United States Patent
Lee et al.

(10) Patent No.: US 10,249,825 B2
(45) Date of Patent: Apr. 2, 2019

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicants: DUK SAN NEOLUX CO., LTD., Cheonan-si, Chungcheongnam-do (KR); SAMSUNG DISPLAY CO., LTD., Yongin-si, Gyeonggi-do (KR)

(72) Inventors: Bumsung Lee, Cheonan-si (KR); Yeonhee Choi, Cheonan-si (KR); Daesung Kim, Yongin-si (KR); Soungyun Mun, Yongin-si (KR); Jungcheol Park, Cheonan-si (KR); Kiho So, Cheonan-si (KR); Jinho Yun, Cheonan-si (KR); Daehwan Oh, Cheonan-si (KR); Seungwon Yeo, Daejeon (KR); Mikyung Kim, Yongin-si (KR); Kwanhee Lee, Yongin-si (KR)

(73) Assignees: DUK SAN NEOLUX CO., LTD., Cheonan-si, Chungcheon (KR); SAMSUNG DISPLAY CO., LTD., Yongin-si, Gyeonggi-do (KR)

( * ) Notice: Subject to any disclaimer, the term of this patent is extended or adjusted under 35 U.S.C. 154(b) by 337 days.

(21) Appl. No.: 14/650,078

(22) PCT Filed: Dec. 3, 2013

(86) PCT No.: PCT/KR2013/011088
§ 371 (c)(1),
(2) Date: Jun. 5, 2015

(87) PCT Pub. No.: WO2014/088284
PCT Pub. Date: Jun. 12, 2014

(65) Prior Publication Data
US 2015/0325795 A1    Nov. 12, 2015

(30) Foreign Application Priority Data

Dec. 6, 2012  (KR) .................. 10-2012-0141364
Nov. 6, 2013  (KR) .................. 10-2013-0133883

(51) Int. Cl.
*H01L 51/00*  (2006.01)
*C07D 209/82*  (2006.01)
(Continued)

(52) U.S. Cl.
CPC ........ *H01L 51/0061* (2013.01); *C07D 209/82* (2013.01); *C07D 209/86* (2013.01);
(Continued)

(58) Field of Classification Search
CPC ............... H01L 51/006; H01L 51/0061; H01L 51/0067; H01L 51/0052; H01L 51/0068;
(Continued)

(56) References Cited

FOREIGN PATENT DOCUMENTS

| JP | 2008-78362 A | 4/2008 |
| JP | 2008078362 A * | 4/2008 |

(Continued)

OTHER PUBLICATIONS

Extended European Search Report for EP Application No. 13861127.2, seven pages, completed on Jul. 5, 2016.
(Continued)

*Primary Examiner* — Ruiyun Zhang
(74) *Attorney, Agent, or Firm* — Vorys, Sater, Seymour & Pease LLP; Mih Suhn Koh

(57) ABSTRACT

Provided are a compound capable of improving light emitting efficiency, stability, and lifespan of the element, an organic element using the same, and an electric device for the same.

13 Claims, 1 Drawing Sheet

(51) Int. Cl.
| | |
|---|---|
| *C09K 11/06* | (2006.01) |
| *H05B 33/14* | (2006.01) |
| *C07D 209/86* | (2006.01) |
| *C07D 401/12* | (2006.01) |
| *C07D 405/04* | (2006.01) |
| *C07D 405/14* | (2006.01) |
| *C07D 409/04* | (2006.01) |
| *C07D 409/12* | (2006.01) |
| *C07D 409/14* | (2006.01) |
| *G09G 3/3225* | (2016.01) |
| *H01L 51/50* | (2006.01) |

(52) U.S. Cl.
CPC ......... *C07D 401/12* (2013.01); *C07D 405/04* (2013.01); *C07D 405/14* (2013.01); *C07D 409/04* (2013.01); *C07D 409/12* (2013.01); *C07D 409/14* (2013.01); *C09K 11/06* (2013.01); *G09G 3/3225* (2013.01); *H01L 51/006* (2013.01); *H01L 51/0072* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0052* (2013.01); *H01L 51/0056* (2013.01); *H01L 51/0058* (2013.01); *H01L 51/0067* (2013.01); *H01L 51/0068* (2013.01); *H01L 51/0073* (2013.01); *H01L 51/0074* (2013.01); *H01L 51/5004* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 2251/552* (2013.01); *Y02E 10/549* (2013.01)

(58) Field of Classification Search
CPC ............. H01L 51/0073; H01L 51/0074; H01L 51/5012; C09K 11/06; C09K 2211/1007; C09K 2211/1011; C09K 2211/1014; C09K 2211/1029; C09K 2211/1044; C09K 2211/1059; C07D 403/04; C07D 403/10; C07D 401/12; C07D 405/04; C07D 405/14
USPC .................. 428/690, 917; 257/40, E51.028; 544/180, 284, 212; 546/1, 276.7; 548/440
See application file for complete search history.

(56) References Cited

FOREIGN PATENT DOCUMENTS

| | | | |
|---|---|---|---|
| JP | 2008-195841 A | | 8/2008 |
| JP | 2013159561 A | * | 8/2013 |
| KR | 10-2010-0021907 A | | 2/2010 |
| KR | 10-2010-0033265 A | | 3/2010 |
| KR | 10-2010-0055351 A | | 5/2010 |
| KR | 10-2010-0131629 A | | 12/2010 |
| KR | 10-2011-0016047 A | | 2/2011 |
| KR | 10-2011-0117549 A | | 10/2011 |
| KR | 10-2011-0134201 A | | 12/2011 |
| KR | 10-2012-0100031 A | | 9/2012 |
| KR | 10-2012-0111670 A | | 10/2012 |
| KR | 20130077473 A | * | 7/2013 |
| KR | 10-2013-0096334 A | | 8/2013 |
| WO | 2011155742 A2 | | 12/2011 |

OTHER PUBLICATIONS

Office Action for JP Application No. 2015-546381, three pages, dated Jun. 7, 2016.

* cited by examiner

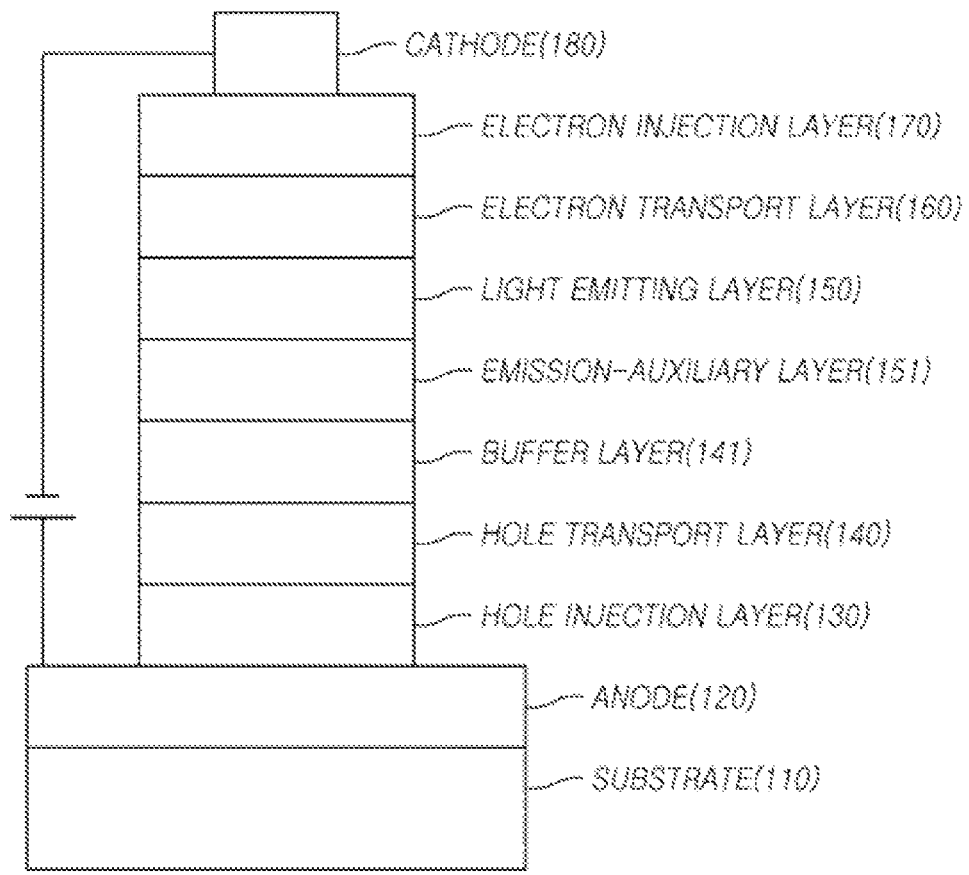

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This application claims priority from and the benefit under 35 U.S.C. § 119(a) of Korean Patent Application No. 10-2012-0141364, filed on Dec. 6, 2012, and Korean Patent Application No. 10-2013-0133883, filed on Nov. 6, 2013, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. Here, in many cases, the organic material layer may have a multi-layered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function.

The most problematic issues in an organic electric element are life span and efficiency, and the situation is such that this life span or efficiency issue must be solved as displays become larger and larger. Efficiency, life span, driving voltage, and the like are correlated with each other.

For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton.

However, since a material used in a hole transporting layer should have a low HOMO value, it mainly has a low T1 value. Due to this, excitons generated from a light emitting layer are transported to the hole transporting layer, resulting in a charge unbalance in the light emitting layer. Thus, light emission occurs in the hole transporting layer or at an interface of the hole transporting layer so that the organic electroluminescent device is reduced in color purity, efficiency, and lifespan.

When used, a material with rapid hole mobility can reduce a driving voltage in the organic electroluminescent device, but is apt to cause a charge unbalance due to its hole mobility being faster than its electron mobility. Hence, the organic electroluminescent device also suffers from the disadvantage of a reduction in color purity, efficiency, and lifespan.

Therefore, there is an urgent need to develop an emission-auxiliary layer which has a high T1 value and the HOMO level of which is between the HOMO energy level of a hole transport layer and the HOMO energy level of a light emitting layer.

In addition, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

An object of the present invention is to provide a compound that is configured to both have a high T1 value and a wide band gap, and which allows for an excellent charge balance by introducing a carbazole core, which is widely used as a hole transporting material, with a non-linear linker (thus, resulting in a bent structure upon linkage with an amine group) and with a bulky substituent at the nitrogen position thereof, thereby guaranteeing that the device has high luminous efficiency, low driving voltage, high thermal resistance, high color purity, and long longevity, an organic electroluminescent device using the same, and an electronic device using the device.

In accordance with an aspect of the present invention, there is provided compounds represented by the formula below.

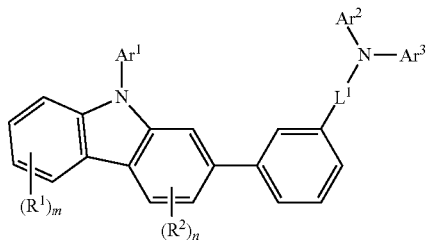

In another aspect of the present invention, there are provided organic electric elements using the compound represented by the formula above and electronic devices including the organic electric element.

By using the compound according to embodiments of the present invention, an organic electric element according to one or more embodiments of the present invention not only has high luminous efficiency, low driving voltage and high heat-resistant and, but can also be significantly improved in color purity, luminous efficiency, and life span.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine, chlorine, bromine, or iodine.

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl" or "halogen alkyl" as used herein includes an alkyl group substituted with a halogen.

Unless otherwise stated, the term "heteroalkyl" as used herein means alkyl substituted one or more carbon atoms with heteroatom.

Unless otherwise stated, the term "alkenyl" or "alkynyl" as used herein has, but not limited to, double or triple bonds of 2 to 60 carbon atoms, and includes a linear alkyl group, or a branched chain alkyl group, Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "alkenoxyl group", "alkenoxy group", "alkenyloxy group" or "alkenyloxy group" as used herein means an oxygen radical attached to an alkenyl group, but not limited to, and has 2 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_2$ to $C_{60}$ aryl or arylene group containing one or more heteroatoms, includes both monocyclic and polycyclic rings, and may also be formed in conjunction with an adjacent group.

Unless otherwise stated, the term "heterocyclic group" as used herein contains one or more heteroatoms, but not limited to, has 2 to 60 carbon atoms, includes both monocyclic and polycyclic rings, and may include alicyclic and/or aromatic group containing heteroatoms. Also, the heterocyclic group may also be formed in conjunction with an adjacent group.

Unless otherwise stated, the term "heteroatom" as used herein represents at least one of N, O, S, P, and Si.

Also, the term "heterocyclic group" may include $SO_2$ instead of carbon consisting of cycle. For example, "heterocyclic group" includes compound below.

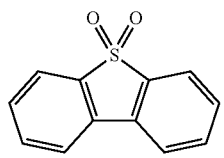 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$' $C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the Formulas used in the present invention are as defined in the index definition of the substituent of the following Formula.

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. When a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

(a = 2)  (a = 3)

The FIGURE illustrates an organic electric element according to an embodiment of the present invention.

Referring to the FIGURE, an organic electric element 100 according to an embodiment of the present invention includes a first electrode 120 formed on a substrate 100, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a light emitting layer or an emission-auxiliary layer by using the compound represented by Formula 1, and thus the life span and efficiency of the organic electric element can be improved at the same time.

The organic electric element according to an embodiment of the present invention may be manufactured using a PVD (physical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R(Red), G(Green), B(Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, which covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

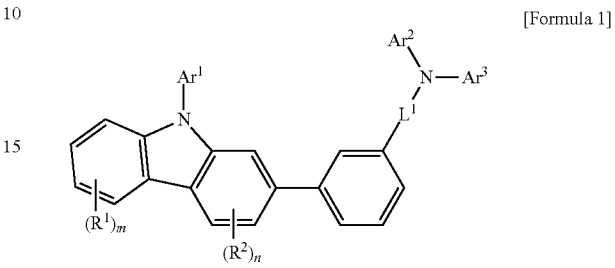

[Formula 1]

In Formula 1 above, m is an integer from 1 to 4, and n is an integer from 1 to 3.

In Formula 1 above, $R^1$ and $R^2$ may be independently selected from the group consisting of hydrogen, deuterium, tritium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, -$L^2$-N($Ar^2$)($Ar^3$), a $C_1$-$C_{30}$ alkoxy group, and a $C_6$-$C_{30}$ aryloxy group. For example, $R^1$ and $R^2$ may be independently hydrogen, a phenyl group, or a naphthyl group and so on.

In Formula 1 above, $Ar^1$ may be selected from the group consisting of a fluorenyl group, a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, a $C_1$-$C_{50}$ alkyl group, -$L^2$-N($Ar^2$)($Ar^3$), and a fused ring group of a $C_3$-$C_{60}$ aliphatic ring and a $C_6$-$C_{60}$ aromatic ring. For example, $Ar^1$ may be an ethyl group, a phenyl group, a biphenylyl group, a naphthyl group, a terphenylyl group, a 9,9-dimethyl-9H-fluorenyl group, a 9,9-diphenyl-9H-fluorenyl group, a 9,9-spiro-bifluorenyl group, a pyridyl group, an isoquinolyl group, a dibenzothienyl group, or a dibenzofuranyl group and so on.

In Formula 1 above, $L^1$ and $L^2$ may be independently selected from the group consisting of a single bond, a $C_6$-$C_{60}$ arylene group, a fluorenylene group, and a $C_2$-$C_{60}$ bivalent heterocyclic group containing at least one heteroatom selected from the group consisting of O, N, S, Si, and P, a bivalent fused ring group of a $C_3$-$C_{60}$ aliphatic ring and a $C_6$-$C_{60}$ aromatic ring, and a bivalent aliphatic hydrocarbon group. For example, $L^1$ and $L^2$ may be independently a single bond, a phenylene group, a biphenylene group, a naphthylene group, a 9,9-dimethyl-9H-fluorenylene group, a 9,9-diphenyl-9H-fluorenylene group, a dibenzothienylene group, or a dibenzofuranylene group and so on.

In Formula 1 above, $Ar^2$ and $Ar^3$ may be independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, and a $C_2$-$C_{20}$ alkenyl group. For example, $Ar^2$ and $Ar^3$ may be independently a phenyl group, a biphenylyl group, a terphenylyl group, a naphthyl group, a phenanthryl group, a 9,9-dimethyl-9H-fluorenyl group, a 9,9-diphenyl-9H-fluorenyl group, a 9,9-spiro-bifluorenyl group, a dibenzothienyl group, a dibenzofuranyl group, a phenyl group substituted by fluoro, a phenyl group substituted by propenyl, a pyridyl group, a isoquinolyl group, a quinolyl group, a phenyl group substituted by methyl, a phenyl group substituted by deuterium, a benzothienyl group, a thienyl group, an indolyl group, or a benzoquinolyl group and so on.

With the provisos that, the aryl group, heterocyclic group, fluorenyl group, alkyl group, alkenyl group, fused ring group, alkoxy group, aryloxy group, arylene group, fluorenylene group and aliphatic hydrocarbon group may be substituted by one or more substituents selected from the group consisting of deuterium, halogen, a silane group, a boron group, a germanium group, a cyano group, a nitro group, -L'-N(R')(R'') (wherein, L' may be selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring, and a $C_2$-$C_{60}$ bivalent aliphatic hydrocarbon group, and the R' and R'' may be independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{20}$ alkyl group, and a $C_2$-$C_{20}$ alkenyl group.), a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

Also, in Formula 1 above, $L^1$ may be any one of groups below.

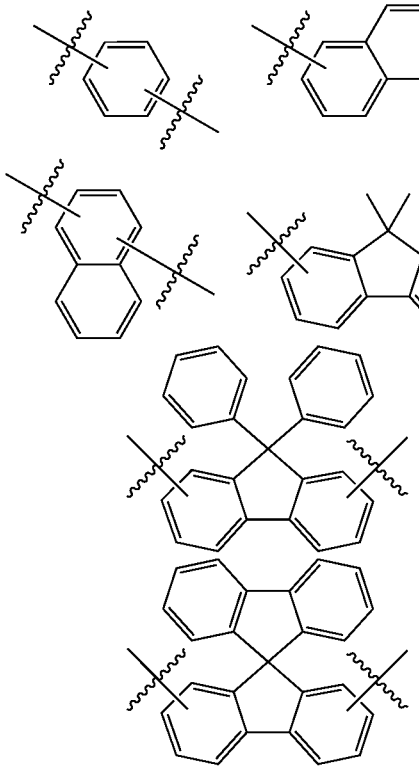

Also, in Formula 1 above, $Ar^e$ and $Ar^a$ are independently any one of groups below.

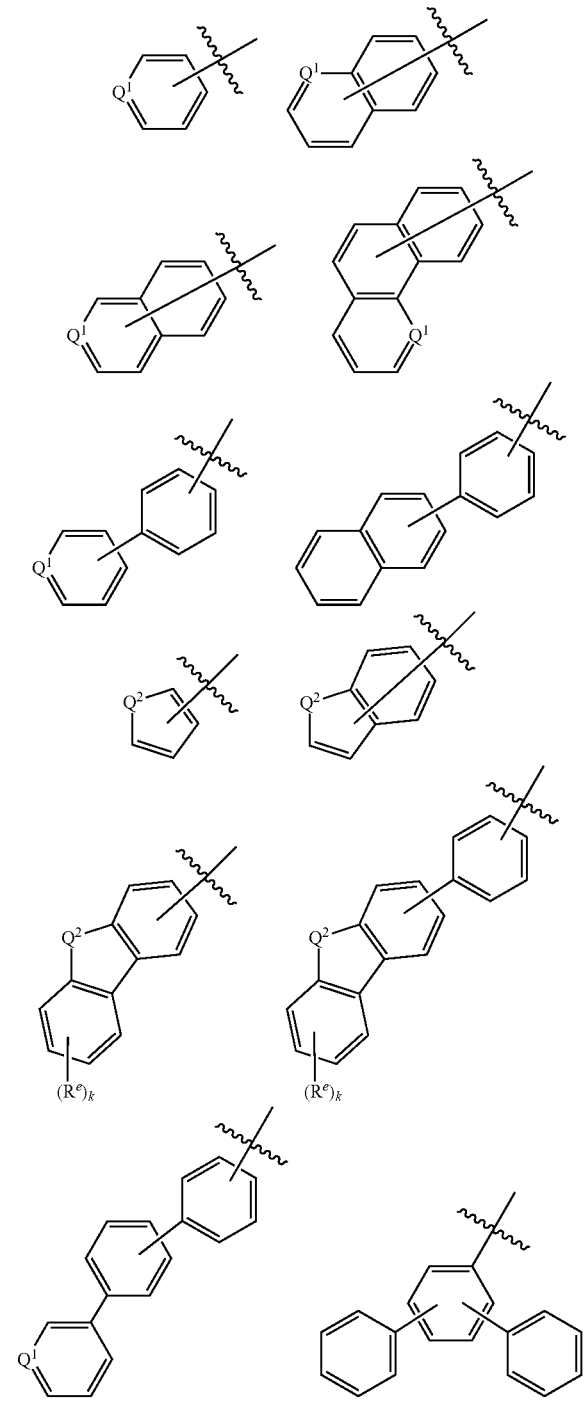

In groups above, $Q^1$ may be $C(R^a)$ or N, and $Q^2$ may be selected from the group consisting of $C(R^b)(R^c)$, $N(R^d)$, S and O. k may be an integer from 1 to 4. $R^a$ and $R^e$ may be independently selected from the group consisting of hydrogen, deuterium, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a fluorenyl group, or any two adjacent groups of $R^e$s can be optionally linked together to form at least one aromatic ring.

$R^b$ to $R^d$ may be independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^b$ and $R^e$ can be optionally linked together to form at least one spiro compound.

Specially, the compound represented by Formula 1 above may be represented by one of Formula 2 or Formula 3 below.

[Formula 2]

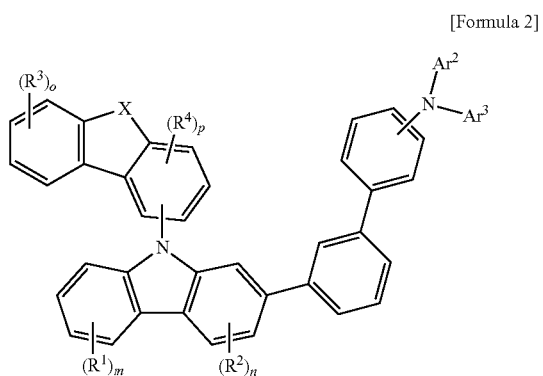

[Formula 3]

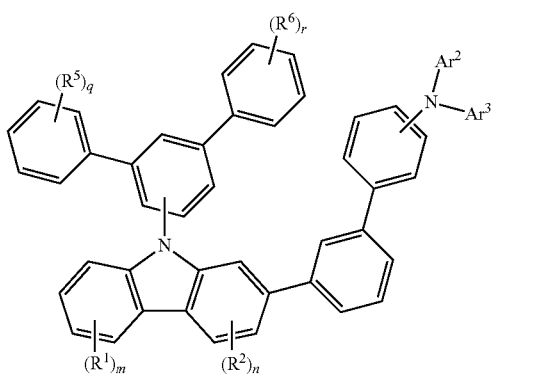

In Formula 2 and Formula 3 above, $Ar^2$, $Ar^3$, $R^1$, $R^2$, m and n may be as defined in Formula 1 above.

In Formula 2 above, X may be selected from the group consisting of $C(R^f)(R^g)$, S and O. $R^f$ and $R^g$ may be independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^f$ and $R^g$ can be optionally linked together to form at least one spiro compound.

In Formula 2 and Formula 3 above, o is an integer from 1 to 4, p is an integer from 1 to 3, and q and r are independently an integer from 1 to 5.

In Formula 2 and Formula 3 above, $R^3$ to $R^6$ may be independently selected from the group consisting of hydrogen, deuterium, tritium, halogen, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a $C_6$-$C_{30}$ aryloxy group, or any two adjacent groups of $R^3$s to $R^6$s can be optionally linked together to form at least one aromatic ring.

Specially, the compound represented by Formula 1 above may be represented by one of Formula 4 or Formula 5 below.

[Formula 4]

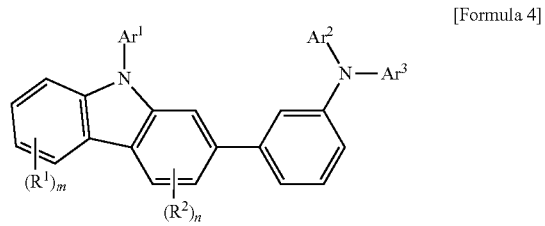

[Formula 5]

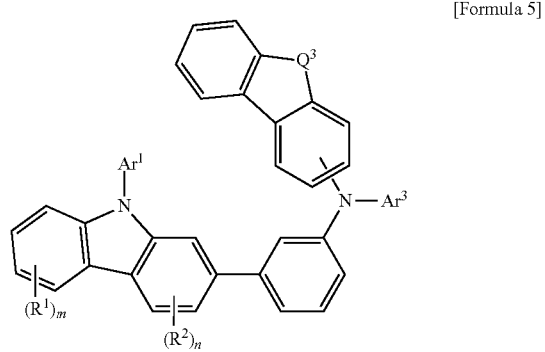

In Formula 4 and Formula 5 above, $Ar^1$ to $Ar^3$, $R^1$, $R^2$, m and n may be as defined in Formula 1 above.

In Formula 5 above, $Q^3$ may be selected from the group consisting of $C(R^h)(R^i)$, $N(R^j)$, S and O. $R^h$ to $R^j$ may be independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^h$ and $R^i$ can be optionally linked together to form at least one spiro compound.

More specially, the compound represented by Formula 1 to Formula 5 above may be represented by one of compounds below.

B1 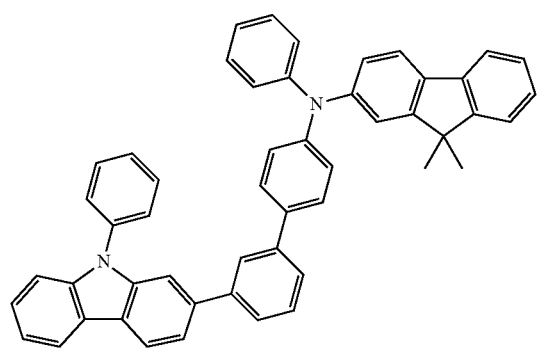
B6 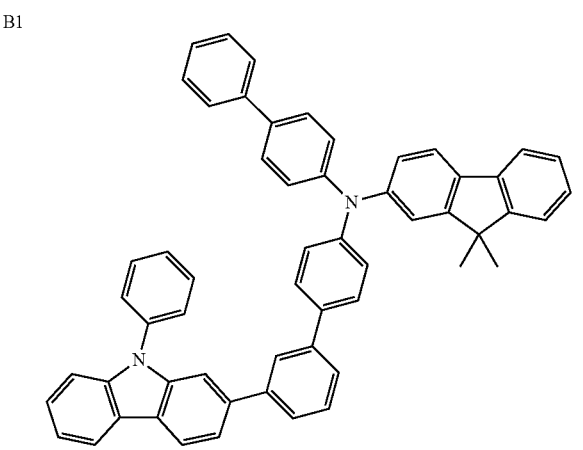
B7 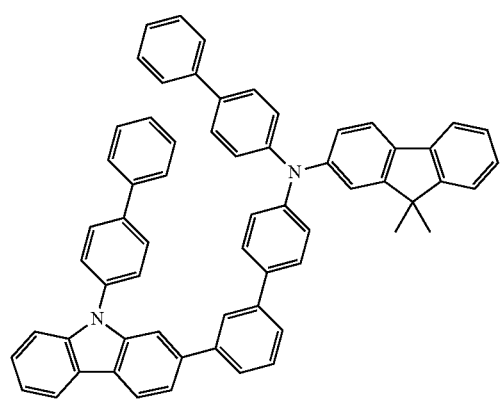
B11 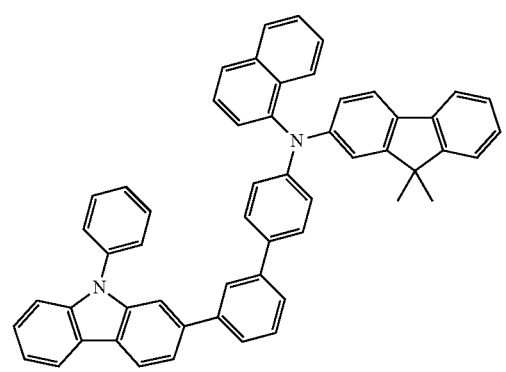
B12 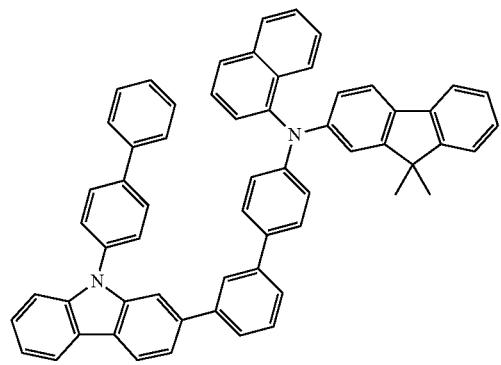
B16 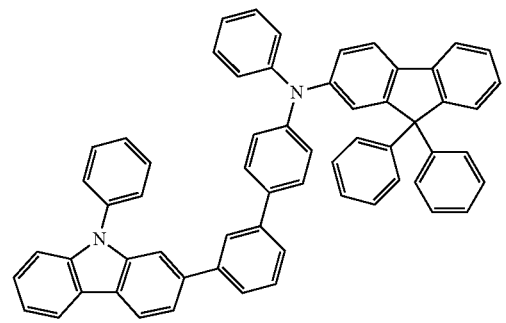
B17 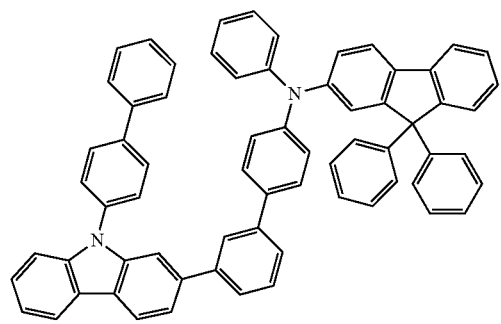
B21 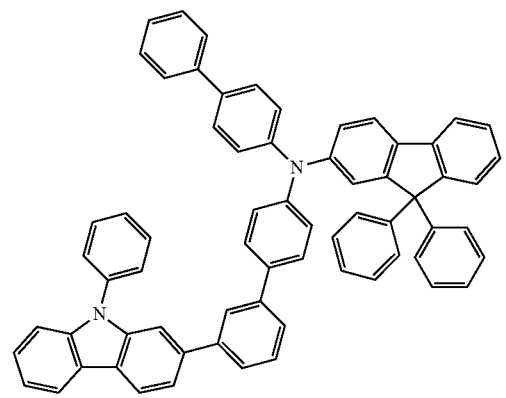

-continued
B22
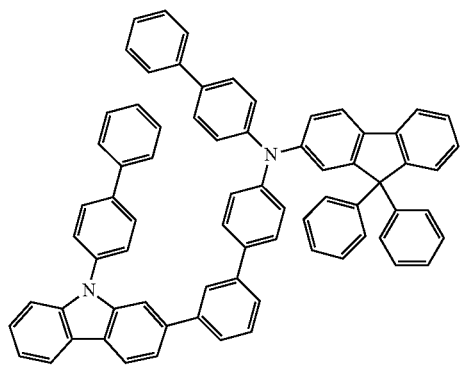
B23
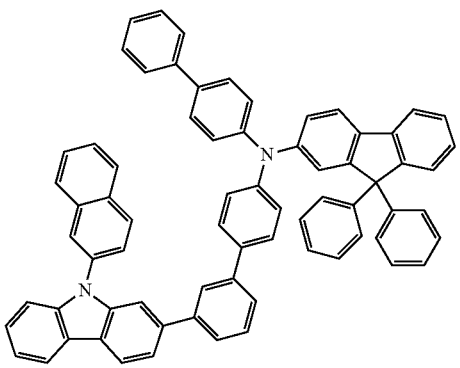
B24
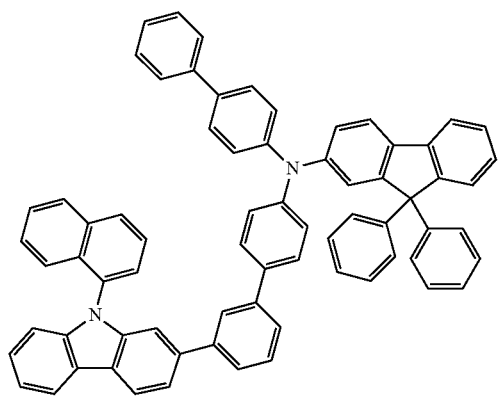
B25
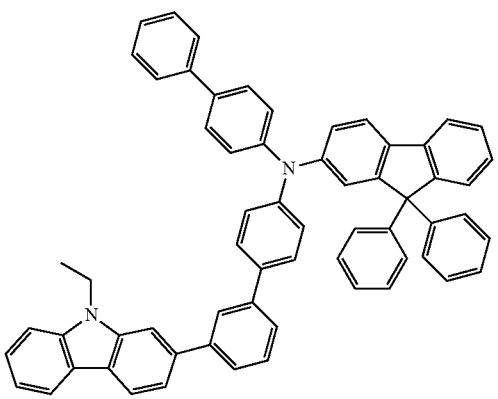
B26
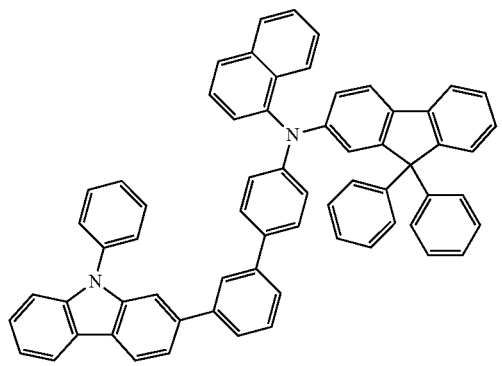
B27
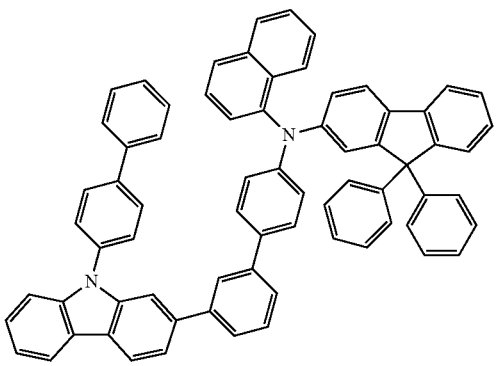
B31
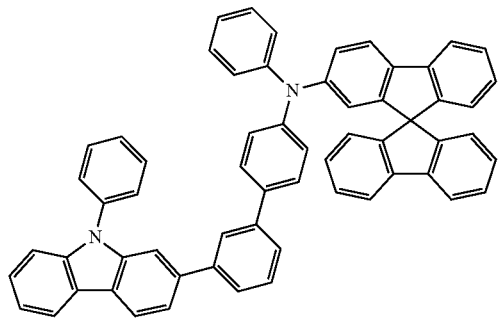
B43
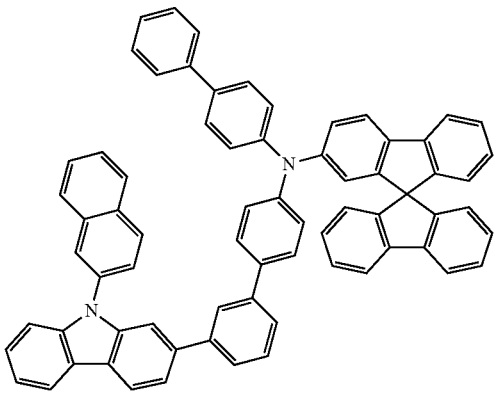

-continued
B47
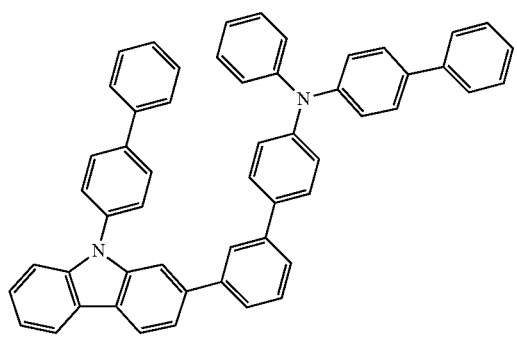
B51
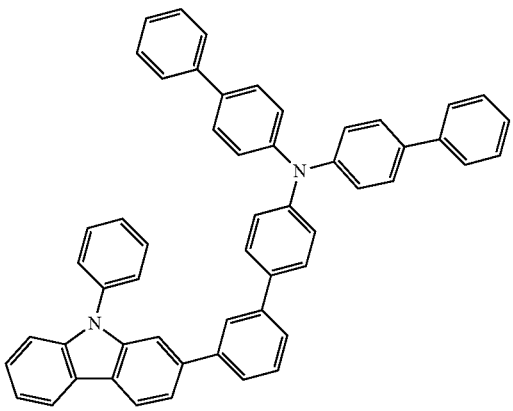
B62
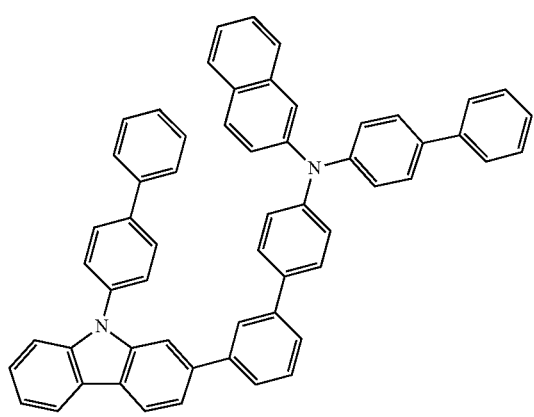
B66
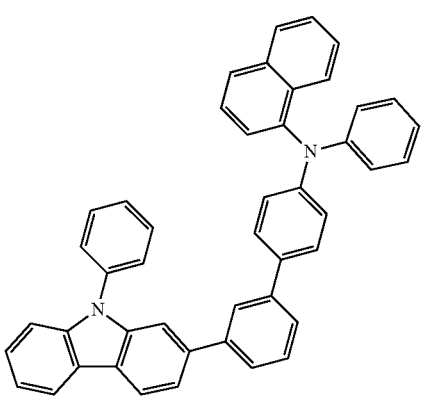
B86
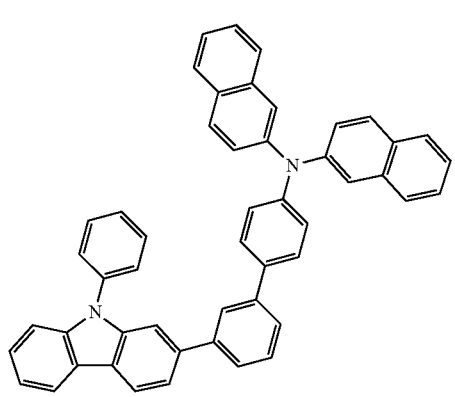
B94
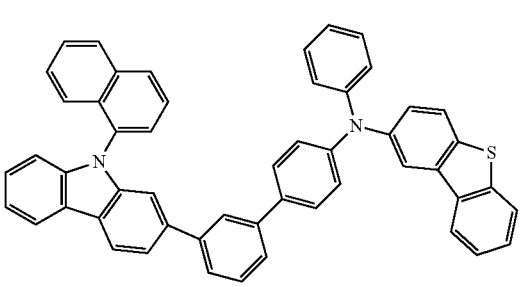
B106
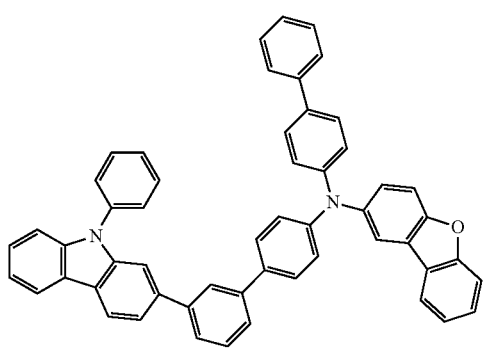
B122
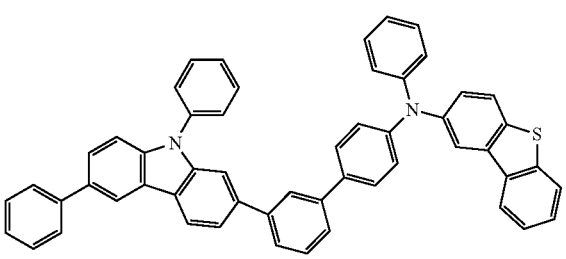

-continued
B124
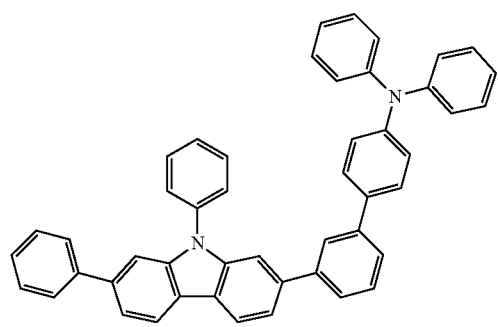
B125
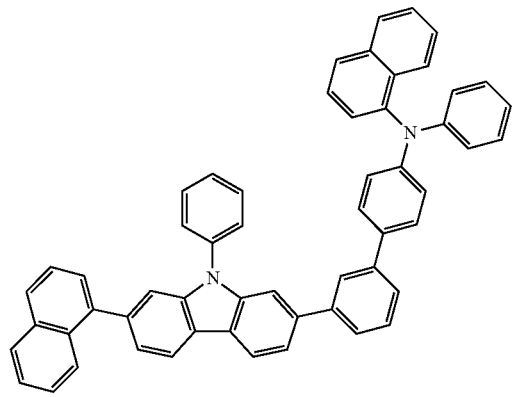
B127
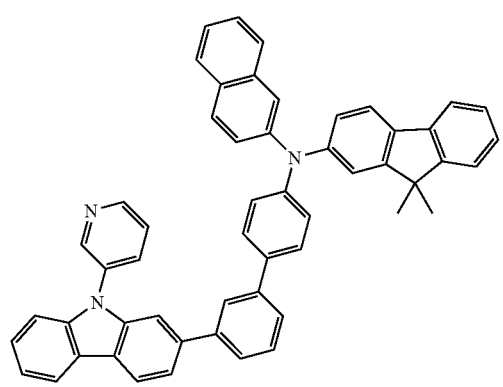
B128
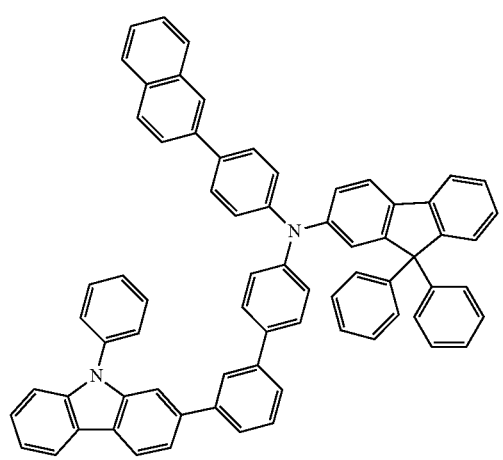
B129
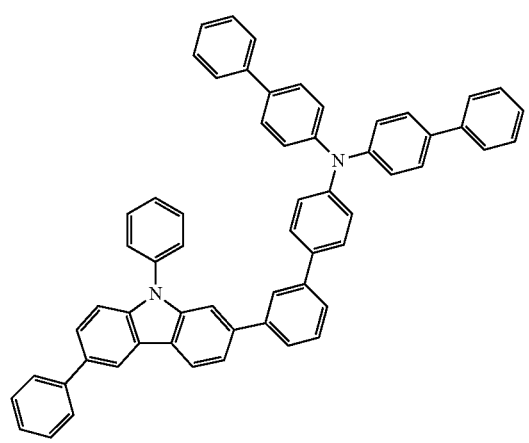
B130
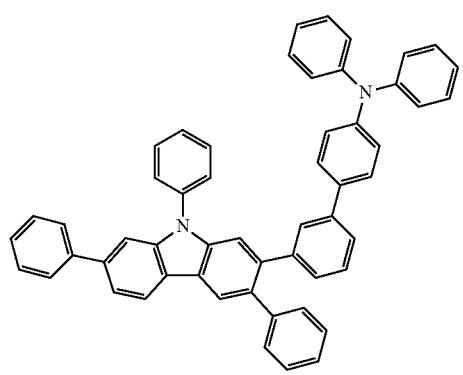

-continued
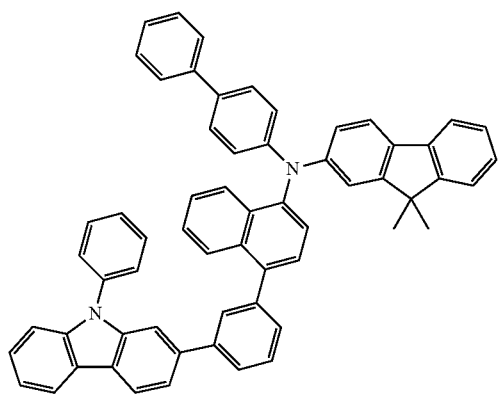
B132
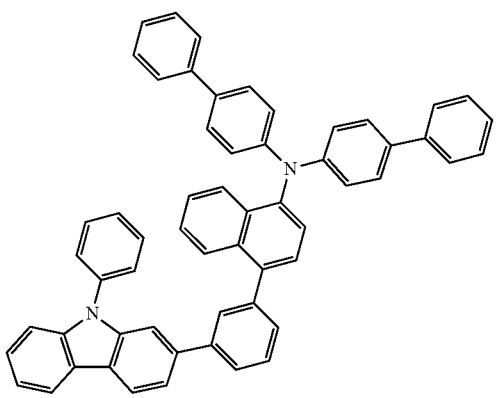
B138
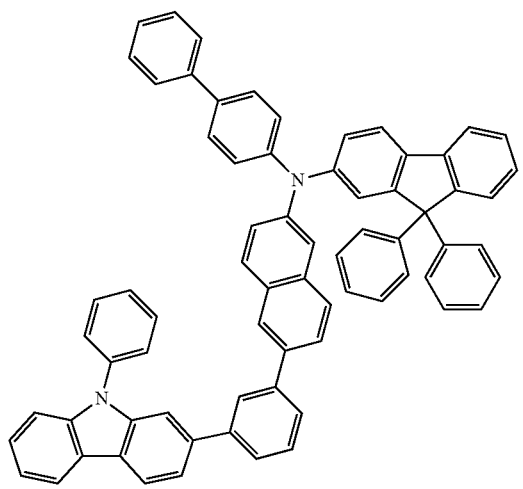
B145
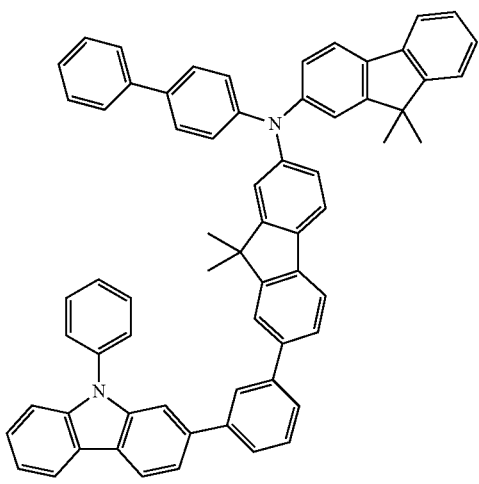
B152
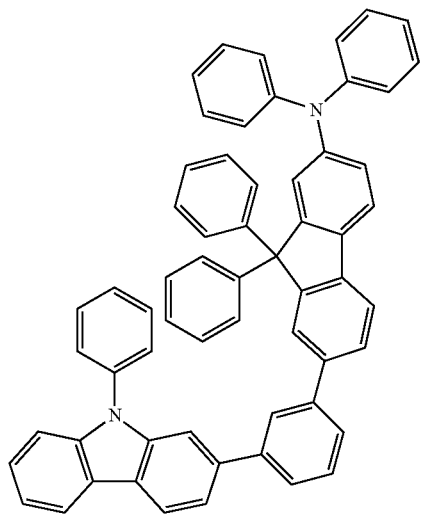
B157
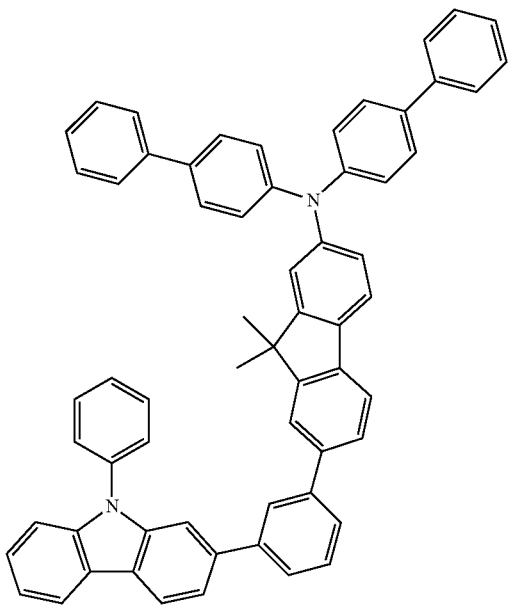
B158

-continued
B161
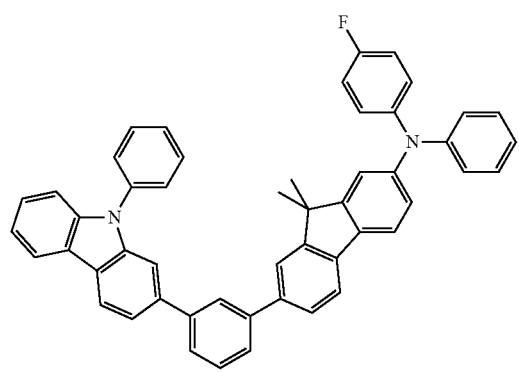
B162
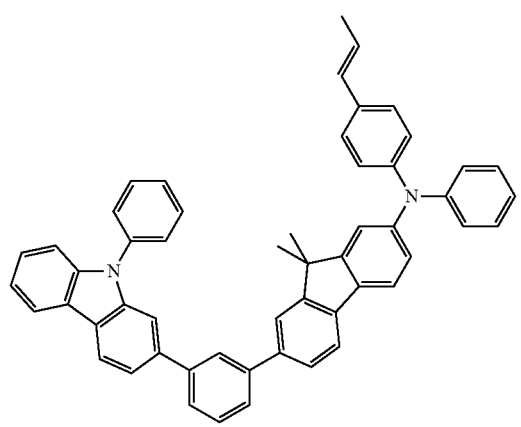
B164
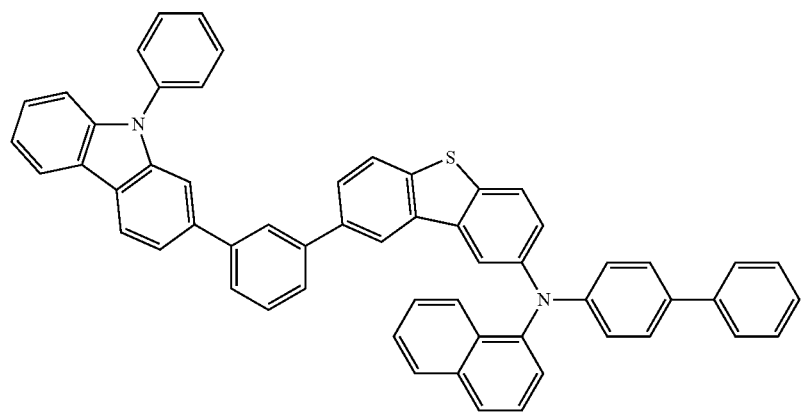
B165
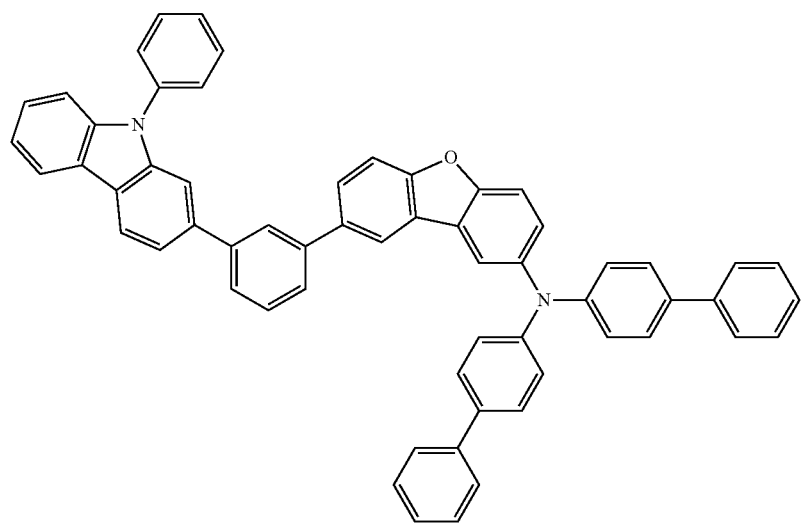

-continued
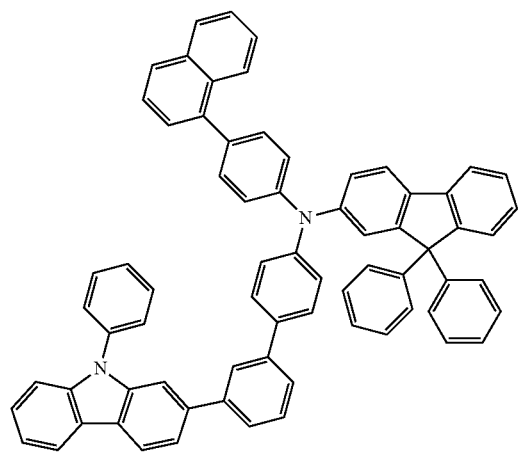
B167
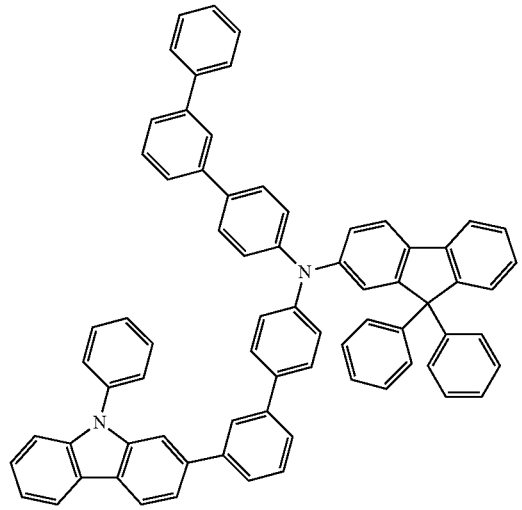
B168
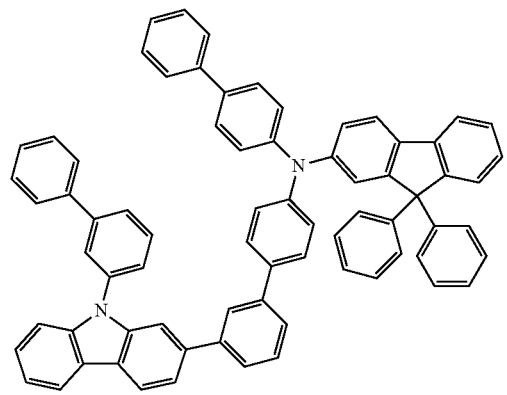
B169
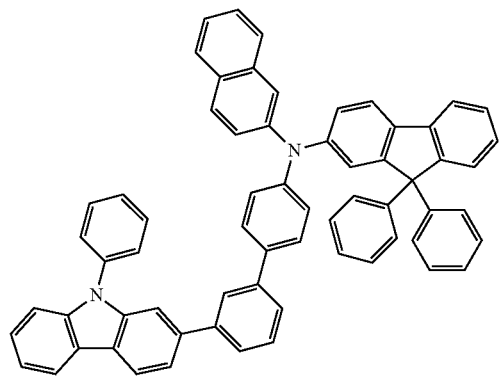
B170
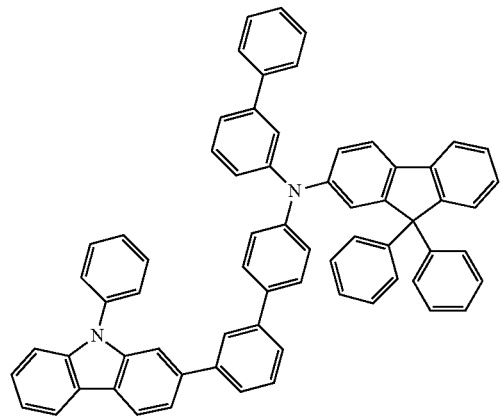
B171
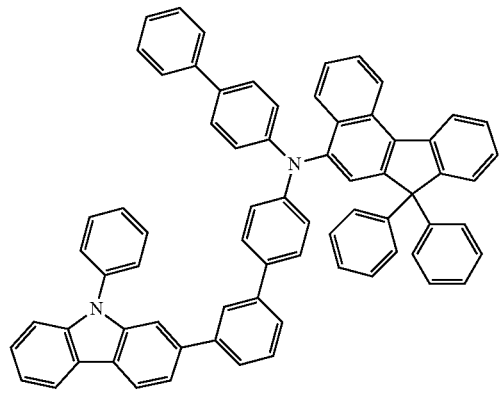
B172

-continued
B173
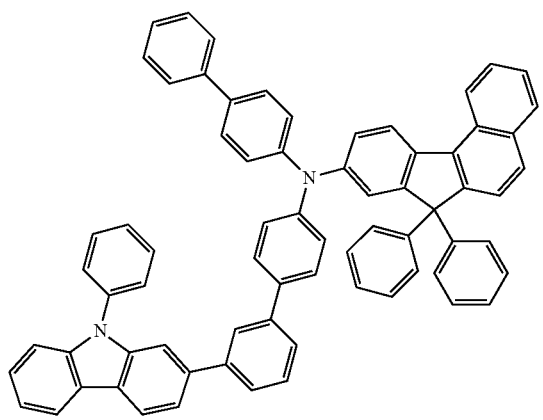
B174
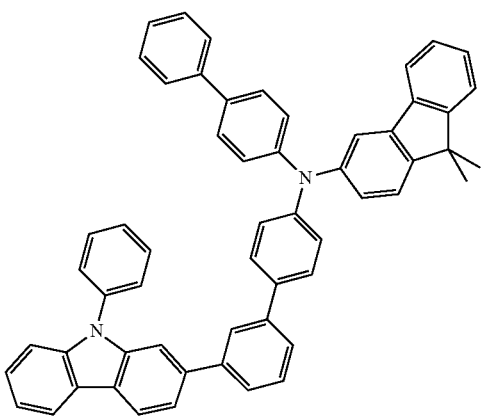
B175
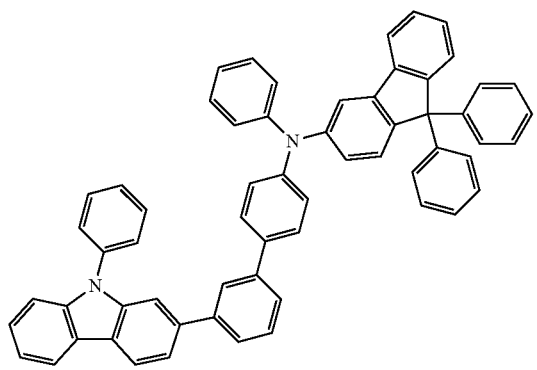
B176
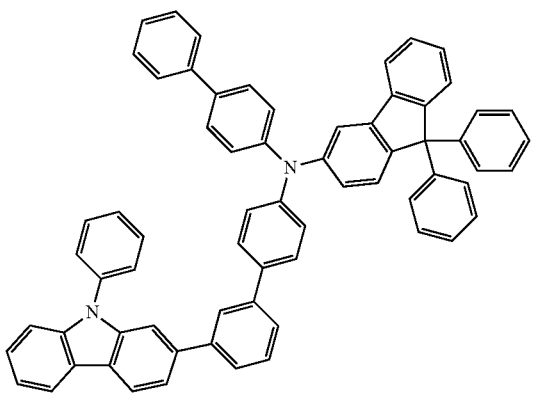
B177
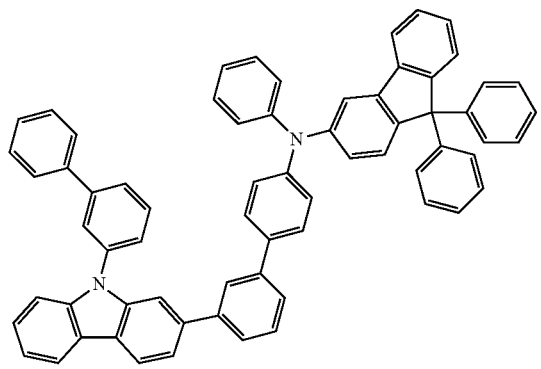
B178
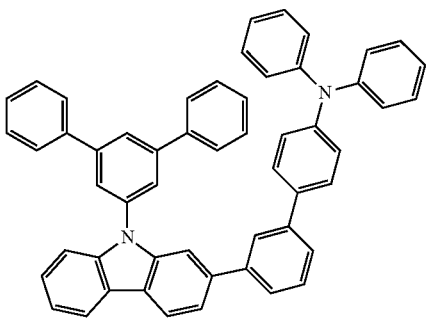
B179
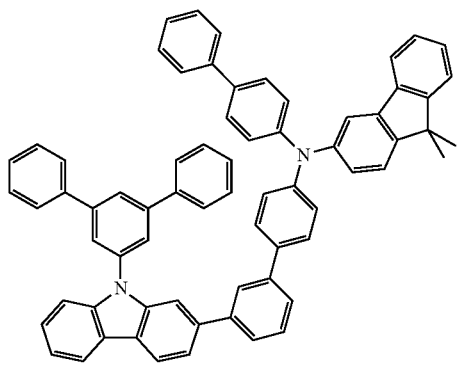
B180
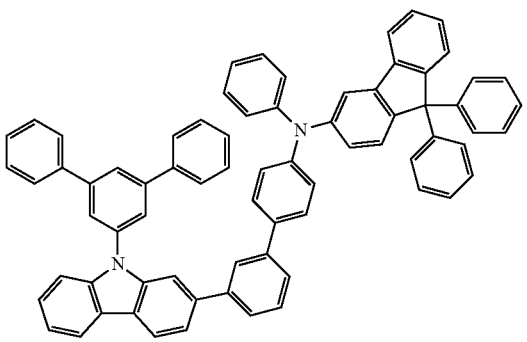

-continued
B181
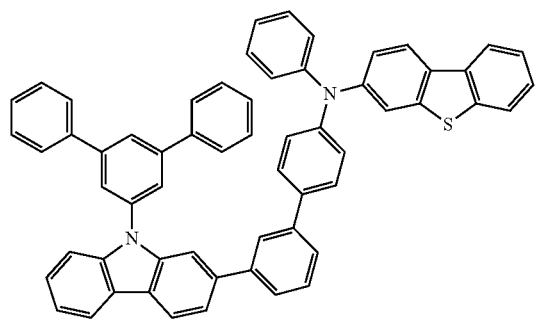
B182
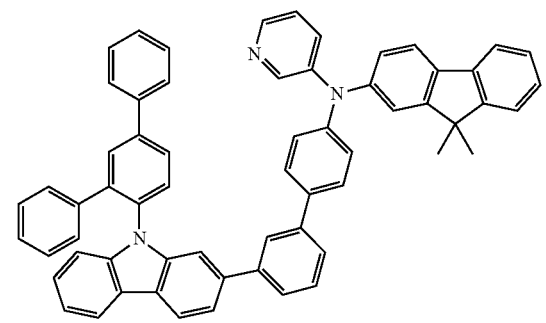
B183
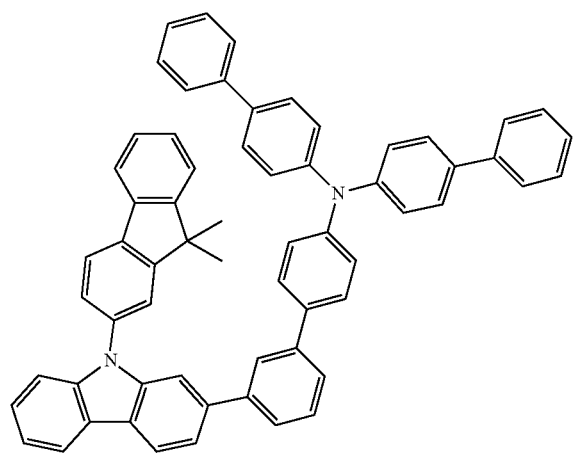
B184
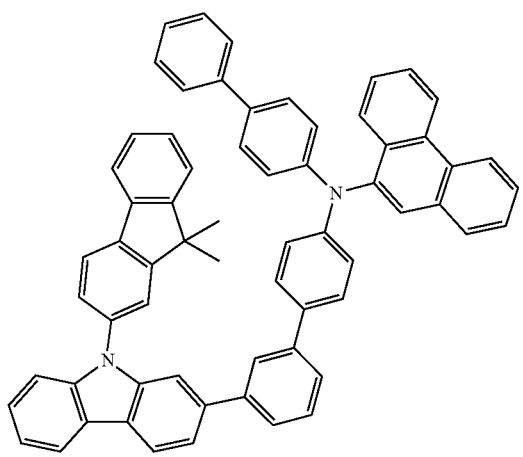
B185
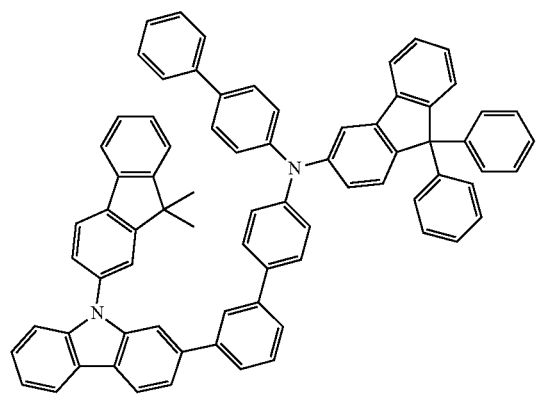
B186
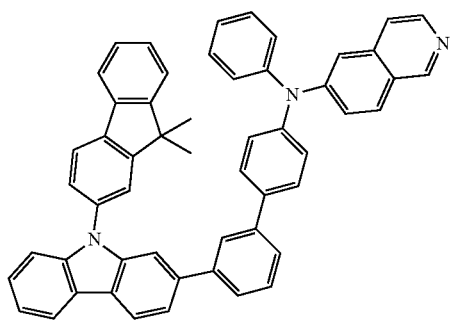

-continued
B187
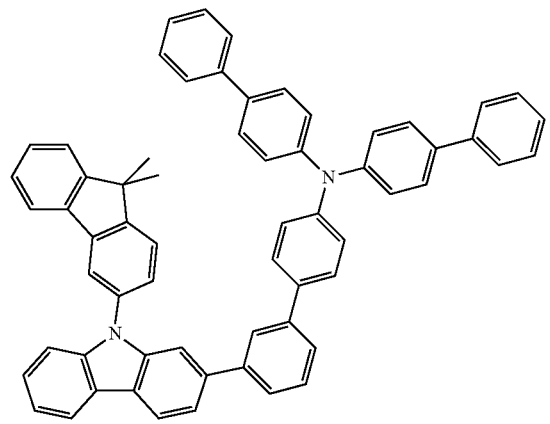
B188
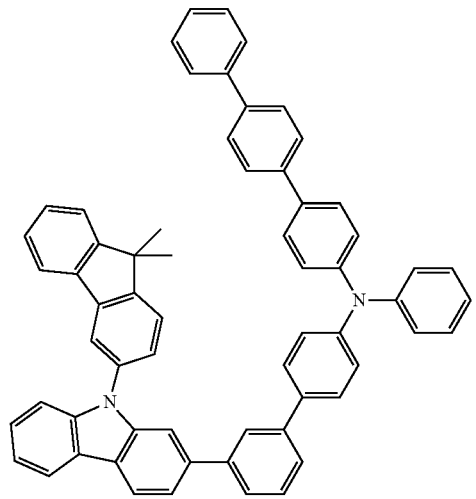
B189
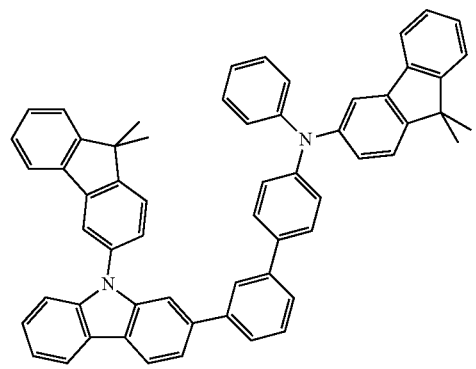
B190
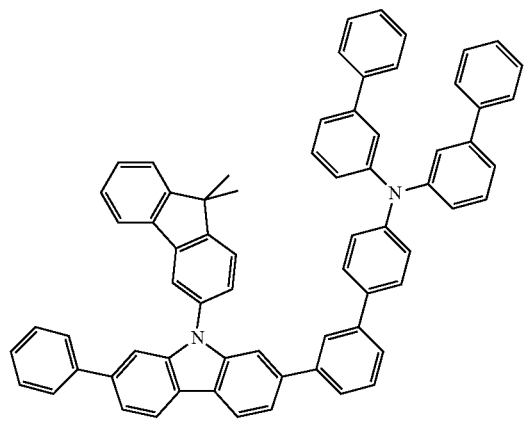
B191
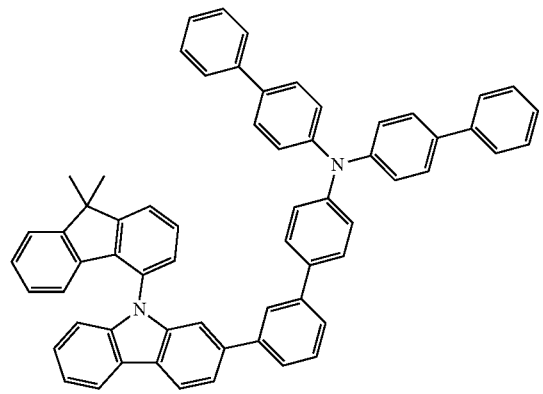
B192
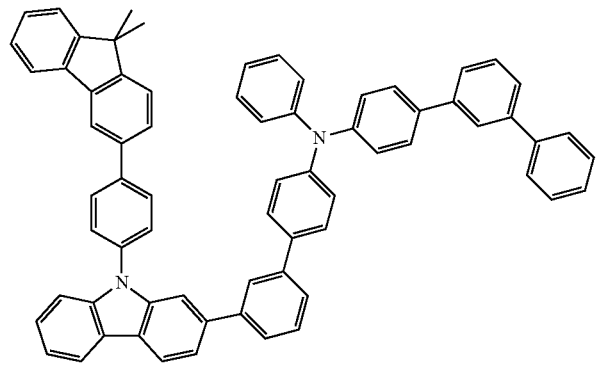

-continued
B193
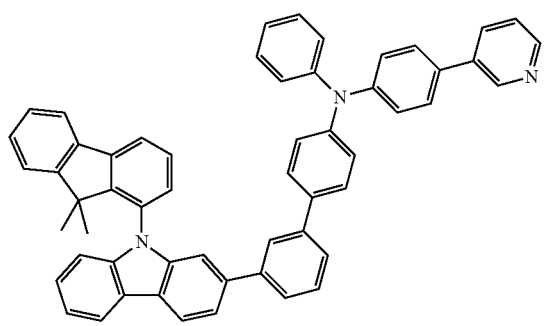
B194
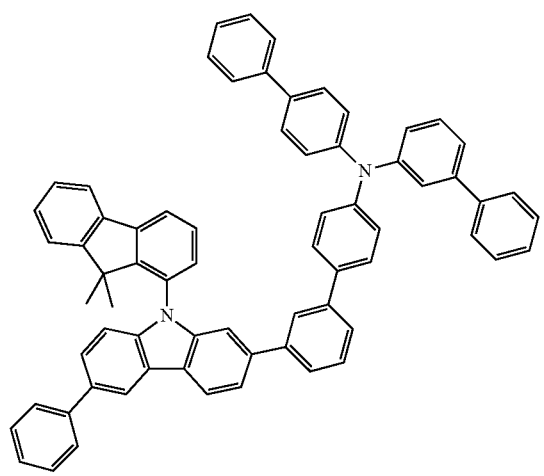
B195
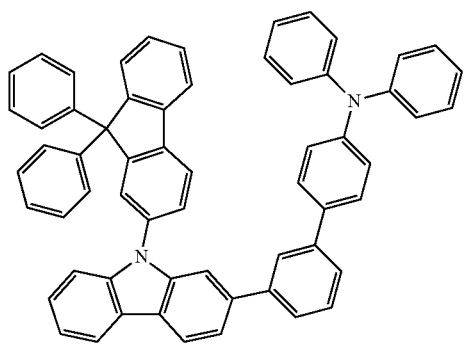
B196
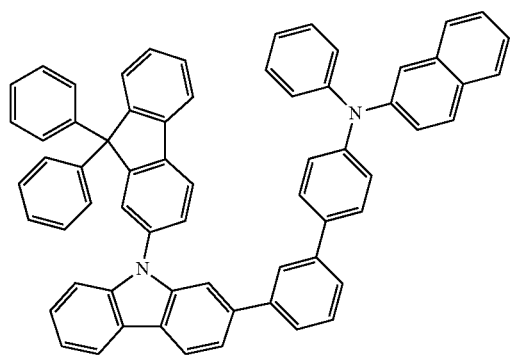
B197
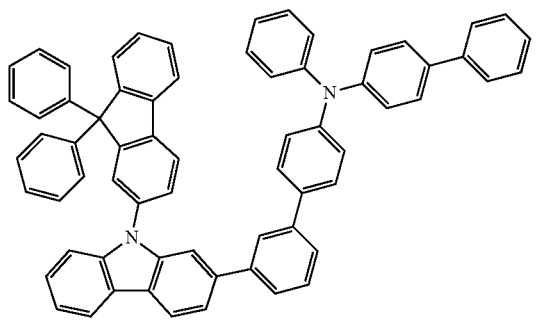
B198
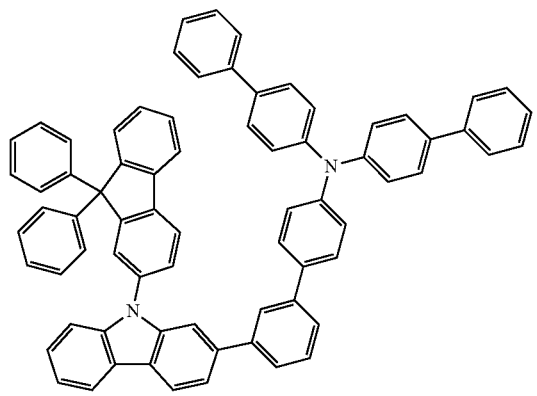
B199
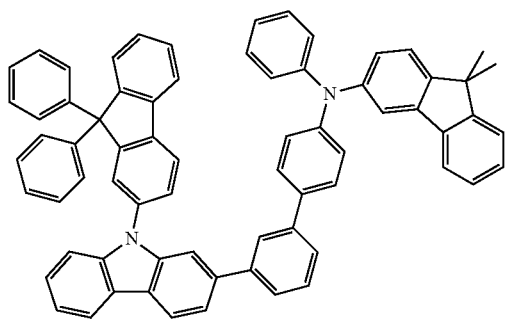
B200
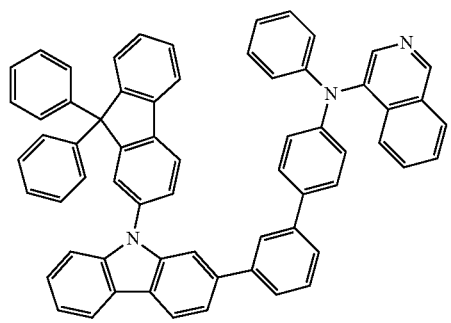

-continued
B201
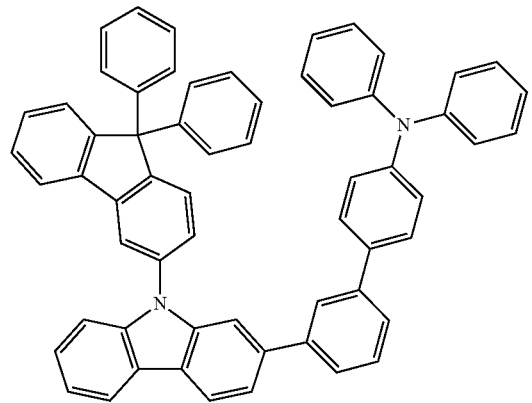
B202
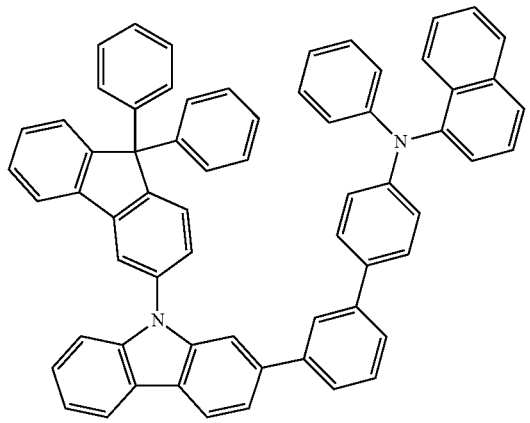
B203
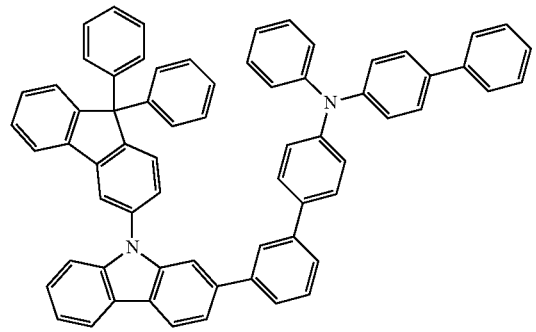
B204
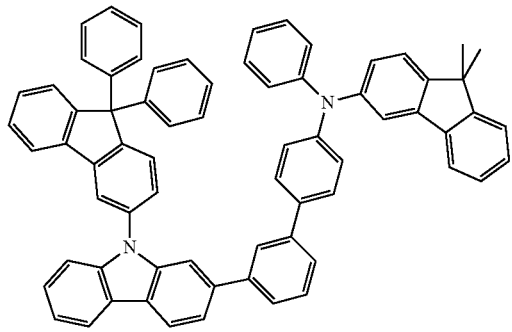
B205
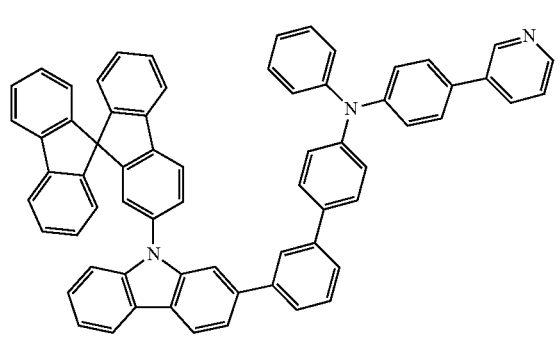
B206
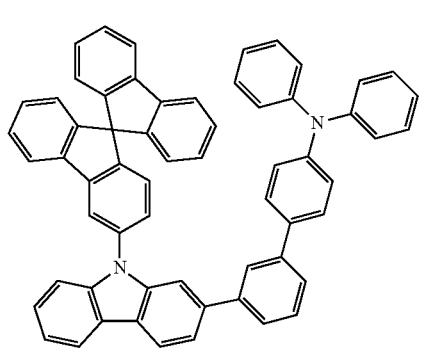
B207
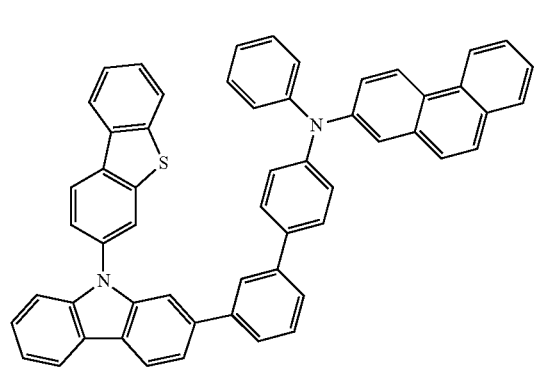
B208
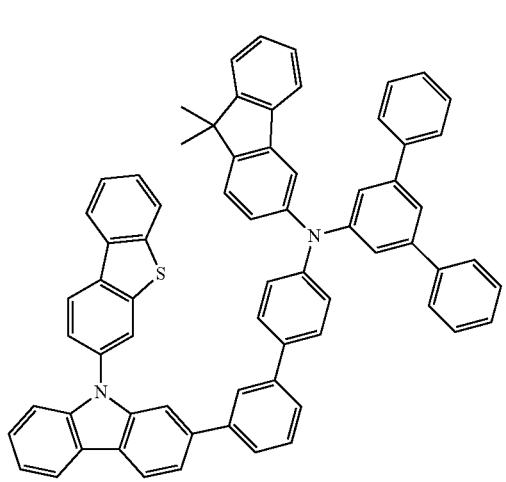

-continued
B209
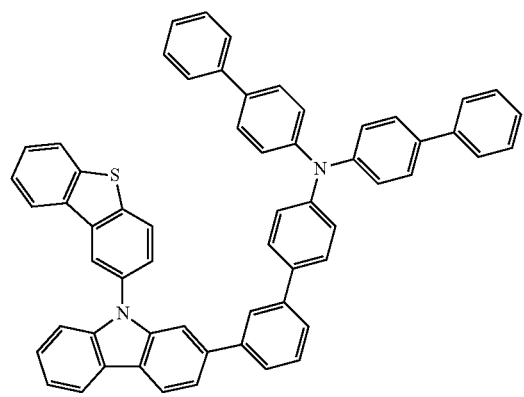
B210
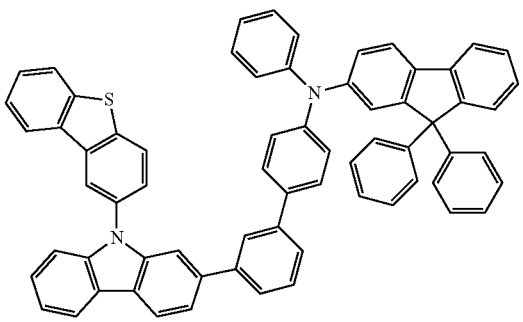
B211
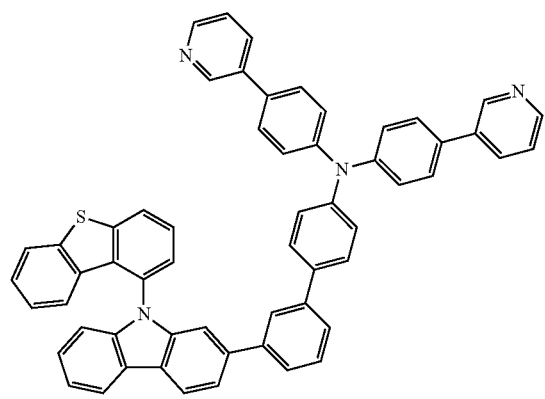
B212
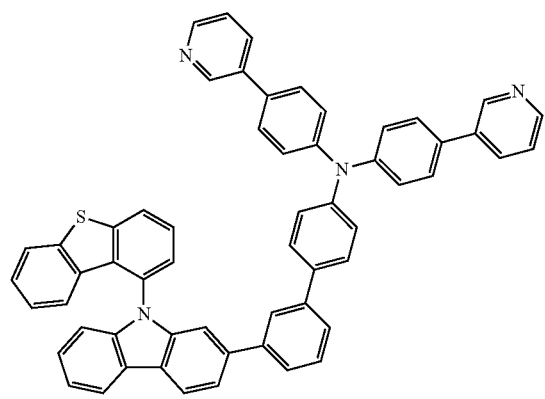
B213
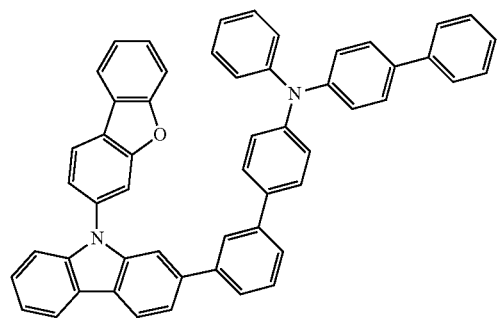
B214
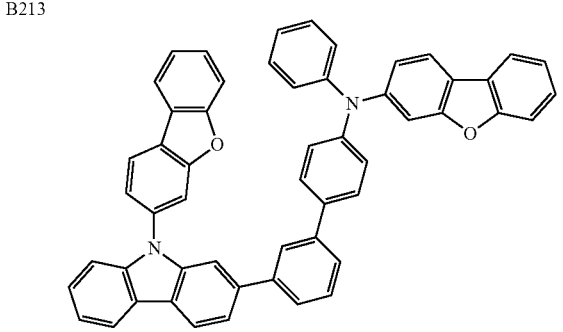
B215
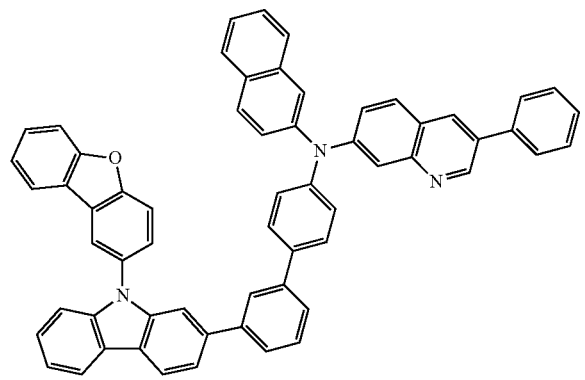
B216
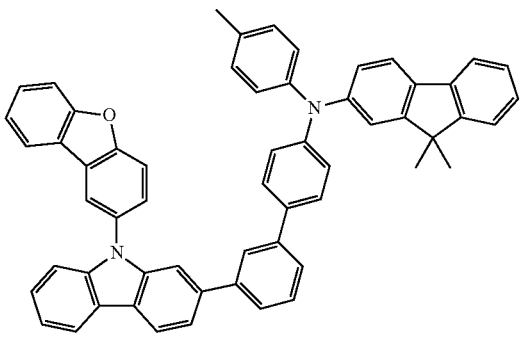

-continued
B217 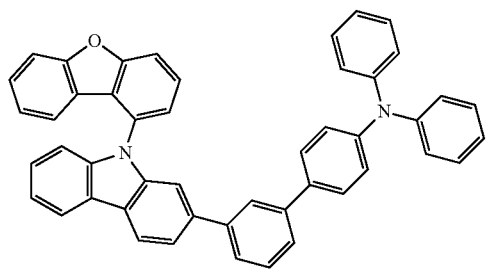
B218 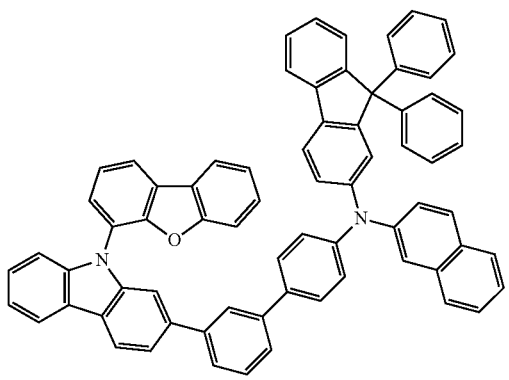
B219 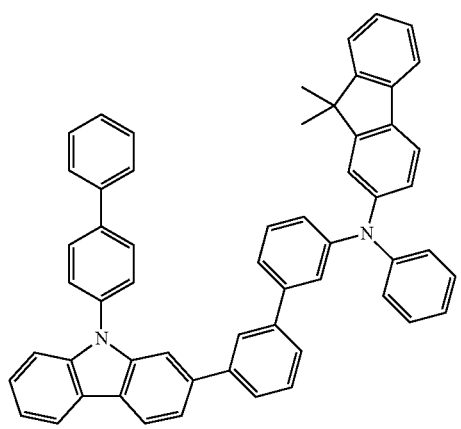
B220 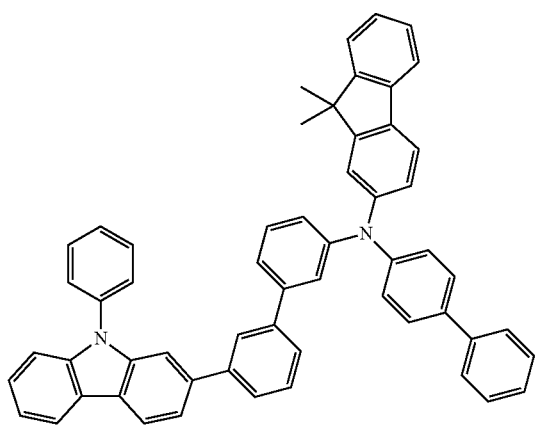
B221 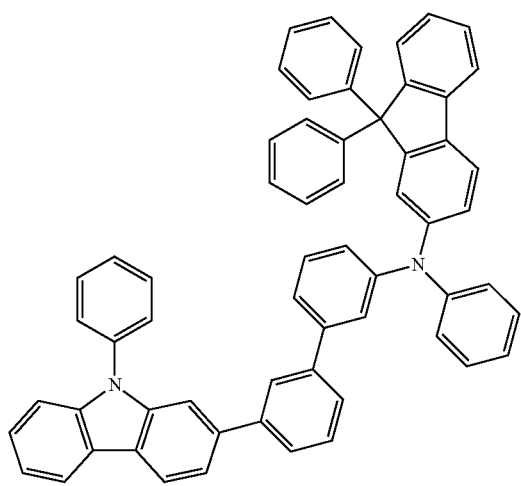
B222 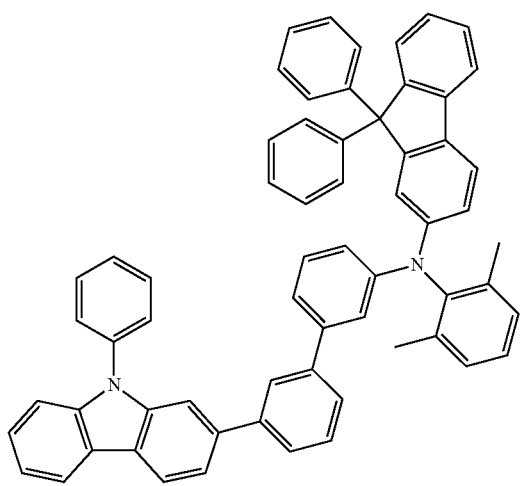

-continued
B223
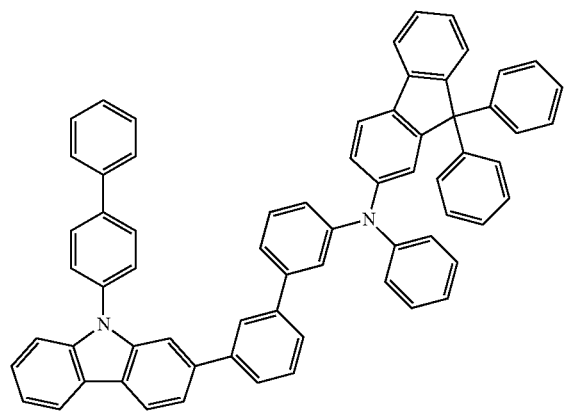
B224
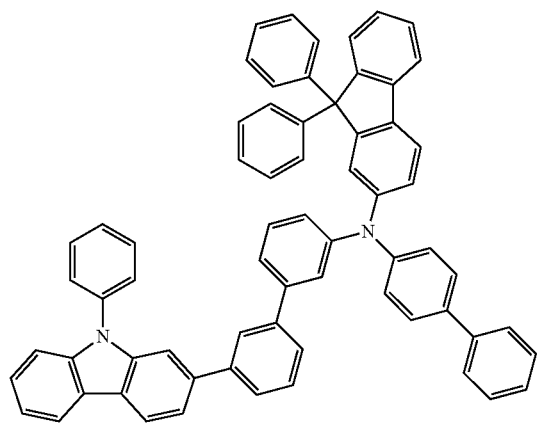
B225
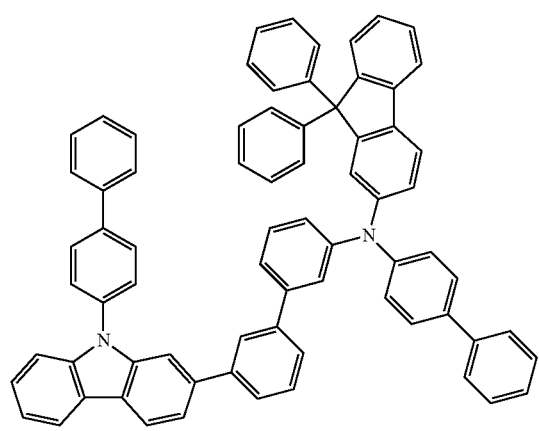
B226
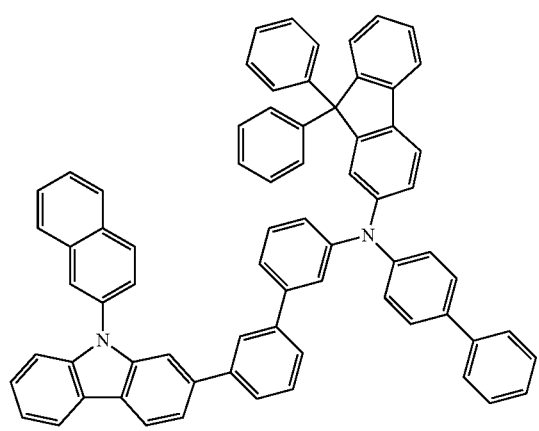
B227
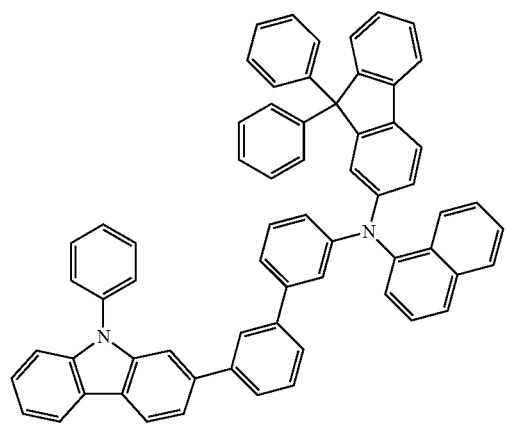
B228
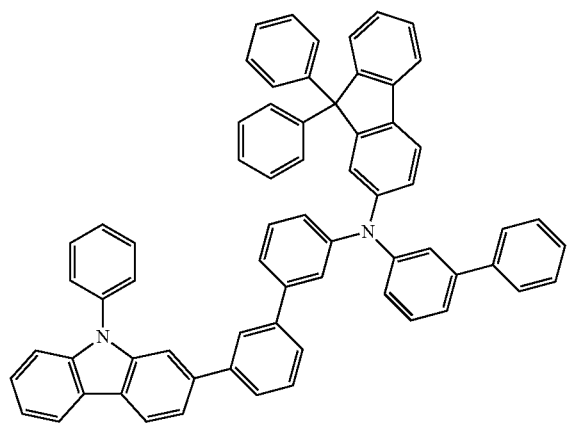

-continued
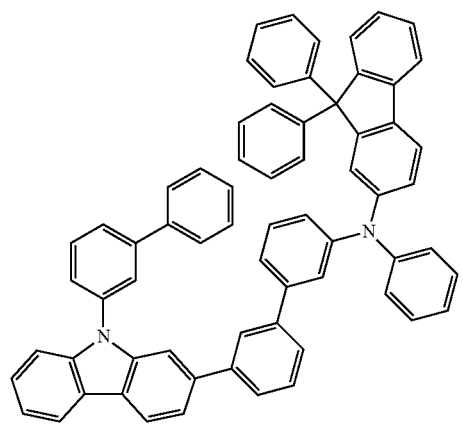
B229
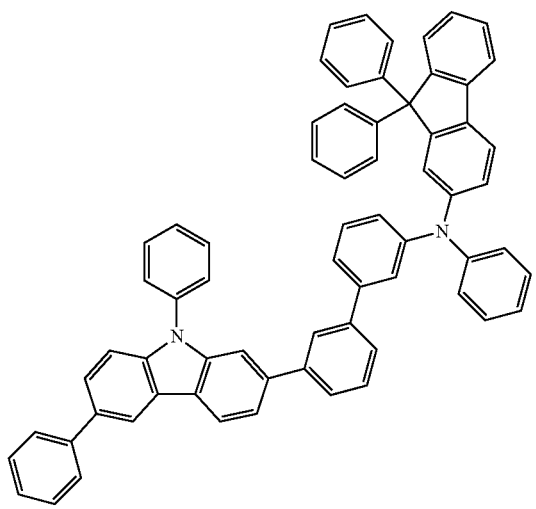
B230
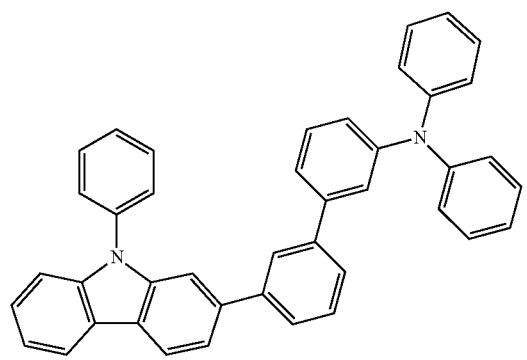
B231
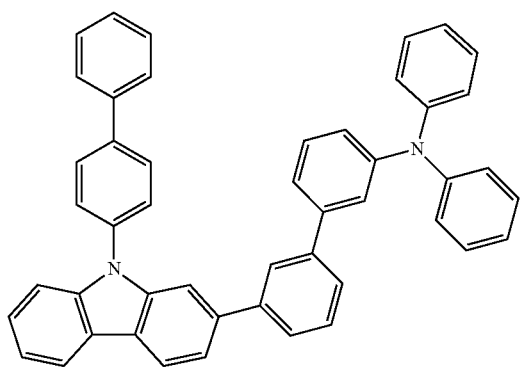
B232
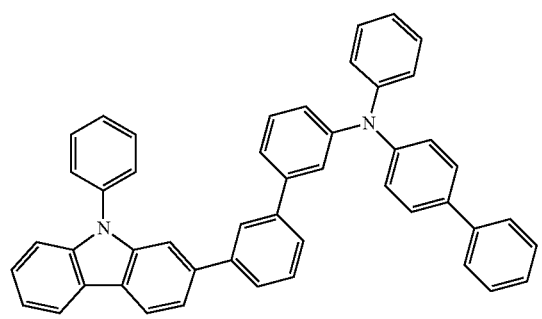
B233
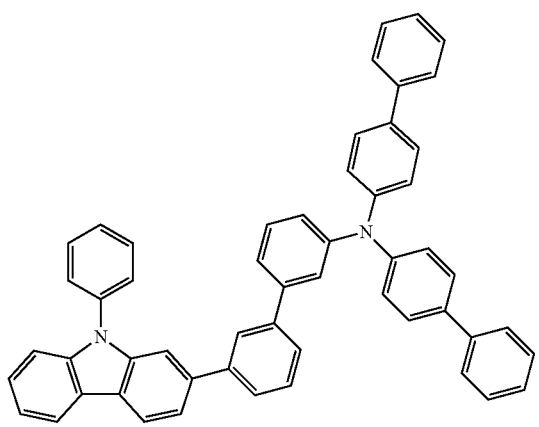
B234

-continued
B235
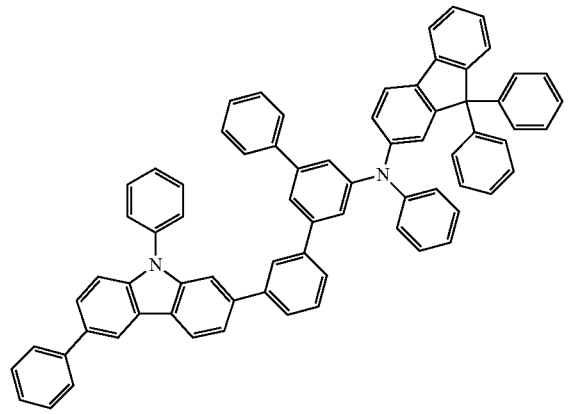
B236
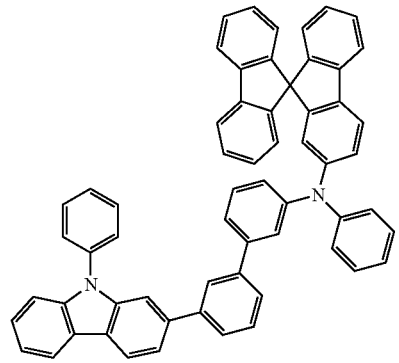
B237
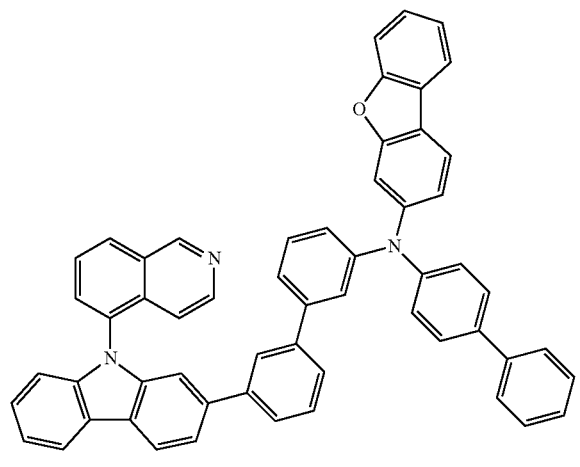
B238
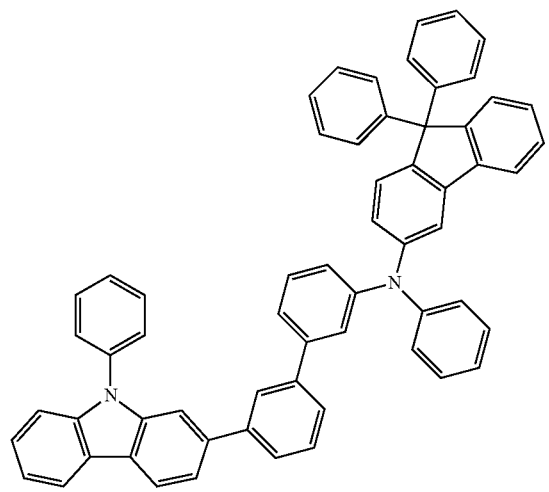
B239
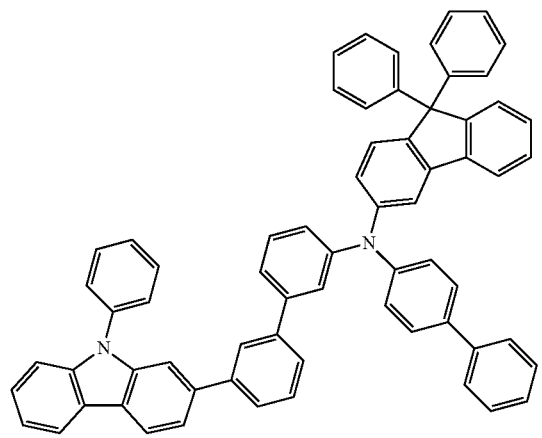
B240
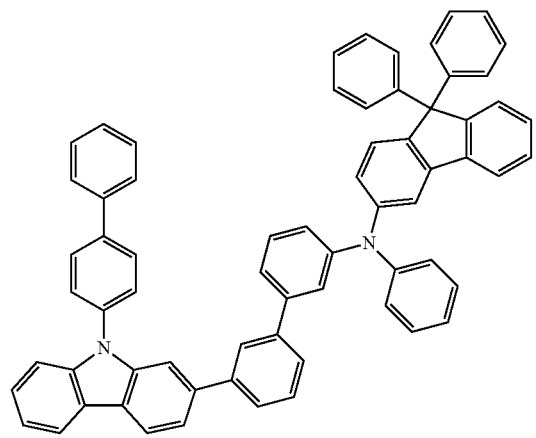

-continued
B241
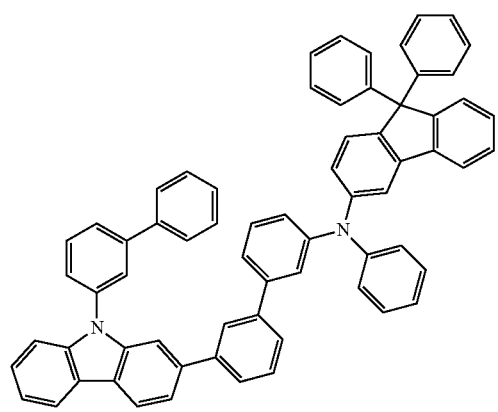
B242
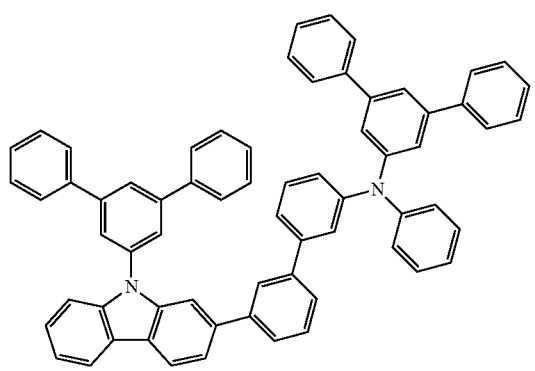
B243
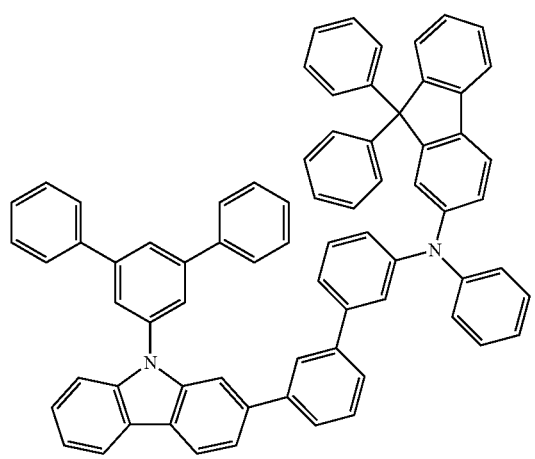
B244
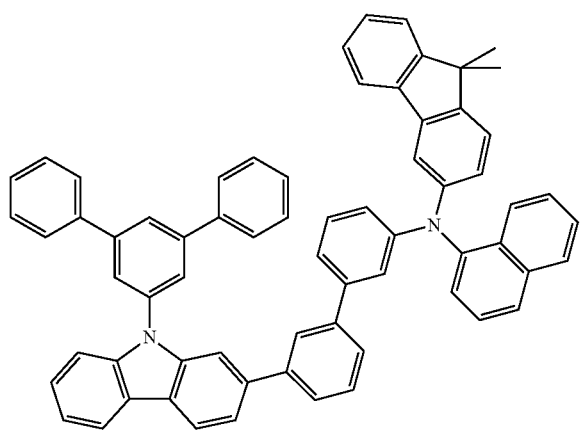
B245
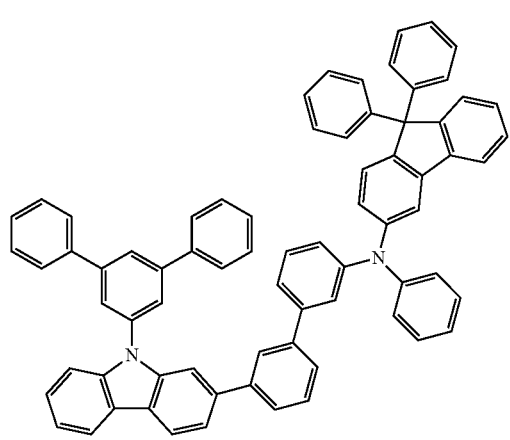
B246
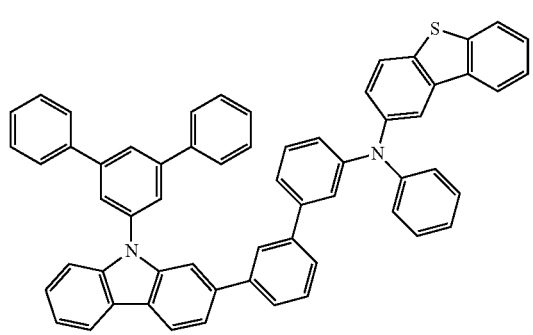

-continued
B247
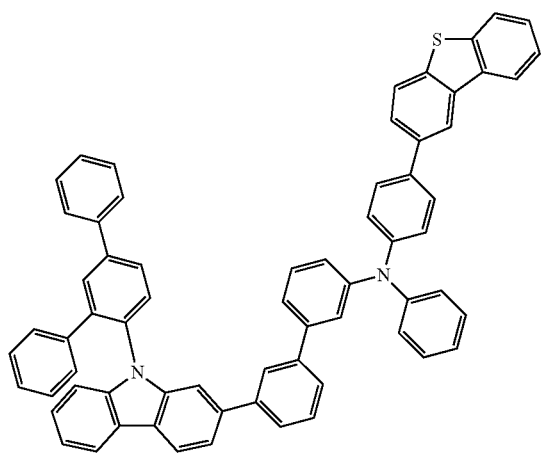
B248
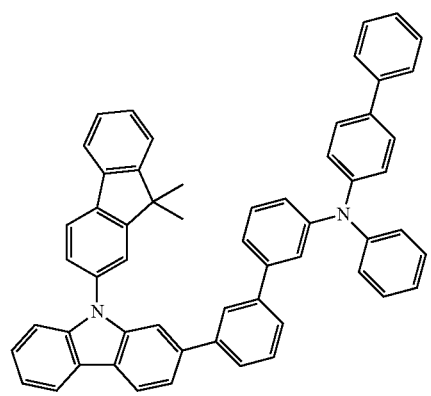
B249
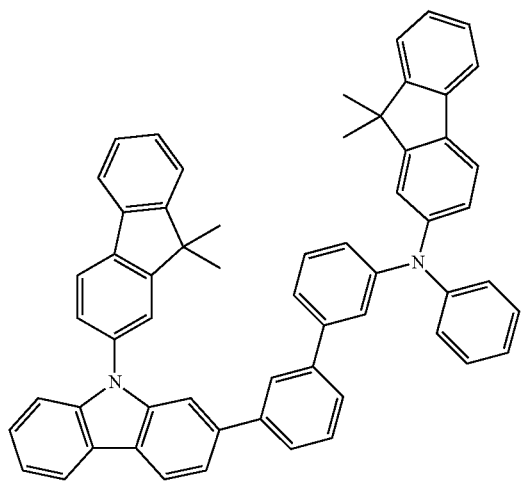
B250
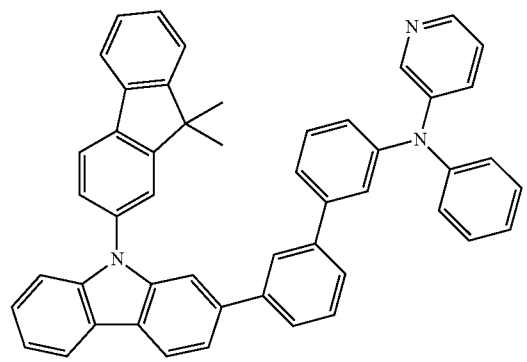
B251
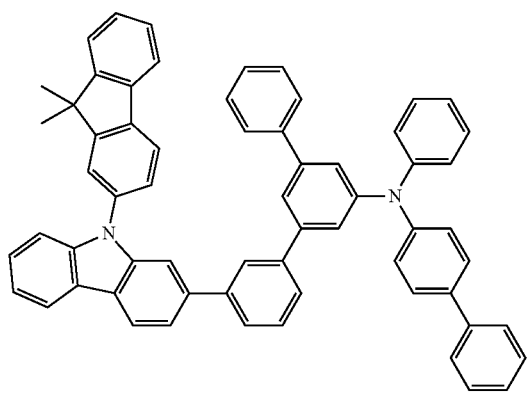
B252
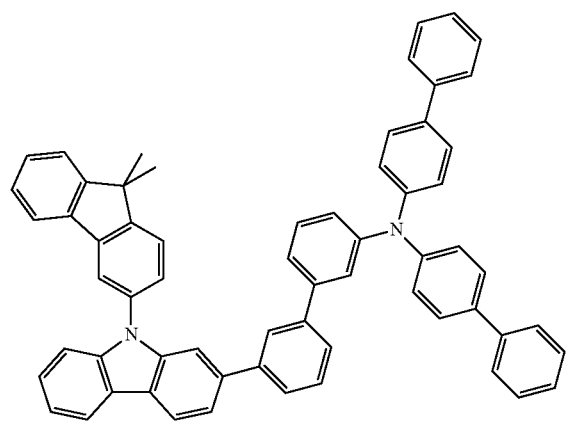

-continued
B253
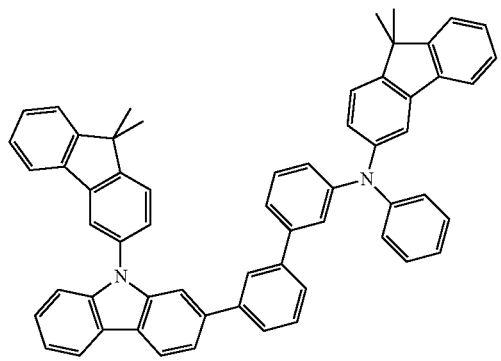
B254
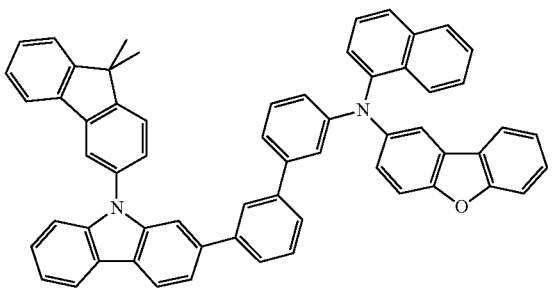
B255
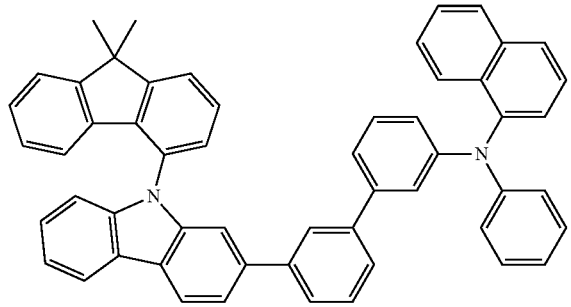
B256
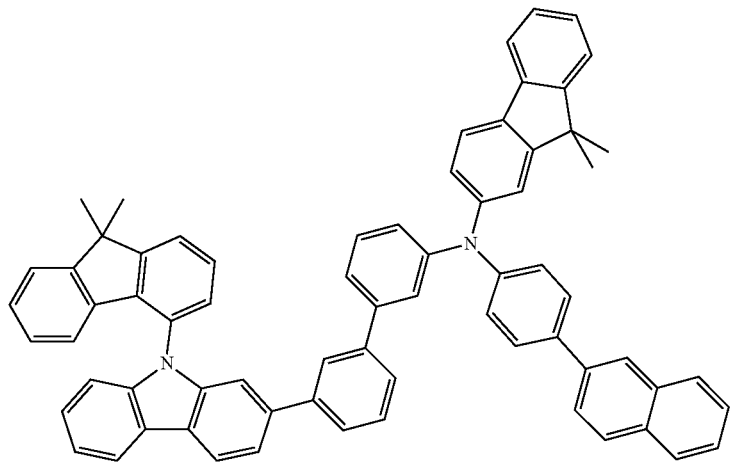
B257
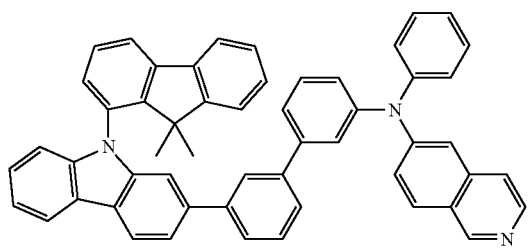
B258
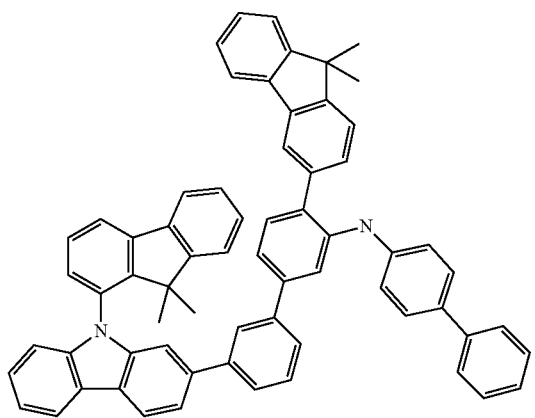

-continued
B259
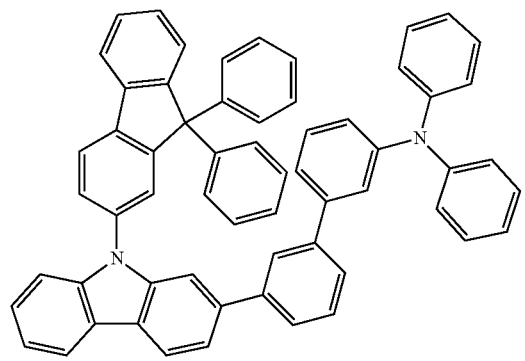
B260
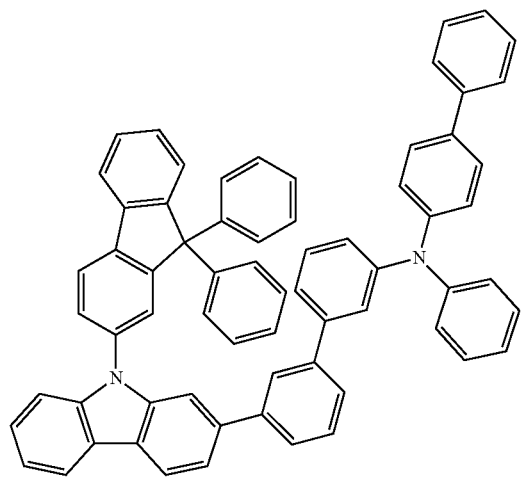
B261
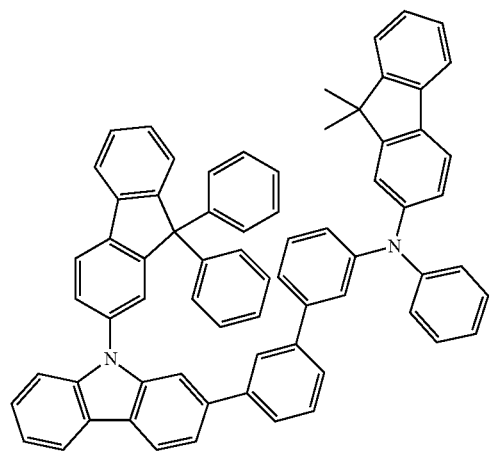
B262
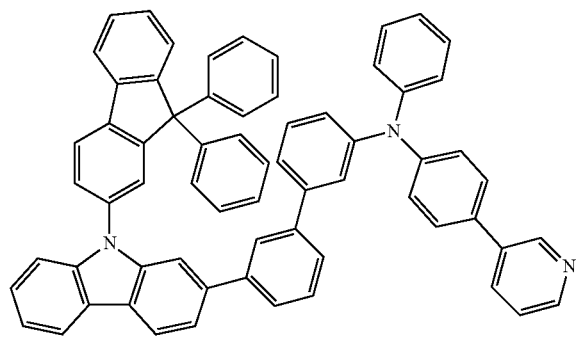
B263
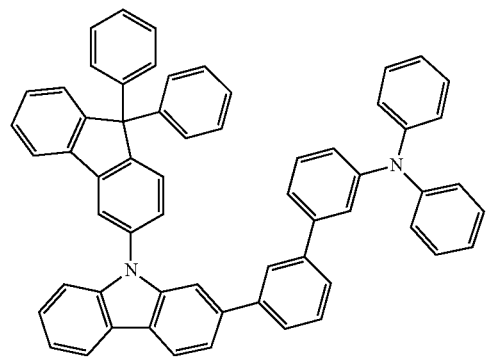
B264
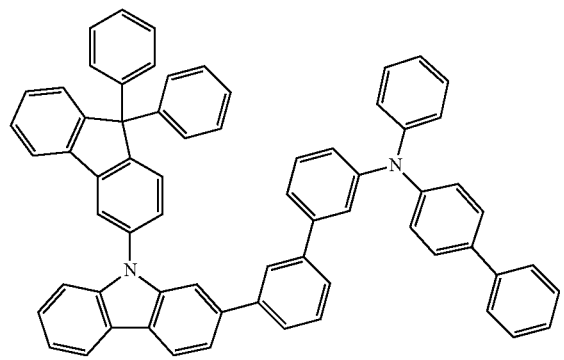

-continued
B265 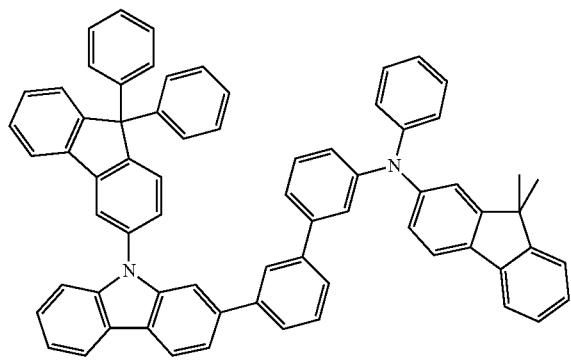
B266 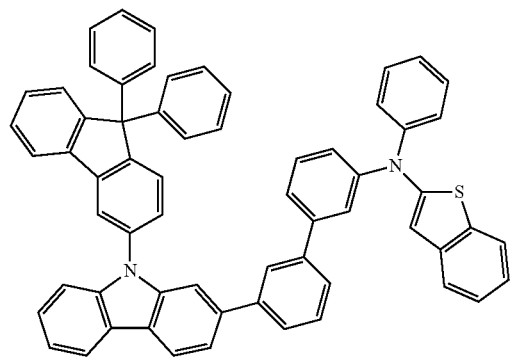
B267 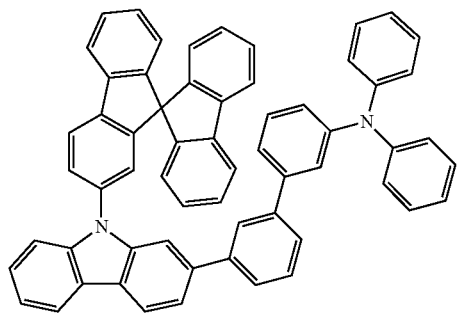
B268 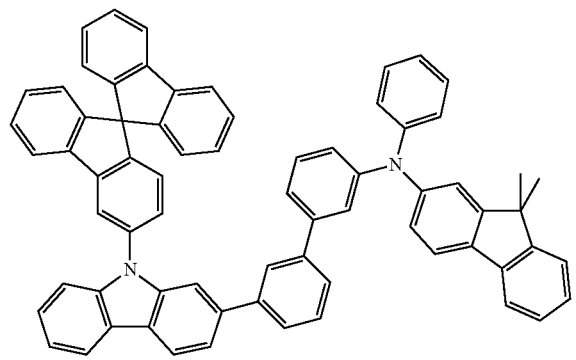
B269 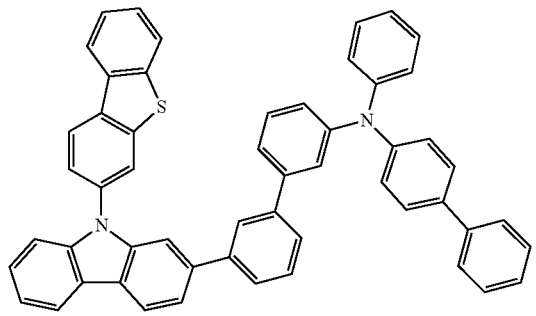
B270 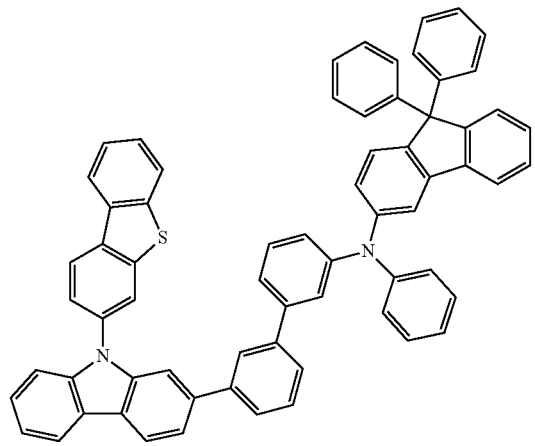
B271 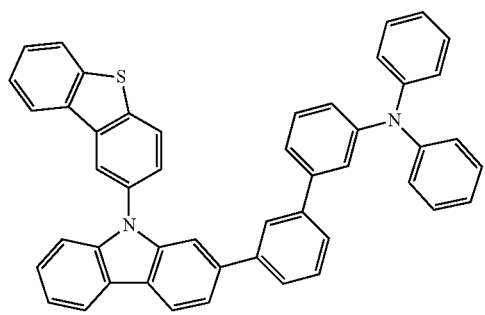
B272 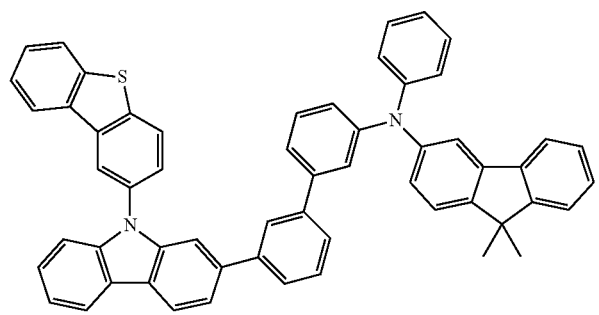

-continued
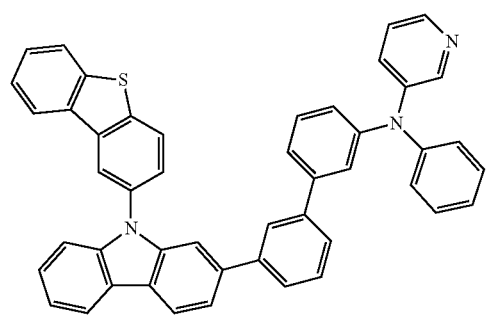
B273
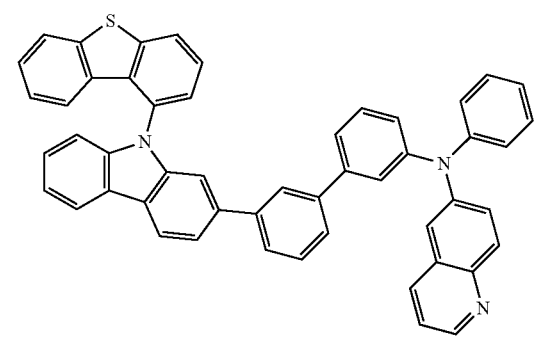
B274
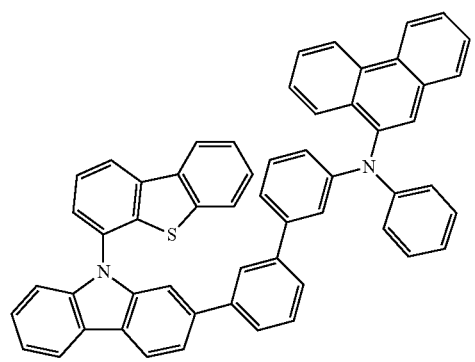
B275
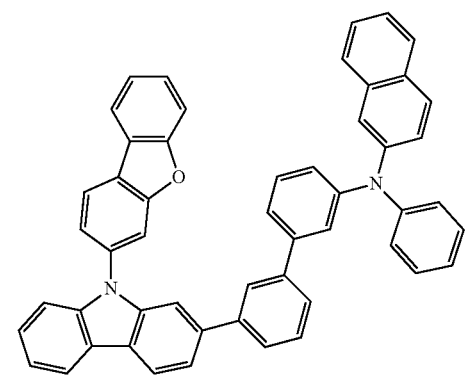
B276
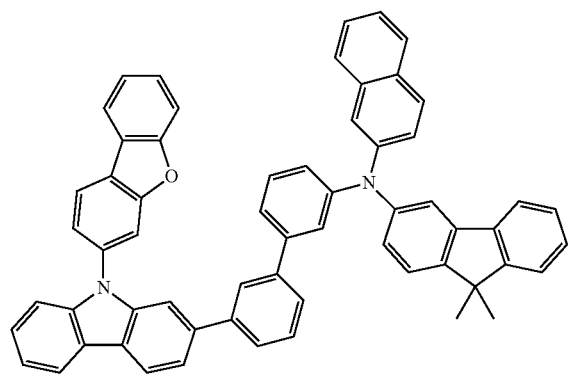
B277
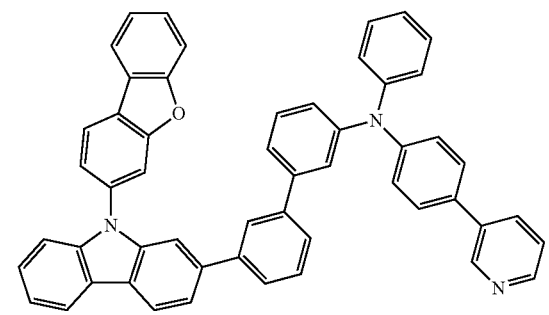
B278
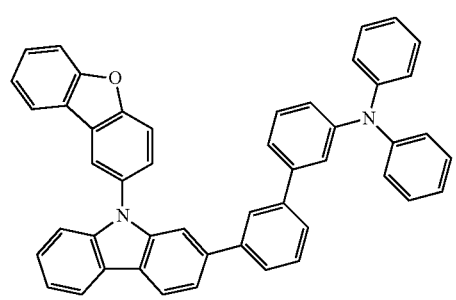
B279
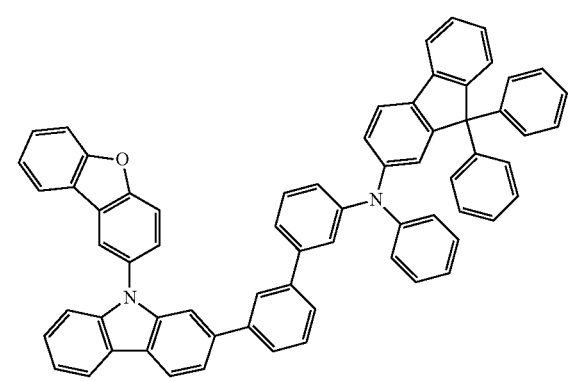
B280

-continued
B281
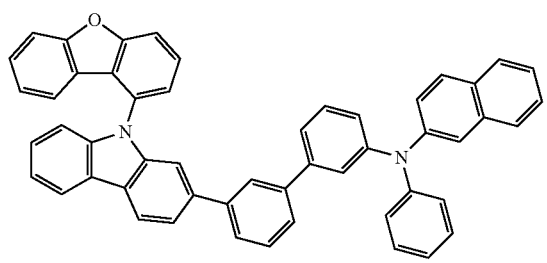
B282
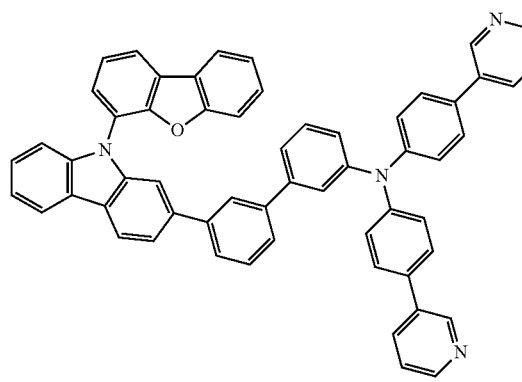
B283
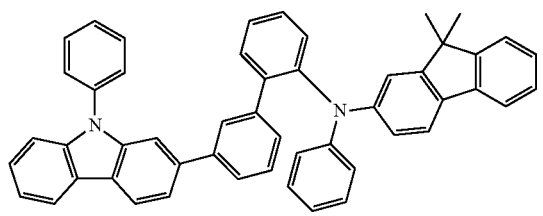
B284
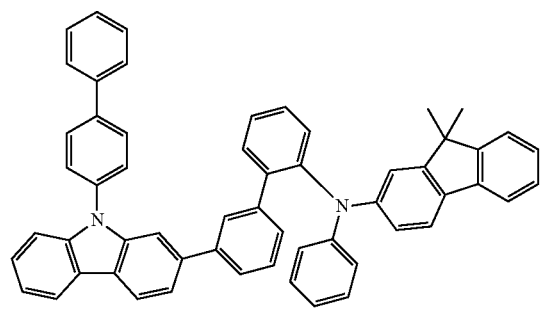
B285
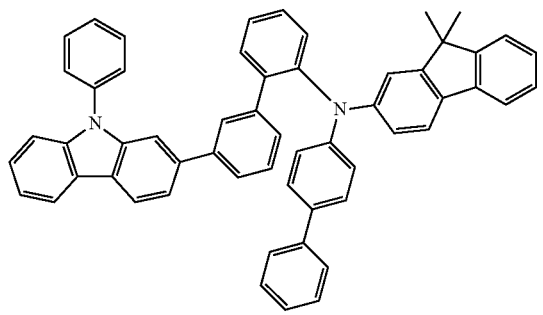
B286
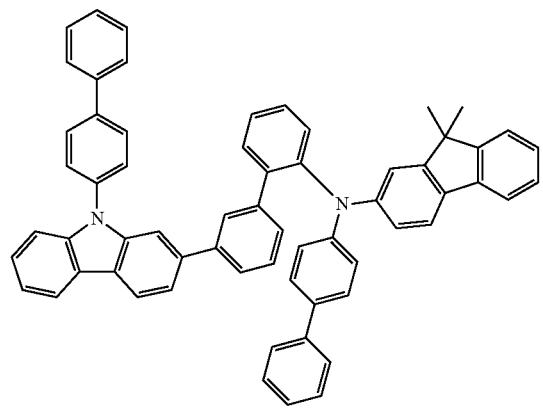
B287
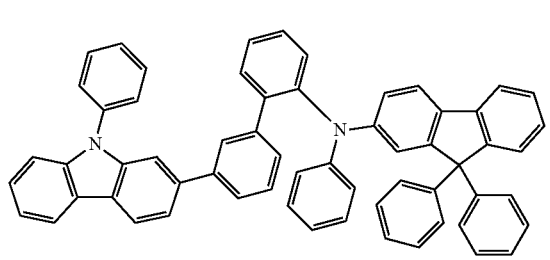
B288
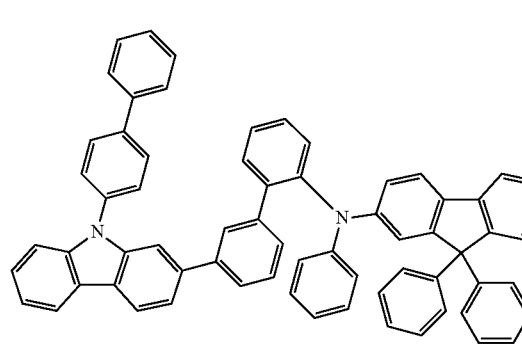

-continued
B289
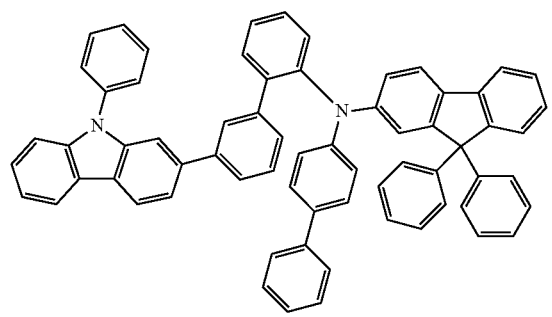
B290
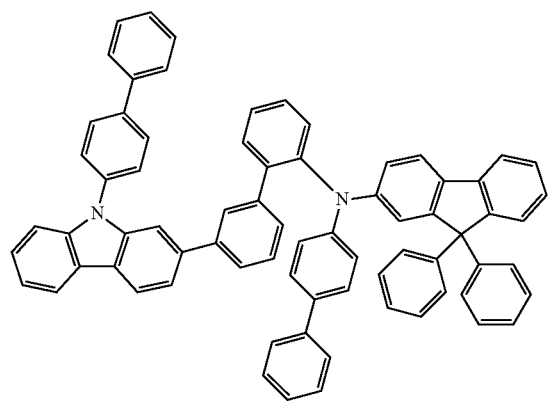
B291
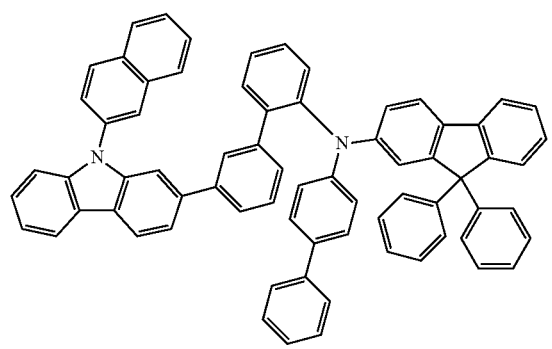
B292
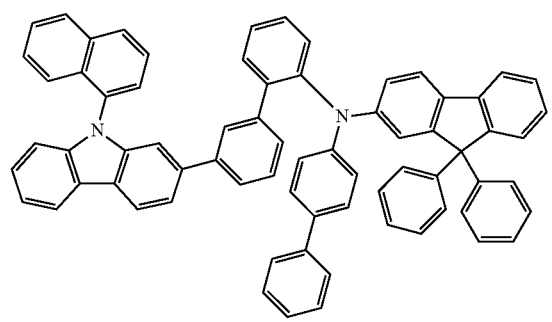
B293
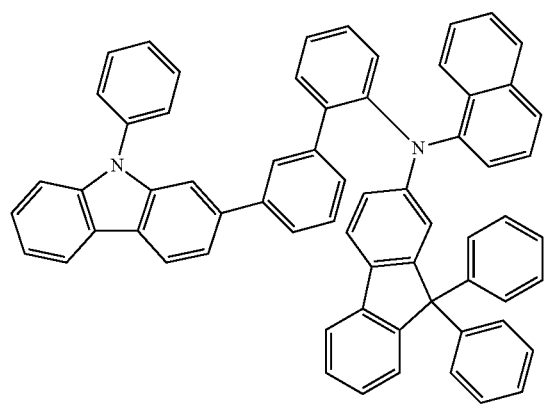
B294
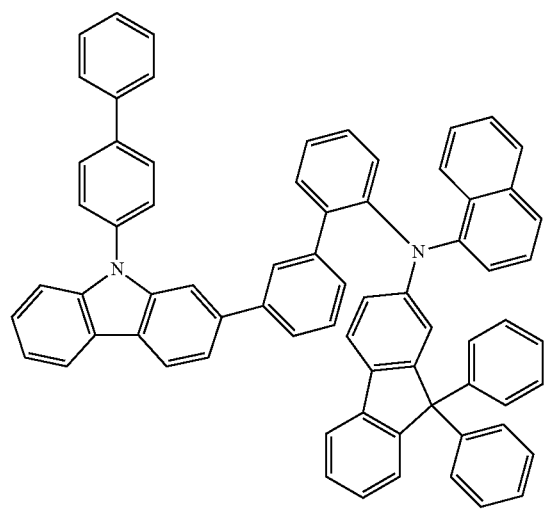

-continued
B295
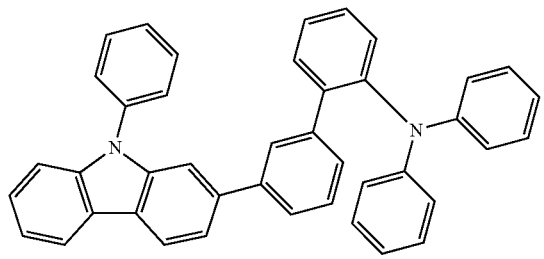
B296
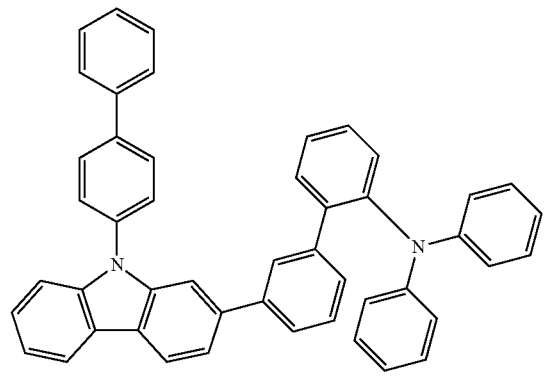
B297
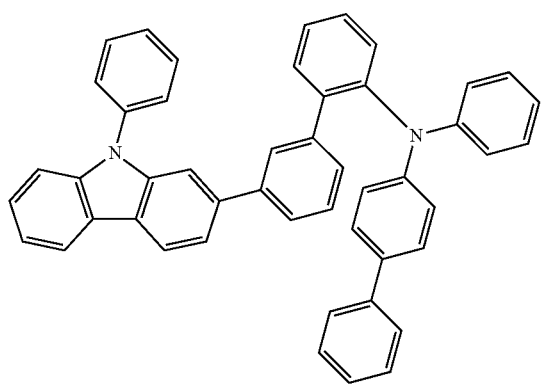
B298
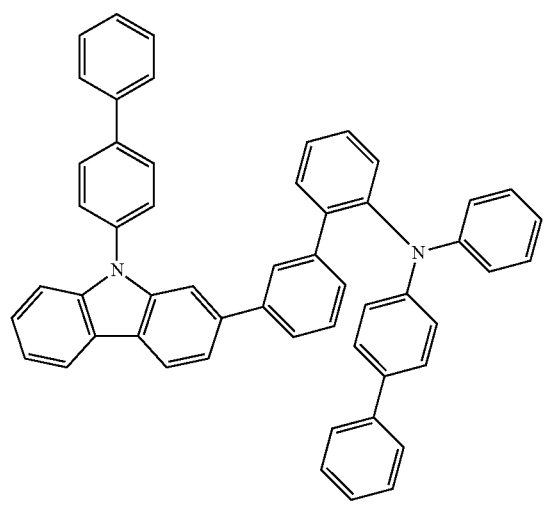
B299
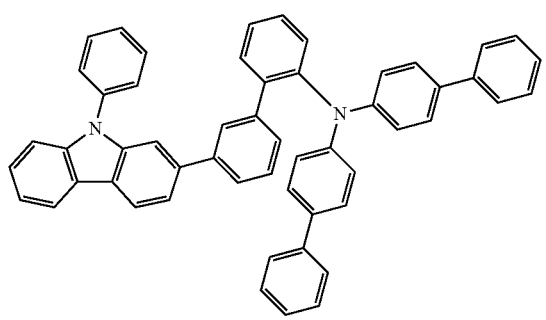
B300
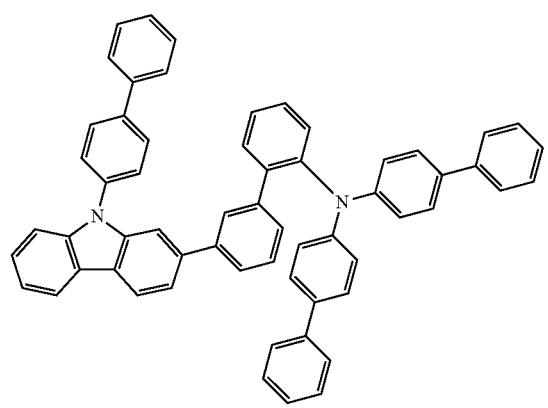

-continued
B301
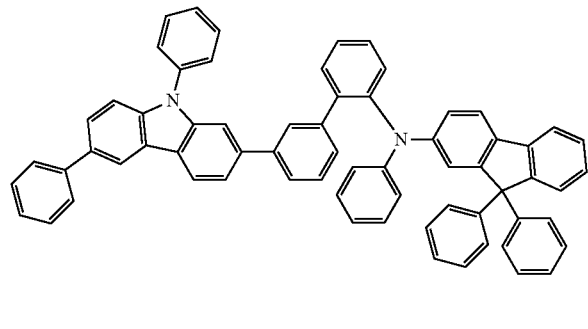
B302
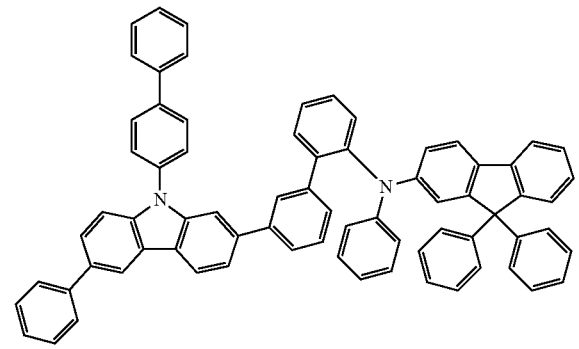
B303
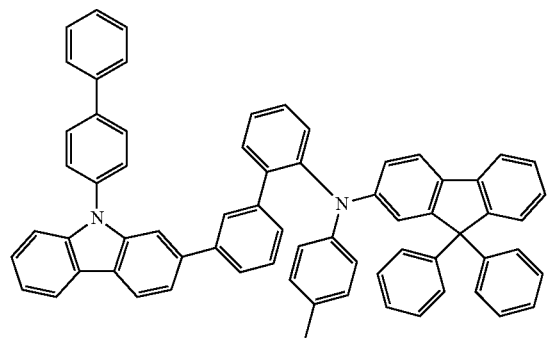
B304
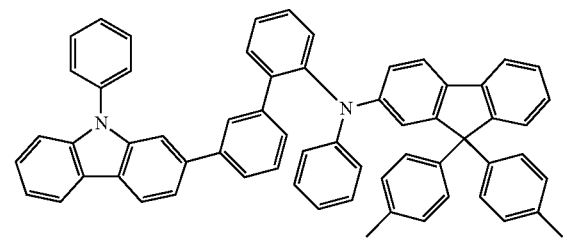
B305
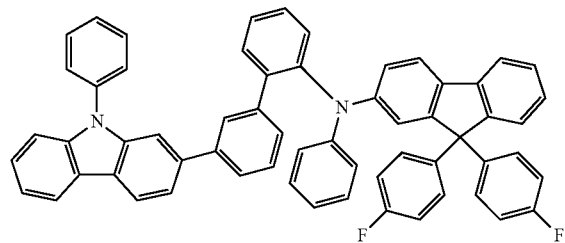
B306
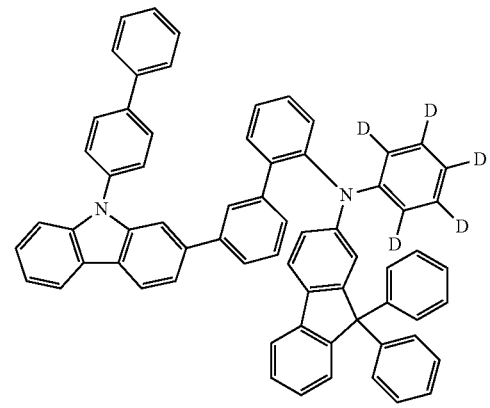
B307
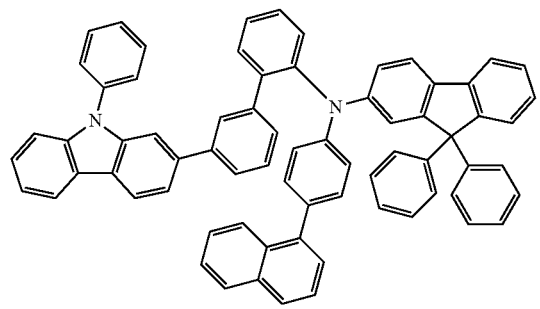
B308
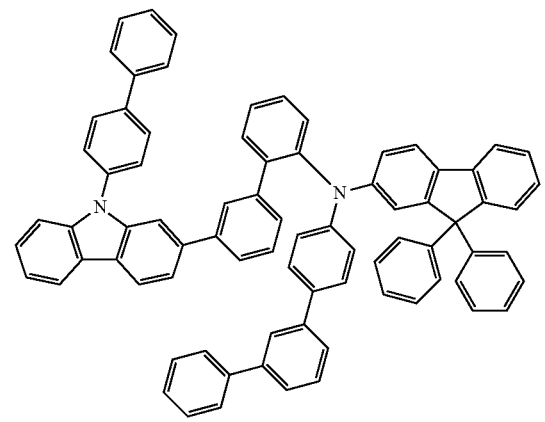

-continued
B309 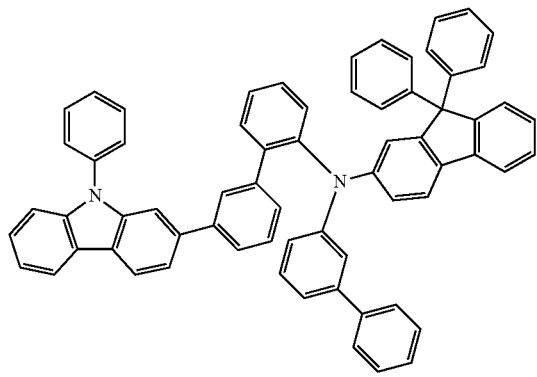
B310 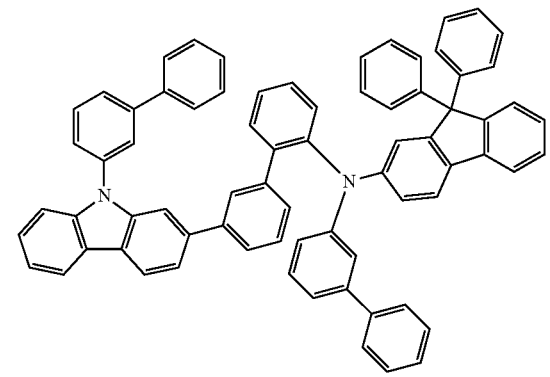
B311 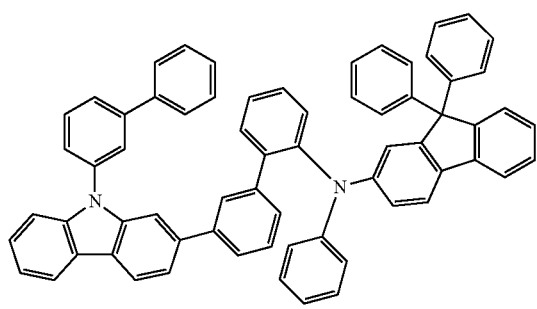
B312 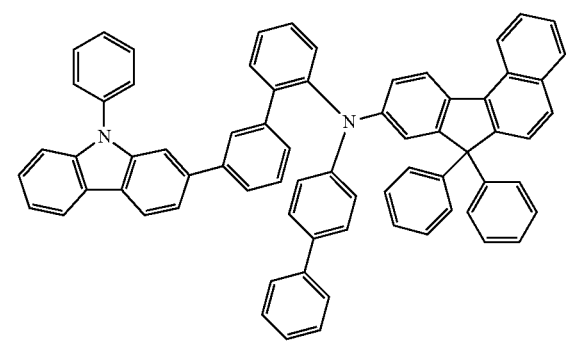
B313 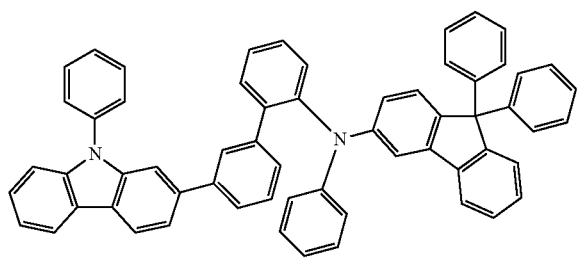
B314 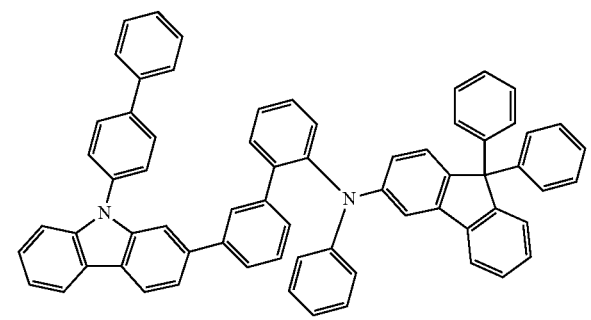
B315 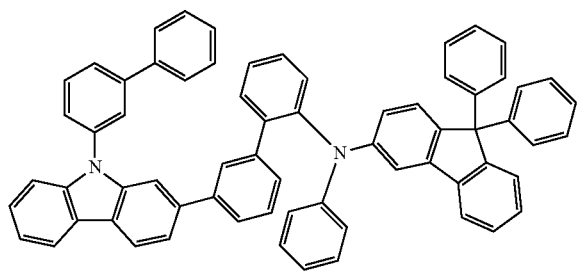
B316 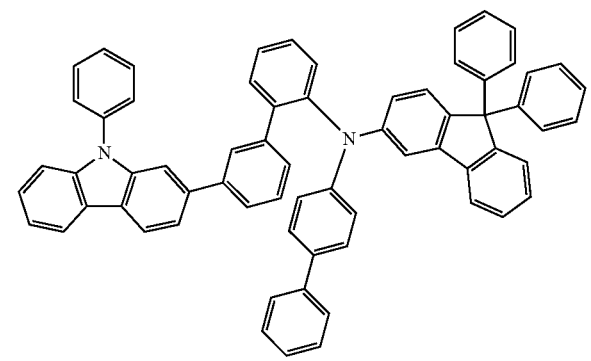

-continued
B317
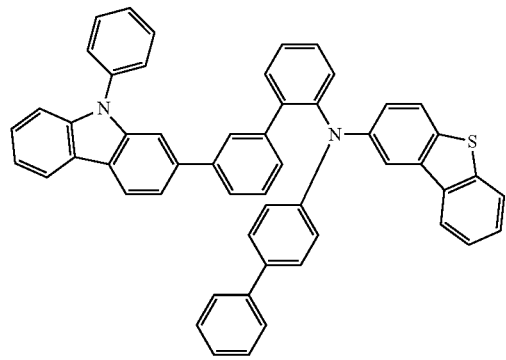
B318
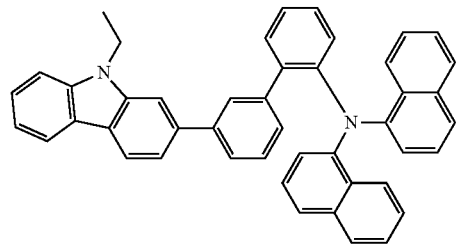
B319
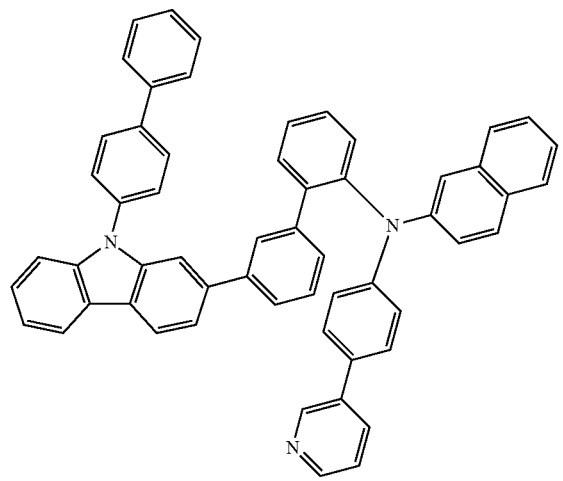
B320
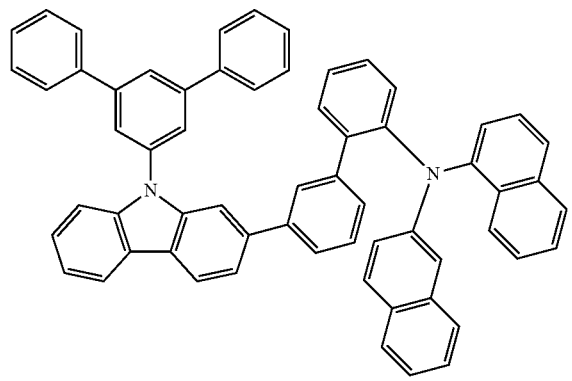
B321
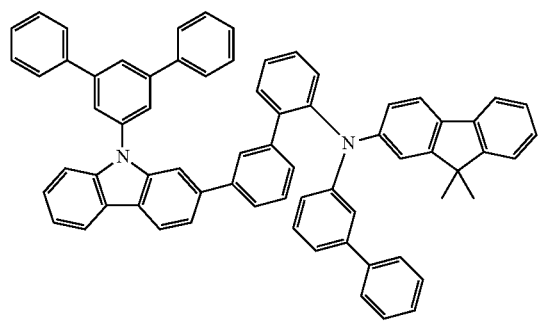
B322
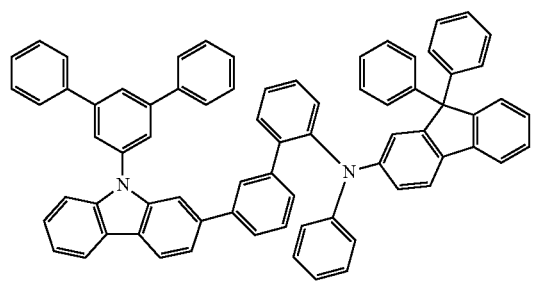
B323
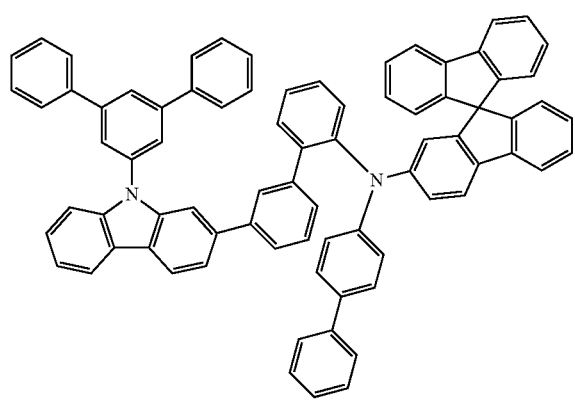
B324
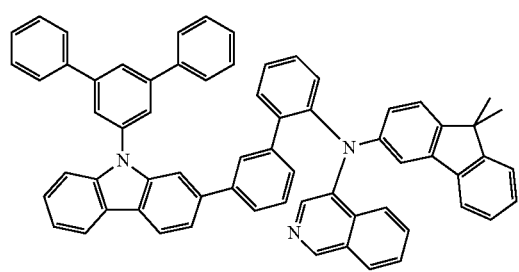

-continued
B325
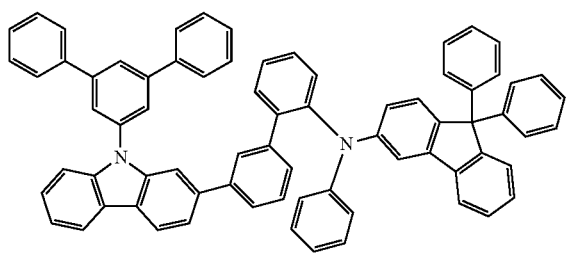
B326
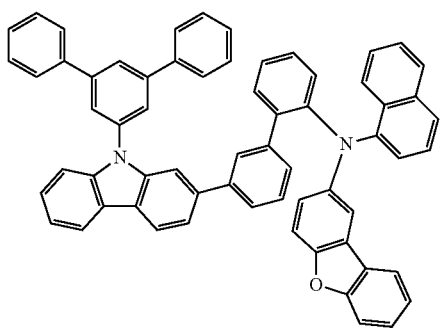
B327
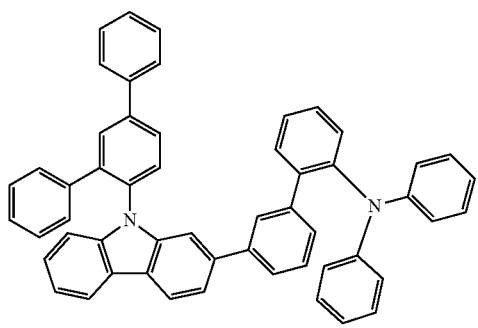
B328
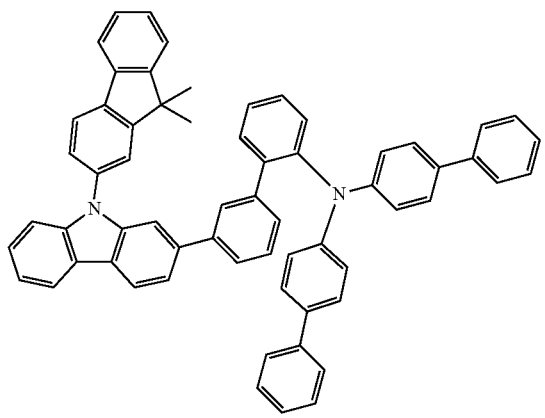
B329
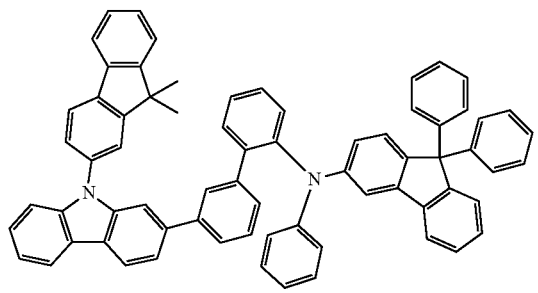
B330
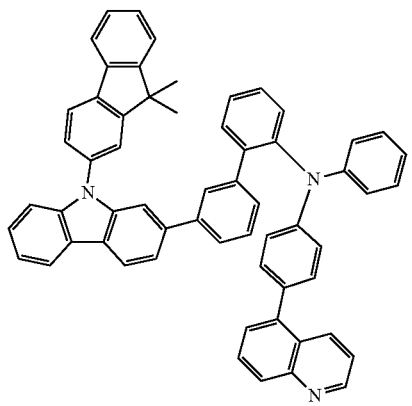
B331
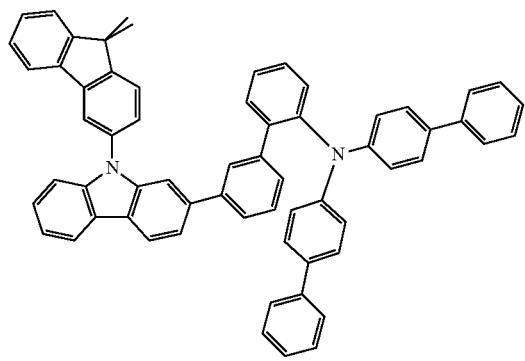
B332
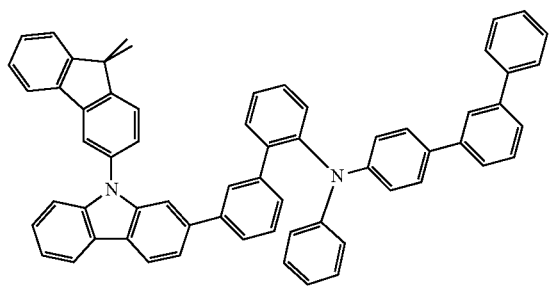

-continued
B333
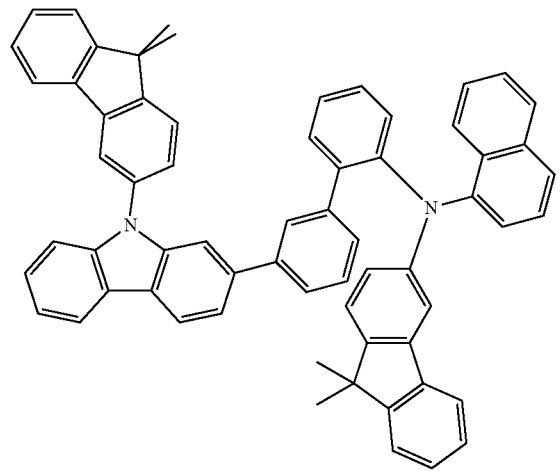
B334
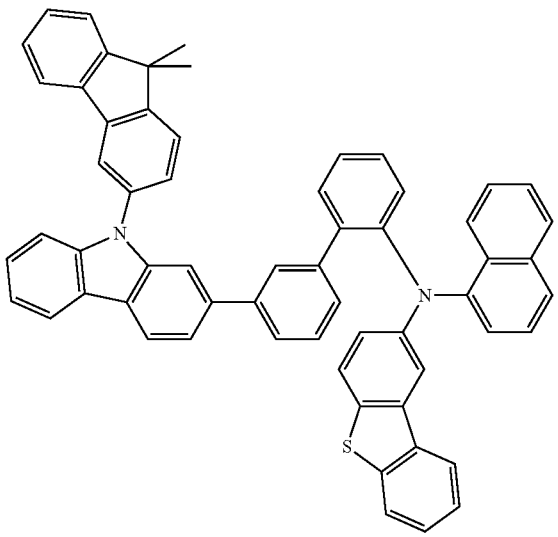
B335
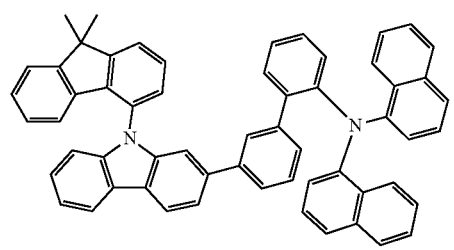
B336
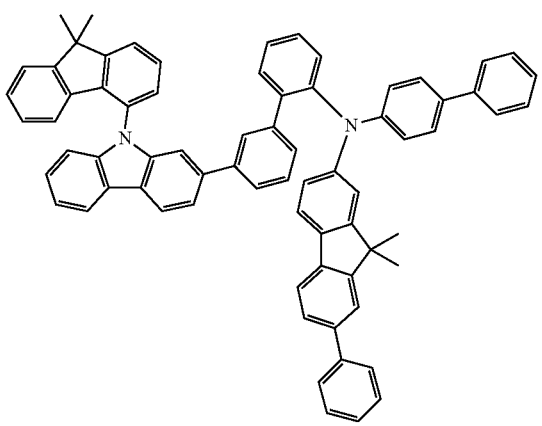
B337
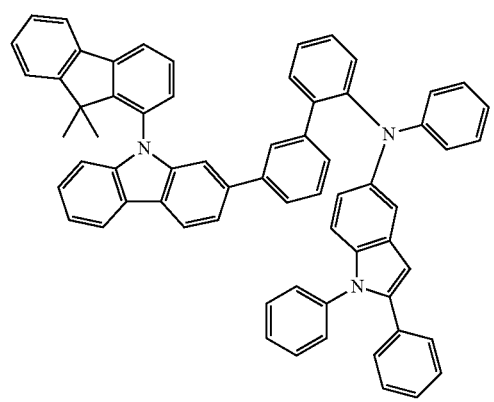
B338
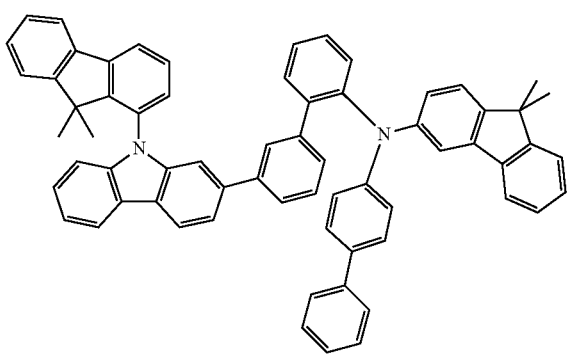

-continued
B339
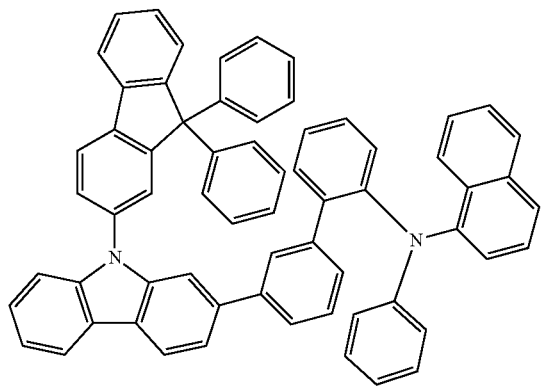
B340
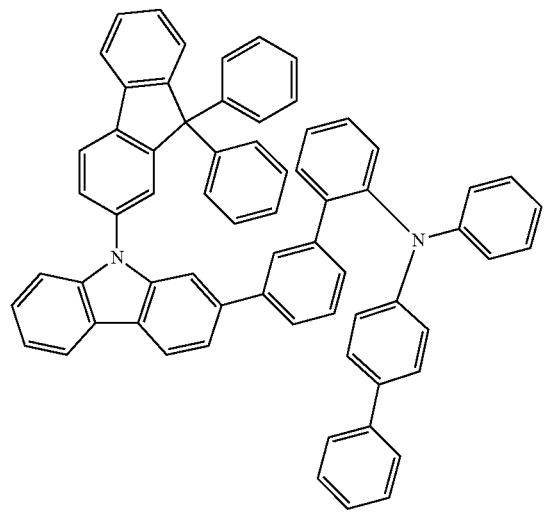
B341
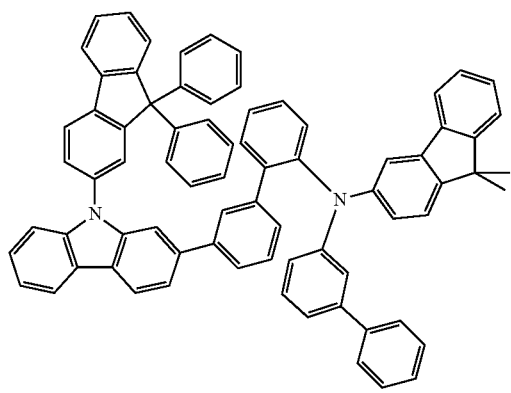
B342
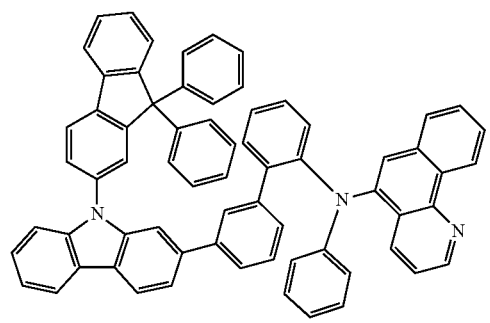
B343
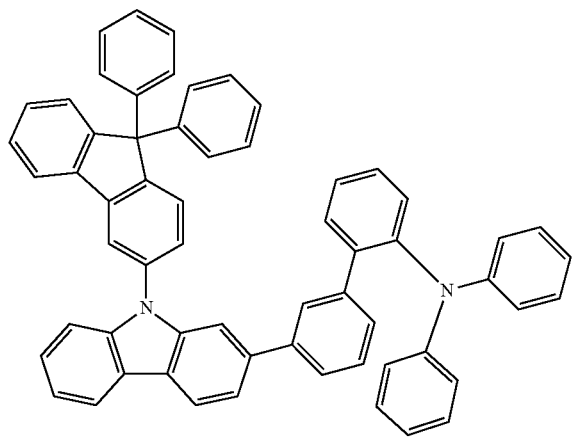
B344
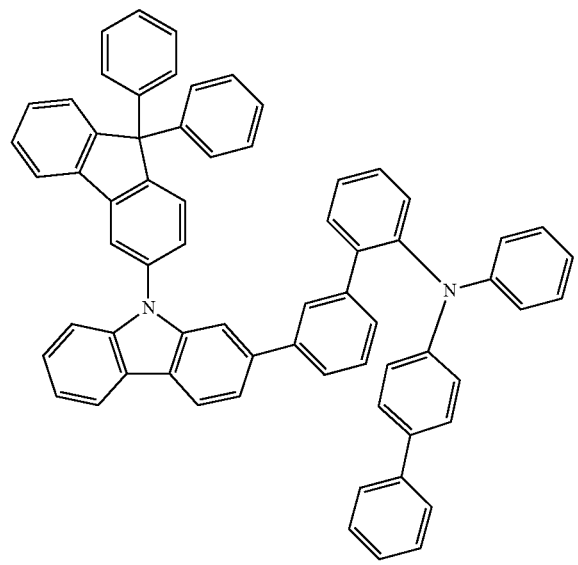

-continued
B345
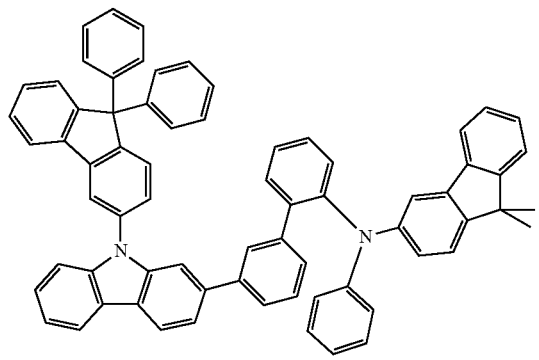
B346
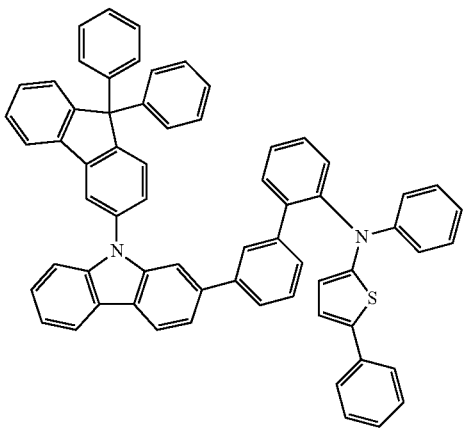
B347
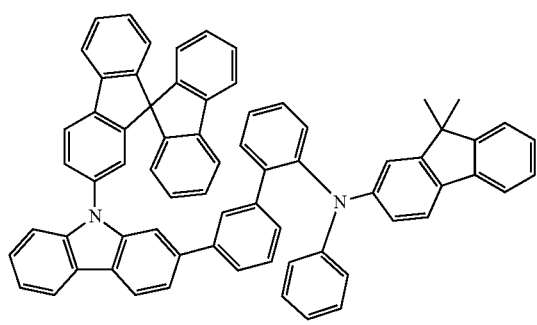
B348
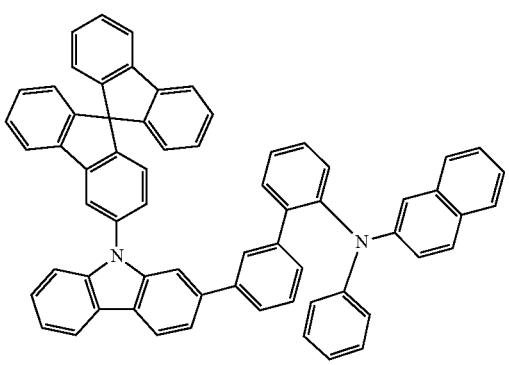
B349
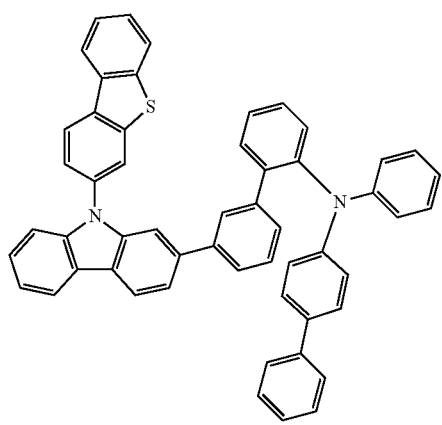
B350
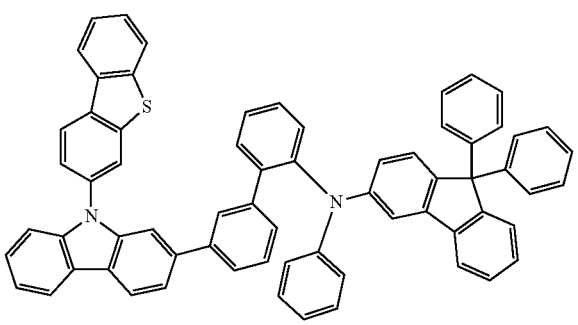

-continued
B351
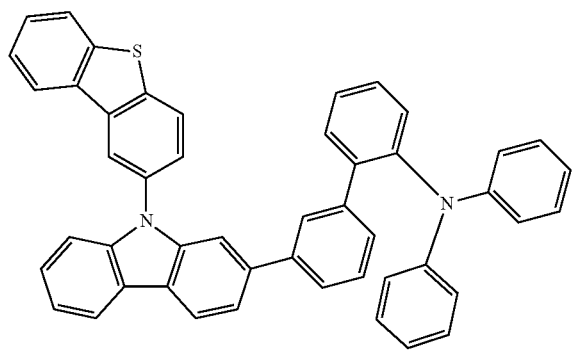
B352
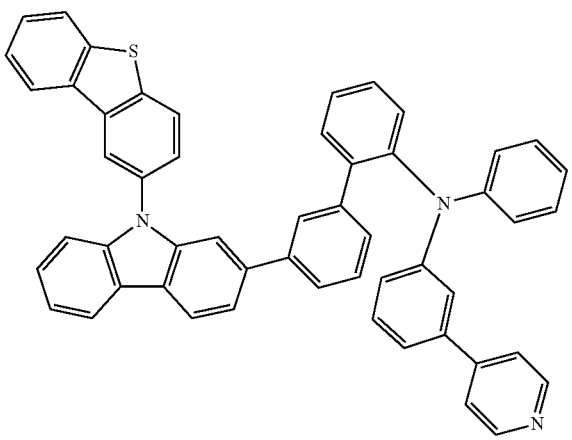
B353
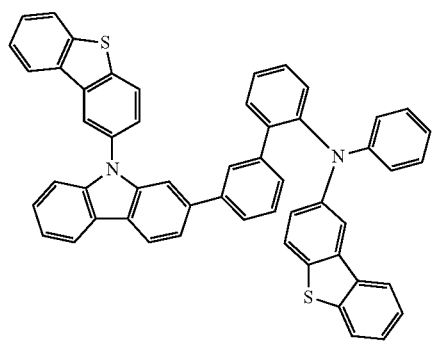
B354
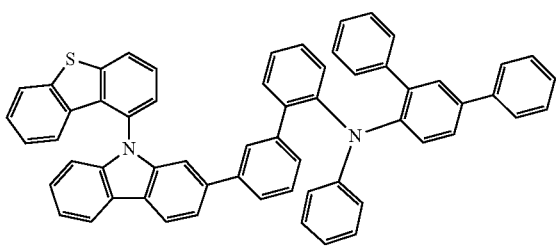
B355
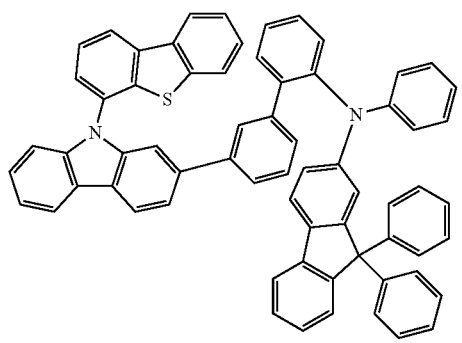
B356
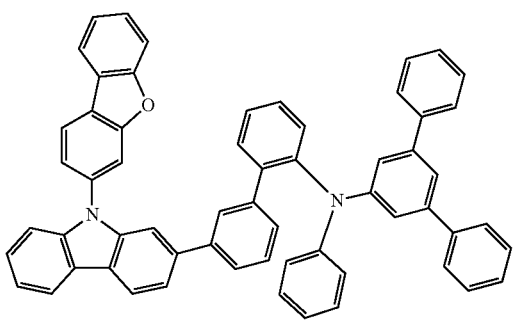

-continued
B357
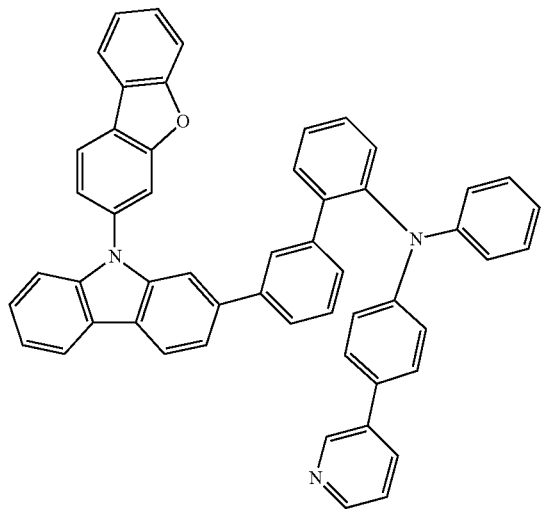
B358
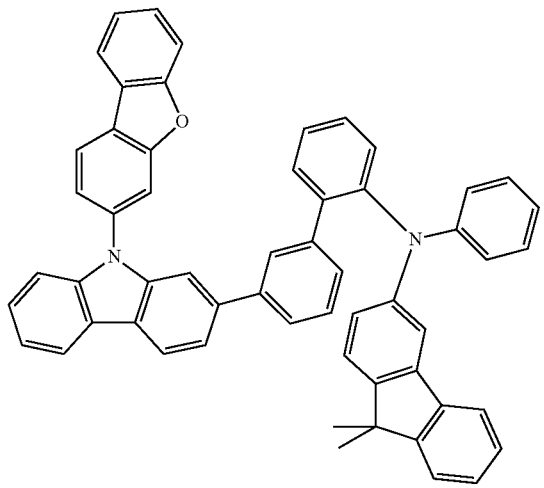
B359
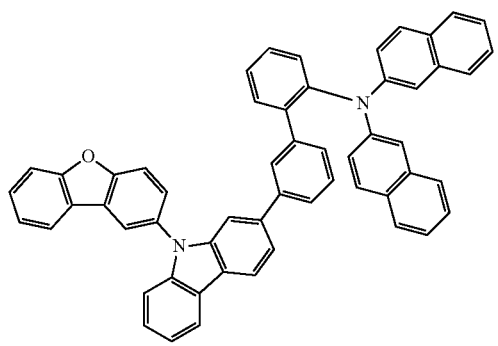
B360
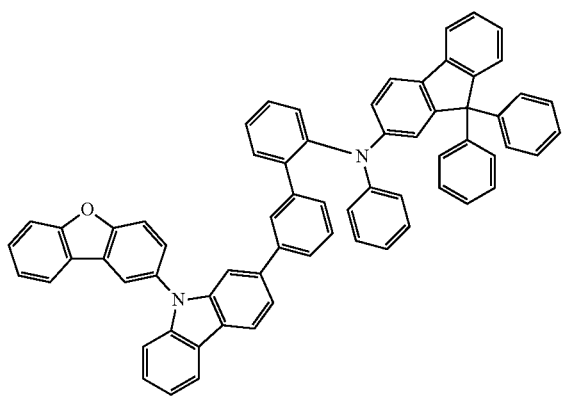
B361
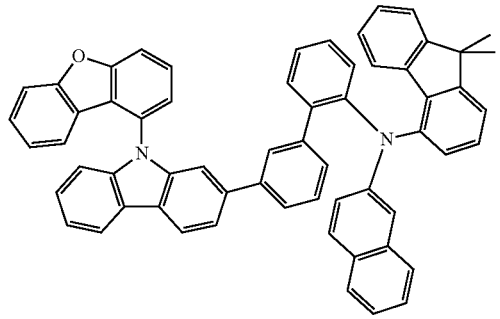
B362
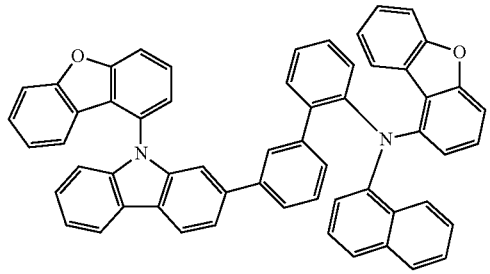
B363
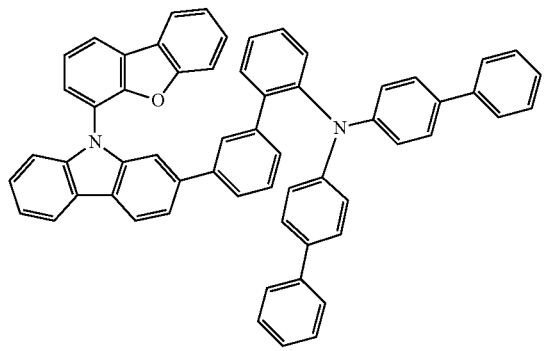
B364
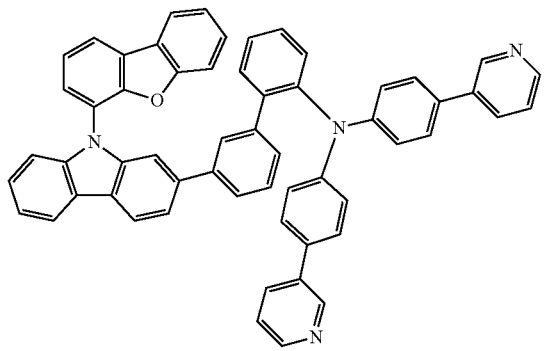

-continued
| B365 | B366 |
|---|---|
| 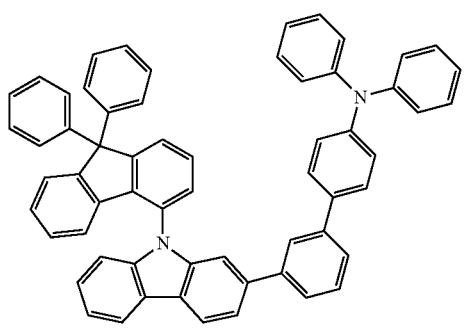 | 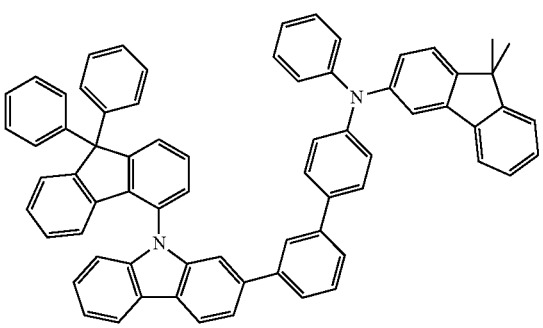 |
| B367 | B368 |
| 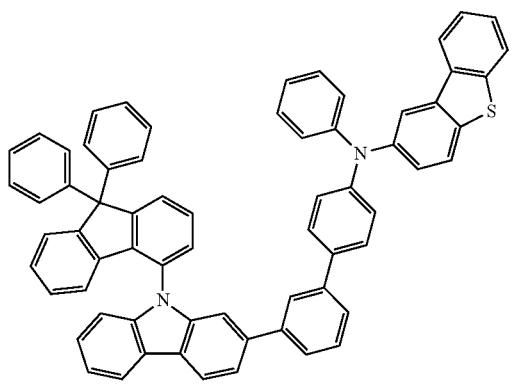 | 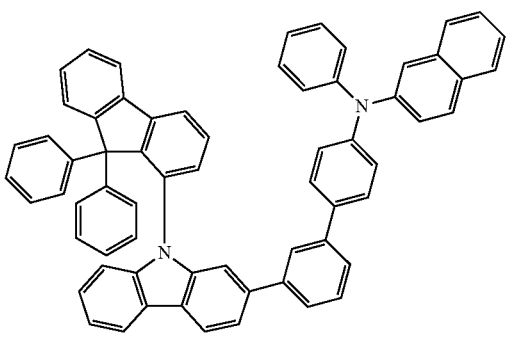 |
| B369 | B370 |
| 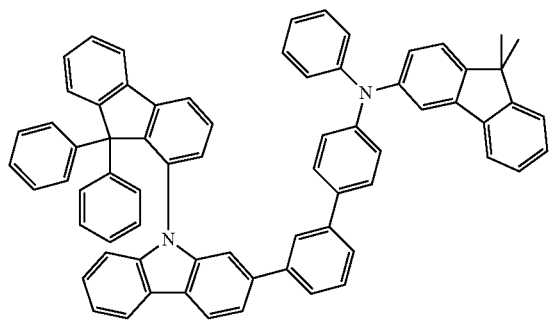 | 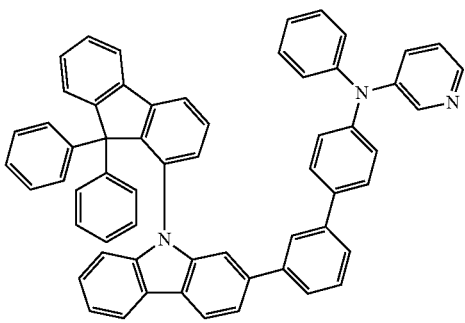 |
| B371 | B372 |
| 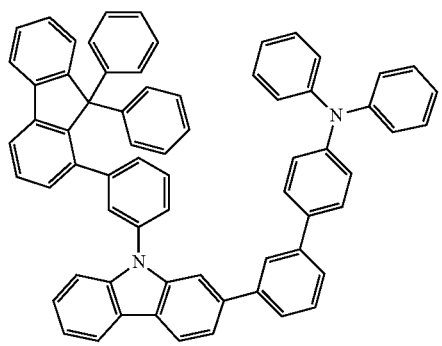 | 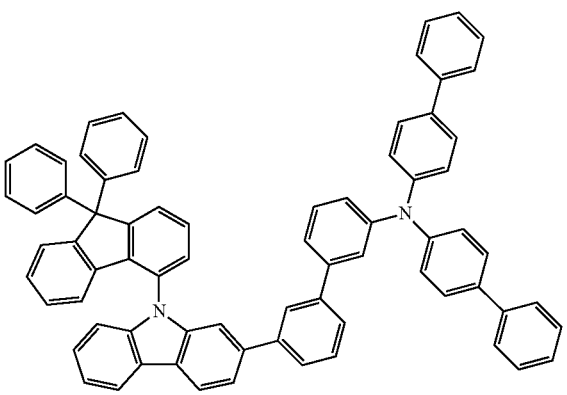 |

-continued
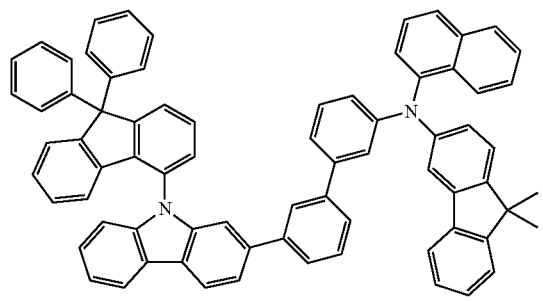
B373
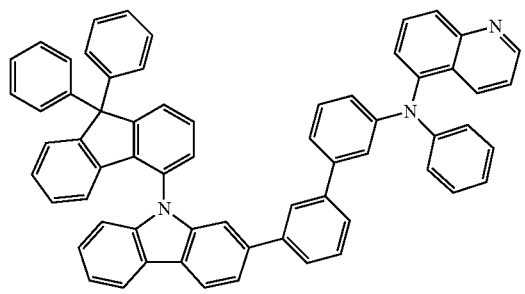
B374
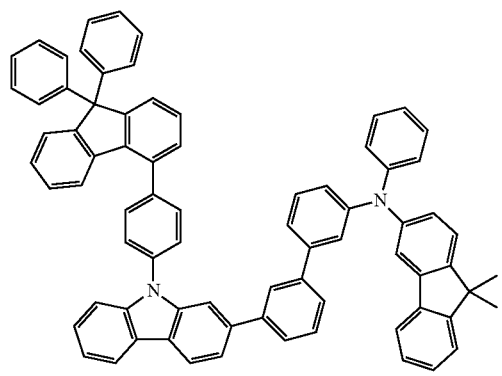
B375
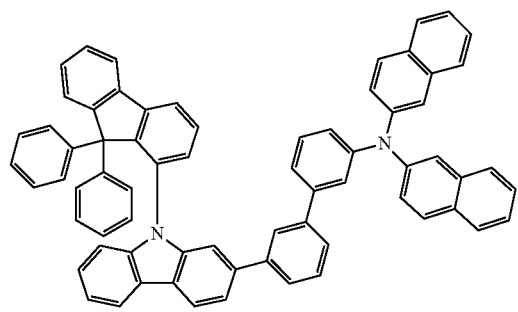
B376
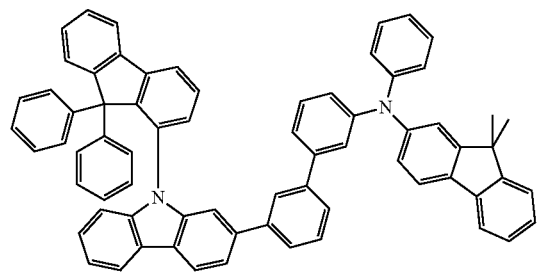
B377
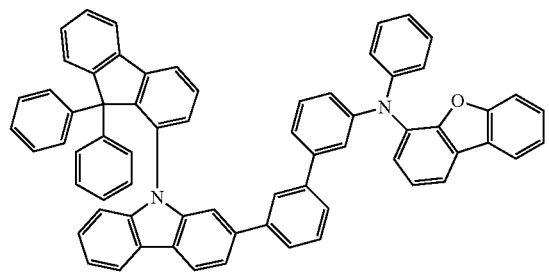
B378
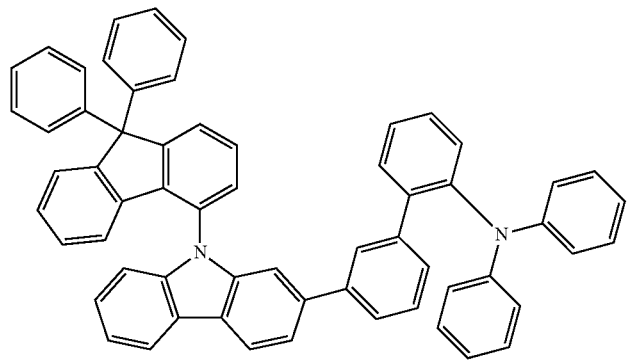
B379

-continued
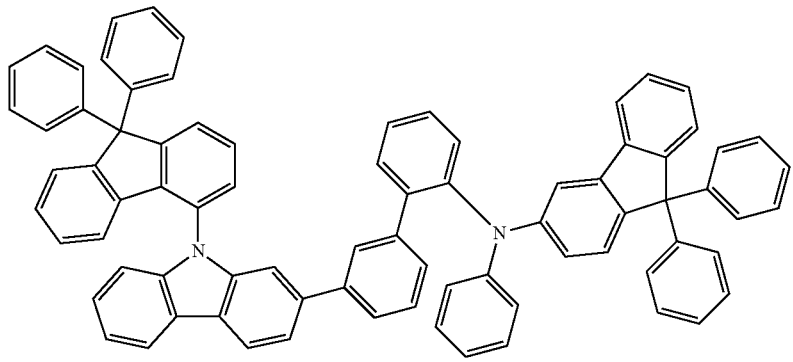
B380
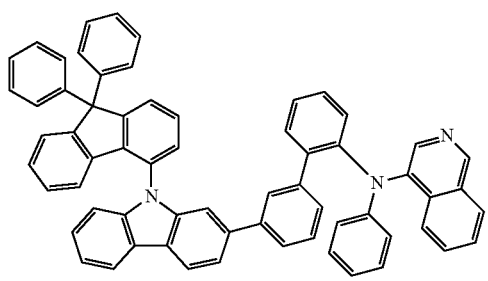
B381
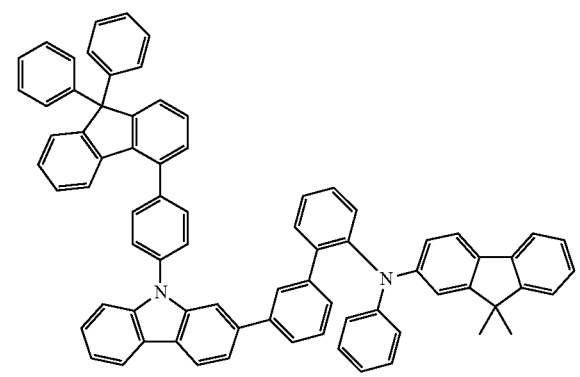
B382
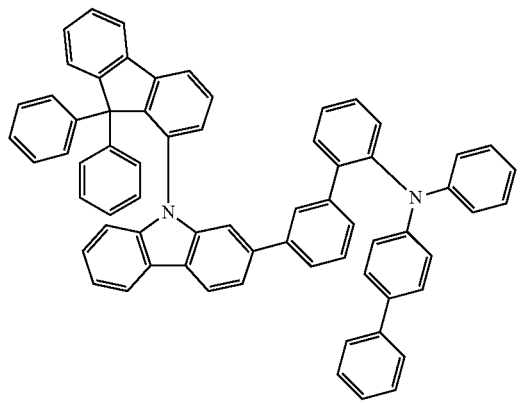
B383
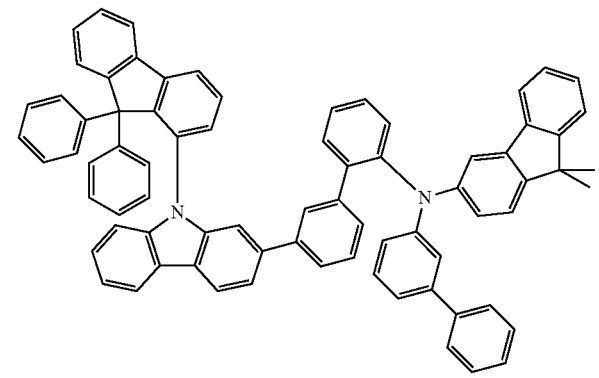
B384
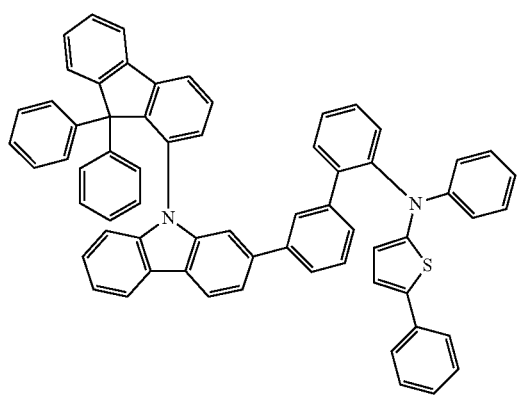
B385
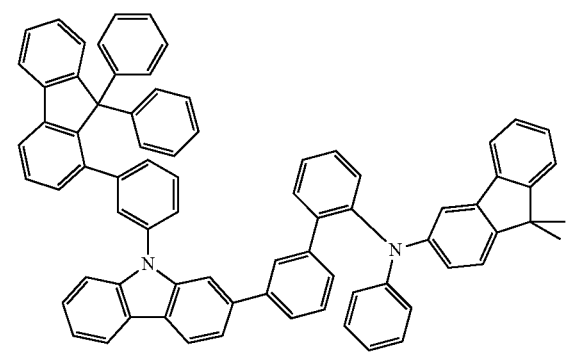
B386

-continued
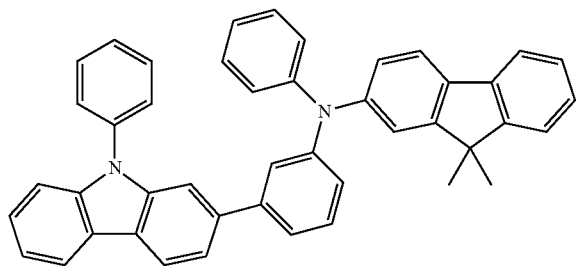
C1
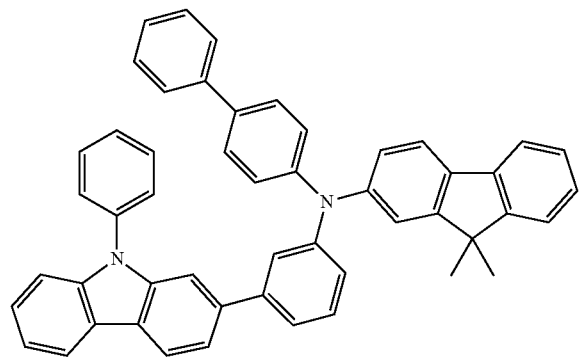
C2
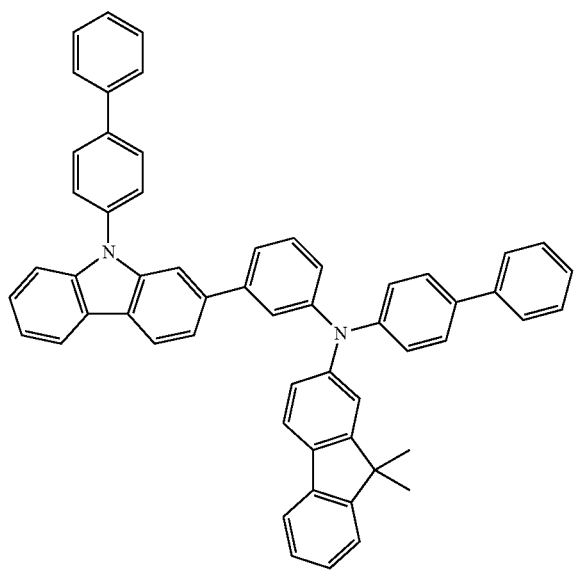
C3
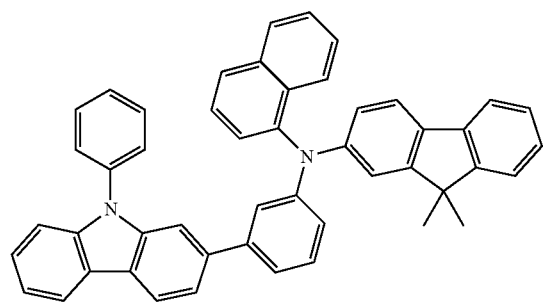
C4
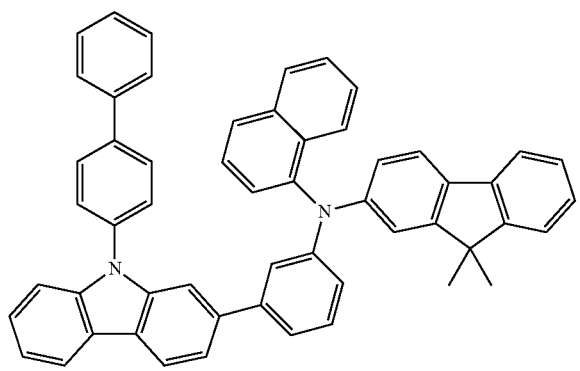
C5
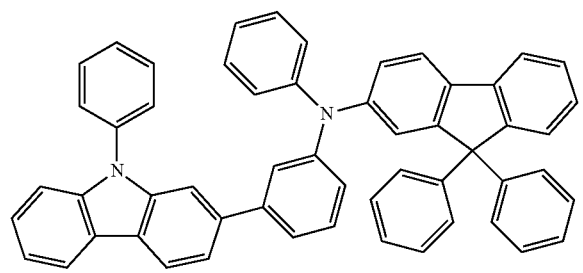
C6

-continued
C7
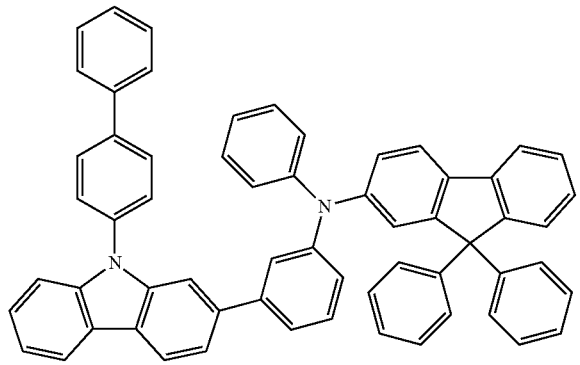
C8
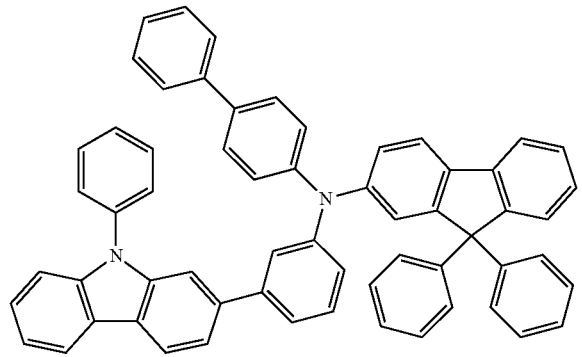
C9
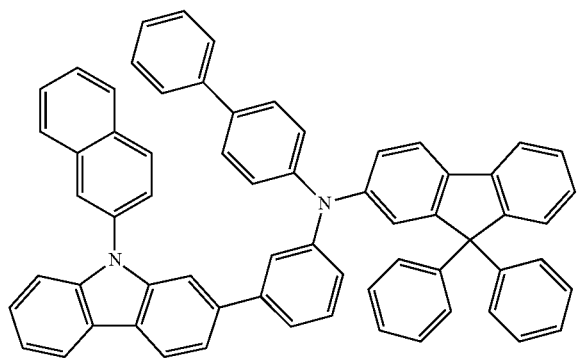
C10
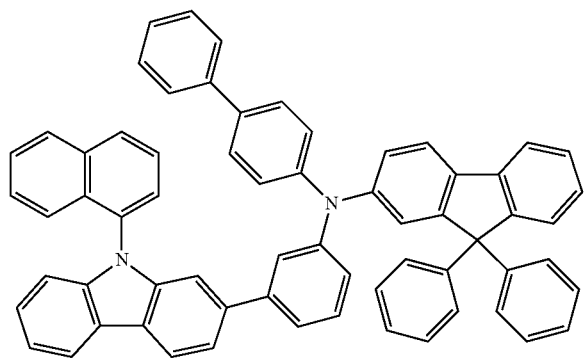
C11
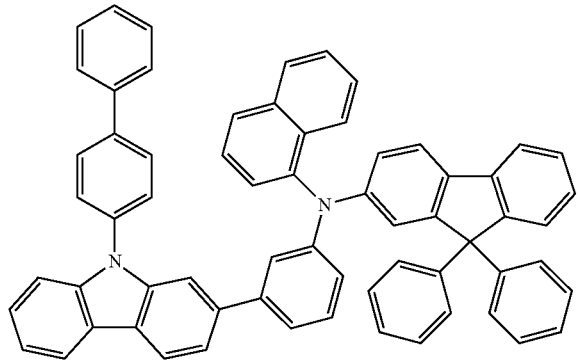
C12
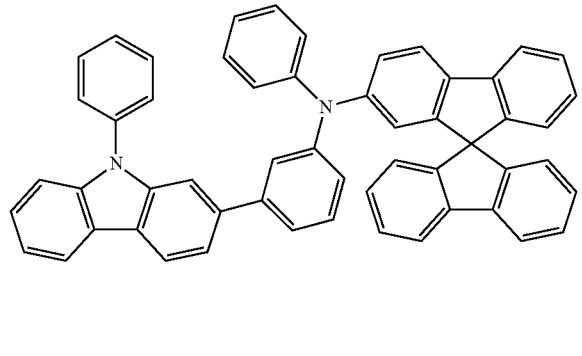
C13
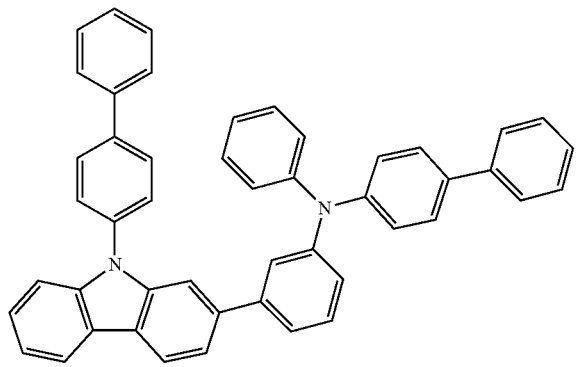
C14
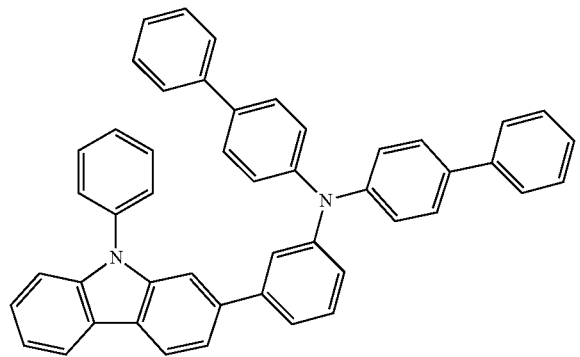

-continued
C15
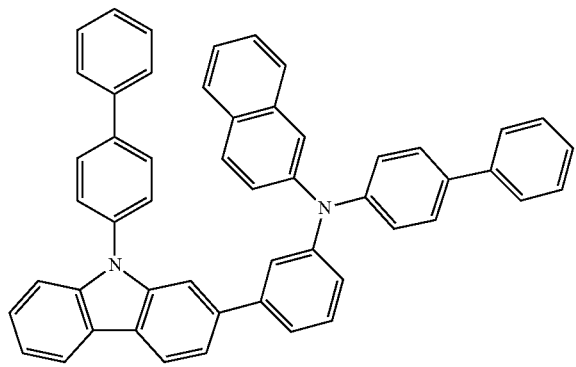
C16
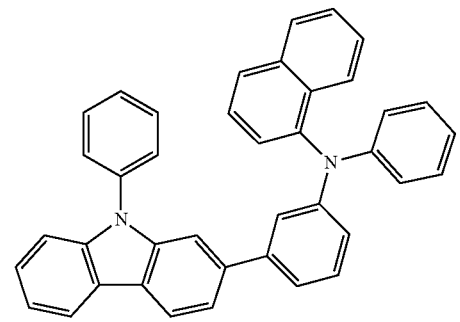
C17
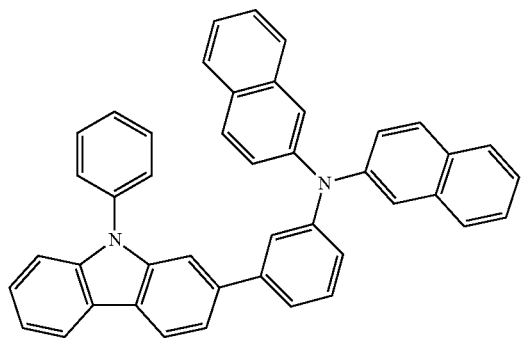
C18
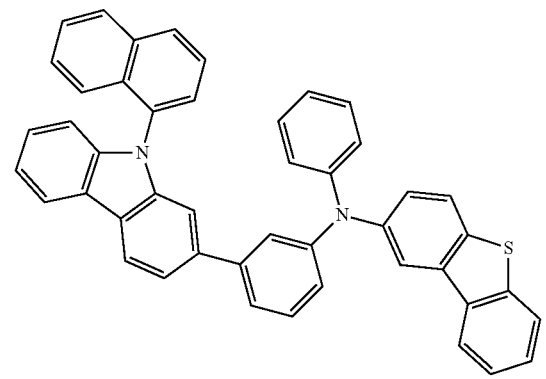
C19
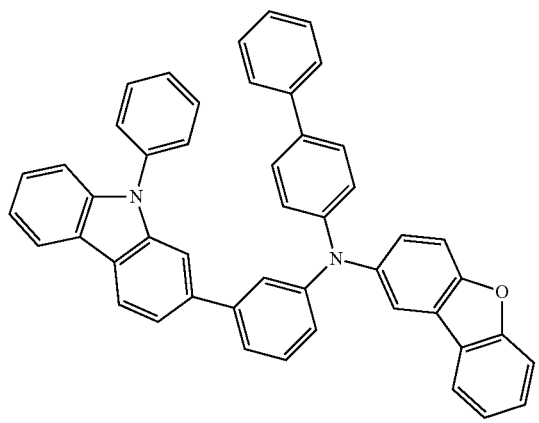
C20
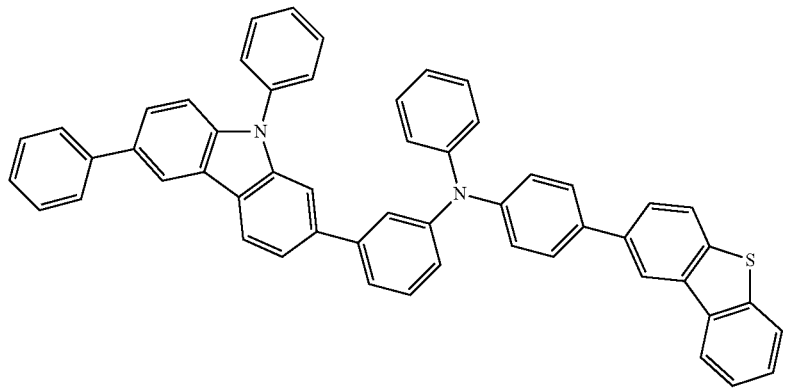

-continued
C21
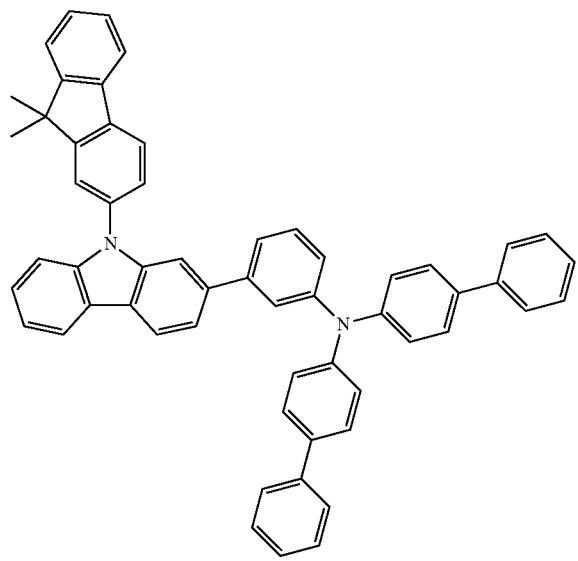
C22
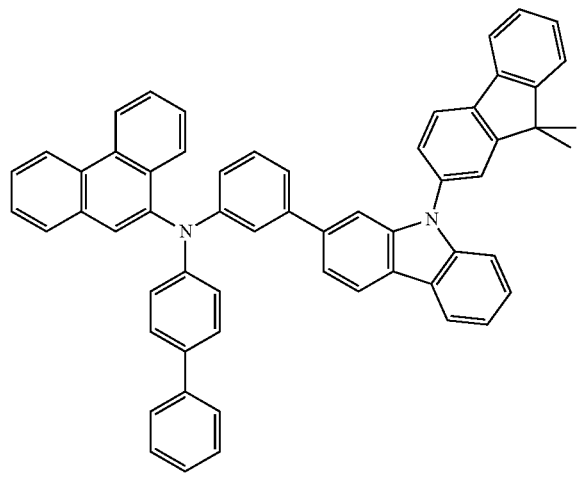
C23
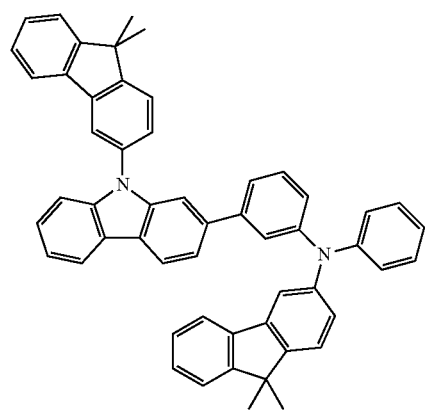
C24
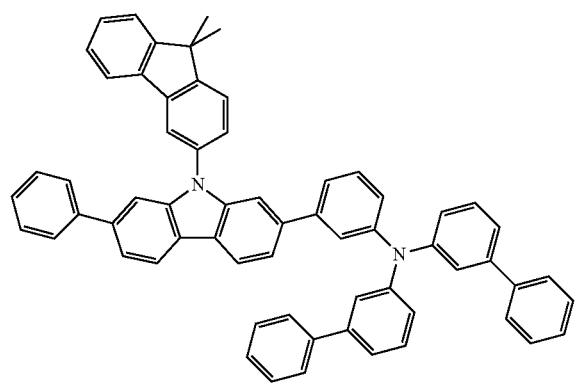
C25
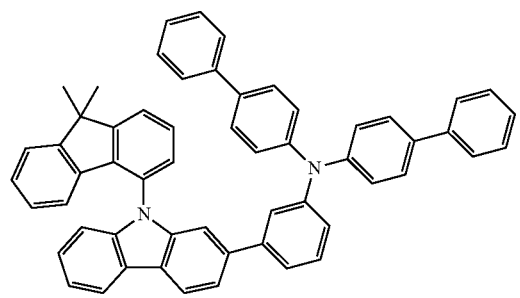
C26
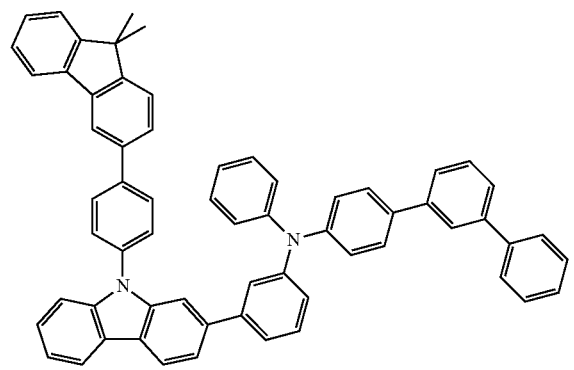

-continued
C27
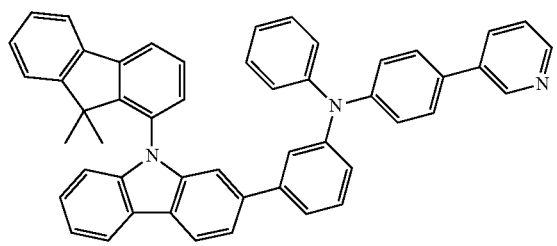
C28
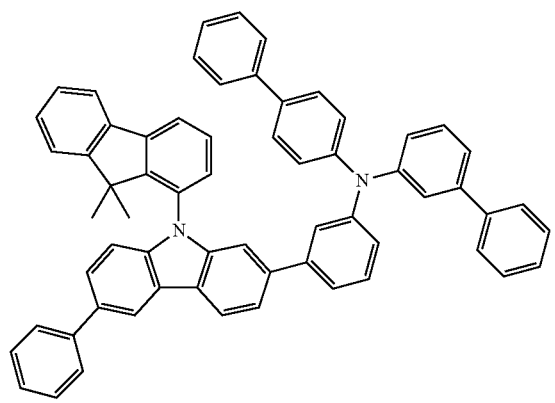
C29
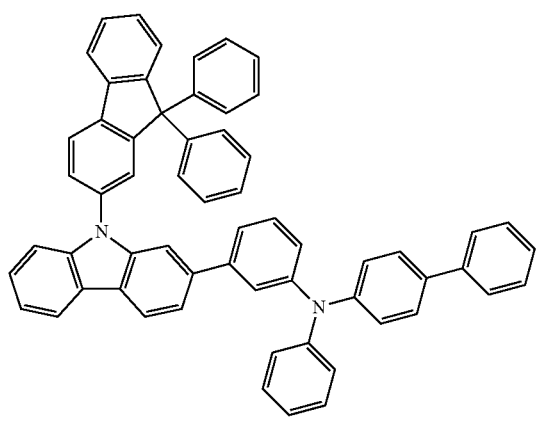
C30
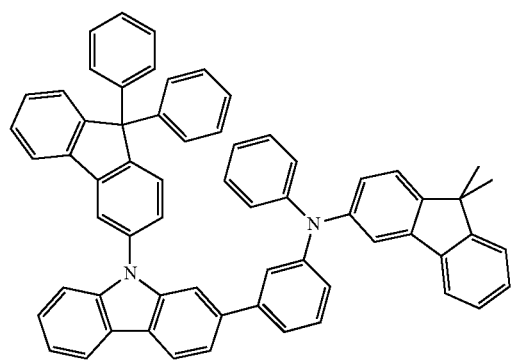
C31
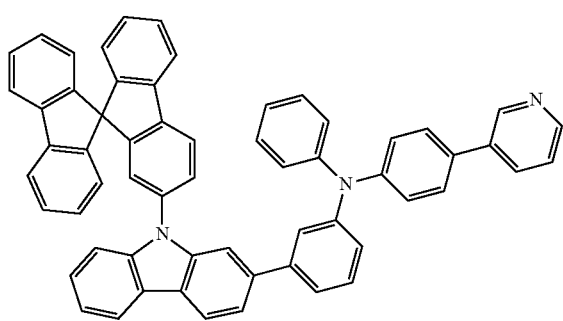
C32
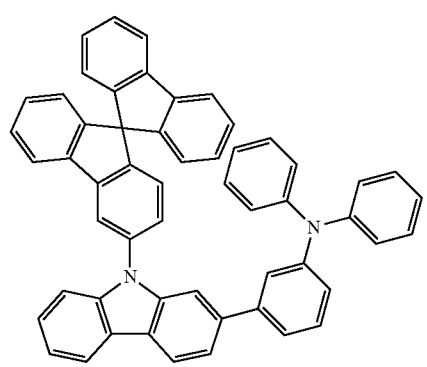

-continued
C33
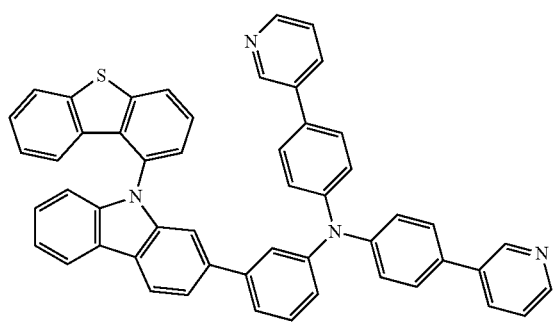
C34
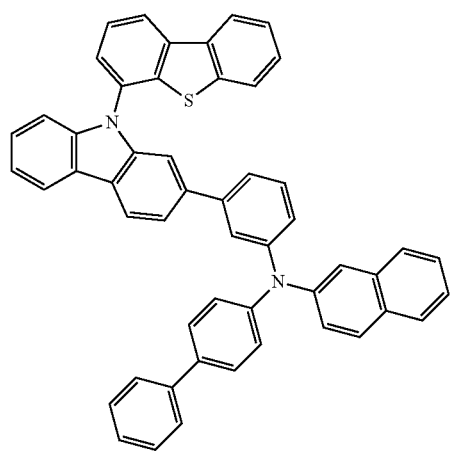
C35
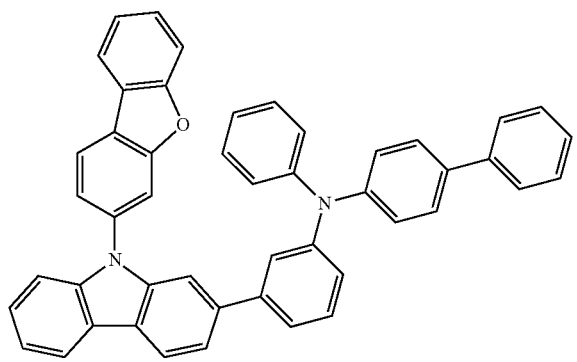
C36
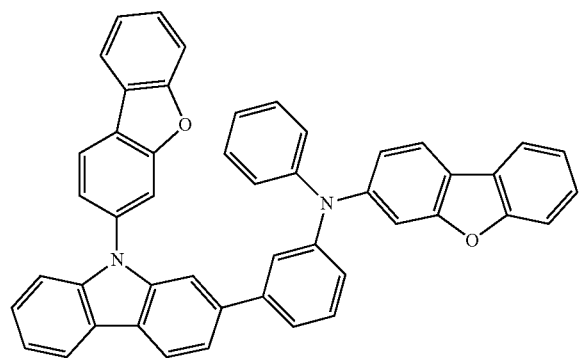
C37
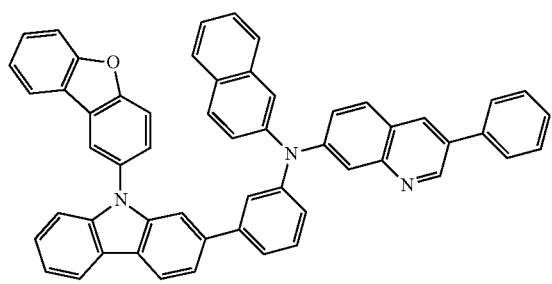
C38
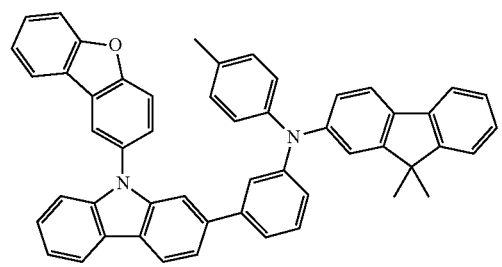

101

C39

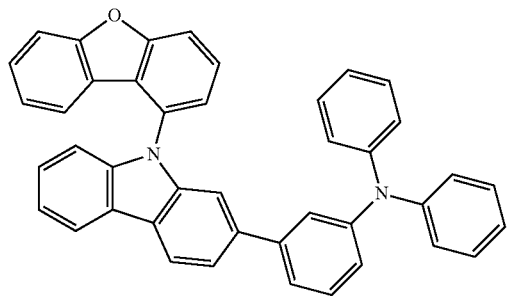

102
-continued
C40

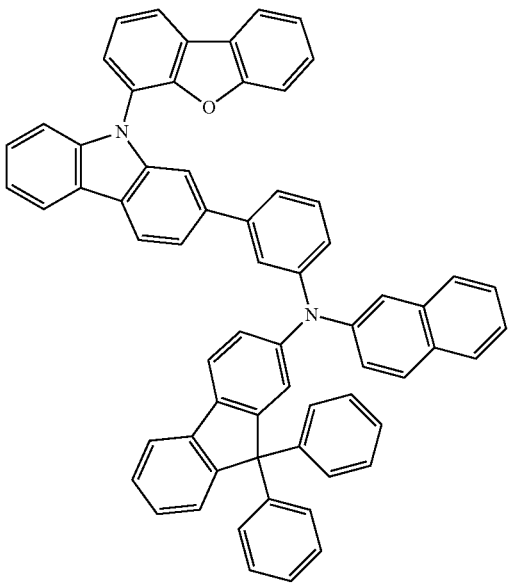

In another aspect of the present invention, there is provided a compound for an organic electric element represented by Formula 1 above.

In another aspect of the present invention, there is provided an organic electric element comprising the compound represented by Formula 1 above.

The organic electric element can comprise a first electrode, a second electrode, and an organic material layer disposed between the first electrode and the second electrode. The organic material layer can comprise the compound represented by Formula 1. The compound by represented Formula 1 can be contained in at least one layer of a hole injection layer, a hole transport layer, an emission-auxiliary layer, or a light emitting layer of the organic material layer. The compound represented by Formula 1 may be used a material in the hole injection layer, a material in the hole transport layer, a material in the emission-auxiliary layer, or a material in the light emitting layer. There is provided the organic electric element comprising the organic material layer comprising at least one of the compounds represented by Formula 2 to Formula 5. Specially, there is provided and the organic electric element comprising the organic material layer comprising at least one of the compounds represented by the individual formulas.

In another aspect of the present invention, the present invention provides an organic electric element further including at least a layer to improve luminous efficiency which is formed on at least one of the sides the first and second electrodes, which is opposite to the organic material layer.

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

SYNTHESIS EXAMPLE

The final product according to the present invention can be synthesized by reaction between Sub 1 and Sub 2 as illustrated in, but not limited to, the following Reaction Scheme 1.

($Ar^1$ to $Ar^3$, $L^1$, $R^1$, $R^2$, m and n are as defined in Formula 1 above. When $L^1$ is a single bond, the Br is directly bonded to a linking group of a phenyl.)

I. Synthesis Method of Sub 1

Sub 1 of Reaction Scheme 1 can be synthesized according to, but not limited to, the following Reaction Scheme 2.

<Reaction Scheme 2>
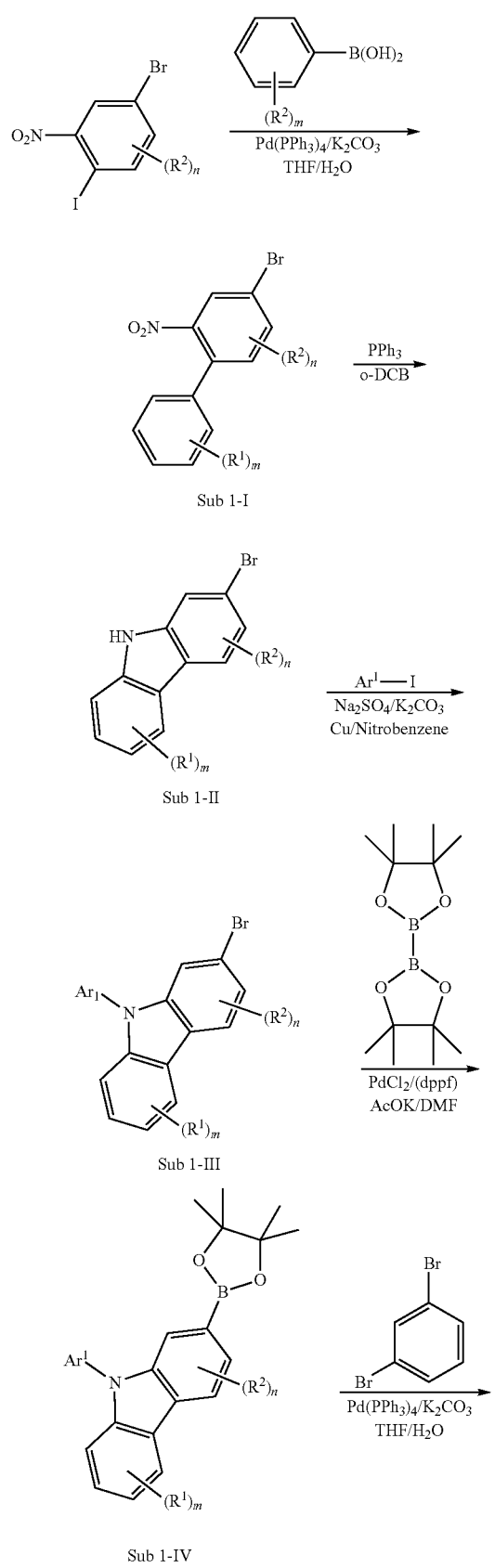
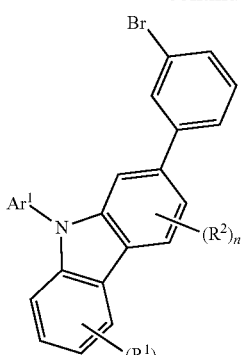
Sub 1-V
Sub 1 (L1 = single bond)
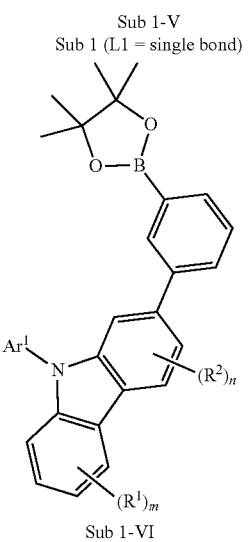
Sub 1-VI
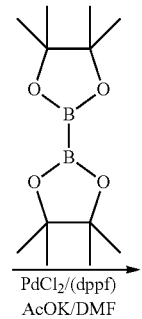
Sub 1
Synthesis Examples of the compounds of Sub 1 will be described in detail.
1. Synthesis Method of Sub 1-B1
<Reaction Scheme 3>
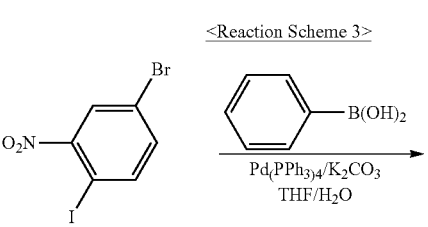

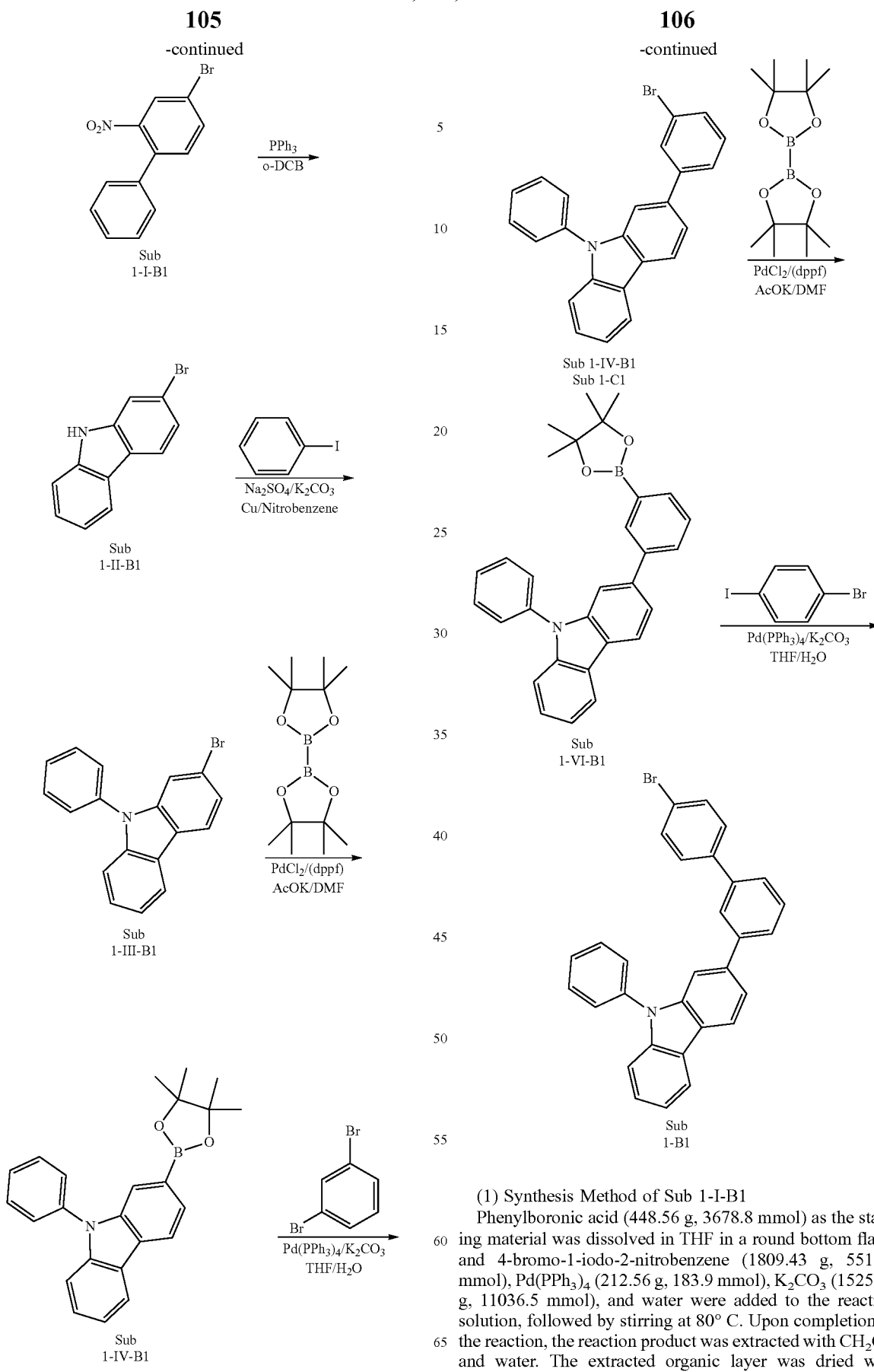

(1) Synthesis Method of Sub 1-I-B1

Phenylboronic acid (448.56 g, 3678.8 mmol) as the starting material was dissolved in THF in a round bottom flask, and 4-bromo-1-iodo-2-nitrobenzene (1809.43 g, 5518.2 mmol), Pd(PPh$_3$)$_4$ (212.56 g, 183.9 mmol), K$_2$CO$_3$ (1525.35 g, 11036.5 mmol), and water were added to the reaction solution, followed by stirring at 80° C. Upon completion of the reaction, the reaction product was extracted with CH$_2$Cl$_2$ and water. The extracted organic layer was dried with MgSO$_4$ and concentrated, and then the produced organic material was separated by a silica gel column and recrystallized to obtain 705.93 g of product (yield: 69%).

(2) Synthesis Method of Sub 1-II-B1

The obtained Sub 1-I-B1 (705.93 g, 2538.4 mmol) was dissolved in o-dichlorobenzene in a round bottom flask, and triphenylphosphine (1664.49 g, 6346 mmol) was added to the reaction solution, followed by stirring at 200° C. Upon completion of the reaction, o-dichlorobenzene was removed by distillation, and the reaction product was extracted with CH₂Cl₂ and water. The extracted organic layer was dried with MgSO₄ and concentrated, and then the produced organic material was separated by a silica gel column and recrystallized to obtain 449.78 g of product (yield: 72%).

(3) Synthesis Method of Sub 1-III-B1

The obtained Sub 1-II-B1 (37.19 g, 151.1 mmol) was dissolved in nitrobenzene in a round bottom flask, and iodobenzene (46.24 g, 226.7 mmol), Na₂SO₄ (21.46 g, 151.1 mmol), K₂CO₃ (20.89 g, 151.1 mmol), and Cu (2.88 g, 45.3 mmol) were added to the reaction solution, followed by stirring at 200° C. Upon completion of the reaction, nitrobenzene was removed by distillation, and the reaction product was extracted with CH₂Cl₂ and water. The extracted organic layer was dried with MgSO₄ and concentrated, and then the produced organic material was separated by a silica gel column and recrystallized to obtain 38.47 g of product (yield: 79%).

(4) Synthesis Method of Sub 1-IV-B1

The obtained Sub 1-III-B1 (38.47 g, 119.4 mmol) was dissolved in DMF in a round bottom flask, and Bis(pinacolato)diboron (33.35 g, 131.3 mmol), Pd(dppf)Cl₂ (2.93 g, 3.6 mmol) and KOAc (35.15 g, 358.2 mmol) were added to the reaction solution, followed by stirring at 90° C. Upon completion of the reaction, DMF was removed by distillation, and the reaction product was extracted with CH₂Cl₂ and water. The extracted organic layer was dried with MgSO₄ and concentrated, and then the produced organic material was separated by a silica gel column and recrystallized to obtain 37.48 g of product (yield: 85%).

(5) Synthesis Method of Sub 1-V-B1(Sub 1-C1)

The obtained Sub 1-IV-B1 (37.48 g, 101.5 mmol) was dissolved in THF in a round bottom flask, and 1,3-dibromobenzene (35.92 g, 152.3 mmol), Pd(PPh₃)₄(5.86 g, 5.1 mmol), K₂CO₃ (42.09 g, 304.5 mmol), and water were added to the reaction solution, followed by stirring at 80° C. Upon completion of the reaction, the reaction product was extracted with CH₂Cl₂ and water. The extracted organic layer was dried with MgSO₄ and concentrated, and then the produced organic material was separated by a silica gel column and recrystallized to obtain 30.32 g of product (yield: 75%).

6) Synthesis Method of Sub 1-VI-B1

The obtained Sub 1-V-B1 (30.32 g, 76.1 mmol) was dissolved in DMF in a round bottom flask, and Bis(pinacolato)diboron (21.26 g, 83.7 mmol), Pd(dppf)Cl₂ (1.87 g, 2.3 mmol) and KOAc (22.41 g, 228.4 mmol) were added to the reaction solution, followed by stirring at 90° C. Upon completion of the reaction, DMF was removed by distillation, and the reaction product was extracted with CH₂Cl₂ and water. The extracted organic layer was dried with MgSO₄ and concentrated, and then the produced organic material was separated by a silica gel column and recrystallized to obtain 28.48 g of product (yield: 84%).

(7) Synthesis Method of Sub 1-B1

The obtained Sub 1-VI-B1 (7.16 g, 16.1 mmol) was dissolved in THF in a round bottom flask, and 1-bromo-4-iodobenzene (6.82 g, 24.1 mmol), Pd(PPh₃)₄(0.93 g, 0.8 mmol), K₂CO₃ (6.67 g, 48.2 mmol) and water were added to the reaction solution, followed by stirring at 80° C. Upon completion of the reaction, the reaction product was extracted with CH₂Cl₂ and water. The extracted organic layer was dried with MgSO₄ and concentrated, and then the produced organic material was separated by a silica gel column and recrystallized to obtain 6.33 g of product (yield: 83%).

2. Synthesis Method of Sub 1-B2

<Reaction Scheme 4>

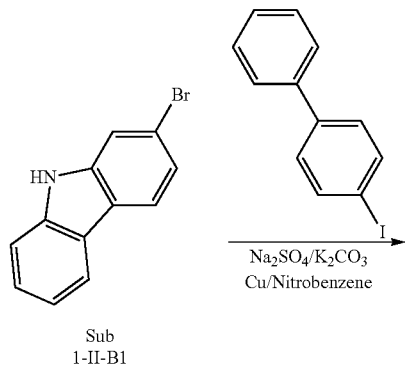

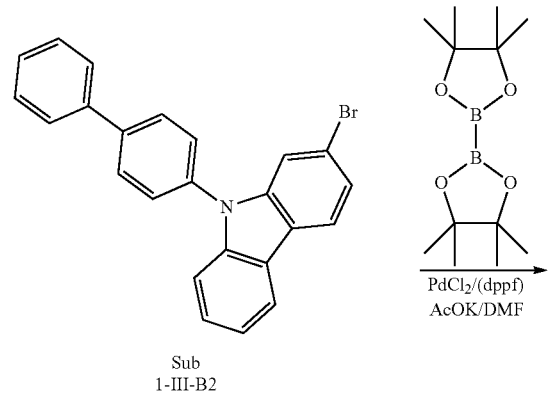

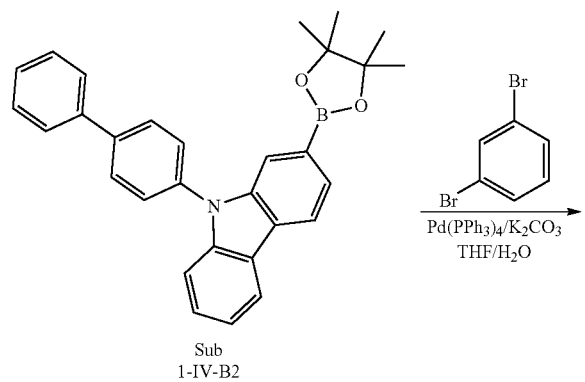

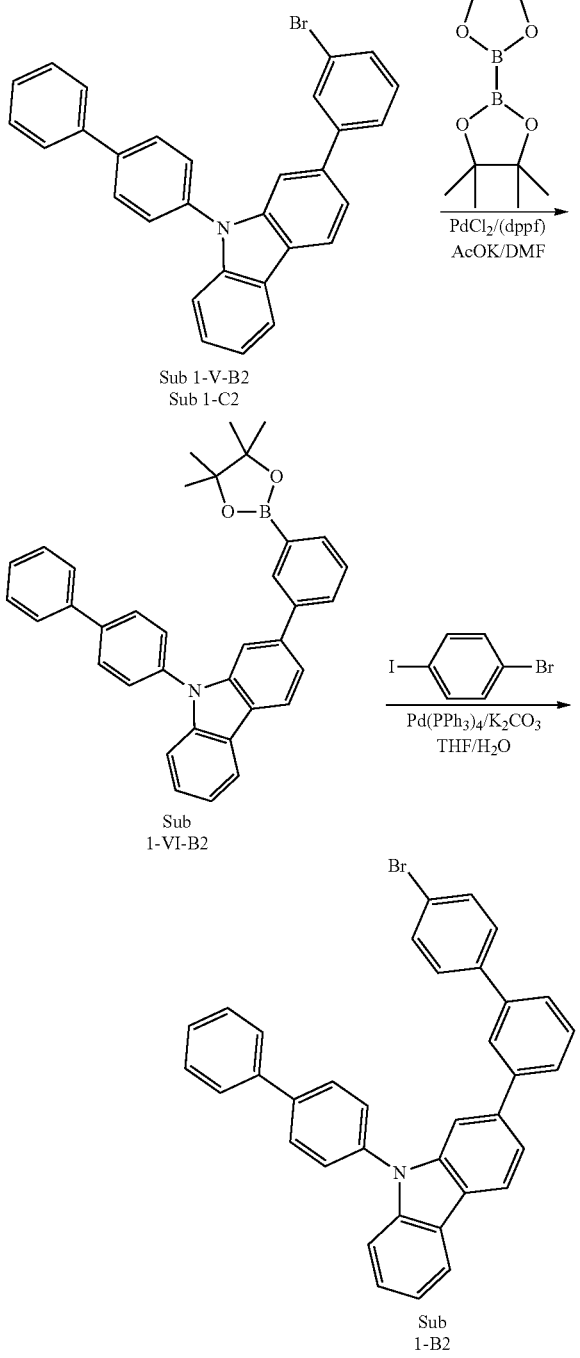

Sub 1-V-B2
Sub 1-C2

Sub 1-VI-B2

Sub 1-B2

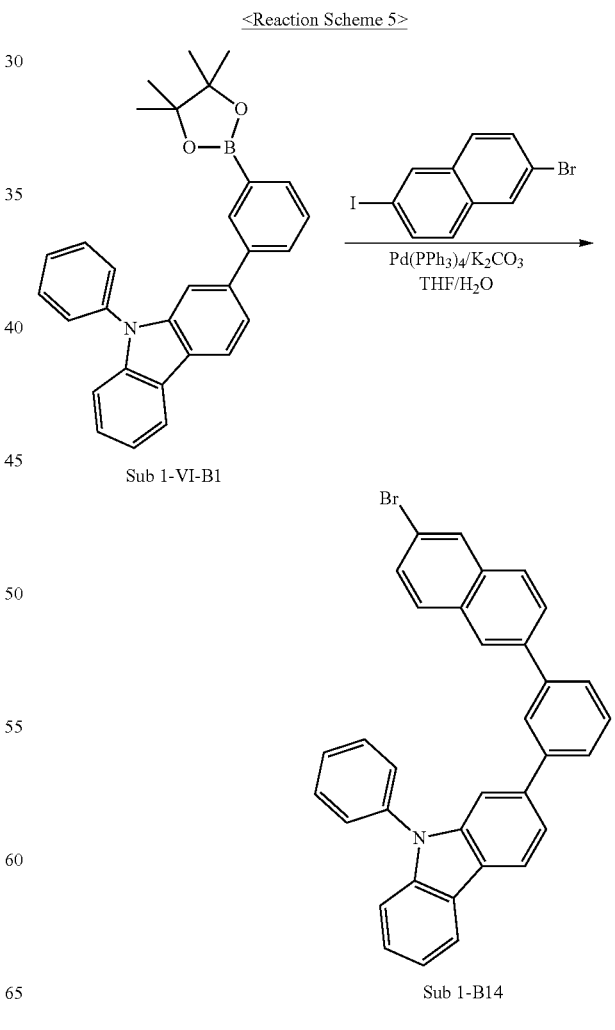

Sub 1-VI-B1

Sub 1-B14

DMF, the same procedure as described in the synthesis method of Sub 1-IV-B1 was carried out to obtain 33.68 g of product (yield: 83%).

(3) Synthesis Method of Sub 1-V-B2(Sub 1-C2)

Using the obtained Sub 1-IV-B2 (33.68 g, 75.6 mmol) plus 1,3-dibromobenzezene (26.76 g, 113.4 mmol), Pd(PPh₃)₄(4.37 g, 3.8 mmol), K₂CO₃ (31.36 g, 226.9 mmol), THF and water, the same procedure as described in the synthesis method of Sub 1-V-B1 was carried out to obtain 26.91 g of product (yield: 75%).

(4) Synthesis Method of Sub 1-VI-B2

Using the obtained Sub 1-V-B2 (26.91 g, 56.7 mmol) plus Bis(pinacolato)diboron (15.85 g, 62.4 mmol), Pd(dppf)Cl₂ (1.39 g, 1.7 mmol), KOAc (16.7 g, 170.2 mmol) and DMF, the same procedure as described in the synthesis method of Sub 1-VI-B1 was carried out to obtain 24.55 g of product (yield: 83%).

(5) Synthesis Method of Sub 1-B2

Using the obtained Sub 1-VI-B2 (12.93 g, 24.8 mmol) plus 1-bromo-4-iodobenzene (10.52 g, 37.2 mmol), Pd(PPh₃)₄(1.43 g, 1.2 mmol), K₂CO₃ (10.28 g, 74.4 mmol), THF and water, the same procedure as described in the synthesis method of Sub 1-B1 was carried out to obtain 10.78 g of product (yield: 79%).

3. Synthesis Method of Sub 1-B14

<Reaction Scheme 5>

(1) Synthesis Method of Sub 1-III-B2

Using the obtained Sub 1-II-B1 (30.72 g, 124.8 mmol) plus 4-iodo-1,1'-biphenyl (52.45 g, 187.2 mmol), Na₂SO₄ (17.73 g, 124.8 mmol), K₂CO₃ (17.25 g, 124.8 mmol), Cu (2.38 g, 37.4 mmol), and nitrobenzene, the same procedure as described in the synthesis method of Sub 1-III-B1 was carried out to obtain 36.29 g of product (yield: 73%).

(2) Synthesis Method of Sub 1-IV-B2

Using the obtained Sub 1-III-B2 (36.29 g, 91.1 mmol) plus Bis(pinacolato)diboron (25.45 g, 100.2 mmol), Pd(dppf)Cl₂ (2.23 g, 2.7 mmol), KOAc (26.83 g, 273.3 mmol) and Using the obtained Sub 1-VI-B1 (7.65 g, 17.2 mmol) plus 2-bromo-6-iodonaphthalene (8.58 g, 25.8 mmol), Pd(PPh$_3$)$_4$ (0.99 g, 0.9 mmol), K$_2$CO$_3$ (7.12 g, 51.5 mmol), THF and water, the same procedure as described in the synthesis method of Sub 1-B1 was carried out to obtain 6.85 g of product (yield: 76%).

4. Synthesis Method of Sub 1-B23

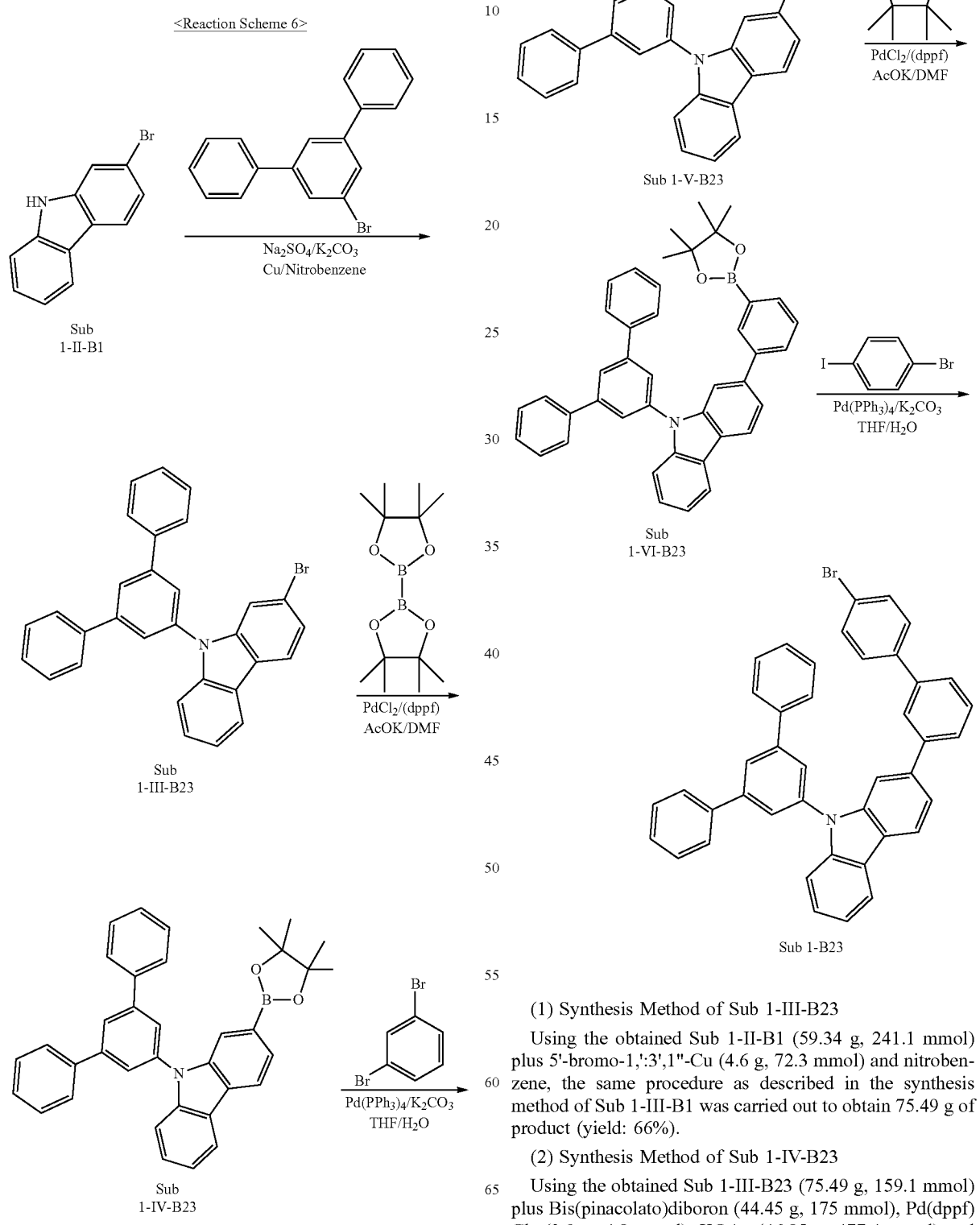

(1) Synthesis Method of Sub 1-III-B23

Using the obtained Sub 1-II-B1 (59.34 g, 241.1 mmol) plus 5'-bromo-1,':3',1''-Cu (4.6 g, 72.3 mmol) and nitrobenzene, the same procedure as described in the synthesis method of Sub 1-III-B1 was carried out to obtain 75.49 g of product (yield: 66%).

(2) Synthesis Method of Sub 1-IV-B23

Using the obtained Sub 1-III-B23 (75.49 g, 159.1 mmol) plus Bis(pinacolato)diboron (44.45 g, 175 mmol), Pd(dppf)Cl$_2$ (3.9 g, 4.8 mmol), KOAc (46.85 g, 477.4 mmol) and DMF, the same procedure as described in the synthesis method of Sub 1-IV-B1 was carried out to obtain 64.72 g of product (yield: 78%).

(3) Synthesis Method of Sub 1-V-B23

Using the obtained Sub 1-IV-B23 (64.72 g, 124.1 mmol) plus 1,3-dibromobenzene (43.92 g, 186.2 mmol), Pd(PPh$_3$)$_4$ (7.17 g, 6.2 mmol), K$_2$CO$_3$ (51.46 g, 372.3 mmol), THF and water, the same procedure as described in the synthesis method of Sub 1-V-B1 was carried out to obtain 49.19 g of product (yield: 72%).

(4) Synthesis Method of Sub 1-VI-B23

Using the obtained Sub 1-V-B23 (49.19 g, 89.4 mmol) plus Bis(pinacolato)diboron (24.96 g, 98.3 mmol), Pd(dppf)Cl$_2$ (2.19 g, 2.7 mmol), KOAc (26.31 g, 268.1 mmol) and DMF, the same procedure as described in the synthesis method of Sub 1-VI-B1 was carried out to obtain 42.72 g of product (yield: 80%).

(5) Synthesis Method of Sub 1-B23

Using the obtained Sub 1-VI-B23 (12.61 g, 21.1 mmol) plus 1-bromo-4-iodobenzene (8.95 g, 31.7 mmol), Pd(PPh$_3$)$_4$ (1.22 g, 1.1 mmol), K$_2$CO$_3$ (8.75 g, 63.3 mmol), THF and water, the same procedure as described in the synthesis method of Sub 1-B1 was carried out to obtain 8.46 g of product (yield: 64%).

5. Synthesis Method of Sub 1-B26

<Reaction Scheme 7>

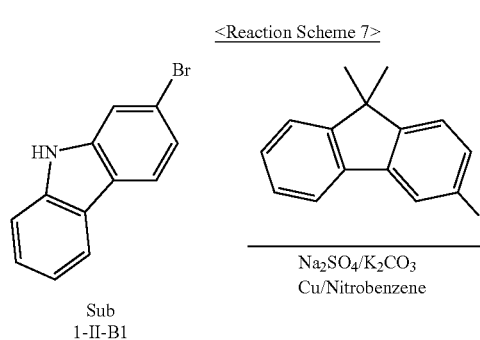

Sub 1-II-B1

Na$_2$SO$_4$/K$_2$CO$_3$
Cu/Nitrobenzene

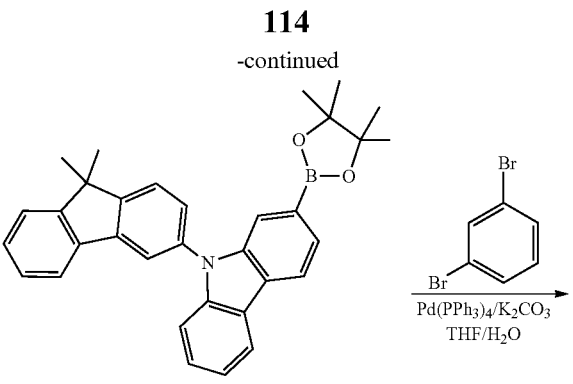

Sub 1-IV-B26

Pd(PPh$_3$)$_4$/K$_2$CO$_3$
THF/H$_2$O

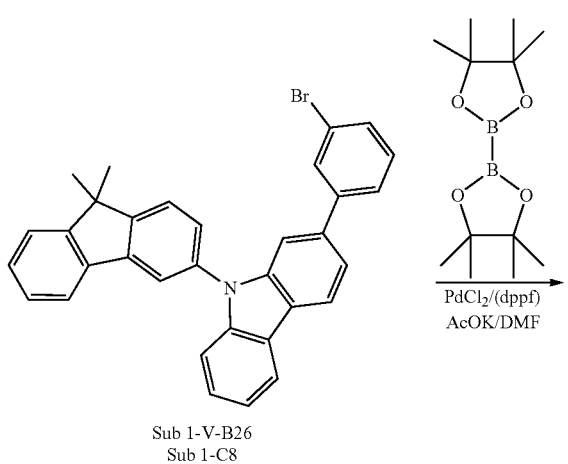

Sub 1-V-B26
Sub 1-C8

PdCl$_2$/(dppf)
AcOK/DMF

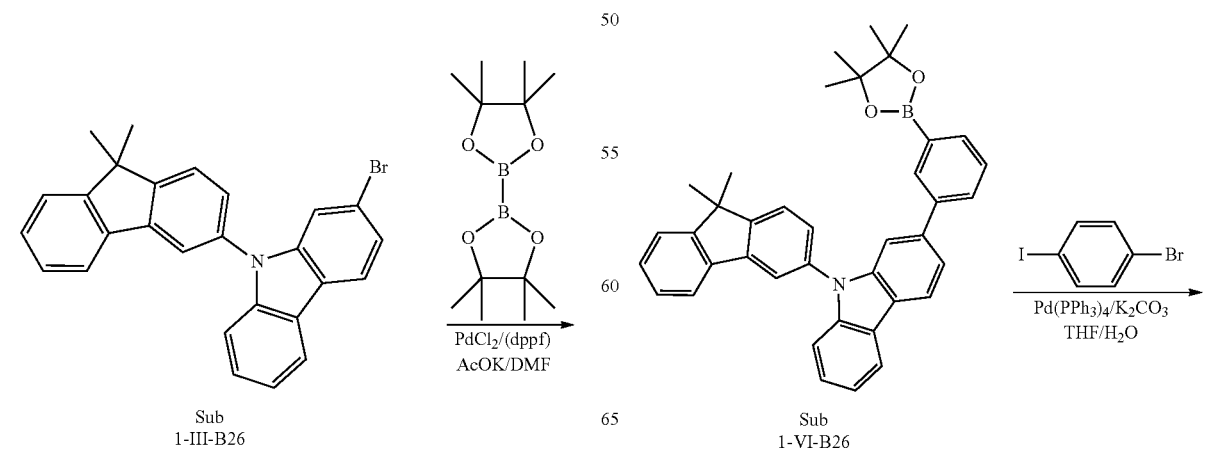

Sub 1-III-B26

PdCl$_2$/(dppf)
AcOK/DMF

Sub 1-VI-B26

Pd(PPh$_3$)$_4$/K$_2$CO$_3$
THF/H$_2$O

115
-continued

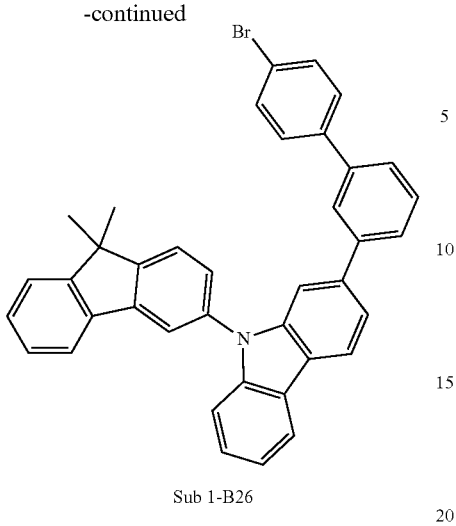

Sub 1-B26

(1) Synthesis Method of Sub 1-III-B26

Using the obtained Sub 1-II-B1 (41.89 g, 170.2 mmol) plus 3-bromo-9,9-dimethyl-9H-fluorene (69.75 g, 255.3 mmol), Na$_2$SO$_4$ (24.18 g, 170.2 mmol), K$_2$CO$_3$ (23.53 g, 170.2 mmol), Cu (3.25 g, 51.1 mmol) and nitrobenzene, the same procedure as described in the synthesis method of Sub 1-III-B1 was carried out to obtain 55.96 g of product (yield: 75%).

(2) Synthesis Method of Sub 1-IV-B26

Using the obtained Sub 1-III-B26 (55.96 g, 127.7 mmol) plus Bis(pinacolato)diboron (35.66 g, 140.4 mmol), Pd(dppf)Cl$_2$ (3.13 g, 3.8 mmol), KOAc (37.58 g, 383 mmol) and DMF, the same procedure as described in the synthesis method of Sub 1-IV-B1 was carried out to obtain 52.05 g of product (yield: 84%).

(3) Synthesis Method of Sub 1-V-B26(Sub 1-C8)

Using the obtained Sub 1-IV-B26 (52.05 g, 107.2 mmol) plus 1,3-dibromobenzene (37.94 g, 160.8 mmol), Pd(PPh$_3$)$_4$ (6.2 g, 5.4 mmol), K$_2$CO$_3$ (44.46 g, 321.7 mmol), THF and water, the same procedure as described in the synthesis method of Sub 1-V-B1 was carried out to obtain 39.72 g of product (yield: 72%).

(4) Synthesis Method of Sub 1-VI-B26

Using the obtained Sub 1-V-B26 (39.72 g, 77.2 mmol) plus Bis(pinacolato)diboron (21.57 g, 84.9 mmol), Pd(dppf)Cl$_2$ (1.89 g, 2.3 mmol), KOAc (22.73 g, 231.6 mmol) and DMF, the same procedure as described in the synthesis method of Sub 1-VI-B1 was carried out to obtain 36.85 g of product (yield: 85%).

(5) Synthesis Method of Sub 1-B26

Using the obtained Sub 1-VI-B26 (9.87 g, 17.6 mmol) plus 1-bromo-4-iodobenzene (7.46 g, 26.4 mmol), Pd(PPh$_3$)$_4$ (1.02 g, 0.9 mmol), K$_2$CO$_3$ (7.29 g, 52.7 mmol), THF and water, the same procedure as described in the synthesis method of Sub 1-B1 was carried out to obtain 8.41 g of product (yield: 81%).

116

6. Synthesis Method of Sub 1-B32

<Reaction Scheme 8>

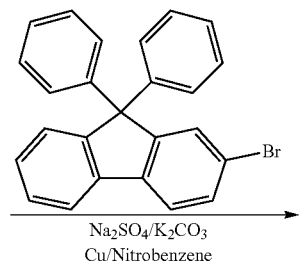

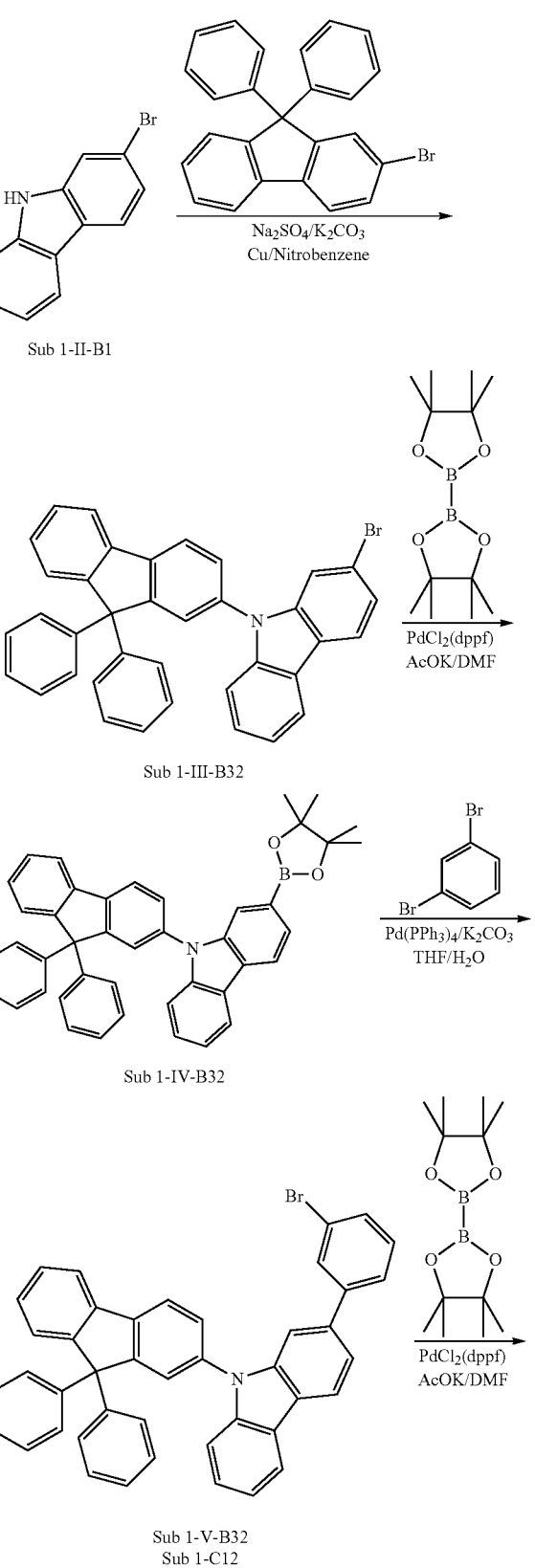

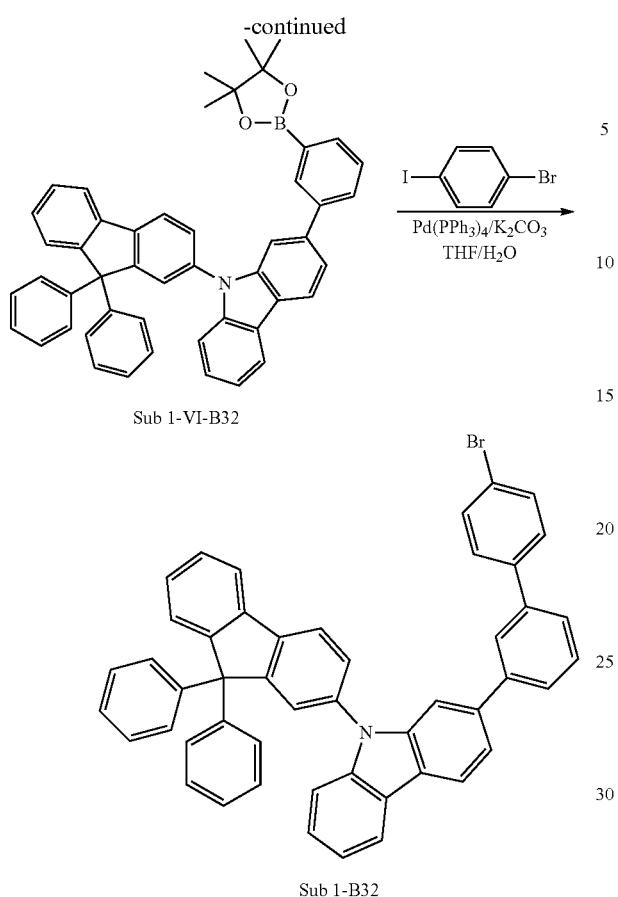

Sub 1-VI-B32

Sub 1-B32

(1) Synthesis Method of Sub 1-III-B32

Using the obtained Sub 1-II-B1 (72.54 g, 294.8 mmol) plus 2-bromo-9,9-diphenyl-9H-fluorene (175.67 g, 442.1 mmol), Na$_2$SO$_4$ (41.87 g, 294.8 mmol), K$_2$CO$_3$ (40.74 g, 294.8 mmol), Cu (5.62 g, 88.4 mmol) and nitrobenzene, the same procedure as described in the synthesis method of Sub 1-III-B1 was carried out to obtain 97.82 g of product (yield: 59%).

(2) Synthesis Method of Sub 1-IV-B32

Using the obtained Sub 1-III-B32 (97.82 g, 173.9 mmol) plus Bis(pinacolato)diboron (48.58 g, 191.3 mmol), Pd(dppf)Cl$_2$ (4.26 g, 5.2 mmol), KOAc (51.2 g, 521.7 mmol) and DMF, the same procedure as described in the synthesis method of Sub 1-IV-B1 was carried out to obtain 83.74 g of product (yield: 79%).

(3) Synthesis Method of Sub 1-V-B32(Sub 1-C12)

Using the obtained Sub 1-IV-B32 (83.74 g, 137.4 mmol) plus 1,3-dibromobenzene (48.61 g, 206.1 mmol), Pd(PPh$_3$)$_4$ (7.94 g, 6.9 mmol), K$_2$CO$_3$ (56.96 g, 412.1 mmol), THF and water, the same procedure as described in the synthesis method of Sub 1-V-B1 was carried out to obtain 64.04 g of product (yield: 73%).

(4) Synthesis Method of Sub 1-VI-B32

Using the obtained Sub 1-V-B32 (64.04 g, 100.3 mmol) plus Bis(pinacolato)diboron (28.01 g, 110.3 mmol), Pd(dppf)Cl$_2$ (2.46 g, 3 mmol), KOAc (29.53 g, 300.9 mmol) and DMF, the same procedure as described in the synthesis method of Sub 1-VI-B1 was carried out to obtain 52.26 g of product (yield: 76%).

(5) Synthesis Method of Sub 1-B32

Using the obtained Sub 1-VI-B32 (17.43 g, 25.4 mmol) plus 1-bromo-4-iodobenzene (10.79 g, 38.1 mmol), Pd(PPh$_3$)$_4$(1.47 g, 1.3 mmol), K$_2$CO$_3$ (10.54 g, 76.3 mmol), THF and water, the same procedure as described in the synthesis method of Sub 1-B1 was carried out to obtain 11.08 g of product (yield: 61%).

7. Synthesis Method of Sub 1-B33

<Reaction Scheme 9>

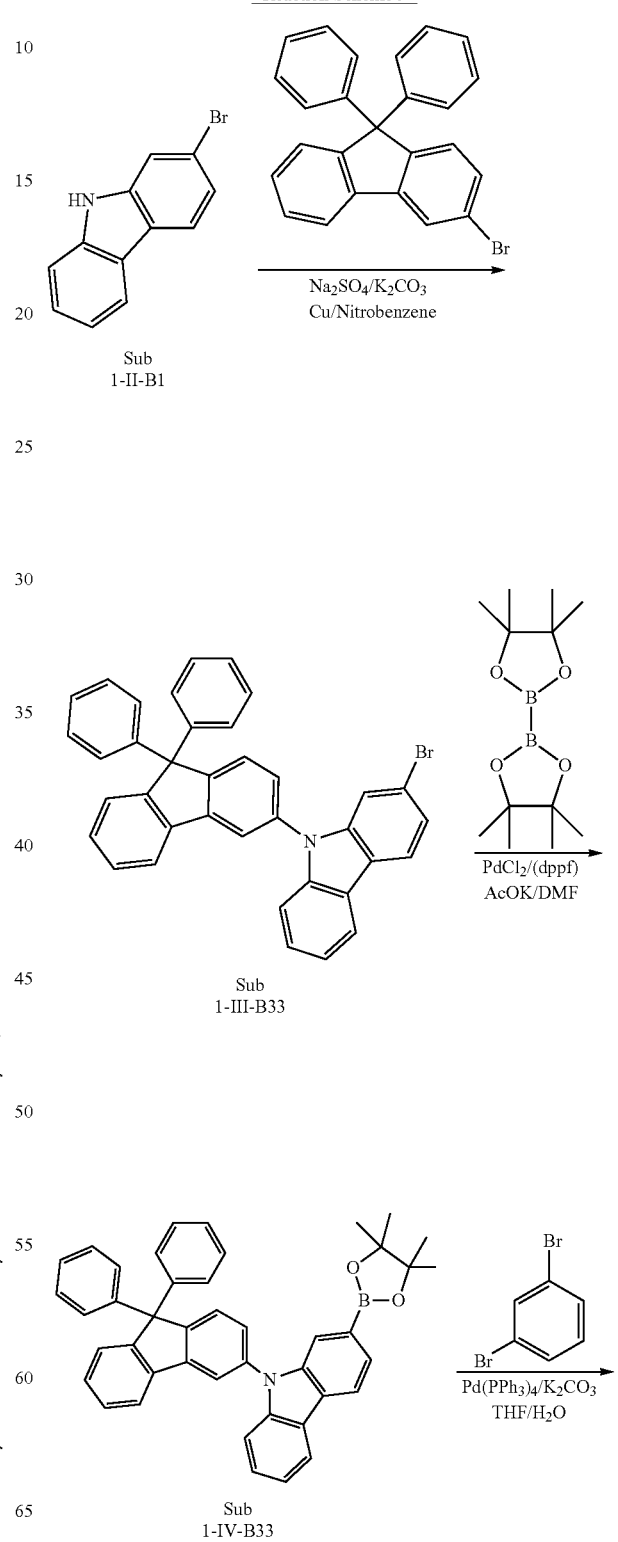

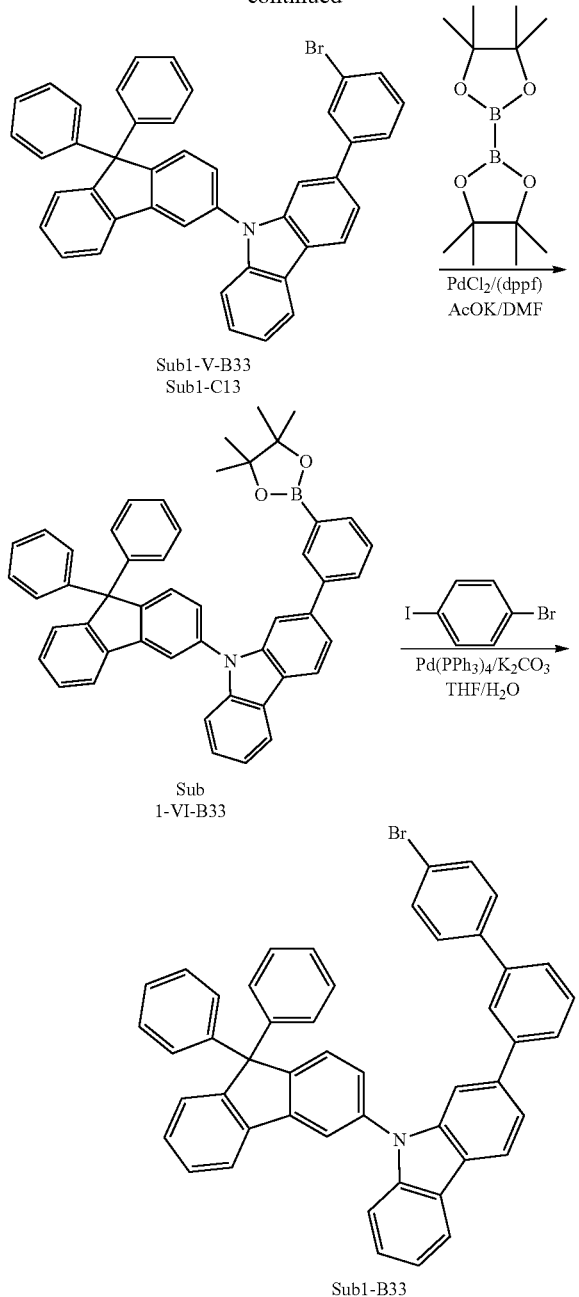

Sub1-V-B33
Sub1-C13

Sub 1-VI-B33

Sub1-B33

(1) Synthesis Method of Sub 1-III-B33

Using the obtained Sub 1-II-B1 (67.82 g, 275.6 mmol) plus 3-bromo-9,9-diphenyl-9H-fluorene (164.24 g, 413.4 mmol), $Na_2SO_4$ (39.14 g, 275.6 mmol), $K_2CO_3$ (38.09 g, 275.6 mmol), Cu (5.25 g, 82.7 mmol) and nitrobenzene, the same procedure as described in the synthesis method of Sub 1-III-B1 was carried out to obtain 96.11 g of product (yield: 62%).

(2) Synthesis Method of Sub 1-IV-B33

Using the obtained Sub 1-III-B33 (96.11 g, 170.9 mmol) plus Bis(pinacolato)diboron (47.73 g, 187.9 mmol), Pd(dppf)$Cl_2$ (4.19 g, 5.1 mmol), KOAc (50.31 g, 512.6 mmol) and DMF, the same procedure as described in the synthesis method of Sub 1-IV-B1 was carried out to obtain 79.15 g of product (yield: 76%).

(3) Synthesis Method of Sub 1-V-B33(Sub 1-C13)

Using the obtained Sub 1-IV-B33 (79.15 g, 129.8 mmol) plus 1,3-dibromobenzene (45.95 g, 194.8 mmol), Pd(PPh$_3$)$_4$ (7.5 g, 6.5 mmol), $K_2CO_3$ (53.84 g, 389.5 mmol), THF and water, the same procedure as described in the synthesis method of Sub 1-V-B1 was carried out to obtain 58.87 g of product (yield: 71%).

(4) Synthesis Method of Sub 1-VI-B33

Using the obtained Sub 1-V-B33 (58.87 g, 92.2 mmol) plus Bis(pinacolato)diboron (25.75 g, 101.4 mmol), Pd(dppf)$Cl_2$ (2.26 g, 2.8 mmol), KOAc (27.14 g, 276.6 mmol) and DMF, the same procedure as described in the synthesis method of Sub 1-VI-B1 was carried out to obtain 48.67 g of product (yield: 77%).

(5) Synthesis Method of Sub 1-B33

Using the obtained Sub 1-VI-B33 (14.61 g, 21.3 mmol) plus 1-bromo-4-iodobenzene (9.04 g, 32 mmol), Pd(PPh$_3$)$_4$ (1.23 g, 1.1 mmol), $K_2CO_3$ (8.83 g, 63.9 mmol), THF and water, the same procedure as described in the synthesis method of Sub 1-B1 was carried out to obtain 9.75 g of product (yield: 64%).

8. Synthesis Method of Sub 1-B40

<Reaction Scheme 10>

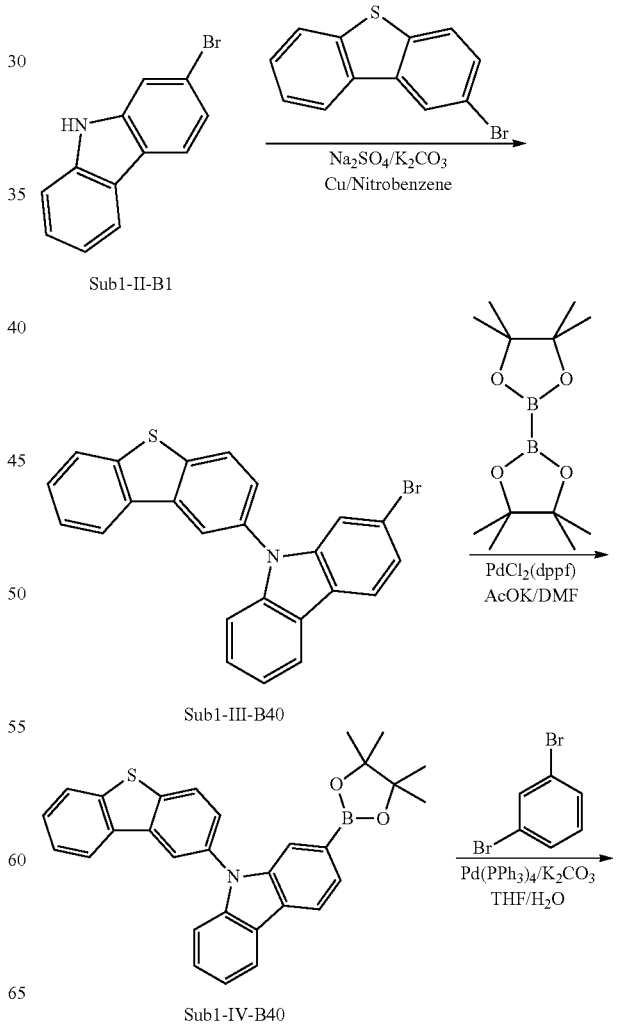

Sub1-II-B1

Sub1-III-B40

Sub1-IV-B40

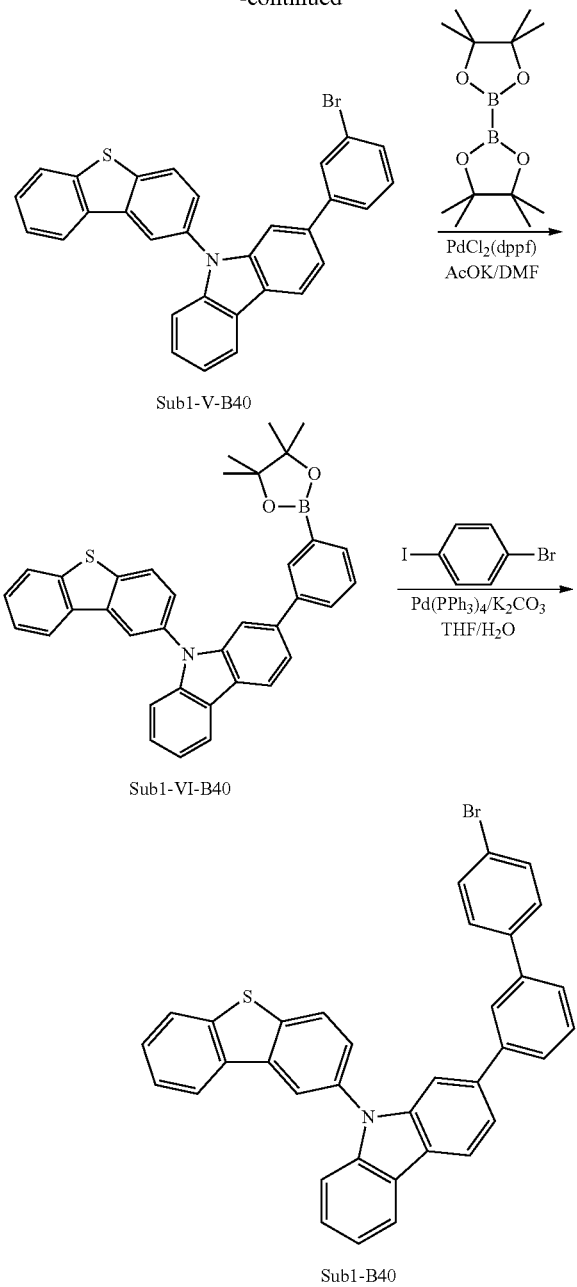

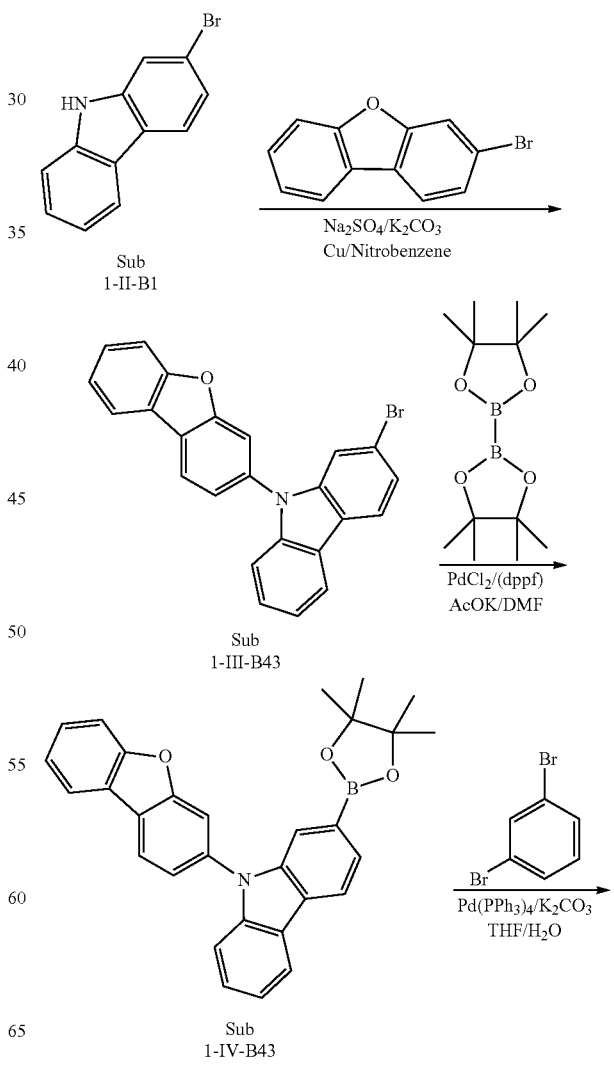

(3) Synthesis Method of Sub 1-V-B40

Using the obtained Sub 1-IV-B40 (58.82 g, 123.7 mmol) plus 1,3-dibromobenzene (43.78 g, 185.6 mmol), Pd(PPh$_3$)$_4$ (7.15 g, 6.2 mmol), K$_2$CO$_3$ (51.3 g, 371.2 mmol), THF and water, the same procedure as described in the synthesis method of Sub 1-V-B1 was carried out to obtain 47.43 g of product (yield: 76%).

(4) Synthesis Method of Sub 1-VI-B40

Using the obtained Sub 1-V-B40 (47.43 g, 94 mmol) plus Bis(pinacolato)diboron (26.26 g, 103.4 mmol), Pd(dppf)Cl$_2$ (2.3 g, 2.8 mmol), KOAc (27.68 g, 282.1 mmol) and DMF, the same procedure as described in the synthesis method of Sub 1-VI-B1 was carried out to obtain 42.52 g of product (yield: 82%).

(5) Synthesis Method of Sub 1-B40

Using the obtained Sub 1-VI-B40 (9.54 g, 17.3 mmol) plus 1-bromo-4-iodobenzene (7.34 g, 25.9 mmol), Pd(PPh$_3$)$_4$ (1 g, 0.9 mmol), K$_2$CO$_3$ (7.17 g, 51.9 mmol), THF and water, the same procedure as described in the synthesis method of Sub 1-B1 was carried out to obtain 7.73 g of product (yield: 77%).

9. Synthesis Method of Sub 1-B43

<Reaction Scheme 11>

(1) Synthesis Method of Sub 1-III-B40

Using the obtained Sub 1-II-B1 (53.61 g, 217.8 mmol) plus 2-bromodibenzo[b,d]thiophene (85.99 g, 326.8 mmol), Na$_2$SO$_4$ (30.94 g, 217.8 mmol), K$_2$CO$_3$ (30.11 g, 217.8 mmol), Cu (4.15 g, 65.4 mmol) and nitrobenzene, the same procedure as described in the synthesis method of Sub 1-III-B1 was carried out to obtain 66.25 g of product (yield: 71%).

(2) Synthesis Method of Sub 1-IV-B40

Using the obtained Sub 1-III-B40 (66.25 g, 154.7 mmol) plus Bis(pinacolato)diboron (43.2 g, 170.1 mmol), Pd(dppf)Cl$_2$ (3.79 g, 4.6 mmol), KOAc (45.54 g, 464 mmol) and DMF, the same procedure as described in the synthesis method of Sub 1-IV-B1 was carried out to obtain 58.82 g of product (yield: 80%).

-continued

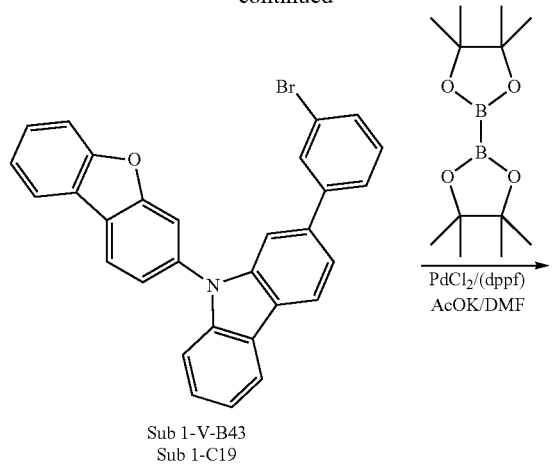

Sub 1-V-B43
Sub 1-C19

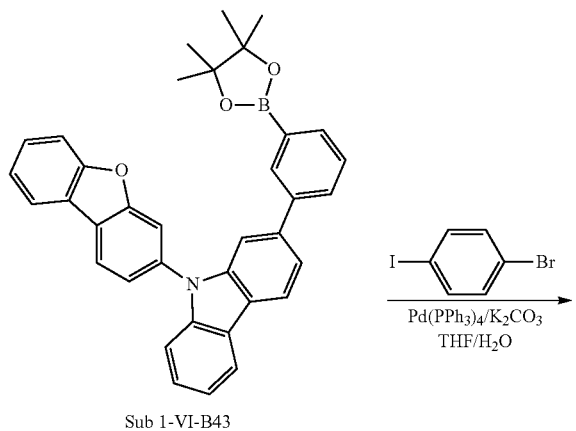

Sub 1-VI-B43

(1) Synthesis Method of Sub 1-III-B43

Using the obtained Sub 1-II-B1 (50.34 g, 204.6 mmol) plus 3-bromodibenzo[b,d]furan (75.81 g, 306.8 mmol), $Na_2SO_4$ (29.05 g, 204.6 mmol), $K_2CO_3$ (28.27 g, 204.6 mmol), Cu (3.9 g, 61.4 mmol) and nitrobenzene, the same procedure as described in the synthesis method of Sub 1-III-B1 was carried out to obtain 64.94 g of product (yield: 77%).

(2) Synthesis Method of Sub 1-IV-B43

Using the obtained Sub 1-III-B43 (64.94 g, 157.5 mmol) plus Bis(pinacolato)diboron (44 g, 173.3 mmol), Pd(dppf)$Cl_2$ (3.86 g, 4.7 mmol), KOAc (46.38 g, 472.5 mmol) and DMF, the same procedure as described in the synthesis method of Sub 1-IV-B1 was carried out to obtain 62.22 g of product (yield: 86%).

(3) Synthesis Method of Sub 1-V-B43(Sub 1-C19)

Using the obtained Sub 1-IV-B43 (62.22 g, 135.5 mmol) plus 1,3-dibromobenzene (47.93 g, 203.2 mmol), Pd(PPh$_3$)$_4$ (7.83 g, 6.8 mmol), $K_2CO_3$ (56.16 g, 406.4 mmol), THF and water, the same procedure as described in the synthesis method of Sub 1-V-B1 was carried out to obtain 46.97 g of product (yield: 71%).

(4) Synthesis Method of Sub 1-VI-B43

Using the obtained Sub 1-V-B43 (46.97 g, 96.2 mmol) plus Bis(pinacolato)diboron (26.87 g, 105.8 mmol), Pd(dppf)Cl$_2$ (2.36 g, 2.9 mmol), KOAc (28.32 g, 288.5 mmol) and DMF, the same procedure as described in the synthesis method of Sub 1-VI-B1 was carried out to obtain 40.68 g of product (yield: 79%).

(5) Synthesis Method of Sub 1-B43

Using the obtained Sub 1-VI-B43 (11.05 g, 20.6 mmol) plus 1-bromo-4-iodobenzene (8.76 g, 31 mmol), Pd(PPh$_3$)$_4$ (1.19 g, 1 mmol), $K_2CO_3$ (8.56 g, 61.9 mmol), THF and water, the same procedure as described in the synthesis method of Sub 1-B1 was carried out to obtain 9.2 g of product (yield: 79%).

10. Synthesis Method of Sub 1-B48

<Reaction Scheme 12>

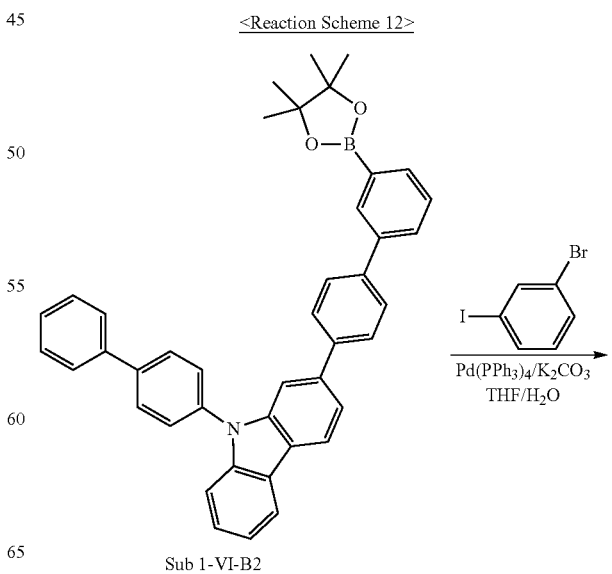

Sub 1-VI-B2

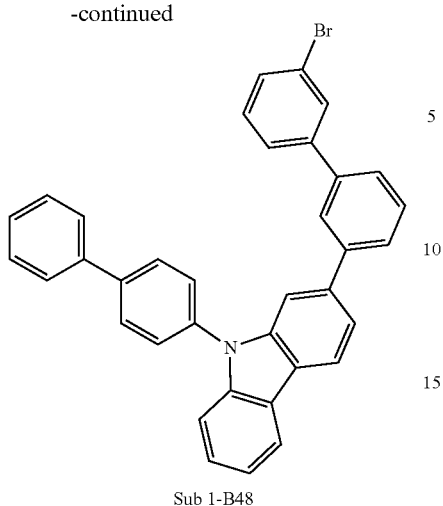

Sub 1-B48

Using the obtained Sub 1-VI-B2 (9.86 g, 18.9 mmol) plus 1-bromo-3-iodobenzene (8.02 g, 28.4 mmol), Pd(PPh₃)₄ (1.09 g, 0.9 mmol), K₂CO₃ (7.84 g, 56.7 mmol), THF and water, the same procedure as described in the synthesis method of Sub 1-B1 was carried out to obtain 7.91 g of product (yield: 76%).

11. Synthesis Method of Sub 1-B54

<Reaction Scheme 13>

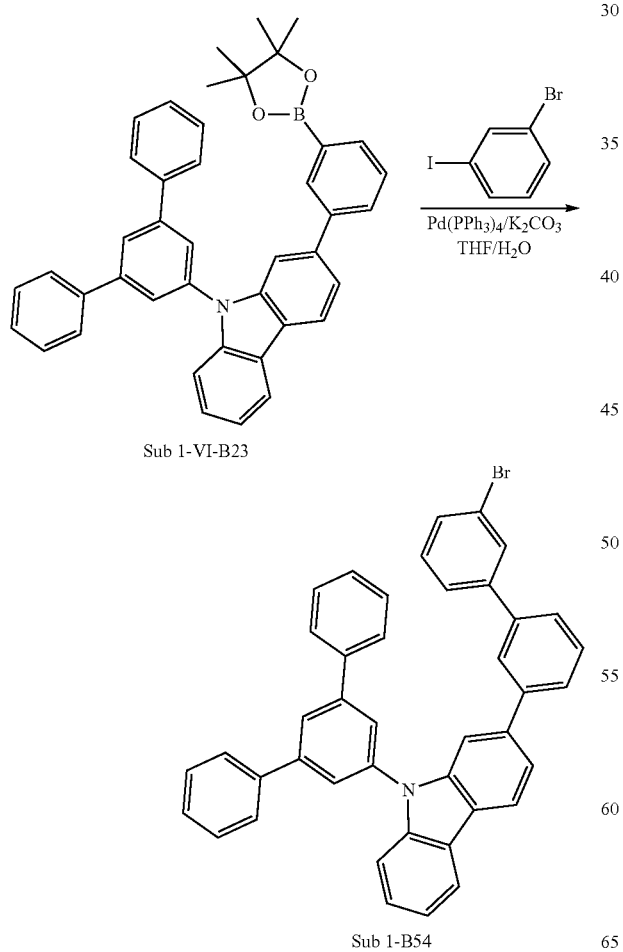

Sub 1-VI-B23

Sub 1-B54

Using the obtained Sub 1-VI-B23 (12.68 g, 21.2 mmol) plus 1-bromo-3-iodobenzene (9 g, 31.8 mmol), Pd(PPh₃)₄ (1.23 g, 1.1 mmol), K₂CO₃ (8.8 g, 63.7 mmol), THF and water, the same procedure as described in the synthesis method of Sub 1-B1 was carried out to obtain 8.24 g of product (yield: 62%).

12. Synthesis Method of Sub 1-B58

<Reaction Scheme 14>

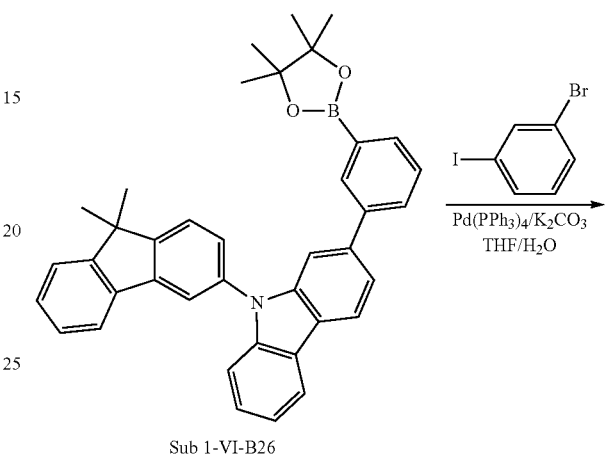

Sub 1-VI-B26

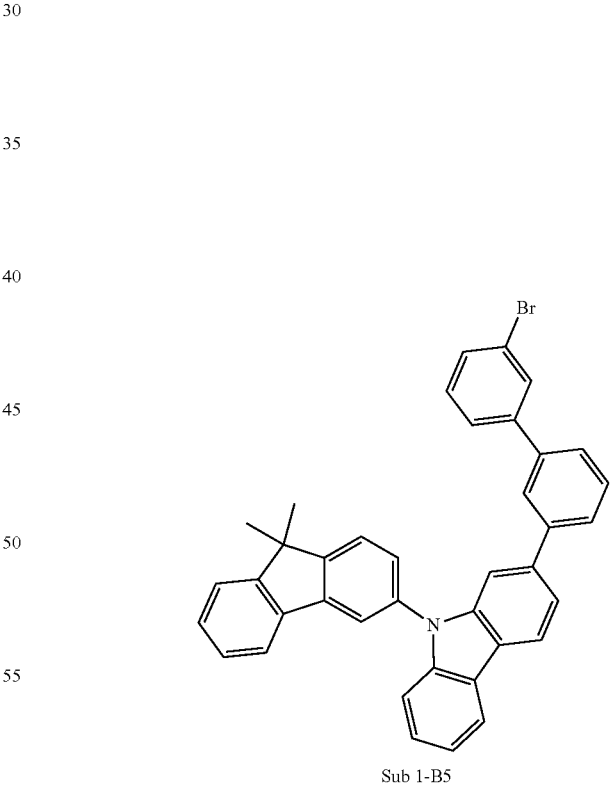

Sub 1-B5

Using the obtained Sub 1-VI-B26 (12.17 g, 21.7 mmol) plus 1-bromo-3-iodobenzene (9.2 g, 32.5 mmol), Pd(PPh₃)₄ (1.25 g, 1.1 mmol), K₂CO₃ (8.99 g, 65 mmol), THF and water, the same procedure as described in the synthesis method of Sub 1-B1 was carried out to obtain 9.34 g of product (yield: 73%).

13. Synthesis Method of Sub 1-B61

<Reaction Scheme 15>

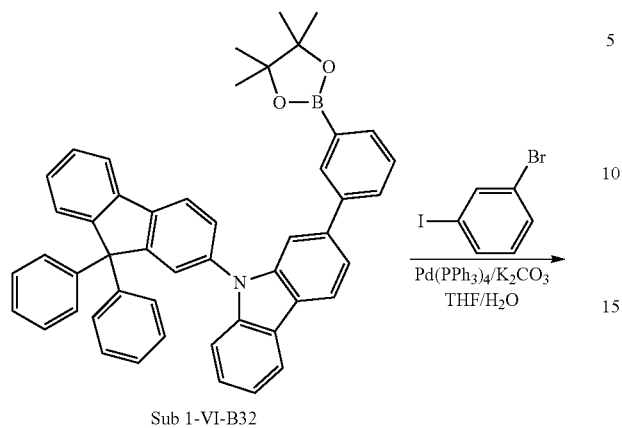

Sub 1-VI-B32 → Sub 1-B61

Using the obtained Sub 1-VI-B32 (16.92 g, 24.7 mmol) plus 1-bromo-3-iodobenzene (10.47 g, 37 mmol), Pd(PPh₃)₄ (1.43 g, 1.2 mmol), K₂CO₃ (10.23 g, 74 mmol), THF and water, the same procedure as described in the synthesis method of Sub 1-B1 was carried out to obtain 10.05 g of product (yield: 57%).

14. Synthesis Method of Sub 1-B62

<Reaction Scheme 16>

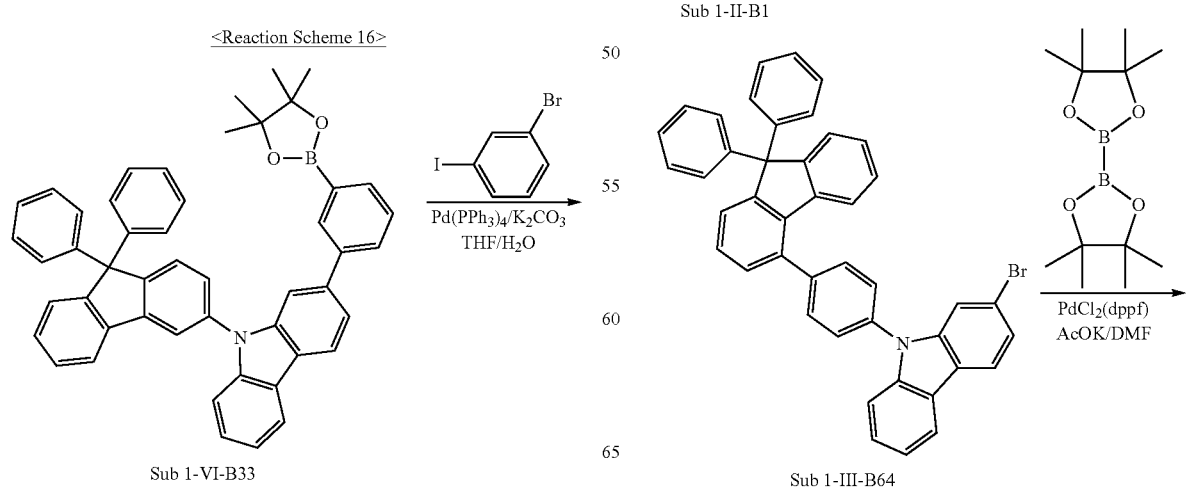

Sub 1-VI-B33 → Sub 1-B62

Using the obtained Sub 1-VI-B33 (16.64 g, 24.3 mmol) plus 1-bromo-3-iodobenzene (10.3 g, 36.4 mmol), Pd(PPh₃)₄ (1.4 g, 1.2 mmol), K₂CO₃ (10.06 g, 72.8 mmol), THF and water, the same procedure as described in the synthesis method of Sub 1-B1 was carried out to obtain 10.41 g of product (yield: 60%).

15. Synthesis Method of Sub 1-B64

<Reaction Scheme 17>

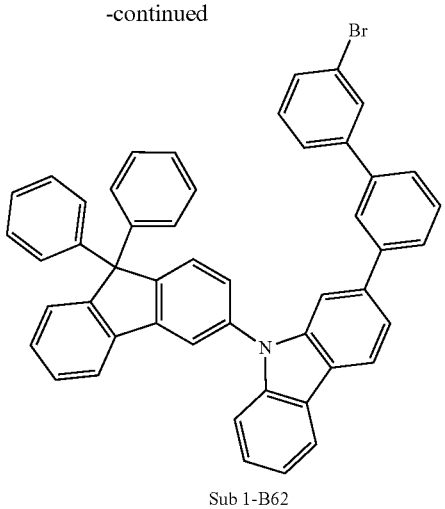

Sub 1-II-B1

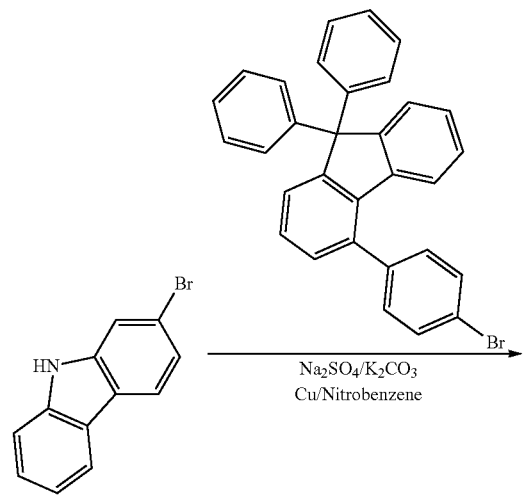

Sub 1-III-B64

-continued

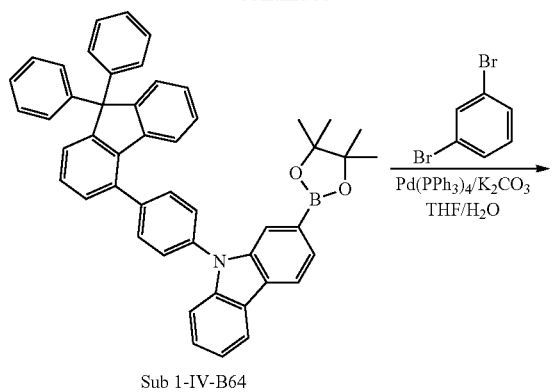

Sub 1-IV-B64

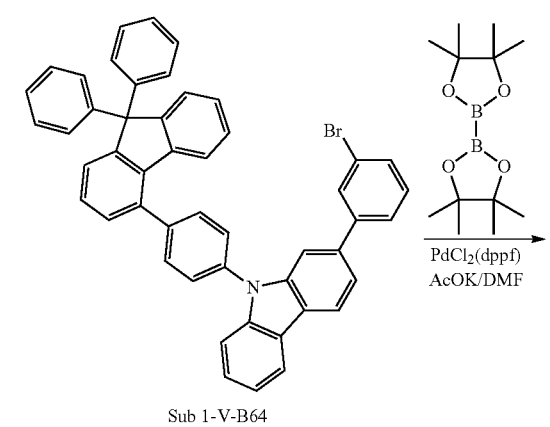

Sub 1-V-B64

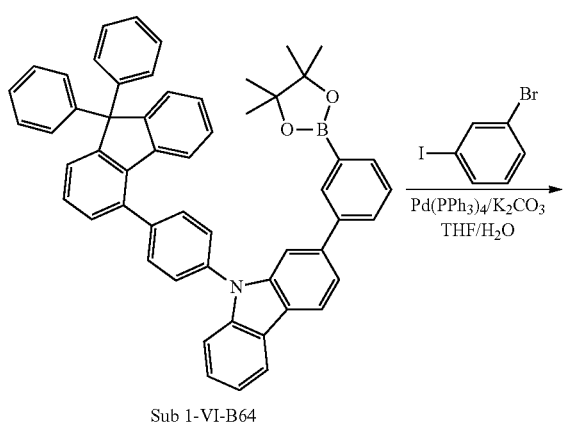

Sub 1-VI-B64

-continued

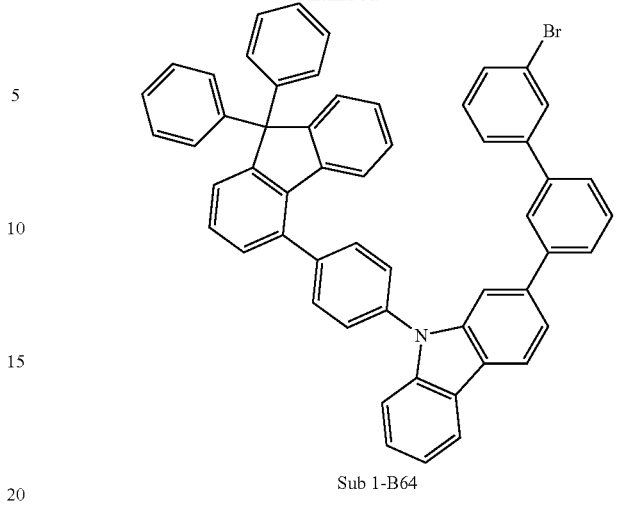

Sub 1-B64

(1) Synthesis Method of Sub 1-III-B64

Using the obtained Sub 1-II-B1 (30.46 g, 123.8 mmol) plus 4-(4-bromophenyl)-9,9-diphenyl-9H-fluorene (87.89 g, 185.7 mmol), $Na_2SO_4$ (17.58 g, 123.8 mmol), $K_2CO_3$ (17.11 g, 123.8 mmol), Cu (2.36 g, 37.1 mmol) and nitrobenzene, the same procedure as described in the synthesis method of Sub 1-III-B1 was carried out to obtain 41.89 g of product (yield: 53%).

(2) Synthesis Method of Sub 1-IV-B64

Using the obtained Sub 1-III-B64 (41.89 g, 65.6 mmol) plus Bis(pinacolato)diboron (18.32 g, 72.2 mmol), Pd(dppf)Cl$_2$ (1.61 g, 2 mmol), KOAc (19.31 g, 196.8 mmol) and DMF, the same procedure as described in the synthesis method of Sub 1-IV-B1 was carried out to obtain 36.88 g of product (yield: 82%).

(3) Synthesis Method of Sub 1-V-B64

Using the obtained Sub 1-IV-B64 (36.88 g, 53.8 mmol) plus 1,3-dibromobenzene (19.03 g, 80.7 mmol), Pd(PPh$_3$)$_4$ (3.11 g, 2.7 mmol), $K_2CO_3$ (22.3 g, 161.4 mmol), THF and water, the same procedure as described in the synthesis method of Sub 1-V-B1 was carried out to obtain 24.99 g of product (yield: 65%).

(4) Synthesis Method of Sub 1-VI-B64

Using the obtained Sub 1-V-B64 (24.99 g, 35 mmol) plus Bis(pinacolato)diboron (9.77 g, 38.5 mmol), Pd(dppf)Cl$_2$ (0.86 g, 1 mmol), KOAc (10.29 g, 104.9 mmol) and DMF, the same procedure as described in the synthesis method of Sub 1-VI-B1 was carried out to obtain 21.31 g of product (yield: 80%).

(5) Synthesis Method of Sub 1-B64

Using the obtained Sub 1-VI-B64 (19.88 g, 26.1 mmol) plus 1-bromo-4-iodobenzene (11.07 g, 39.1 mmol), Pd(PPh$_3$)$_4$ (1.51 g, 1.3 mmol), $K_2CO_3$ (10.82 g, 78.3 mmol), THF and water, the same procedure as described in the synthesis method of Sub 1-B1 was carried out to obtain 10.73 g of product (yield: 52%).

16. Synthesis Method of Sub 1-B69

<Reaction Scheme 18>

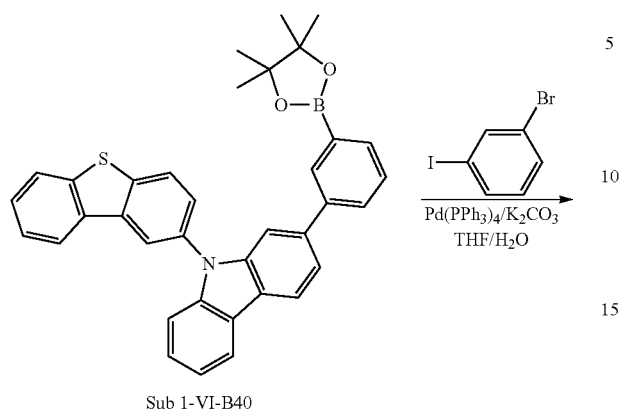

Sub 1-VI-B40

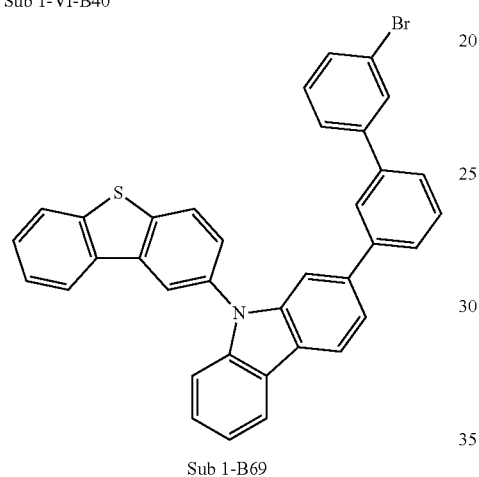

Sub 1-B69

Using the obtained Sub 1-VI-B40 (14.29 g, 25.9 mmol) plus 1-bromo-3-iodobenzene (11 g, 38.9 mmol), Pd(PPh₃)₄ (1.5 g, 1.3 mmol), K₂CO₃ (10.74 g, 77.7 mmol), THF and water, the same procedure as described in the synthesis method of Sub 1-B1 was carried out to obtain 11.88 g of product (yield: 79%).

17. Synthesis Method of Sub 1-B72

<Reaction Scheme 19>

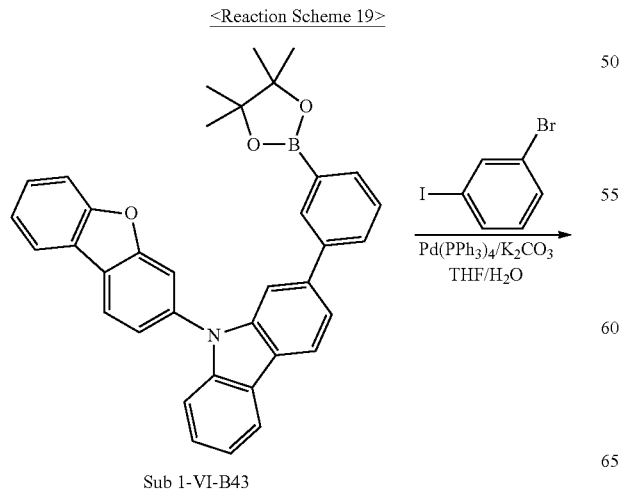

Sub 1-VI-B43

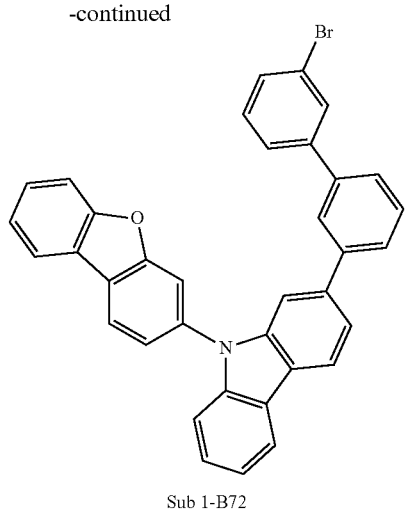

Sub 1-B72

Using the obtained Sub 1-VI-B43 (14.17 g, 26.5 mmol) plus 1-bromo-3-iodobenzene (11.23 g, 39.7 mmol), Pd(PPh₃)₄ (1.53 g, 1.3 mmol), K₂CO₃ (10.97 g, 79.4 mmol), THF and water, the same procedure as described in the synthesis method of Sub 1-B1 was carried out to obtain 10.61 g of product (yield: 71%).

18. Synthesis Method of Sub 1-B76

<Reaction Scheme 20>

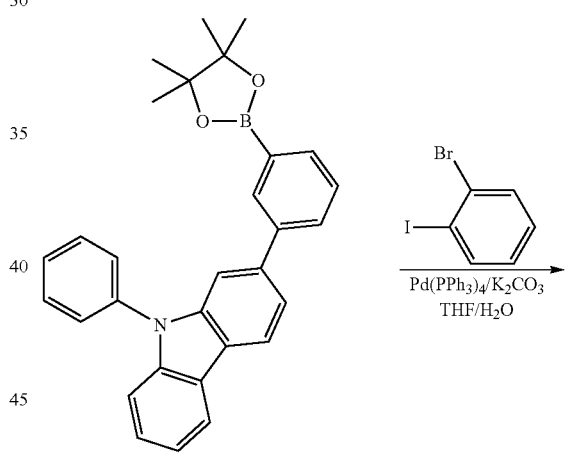

Sub 1-VI-B1

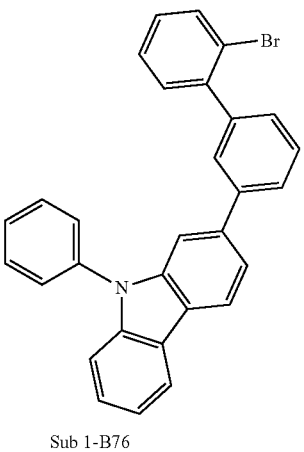

Sub 1-B76

Using the obtained Sub 1-VI-B1 (11.32 g, 25.4 mmol) plus 1-bromo-2-iodobenzene (10.79 g, 38.1 mmol), Pd(PPh₃)₄(1.47 g, 1.3 mmol), K₂CO₃ (10.54 g, 76.3 mmol), THF and water, the same procedure as described in the synthesis method of Sub 1-B1 was carried out to obtain 7.11 g of product (yield: 59%).

19. Synthesis Method of Sub 1-B84

<Reaction Scheme 21>

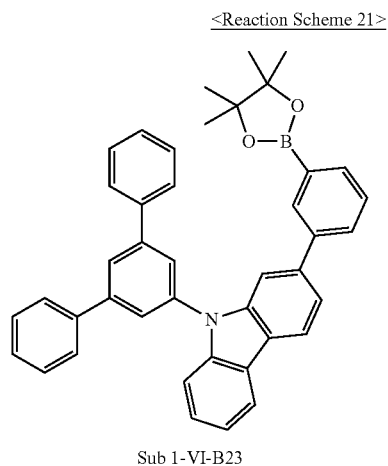

Sub 1-VI-B23

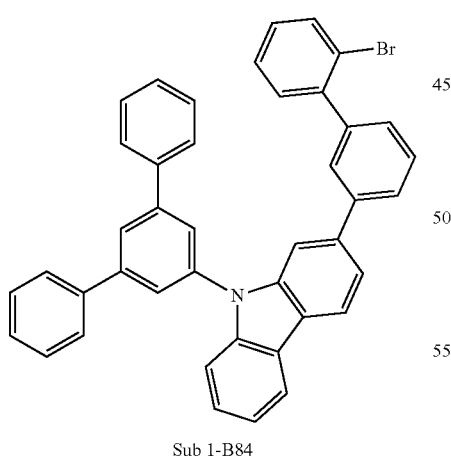

Sub 1-B84

Using the obtained Sub 1-VI-B23 (16.14 g, 27 mmol) plus 1-bromo-2-iodobenzene (11.46 g, 40.5 mmol), Pd(PPh₃)₄ (1.56 g, 1.4 mmol), K₂CO₃ (11.2 g, 81 mmol), THF and water, the same procedure as described in the synthesis method of Sub 1-B1 was carried out to obtain 8.97 g of product (yield: 53%).

20. Synthesis Method of Sub 1-B87

<Reaction Scheme 22>

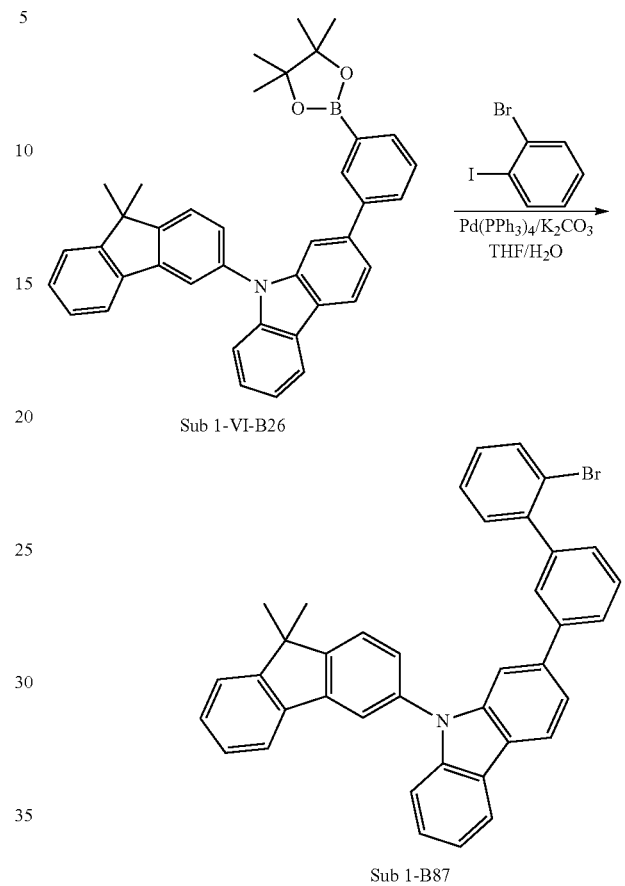

Sub 1-VI-B26

Sub 1-B87

Using the obtained Sub 1-VI-B26 (12.67 g, 22.6 mmol) plus 1-bromo-2-iodobenzene (9.57 g, 33.8 mmol), Pd(PPh₃)₄ (1.3 g, 1.1 mmol), K₂CO₃ (9.36 g, 67.7 mmol), THF and water, the same procedure as described in the synthesis method of Sub 1-B1 was carried out to obtain 8.13 g of product (yield: 61%).

21. Synthesis Method of Sub 1-B90

<Reaction Scheme 23>

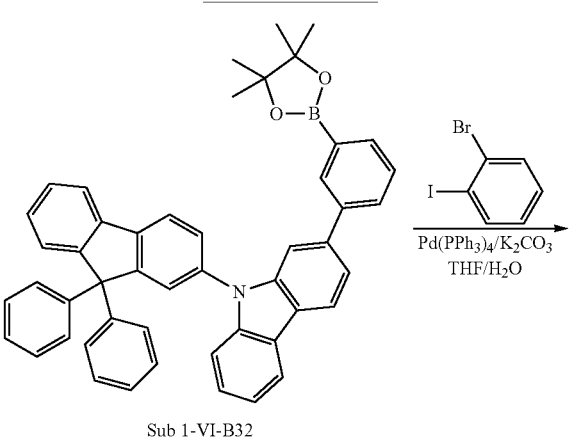

Sub 1-VI-B32

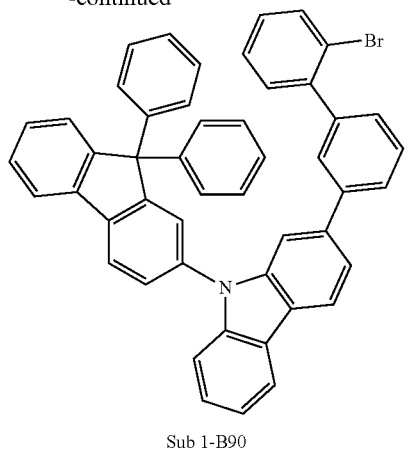

Sub 1-B90

Using the obtained Sub 1-VI-B32 (17.39 g, 25.4 mmol) plus 1-bromo-2-iodobenzene (10.76 g, 38 mmol), Pd(PPh₃)₄ (1.47 g, 1.3 mmol), K₂CO₃ (10.52 g, 76.1 mmol), THF and water, the same procedure as described in the synthesis method of Sub 1-B1 was carried out to obtain 10.15 g of product (yield: 56%).

22. Synthesis Method of Sub 1-B91

Using the obtained Sub 1-VI-B33 (15.63 g, 22.8 mmol) plus 1-bromo-2-iodobenzene (9.67 g, 34.2 mmol), Pd(PPh₃)₄ (1.32 g, 1.1 mmol), K₂CO₃ (9.45 g, 68.4 mmol), THF and water, the same procedure as described in the synthesis method of Sub 1-B1 was carried out to obtain 9.78 g of product (yield: 60%).

23. Synthesis Method of Sub 1-B99

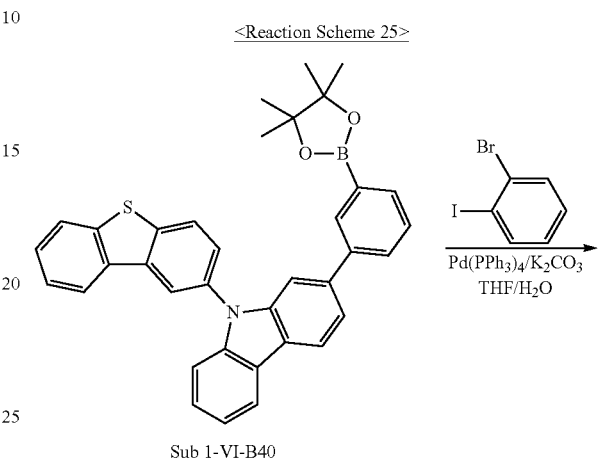

<Reaction Scheme 25>

Sub 1-VI-B40

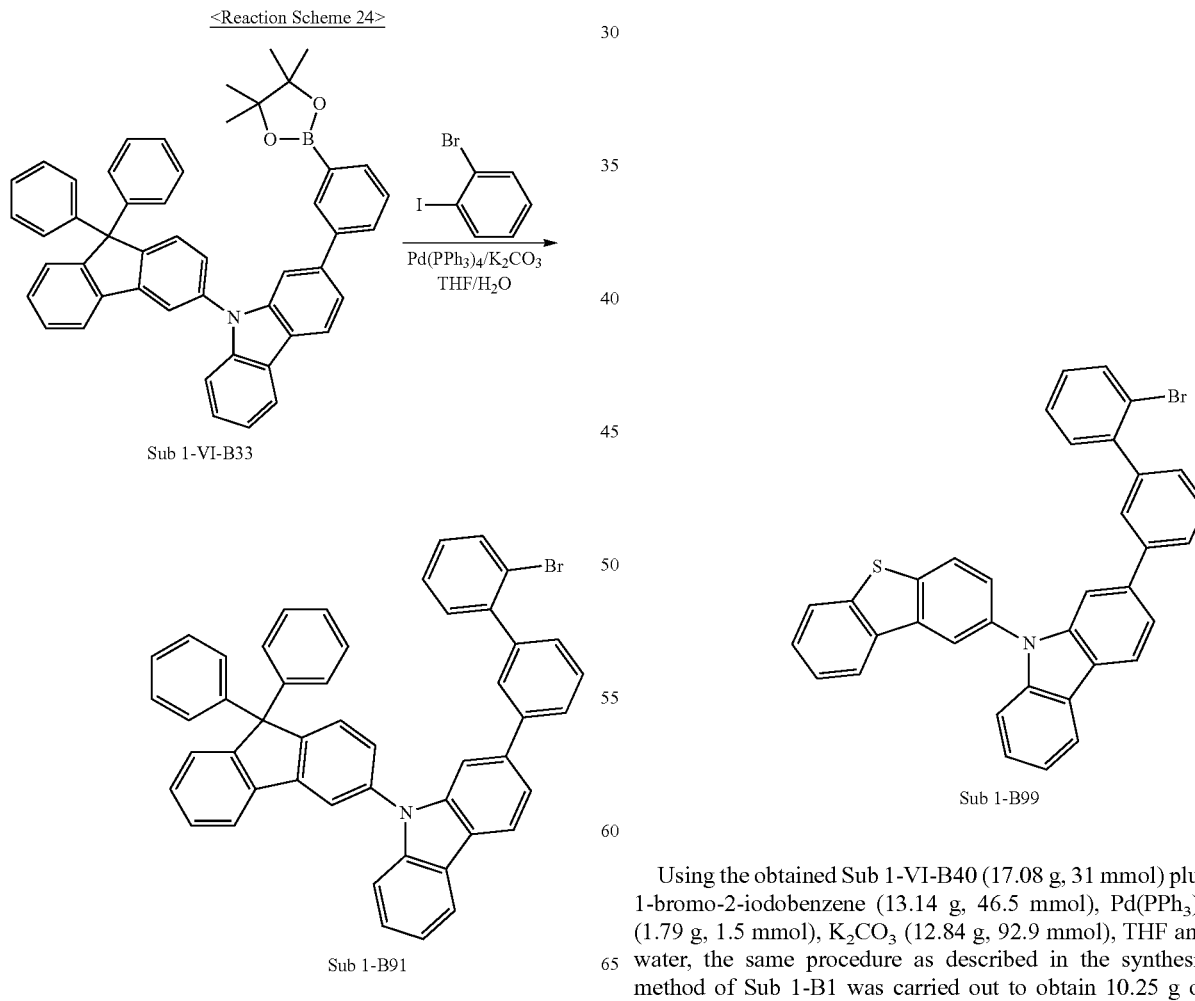

<Reaction Scheme 24>

Sub 1-VI-B33

Sub 1-B91

Sub 1-B99

Using the obtained Sub 1-VI-B40 (17.08 g, 31 mmol) plus 1-bromo-2-iodobenzene (13.14 g, 46.5 mmol), Pd(PPh₃)₄ (1.79 g, 1.5 mmol), K₂CO₃ (12.84 g, 92.9 mmol), THF and water, the same procedure as described in the synthesis method of Sub 1-B1 was carried out to obtain 10.25 g of product (yield: 57%).

24. Synthesis Method of Sub 1-B102

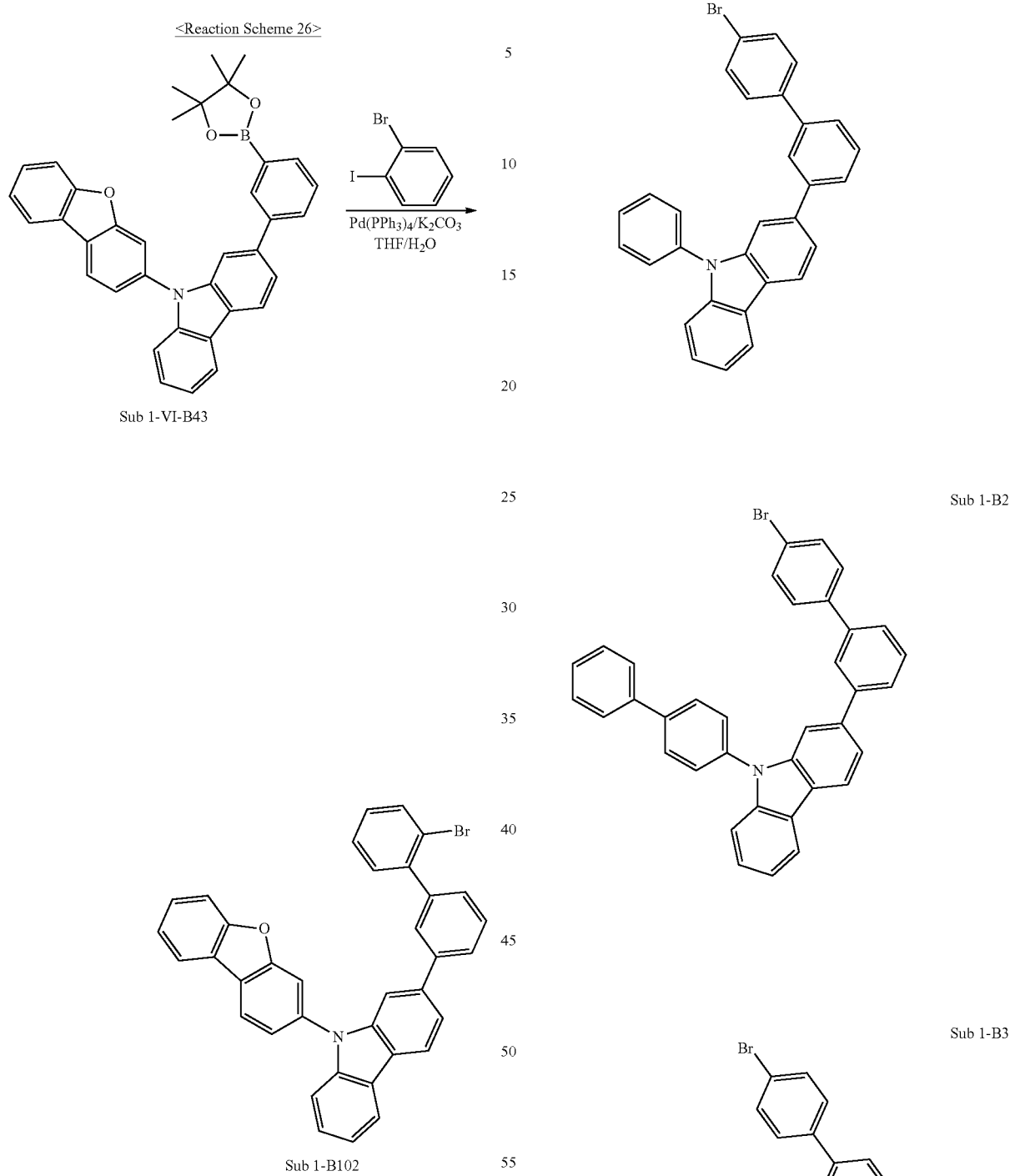

Using the obtained Sub 1-VI-B43 (13.96 g, 26.1 mmol) plus 1-bromo-2-iodobenzene (11.06 g, 39.1 mmol), Pd(PPh$_3$)$_4$ (1.51 g, 1.3 mmol), K$_2$CO$_3$ (10.81 g, 78.2 mmol), THF and water, the same procedure as described in the synthesis method of Sub 1-B1 was carried out to obtain 9.12 g of product (yield: 62%).

Meanwhile, examples of Sub 1 compounds include, but are not limited to, the following compounds, and Field Desorption Mass Spectrometry (FD-MS) data of the Sub 1 compounds are given in Table 1 below.

Sub 1-B4
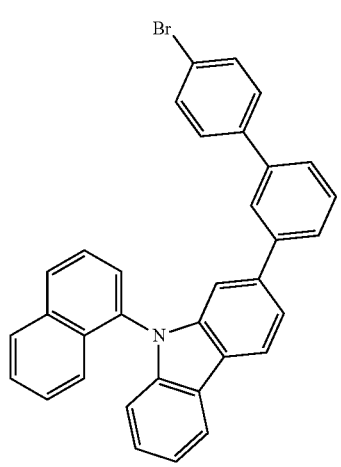
Sub 1-B5
Sub 1-B6
Sub 1-B7
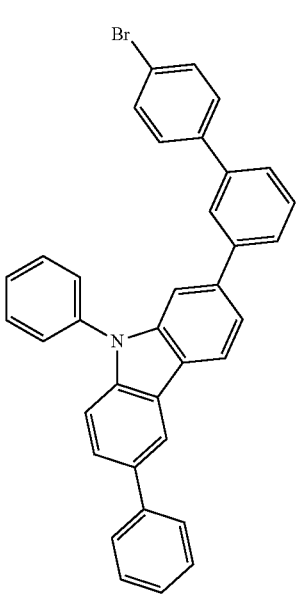
Sub 1-B8
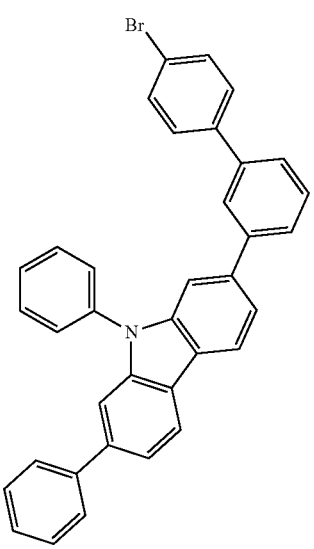
Sub 1-B9
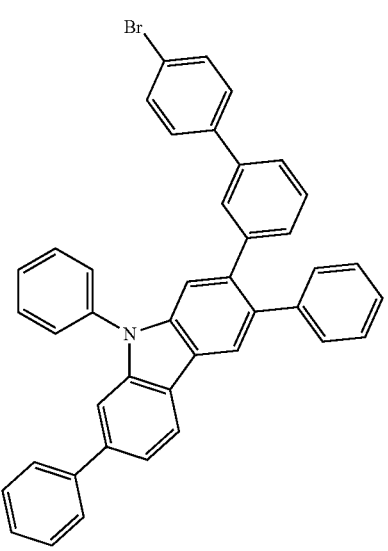

-continued
Sub 1-B10
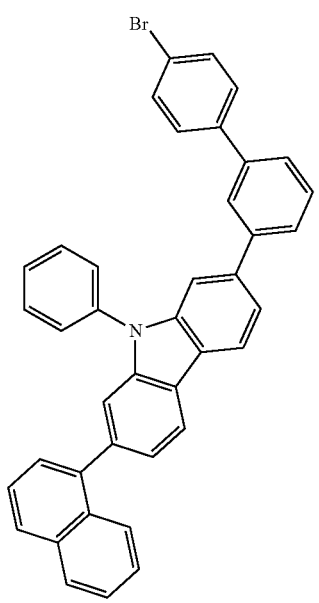
Sub 1-B11
Sub 1-B14
-continued
Sub 1-B18
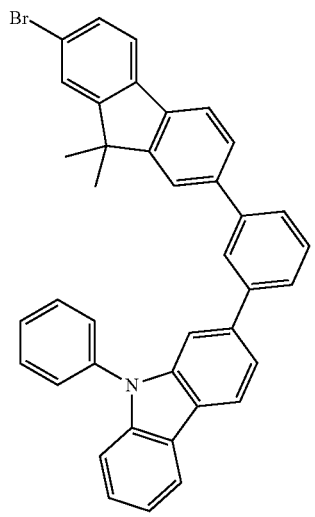
Sub 1-B19
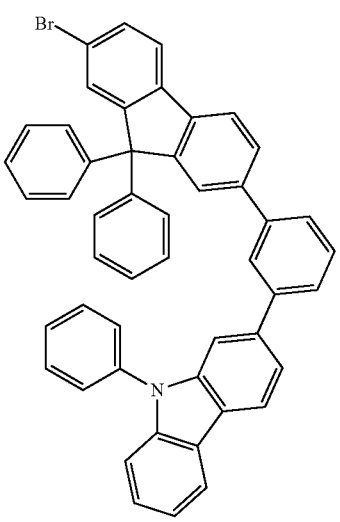
Sub 1-B20
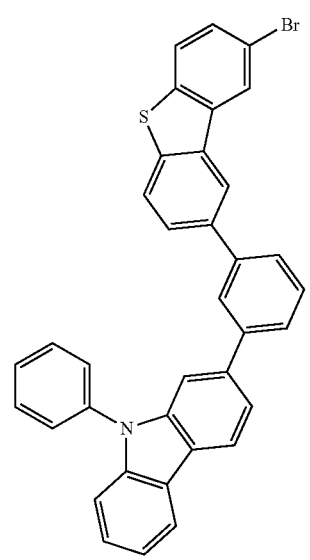

Sub 1-B21
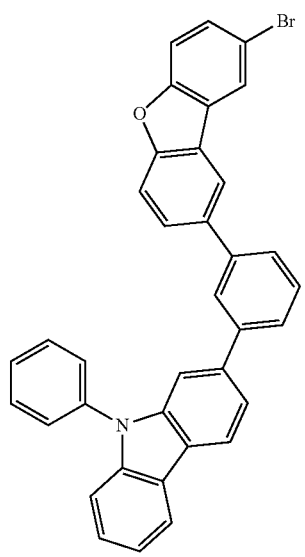
Sub 1-B22
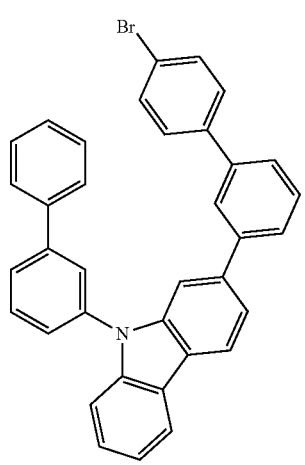
Sub 1-B23
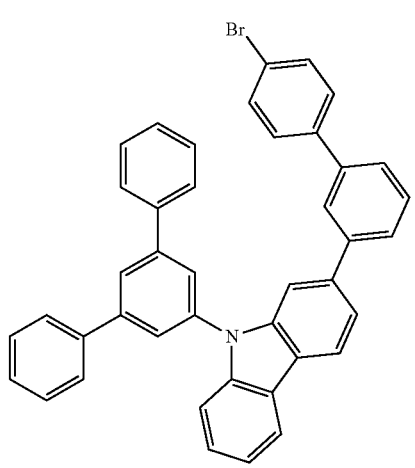
Sub 1-B24
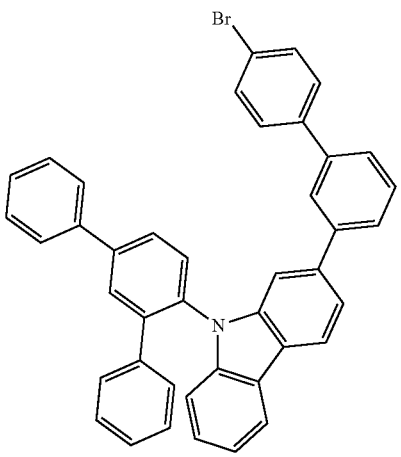
Sub 1-B25
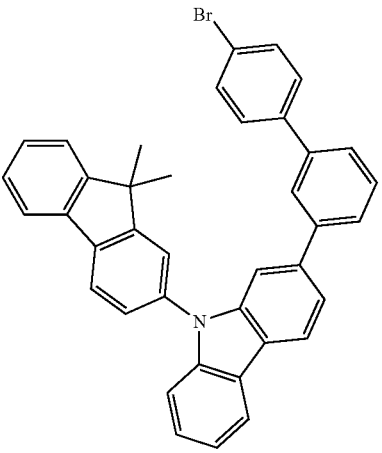
Sub 1-B26
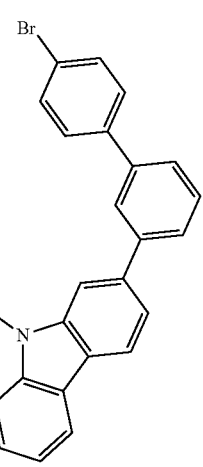

Sub 1-B27
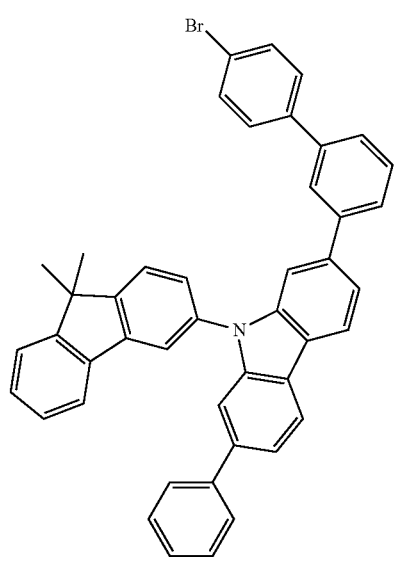
Sub 1-B28
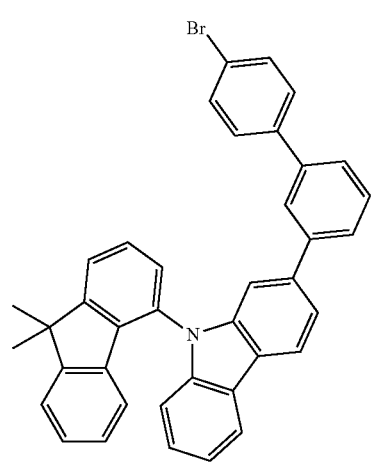
Sub 1-B29
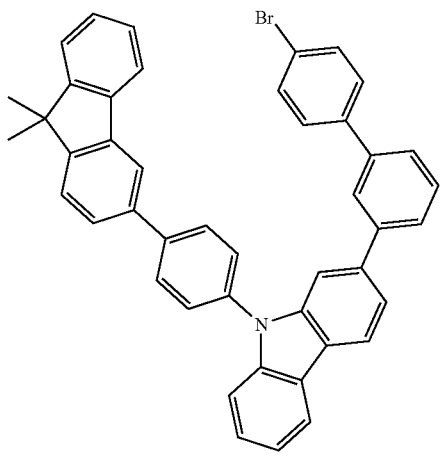
Sub 1-B30
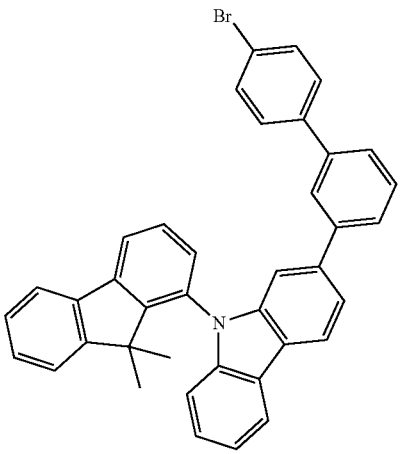
Sub 1-B31
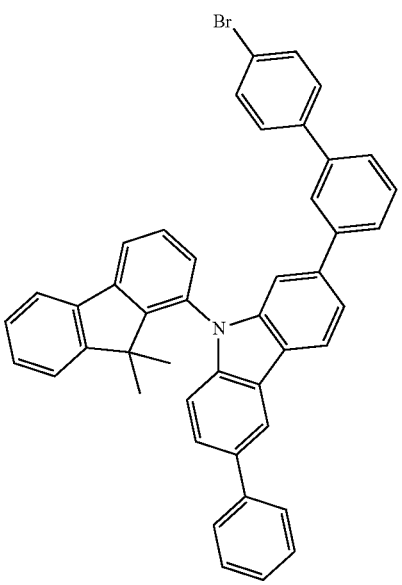
Sub 1-B32
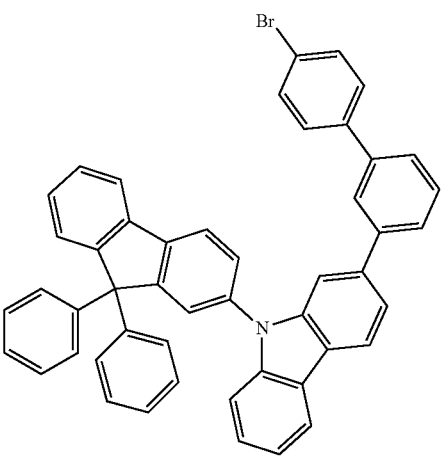

Sub 1-B33
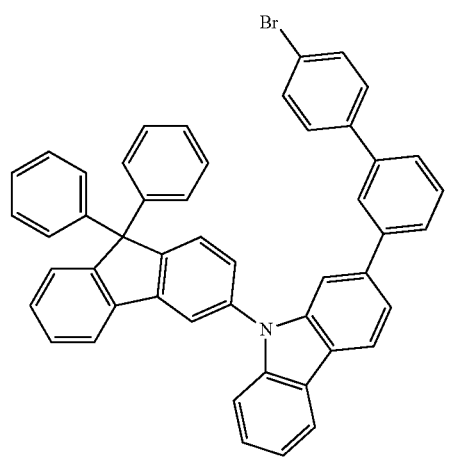
Sub 1-B36
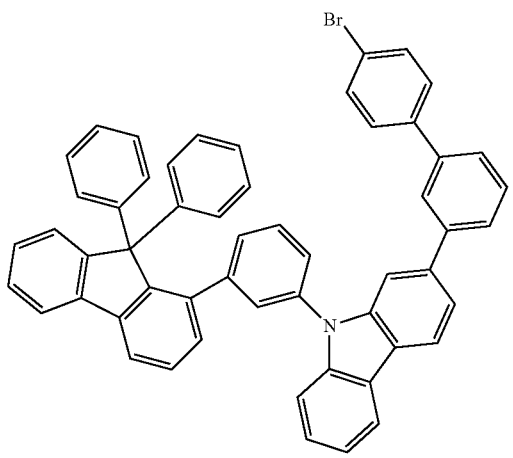
Sub 1-B34
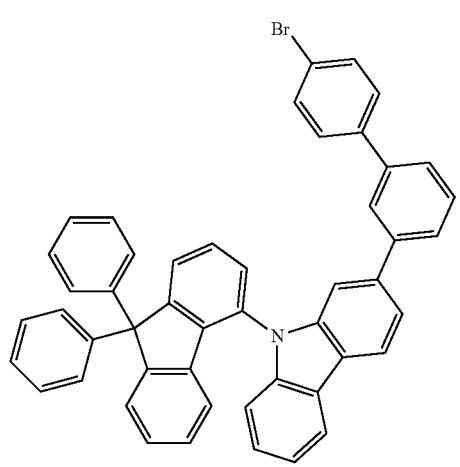
Sub 1-B37
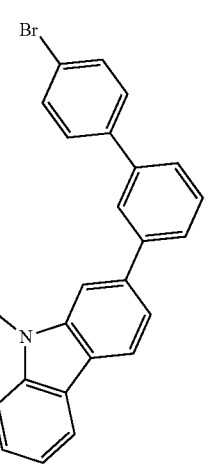
Sub 1-B35
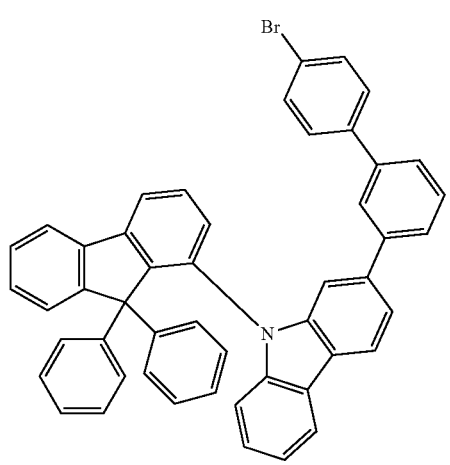
Sub 1-B38
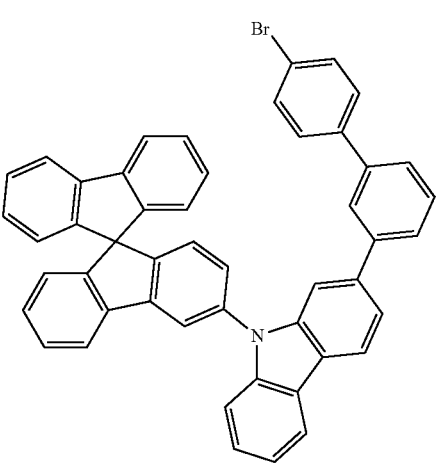

Sub 1-B39
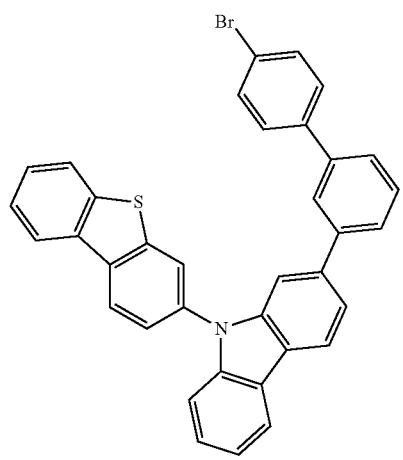
Sub 1-B42
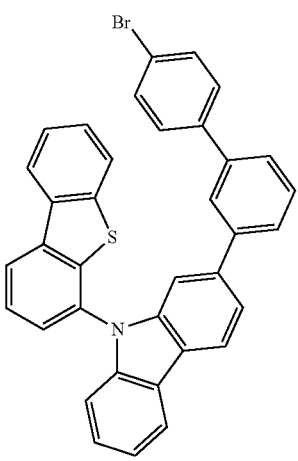
Sub 1-B40
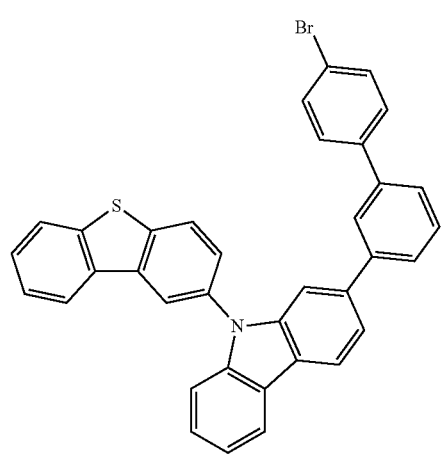
Sub 1-B43
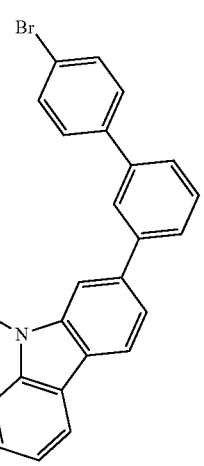
Sub 1-B41
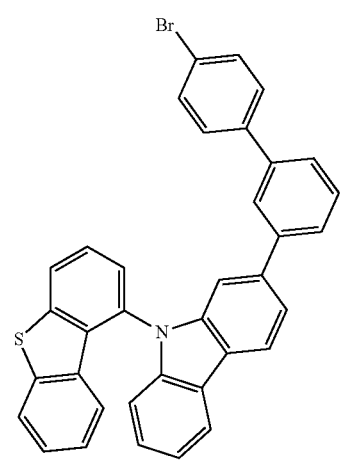
Sub 1-B44
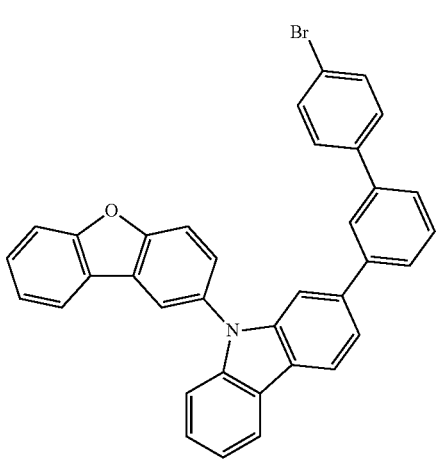

-continued
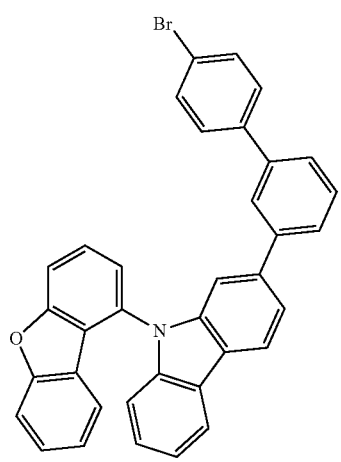 Sub 1-B45
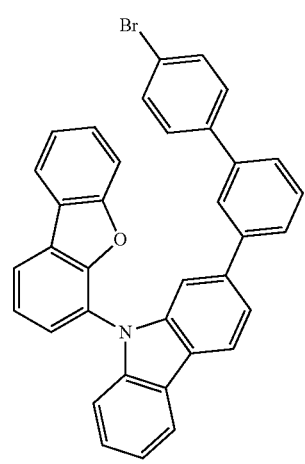 Sub 1-B46
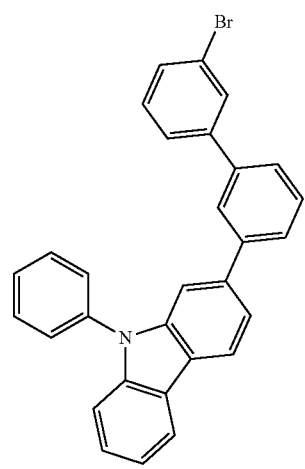 Sub 1-B47
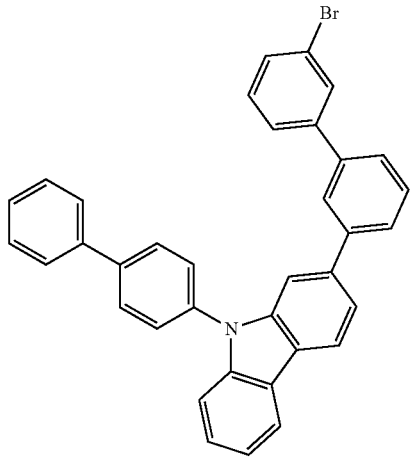 Sub 1-B48
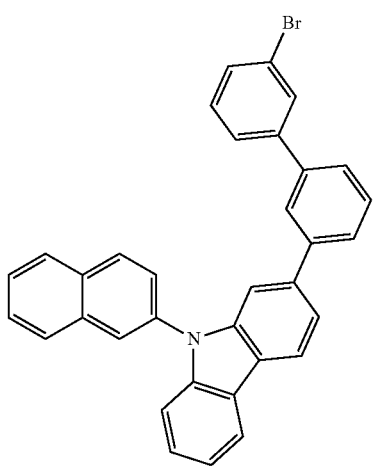 Sub 1-B49
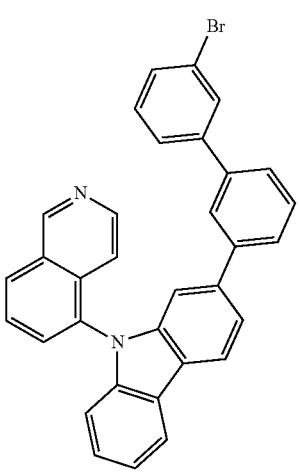 Sub 1-B50

Sub 1-B51
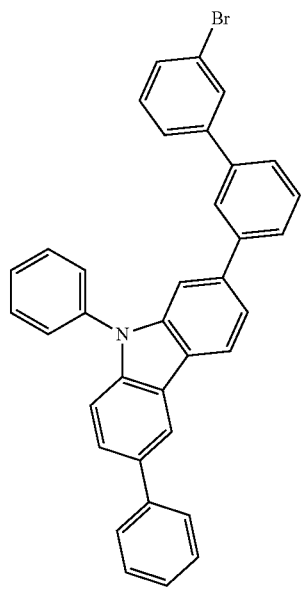
Sub 1-B52
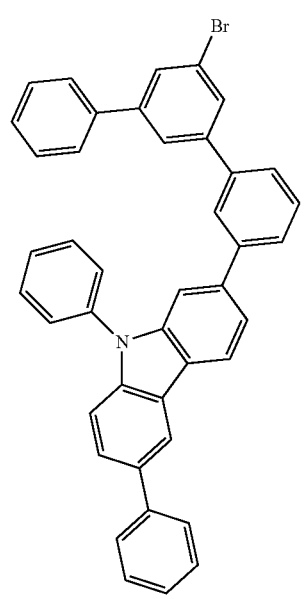
Sub 1-B53
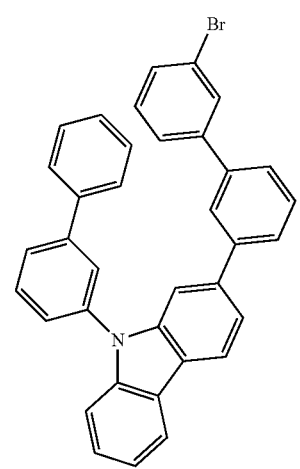
Sub 1-B54
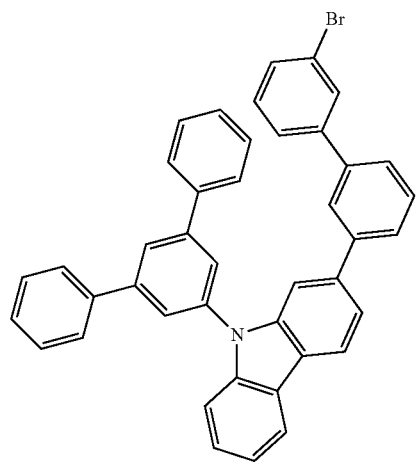
Sub 1-B55
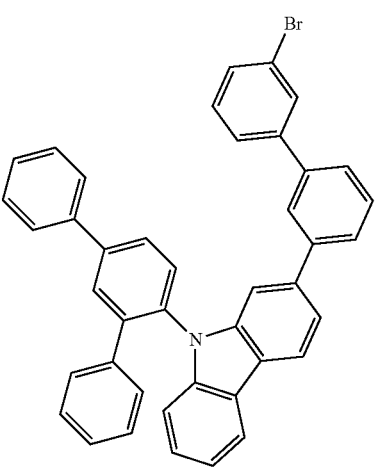
Sub 1-B56
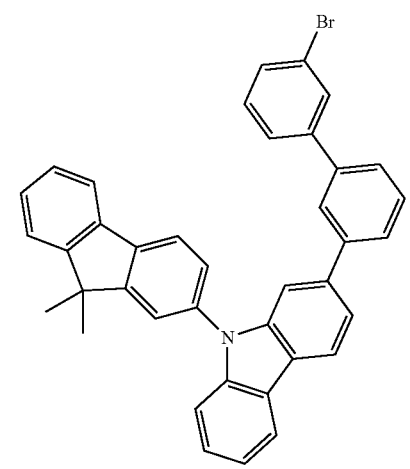

Sub 1-B57
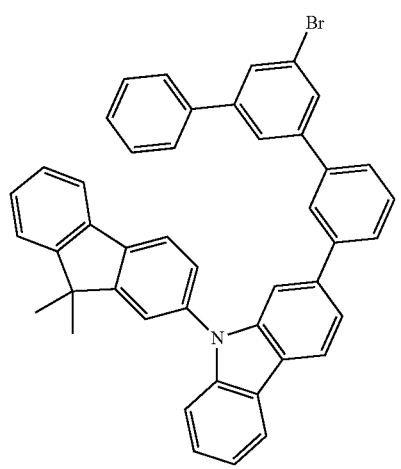
Sub 1-B60
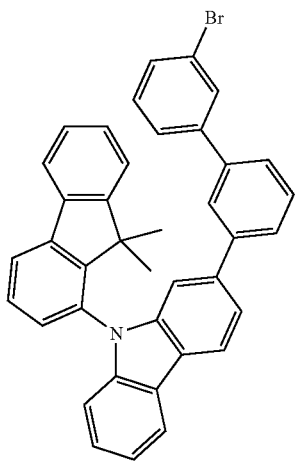
Sub 1-B58
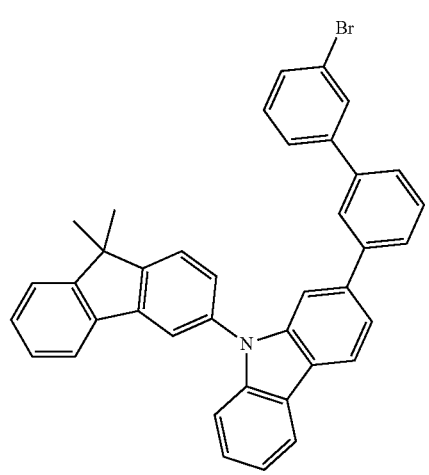
Sub 1-B61
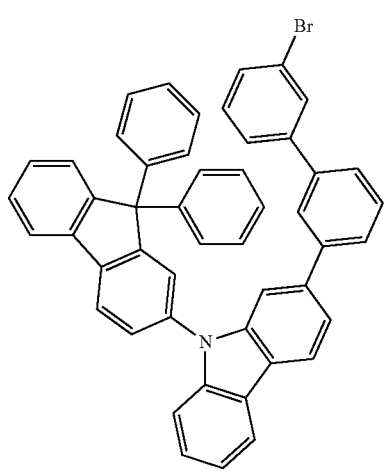
Sub 1-B59
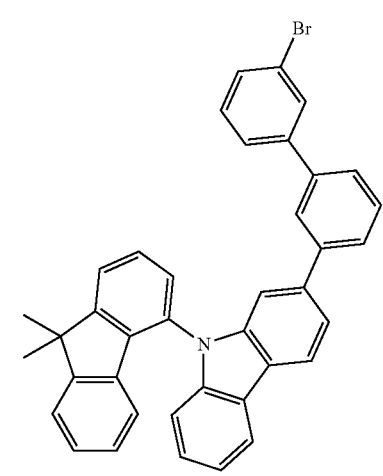
Sub 1-B62
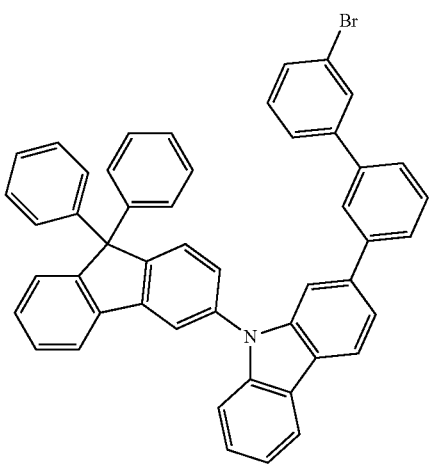

Sub 1-B63
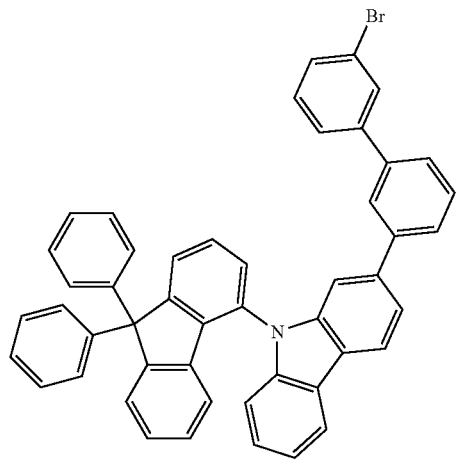
Sub 1-B64
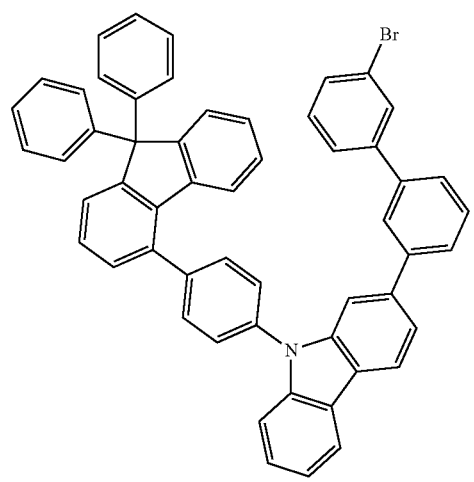
Sub 1-B65
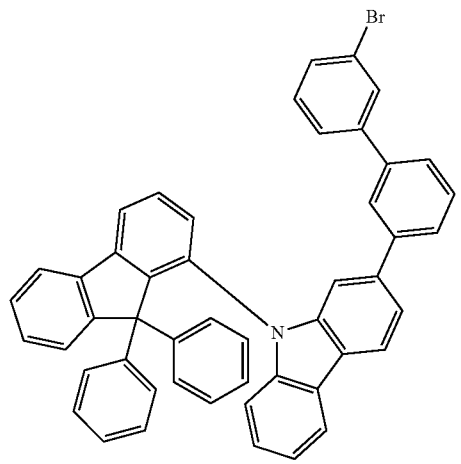
Sub 1-B66
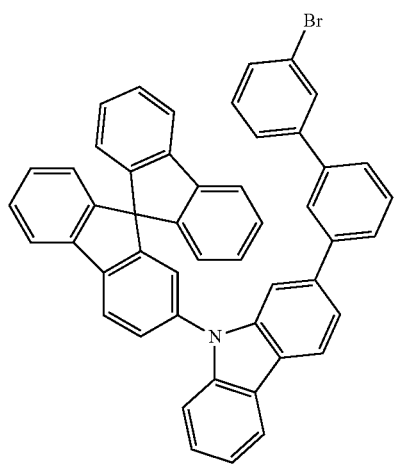
Sub 1-B67
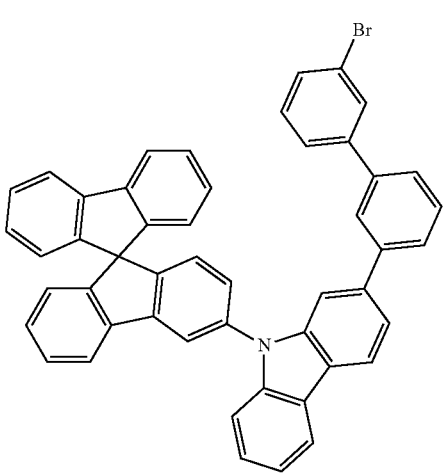
Sub 1-B68
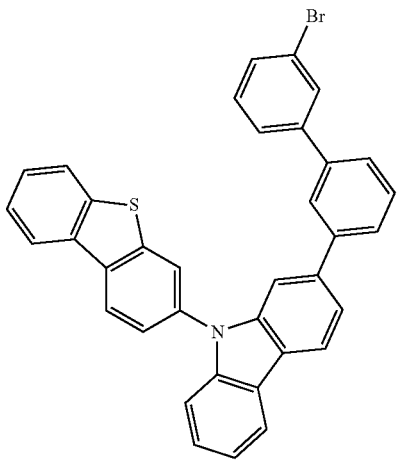

Sub 1-B69
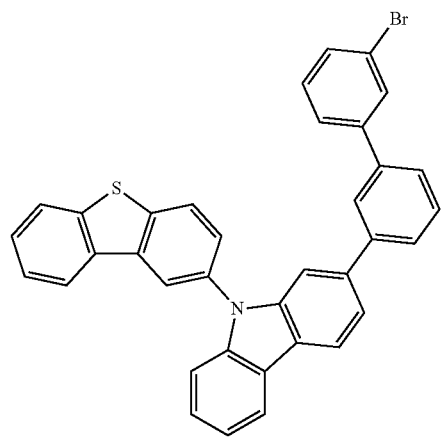
Sub 1-B72
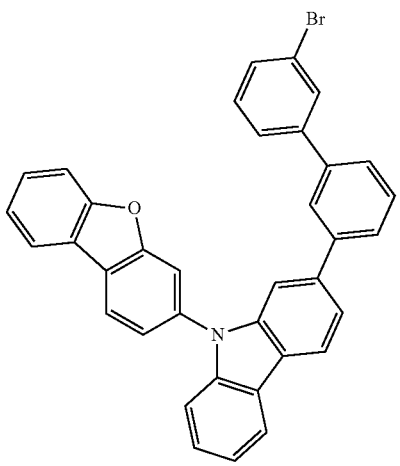
Sub 1-B70
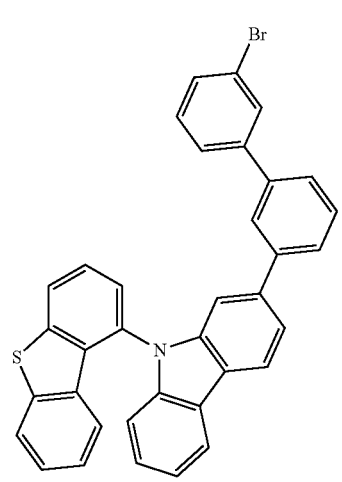
Sub 1-B73
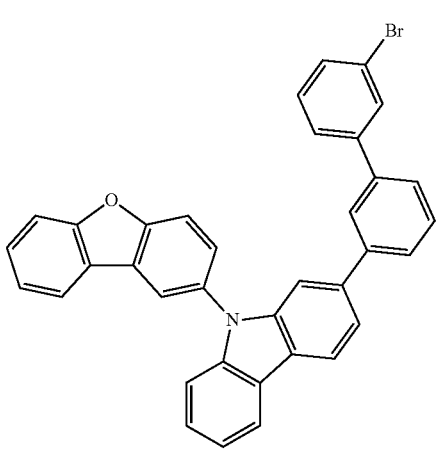
Sub 1-B71
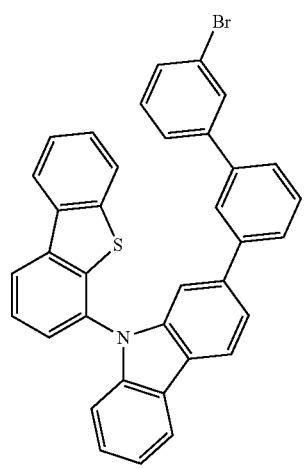
Sub 1-B74
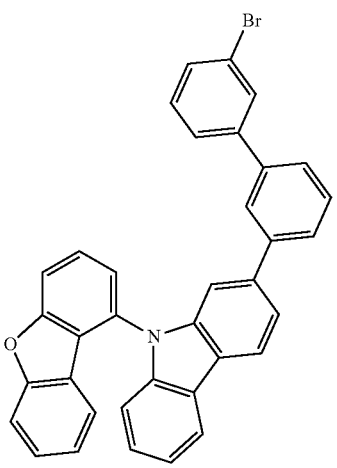

Sub 1-B75
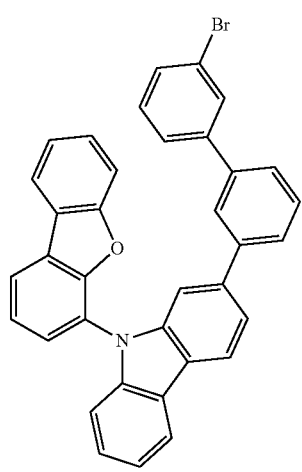
Sub 1-B76
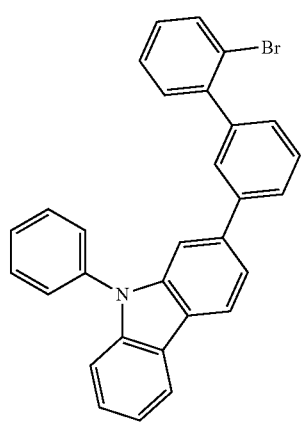
Sub 1-B77
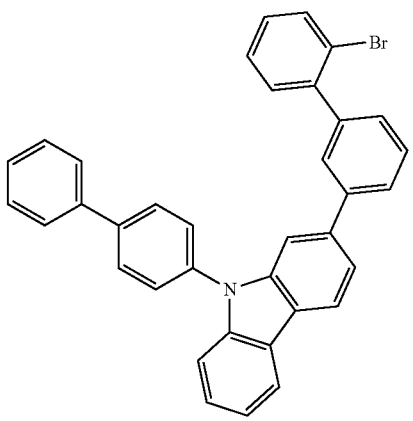
Sub 1-B78
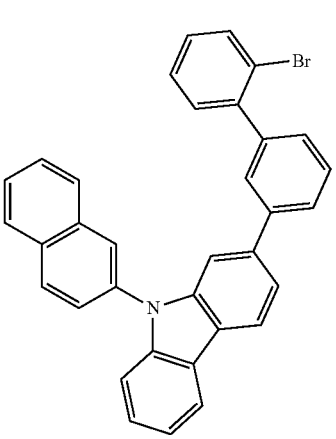
Sub 1-B79
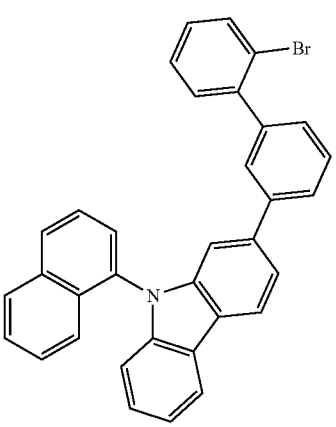
Sub 1-B80
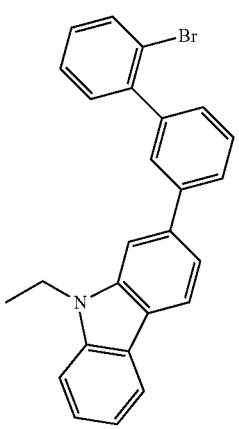

Sub 1-B81
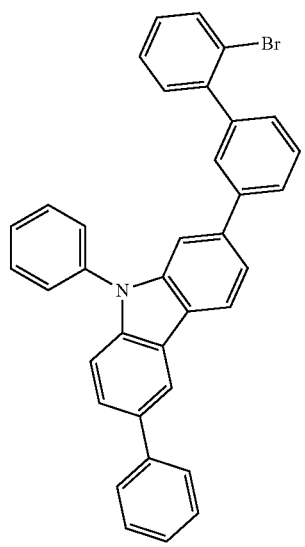
Sub 1-B82
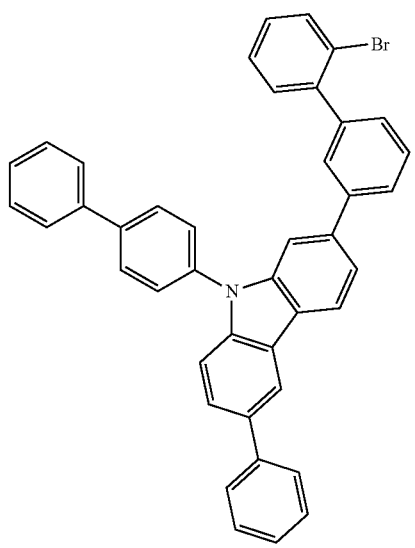
Sub 1-B83
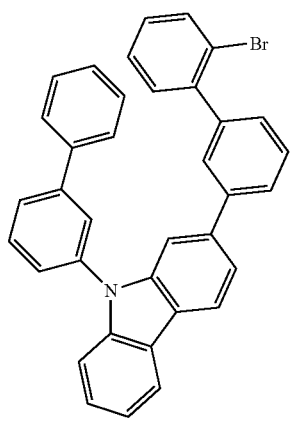
Sub 1-B84
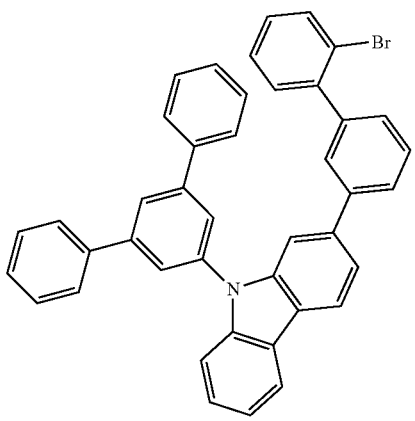
Sub 1-B85
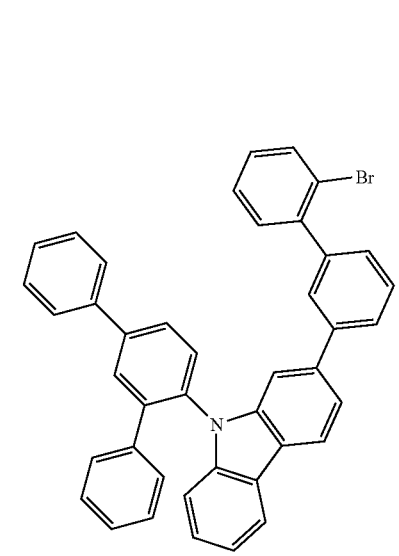
Sub 1-B86
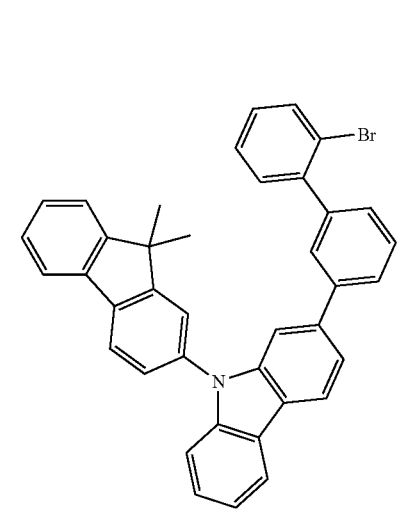

-continued
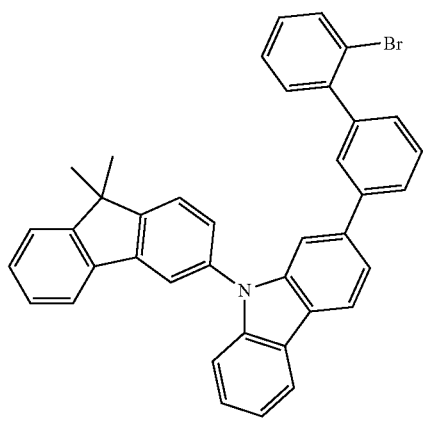
Sub 1-B87
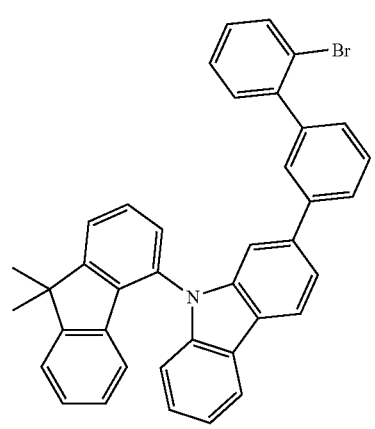
Sub 1-B88
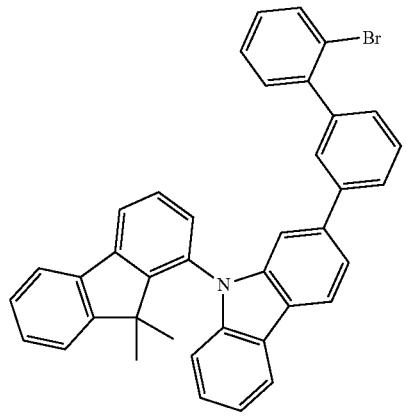
Sub 1-B89
-continued
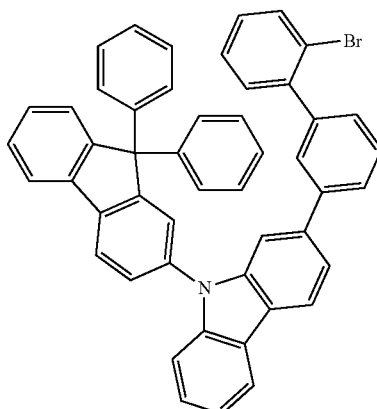
Sub 1-B90
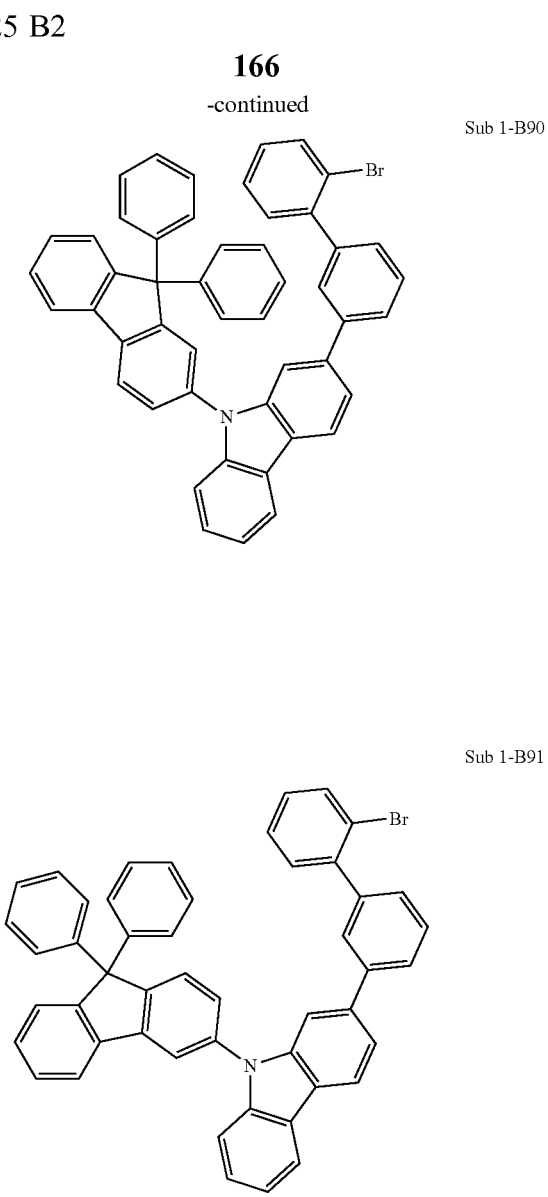
Sub 1-B91
Sub 1-B92

-continued
Sub 1-B93
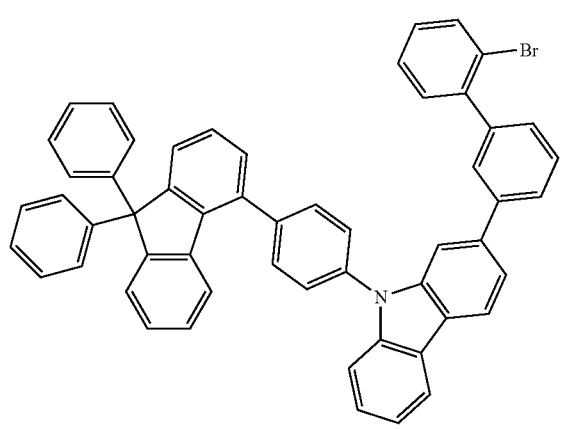
Sub 1-B94
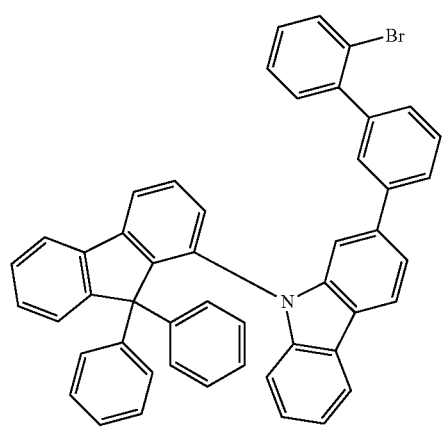
Sub 1-B95
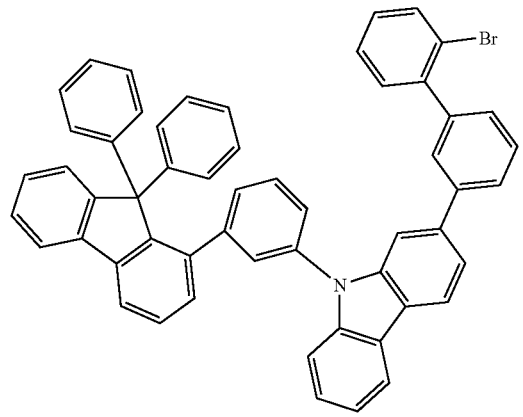
-continued
Sub 1-B96
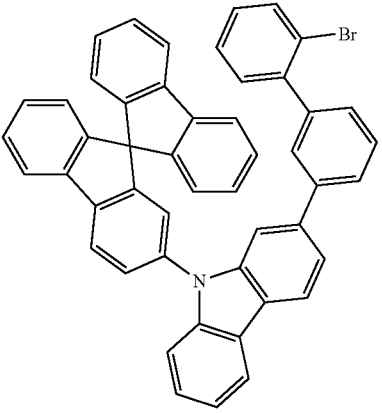
Sub 1-B97
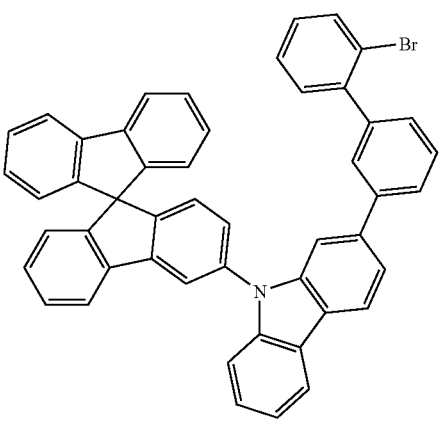
Sub 1-B98
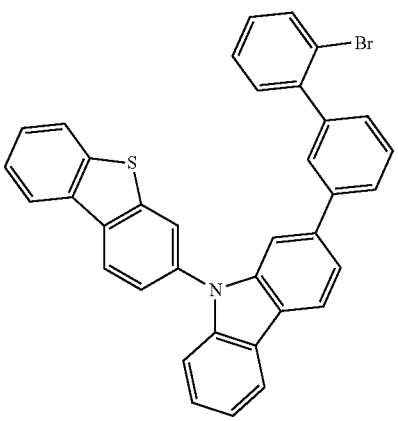

Sub 1-B99
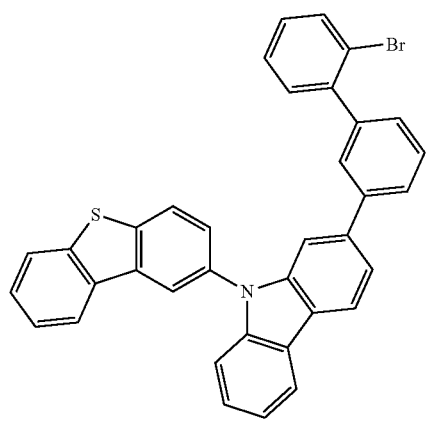
Sub 1-B100
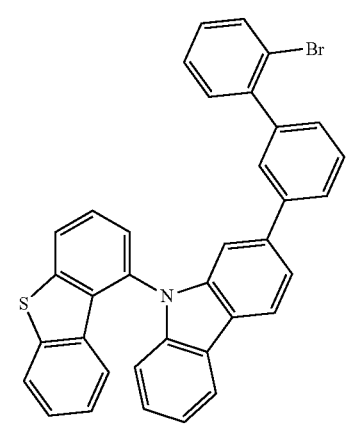
Sub 1-B101
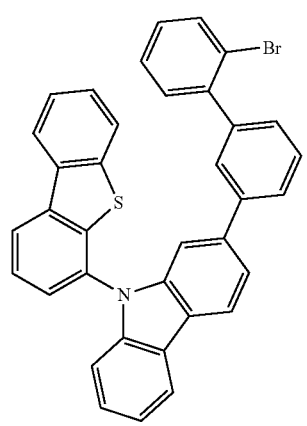
Sub 1-B102
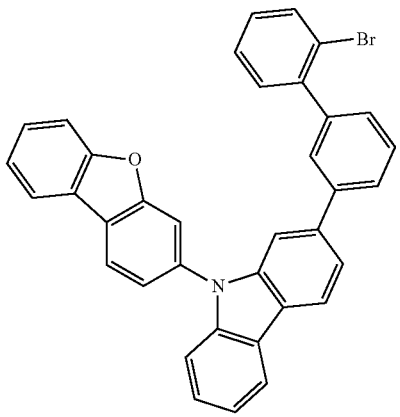
Sub 1-B103
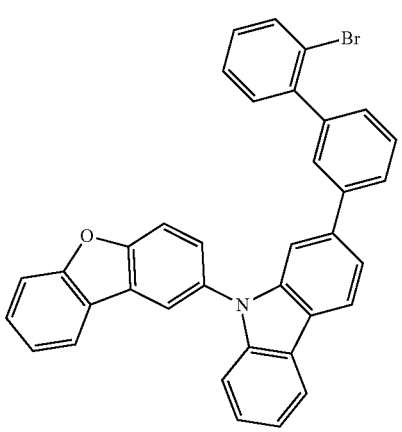
Sub 1-B104
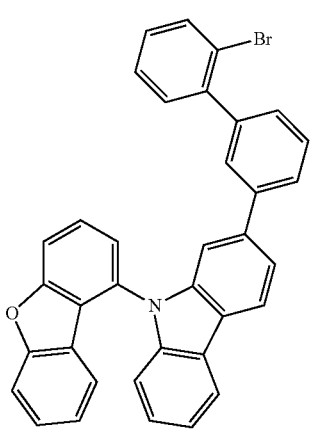

Sub 1-B105
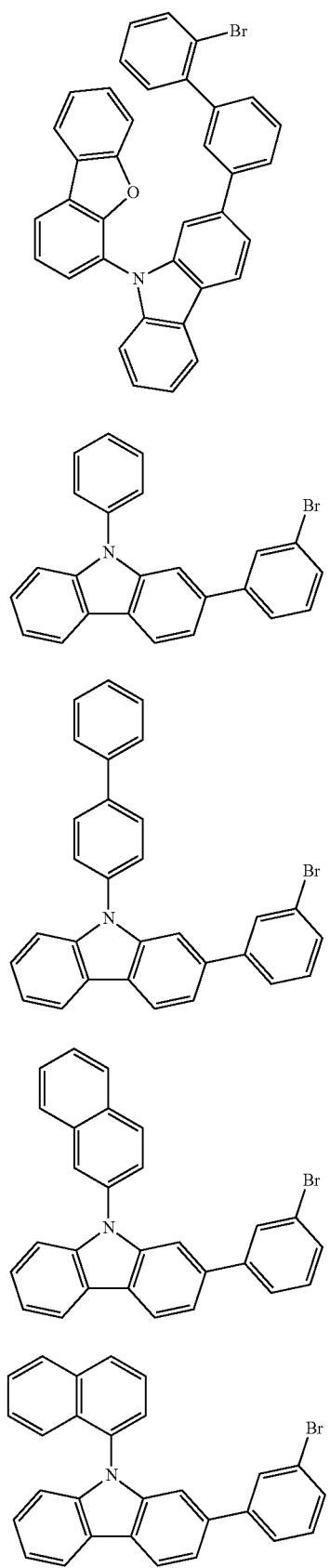
Sub 1-C1
Sub 1-C2
Sub 1-C3
Sub 1-C4
Sub 1-C5
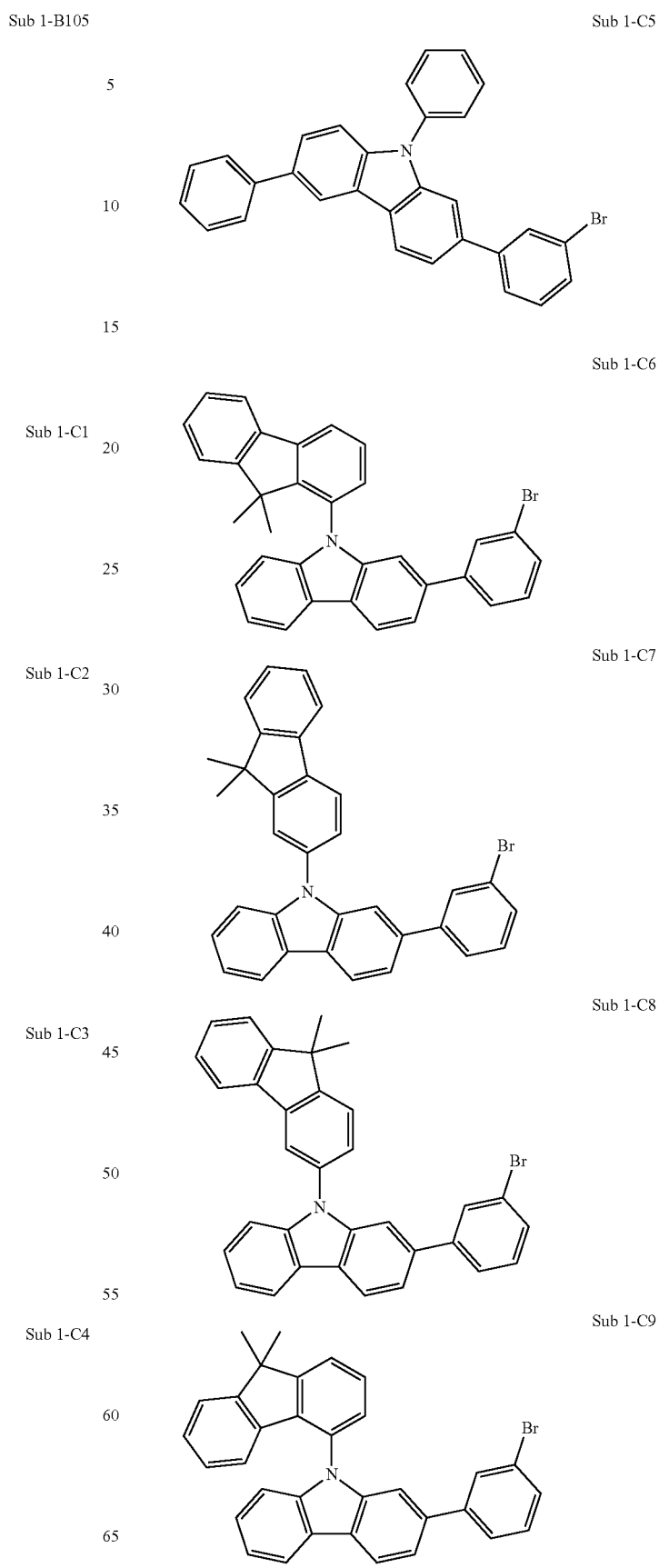
Sub 1-C6
Sub 1-C7
Sub 1-C8
Sub 1-C9

-continued
Sub 1-C10
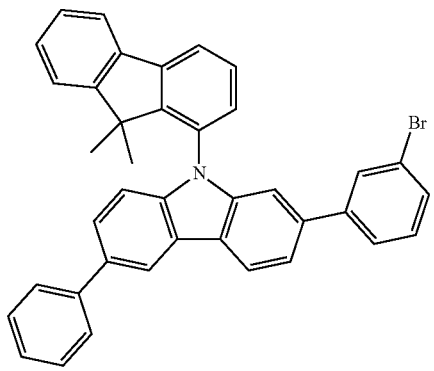
Sub 1-C11
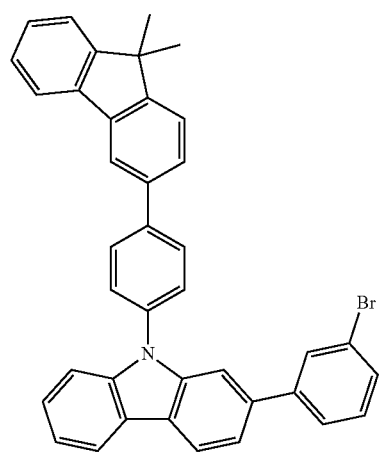
Sub 1-C12
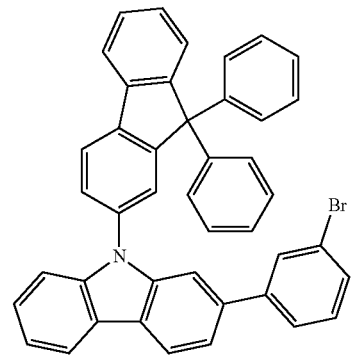
Sub 1-C13
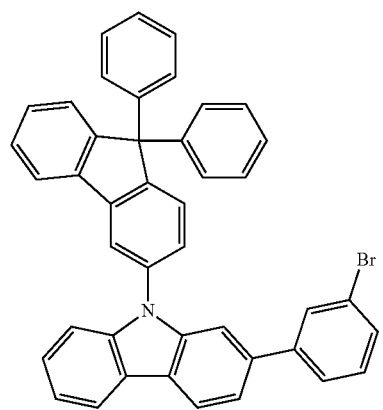
Sub 1-C14
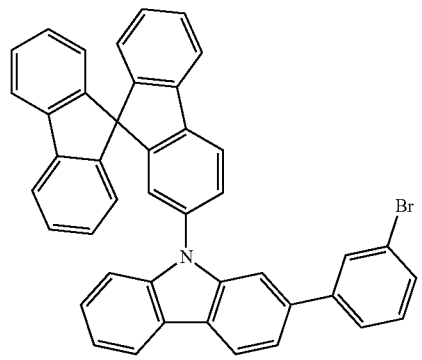
Sub 1-C15
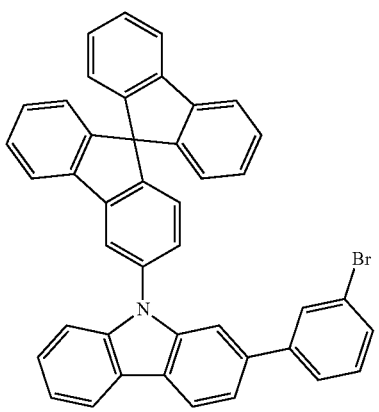
Sub 1-C16
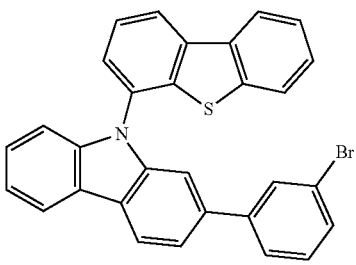
Sub 1-C17
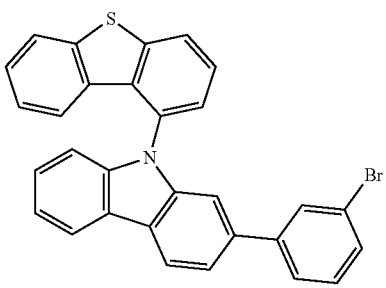

-continued

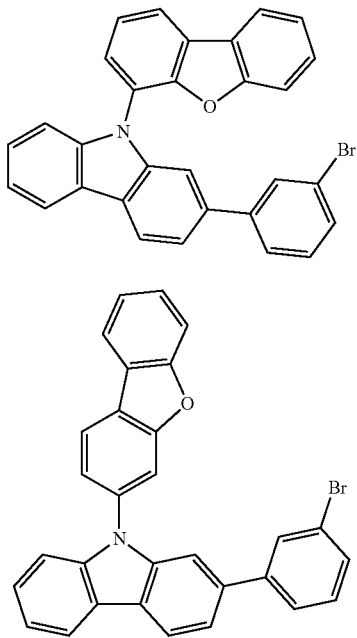

Sub 1-C18

Sub 1-C19

-continued

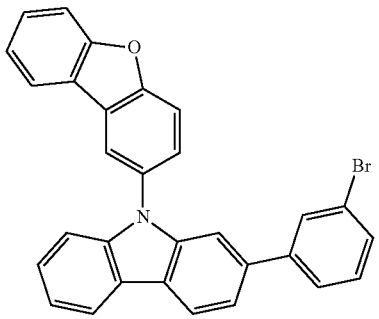

Sub 1-C20

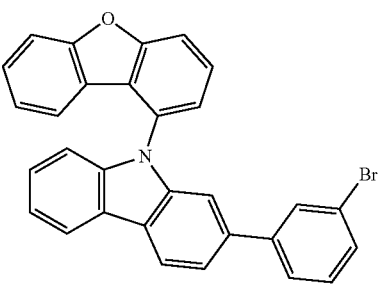

Sub 1-C21

TABLE 1

| Compound | FD-MS | Compound | FD-MS |
| --- | --- | --- | --- |
| Sub1-B1 | m/z = 473.08($C_{30}H_{20}BrN$ = 474.39) | Sub1-B2 | m/z = 549.11($C_{36}H_{24}BrN$ = 550.49) |
| Sub1-B3 | m/z = 523.09($C_{34}H_{22}BrN$ = 524.45) | Sub1-B4 | m/z = 523.09($C_{34}H_{22}BrN$ = 524.45) |
| Sub1-B5 | m/z = 425.08($C_{26}H_{20}BrN$ = 426.35) | Sub1-B6 | m/z = 474.07($C_{29}H_{19}BrN_2$ = 475.38) |
| Sub1-B7 | m/z = 549.11($C_{36}H_{24}BrN$ = 550.49) | Sub1-B8 | m/z = 549.11($C_{36}H_{24}BrN$ = 550.49) |
| Sub1-B9 | m/z = 625.14($C_{42}H_{28}BrN$ = 626.58) | Sub1-B10 | m/z = 599.12($C_{40}H_{26}BrN$ = 600.55) |
| Sub1-B11 | m/z = 523.09($C_{34}H_{22}BrN$ = 524.45) | Sub1-B14 | m/z = 523.09($C_{34}H_{22}BrN$ = 524.45) |
| Sub1-B18 | m/z = 589.14($C_{39}H_{28}BrN$ = 590.55) | Sub1-B19 | m/z = 713.17($C_{49}H_{32}BrN$ = 714.69) |
| Sub1-B20 | m/z = 579.07($C_{36}H_{22}BrNS$ = 580.54) | Sub1-B21 | m/z = 563.09($C_{36}H_{22}BrNO$ = 564.47) |
| Sub1-B22 | m/z = 549.11($C_{36}H_{24}BrN$ = 550.49) | Sub1-B23 | m/z = 625.14($C_{42}H_{28}BrN$ = 626.58) |
| Sub1-B24 | m/z = 625.14($C_{42}H_{28}BrN$ = 626.58) | Sub1-B25 | m/z = 589.14($C_{39}H_{28}BrN$ = 590.55) |
| Sub1-B26 | m/z = 589.14($C_{39}H_{28}BrN$ = 590.55) | Sub1-B27 | m/z = 665.17($C_{45}H_{32}BrN$ = 666.65) |
| Sub1-B28 | m/z = 589.14($C_{39}H_{28}BrN$ = 590.55) | Sub1-B29 | m/z = 665.17($C_{45}H_{32}BrN$ = 666.65) |
| Sub1-B30 | m/z = 589.14($C_{39}H_{28}BrN$ = 590.55) | Sub1-B31 | m/z = 665.17($C_{45}H_{32}BrN$ = 666.65) |
| Sub1-B32 | m/z = 713.17($C_{49}H_{32}BrN$ = 714.69) | Sub1-B33 | m/z = 713.17($C_{49}H_{32}BrN$ = 714.69) |
| Sub1-B34 | m/z = 713.17($C_{49}H_{32}BrN$ = 714.69) | Sub1-B35 | m/z = 713.17($C_{49}H_{32}BrN$ = 714.69) |
| Sub1-B36 | m/z = 789.20($C_{55}H_{36}BrN$ = 790.79) | Sub1-B37 | m/z = 711.16($C_{49}H_{30}BrN$ = 712.67) |
| Sub1-B38 | m/z = 711.16($C_{49}H_{30}BrN$ = 712.67) | Sub1-B39 | m/z = 579.07($C_{36}H_{22}BrNS$ = 580.54) |
| Sub1-B40 | m/z = 579.07($C_{36}H_{22}BrNS$ = 580.54) | Sub1-B41 | m/z = 579.07($C_{36}H_{22}BrNS$ = 580.54) |
| Sub1-B42 | m/z = 579.07($C_{36}H_{22}BrNS$ = 580.54) | Sub1-B43 | m/z = 563.09($C_{36}H_{22}BrNO$ = 564.47) |
| Sub1-B44 | m/z = 563.09($C_{36}H_{22}BrNO$ = 564.47) | Sub1-B45 | m/z = 563.09($C_{36}H_{22}BrNO$ = 564.47) |
| Sub1-B46 | m/z = 563.09($C_{36}H_{22}BrNO$ = 564.47) | Sub1-B47 | m/z = 473.08($C_{30}H_{20}BrN$ = 474.39) |
| Sub1-B48 | m/z = 549.11($C_{36}H_{24}BrN$ = 550.49) | Sub1-B49 | m/z = 523.09($C_{34}H_{22}BrN$ = 524.45) |
| Sub1-B50 | m/z = 524.09($C_{33}H_{21}BrN_2$ = 525.44) | Sub1-B51 | m/z = 549.11($C_{36}H_{24}BrN$ = 550.49) |
| Sub1-B52 | m/z = 625.14($C_{42}H_{28}BrN$ = 626.58) | Sub1-B53 | m/z = 549.11($C_{36}H_{24}BrN$ = 550.49) |
| Sub1-B54 | m/z = 625.14($C_{42}H_{28}BrN$ = 626.58) | Sub1-B55 | m/z = 625.14($C_{42}H_{28}BrN$ = 626.58) |
| Sub1-B56 | m/z = 589.14($C_{39}H_{28}BrN$ = 590.55) | Sub1-B57 | m/z = 665.17($C_{45}H_{32}BrN$ = 666.65) |
| Sub1-B58 | m/z = 589.14($C_{39}H_{28}BrN$ = 590.55) | Sub1-B59 | m/z = 589.14($C_{39}H_{28}BrN$ = 590.55) |
| Sub1-B60 | m/z = 589.14($C_{39}H_{28}BrN$ = 590.55) | Sub1-B61 | m/z = 713.17($C_{49}H_{32}BrN$ = 714.69) |
| Sub1-B62 | m/z = 713.17($C_{49}H_{32}BrN$ = 714.69) | Sub1-B63 | m/z = 713.17($C_{49}H_{32}BrN$ = 714.69) |
| Sub1-B64 | m/z = 789.20($C_{55}H_{36}BrN$ = 790.79) | Sub1-B65 | m/z = 713.17($C_{49}H_{32}BrN$ = 714.69) |
| Sub1-B66 | m/z = 711.16($C_{49}H_{30}BrN$ = 712.67) | Sub1-B67 | m/z = 711.16($C_{49}H_{30}BrN$ = 712.67) |
| Sub1-B68 | m/z = 579.07($C_{36}H_{22}BrNS$ = 580.54) | Sub1-B69 | m/z = 579.07($C_{36}H_{22}BrNS$ = 580.54) |
| Sub1-B70 | m/z = 579.07($C_{36}H_{22}BrNS$ = 580.54) | Sub1-B71 | m/z = 579.07($C_{36}H_{22}BrNS$ = 580.54) |
| Sub1-B72 | m/z = 563.09($C_{36}H_{22}BrNO$ = 564.47) | Sub1-B73 | m/z = 563.09($C_{36}H_{22}BrNO$ = 564.47) |
| Sub1-B74 | m/z = 563.09($C_{36}H_{22}BrNO$ = 564.47) | Sub1-B75 | m/z = 563.09($C_{36}H_{22}BrNO$ = 564.47) |
| Sub1-B76 | m/z = 473.08($C_{30}H_{20}BrN$ = 474.39) | Sub1-B77 | m/z = 549.11($C_{36}H_{24}BrN$ = 550.49) |
| Sub1-B78 | m/z = 523.09($C_{34}H_{22}BrN$ = 524.45) | Sub1-B79 | m/z = 523.09($C_{34}H_{22}BrN$ = 524.45) |
| Sub1-B80 | m/z = 425.08($C_{26}H_{20}BrN$ = 426.35) | Sub1-B81 | m/z = 549.11($C_{36}H_{24}BrN$ = 550.49) |
| Sub1-B82 | m/z = 625.14($C_{42}H_{28}BrN$ = 626.58) | Sub1-B83 | m/z = 549.11($C_{36}H_{24}BrN$ = 550.49) |
| Sub1-B84 | m/z = 625.14($C_{42}H_{28}BrN$ = 626.58) | Sub1-B85 | m/z = 625.14($C_{42}H_{28}BrN$ = 626.58) |
| Sub1-B86 | m/z = 589.14($C_{39}H_{28}BrN$ = 590.55) | Sub1-B87 | m/z = 589.14($C_{39}H_{28}BrN$ = 590.55) |

TABLE 1-continued

| Compound | FD-MS | Compound | FD-MS |
| --- | --- | --- | --- |
| Sub1-B88 | m/z = 589.14($C_{39}H_{28}BrN$ = 590.55) | Sub1-B89 | m/z = 589.14($C_{39}H_{28}BrN$ = 590.55) |
| Sub1-B90 | m/z = 713.17($C_{49}H_{32}BrN$ = 714.69) | Sub1-B91 | m/z = 713.17($C_{49}H_{32}BrN$ = 714.69) |
| Sub1-B92 | m/z = 713.17($C_{49}H_{32}BrN$ = 714.69) | Sub1-B93 | m/z = 789.20($C_{55}H_{36}BrN$ = 790.79) |
| Sub1-B94 | m/z = 713.17($C_{49}H_{32}BrN$ = 714.69) | Sub1-B95 | m/z = 789.20($C_{55}H_{36}BrN$ = 790.79) |
| Sub1-B96 | m/z = 711.16($C_{49}H_{30}BrN$ = 712.67) | Sub1-B97 | m/z = 711.16($C_{49}H_{30}BrN$ = 712.67) |
| Sub1-B98 | m/z = 579.07($C_{36}H_{22}BrNS$ = 580.54) | Sub1-B99 | m/z = 579.07($C_{36}H_{22}BrNS$ = 580.54) |
| Sub1-B100 | m/z = 579.07($C_{36}H_{22}BrNS$ = 580.54) | Sub1-B101 | m/z = 579.07($C_{36}H_{22}BrNS$ = 580.54) |
| Sub1-B102 | m/z = 563.09($C_{36}H_{22}BrNO$ = 564.47) | Sub1-B103 | m/z = 563.09($C_{36}H_{22}BrNO$ = 564.47) |
| Sub1-B104 | m/z = 563.09($C_{36}H_{22}BrNO$ = 564.47) | Sub1-B105 | m/z = 563.09($C_{36}H_{22}BrNO$ = 564.47) |
| Sub1-C1 | m/z = 397.05($C_{24}H_{16}BrN$ = 398.29) | Sub1-C2 | m/z = 473.08($C_{30}H_{20}BrN$ = 474.39) |
| Sub1-C3 | m/z = 447.06($C_{28}H_{18}BrN$ = 448.35) | Sub1-C4 | m/z = 447.06($C_{28}H_{18}BrN$ = 448.35) |
| Sub1-C5 | m/z = 473.08($C_{30}H_{20}BrN$ = 474.39) | Sub1-C6 | m/z = 513.11($C_{33}H_{24}BrN$ = 514.45) |
| Sub1-C7 | m/z = 513.11($C_{33}H_{24}BrN$ = 514.45) | Sub1-C8 | m/z = 513.11($C_{33}H_{24}BrN$ = 514.45) |
| Sub1-C9 | m/z = 513.11($C_{33}H_{24}BrN$ = 514.45) | Sub1-C10 | m/z = 589.14($C_{39}H_{28}BrN$ = 590.55) |
| Sub1-C11 | m/z = 589.14($C_{39}H_{28}BrN$ = 590.55) | Sub1-C12 | m/z = 637.14($C_{43}H_{28}BrN$ = 638.59) |
| Sub1-C13 | m/z = 637.14($C_{43}H_{28}BrN$ = 638.59) | Sub1-C14 | m/z = 635.12($C_{43}H_{26}BrN$ = 636.58) |
| Sub1-C15 | m/z = 635.12($C_{43}H_{26}BrN$ = 636.58) | Sub1-C16 | m/z = 503.03($C_{30}H_{18}BrNS$ = 504.44) |
| Sub1-C17 | m/z = 503.03($C_{30}H_{18}BrNS$ = 504.44) | Sub1-C18 | m/z = 487.06($C_{30}H_{18}BrNO$ = 488.37) |
| Sub1-C19 | m/z = 487.06($C_{30}H_{18}BrNO$ = 488.37) | Sub1-C20 | m/z = 487.06($C_{30}H_{18}BrNO$ = 488.37) |
| Sub1-C21 | m/z = 487.06($C_{30}H_{18}BrNO$ = 488.37) | | |

II. Synthesis Method of Sub 2

Sub 2 of Reaction Scheme 1 can be synthesized according to, but not limited to, the following Reaction Scheme 27.

<Reaction Scheme 27>

$$Br-Ar^2 + Ar^3-NH_2 \xrightarrow[\text{NaOt-Bu/Toluene}]{Pd_2(dba)_3/P(t-Bu)_3} HN\begin{smallmatrix}Ar^2\\Ar^3\end{smallmatrix}$$

Sub 2

Synthesis Examples of the compounds of Sub 2 will be described in detail.

1. Synthesis Method of Sub 2-6

<Reaction Scheme 28>

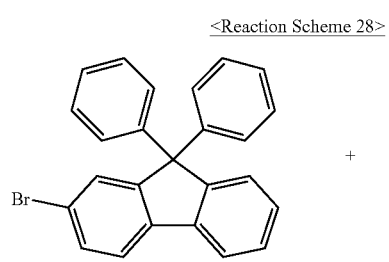

+

-continued

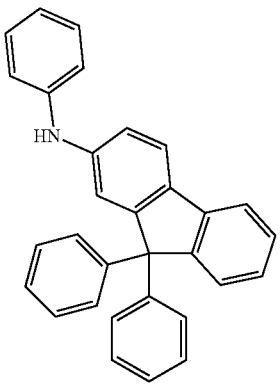

Sub 2-6

2-bromo-9,9-diphenyl-9H-fluorene (35.27 g, 88.8 mmol) as the starting material was dissolved in toluene in a round bottom flask, and aniline (16.53 g, 177.5 mmol), $Pd_2(dba)_3$ (2.44 g, 2.7 mmol), 50% $P(t-Bu)_3$ (3.5 ml, 7.1 mmol), and NaOt-Bu (25.6 g, 266.3 mmol) were added to the reaction solution, followed by stirring at 40° C. Upon completion of the reaction, the reaction product was extracted with $CH_2Cl_2$ and water. The extracted organic layer was dried with $MgSO_4$ and concentrated, and then the produced organic material was separated by a silica gel column and recrystallized to obtain 27.27 g of product (yield: 75%).

2. Synthesis Method of Sub 2-7

<Reaction Scheme 29>

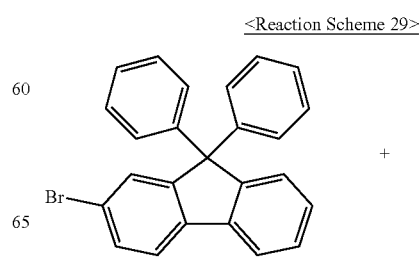

+

-continued

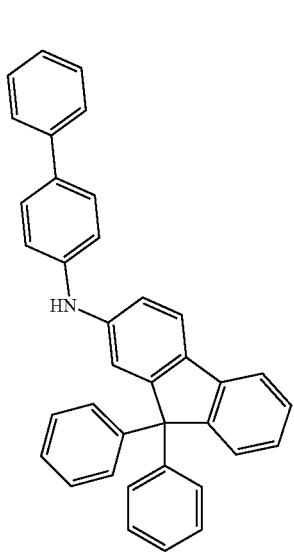

Sub 2-7

Using 2-bromo-9,9-diphenyl-9H-fluorene (11.89 g, 29.9 mmol) as the starting material and using [1,1'-biphenyl]-4-amine (10.13 g, 59.9 mmol), Pd$_2$(dba)$_3$ (0.82 g, 0.9 mmol), 50% P(t-Bu)$_3$ (1.2 ml, 2.4 mmol), NaOt-Bu (8.63 g, 89.8 mmol), and toluene, the same procedure as described in the synthesis method of Sub 2-6 was carried out to obtain 11.04 g of product (yield: 76%).

3. Synthesis Method of Sub 2-13

<Reaction Scheme 30>

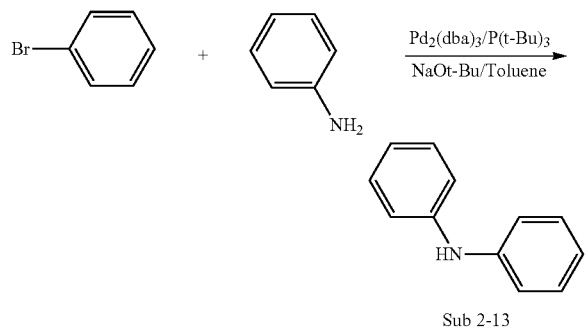

Sub 2-13

Using bromobenzene (11.16 g, 71.1 mmol) as the starting material and using aniline (13.24 g, 142.2 mmol), Pd$_2$(dba)$_3$ (1.95 g, 2.1 mmol), 50% P(t-Bu)$_3$ (2.8 ml, 5.7 mmol), NaOt-Bu (20.49 g, 213.2 mmol), and toluene, the same procedure as described in the synthesis method of Sub 2-6 was carried out to obtain 9.62 g of product (yield: 80%).

4. Synthesis Method of Sub 2-16

<Reaction Scheme 31>

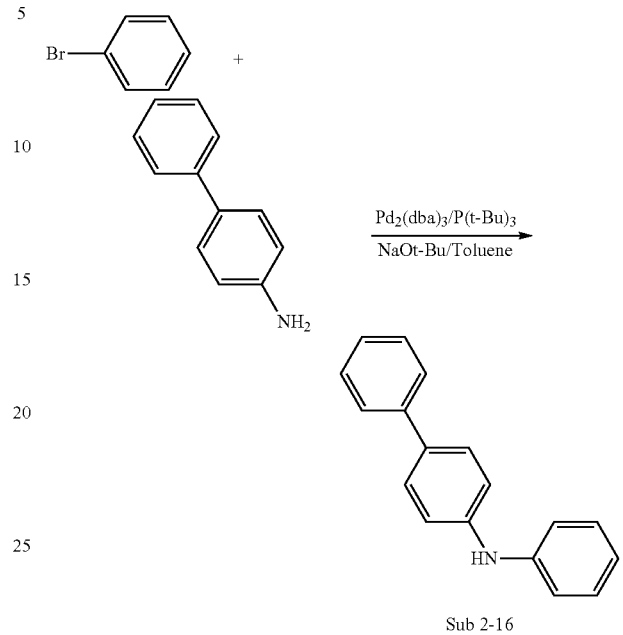

Sub 2-16

Using bromobenzene (7.61 g, 48.5 mmol) as the starting material and using [1,1'-biphenyl]-4-amine (16.4 g, 96.9 mmol), Pd$_2$(dba)$_3$ (1.33 g, 1.5 mmol), 50% P(t-Bu)$_3$ (1.9 ml, 3.9 mmol), NaOt-Bu (13.97 g, 145.4 mmol), and toluene, the same procedure as described in the synthesis method of Sub 2-6 was carried out to obtain 9.87 g of product (yield: 83%).

5. Synthesis Method of Sub 2-17

<Reaction Scheme 32>

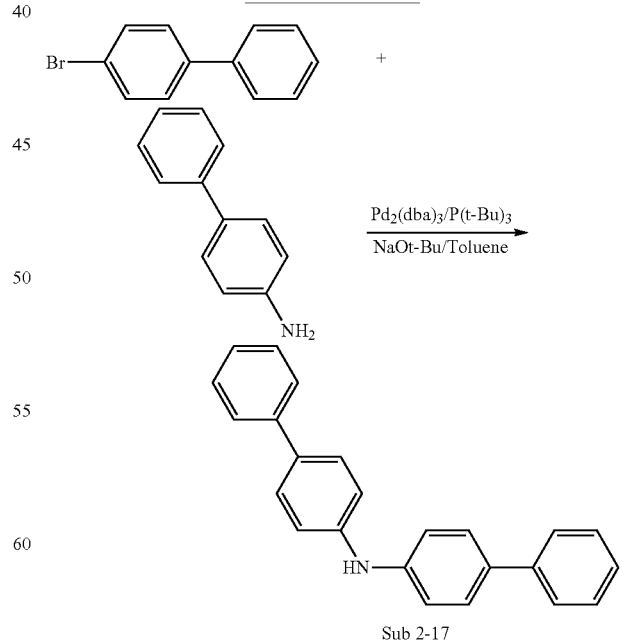

Sub 2-17

Using 4-bromo-1,1'-biphenyl (9.74 g, 41.8 mmol) as the starting material and using [1,1'-biphenyl]-4-amine (14.14 g, 83.6 mmol), Pd$_2$(dba)$_3$ (1.15 g, 1.3 mmol), 50% P(t-Bu)$_3$ (1.6 ml, 3.3 mmol), NaOt-Bu (12.05 g, 125.4 mmol), and toluene, the same procedure as described in the synthesis method of Sub 2-6 was carried out to obtain 10.61 g of product (yield: 79%).

6. Synthesis Method of Sub 2-39

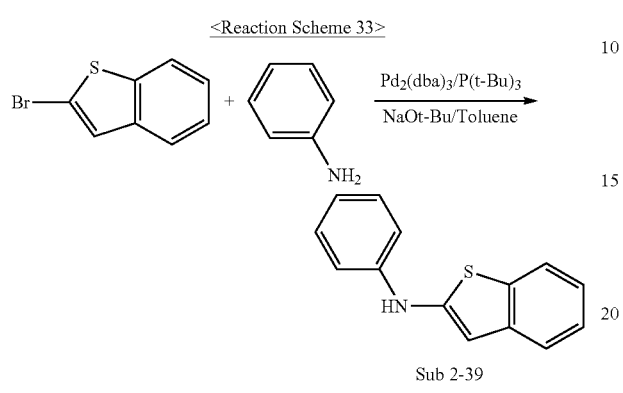

Sub 2-39

Using 2-bromobenzo[b]thiophene (8.92 g, 41.9 mmol) as the starting material and using aniline (7.8 g, 83.7 mmol), Pd$_2$(dba)$_3$ (1.15 g, 1.3 mmol), 50% P(t-Bu)$_3$ (1.6 ml, 3.3 mmol), NaOt-Bu (12.07 g, 125.6 mmol), and toluene, the same procedure as described in the synthesis method of Sub 2-6 was carried out to obtain 6.51 g of product (yield: 69%).

7. Synthesis Method of Sub 2-67

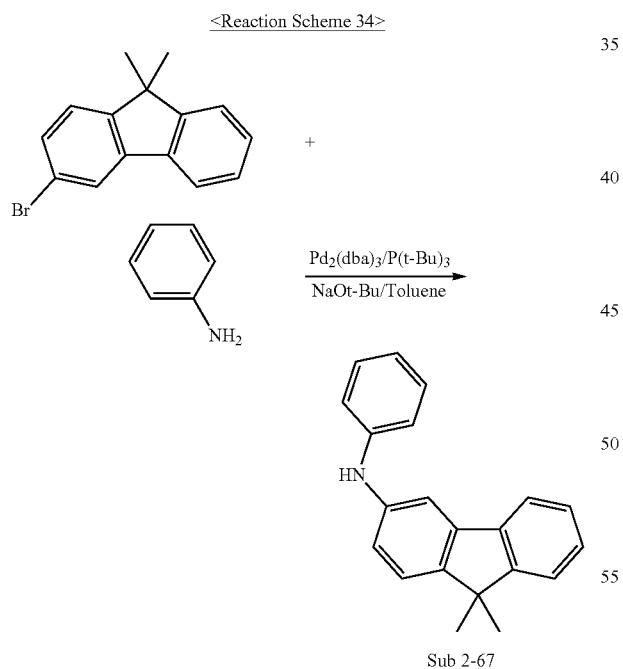

Sub 2-67

Using 3-bromo-9,9-dimethyl-9H-fluorene (16.33 g, 59.8 mmol) as the starting material and using aniline (11.13 g, 119.6 mmol), Pd$_2$(dba)$_3$ (1.64 g, 1.8 mmol), 50% P(t-Bu)$_3$ (2.3 ml, 4.8 mmol), NaOt-Bu (17.24 g, 179.3 mmol), and toluene, the same procedure as described in the synthesis method of Sub 2-6 was carried out to obtain 14.33 g of product (yield: 84%).

8. Synthesis Method of Sub 2-68

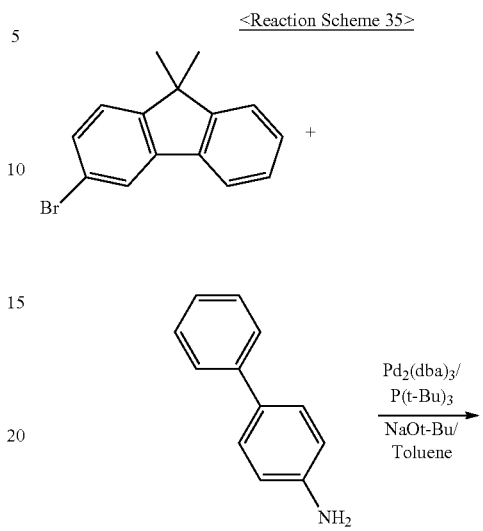

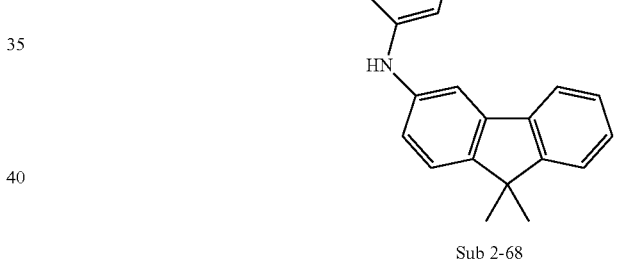

Sub 2-68

Using 3-bromo-9,9-dimethyl-9H-fluorene (8.09 g, 29.6 mmol) as the starting material and using [1,1'-biphenyl]-4-amine (10.02 g, 59.2 mmol), Pd$_2$(dba)$_3$ (0.81 g, 0.9 mmol), 50% P(t-Bu)$_3$ (1.2 ml, 2.4 mmol), NaOt-Bu (8.54 g, 88.8 mmol), and toluene, the same procedure as described in the synthesis method of Sub 2-6 was carried out to obtain 8.78 g of product (yield: 82%).

9. Synthesis Method of Sub 2-72

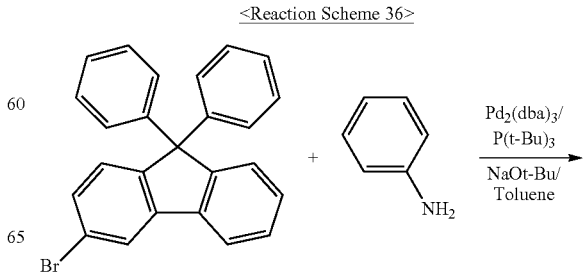

-continued

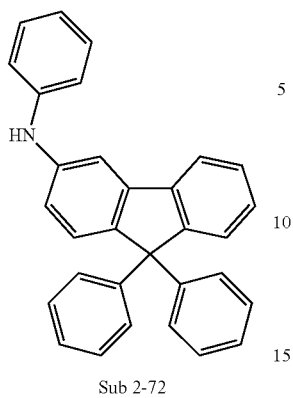
Sub 2-72

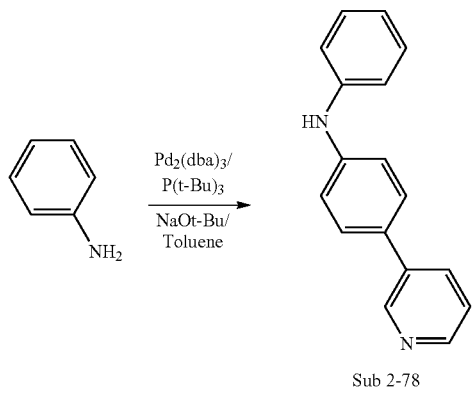
Sub 2-78

Using 3-bromo-9,9-diphenyl-9H-fluorene (11.67 g, 29.4 mmol) as the starting material and using aniline (5.47 g, 58.7 mmol), Pd$_2$(dba)$_3$ (0.81 g, 0.9 mmol), 50% P(t-Bu)$_3$ (1.1 ml, 2.3 mmol), NaOt-Bu (8.47 g, 88.1 mmol), and toluene, the same procedure as described in the synthesis method of Sub 2-6 was carried out to obtain 9.02 g of product (yield: 75%).

10. Synthesis Method of Sub 2-77

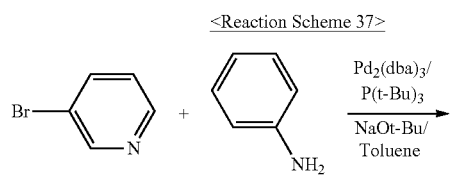
<Reaction Scheme 37>

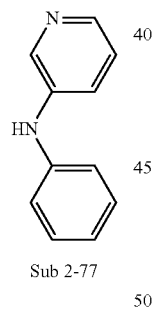
Sub 2-77

Using 3-bromopyridine (10.41 g, 65.9 mmol) as the starting material and using aniline (12.27 g, 131.8 mmol), Pd$_2$(dba)$_3$ (1.81 g, 2 mmol), 50% P(t-Bu)$_3$ (2.6 ml, 5.3 mmol), NaOt-Bu (19 g, 197.7 mmol), and toluene, the same procedure as described in the synthesis method of Sub 2-6 was carried out to obtain 7.51 g of product (yield: 67%).

11. Synthesis Method of Sub 2-78

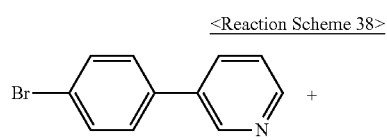
<Reaction Scheme 38>

Using 3-(4-bromophenyl)pyridine (10.98 g, 46.9 mmol) as the starting material and using aniline (8.74 g, 93.8 mmol), Pd$_2$(dba)$_3$ (1.29 g, 1.4 mmol), 50% P(t-Bu)$_3$ (1.8 ml, 3.8 mmol), NaOt-Bu (13.52 g, 140.7 mmol), and toluene, the same procedure as described in the synthesis method of Sub 2-6 was carried out to obtain 7.97 g of product (yield: 69%).

12. Synthesis Method of Sub 2-82

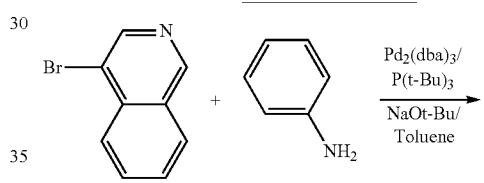
<Reaction Scheme 39>

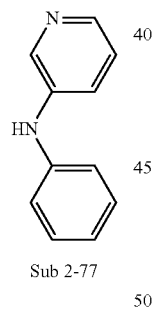
Sub 2-82

Using 4-bromoisoquinoline (9.83 g, 47.2 mmol) as the starting material and using aniline (8.8 g, 94.5 mmol), Pd$_2$(dba)$_3$ (1.3 g, 1.4 mmol), 50% P(t-Bu)$_3$ (1.8 ml, 3.8 mmol), NaOt-Bu (13.62 g, 141.7 mmol), and toluene, the same procedure as described in the synthesis method of Sub 2-6 was carried out to obtain 6.24 g of product (yield: 60%).

Meanwhile, examples of Sub 2 compounds include, but are not limited to, the following compounds, and FD-MS data of the Sub 2 compounds are given in Table 2 below.

Sub 2-1
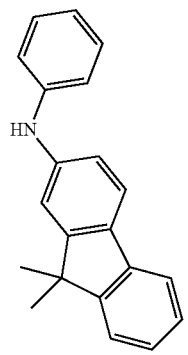
Sub 2-2
Sub 2-3
Sub 2-4
Sub 2-5
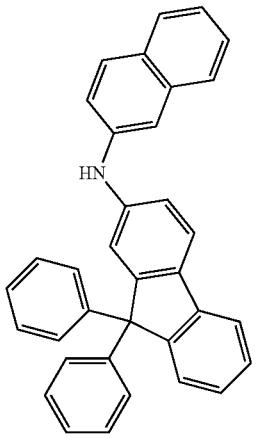
Sub 2-6
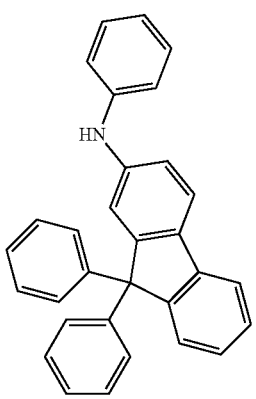
Sub 2-7
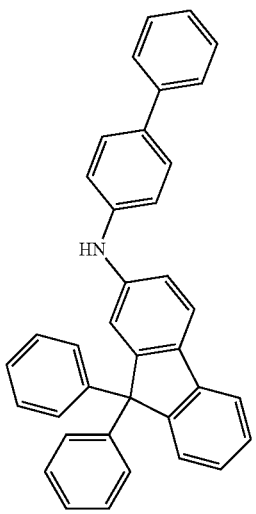

Sub 2-8
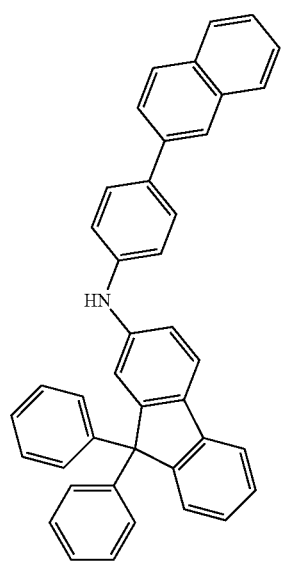
Sub 2-9
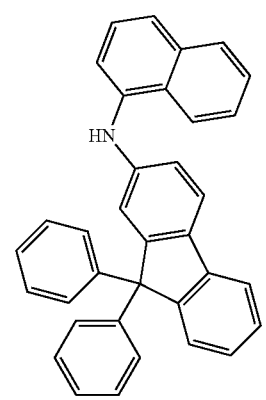
Sub 2-10
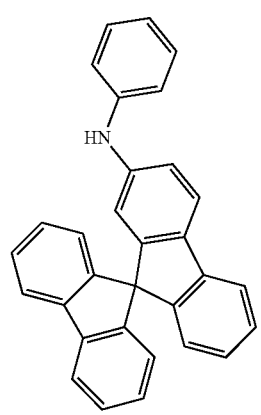
Sub 2-11
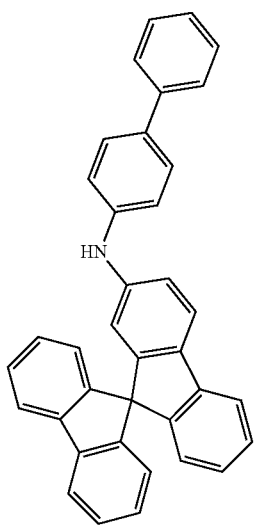
Sub 2-13
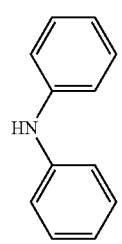
Sub 2-14
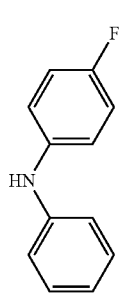
Sub 2-15
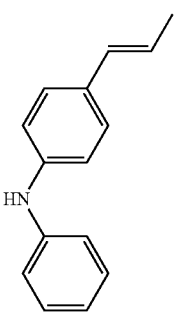

Sub 2-16
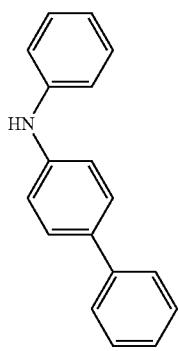
Sub 2-17
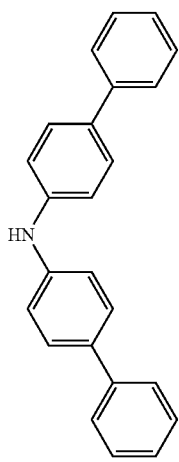
Sub 2-18
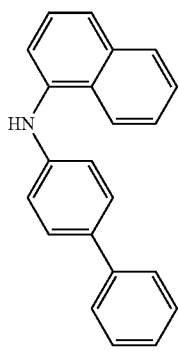
Sub 2-19
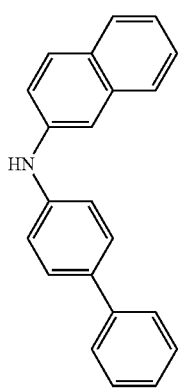
Sub 2-20
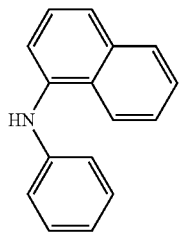
Sub 2-21
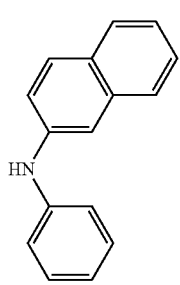
Sub 2-22
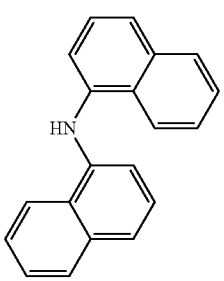
Sub 2-23
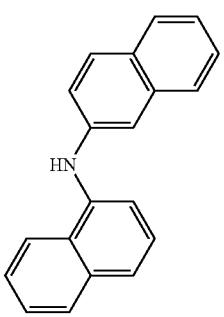
Sub 2-24
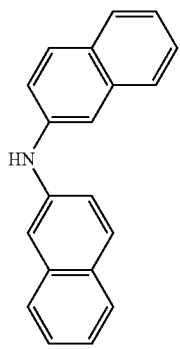

Sub 2-25
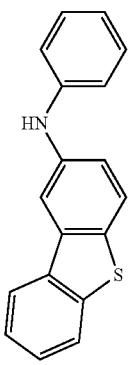
Sub 2-28
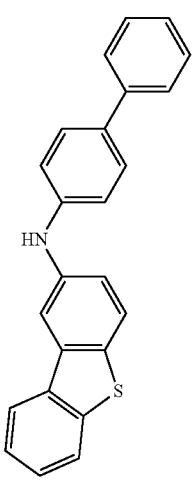
Sub 2-29
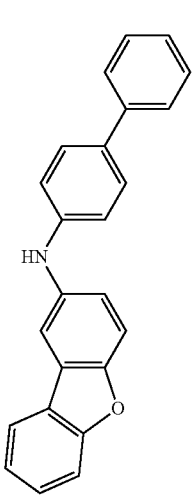
Sub 2-30
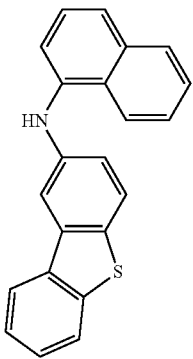
Sub 2-31
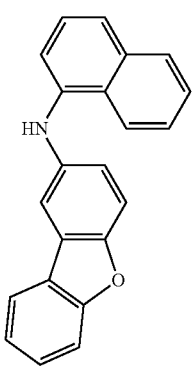
Sub 2-32
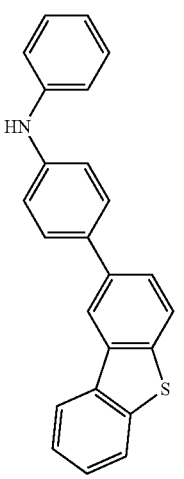
Sub 2-37
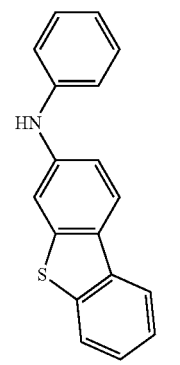

Sub 2-38
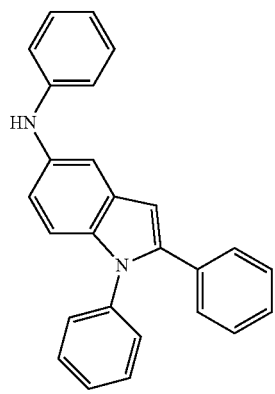
Sub 2-42
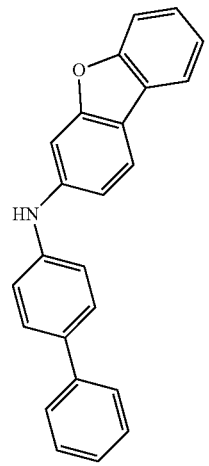
Sub 2-39
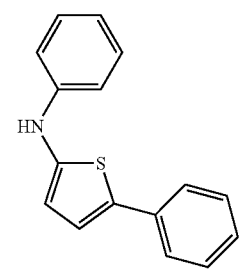
Sub 2-43
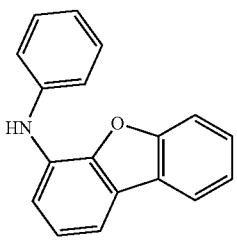
Sub 2-44
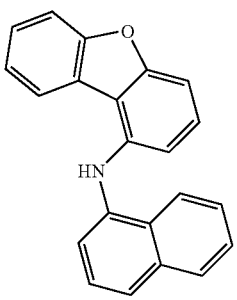
Sub 2-40
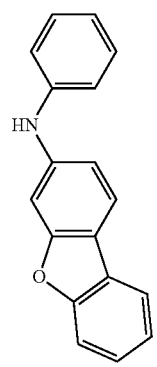
Sub 2-45
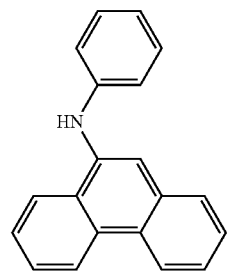
Sub 2-41
Sub 2-46
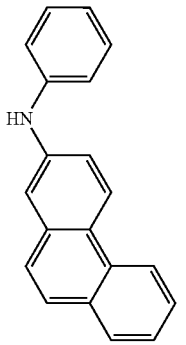

Sub 2-47
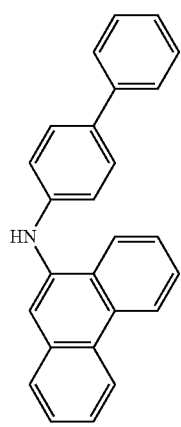
Sub 2-48
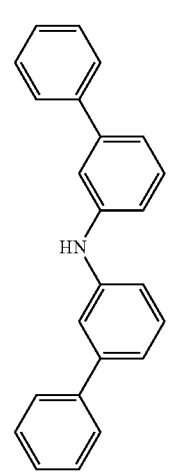
Sub 2-49
Sub 2-50
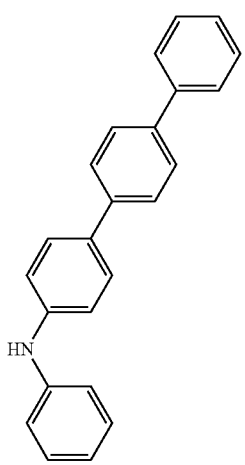
Sub 2-51
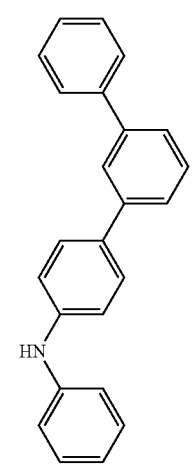
Sub 2-52
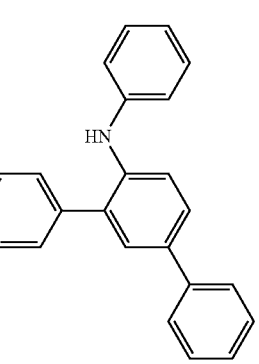
Sub 2-53
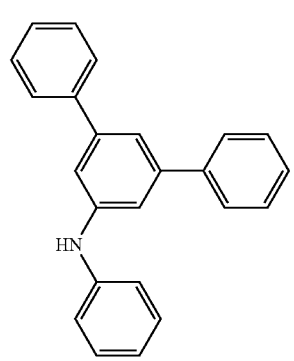

Sub 2-54
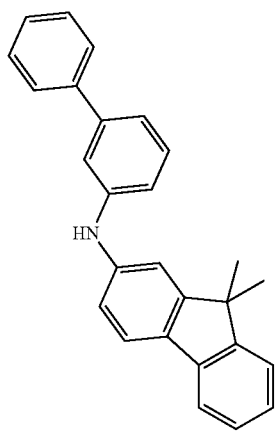
Sub 2-55
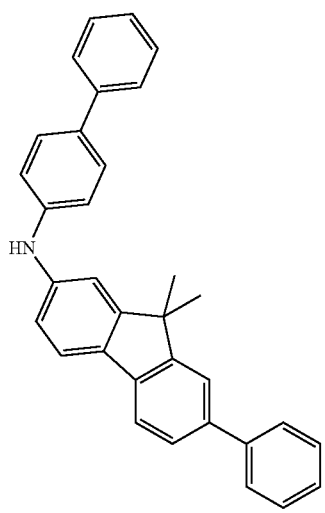
Sub 2-56
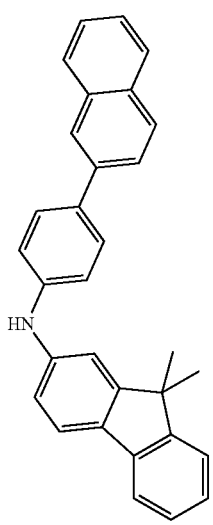
Sub 2-57
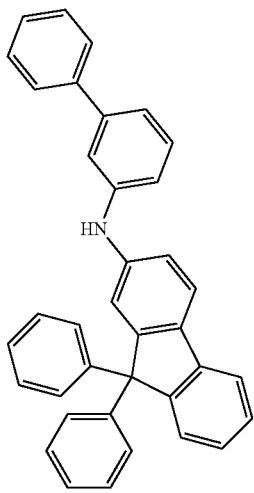
Sub 2-58
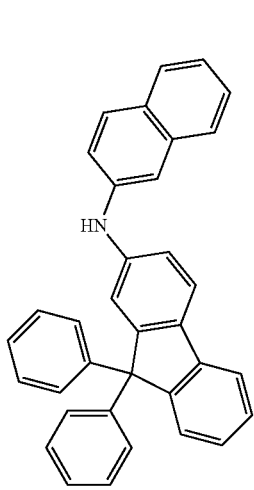
Sub 2-59
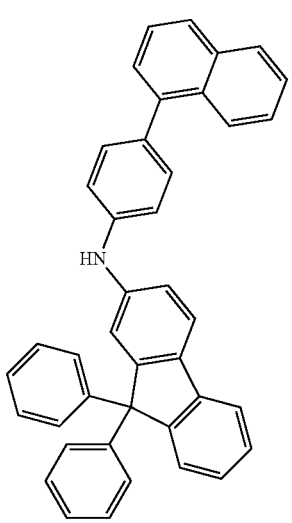

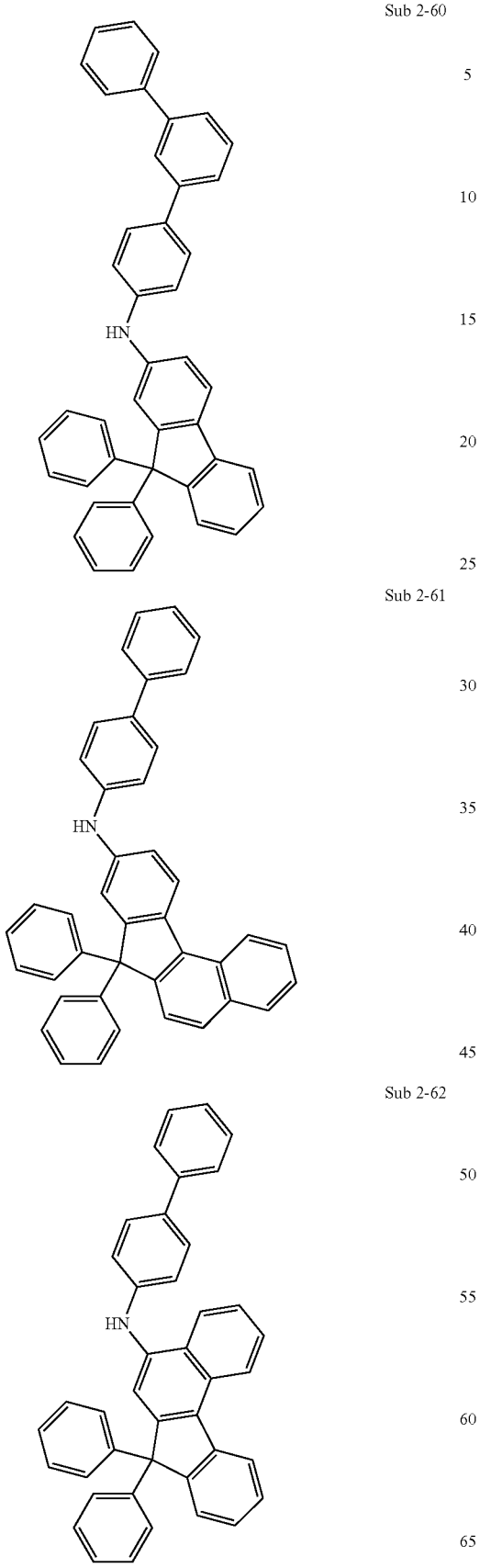
Sub 2-60
Sub 2-61
Sub 2-62
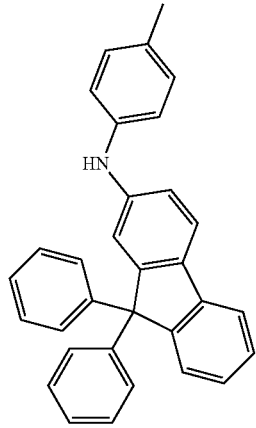
Sub 2-63
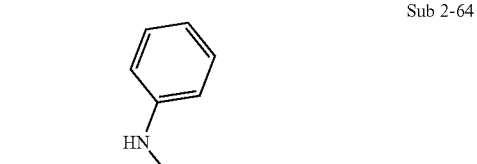
Sub 2-64
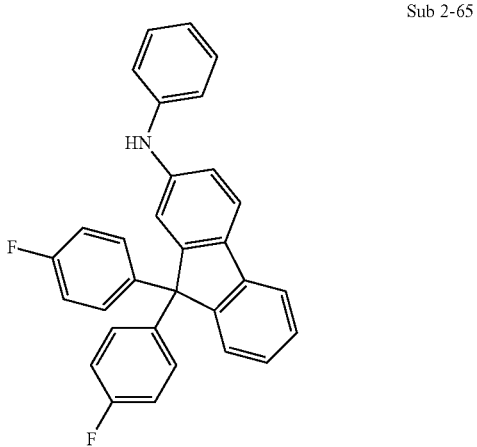
Sub 2-65

Sub 2-66
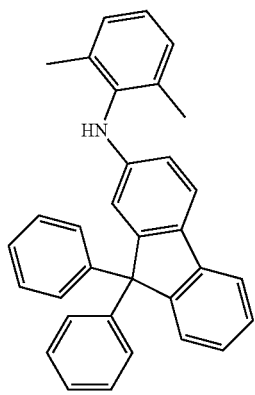
Sub 2-67
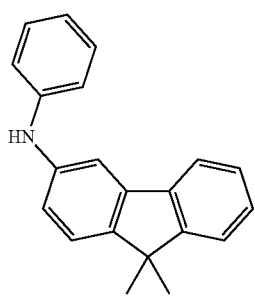
Sub 2-68
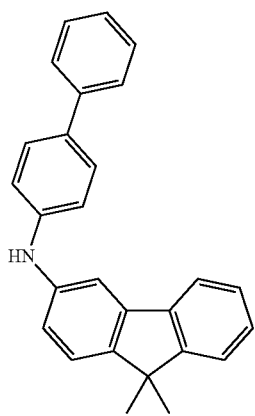
Sub 2-69
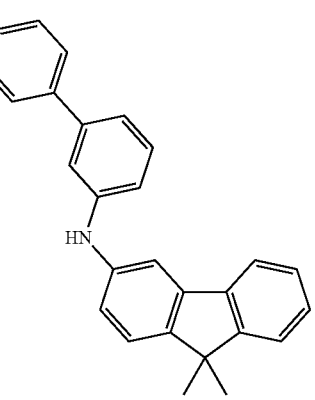
Sub 2-70
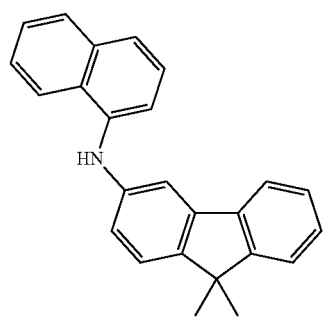
Sub 2-71
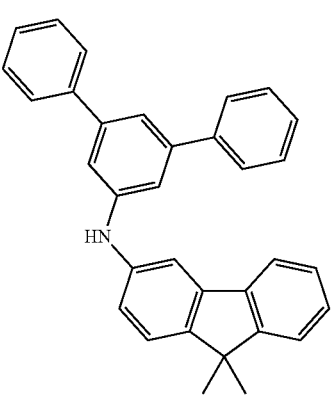
Sub 2-72
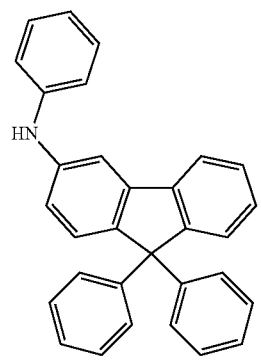
Sub 2-73
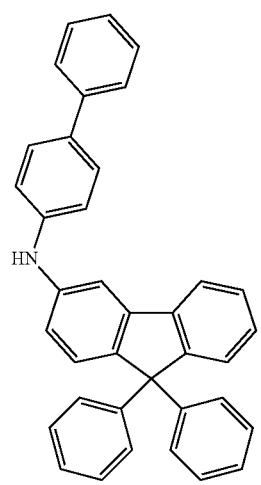

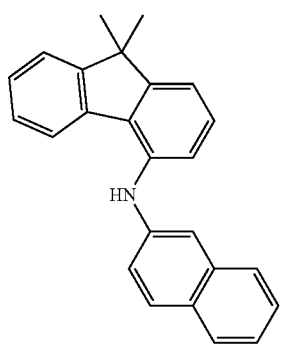
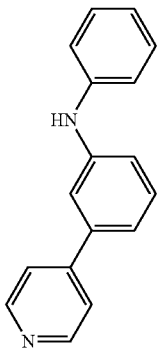
Sub 2-74
Sub 2-75
Sub 2-76
Sub 2-77
Sub 2-78
Sub 2-79
Sub 2-80
Sub 2-81
Sub 2-82

Sub 2-83
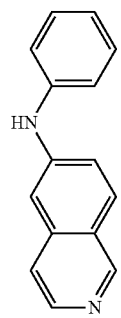
Sub 2-84
Sub 2-85
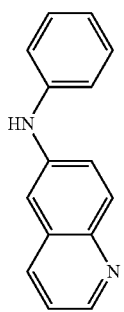
Sub 2-86
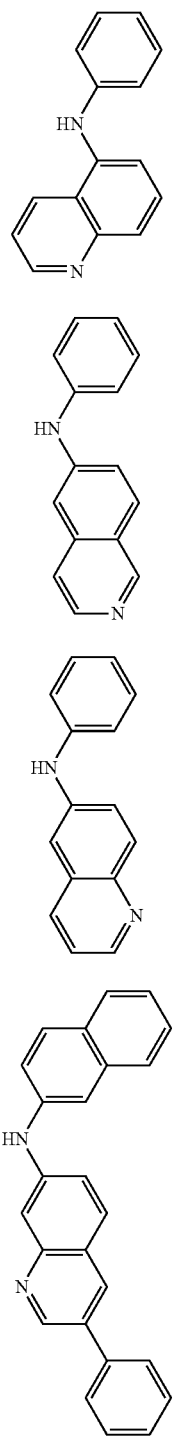
Sub 2-87
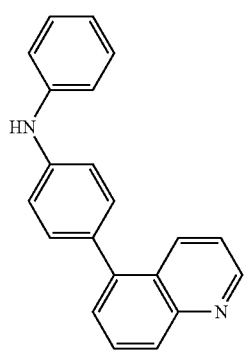
Sub 2-88
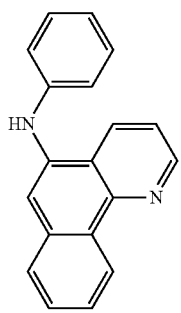
Sub 2-89
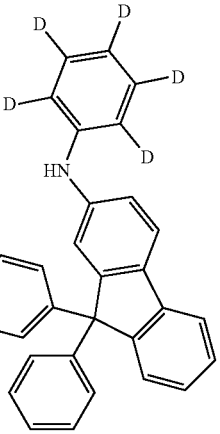
TABLE 2
| Compound | FD-MS | Compound | FD-MS |
| --- | --- | --- | --- |
| Sub 2-1 | m/z = 285.15($C_{21}H_{19}N$ = 285.38) | Sub 2-2 | m/z = 299.17($C_{22}H_{21}N$ = 299.41) |
| Sub 2-3 | m/z = 361.18($C_{27}H_{23}N$ = 361.48) | Sub 2-4 | m/z = 335.17($C_{25}H_{21}N$ = 335.44) |
| Sub 2-5 | m/z = 335.17($C_{25}H_{21}N$ = 335.44) | Sub 2-6 | m/z = 409.18($C_{31}H_{23}N$ = 409.52) |
| Sub 2-7 | m/z = 485.21($C_{37}H_{27}N$ = 485.62) | Sub 2-8 | m/z = 535.23($C_{41}H_{29}N$ = 535.68) |
| Sub 2-9 | m/z = 459.20($C_{35}H_{25}N$ = 459.58) | Sub 2-10 | m/z = 407.17($C_{31}H_{21}N$ = 407.51) |
| Sub 2-11 | m/z = 483.20($C_{37}H_{25}N$ = 483.60) | Sub 2-13 | m/z = 169.09($C_{12}H_{11}N$ = 169.22) |

TABLE 2-continued

| Compound | FD-MS | Compound | FD-MS |
|---|---|---|---|
| Sub 2-14 | m/z = 187.08($C_{12}H_{10}FN$ = 187.21) | Sub 2-15 | m/z = 209.12($C_{15}H_{15}N$ = 209.29) |
| Sub 2-16 | m/z = 245.12($C_{18}H_{15}N$ = 245.32) | Sub 2-17 | m/z = 321.15($C_{24}H_{19}N$ = 321.41) |
| Sub 2-18 | m/z = 295.14($C_{22}H_{17}N$ = 295.38) | Sub 2-19 | m/z = 295.14($C_{22}H_{17}N$ = 295.38) |
| Sub 2-20 | m/z = 219.10($C_{16}H_{13}N$ = 219.28) | Sub 2-21 | m/z = 219.10($C_{16}H_{13}N$ = 219.28) |
| Sub 2-22 | m/z = 269.12($C_{20}H_{15}N$ = 269.34) | Sub 2-23 | m/z = 269.12($C_{20}H_{15}N$ = 269.34) |
| Sub 2-24 | m/z = 269.12($C_{20}H_{15}N$ = 269.34) | Sub 2-25 | m/z = 275.08($C_{18}H_{13}NS$ = 275.37) |
| Sub 2-28 | m/z = 351.11($C_{24}H_{17}NS$ = 351.46) | Sub 2-29 | m/z = 335.13($C_{24}H_{17}NO$ = 335.40) |
| Sub 2-30 | m/z = 325.09($C_{22}H_{15}NS$ = 325.43) | Sub 2-31 | m/z = 309.12($C_{22}H_{15}NO$ = 309.36) |
| Sub 2-32 | m/z = 351.11($C_{24}H_{17}NS$ = 351.46) | Sub 2-37 | m/z = 275.08($C_{18}H_{13}NS$ = 275.37) |
| Sub 2-38 | m/z = 360.16($C_{26}H_{20}N_2$ = 360.45) | Sub 2-39 | m/z = 225.06($C_{14}H_{11}NS$ = 225.31) |
| Sub 2-40 | m/z = 251.08($C_{16}H_{13}NS$ = 251.35) | Sub 2-41 | m/z = 259.10($C_{18}H_{13}NO$ = 259.30) |
| Sub 2-42 | m/z = 335.13($C_{24}H_{17}NO$ = 335.40) | Sub 2-43 | m/z = 259.10($C_{18}H_{13}NO$ = 259.30) |
| Sub 2-44 | m/z = 309.12($C_{22}H_{15}NO$ = 309.36) | Sub 2-45 | m/z = 269.12($C_{20}H_{15}N$ = 269.34) |
| Sub 2-46 | m/z = 269.12($C_{20}H_{15}N$ = 269.34) | Sub 2-47 | m/z = 345.15($C_{26}H_{19}N$ = 345.44) |
| Sub 2-48 | m/z = 321.15($C_{24}H_{19}N$ = 321.41) | Sub 2-49 | m/z = 321.15($C_{24}H_{19}N$ = 321.41) |
| Sub 2-50 | m/z = 321.15($C_{24}H_{19}N$ = 321.41) | Sub 2-51 | m/z = 321.15($C_{24}H_{19}N$ = 321.41) |
| Sub 2-52 | m/z = 321.15($C_{24}H_{19}N$ = 321.41) | Sub 2-53 | m/z = 321.15($C_{24}H_{19}N$ = 321.41) |
| Sub 2-54 | m/z = 361.18($C_{27}H_{23}N$ = 361.48) | Sub 2-55 | m/z = 437.21($C_{33}H_{27}N$ = 437.57) |
| Sub 2-56 | m/z = 411.20($C_{31}H_{25}N$ = 411.54) | Sub 2-57 | m/z = 485.21($C_{37}H_{27}N$ = 485.62) |
| Sub 2-58 | m/z = 459.20($C_{35}H_{25}N$ = 459.58) | Sub 2-59 | m/z = 535.23($C_{41}H_{29}N$ = 535.68) |
| Sub 2-60 | m/z = 561.25($C_{43}H_{31}N$ = 561.71) | Sub 2-61 | m/z = 535.23($C_{41}H_{29}N$ = 535.68) |
| Sub 2-62 | m/z = 535.23($C_{41}H_{29}N$ = 535.68) | Sub 2-63 | m/z = 423.20($C_{32}H_{25}N$ = 423.55) |
| Sub 2-64 | m/z = 437.21($C_{33}H_{27}N$ = 437.57) | Sub 2-65 | m/z = 445.16($C_{31}H_{21}F_2N$ = 445.50) |
| Sub 2-66 | m/z = 437.21($C_{33}H_{27}N$ = 437.57) | Sub 2-67 | m/z = 285.15($C_{21}H_{19}N$ = 285.38) |
| Sub 2-68 | m/z = 361.18($C_{27}H_{23}N$ = 361.48) | Sub 2-69 | m/z = 361.18($C_{27}H_{23}N$ = 361.48) |
| Sub 2-70 | m/z = 335.17($C_{25}H_{21}N$ = 335.44) | Sub 2-71 | m/z = 437.21($C_{33}H_{27}N$ = 437.57) |
| Sub 2-72 | m/z = 409.18($C_{31}H_{23}N$ = 409.52) | Sub 2-73 | m/z = 485.21($C_{37}H_{27}N$ = 485.62) |
| Sub 2-74 | m/z = 335.17($C_{25}H_{21}N$ = 335.44) | Sub 2-75 | m/z = 286.15($C_{20}H_{18}N_2$ = 286.37) |
| Sub 2-76 | m/z = 336.16($C_{24}H_{20}N_2$ = 336.43) | Sub 2-77 | m/z = 170.08($C_{11}H_{10}N_2$ = 170.21) |
| Sub 2-78 | m/z = 246.12($C_{17}H_{14}N_2$ = 246.31) | Sub 2-79 | m/z = 246.12($C_{17}H_{14}N_2$ = 246.31) |
| Sub 2-80 | m/z = 296.13($C_{21}H_{16}N_2$ = 296.37) | Sub 2-81 | m/z = 323.14($C_{22}H_{17}N_3$ = 323.39) |
| Sub 2-82 | m/z = 220.10($C_{15}H_{12}N_2$ = 220.27) | Sub 2-83 | m/z = 220.10($C_{15}H_{12}N_2$ = 220.27) |
| Sub 2-84 | m/z = 220.10($C_{15}H_{12}N_2$ = 220.27) | Sub 2-85 | m/z = 220.10($C_{15}H_{12}N_2$ = 220.27) |
| Sub 2-86 | m/z = 346.15($C_{25}H_{18}N_2$ = 346.42) | Sub 2-87 | m/z = 296.13($C_{21}H_{16}N_2$ = 296.37) |
| Sub 2-88 | m/z = 270.12($C_{19}H_{14}N_2$ = 270.33) | Sub 2-89 | m/z = 414.21($C_{31}H_{18}D_5N$ = 414.55) |

III. Synthesis Method of Final Product

Sub 2 (1 eq.) was dissolved in toluene in a round bottom flask, and Sub 1 (1.2 eq.), $Pd_2(dba)_3$ (0.03 eq.), $P(t-Bu)_3$ (0.08 eq.), NaOt-Bu (3 eq.) were added to the reaction solution, followed by stirring at 100° C. Upon completion of the reaction, the reaction product was extracted with $CH_2Cl_2$ and water. The extracted organic layer was dried with $MgSO_4$ and concentrated, and then the produced organic material was separated by a silica gel column and recrystallized to obtain Final Product.

1. Synthesis Method of Product B17

<Reaction Scheme 40>

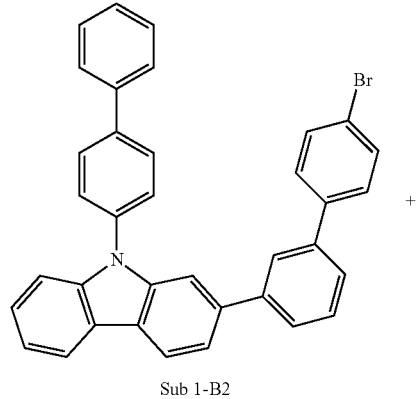

Sub 1-B2

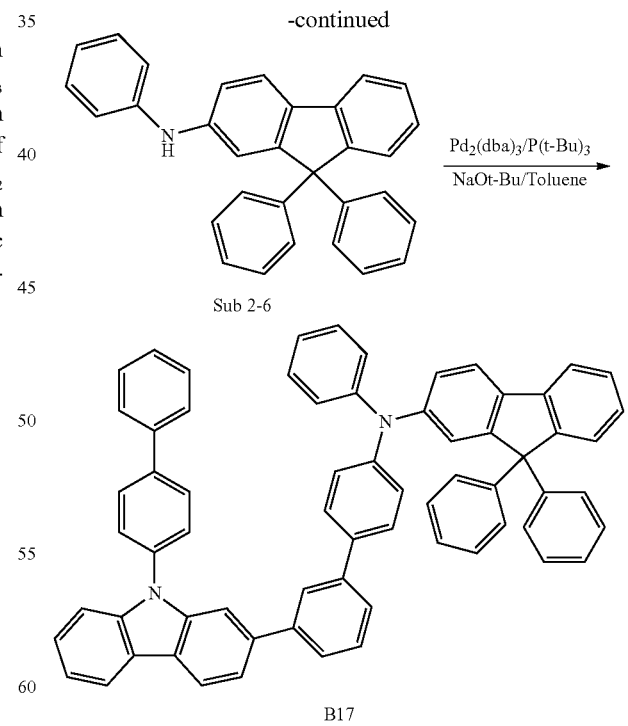

The obtained Sub 2-6 (6.39 g, 15.6 mmol) was dissolved in toluene in a round bottom flask, and Sub 1-B2 (10.31 g, 18.7 mmol), $Pd_2(dba)_3$ (0.43 g, 0.5 mmol), 50% $P(t-Bu)_3$ (0.6 ml, 1.2 mmol), and NaOt-Bu (4.5 g, 46.8 mmol) were added to the reaction solution, followed by stirring at 100° C. Upon completion of the reaction, the reaction product was extracted with CH₂Cl₂ and water. The extracted organic layer was dried with MgSO₄ and concentrated, and then the produced organic material was separated by a silica gel column and recrystallized to obtain 9.46 g of product (yield: 69%).

2. Synthesis Method of Product B21

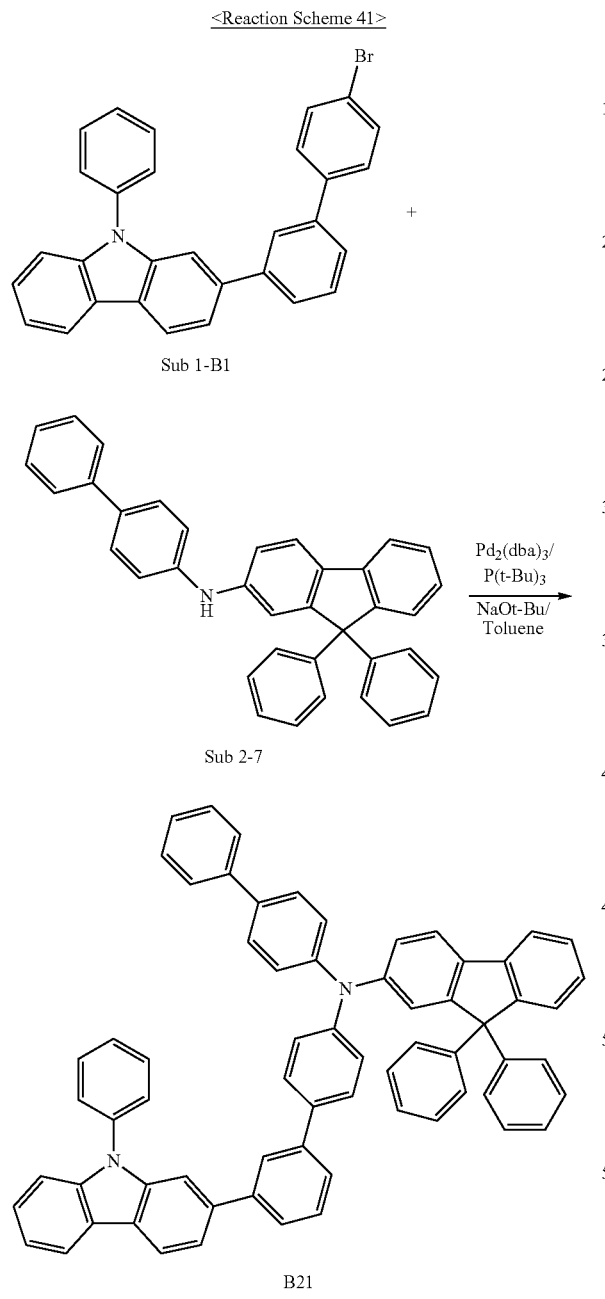

3. Synthesis Method of Product B145

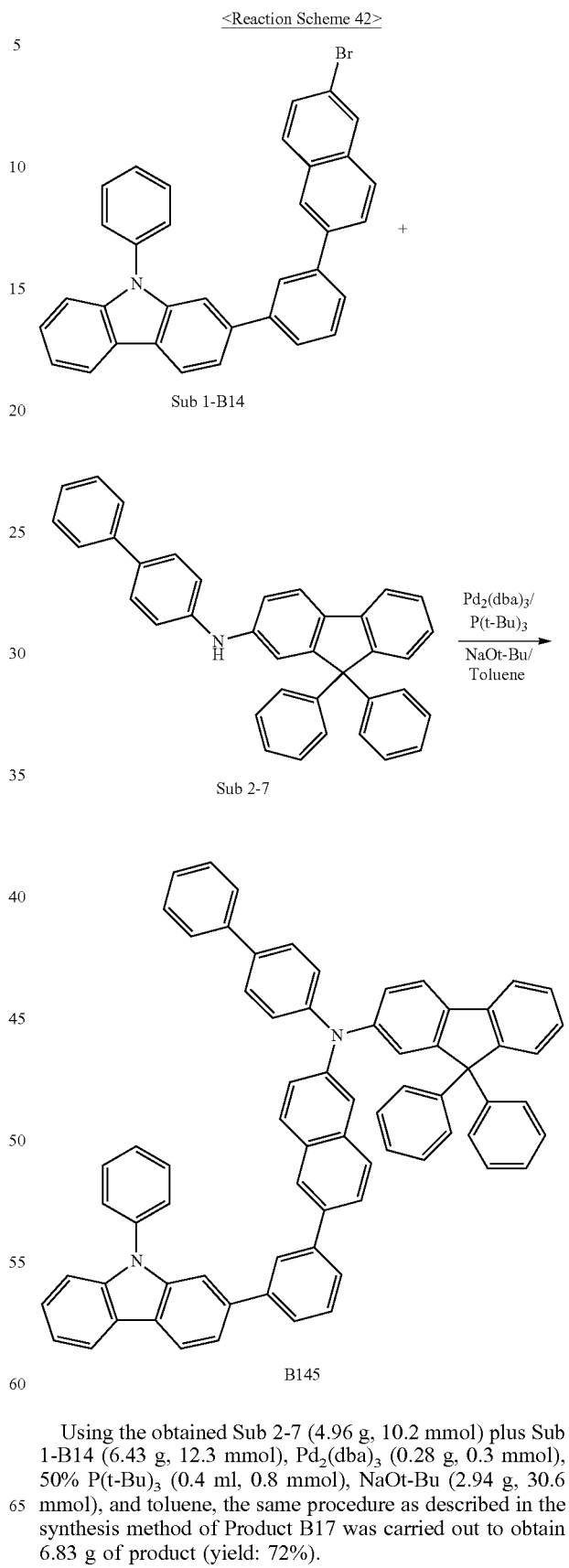

Using the obtained Sub 2-7 (5.18 g, 10.7 mmol) plus Sub 1-B1 (6.07 g, 12.8 mmol), Pd₂(dba)₃ (0.29 g, 0.3 mmol), 50% P(t-Bu)₃ (0.4 ml, 0.9 mmol), NaOt-Bu (3.08 g, 32 mmol), and toluene, the same procedure as described in the synthesis method of Product B17 was carried out to obtain 7.22 g of product (yield: 77%).

Using the obtained Sub 2-7 (4.96 g, 10.2 mmol) plus Sub 1-B14 (6.43 g, 12.3 mmol), Pd₂(dba)₃ (0.28 g, 0.3 mmol), 50% P(t-Bu)₃ (0.4 ml, 0.8 mmol), NaOt-Bu (2.94 g, 30.6 mmol), and toluene, the same procedure as described in the synthesis method of Product B17 was carried out to obtain 6.83 g of product (yield: 72%).

4. Synthesis Method of Product B179

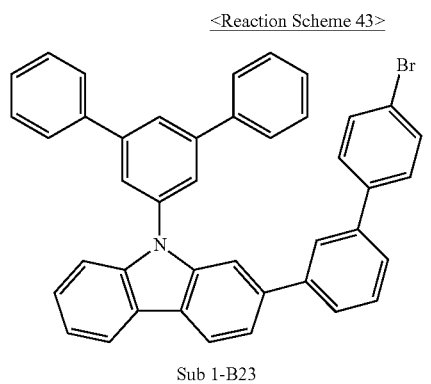

5. Synthesis Method of Product B187

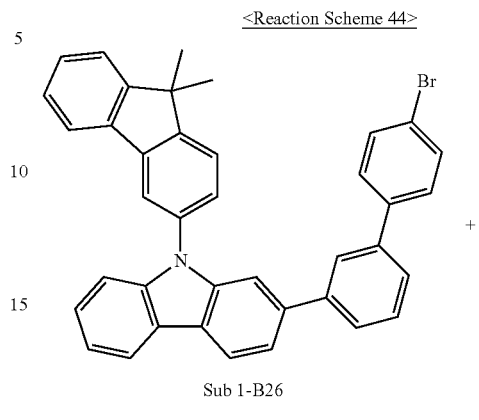

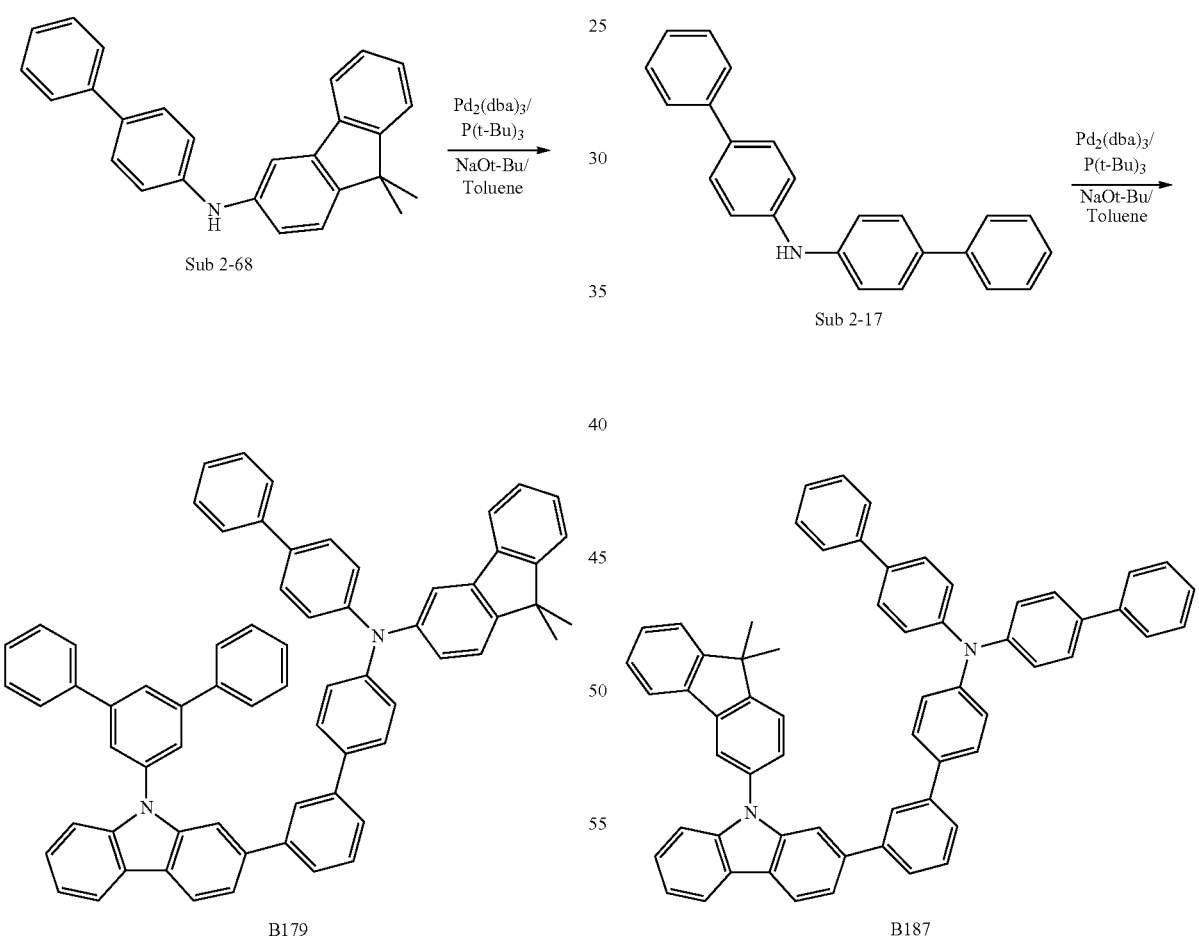

Using the obtained Sub 2-68 (3.91 g, 10.8 mmol) plus Sub 1-B23 (8.13 g, 13 mmol), Pd$_2$(dba)$_3$ (0.3 g, 0.3 mmol), 50% P(t-Bu)$_3$ (0.4 ml, 0.9 mmol), NaOt-Bu (3.12 g, 32.4 mmol), and toluene, the same procedure as described in the synthesis method of Product B17 was carried out to obtain 6.18 g of product (yield: 63%).

Using the obtained Sub 2-17 (3.64 g, 11.3 mmol) plus Sub 1-B26 (8.03 g, 13.6 mmol), Pd$_2$(dba)$_3$ (0.31 g, 0.3 mmol), 50% P(t-Bu)$_3$ (0.4 ml, 0.9 mmol), NaOt-Bu (3.27 g, 34 mmol), and toluene, the same procedure as described in the synthesis method of Product B17 was carried out to obtain 7.06 g of product (yield: 75%).

6. Synthesis Method of Product B200

<Reaction Scheme 45>

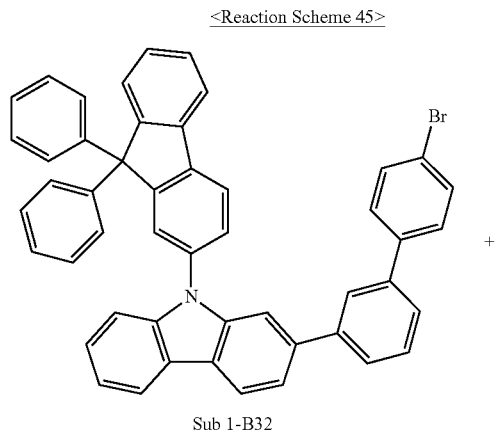

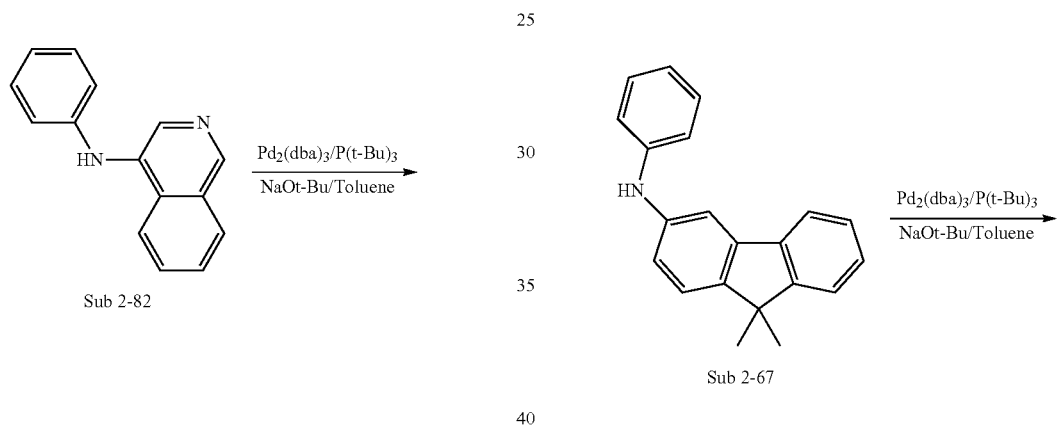

Using the obtained Sub 2-82 (2.76 g, 12.5 mmol) plus Sub 1-B32 (10.75 g, 15 mmol), Pd$_2$(dba)$_3$ (0.34 g, 0.4 mmol), 50% P(t-Bu)$_3$ (0.5 ml, 1 mmol), NaOt-Bu (3.61 g, 37.6 mmol), and toluene, the same procedure as described in the synthesis method of Product B17 was carried out to obtain 6.21 g of product (yield: 58%).

7. Synthesis Method of Product B204

<Reaction Scheme 46>

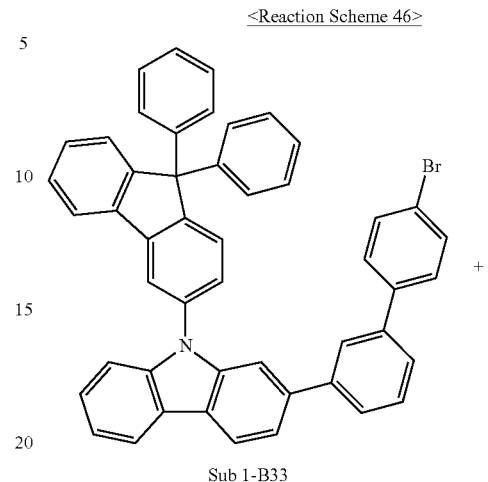

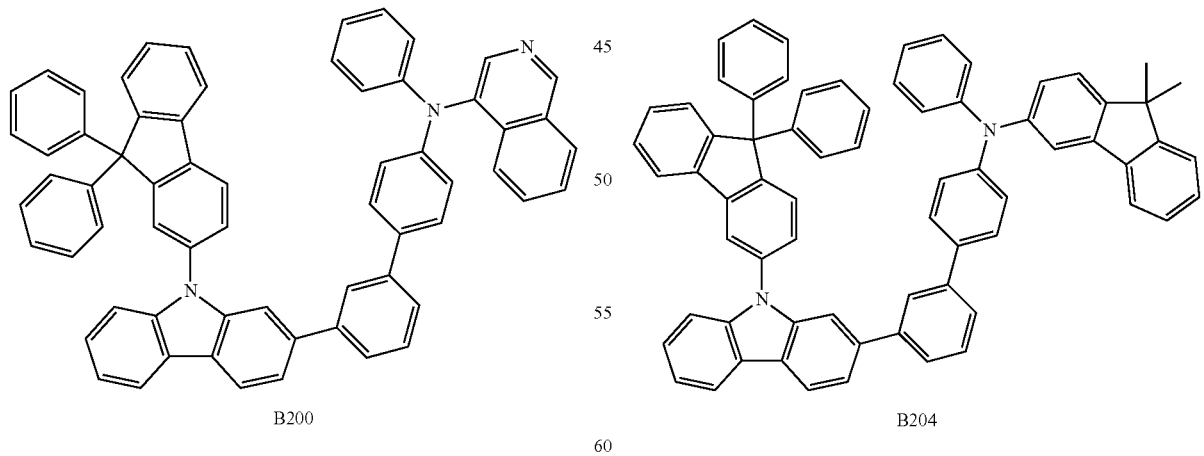

Using the obtained Sub 2-67 (3.07 g, 10.8 mmol) plus Sub 1-B33 (9.23 g, 12.9 mmol), Pd$_2$(dba)$_3$ (0.3 g, 0.3 mmol), 50% P(t-Bu)$_3$ (0.4 ml, 0.9 mmol), NaOt-Bu (3.1 g, 32.3 mmol), and toluene, the same procedure as described in the synthesis method of Product B17 was carried out to obtain 6.62 g of product (yield: 67%).

8. Synthesis Method of Product B210

<Reaction Scheme 47>

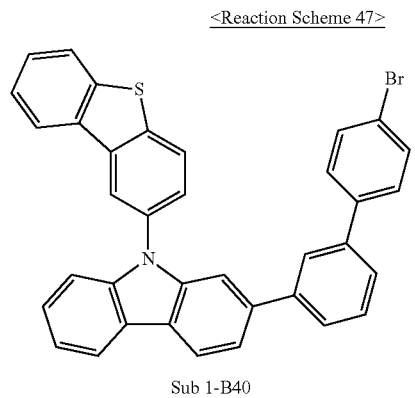

Sub 1-B40

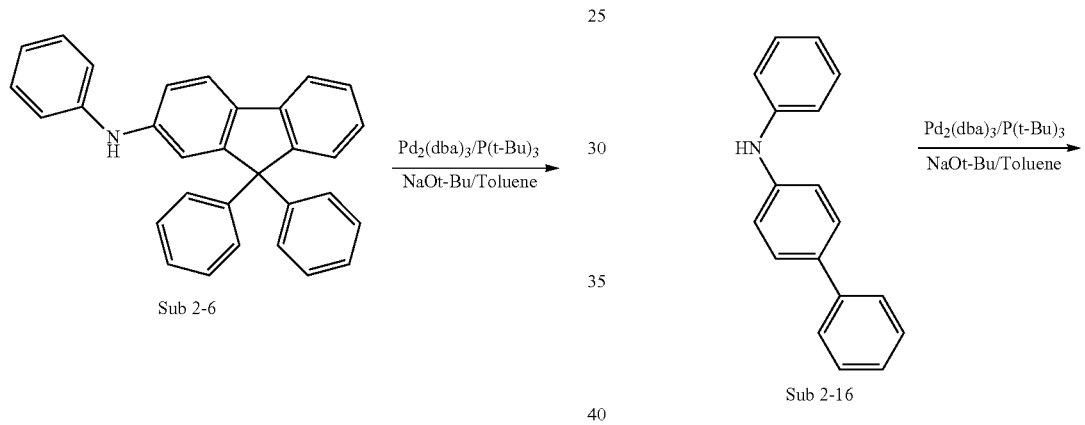

Sub 2-6

B210

Using the obtained Sub 2-6 (4.28 g, 10.5 mmol) plus Sub 1-B40 (7.28 g, 12.5 mmol), Pd$_2$(dba)$_3$ (0.29 g, 0.3 mmol), 50% P(t-Bu)$_3$ (0.4 ml, 0.8 mmol), NaOt-Bu (3.01 g, 31.4 mmol), and toluene, the same procedure as described in the synthesis method of Product B17 was carried out to obtain 6.75 g of product (yield: 71%).

9. Synthesis Method of Product B213

<Reaction Scheme 48>

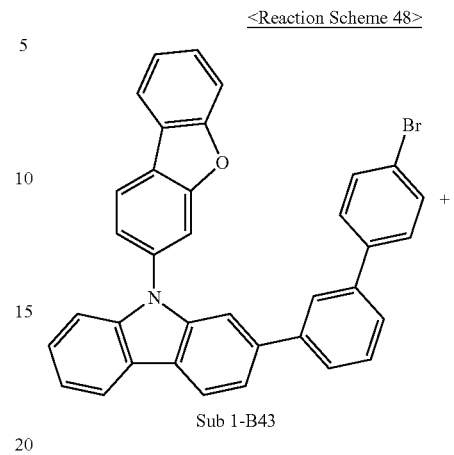

Sub 1-B43

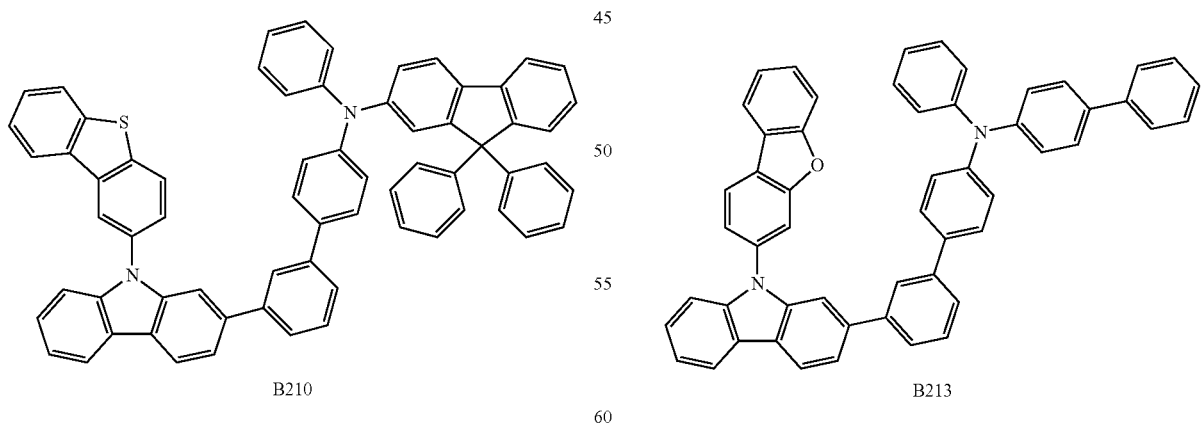

Sub 2-16

B213

Using the obtained Sub 2-16 (3.15 g, 12.8 mmol) plus Sub 1-B43 (8.7 g, 15.4 mmol), Pd$_2$(dba)$_3$ (0.35 g, 0.4 mmol), 50% P(t-Bu)$_3$ (0.5 ml, 1 mmol), NaOt-Bu (3.7 g, 38.5 mmol), and toluene, the same procedure as described in the synthesis method of Product B17 was carried out to obtain 6.93 g of product (yield: 74%).

10. Synthesis Method of Product B223

11. Synthesis Method of Product B245

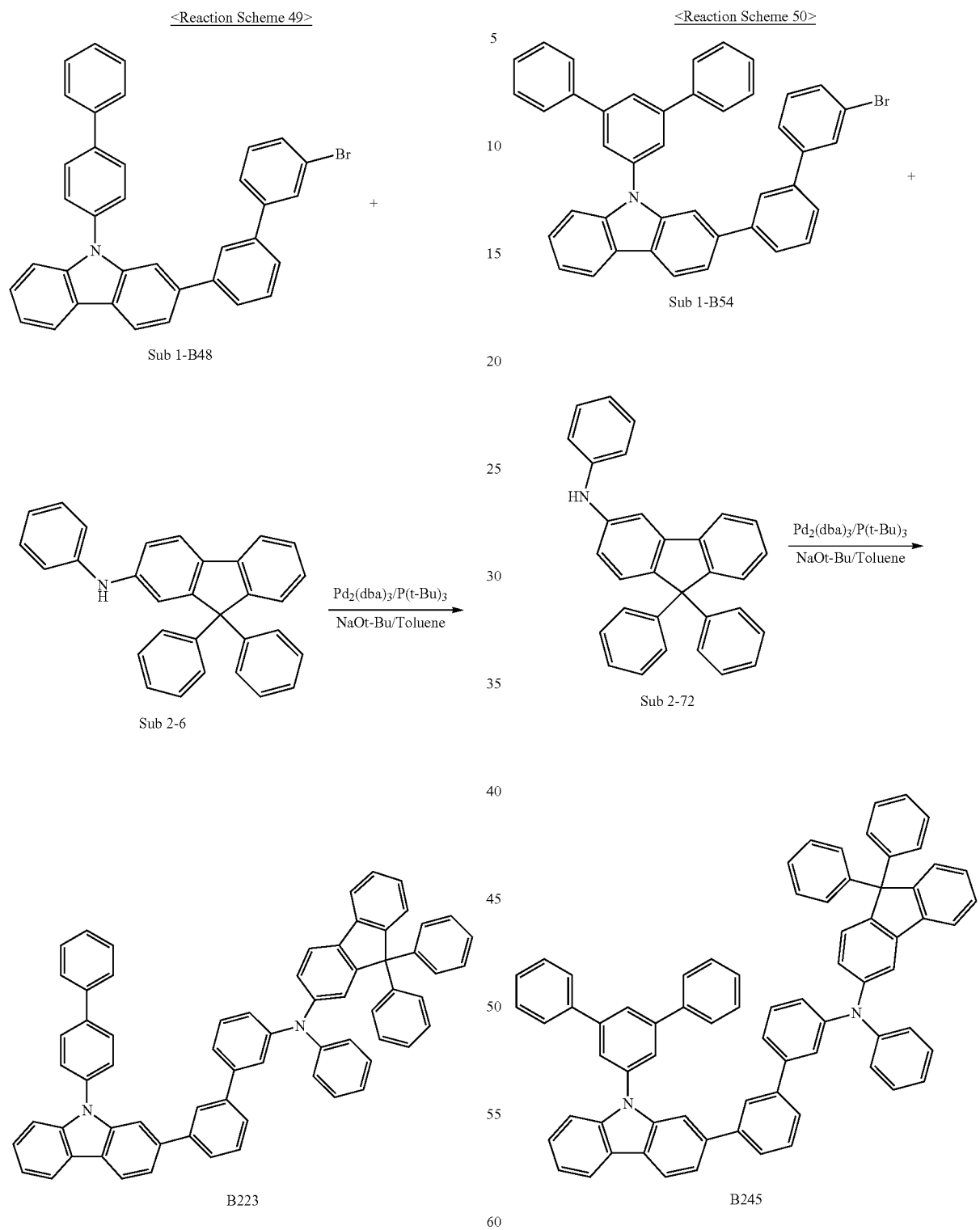

Using the obtained Sub 2-6 (4.47 g, 10.9 mmol) plus Sub 1-B48 (7.21 g, 13.1 mmol), $Pd_2(dba)_3$ (0.3 g, 0.3 mmol), 50% P(t-Bu)$_3$ (0.4 ml, 0.9 mmol), NaOt-Bu (3.15 g, 32.7 mmol), and toluene, the same procedure as described in the synthesis method of Product B17 was carried out to obtain 7.2 g of product (yield: 75%).

Using the obtained Sub 2-72 (4.32 g, 10.5 mmol) plus Sub 1-B54 (7.93 g, 12.7 mmol), $Pd_2(dba)_3$ (0.29 g, 0.3 mmol), 50% P(t-Bu)$_3$ (0.4 ml, 0.8 mmol), NaOt-Bu (3.04 g, 31.6 mmol), and toluene, the same procedure as described in the synthesis method of Product B17 was carried out to obtain 6.35 g of product (yield: 63%).

12. Synthesis Method of Product B253

<Reaction Scheme 51>

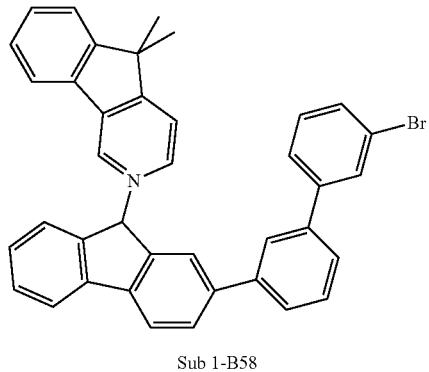

Sub 1-B58

+

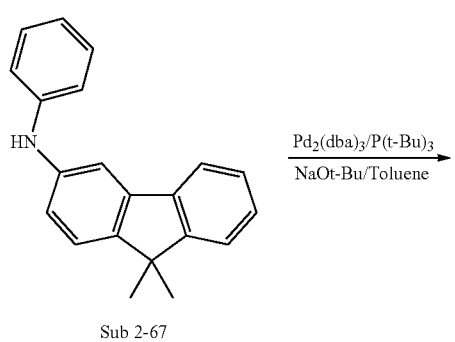

Sub 2-67

→ (Pd₂(dba)₃/P(t-Bu)₃, NaOt-Bu/Toluene)

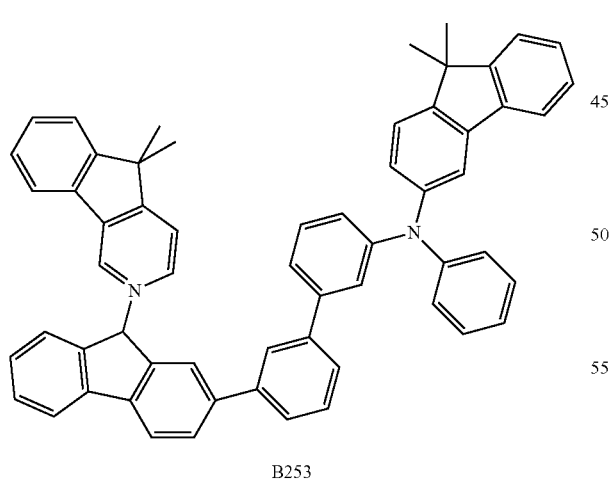

B253

Using the obtained Sub 2-67 (3.56 g, 12.5 mmol) plus Sub 1-B58 (8.84 g, 15 mmol), Pd₂(dba)₃ (0.34 g, 0.4 mmol), 50% P(t-Bu)₃ (0.5 ml, 1 mmol), NaOt-Bu (3.6 g, 37.4 mmol), and toluene, the same procedure as described in the synthesis method of Product B17 was carried out to obtain 7.44 g of product (yield: 75%).

13. Synthesis Method of Product B259

<Reaction Scheme 52>

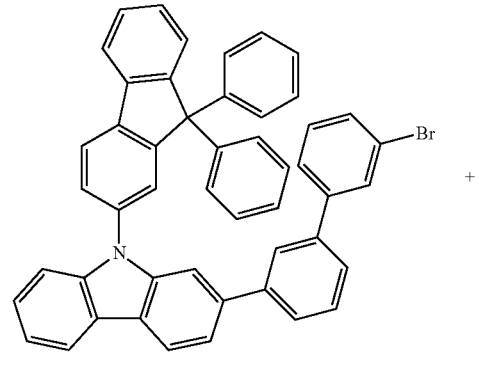

Sub 1-B61

+

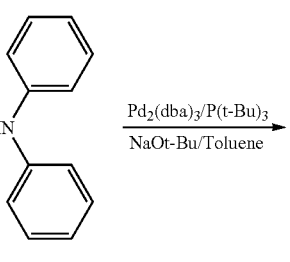

Sub 2-13

→ (Pd₂(dba)₃/P(t-Bu)₃, NaOt-Bu/Toluene)

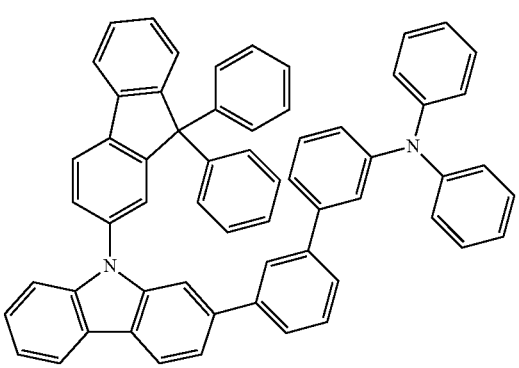

B259

Using the obtained Sub 2-13 (1.88 g, 11.1 mmol) plus Sub 1-B61 (9.53 g, 13.3 mmol), Pd₂(dba)₃ (0.31 g, 0.3 mmol), 50% P(t-Bu)₃ (0.4 ml, 0.9 mmol), NaOt-Bu (3.2 g, 33.3 mmol), and toluene, the same procedure as described in the synthesis method of Product B17 was carried out to obtain 6.96 g of product (yield: 78%).

14. Synthesis Method of Product B266

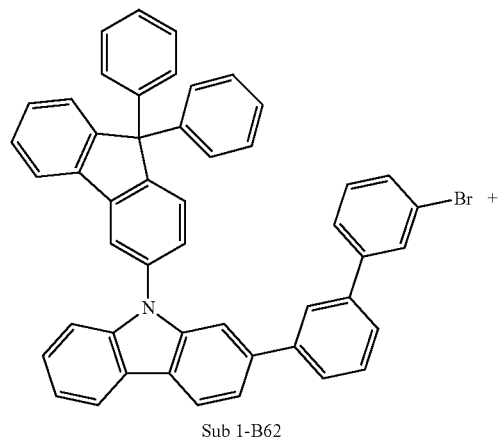

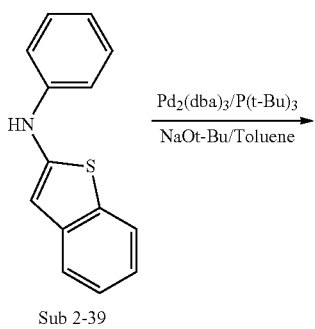

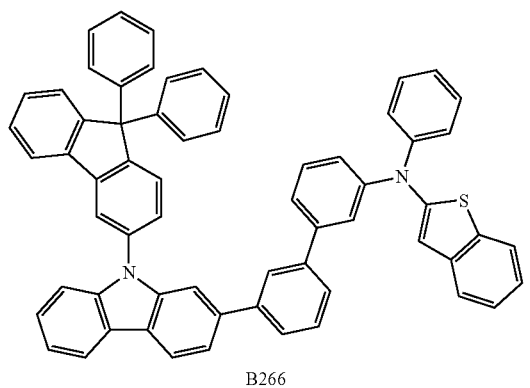

Using the obtained Sub 2-39 (2.56 g, 11.4 mmol) plus Sub 1-B62 (9.74 g, 13.6 mmol), $Pd_2(dba)_3$ (0.31 g, 0.3 mmol), 50% P(t-Bu)$_3$ (0.4 ml, 0.9 mmol), NaOt-Bu (3.28 g, 34.1 mmol), and toluene, the same procedure as described in the synthesis method of Product B17 was carried out to obtain 6.54 g of product (yield: 67%).

15. Synthesis Method of Product B273

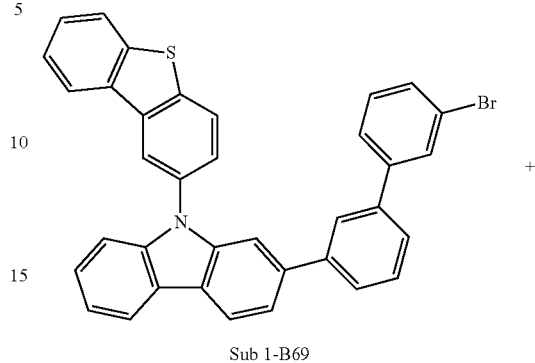

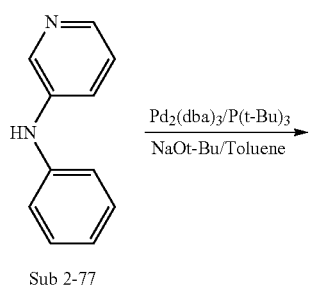

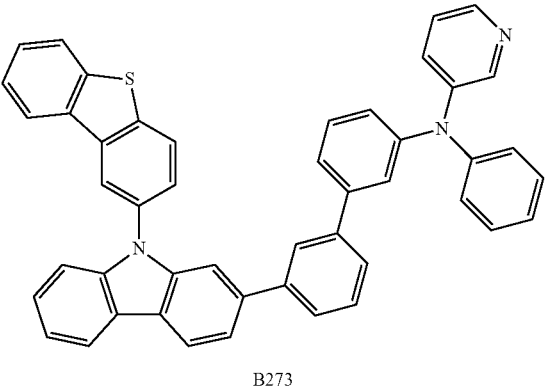

Using the obtained Sub 2-77 (2.83 g, 16.6 mmol) plus Sub 1-B69 (11.58 g, 20 mmol), $Pd_2(dba)_3$ (0.46 g, 0.5 mmol), 50% P(t-Bu)$_3$ (0.6 ml, 1.3 mmol), NaOt-Bu (4.79 g, 49.9 mmol), and toluene, the same procedure as described in the synthesis method of Product B17 was carried out to obtain 6.79 g of product (yield: 61%).

16. Synthesis Method of Product B278

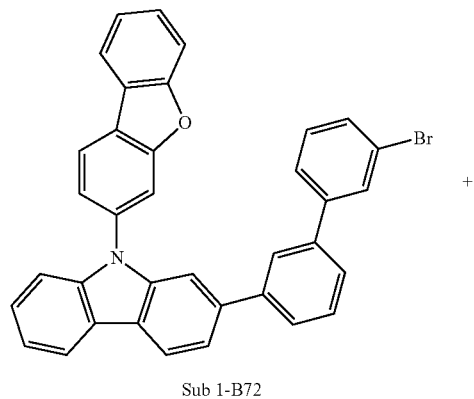

Sub 1-B72

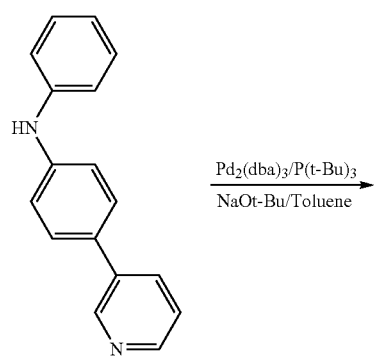

Sub 2-78

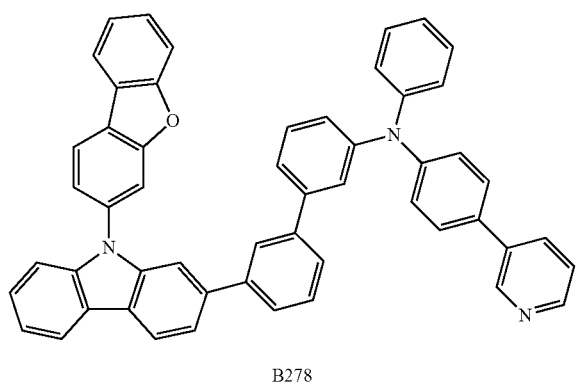

B278

Using the obtained Sub 2-78 (3.71 g, 15.1 mmol) plus Sub 1-B72 (10.2 g, 18.1 mmol), Pd$_2$(dba)$_3$ (0.41 g, 0.5 mmol), 50% P(t-Bu)$_3$ (0.6 ml, 1.2 mmol), NaOt-Bu (4.34 g, 45.2 mmol), and toluene, the same procedure as described in the synthesis method of Product B17 was carried out to obtain 6.93 g of product (yield: 63%).

17. Synthesis Method of Product B287

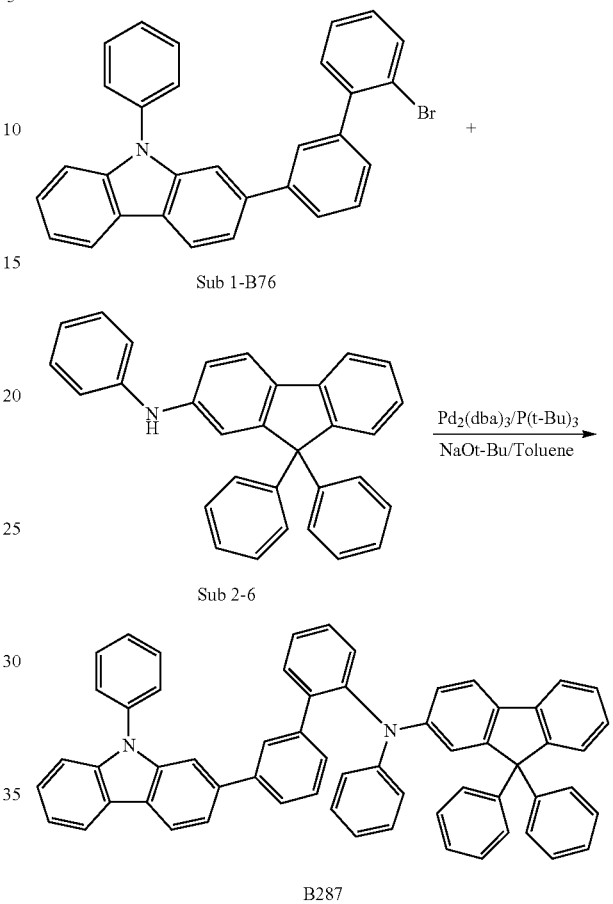

Using the obtained Sub 2-6 (4.97 g, 12.1 mmol) plus Sub 1-B76 (6.91 g, 14.6 mmol), Pd$_2$(dba)$_3$ (0.33 g, 0.4 mmol), 50% P(t-Bu)$_3$ (0.5 ml, 1 mmol), NaOt-Bu 3.5 g, 36.4 mmol), and toluene, the same procedure as described in the synthesis method of Product B17 was carried out to obtain 6.33 g of product (yield: 65%).

18. Synthesis Method of Product B322

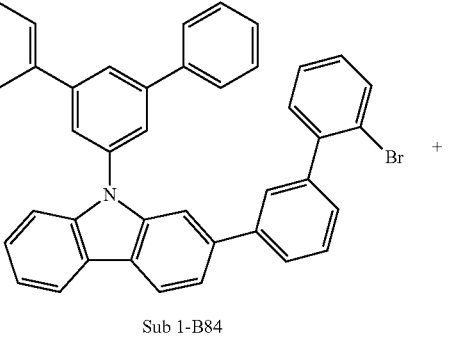

Sub 1-B84

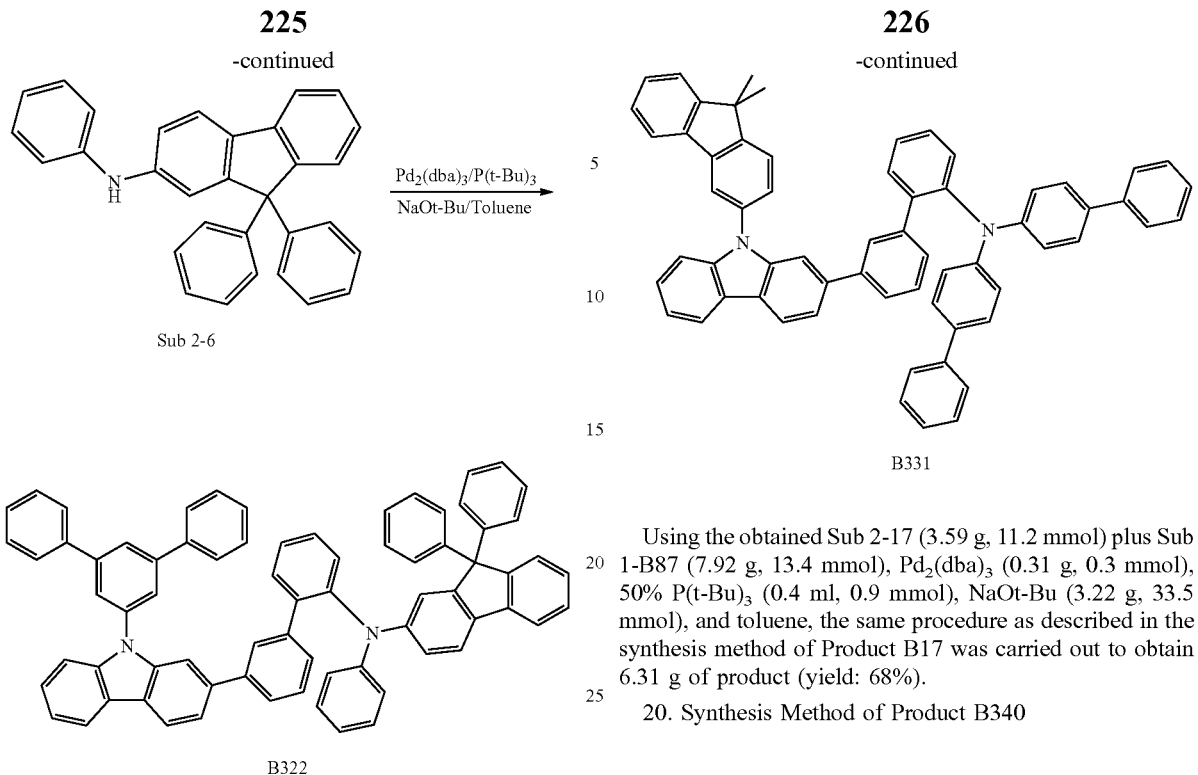

Using the obtained Sub 2-6 (4.72 g, 11.5 mmol) plus Sub 1-B84 (8.67 g, 13.8 mmol), Pd$_2$(dba)$_3$ (0.32 g, 0.3 mmol), 50% P(t-Bu)$_3$ (0.4 ml, 0.9 mmol), NaOt-Bu (3.32 g, 34.6 mmol), and toluene, the same procedure as described in the synthesis method of Product B17 was carried out to obtain 6.61 g of product (yield: 60%).

19. Synthesis Method of Product B331

Using the obtained Sub 2-17 (3.59 g, 11.2 mmol) plus Sub 1-B87 (7.92 g, 13.4 mmol), Pd$_2$(dba)$_3$ (0.31 g, 0.3 mmol), 50% P(t-Bu)$_3$ (0.4 ml, 0.9 mmol), NaOt-Bu (3.22 g, 33.5 mmol), and toluene, the same procedure as described in the synthesis method of Product B17 was carried out to obtain 6.31 g of product (yield: 68%).

20. Synthesis Method of Product B340

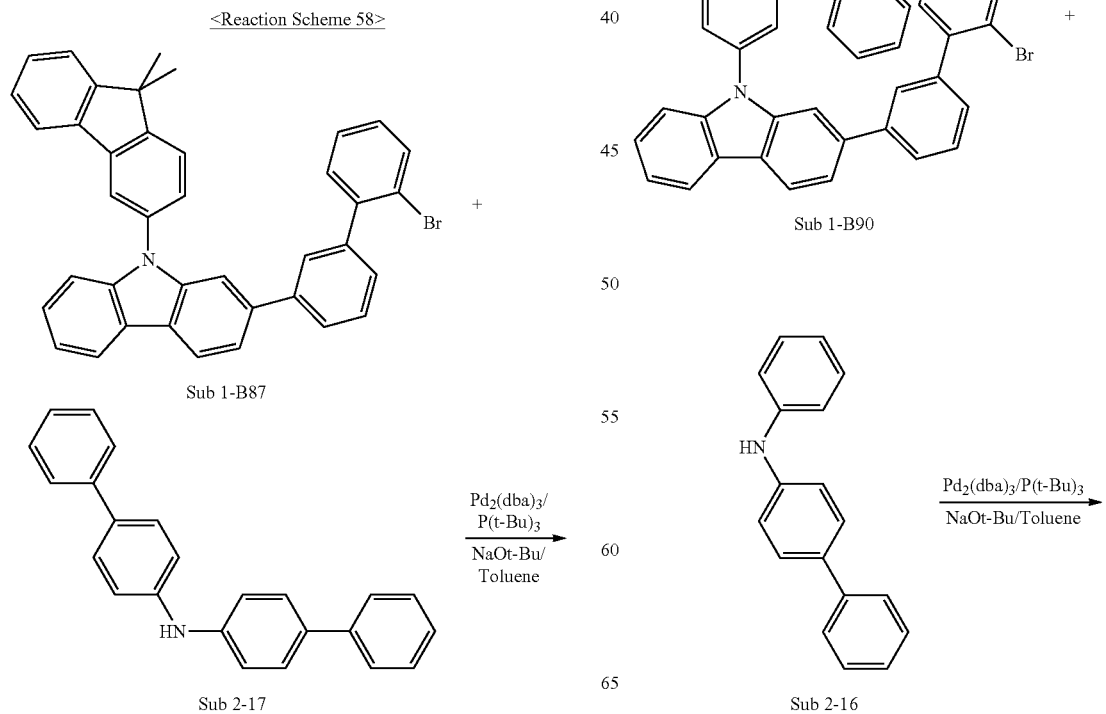

227
-continued

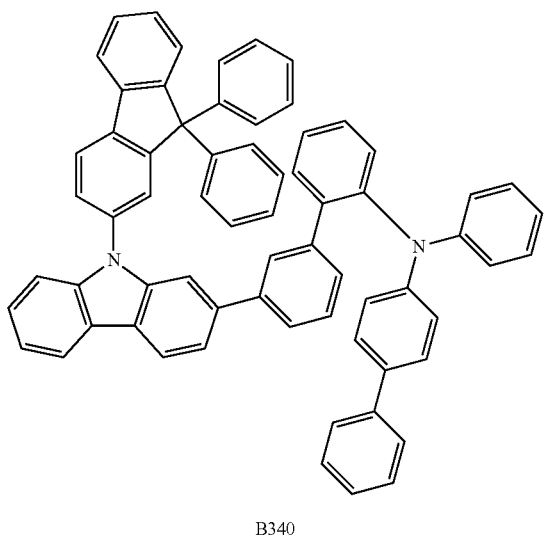

B340

Using the obtained Sub 2-16 (2.82 g, 11.5 mmol) plus Sub 1-B90 (9.86 g, 13.8 mmol), Pd$_2$(dba)$_3$ (0.32 g, 0.3 mmol), 50% P(t-Bu)$_3$ (0.4 ml, 0.9 mmol), NaOt-Bu (3.31 g, 34.5 mmol), and toluene, the same procedure as described in the synthesis method of Product B17 was carried out to obtain 6.37 g of product (yield: 63%).

21. Synthesis Method of Product B343

<Reaction Scheme 60>

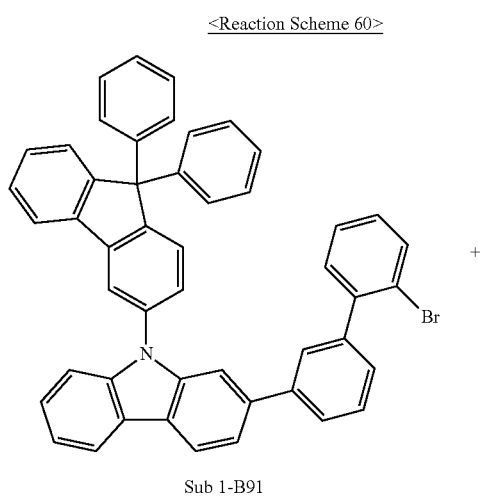

Sub 1-B91

228
-continued

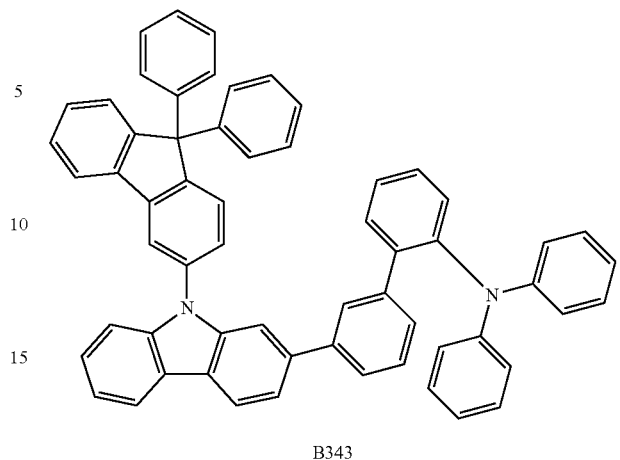

B343

Using the obtained Sub 2-13 (1.86 g, 11 mmol) plus Sub 1-B91 (9.43 g, 13.2 mmol), Pd$_2$(dba)$_3$ (0.3 g, 0.3 mmol), 50% P(t-Bu)$_3$ (0.4 ml, 0.9 mmol), NaOt-Bu (3.17 g, 33 mmol), and toluene, the same procedure as described in the synthesis method of Product B17 was carried out to obtain 6.27 g of product (yield: 71%).

22. Synthesis Method of Product B351

<Reaction Scheme 61>

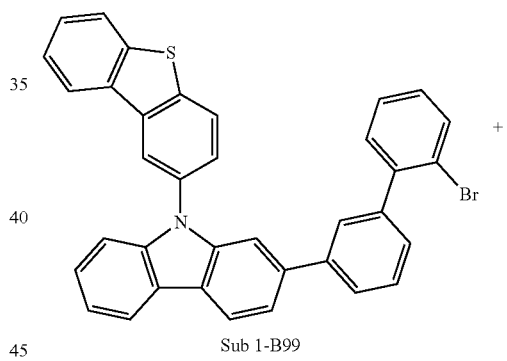

Sub 1-B99

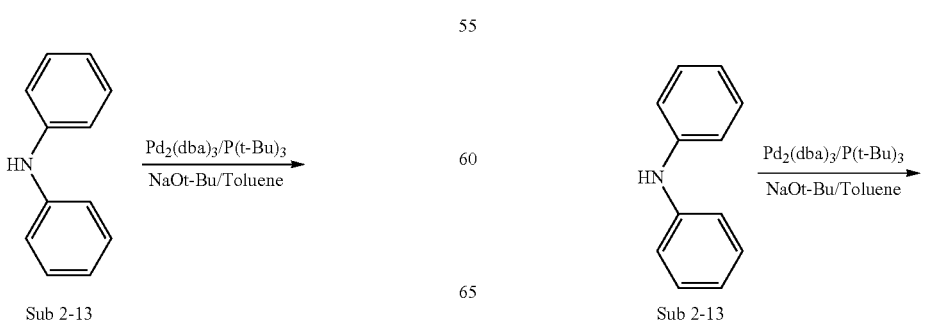

Sub 2-13                              Sub 2-13

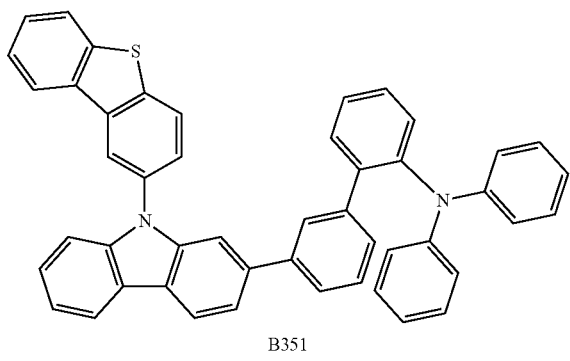

B351

Using the obtained Sub 2-13 (2.41 g, 14.2 mmol) plus Sub 1-B99 (9.92 g, 17.1 mmol), Pd$_2$(dba)$_3$ (0.39 g, 0.4 mmol), 50% P(t-Bu)$_3$ (0.6 ml, 1.1 mmol), NaOt-Bu (4.11 g, 42.7 mmol), and toluene, the same procedure as described in the synthesis method of Product B17 was carried out to obtain 6.48 g of product (yield: 68%).

23. Synthesis Method of Product B358

<Reaction Scheme 62>

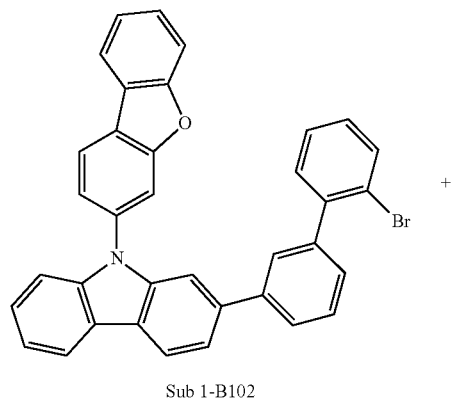

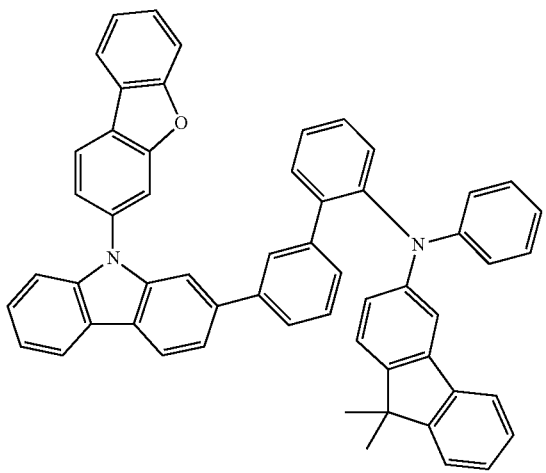

B358

Using the obtained Sub 2-67 (3.78 g, 13.2 mmol) plus Sub 1-B102 (8.97 g, 15.9 mmol), Pd$_2$(dba)$_3$ (0.36 g, 0.4 mmol), 50% P(t-Bu)$_3$ (0.5 ml, 1.1 mmol), NaOt-Bu (3.82 g, 39.7 mmol), and toluene, the same procedure as described in the synthesis method of Product B17 was carried out to obtain 6.31 g of product (yield: 62%).

24. Synthesis Method of Product B375

<Reaction Scheme 63>

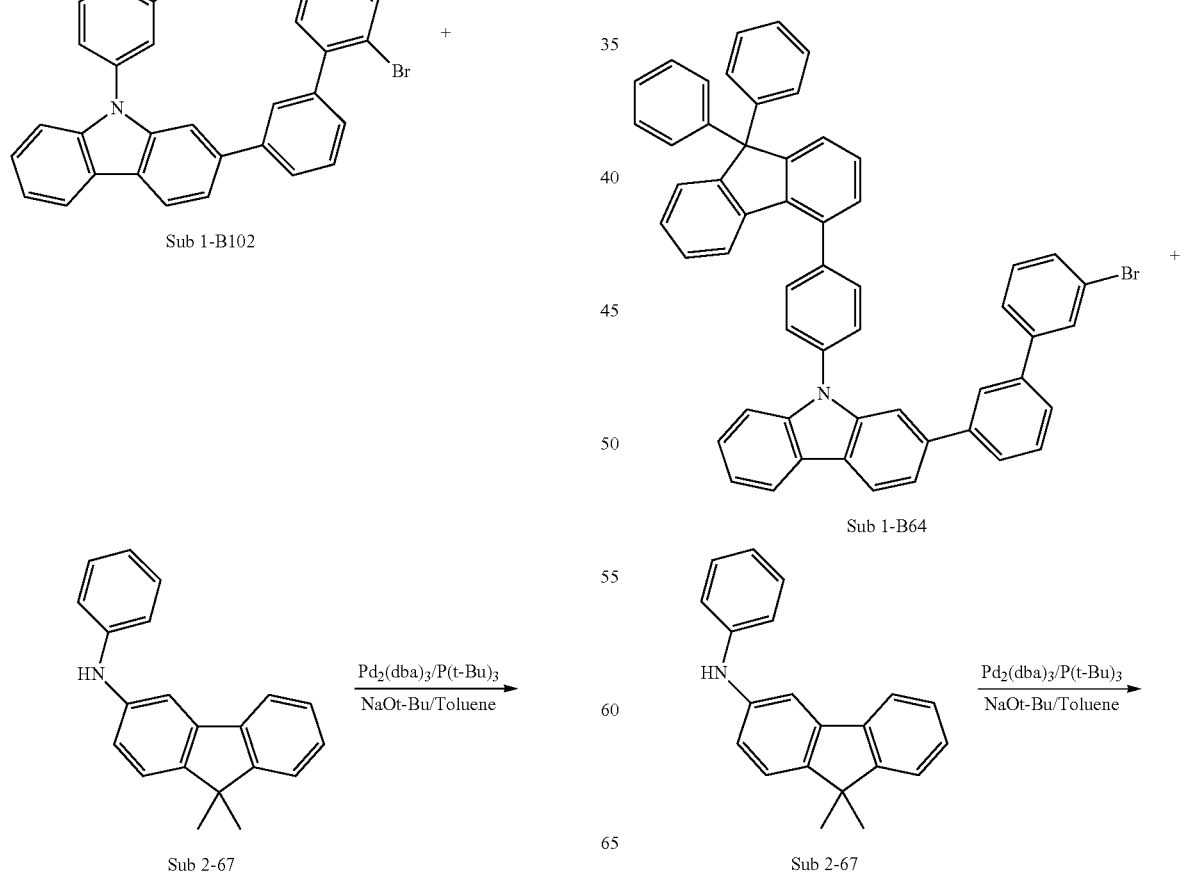

-continued

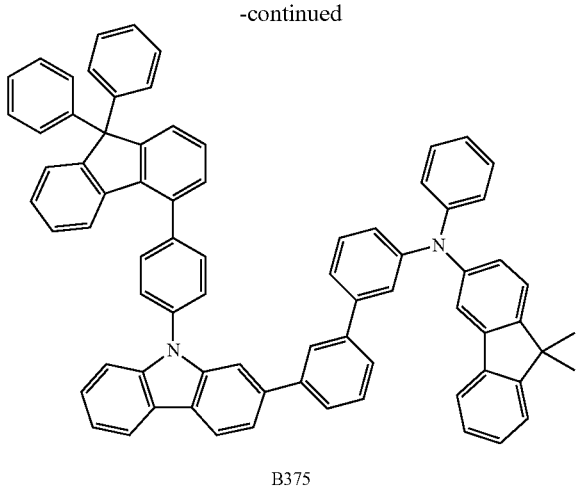

B375

Using the obtained Sub 2-67 (3.11 g, 10.9 mmol) plus Sub 1-B64 (10.34 g, 13.1 mmol), Pd₂(dba)₃ (0.3 g, 0.3 mmol), 50% P(t-Bu)₃ (0.4 ml, 0.9 mmol), NaOt-Bu (3.14 g, 32.7 mmol), and toluene, the same procedure as described in the synthesis method of Product B17 was carried out to obtain 6.18 g of product (yield: 57%).

25. Synthesis Method of Product C2

<Reaction Scheme 64>

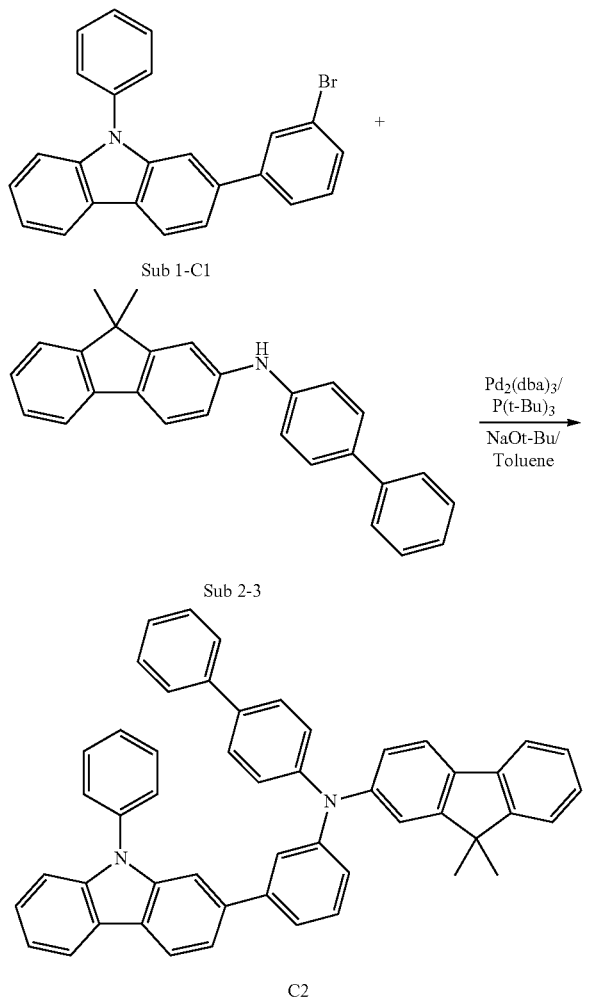

Using the obtained Sub 2-3 (6 g, 16.6 mmol) plus Sub 1-C1 (7.93 g, 19.9 mmol), Pd₂(dba)₃ (1.21 g, 1.3 mmol), 50% P(t-Bu)₃ (0.7 ml, 1.66 mmol), NaOt-Bu (73.03 g, 49.8 mmol), and toluene, the same procedure as described in the synthesis method of Product B17 was carried out to obtain 7.54 g of product (yield: 67%).

26. Synthesis Method of Product C8

<Reaction Scheme 65>

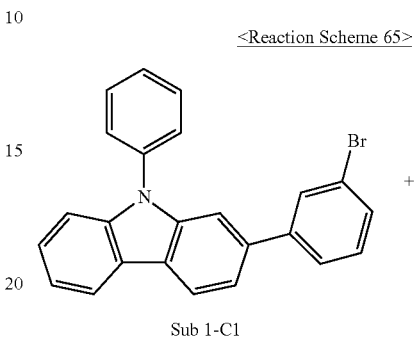

Sub 1-C1

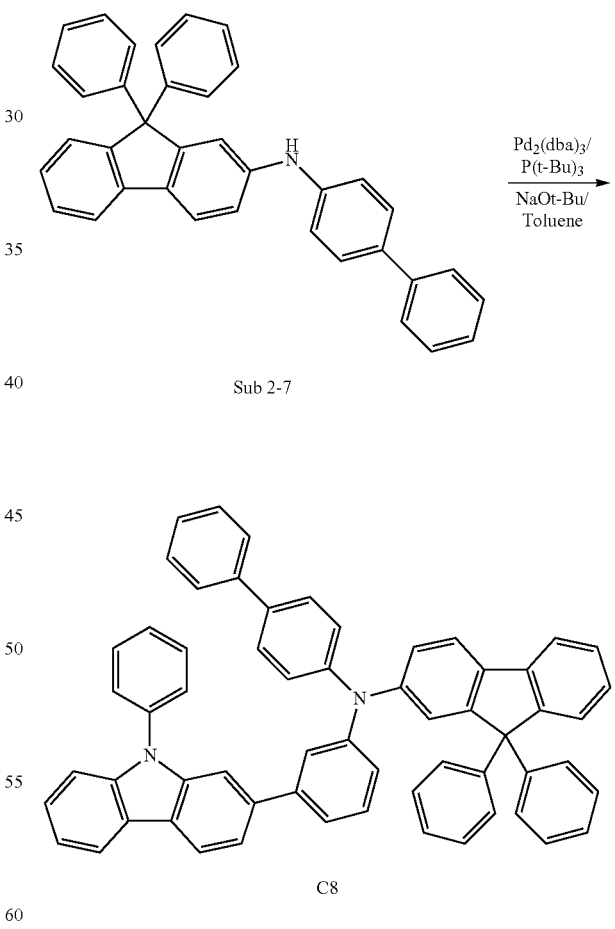

Using the obtained Sub 2-7 (5.18 g, 10.7 mmol) plus Sub 1-C1 (5.1 g, 12.8 mmol), Pd₂(dba)₃ (0.29 g, 0.3 mmol), 50% P(t-Bu)₃ (0.4 ml, 0.9 mmol), NaOt-Bu (3.08 g, 32 mmol), and toluene, the same procedure as described in the synthesis method of Product B17 was carried out to obtain 6.34 g of product (yield: 74%).

27. Synthesis Method of Product C21

<Reaction Scheme 66>

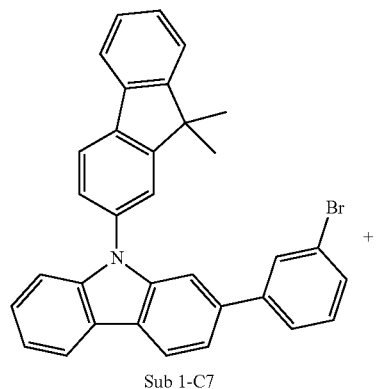

Sub 1-C7

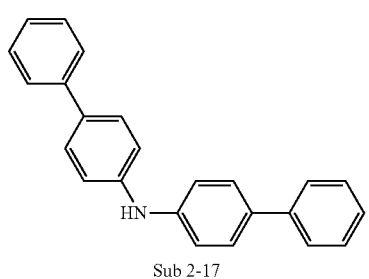

Sub 2-17

$\xrightarrow{\text{Pd}_2(\text{dba})_3/\text{P}(t\text{-Bu})_3}{\text{NaOt-Bu/Toluene}}$

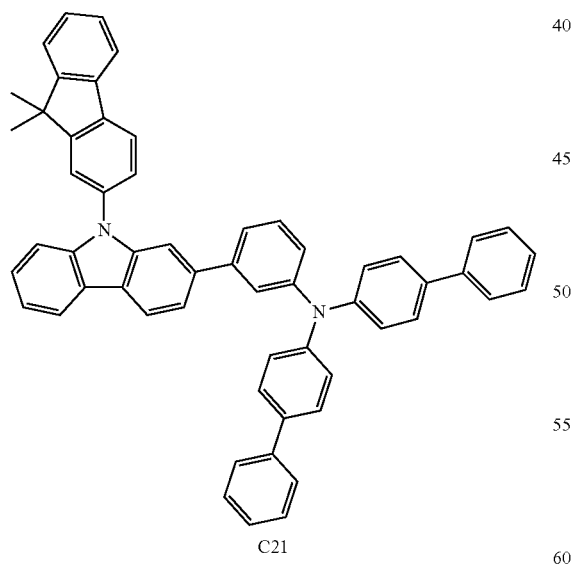

C21

Using the obtained Sub 2-17 (3.59 g, 11.2 mmol) plus Sub 1-C7 (6.9 g, 13.4 mmol), Pd$_2$(dba)$_3$ (0.31 g, 0.3 mmol), 50% P(t-Bu)$_3$ (0.4 ml, 0.9 mmol), NaOt-Bu (3.22 g, 33.5 mmol), and toluene, the same procedure as described in the synthesis method of Product B17 was carried out to obtain 6 g of product (yield: 71%).

28. Synthesis Method of Product C23

<Reaction Scheme 67>

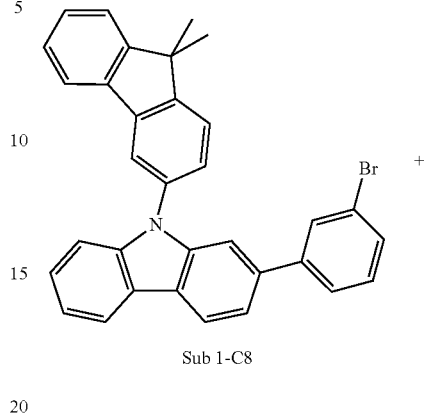

Sub 1-C8

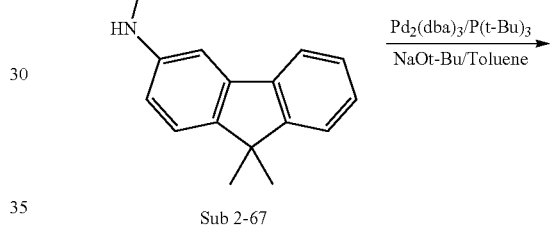

Sub 2-67

$\xrightarrow{\text{Pd}_2(\text{dba})_3/\text{P}(t\text{-Bu})_3}{\text{NaOt-Bu/Toluene}}$

C23

Using the obtained Sub 2-67 (3.56 g, 12.5 mmol) plus Sub 1-C8 (7.7 g, 15 mmol), Pd$_2$(dba)$_3$ (0.34 g, 0.4 mmol), 50% P(t-Bu)$_3$ (0.5 ml, 1 mmol), NaOt-Bu (3.6 g, 37.4 mmol), and toluene, the same procedure as described in the synthesis method of Product B17 was carried out to obtain 6.82 g of product (yield: 76%).

In Table 3 below, FD-MS data of the compounds B1 to B386 and C1 to C40 prepared in the Synthesis Examples of the present invention are given.

TABLE 3

| Compound | FD-MS | Compound | FD-MS |
|---|---|---|---|
| B1 | m/z = 678.30($C_{51}H_{38}N_2$ = 678.86) | B6 | m/z = 754.33($C_{57}H_{42}N_2$ = 754.96) |
| B7 | m/z = 830.37($C_{63}H_{46}N_2$ = 831.05) | B11 | m/z = 728.32($C_{55}H_{40}N_2$ = 728.92) |
| B12 | m/z = 804.35($C_{61}H_{44}N_2$ = 805.02) | B16 | m/z = 802.33($C_{61}H_{42}N_2$ = 803.00) |
| B17 | m/z = 878.37($C_{67}H_{46}N_2$ = 879.10) | B21 | m/z = 878.37($C_{67}H_{46}N_2$ = 879.10) |
| B22 | m/z = 954.40($C_{73}H_{50}N_2$ = 955.19) | B23 | m/z = 928.38($C_{71}H_{48}N_2$ = 929.15) |
| B24 | m/z = 928.38($C_{71}H_{48}N_2$ = 929.15) | B25 | m/z = 830.37($C_{63}H_{46}N_2$ = 831.05) |
| B26 | m/z = 852.35($C_{65}H_{44}N_2$ = 853.06) | B27 | m/z = 928.38($C_{71}H_{48}N_2$ = 929.15) |
| B31 | m/z = 800.32($C_{61}H_{40}N_2$ = 800.98) | B43 | m/z = 926.37($C_{71}H_{46}N_2$ = 927.14) |
| B47 | m/z = 714.30($C_{54}H_{38}N_2$ = 714.89) | B51 | m/z = 714.30($C_{54}H_{38}N_2$ = 714.89) |
| B62 | m/z = 764.32($C_{58}H_{40}N_2$ = 764.95) | B66 | m/z = 612.26($C_{46}H_{32}N_2$ = 612.76) |
| B86 | m/z = 662.27($C_{50}H_{34}N_2$ = 662.82) | B94 | m/z = 718.24($C_{52}H_{34}N_2$ = 718.90) |
| B106 | m/z = 728.28($C_{54}H_{36}N_2O$ = 728.88) | B122 | m/z = 820.29($C_{60}H_{40}N_2S$ = 821.04) |
| B124 | m/z = 638.27($C_{48}H_{34}N_2$ = 638.80) | B125 | m/z = 738.30($C_{56}H_{38}N_2$ = 738.91) |
| B127 | m/z = 729.31($C_{54}H_{39}N_3$ = 729.91) | B128 | m/z = 928.38($C_{71}H_{48}N_2$ = 929.15) |
| B129 | m/z = 790.33($C_{60}H_{42}N_2$ = 790.99) | B130 | m/z = 714.30($C_{54}H_{38}N_2$ = 714.89) |
| B132 | m/z = 804.35($C_{61}H_{44}N_2$ = 805.02) | B138 | m/z = 764.32($C_{58}H_{40}N_2$ = 764.95) |
| B145 | m/z = 928.38($C_{71}H_{48}N_2$ = 929.15) | B152 | m/z = 870.40($C_{66}H_{50}N_2$ = 871.12) |
| B157 | m/z = 802.33($C_{61}H_{42}N_2$ = 803.00) | B158 | m/z = 830.37($C_{63}H_{46}N_2$ = 831.05) |
| B161 | m/z = 696.29($C_{51}H_{37}FN_2$ = 696.85) | B162 | m/z = 718.33($C_{54}H_{42}N_2$ = 718.92) |
| B164 | m/z = 794.28($C_{58}H_{38}N_2S$ = 795.00) | B165 | m/z = 804.31($C_{60}H_{40}N_2O$ = 804.97) |
| B167 | m/z = 928.38($C_{71}H_{48}N_2$ = 929.15) | B168 | m/z = 954.40($C_{73}H_{50}N_2$ = 955.19) |
| B169 | m/z = 954.40($C_{73}H_{50}N_2$ = 955.19) | B170 | m/z = 852.35($C_{65}H_{44}N_2$ = 853.06) |
| B171 | m/z = 878.37($C_{67}H_{46}N_2$ = 879.10) | B172 | m/z = 928.38($C_{71}H_{48}N_2$ = 929.15) |
| B173 | m/z = 928.38($C_{71}H_{48}N_2$ = 929.15) | B174 | m/z = 754.33($C_{57}H_{42}N_2$ = 754.96) |
| B175 | m/z = 802.33($C_{61}H_{42}N_2$ = 803.00) | B176 | m/z = 878.37($C_{67}H_{46}N_2$ = 879.10) |
| B177 | m/z = 878.37($C_{67}H_{46}N_2$ = 879.10) | B178 | m/z = 714.30($C_{54}H_{38}N_2$ = 714.89) |
| B179 | m/z = 906.40($C_{69}H_{50}N_2$ = 907.15) | B180 | m/z = 954.40($C_{73}H_{50}N_2$ = 955.19) |
| B181 | m/z = 820.29($C_{60}H_{40}N_2S$ = 821.04) | B182 | m/z = 831.36($C_{62}H_{45}N_3$ = 832.04) |
| B183 | m/z = 830.37($C_{63}H_{46}N_2$ = 831.05) | B184 | m/z = 854.37($C_{65}H_{46}N_2$ = 855.07) |
| B185 | m/z = 994.43($C_{76}H_{54}N_2$ = 995.26) | B186 | m/z = 729.31($C_{54}H_{39}N_3$ = 729.91) |
| B187 | m/z = 830.37($C_{63}H_{46}N_2$ = 831.05) | B188 | m/z = 830.37($C_{63}H_{46}N_2$ = 831.05) |
| B189 | m/z = 794.37($C_{60}H_{46}N_2$ = 795.02) | B190 | m/z = 906.40($C_{69}H_{50}N_2$ = 907.15) |
| B191 | m/z = 830.37($C_{63}H_{46}N_2$ = 831.05) | B192 | m/z = 906.40($C_{69}H_{50}N_2$ = 907.15) |
| B193 | m/z = 755.33($C_{56}H_{41}N_3$ = 755.94) | B194 | m/z = 906.40($C_{69}H_{50}N_2$ = 907.15) |
| B195 | m/z = 802.33($C_{61}H_{42}N_2$ = 803.00) | B196 | m/z = 852.35($C_{65}H_{44}N_2$ = 853.06) |
| B197 | m/z = 878.37($C_{67}H_{46}N_2$ = 879.10) | B198 | m/z = 954.40($C_{73}H_{50}N_2$ = 955.19) |
| B199 | m/z = 918.40($C_{70}H_{50}N_2$ = 919.16) | B200 | m/z = 853.35($C_{64}H_{43}N_3$ = 854.05) |
| B201 | m/z = 802.33($C_{61}H_{42}N_2$ = 803.00) | B202 | m/z = 852.35($C_{65}H_{44}N_2$ = 853.06) |
| B203 | m/z = 878.37($C_{67}H_{46}N_2$ = 879.10) | B204 | m/z = 918.40($C_{70}H_{50}N_2$ = 919.16) |
| B205 | m/z = 877.35($C_{66}H_{43}N_3$ = 878.07) | B206 | m/z = 800.32($C_{61}H_{40}N_2$ = 800.98) |
| B207 | m/z = 768.26($C_{56}H_{36}N_2S$ = 768.96) | B208 | m/z = 936.35($C_{60}H_{40}N_2S$ = 937.20) |
| B209 | m/z = 820.29($C_{60}H_{40}N_2S$ = 821.04) | B210 | m/z = 908.32($C_{67}H_{44}N_2S$ = 909.14) |
| B211 | m/z = 822.28($C_{58}H_{38}N_4S$ = 823.01) | B212 | m/z = 794.28($C_{58}H_{30}N_2S$ = 795.00) |
| B213 | m/z = 728.28($C_{54}H_{36}N_2O$ = 728.88) | B214 | m/z = 742.26($C_{54}H_{34}N_2O_2$ = 742.86) |
| B215 | m/z = 829.31($C_{62}H_{30}N_3O$ = 829.98) | B216 | m/z = 782.33($C_{58}H_{42}N_2O$ = 782.97) |
| B217 | m/z = 652.25($C_{48}H_{32}N_2O$ = 652.78) | B218 | m/z = 942.36($C_{71}H_{46}N_2O$ = 943.14) |
| B219 | m/z = 754.33($C_{57}H_{42}N_2$ = 754.96) | B220 | m/z = 754.33($C_{57}H_{42}N_2$ = 754.96) |
| B221 | m/z = 802.33($C_{61}H_{42}N_2$ = 803.00) | B222 | m/z = 830.37($C_{63}H_{46}N_2$ = 831.05) |
| B223 | m/z = 878.37($C_{67}H_{46}N_2$ = 879.10) | B224 | m/z = 878.37($C_{67}H_{46}N_2$ = 879.10) |
| B225 | m/z = 954.40($C_{73}H_{50}N_2$ = 955.19) | B226 | m/z = 928.38($C_{72}H_{48}N_2$ = 929.15) |
| B227 | m/z = 852.35($C_{65}H_{44}N_2$ = 853.06) | B228 | m/z = 878.37($C_{67}H_{46}N_2$ = 879.10) |
| B229 | m/z = 878.37($C_{67}H_{46}N_2$ = 879.10) | B230 | m/z = 878.37($C_{67}H_{46}N_2$ = 879.10) |
| B231 | m/z = 562.24($C_{42}H_{30}N_2$ = 562.70) | B232 | m/z = 638.27($C_{48}H_{34}N_2$ = 638.80) |
| B233 | m/z = 638.27($C_{40}H_{34}N_2$ = 638.80) | B234 | m/z = 714.30($C_{54}H_{38}N_2$ = 714.89) |
| B235 | m/z = 954.40($C_{73}H_{50}N_2$ = 955.19) | B236 | m/z = 800.32($C_{61}H_{40}N_2$ = 800.98) |
| B237 | m/z = 779.29($C_{57}H_{37}N_3O$ = 779.92) | B238 | m/z = 802.33($C_{61}H_{42}N_2$ = 803.00) |
| B239 | m/z = 878.37($C_{67}H_{46}N_2$ = 879.10) | B240 | m/z = 878.37($C_{67}H_{46}N_2$ = 879.10) |
| B241 | m/z = 878.37($C_{67}H_{46}N_2$ = 879.10) | B242 | m/z = 866.37($C_{66}H_{46}N_2$ = 867.08) |
| B243 | m/z = 954.40($C_{73}H_{50}N_2$ = 955.19) | B244 | m/z = 880.38($C_{67}H_{48}N_2$ = 881.11) |
| B245 | m/z = 954.40($C_{73}H_{50}N_2$ = 955.19) | B246 | m/z = 820.29($C_{60}H_{40}N_2S$ = 821.04) |
| B247 | m/z = 896.32($C_{66}H_{44}N_2S$ = 897.13) | B248 | m/z = 754.33($C_{57}H_{42}N_2$ = 754.96) |
| B249 | m/z = 794.37($C_{60}H_{46}N_2$ = 795.02) | B250 | m/z = 679.30($C_{50}H_{37}N_3$ = 679.85) |
| B251 | m/z = 830.37($C_{63}H_{46}N_2$ = 831.05) | B252 | m/z = 830.37($C_{63}H_{46}N_2$ = 831.05) |
| B253 | m/z = 794.37($C_{60}H_{46}N_2$ = 795.02) | B254 | m/z = 818.33($C_{61}H_{42}N_2O$ = 819.00) |
| B255 | m/z = 728.32($C_{55}H_{40}N_2$ = 728.92) | B256 | m/z = 920.41($C_{70}H_{52}N_2$ = 921.18) |
| B257 | m/z = 729.31($C_{54}H_{30}N_3$ = 729.91) | B258 | m/z = 870.40($C_{66}H_{50}N_2$ = 871.12) |
| B259 | m/z = 802.33($C_{61}H_{42}N_2$ = 803.00) | B260 | m/z = 878.37($C_{67}H_{46}N_2$ = 879.10) |
| B261 | m/z = 918.40($C_{70}H_{50}N_2$ = 919.16) | B262 | m/z = 879.36($C_{66}H_{45}N_3$ = 880.08) |
| B263 | m/z = 802.33($C_{61}H_{42}N_2$ = 803.00) | B264 | m/z = 878.37($C_{67}H_{46}N_2$ = 879.10) |
| B265 | m/z = 918.40($C_{70}H_{50}N_2$ = 919.16) | B266 | m/z = 858.31($C_{63}H_{42}N_2S$ = 859.09) |
| B267 | m/z = 800.32($C_{61}H_{40}N_2$ = 800.98) | B268 | m/z = 916.38($C_{70}H_{48}N_2$ = 917.14) |
| B269 | m/z = 744.26($C_{54}H_{36}N_2S$ = 744.94) | B270 | m/z = 908.32($C_{67}H_{44}N_2S$ = 909.14) |
| B271 | m/z = 668.23($C_{40}H_{32}N_2S$ = 668.85) | B272 | m/z = 784.29($C_{57}H_{40}N_2S$ = 785.01) |
| B273 | m/z = 669.22($C_{47}H_{32}N_3S$ = 669.83) | B274 | m/z = 719.24($C_{52}H_{33}N_3S$ = 719.89) |
| B275 | m/z = 768.26($C_{56}H_{36}N_2S$ = 768.96) | B276 | m/z = 702.27($C_{52}H_{34}N_2O$ = 702.84) |
| B277 | m/z = 818.33($C_{61}H_{42}N_2O$ = 819.00) | B278 | m/z = 729.28($C_{53}H_{35}N_3O$ = 729.86) |
| B279 | m/z = 652.25($C_{48}H_{32}N_2O$ = 652.78) | B280 | m/z = 892.35($C_{67}H_{44}N_2O$ = 893.08) |
| B281 | m/z = 702.27($C_{52}H_{34}N_2O$ = 702.84) | B282 | m/z = 806.30($C_{50}H_{30}N_4O$ = 806.95) |

TABLE 3-continued

| Compound | FD-MS | Compound | FD-MS |
|---|---|---|---|
| B283 | m/z = 678.30($C_{51}H_{38}N_2$ = 678.86) | B284 | m/z = 754.33($C_{57}H_{42}N_2$ = 754.96) |
| B285 | m/z = 754.33($C_{57}H_{42}N_2$ = 754.96) | B286 | m/z = 830.37($C_{63}H_{46}N_2$ = 831.05) |
| B287 | m/z = 802.33($C_{61}H_{42}N_2$ = 803.00) | B288 | m/z = 878.37($C_{67}H_{46}N_2$ = 879.10) |
| B289 | m/z = 878.37($C_{67}H_{46}N_2$ = 879.10) | B290 | m/z = 954.40($C_{73}H_{50}N_2$ = 955.19) |
| B291 | m/z = 928.38($C_{72}H_{48}N_2$ = 929.15) | B292 | m/z = 928.38($C_{71}H_{48}N_2$ = 929.15) |
| B293 | m/z = 852.35($C_{65}H_{44}N_2$ = 853.06) | B294 | m/z = 928.38($C_{71}H_{48}N_2$ = 929.15) |
| B295 | m/z = 562.24($C_{42}H_{30}N_2$ = 562.70) | B296 | m/z = 638.27($C_{48}H_{34}N_2$ = 638.80) |
| B297 | m/z = 638.27($C_{40}H_{34}N_2$ = 638.80) | B298 | m/z = 714.30($C_{54}H_{38}N_2$ = 714.89) |
| B299 | m/z = 714.30($C_{54}H_{38}N_2$ = 714.89) | B300 | m/z = 790.33($C_{60}H_{42}N_2$ = 790.99) |
| B301 | m/z = 878.37($C_{67}H_{46}N_2$ = 879.10) | B302 | m/z = 954.40($C_{73}H_{50}N_2$ = 955.19) |
| B303 | m/z = 892.38($C_{68}H_{48}N_2$ = 893.12) | B304 | m/z = 830.37($C_{63}H_{46}N_2$ = 831.05) |
| B305 | m/z = 838.32($C_{61}H_{40}F_2N_2$ = 838.98) | B306 | m/z = 883.40($C_{67}H_{41}D_5N_2$ = 884.13) |
| B307 | m/z = 928.38($C_{71}H_{48}N_2$ = 929.15) | B308 | m/z = 1030.43($C_{79}H_{54}N_2$ = 1031.29) |
| B309 | m/z = 878.37($C_{67}H_{46}N_2$ = 879.10) | B310 | m/z = 954.40($C_{73}H_{50}N_2$ = 955.19) |
| B311 | m/z = 878.37($C_{67}H_{46}N_2$ = 879.10) | B312 | m/z = 928.38($C_{72}H_{40}N_2$ = 929.15) |
| B313 | m/z = 802.33($C_{61}H_{42}N_2$ = 803.00) | B314 | m/z = 878.37($C_{67}H_{46}N_2$ = 879.10) |
| B315 | m/z = 878.37($C_{67}H_{46}N_2$ = 879.10) | B316 | m/z = 878.37($C_{67}H_{46}N_2$ = 879.10) |
| B317 | m/z = 744.26($C_{54}H_{36}N_2S$ = 744.94) | B318 | m/z = 614.27($C_{46}H_{34}N_2$ = 614.78) |
| B319 | m/z = 765.31($C_{57}H_{39}N_3$ = 765.94) | B320 | m/z = 814.33($C_{62}H_{42}N_2$ = 815.01) |
| B321 | m/z = 906.40($C_{69}H_{50}N_2$ = 907.15) | B322 | m/z = 954.40($C_{73}H_{50}N_2$ = 955.19) |
| B323 | m/z = 1028.41($C_{79}H_{52}N_2$ = 1029.27) | B324 | m/z = 881.38($C_{66}H_{47}N_3$ = 882.10) |
| B325 | m/z = 954.40($C_{73}H_{50}N_2$ = 955.19) | B326 | m/z = 854.33($C_{64}H_{42}N_2O$ = 855.03) |
| B327 | m/z = 714.30($C_{54}H_{38}N_2$ = 714.89) | B328 | m/z = 830.37($C_{63}H_{46}N_2$ = 831.05) |
| B329 | m/z = 918.40($C_{70}H_{50}N_2$ = 919.16) | B330 | m/z = 805.35($C_{60}H_{43}N_3$ = 806.00) |
| B331 | m/z = 830.37($C_{63}H_{46}N_2$ = 831.05) | B332 | m/z = 830.37($C_{63}H_{46}N_2$ = 831.05) |
| B333 | m/z = 844.38($C_{64}H_{48}N_2$ = 845.08) | B334 | m/z = 834.31($C_{61}H_{42}N_2S$ = 835.06) |
| B335 | m/z = 778.33($C_{59}H_{42}N_2$ = 778.98) | B336 | m/z = 946.43($C_{72}H_{54}N_2$ = 947.21) |
| B337 | m/z = 869.38($C_{65}H_{47}N_3$ = 870.09) | B338 | m/z = 870.40($C_{66}H_{50}N_2$ = 871.12) |
| B339 | m/z = 852.35($C_{65}H_{44}N_2$ = 853.06) | B340 | m/z = 878.37($C_{67}H_{46}N_2$ = 879.10) |
| B341 | m/z = 994.43($C_{76}H_{54}N_2$ = 995.26) | B342 | m/z = 903.36($C_{68}H_{45}N_3$ = 904.10) |
| B343 | m/z = 802.33($C_{61}H_{42}N_2$ = 803.00) | B344 | m/z = 878.37($C_{67}H_{46}N_2$ = 879.10) |
| B345 | m/z = 918.40($C_{70}H_{50}N_2$ = 919.16) | B346 | m/z = 884.32($C_{65}H_{44}N_2S$ = 885.12) |
| B347 | m/z = 916.38($C_{70}H_{48}N_2$ = 917.14) | B348 | m/z = 850.33($C_{65}H_{42}N_2$ = 851.04) |
| B349 | m/z = 744.26($C_{54}H_{36}N_2S$ = 744.94) | B350 | m/z = 908.32($C_{67}H_{44}N_2S$ = 909.14) |
| B351 | m/z = 668.23($C_{48}H_{32}N_2S$ = 668.85) | B352 | m/z = 745.26($C_{53}H_{35}N_3S$ = 745.93) |
| B353 | m/z = 774.22($C_{54}H_{34}N_2S_2$ = 774.99) | B354 | m/z = 820.29($C_{60}H_{40}N_2S$ = 821.04) |
| B355 | m/z = 908.32($C_{67}H_{44}N_2S$ = 909.14) | B356 | m/z = 804.31($C_{60}H_{40}N_2O$ = 804.97) |
| B357 | m/z = 729.28($C_{53}H_{35}N_3O$ = 729.86) | B358 | m/z = 768.31($C_{57}H_{40}N_2O$ = 768.94) |
| B359 | m/z = 752.28($C_{56}H_{36}N_2O$ = 752.90) | B360 | m/z = 892.35($C_{67}H_{44}N_2O$ = 893.08) |
| B361 | m/z = 818.33($C_{61}H_{42}N_2O$ = 819.00) | B362 | m/z = 792.28($C_{58}H_{36}N_2O_2$ = 792.92) |
| B363 | m/z = 804.31($C_{60}H_{40}N_2O$ = 804.97) | B364 | m/z = 806.30($C_{58}H_{38}N_4O$ = 806.95) |
| B365 | m/z = 802.33($C_{61}H_{42}N_2$ = 803.00) | B366 | m/z = 918.40($C_{70}H_{50}N_2$ = 919.16) |
| B367 | m/z = 908.32($C_{67}H_{44}N_2S$ = 909.14) | B368 | m/z = 852.35($C_{65}H_{44}N_2$ = 853.06) |
| B369 | m/z = 918.40($C_{70}H_{50}N_2$ = 919.16) | B370 | m/z = 803.33($C_{60}H_{41}N_3$ = 803.99) |
| B371 | m/z = 878.37($C_{67}H_{46}N_2$ = 879.10) | B372 | m/z = 954.40($C_{73}H_{50}N_2$ = 955.19) |
| B373 | m/z = 968.41($C_{74}H_{52}N_2$ = 969.22) | B374 | m/z = 853.35($C_{64}H_{43}N_3$ = 854.05) |
| B375 | m/z = 994.43($C_{76}H_{54}N_2$ = 995.26) | B376 | m/z = 902.37($C_{69}H_{46}N_2$ = 903.12) |
| B377 | m/z = 918.40($C_{70}H_{50}N_2$ = 919.16) | B378 | m/z = 892.35($C_{67}H_{44}N_2O$ = 893.08) |
| B379 | m/z = 802.33($C_{61}H_{42}N_2$ = 803.00) | B380 | m/z = 1042.43($C_{80}H_{54}N_2$ = 1043.30) |
| B381 | m/z = 853.35($C_{64}H_{43}N_3$ = 854.05) | B382 | m/z = 994.43($C_{76}H_{54}N_2$ = 995.26) |
| B383 | m/z = 878.37($C_{67}H_{46}N_2$ = 879.10) | B384 | m/z = 994.43($C_{76}H_{54}N_2$ = 995.26) |
| B385 | m/z = 884.32($C_{65}H_{44}N_2S$ = 885.12) | B386 | m/z = 994.43($C_{76}H_{54}N_2$ = 995.26) |
| C1 | m/z = 602.27($C_{45}H_{34}N_2$ = 602.76) | C2 | m/z = 678.30($C_{51}H_{38}N_2$ = 678.86) |
| C3 | m/z = 754.33($C_{57}H_{42}N_2$ = 754.96) | C4 | m/z = 652.29($C_{49}H_{36}N_2$ = 652.82) |
| C5 | m/z = 728.32($C_{55}H_{40}N_2$ = 728.92) | C6 | m/z = 726.30($C_{55}H_{38}N_2$ = 726.90) |
| C7 | m/z = 802.33($C_{61}H_{42}N_2$ = 803.00) | C8 | m/z = 802.33($C_{61}H_{42}N_2$ = 803.00) |
| C9 | m/z = 852.35($C_{65}H_{44}N_2$ = 853.06) | C10 | m/z = 852.35($C_{65}H_{44}N_2$ = 853.06) |
| C11 | m/z = 852.35($C_{65}H_{44}N_2$ = 853.06) | C12 | m/z = 724.29($C_{55}H_{36}N_2$ = 724.89) |
| C13 | m/z = 638.27($C_{48}H_{34}N_2$ = 638.80) | C14 | m/z = 638.27($C_{48}H_{34}N_2$ = 638.80) |
| C15 | m/z = 688.29($C_{52}H_{36}N_2$ = 688.86) | C16 | m/z = 536.23($C_{40}H_{28}N_2$ = 536.66) |
| C17 | m/z = 586.24($C_{44}H_{30}N_2$ = 586.72) | C18 | m/z = 642.21($C_{46}H_{30}N_2S$ = 642.81) |
| C19 | m/z = 652.25($C_{48}H_{32}N_2O$ = 652.78) | C20 | m/z = 744.26($C_{54}H_{36}N_2S$ = 744.94) |
| C21 | m/z = 754.33($C_{57}H_{42}N_2$ = 754.96) | C22 | m/z = 778.33($C_{59}H_{42}N_2$ = 778.98) |
| C23 | m/z = 718.33($C_{54}H_{42}N_2$ = 718.92) | C24 | m/z = 830.37($C_{63}H_{46}N_2$ = 831.05) |
| C25 | m/z = 754.33($C_{57}H_{42}N_2$ = 754.96) | C26 | m/z = 830.37($C_{63}H_{46}N_2$ = 831.05) |
| C27 | m/z = 679.30($C_{50}H_{37}N_3$ = 679.85) | C28 | m/z = 830.37($C_{63}H_{46}N_2$ = 831.05) |
| C29 | m/z = 802.33($C_{61}H_{42}N_2$ = 803.00) | C30 | m/z = 842.37($C_{64}H_{46}N_2$ = 843.06) |
| C31 | m/z = 801.31($C_{60}H_{39}N_3$ = 801.97) | C32 | m/z = 724.29($C_{55}H_{36}N_2$ = 724.89) |
| C33 | m/z = 746.25($C_{52}H_{34}N_4S$ = 746.92) | C34 | m/z = 718.24($C_{52}H_{34}N_2S$ = 718.90) |
| C35 | m/z = 652.25($C_{48}H_{32}N_2O$ = 652.78) | C36 | m/z = 666.23($C_{48}H_{30}N_2O_2$ = 666.76) |
| C37 | m/z = 753.28($C_{55}H_{35}N_3O$ = 753.89) | C38 | m/z = 706.30($C_{52}H_{38}N_2O$ = 706.87) |
| C39 | m/z = 576.22($C_{42}H_{28}N_2O$ = 576.68) | C40 | m/z = 866.33($C_{65}H_{42}N_2O$ = 867.04) |

Meanwhile, even though the compounds of the present invention, represented by Chemical Formula 1, have been synthesized in the Synthesis Examples above, they are based on a Suzuki cross-coupling reaction, an Ullmann reaction, a Miyaura boration reaction, a Buchwald-Hartwig cross coupling reaction, and the like. Therefore, it should be apparent to those having ordinary skill in the art that the reactions could proceed even though substituents (such as $R^1$, $R^2$, $L^1$, $Ar^1$, $Ar^2$, and $Ar^3$) defined in Chemical Formula 1, other than those specified in the Synthesis Examples, are used.

In Reaction Scheme 2, for example, all reactions of the starting material→Sub 1-I, Sub 1-IV→Sub 1-V, and Sub 1-VI→Sub 1 are based on the Suzuki cross-coupling reaction, the reaction of Sub 1-II→Sub 1-III on the Ullmann reaction, and the reactions of Sub 1-III→Sub 1-IV and Sub 1-V→Sub 1-VI on the Miyaura boration reaction; and in Reaction Scheme 27, all the reactions of the starting material→Sub 2, and the product synthesis reactions (Reaction Schemes 40 to 67) are based on the Buchwald-Hartwig cross coupling reaction. These reactions can be conducted even with substituents that are not specifically stated.

Fabrication and Evaluation of Organic Electronic Element

[Test Example I-1] Green Organic Light Emitting Diode (a Hole Transport Layer)

Organic light emitting diodes (OLEDs) were fabricated according to a conventional method by using a compound of the present invention as a hole transport layer material. First, an ITO layer (anode) was formed on a glass substrate, and a film of 4,4',4"-Tris[2-naphthyl(phenyl)amino]triphenylamine (hereinafter abbreviated as "2-TNATA") was vacuum-deposited on the ITO layer to form a hole injection layer with a thickness of 60 nm.

Subsequently, a film of the compound B 1 of the present invention was vacuum-deposited on the hole injection layer to form a hole transport layer with a thickness of 60 nm. Subsequently, a light emitting layer with a thickness of 30 nm was deposited on the hole transport layer by doping the hole transport layer with the 4,4'-N,N'-dicarbazole-biphenyl (hereinafter abbreviated as "CBP") as a host material and tris(2-phenylpyridine)-iridium (hereinafter abbreviated as "Ir(ppy)$_3$") as a dopant material in a weight ratio of 90:10. Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Test Example I-2] to [Test Example I-300] Green Organic Light Emitting Diode (a Hole Transport Layer)

The OLED was manufactured in the same manner as described in Test Example I-1, except that any one of the compounds B6 to C40 of the present invention in the Table 4 below was used as the hole transport layer material, instead of the inventive compound B1.

Comparative Example 1

An OLED was manufactured in the same manner as described in Test Example I-1, except that Comparative Compound 1 represented below was used as the hole transport layer material, instead of the inventive compound B1.

<Comparative Compound 1>

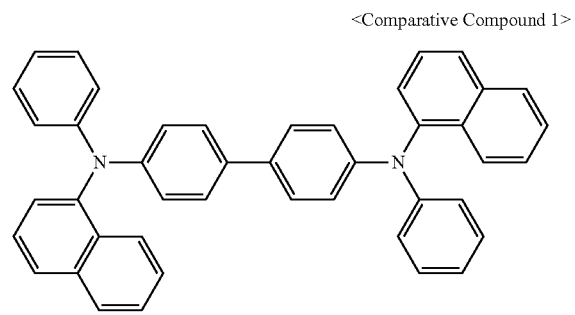 [SMILES: c1ccc(N(c2ccc(-c3ccc(N(c4ccccc4)c4cccc5ccccc45)cc3)cc2)c2cccc3ccccc23)cc1]

Comparative Example 2

An OLED was manufactured in the same manner as described in Test Example I-1, except that Comparative Compound 2 represented below was used as the hole transport layer material, instead of the inventive compound B1.

<Comparative Compound 2>

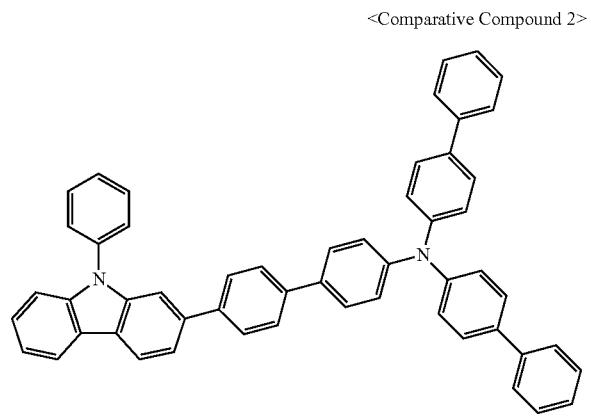 [SMILES: c1ccc(-c2ccc(N(c3ccc(-c4ccccc4)cc3)c3ccc(-c4ccc(-c5ccc6c7ccccc7n(-c7ccccc7)c6c5)cc4)cc3)cc2)cc1]

Comparative Example 3

An OLED was manufactured in the same manner as described in Test Example I-1, except that Comparative Compound 3 represented below was used as the hole transport layer material, instead of the inventive compound B1.

<Comparative Compound 3>

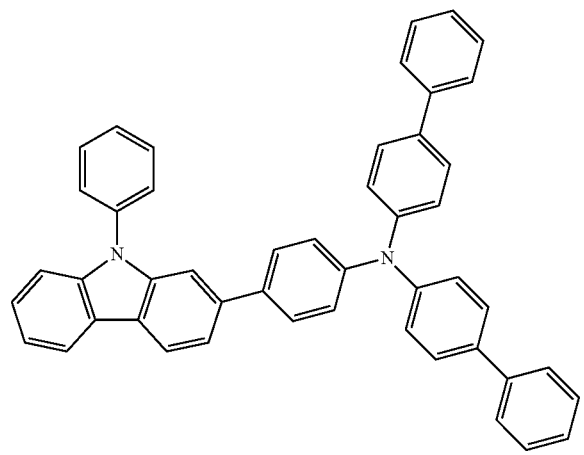

Comparative Example 4

An OLED was manufactured in the same manner as described in Test Example I-1, except that Comparative Compound 4 represented below was used as the hole transport layer material, instead of the inventive compound B1.

<Comparative Compound 4>

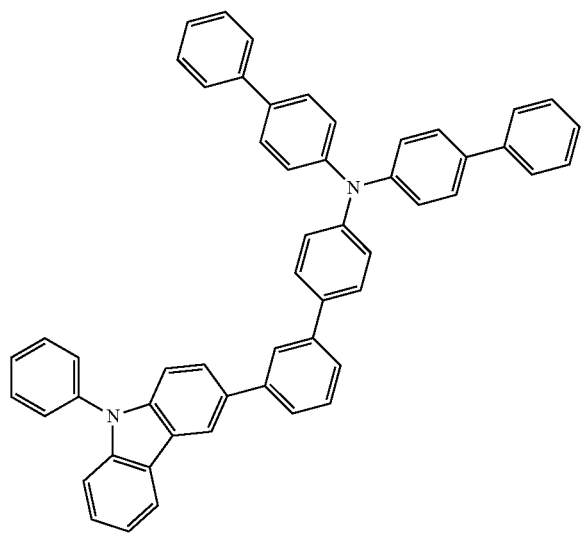

Comparative Example 5

An OLED was manufactured in the same manner as described in Test Example I-1, except that Comparative Compound 5 represented below was used as the hole transport layer material, instead of the inventive compound B1.

<Comparative Compound 5>

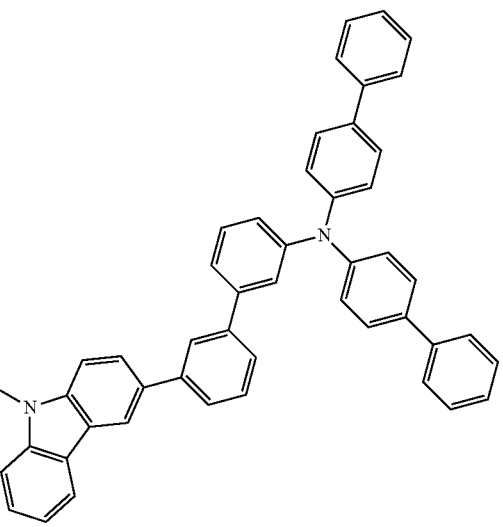

Comparative Example 6

An OLED was manufactured in the same manner as described in Test Example I-1, except that Comparative Compound 6 represented below was used as the hole transport layer material, instead of the inventive compound B1.

<Comparative Compound 6>

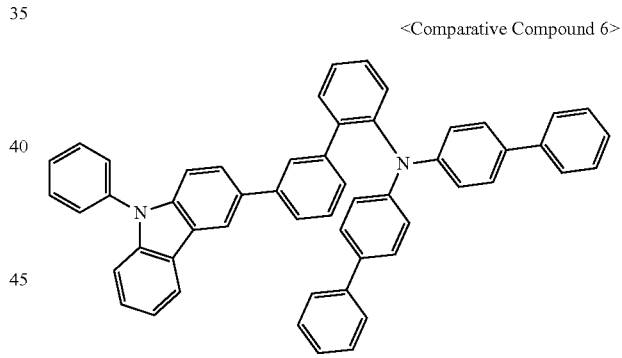

A forward bias DC voltage was applied to each of the OLEDs manufactured through Test Examples (I-1) to (1-300) and Comparative Example (1) to (6), and electroluminescence (EL) characteristics of the OLED were measured by PR-650 (Photoresearch). Also, T95 life span was measured by life span measuring equipment (Mcscience) at a reference brightness of 5000 cd/m². Table 4 below shows evaluation results of OLEDs manufactured Test Examples and Comparative Examples.

TABLE 4

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp. Ex (1) | comp. Com1 | 6.0 | 20.8 | 5000.0 | 24.0 | 53.0 | 0.33 | 0.61 |
| comp. Ex (2) | comp. Com 2 | 5.7 | 18.0 | 5000.0 | 27.8 | 82.3 | 0.33 | 0.62 |

TABLE 4-continued

|  | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex (3) | comp. Com 3 | 5.6 | 18.4 | 5000.0 | 27.2 | 83.4 | 0.33 | 0.62 |
| comp. Ex (4) | comp. Com 4 | 5.2 | 15.3 | 5000.0 | 32.7 | 123.7 | 0.33 | 0.62 |
| comp. Ex (5) | comp. Com 5 | 4.9 | 15.1 | 5000.0 | 33.0 | 125.8 | 0.33 | 0.62 |
| comp. Ex (6) | comp. Com 6 | 5.2 | 14.8 | 5000.0 | 33.8 | 138.7 | 0.33 | 0.61 |
| Ex. (I-1) | Com. (B1) | 5.1 | 14.4 | 5000.0 | 34.6 | 149.7 | 0.33 | 0.61 |
| Ex. (I-2) | Com. (B6) | 5.1 | 13.7 | 5000.0 | 36.4 | 152.9 | 0.33 | 0.61 |
| Ex. (I-3) | Com. (B7) | 5.2 | 14.3 | 5000.0 | 35.1 | 153.3 | 0.33 | 0.61 |
| Ex. (I-4) | Com. (B11) | 4.9 | 14.0 | 5000.0 | 35.6 | 156.2 | 0.33 | 0.62 |
| Ex. (I-5) | Com. (B12) | 5.2 | 14.7 | 5000.0 | 33.9 | 150.5 | 0.33 | 0.62 |
| Ex. (I-6) | Com. (B16) | 5.3 | 14.3 | 5000.0 | 35.0 | 160.3 | 0.33 | 0.62 |
| Ex. (I-7) | Com. (B17) | 5.0 | 14.0 | 5000.0 | 35.7 | 150.4 | 0.33 | 0.62 |
| Ex. (I-8) | Com. (B21) | 5.0 | 13.2 | 5000.0 | 38.0 | 166.6 | 0.33 | 0.62 |
| Ex. (I-9) | Com. (B22) | 5.1 | 13.7 | 5000.0 | 36.4 | 158.7 | 0.33 | 0.62 |
| Ex. (I-10) | Com. (B23) | 5.0 | 14.1 | 5000.0 | 35.3 | 155.7 | 0.33 | 0.61 |
| Ex. (I-11) | Com. (B24) | 5.1 | 14.0 | 5000.0 | 35.8 | 152.8 | 0.33 | 0.61 |
| Ex. (I-12) | Com. (B25) | 5.1 | 13.9 | 5000.0 | 35.9 | 160.4 | 0.33 | 0.61 |
| Ex. (I-13) | Com. (B26) | 5.1 | 13.5 | 5000.0 | 37.0 | 157.3 | 0.33 | 0.62 |
| Ex. (I-14) | Com. (B27) | 5.3 | 14.1 | 5000.0 | 35.6 | 158.9 | 0.33 | 0.61 |
| Ex. (I-15) | Com. (B31) | 5.3 | 14.4 | 5000.0 | 34.7 | 148.7 | 0.33 | 0.61 |
| Ex. (I-16) | Com. (B43) | 5.3 | 14.9 | 5000.0 | 33.5 | 134.6 | 0.33 | 0.61 |
| Ex. (I-17) | Com. (B47) | 5.3 | 15.0 | 5000.0 | 33.4 | 131.6 | 0.33 | 0.61 |
| Ex. (I-18) | Com. (B51) | 5.1 | 13.8 | 5000.0 | 36.2 | 156.4 | 0.33 | 0.61 |
| Ex. (I-19) | Com. (B62) | 5.3 | 14.5 | 5000.0 | 34.5 | 146.4 | 0.33 | 0.61 |
| Ex. (I-20) | Com. (B66) | 5.1 | 14.5 | 5000.0 | 34.6 | 145.5 | 0.33 | 0.61 |
| Ex. (I-21) | Com. (B86) | 5.1 | 14.7 | 5000.0 | 33.9 | 146.9 | 0.33 | 0.62 |
| Ex. (I-22) | Com. (B94) | 5.2 | 15.2 | 5000.0 | 32.8 | 131.8 | 0.33 | 0.62 |
| Ex. (I-23) | Com. (B106) | 5.0 | 14.2 | 5000.0 | 35.3 | 155.8 | 0.33 | 0.62 |
| Ex. (I-24) | Com. (B122) | 5.1 | 15.1 | 5000.0 | 33.0 | 136.4 | 0.33 | 0.61 |
| Ex. (I-25) | Com. (B124) | 5.1 | 14.8 | 5000.0 | 33.8 | 135.3 | 0.33 | 0.61 |
| Ex. (I-26) | Com. (B125) | 5.3 | 14.7 | 5000.0 | 34.0 | 136.8 | 0.33 | 0.61 |
| Ex. (I-27) | Com. (B127) | 5.2 | 15.0 | 5000.0 | 33.3 | 139.2 | 0.33 | 0.61 |
| Ex. (I-28) | Com. (B128) | 5.1 | 14.8 | 5000.0 | 33.8 | 134.8 | 0.33 | 0.61 |
| Ex. (I-29) | Com. (B129) | 5.0 | 15.0 | 5000.0 | 33.4 | 130.5 | 0.33 | 0.61 |
| Ex. (I-30) | Com. (B130) | 5.3 | 15.0 | 5000.0 | 33.4 | 132.6 | 0.33 | 0.61 |
| Ex. (I-31) | Com. (B132) | 5.0 | 14.8 | 5000.0 | 33.7 | 131.9 | 0.33 | 0.61 |
| Ex. (I-32) | Com. (B138) | 5.2 | 15.2 | 5000.0 | 32.9 | 133.5 | 0.33 | 0.61 |
| Ex. (I-33) | Com. (B145) | 5.1 | 15.2 | 5000.0 | 32.9 | 137.0 | 0.33 | 0.62 |
| Ex. (I-34) | Com. (B152) | 5.0 | 15.2 | 5000.0 | 33.0 | 136.0 | 0.33 | 0.62 |
| Ex. (I-35) | Com. (B157) | 5.3 | 14.7 | 5000.0 | 33.9 | 139.2 | 0.33 | 0.61 |
| Ex. (I-36) | Com. (B158) | 5.3 | 15.3 | 5000.0 | 32.7 | 139.1 | 0.33 | 0.62 |
| Ex. (I-37) | Com. (B161) | 5.2 | 14.8 | 5000.0 | 33.9 | 140.0 | 0.33 | 0.62 |
| Ex. (I-38) | Com. (B162) | 5.2 | 14.9 | 5000.0 | 33.6 | 136.7 | 0.33 | 0.62 |
| Ex. (I-39) | Com. (B164) | 5.2 | 14.8 | 5000.0 | 33.7 | 139.7 | 0.33 | 0.61 |
| Ex. (I-40) | Com. (B165) | 5.2 | 14.8 | 5000.0 | 33.9 | 133.3 | 0.33 | 0.61 |
| Ex. (I-41) | Com. (B167) | 5.0 | 14.7 | 5000.0 | 34.1 | 148.7 | 0.33 | 0.61 |
| Ex. (I-42) | Com. (B168) | 5.2 | 14.5 | 5000.0 | 34.4 | 148.9 | 0.33 | 0.62 |
| Ex. (I-43) | Com. (B169) | 5.0 | 13.9 | 5000.0 | 35.9 | 160.5 | 0.33 | 0.62 |
| Ex. (I-44) | Com. (B170) | 5.2 | 14.4 | 5000.0 | 34.7 | 140.2 | 0.33 | 0.61 |
| Ex. (I-45) | Com. (B171) | 5.1 | 14.5 | 5000.0 | 34.4 | 143.6 | 0.33 | 0.62 |
| Ex. (I-46) | Com. (B172) | 5.2 | 14.7 | 5000.0 | 34.1 | 145.9 | 0.33 | 0.62 |
| Ex. (I-47) | Com. (B173) | 5.1 | 14.6 | 5000.0 | 34.3 | 147.8 | 0.33 | 0.61 |
| Ex. (I-48) | Com. (B174) | 5.0 | 14.0 | 5000.0 | 35.8 | 156.2 | 0.33 | 0.62 |
| Ex. (I-49) | Com. (B175) | 4.9 | 14.0 | 5000.0 | 35.8 | 154.5 | 0.33 | 0.61 |
| Ex. (I-50) | Com. (B176) | 5.0 | 13.9 | 5000.0 | 36.0 | 155.8 | 0.33 | 0.62 |
| Ex. (I-51) | Com. (B177) | 5.1 | 13.6 | 5000.0 | 36.6 | 156.5 | 0.33 | 0.62 |
| Ex. (I-52) | Com. (B178) | 5.1 | 14.5 | 5000.0 | 34.5 | 144.7 | 0.33 | 0.62 |
| Ex. (I-53) | Com. (B179) | 5.1 | 14.0 | 5000.0 | 35.7 | 160.7 | 0.33 | 0.62 |
| Ex. (I-54) | Com. (B180) | 5.0 | 14.0 | 5000.0 | 35.6 | 153.6 | 0.33 | 0.62 |
| Ex. (I-55) | Com. (B181) | 5.3 | 14.6 | 5000.0 | 34.2 | 144.8 | 0.33 | 0.61 |
| Ex. (I-56) | Com. (B182) | 5.2 | 15.0 | 5000.0 | 33.4 | 141.0 | 0.33 | 0.61 |
| Ex. (I-57) | Com. (B183) | 5.0 | 14.2 | 5000.0 | 35.2 | 153.1 | 0.33 | 0.61 |
| Ex. (I-58) | Com. (B184) | 5.1 | 14.5 | 5000.0 | 34.5 | 149.5 | 0.33 | 0.61 |
| Ex. (I-59) | Com. (B185) | 5.3 | 14.5 | 5000.0 | 34.4 | 151.1 | 0.33 | 0.62 |
| Ex. (I-60) | Com. (B186) | 5.2 | 14.9 | 5000.0 | 33.6 | 136.7 | 0.33 | 0.61 |
| Ex. (I-61) | Com. (B187) | 5.0 | 13.8 | 5000.0 | 36.2 | 151.6 | 0.33 | 0.61 |
| Ex. (I-62) | Com. (B188) | 5.2 | 14.0 | 5000.0 | 35.6 | 153.6 | 0.33 | 0.61 |
| Ex. (I-63) | Com. (B189) | 5.2 | 14.2 | 5000.0 | 35.2 | 161.4 | 0.33 | 0.61 |
| Ex. (I-64) | Com. (B190) | 5.0 | 14.0 | 5000.0 | 35.6 | 153.8 | 0.33 | 0.61 |
| Ex. (I-65) | Com. (B191) | 4.9 | 14.6 | 5000.0 | 34.3 | 150.6 | 0.33 | 0.62 |
| Ex. (I-66) | Com. (B192) | 5.3 | 15.1 | 5000.0 | 33.1 | 133.0 | 0.33 | 0.61 |
| Ex. (I-67) | Com. (B193) | 5.3 | 15.1 | 5000.0 | 33.2 | 131.7 | 0.33 | 0.62 |
| Ex. (I-68) | Com. (B194) | 4.9 | 14.6 | 5000.0 | 34.2 | 143.6 | 0.33 | 0.61 |
| Ex. (I-69) | Com. (B195) | 5.0 | 13.7 | 5000.0 | 36.5 | 159.7 | 0.33 | 0.61 |
| Ex. (I-70) | Com. (B196) | 4.9 | 13.8 | 5000.0 | 36.2 | 156.3 | 0.33 | 0.62 |
| Ex. (I-71) | Com. (B197) | 4.9 | 13.2 | 5000.0 | 37.9 | 164.8 | 0.33 | 0.61 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (I-72) | Com. (B198) | 5.0 | 13.6 | 5000.0 | 36.7 | 151.5 | 0.33 | 0.61 |
| Ex. (I-73) | Com. (B199) | 5.2 | 14.0 | 5000.0 | 35.7 | 161.7 | 0.33 | 0.62 |
| Ex. (I-74) | Com. (B200) | 5.0 | 14.5 | 5000.0 | 34.5 | 145.6 | 0.33 | 0.62 |
| Ex. (I-75) | Com. (B201) | 5.2 | 13.4 | 5000.0 | 37.2 | 163.2 | 0.33 | 0.62 |
| Ex. (I-76) | Com. (B202) | 5.1 | 13.3 | 5000.0 | 37.6 | 160.7 | 0.33 | 0.61 |
| Ex. (I-77) | Com. (B203) | 5.0 | 13.5 | 5000.0 | 37.1 | 160.3 | 0.33 | 0.61 |
| Ex. (I-78) | Com. (B204) | 5.2 | 13.8 | 5000.0 | 36.3 | 150.3 | 0.33 | 0.61 |
| Ex. (I-79) | Com. (B205) | 5.3 | 15.2 | 5000.0 | 32.8 | 130.5 | 0.33 | 0.61 |
| Ex. (I-80) | Com. (B206) | 5.2 | 14.7 | 5000.0 | 34.1 | 144.6 | 0.33 | 0.61 |
| Ex. (I-81) | Com. (B207) | 4.9 | 14.6 | 5000.0 | 34.2 | 148.3 | 0.33 | 0.61 |
| Ex. (I-82) | Com. (B208) | 5.3 | 14.3 | 5000.0 | 34.9 | 146.7 | 0.33 | 0.62 |
| Ex. (I-83) | Com. (B209) | 5.0 | 14.4 | 5000.0 | 34.8 | 145.0 | 0.33 | 0.62 |
| Ex. (I-84) | Com. (B210) | 5.0 | 14.3 | 5000.0 | 34.9 | 150.3 | 0.33 | 0.62 |
| Ex. (I-85) | Com. (B211) | 5.0 | 15.2 | 5000.0 | 33.0 | 130.3 | 0.33 | 0.61 |
| Ex. (I-86) | Com. (B212) | 5.0 | 14.6 | 5000.0 | 34.3 | 150.3 | 0.33 | 0.61 |
| Ex. (I-87) | Com. (B213) | 5.2 | 14.4 | 5000.0 | 34.8 | 151.7 | 0.33 | 0.61 |
| Ex. (I-88) | Com. (B214) | 5.0 | 14.5 | 5000.0 | 34.5 | 151.8 | 0.33 | 0.61 |
| Ex. (I-89) | Com. (B215) | 5.1 | 15.1 | 5000.0 | 33.2 | 135.7 | 0.33 | 0.62 |
| Ex. (I-90) | Com. (B216) | 5.0 | 15.3 | 5000.0 | 32.8 | 132.0 | 0.33 | 0.62 |
| Ex. (I-91) | Com. (B217) | 5.1 | 14.7 | 5000.0 | 34.1 | 147.6 | 0.33 | 0.62 |
| Ex. (I-92) | Com. (B218) | 4.9 | 14.4 | 5000.0 | 34.7 | 150.3 | 0.33 | 0.61 |
| Ex. (I-93) | Com. (B219) | 4.9 | 14.3 | 5000.0 | 34.9 | 159.9 | 0.33 | 0.62 |
| Ex. (I-94) | Com. (B220) | 5.0 | 13.9 | 5000.0 | 36.0 | 157.2 | 0.33 | 0.62 |
| Ex. (I-95) | Com. (B221) | 5.0 | 13.8 | 5000.0 | 36.3 | 151.2 | 0.33 | 0.62 |
| Ex. (I-96) | Com. (B222) | 5.1 | 13.7 | 5000.0 | 36.4 | 152.0 | 0.33 | 0.61 |
| Ex. (I-97) | Com. (B223) | 5.1 | 13.3 | 5000.0 | 37.6 | 165.2 | 0.33 | 0.62 |
| Ex. (I-98) | Com. (B224) | 5.3 | 13.8 | 5000.0 | 36.2 | 156.6 | 0.33 | 0.62 |
| Ex. (I-99) | Com. (B225) | 4.9 | 13.8 | 5000.0 | 36.1 | 161.0 | 0.33 | 0.61 |
| Ex. (I-100) | Com. (B226) | 5.1 | 13.8 | 5000.0 | 36.3 | 158.9 | 0.33 | 0.62 |
| Ex. (I-101) | Com. (B227) | 5.0 | 13.8 | 5000.0 | 36.1 | 150.6 | 0.33 | 0.61 |
| Ex. (I-102) | Com. (B228) | 5.2 | 13.7 | 5000.0 | 36.5 | 150.7 | 0.33 | 0.61 |
| Ex. (I-103) | Com. (B229) | 5.0 | 13.7 | 5000.0 | 36.5 | 151.7 | 0.33 | 0.61 |
| Ex. (I-104) | Com. (B230) | 5.1 | 14.2 | 5000.0 | 35.2 | 154.9 | 0.33 | 0.61 |
| Ex. (I-105) | Com. (B231) | 5.1 | 13.5 | 5000.0 | 37.0 | 152.7 | 0.33 | 0.61 |
| Ex. (I-106) | Com. (B232) | 5.2 | 13.8 | 5000.0 | 36.2 | 156.6 | 0.33 | 0.62 |
| Ex. (I-107) | Com. (B233) | 5.3 | 13.8 | 5000.0 | 36.3 | 152.5 | 0.33 | 0.61 |
| Ex. (I-108) | Com. (B234) | 5.3 | 13.6 | 5000.0 | 36.7 | 150.0 | 0.33 | 0.61 |
| Ex. (I-109) | Com. (B235) | 5.2 | 14.4 | 5000.0 | 34.8 | 148.0 | 0.33 | 0.62 |
| Ex. (I-110) | Com. (B236) | 5.2 | 14.2 | 5000.0 | 35.3 | 150.3 | 0.33 | 0.62 |
| Ex. (I-111) | Com. (B237) | 5.0 | 14.6 | 5000.0 | 34.3 | 140.4 | 0.33 | 0.61 |
| Ex. (I-112) | Com. (B238) | 5.2 | 13.8 | 5000.0 | 36.2 | 156.3 | 0.33 | 0.61 |
| Ex. (I-113) | Com. (B239) | 4.9 | 13.7 | 5000.0 | 36.6 | 161.5 | 0.33 | 0.62 |
| Ex. (I-114) | Com. (B240) | 5.0 | 13.4 | 5000.0 | 37.4 | 163.5 | 0.33 | 0.61 |
| Ex. (I-115) | Com. (B241) | 5.3 | 13.3 | 5000.0 | 37.6 | 163.1 | 0.33 | 0.61 |
| Ex. (I-116) | Com. (B242) | 5.1 | 14.0 | 5000.0 | 35.7 | 150.2 | 0.33 | 0.62 |
| Ex. (I-117) | Com. (B243) | 5.0 | 14.0 | 5000.0 | 35.8 | 157.5 | 0.33 | 0.61 |
| Ex. (I-118) | Com. (B244) | 5.1 | 14.0 | 5000.0 | 35.6 | 155.6 | 0.33 | 0.61 |
| Ex. (I-119) | Com. (B245) | 5.2 | 14.2 | 5000.0 | 35.1 | 150.8 | 0.33 | 0.62 |
| Ex. (I-120) | Com. (B246) | 5.0 | 14.1 | 5000.0 | 35.4 | 155.2 | 0.33 | 0.62 |
| Ex. (I-121) | Com. (B247) | 5.1 | 14.0 | 5000.0 | 35.8 | 150.8 | 0.33 | 0.62 |
| Ex. (I-122) | Com. (B248) | 5.1 | 13.7 | 5000.0 | 36.6 | 151.7 | 0.33 | 0.62 |
| Ex. (I-123) | Com. (B249) | 5.1 | 14.2 | 5000.0 | 35.3 | 157.8 | 0.33 | 0.61 |
| Ex. (I-124) | Com. (B250) | 5.2 | 14.5 | 5000.0 | 34.5 | 142.8 | 0.33 | 0.62 |
| Ex. (I-125) | Com. (B251) | 4.9 | 14.3 | 5000.0 | 35.0 | 157.2 | 0.33 | 0.62 |
| Ex. (I-126) | Com. (B252) | 5.1 | 13.4 | 5000.0 | 37.2 | 161.7 | 0.33 | 0.62 |
| Ex. (I-127) | Com. (B253) | 5.2 | 13.8 | 5000.0 | 36.2 | 152.0 | 0.33 | 0.62 |
| Ex. (I-128) | Com. (B254) | 5.0 | 13.7 | 5000.0 | 36.5 | 156.9 | 0.33 | 0.61 |
| Ex. (I-129) | Com. (B255) | 5.2 | 14.0 | 5000.0 | 35.7 | 156.5 | 0.33 | 0.62 |
| Ex. (I-130) | Com. (B256) | 5.1 | 14.0 | 5000.0 | 35.8 | 156.9 | 0.33 | 0.61 |
| Ex. (I-131) | Com. (B257) | 5.0 | 14.6 | 5000.0 | 34.3 | 147.5 | 0.33 | 0.61 |
| Ex. (I-132) | Com. (B258) | 5.1 | 14.2 | 5000.0 | 35.1 | 157.2 | 0.33 | 0.61 |
| Ex. (I-133) | Com. (B259) | 5.2 | 13.5 | 5000.0 | 37.1 | 164.4 | 0.33 | 0.61 |
| Ex. (I-134) | Com. (B260) | 4.9 | 13.3 | 5000.0 | 37.6 | 165.1 | 0.33 | 0.62 |
| Ex. (I-135) | Com. (B261) | 5.1 | 13.8 | 5000.0 | 36.2 | 155.1 | 0.33 | 0.62 |
| Ex. (I-136) | Com. (B262) | 5.1 | 14.3 | 5000.0 | 35.0 | 154.8 | 0.33 | 0.62 |
| Ex. (I-137) | Com. (B263) | 5.3 | 13.1 | 5000.0 | 38.3 | 166.6 | 0.33 | 0.62 |
| Ex. (I-138) | Com. (B264) | 4.9 | 13.0 | 5000.0 | 38.4 | 165.3 | 0.33 | 0.61 |
| Ex. (I-139) | Com. (B265) | 5.3 | 13.4 | 5000.0 | 37.4 | 165.0 | 0.33 | 0.61 |
| Ex. (I-140) | Com. (B266) | 5.0 | 13.9 | 5000.0 | 35.9 | 161.9 | 0.33 | 0.61 |
| Ex. (I-141) | Com. (B267) | 4.9 | 14.0 | 5000.0 | 35.7 | 158.5 | 0.33 | 0.61 |
| Ex. (I-142) | Com. (B268) | 5.3 | 14.0 | 5000.0 | 35.6 | 155.7 | 0.33 | 0.62 |
| Ex. (I-143) | Com. (B269) | 5.0 | 14.0 | 5000.0 | 35.6 | 156.7 | 0.33 | 0.62 |
| Ex. (I-144) | Com. (B270) | 5.0 | 14.1 | 5000.0 | 35.4 | 152.3 | 0.33 | 0.61 |
| Ex. (I-145) | Com. (B271) | 5.0 | 14.2 | 5000.0 | 35.2 | 150.3 | 0.33 | 0.61 |
| Ex. (I-146) | Com. (B272) | 4.9 | 14.2 | 5000.0 | 35.3 | 160.9 | 0.33 | 0.62 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (I-147) | Com. (B273) | 5.3 | 14.5 | 5000.0 | 34.5 | 144.8 | 0.33 | 0.62 |
| Ex. (I-148) | Com. (B274) | 4.9 | 14.3 | 5000.0 | 34.9 | 142.1 | 0.33 | 0.62 |
| Ex. (I-149) | Com. (B275) | 5.1 | 14.2 | 5000.0 | 35.2 | 152.3 | 0.33 | 0.62 |
| Ex. (I-150) | Com. (B276) | 5.3 | 14.0 | 5000.0 | 35.7 | 156.8 | 0.33 | 0.62 |
| Ex. (I-151) | Com. (B277) | 5.0 | 14.2 | 5000.0 | 35.1 | 153.0 | 0.33 | 0.61 |
| Ex. (I-152) | Com. (B278) | 5.1 | 14.3 | 5000.0 | 34.8 | 145.2 | 0.33 | 0.62 |
| Ex. (I-153) | Com. (B279) | 5.3 | 14.1 | 5000.0 | 35.4 | 160.9 | 0.33 | 0.62 |
| Ex. (I-154) | Com. (B280) | 5.2 | 14.1 | 5000.0 | 35.5 | 153.6 | 0.33 | 0.61 |
| Ex. (I-155) | Com. (B281) | 5.0 | 14.2 | 5000.0 | 35.1 | 157.4 | 0.33 | 0.61 |
| Ex. (I-156) | Com. (B282) | 5.0 | 14.6 | 5000.0 | 34.2 | 152.0 | 0.33 | 0.62 |
| Ex. (I-157) | Com. (B283) | 4.9 | 13.6 | 5000.0 | 36.8 | 161.9 | 0.33 | 0.62 |
| Ex. (I-158) | Com. (B284) | 5.0 | 13.8 | 5000.0 | 36.1 | 156.8 | 0.33 | 0.61 |
| Ex. (I-159) | Com. (B285) | 5.2 | 13.4 | 5000.0 | 37.3 | 166.5 | 0.33 | 0.61 |
| Ex. (I-160) | Com. (B286) | 5.2 | 13.3 | 5000.0 | 37.6 | 161.0 | 0.33 | 0.62 |
| Ex. (I-161) | Com. (B287) | 5.2 | 12.9 | 5000.0 | 38.7 | 166.5 | 0.33 | 0.62 |
| Ex. (I-162) | Com. (B288) | 5.2 | 13.3 | 5000.0 | 37.7 | 161.2 | 0.33 | 0.61 |
| Ex. (I-163) | Com. (B289) | 5.1 | 13.2 | 5000.0 | 37.9 | 163.5 | 0.33 | 0.61 |
| Ex. (I-164) | Com. (B290) | 4.9 | 13.4 | 5000.0 | 37.2 | 164.8 | 0.33 | 0.62 |
| Ex. (I-165) | Com. (B291) | 5.3 | 13.2 | 5000.0 | 37.9 | 166.2 | 0.33 | 0.61 |
| Ex. (I-166) | Com. (B292) | 5.1 | 13.1 | 5000.0 | 38.0 | 165.6 | 0.33 | 0.61 |
| Ex. (I-167) | Com. (B293) | 5.2 | 13.4 | 5000.0 | 37.4 | 160.6 | 0.33 | 0.62 |
| Ex. (I-168) | Com. (B294) | 5.0 | 13.2 | 5000.0 | 37.8 | 164.4 | 0.33 | 0.62 |
| Ex. (I-169) | Com. (B295) | 5.1 | 13.4 | 5000.0 | 37.3 | 160.2 | 0.33 | 0.61 |
| Ex. (I-170) | Com. (B296) | 5.3 | 13.2 | 5000.0 | 37.8 | 162.6 | 0.33 | 0.61 |
| Ex. (I-171) | Com. (B297) | 5.0 | 13.2 | 5000.0 | 37.9 | 162.8 | 0.33 | 0.62 |
| Ex. (I-172) | Com. (B298) | 5.0 | 13.2 | 5000.0 | 38.0 | 164.7 | 0.33 | 0.62 |
| Ex. (I-173) | Com. (B299) | 5.0 | 13.2 | 5000.0 | 37.8 | 166.4 | 0.33 | 0.62 |
| Ex. (I-174) | Com. (B300) | 5.3 | 13.4 | 5000.0 | 37.4 | 165.3 | 0.33 | 0.61 |
| Ex. (I-175) | Com. (B301) | 5.2 | 13.7 | 5000.0 | 36.4 | 161.2 | 0.33 | 0.62 |
| Ex. (I-176) | Com. (B302) | 5.1 | 13.5 | 5000.0 | 36.9 | 161.5 | 0.33 | 0.62 |
| Ex. (I-177) | Com. (B303) | 5.2 | 14.2 | 5000.0 | 35.1 | 159.5 | 0.33 | 0.61 |
| Ex. (I-178) | Com. (B304) | 4.9 | 14.2 | 5000.0 | 35.2 | 152.5 | 0.33 | 0.62 |
| Ex. (I-179) | Com. (B305) | 5.2 | 14.3 | 5000.0 | 35.0 | 158.4 | 0.33 | 0.61 |
| Ex. (I-180) | Com. (B306) | 5.2 | 14.2 | 5000.0 | 35.2 | 153.3 | 0.33 | 0.62 |
| Ex. (I-181) | Com. (B307) | 4.9 | 13.9 | 5000.0 | 36.1 | 153.4 | 0.33 | 0.61 |
| Ex. (I-182) | Com. (B308) | 5.2 | 13.8 | 5000.0 | 36.3 | 158.8 | 0.33 | 0.61 |
| Ex. (I-183) | Com. (B309) | 4.9 | 13.9 | 5000.0 | 36.0 | 161.5 | 0.33 | 0.62 |
| Ex. (I-184) | Com. (B310) | 4.9 | 13.5 | 5000.0 | 37.1 | 162.0 | 0.33 | 0.62 |
| Ex. (I-185) | Com. (B311) | 5.0 | 13.2 | 5000.0 | 37.9 | 162.1 | 0.33 | 0.62 |
| Ex. (I-186) | Com. (B312) | 5.3 | 13.7 | 5000.0 | 36.5 | 153.7 | 0.33 | 0.62 |
| Ex. (I-187) | Com. (B313) | 5.0 | 13.5 | 5000.0 | 37.2 | 165.6 | 0.33 | 0.62 |
| Ex. (I-188) | Com. (B314) | 5.0 | 13.2 | 5000.0 | 38.0 | 160.9 | 0.33 | 0.62 |
| Ex. (I-189) | Com. (B315) | 5.3 | 12.8 | 5000.0 | 38.9 | 164.6 | 0.33 | 0.61 |
| Ex. (I-190) | Com. (B316) | 5.1 | 13.1 | 5000.0 | 38.2 | 166.0 | 0.33 | 0.62 |
| Ex. (I-191) | Com. (B317) | 4.9 | 13.7 | 5000.0 | 36.6 | 151.5 | 0.33 | 0.62 |
| Ex. (I-192) | Com. (B318) | 5.3 | 14.0 | 5000.0 | 35.7 | 152.6 | 0.33 | 0.61 |
| Ex. (I-193) | Com. (B319) | 5.0 | 14.2 | 5000.0 | 35.3 | 151.9 | 0.33 | 0.61 |
| Ex. (I-194) | Com. (B320) | 5.2 | 13.7 | 5000.0 | 36.6 | 157.1 | 0.33 | 0.62 |
| Ex. (I-195) | Com. (B321) | 5.1 | 13.9 | 5000.0 | 36.0 | 155.2 | 0.33 | 0.61 |
| Ex. (I-196) | Com. (B322) | 5.0 | 13.6 | 5000.0 | 36.6 | 155.7 | 0.33 | 0.62 |
| Ex. (I-197) | Com. (B323) | 4.9 | 13.9 | 5000.0 | 36.0 | 154.2 | 0.33 | 0.61 |
| Ex. (I-198) | Com. (B324) | 5.1 | 14.2 | 5000.0 | 35.2 | 153.8 | 0.33 | 0.61 |
| Ex. (I-199) | Com. (B325) | 5.0 | 13.7 | 5000.0 | 36.5 | 155.6 | 0.33 | 0.61 |
| Ex. (I-200) | Com. (B326) | 5.1 | 13.8 | 5000.0 | 36.2 | 156.3 | 0.33 | 0.62 |
| Ex. (I-201) | Com. (B327) | 4.9 | 13.8 | 5000.0 | 36.2 | 152.3 | 0.33 | 0.62 |
| Ex. (I-202) | Com. (B328) | 5.1 | 13.4 | 5000.0 | 37.3 | 165.8 | 0.33 | 0.61 |
| Ex. (I-203) | Com. (B329) | 5.0 | 13.8 | 5000.0 | 36.1 | 161.8 | 0.33 | 0.62 |
| Ex. (I-204) | Com. (B330) | 5.1 | 14.1 | 5000.0 | 35.6 | 152.5 | 0.33 | 0.62 |
| Ex. (I-205) | Com. (B331) | 5.2 | 12.8 | 5000.0 | 39.0 | 165.1 | 0.33 | 0.62 |
| Ex. (I-206) | Com. (B332) | 5.2 | 13.2 | 5000.0 | 37.8 | 164.6 | 0.33 | 0.61 |
| Ex. (I-207) | Com. (B333) | 5.2 | 13.1 | 5000.0 | 38.2 | 165.1 | 0.33 | 0.61 |
| Ex. (I-208) | Com. (B334) | 5.1 | 13.2 | 5000.0 | 37.9 | 160.5 | 0.33 | 0.61 |
| Ex. (I-209) | Com. (B335) | 5.2 | 13.8 | 5000.0 | 36.1 | 152.3 | 0.33 | 0.61 |
| Ex. (I-210) | Com. (B336) | 5.0 | 13.8 | 5000.0 | 36.2 | 153.3 | 0.33 | 0.62 |
| Ex. (I-211) | Com. (B337) | 5.2 | 14.2 | 5000.0 | 35.1 | 154.2 | 0.33 | 0.61 |
| Ex. (I-212) | Com. (B338) | 5.0 | 13.6 | 5000.0 | 36.8 | 152.4 | 0.33 | 0.61 |
| Ex. (I-213) | Com. (B339) | 5.2 | 12.8 | 5000.0 | 39.0 | 164.6 | 0.33 | 0.61 |
| Ex. (I-214) | Com. (B340) | 5.0 | 12.9 | 5000.0 | 38.6 | 164.1 | 0.33 | 0.61 |
| Ex. (I-215) | Com. (B341) | 5.0 | 13.4 | 5000.0 | 37.4 | 165.0 | 0.33 | 0.62 |
| Ex. (I-216) | Com. (B342) | 5.1 | 13.9 | 5000.0 | 36.1 | 160.8 | 0.33 | 0.62 |
| Ex. (I-217) | Com. (B343) | 5.2 | 12.5 | 5000.0 | 40.1 | 169.1 | 0.33 | 0.62 |
| Ex. (I-218) | Com. (B344) | 5.0 | 12.4 | 5000.0 | 40.2 | 167.1 | 0.33 | 0.62 |
| Ex. (I-219) | Com. (B345) | 5.3 | 12.9 | 5000.0 | 38.9 | 166.5 | 0.33 | 0.61 |
| Ex. (I-220) | Com. (B346) | 5.3 | 13.2 | 5000.0 | 37.9 | 163.2 | 0.33 | 0.62 |
| Ex. (I-221) | Com. (B347) | 5.1 | 13.7 | 5000.0 | 36.5 | 154.0 | 0.33 | 0.61 |

TABLE 4-continued

|  | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (I-222) | Com. (B348) | 5.3 | 13.9 | 5000.0 | 36.0 | 151.4 | 0.33 | 0.61 |
| Ex. (I-223) | Com. (B349) | 5.2 | 13.5 | 5000.0 | 37.1 | 150.3 | 0.33 | 0.61 |
| Ex. (I-224) | Com. (B350) | 5.1 | 13.6 | 5000.0 | 36.6 | 150.7 | 0.33 | 0.62 |
| Ex. (I-225) | Com. (B351) | 5.0 | 13.7 | 5000.0 | 36.5 | 156.8 | 0.33 | 0.61 |
| Ex. (I-226) | Com. (B352) | 4.9 | 13.9 | 5000.0 | 36.0 | 152.7 | 0.33 | 0.62 |
| Ex. (I-227) | Com. (B353) | 5.0 | 13.5 | 5000.0 | 37.0 | 156.0 | 0.33 | 0.61 |
| Ex. (I-228) | Com. (B354) | 5.2 | 13.8 | 5000.0 | 36.1 | 151.3 | 0.33 | 0.61 |
| Ex. (I-229) | Com. (B355) | 4.9 | 13.8 | 5000.0 | 36.3 | 158.6 | 0.33 | 0.61 |
| Ex. (I-230) | Com. (B356) | 5.2 | 13.7 | 5000.0 | 36.6 | 157.9 | 0.33 | 0.61 |
| Ex. (I-231) | Com. (B357) | 5.1 | 14.0 | 5000.0 | 35.7 | 161.5 | 0.33 | 0.61 |
| Ex. (I-232) | Com. (B358) | 5.1 | 13.8 | 5000.0 | 36.4 | 156.8 | 0.33 | 0.61 |
| Ex. (I-233) | Com. (B359) | 5.2 | 13.6 | 5000.0 | 36.8 | 155.4 | 0.33 | 0.62 |
| Ex. (I-234) | Com. (B360) | 4.9 | 13.5 | 5000.0 | 37.0 | 156.9 | 0.33 | 0.62 |
| Ex. (I-235) | Com. (B361) | 5.2 | 13.8 | 5000.0 | 36.3 | 155.8 | 0.33 | 0.62 |
| Ex. (I-236) | Com. (B362) | 5.1 | 13.7 | 5000.0 | 36.5 | 158.1 | 0.33 | 0.62 |
| Ex. (I-237) | Com. (B363) | 5.0 | 13.5 | 5000.0 | 37.1 | 157.6 | 0.33 | 0.61 |
| Ex. (I-238) | Com. (B364) | 5.1 | 14.2 | 5000.0 | 35.1 | 155.4 | 0.33 | 0.62 |
| Ex. (I-239) | Com. (B365) | 5.1 | 15.0 | 5000.0 | 33.3 | 132.0 | 0.33 | 0.62 |
| Ex. (I-240) | Com. (B366) | 5.0 | 14.8 | 5000.0 | 33.7 | 139.4 | 0.33 | 0.62 |
| Ex. (I-241) | Com. (B367) | 5.2 | 14.9 | 5000.0 | 33.5 | 134.2 | 0.33 | 0.61 |
| Ex. (I-242) | Com. (B368) | 5.3 | 15.0 | 5000.0 | 33.4 | 136.1 | 0.33 | 0.62 |
| Ex. (I-243) | Com. (B369) | 5.2 | 15.2 | 5000.0 | 32.9 | 134.8 | 0.33 | 0.61 |
| Ex. (I-244) | Com. (B370) | 5.1 | 15.1 | 5000.0 | 33.2 | 133.7 | 0.33 | 0.61 |
| Ex. (I-245) | Com. (B371) | 5.3 | 15.1 | 5000.0 | 33.0 | 130.4 | 0.33 | 0.61 |
| Ex. (I-246) | Com. (B372) | 5.1 | 14.3 | 5000.0 | 35.0 | 139.6 | 0.33 | 0.62 |
| Ex. (I-247) | Com. (B373) | 5.1 | 14.7 | 5000.0 | 34.0 | 144.9 | 0.33 | 0.62 |
| Ex. (I-248) | Com. (B374) | 5.4 | 14.6 | 5000.0 | 34.4 | 145.3 | 0.33 | 0.61 |
| Ex. (I-249) | Com. (B375) | 5.1 | 14.6 | 5000.0 | 34.2 | 150.0 | 0.33 | 0.61 |
| Ex. (I-250) | Com. (B376) | 5.0 | 14.7 | 5000.0 | 33.9 | 143.8 | 0.33 | 0.62 |
| Ex. (I-251) | Com. (B377) | 5.1 | 14.6 | 5000.0 | 34.4 | 146.5 | 0.33 | 0.61 |
| Ex. (I-252) | Com. (B378) | 5.0 | 14.3 | 5000.0 | 35.0 | 144.5 | 0.33 | 0.62 |
| Ex. (I-253) | Com. (B379) | 5.3 | 14.0 | 5000.0 | 35.8 | 160.2 | 0.33 | 0.62 |
| Ex. (I-254) | Com. (B380) | 5.1 | 14.0 | 5000.0 | 35.7 | 154.5 | 0.33 | 0.61 |
| Ex. (I-255) | Com. (B381) | 5.1 | 14.1 | 5000.0 | 35.5 | 159.2 | 0.33 | 0.62 |
| Ex. (I-256) | Com. (B382) | 5.3 | 14.0 | 5000.0 | 35.8 | 145.5 | 0.33 | 0.62 |
| Ex. (I-257) | Com. (B383) | 5.2 | 14.3 | 5000.0 | 34.9 | 147.8 | 0.33 | 0.61 |
| Ex. (I-258) | Com. (B384) | 5.2 | 13.8 | 5000.0 | 36.2 | 150.5 | 0.33 | 0.61 |
| Ex. (I-259) | Com. (B385) | 5.3 | 14.0 | 5000.0 | 35.6 | 151.7 | 0.33 | 0.62 |
| Ex. (I-260) | Com. (B386) | 5.2 | 14.0 | 5000.0 | 35.7 | 145.4 | 0.33 | 0.61 |
| Ex. (I-261) | Com. (C1) | 5.1 | 13.0 | 5000.0 | 38.4 | 149.6 | 0.33 | 0.61 |
| Ex. (I-262) | Com. (C2) | 5.2 | 14.3 | 5000.0 | 34.9 | 147.4 | 0.33 | 0.61 |
| Ex. (I-263) | Com. (C3) | 5.1 | 13.7 | 5000.0 | 36.6 | 149.8 | 0.33 | 0.61 |
| Ex. (I-264) | Com. (C4) | 5.2 | 14.8 | 5000.0 | 33.8 | 138.2 | 0.33 | 0.62 |
| Ex. (I-265) | Com. (C5) | 5.2 | 13.5 | 5000.0 | 37.1 | 148.4 | 0.33 | 0.61 |
| Ex. (I-266) | Com. (C6) | 5.3 | 14.8 | 5000.0 | 33.8 | 140.9 | 0.33 | 0.62 |
| Ex. (I-267) | Com. (C7) | 5.2 | 14.0 | 5000.0 | 35.8 | 136.0 | 0.33 | 0.61 |
| Ex. (I-268) | Com. (C8) | 5.0 | 14.4 | 5000.0 | 34.8 | 152.0 | 0.33 | 0.61 |
| Ex. (I-269) | Com. (C9) | 5.3 | 14.9 | 5000.0 | 33.5 | 147.2 | 0.33 | 0.61 |
| Ex. (I-270) | Com. (C10) | 5.2 | 13.5 | 5000.0 | 37.2 | 145.7 | 0.33 | 0.61 |
| Ex. (I-271) | Com. (C11) | 5.1 | 13.7 | 5000.0 | 36.5 | 138.7 | 0.33 | 0.61 |
| Ex. (I-272) | Com. (C12) | 5.3 | 14.9 | 5000.0 | 33.6 | 149.1 | 0.33 | 0.61 |
| Ex. (I-273) | Com. (C13) | 5.2 | 13.4 | 5000.0 | 37.3 | 138.9 | 0.33 | 0.62 |
| Ex. (I-274) | Com. (C14) | 5.1 | 13.9 | 5000.0 | 36.0 | 149.7 | 0.33 | 0.62 |
| Ex. (I-275) | Com. (C15) | 5.1 | 14.3 | 5000.0 | 35.0 | 137.7 | 0.33 | 0.62 |
| Ex. (I-276) | Com. (C16) | 5.2 | 14.9 | 5000.0 | 33.6 | 146.2 | 0.33 | 0.62 |
| Ex. (I-277) | Com. (C17) | 5.0 | 13.5 | 5000.0 | 37.1 | 135.4 | 0.33 | 0.61 |
| Ex. (I-278) | Com. (C18) | 5.3 | 14.3 | 5000.0 | 35.1 | 148.6 | 0.33 | 0.62 |
| Ex. (I-279) | Com. (C19) | 5.1 | 14.0 | 5000.0 | 35.6 | 147.0 | 0.33 | 0.62 |
| Ex. (I-280) | Com. (C20) | 5.1 | 14.6 | 5000.0 | 34.2 | 149.6 | 0.33 | 0.62 |
| Ex. (I-281) | Com. (C21) | 5.1 | 13.4 | 5000.0 | 37.2 | 140.0 | 0.33 | 0.61 |
| Ex. (I-282) | Com. (C22) | 5.2 | 14.4 | 5000.0 | 34.6 | 147.1 | 0.33 | 0.62 |
| Ex. (I-283) | Com. (C23) | 5.3 | 13.6 | 5000.0 | 36.9 | 143.7 | 0.33 | 0.61 |
| Ex. (I-284) | Com. (C24) | 5.1 | 13.0 | 5000.0 | 38.5 | 141.8 | 0.33 | 0.61 |
| Ex. (I-285) | Com. (C25) | 5.1 | 14.6 | 5000.0 | 34.2 | 140.2 | 0.33 | 0.61 |
| Ex. (I-286) | Com. (C26) | 5.1 | 13.9 | 5000.0 | 36.0 | 146.8 | 0.33 | 0.62 |
| Ex. (I-287) | Com. (C27) | 5.0 | 14.2 | 5000.0 | 35.3 | 145.9 | 0.33 | 0.62 |
| Ex. (I-288) | Com. (C28) | 5.3 | 14.3 | 5000.0 | 34.9 | 142.1 | 0.33 | 0.61 |
| Ex. (I-289) | Com. (C29) | 5.1 | 13.4 | 5000.0 | 37.4 | 137.1 | 0.33 | 0.61 |
| Ex. (I-290) | Com. (C30) | 5.3 | 13.1 | 5000.0 | 38.1 | 146.0 | 0.33 | 0.61 |
| Ex. (I-291) | Com. (C31) | 5.1 | 13.3 | 5000.0 | 37.6 | 139.8 | 0.33 | 0.62 |
| Ex. (I-292) | Com. (C32) | 5.0 | 13.6 | 5000.0 | 36.8 | 147.9 | 0.33 | 0.61 |
| Ex. (I-293) | Com. (C33) | 5.1 | 14.2 | 5000.0 | 35.3 | 135.8 | 0.33 | 0.62 |
| Ex. (I-294) | Com. (C34) | 5.1 | 13.0 | 5000.0 | 38.4 | 142.8 | 0.33 | 0.61 |
| Ex. (I-295) | Com. (C35) | 5.1 | 14.1 | 5000.0 | 35.3 | 143.0 | 0.33 | 0.61 |
| Ex. (I-296) | Com. (C36) | 5.3 | 13.0 | 5000.0 | 38.4 | 147.8 | 0.33 | 0.61 |

TABLE 4-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (I-297) | Com. (C37) | 5.2 | 13.3 | 5000.0 | 37.6 | 148.1 | 0.33 | 0.61 |
| Ex. (I-298) | Com. (C38) | 5.0 | 14.8 | 5000.0 | 33.8 | 145.0 | 0.33 | 0.61 |
| Ex. (I-299) | Com. (C39) | 5.3 | 14.1 | 5000.0 | 35.4 | 147.0 | 0.33 | 0.61 |
| Ex. (I-300) | Com. (C40) | 5.0 | 14.1 | 5000.0 | 35.5 | 135.3 | 0.33 | 0.62 |

As can be seen from the results of Table 4, organic electroluminescent devices utilizing the compounds of the present invention as materials of the hole transporting layer can be operated at a relatively low driving voltage, and with significantly improved luminous efficiency and lifespan, compared to the organic electroluminescent devices utilizing Comparative Compounds 1 to 6 as materials of the hole transporting layer.

In particular, the data shows that different results are obtained according to linkage type (linear or non-linear type) as demonstrated by comparison between the compounds of the present invention (non-linear linkers) and comparative compounds (linear-type linkers).

The linker between carbazole and amine (—NAr$^2$Ar$^3$) allows for a deeper HOMO energy level, a higher T1 value, and higher thermal stability at a meta position (non-linear type), compared to a para position (linear type), as demonstrated by the superiority of the compounds of the present invention to Comparative Compounds 2 and 3 in terms of driving voltage, luminous efficiency, and lifespan.

A linker at a meta position (non-linear type) allows for a shorter conjugation length than that at a para position (linear type), thus guaranteeing a wider band gap and a higher T1 value.

Accordingly, the linker at a meta position (non-linear type) is believed to positively contribute to the ability to block electrons thanks to the high T1 value, and to help a hole be smoothly transported to the light emitting layer thanks to a deep HOMO energy level, so that excitons can be more easily and efficiently created in the light emitting layer. Also, the high thermal stability was observed to increase the lifespan.

Furthermore, compared to Comparative Compounds 4 to 6 in which linkers are linked directly to the carbazole backbone at position 2, the compounds of the present invention in which linkers are linked at position 2 have shorter conjugation lengths, and thus have improved luminous efficiency and lifespan.

When the previously described properties (the deep HOMO energy level, high T1 value, and high thermal stability) are taken into consideration, the position of the linker between the carbazole and amine (—NAr$^2$Ar$^3$) has great influence on the band gap and electrical and interfacial properties, and serves as the main factor for improving performance of the device.

Additionally, for the hole transporting layer, account must be taken of a correlation with the light emitting layer (host). Thus, even though a similar core is used in the hole transporting layer, it would be very difficult for those having ordinary skill in the art to analogize the features of the hole transporting layer in which the compound according to the present invention is used.

[Test Example II-1] Blue Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, N,N'-Bis(1-naphthalenyl)-N,N'-bis-phenyl-(1,1'-biphenyl)-4,4'-diamine (hereinafter abbreviated as "NPB") was vacuum-deposited with a thickness of 60 nm on the hole injection layer to form a hole transport layer. Next, the inventive compound B6 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with 9,10-di(naphthalen-2-yl)anthracene (hereinafter abbreviated as "ADN") as a host material and BD-052X (made by Idemitsu kosan) as a dopant material in a weight ratio of 93:7. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

[Test Example II-2] to [Test Example II-86] Blue Organic Light Emitting Diode (Emission-Auxiliary Layer)

The OLED was manufactured in the same manner as described in Test Example II-1, except that any one of the compounds B7 to B386 of the present invention in the Table 5 below was used as the Emission-Auxiliary Layer material, instead of the inventive compound B6.

Comparative Example 7

The OLED was manufactured in the same manner as described in Test Example II-1, except that Comparative Compound 2 represented above was used as the Emission-Auxiliary Layer material, instead of the inventive compound B6.

Comparative Example 8

The OLED was manufactured in the same manner as described in Test Example II-1, except that Comparative Compound 4 represented above was used as the Emission-Auxiliary Layer material, instead of the inventive compound B6.

Comparative Example 9

The OLED was manufactured in the same manner as described in Test Example II-1, except that Comparative Compound 5 represented above was used as the Emission-Auxiliary Layer material, instead of the inventive compound B6.

Comparative Example 10

The OLED was manufactured in the same manner as described in Test Example II-1, except that Comparative Compound 6 represented above was used as the Emission-Auxiliary Layer material, instead of the inventive compound B6.

Comparative Example 11

The OLED was manufactured in the same manner as described in Test Example II-1, except that Comparative Compound 7 represented below above was used as the Emission-Auxiliary Layer material, instead of the inventive compound B6.

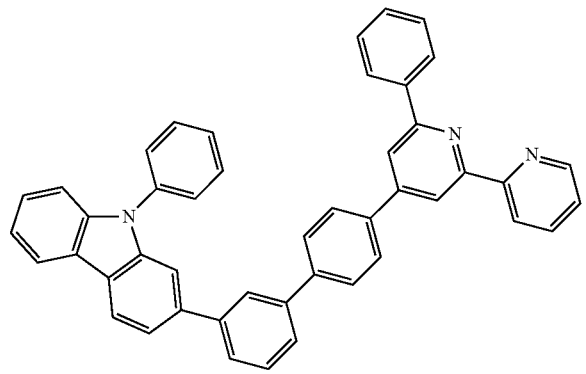

<Comparative Compound 7>

Comparative Example 12

An OLED was manufactured in the same manner as described in Test Example II-1, except that an emission-auxiliary layer was not formed.

A forward bias DC voltage was applied to each of the OLEDs manufactured through Test Examples (II-1) to (11-86) and Comparative Example (7) to (12), and electroluminescence (EL) characteristics of the OLED were measured by PR-650 (Photoresearch). Also, T95 life span was measured by life span measuring equipment (Mcscience) at a reference brightness of 500 cd/m$^2$. Table 5 below shows evaluation results of OLEDs manufactured Test Examples and Comparative Examples.

TABLE 5

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex (7) | comp. Com 2 | 5.1 | 10.6 | 500.0 | 4.7 | 85.6 | 0.14 | 0.12 |
| comp. Ex (8) | comp. Com 4 | 5.2 | 8.2 | 500.0 | 6.1 | 122.2 | 0.14 | 0.12 |
| comp. Ex (9) | comp. Com 5 | 5.1 | 7.9 | 500.0 | 6.3 | 129.3 | 0.14 | 0.11 |
| comp. Ex (10) | comp. Com 6 | 5.1 | 7.1 | 500.0 | 7.0 | 133.4 | 0.14 | 0.12 |
| comp. Ex (11) | comp. Com 7 | 5.5 | 11.9 | 500.0 | 4.2 | 75.7 | 0.14 | 0.12 |
| comp. Ex (12) | — | 5.0 | 14.3 | 500.0 | 3.5 | 56.4 | 0.14 | 0.15 |
| Ex. (II-1) | Com. (B6) | 5.1 | 6.4 | 500.0 | 7.9 | 139.7 | 0.14 | 0.12 |
| Ex. (II-2) | Com. (B7) | 5.0 | 6.7 | 500.0 | 7.5 | 133.1 | 0.14 | 0.11 |
| Ex. (II-3) | Com. (B11) | 5.2 | 6.5 | 500.0 | 7.7 | 140.2 | 0.14 | 0.11 |
| Ex. (II-4) | Com. (B12) | 5.0 | 6.7 | 500.0 | 7.5 | 131.0 | 0.14 | 0.12 |
| Ex. (II-5) | Com. (B17) | 5.1 | 5.8 | 500.0 | 8.6 | 143.6 | 0.14 | 0.11 |
| Ex. (II-6) | Com. (B21) | 5.1 | 5.9 | 500.0 | 8.4 | 144.5 | 0.14 | 0.11 |
| Ex. (II-7) | Com. (B22) | 5.2 | 6.3 | 500.0 | 8.0 | 138.1 | 0.14 | 0.12 |
| Ex. (II-8) | Com. (B23) | 5.1 | 6.5 | 500.0 | 7.8 | 136.3 | 0.14 | 0.11 |
| Ex. (II-9) | Com. (B24) | 5.2 | 6.4 | 500.0 | 7.8 | 137.0 | 0.14 | 0.11 |
| Ex. (II-10) | Com. (B25) | 5.3 | 6.4 | 500.0 | 7.9 | 138.2 | 0.14 | 0.11 |
| Ex. (II-11) | Com. (B26) | 5.1 | 6.2 | 500.0 | 8.0 | 138.8 | 0.14 | 0.12 |
| Ex. (II-12) | Com. (B27) | 5.1 | 6.4 | 500.0 | 7.9 | 138.4 | 0.14 | 0.11 |
| Ex. (II-13) | Com. (B47) | 5.1 | 6.9 | 500.0 | 7.3 | 130.1 | 0.14 | 0.11 |
| Ex. (II-14) | Com. (B51) | 5.1 | 6.1 | 500.0 | 8.2 | 135.0 | 0.14 | 0.11 |
| Ex. (II-15) | Com. (B106) | 5.0 | 6.4 | 500.0 | 7.9 | 142.2 | 0.14 | 0.11 |
| Ex. (II-16) | Com. (B128) | 5.2 | 6.7 | 500.0 | 7.4 | 131.0 | 0.14 | 0.12 |
| Ex. (II-17) | Com. (B129) | 5.2 | 7.0 | 500.0 | 7.1 | 127.6 | 0.14 | 0.12 |
| Ex. (II-18) | Com. (B132) | 5.2 | 7.1 | 500.0 | 7.0 | 131.0 | 0.14 | 0.11 |
| Ex. (II-19) | Com. (B138) | 5.0 | 7.0 | 500.0 | 7.2 | 129.1 | 0.14 | 0.11 |
| Ex. (II-20) | Com. (B145) | 5.0 | 7.1 | 500.0 | 7.0 | 129.5 | 0.14 | 0.11 |
| Ex. (II-21) | Com. (B157) | 5.2 | 7.3 | 500.0 | 6.9 | 128.4 | 0.14 | 0.12 |
| Ex. (II-22) | Com. (B158) | 5.2 | 7.1 | 500.0 | 7.0 | 128.0 | 0.14 | 0.12 |
| Ex. (II-23) | Com. (B164) | 5.3 | 7.1 | 500.0 | 7.0 | 127.5 | 0.14 | 0.11 |

TABLE 5-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (II-24) | Com. (B165) | 5.1 | 7.0 | 500.0 | 7.1 | 130.2 | 0.14 | 0.11 |
| Ex. (II-25) | Com. (B167) | 5.2 | 6.8 | 500.0 | 7.4 | 130.3 | 0.14 | 0.12 |
| Ex. (II-26) | Com. (B168) | 5.3 | 6.7 | 500.0 | 7.4 | 128.8 | 0.14 | 0.11 |
| Ex. (II-27) | Com. (B169) | 5.3 | 6.5 | 500.0 | 7.7 | 138.3 | 0.14 | 0.11 |
| Ex. (II-28) | Com. (B171) | 5.2 | 7.0 | 500.0 | 7.1 | 133.9 | 0.14 | 0.11 |
| Ex. (II-29) | Com. (B175) | 5.1 | 6.7 | 500.0 | 7.4 | 140.1 | 0.14 | 0.12 |
| Ex. (II-30) | Com. (B176) | 5.2 | 6.6 | 500.0 | 7.6 | 133.1 | 0.14 | 0.12 |
| Ex. (II-31) | Com. (B177) | 5.1 | 6.1 | 500.0 | 8.2 | 141.2 | 0.14 | 0.11 |
| Ex. (II-32) | Com. (B179) | 5.2 | 6.5 | 500.0 | 7.7 | 141.9 | 0.14 | 0.12 |
| Ex. (II-33) | Com. (B183) | 5.1 | 6.6 | 500.0 | 7.6 | 139.1 | 0.14 | 0.11 |
| Ex. (II-34) | Com. (B187) | 5.1 | 6.1 | 500.0 | 8.2 | 142.9 | 0.14 | 0.12 |
| Ex. (II-35) | Com. (B195) | 5.1 | 6.4 | 500.0 | 7.9 | 141.7 | 0.14 | 0.12 |
| Ex. (II-36) | Com. (B197) | 5.2 | 6.1 | 500.0 | 8.3 | 144.8 | 0.14 | 0.12 |
| Ex. (II-37) | Com. (B198) | 5.0 | 6.3 | 500.0 | 7.9 | 141.5 | 0.14 | 0.12 |
| Ex. (II-38) | Com. (B203) | 5.2 | 6.0 | 500.0 | 8.3 | 145.0 | 0.14 | 0.11 |
| Ex. (II-39) | Com. (B204) | 5.1 | 6.3 | 500.0 | 7.9 | 136.6 | 0.14 | 0.11 |
| Ex. (II-40) | Com. (B206) | 5.0 | 6.7 | 500.0 | 7.4 | 128.8 | 0.14 | 0.12 |
| Ex. (II-41) | Com. (B210) | 5.2 | 7.1 | 500.0 | 7.1 | 133.8 | 0.14 | 0.12 |
| Ex. (II-42) | Com. (B213) | 5.1 | 6.8 | 500.0 | 7.3 | 131.3 | 0.14 | 0.11 |
| Ex. (II-43) | Com. (B219) | 5.2 | 6.6 | 500.0 | 7.6 | 136.9 | 0.14 | 0.12 |
| Ex. (II-44) | Com. (B220) | 5.1 | 6.1 | 500.0 | 8.3 | 142.1 | 0.14 | 0.12 |
| Ex. (II-45) | Com. (B221) | 5.1 | 6.1 | 500.0 | 8.2 | 145.6 | 0.14 | 0.11 |
| Ex. (II-46) | Com. (B222) | 5.0 | 6.0 | 500.0 | 8.3 | 147.1 | 0.14 | 0.11 |
| Ex. (II-47) | Com. (B223) | 5.1 | 5.8 | 500.0 | 8.6 | 150.7 | 0.14 | 0.11 |
| Ex. (II-48) | Com. (B224) | 5.1 | 6.4 | 500.0 | 7.9 | 145.3 | 0.14 | 0.11 |
| Ex. (II-49) | Com. (B225) | 5.0 | 6.2 | 500.0 | 8.0 | 139.0 | 0.14 | 0.12 |
| Ex. (II-50) | Com. (B226) | 5.0 | 6.2 | 500.0 | 8.1 | 141.7 | 0.14 | 0.12 |
| Ex. (II-51) | Com. (B227) | 5.2 | 6.1 | 500.0 | 8.2 | 142.5 | 0.14 | 0.11 |
| Ex. (II-52) | Com. (B228) | 5.0 | 6.1 | 500.0 | 8.2 | 143.6 | 0.14 | 0.11 |
| Ex. (II-53) | Com. (B229) | 5.0 | 6.0 | 500.0 | 8.3 | 144.5 | 0.14 | 0.12 |
| Ex. (II-54) | Com. (B232) | 5.1 | 6.2 | 500.0 | 8.1 | 146.5 | 0.14 | 0.11 |
| Ex. (II-55) | Com. (B234) | 5.1 | 6.1 | 500.0 | 8.1 | 142.3 | 0.14 | 0.12 |
| Ex. (II-56) | Com. (B238) | 5.1 | 6.1 | 500.0 | 8.2 | 142.1 | 0.14 | 0.12 |
| Ex. (II-57) | Com. (B239) | 5.0 | 6.2 | 500.0 | 8.0 | 148.5 | 0.14 | 0.11 |
| Ex. (II-58) | Com. (B240) | 5.0 | 6.0 | 500.0 | 8.3 | 146.7 | 0.14 | 0.12 |
| Ex. (II-59) | Com. (B241) | 5.1 | 5.9 | 500.0 | 8.5 | 140.4 | 0.14 | 0.12 |
| Ex. (II-60) | Com. (B245) | 5.3 | 6.7 | 500.0 | 7.5 | 135.3 | 0.14 | 0.11 |
| Ex. (II-61) | Com. (B248) | 5.2 | 6.1 | 500.0 | 8.1 | 139.0 | 0.14 | 0.11 |
| Ex. (II-62) | Com. (B252) | 5.2 | 5.9 | 500.0 | 8.5 | 141.7 | 0.14 | 0.12 |
| Ex. (II-63) | Com. (B259) | 5.2 | 6.0 | 500.0 | 8.3 | 139.2 | 0.14 | 0.11 |
| Ex. (II-64) | Com. (B260) | 5.2 | 5.9 | 500.0 | 8.5 | 139.1 | 0.14 | 0.12 |
| Ex. (II-65) | Com. (B264) | 5.1 | 5.9 | 500.0 | 8.5 | 150.8 | 0.14 | 0.12 |
| Ex. (II-66) | Com. (B267) | 5.2 | 6.5 | 500.0 | 7.7 | 134.1 | 0.14 | 0.11 |
| Ex. (II-67) | Com. (B271) | 5.1 | 6.6 | 500.0 | 7.6 | 136.7 | 0.14 | 0.11 |
| Ex. (II-68) | Com. (B276) | 5.1 | 6.6 | 500.0 | 7.6 | 135.9 | 0.14 | 0.12 |
| Ex. (II-69) | Com. (B285) | 5.0 | 6.0 | 500.0 | 8.3 | 152.1 | 0.14 | 0.11 |
| Ex. (II-70) | Com. (B287) | 5.1 | 5.7 | 500.0 | 8.7 | 154.0 | 0.14 | 0.12 |
| Ex. (II-71) | Com. (B289) | 5.1 | 5.8 | 500.0 | 8.5 | 153.5 | 0.14 | 0.12 |
| Ex. (II-72) | Com. (B293) | 5.2 | 6.0 | 500.0 | 8.4 | 152.4 | 0.14 | 0.12 |
| Ex. (II-73) | Com. (B296) | 5.0 | 5.8 | 500.0 | 8.6 | 151.7 | 0.14 | 0.12 |
| Ex. (II-74) | Com. (B297) | 5.1 | 5.9 | 500.0 | 8.5 | 148.9 | 0.14 | 0.12 |
| Ex. (II-75) | Com. (B299) | 5.0 | 6.1 | 500.0 | 8.2 | 150.5 | 0.14 | 0.12 |
| Ex. (II-76) | Com. (B311) | 5.1 | 5.9 | 500.0 | 8.5 | 152.6 | 0.14 | 0.12 |
| Ex. (II-77) | Com. (B322) | 5.1 | 6.2 | 500.0 | 8.0 | 145.6 | 0.14 | 0.12 |
| Ex. (II-78) | Com. (B328) | 5.1 | 5.9 | 500.0 | 8.4 | 154.4 | 0.14 | 0.12 |
| Ex. (II-79) | Com. (B331) | 5.1 | 5.6 | 500.0 | 8.9 | 150.9 | 0.14 | 0.11 |
| Ex. (II-80) | Com. (B340) | 5.1 | 5.6 | 500.0 | 9.0 | 154.0 | 0.14 | 0.12 |
| Ex. (II-81) | Com. (B343) | 5.0 | 5.4 | 500.0 | 9.2 | 156.6 | 0.14 | 0.12 |
| Ex. (II-82) | Com. (B348) | 5.2 | 6.4 | 500.0 | 7.8 | 142.4 | 0.14 | 0.12 |
| Ex. (II-83) | Com. (B351) | 5.1 | 6.2 | 500.0 | 8.0 | 144.5 | 0.14 | 0.12 |
| Ex. (II-84) | Com. (B363) | 5.1 | 6.1 | 500.0 | 8.3 | 144.4 | 0.14 | 0.11 |
| Ex. (II-85) | Com. (B372) | 5.0 | 6.6 | 500.0 | 7.6 | 133.1 | 0.14 | 0.12 |
| Ex. (II-86) | Com. (B386) | 5.2 | 6.5 | 500.0 | 7.7 | 136.3 | 0.14 | 0.12 |

[Test Example III-1] Green Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, NPB was vacuum-deposited with a thickness of 60 nm on the hole injection layer to form a hole transport layer. Next, the inventive compound B6 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with CBP as a host material and Ir(ppy)₃ as a dopant material in a weight ratio of 95:5. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

[Test Example III-2] to [Test Example III-136]
Green Organic Light Emitting Diode
(Emission-Auxiliary Layer)

The OLED was manufactured in the same manner as described in Test Example III-1, except that any one of the compounds B7 to C16 of the present invention in the Table 6 below was used as the Emission-Auxiliary Layer material, instead of the inventive compound B6.

Comparative Example 13

The OLED was manufactured in the same manner as described in Test Example III-1, except that Comparative Compound 2 represented above was used as the Emission-Auxiliary Layer material, instead of the inventive compound B6.

Comparative Example 14

The OLED was manufactured in the same manner as described in Test Example III-1, except that Comparative Compound 3 represented above was used as the Emission-Auxiliary Layer material, instead of the inventive compound B6.

Comparative Example 15

The OLED was manufactured in the same manner as described in Test Example III-1, except that Comparative Compound 4 represented above was used as the Emission-Auxiliary Layer material, instead of the inventive compound B6.

Comparative Example 16

The OLED was manufactured in the same manner as described in Test Example III-1, except that Comparative Compound 5 represented above was used as the Emission-Auxiliary Layer material, instead of the inventive compound B6.

Comparative Example 17

The OLED was manufactured in the same manner as described in Test Example III-1, except that Comparative Compound 6 represented above was used as the Emission-Auxiliary Layer material, instead of the inventive compound B6.

Comparative Example 18

The OLED was manufactured in the same manner as described in Test Example III-1, except that Comparative Compound 7 represented above was used as the Emission-Auxiliary Layer material, instead of the inventive compound B6.

Comparative Example 19

An OLED was manufactured in the same manner as described in Test Example III-1, except that an emission-auxiliary layer was not formed.

A forward bias DC voltage was applied to each of the OLEDs manufactured through Test Examples (III-1) to (111-136) and Comparative Example (13) to (19), and electro-luminescence (EL) characteristics of the OLED were measured by PR-650 (Photoresearch).

Also, T95 life span was measured by life span measuring equipment (Mcscience) at a reference brightness of 5000 cd/m². Table 6 below shows evaluation results of OLEDs manufactured Test Examples and Comparative Examples.

TABLE 6

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp. Ex (13) | comp. Com 2 | 6.0 | 14.5 | 5000.0 | 34.5 | 92.8 | 0.33 | 0.62 |
| comp. Ex (14) | comp. Com 3 | 6.0 | 13.6 | 5000.0 | 36.9 | 91.5 | 0.33 | 0.62 |
| comp. Ex (15) | comp. Com 4 | 6.0 | 11.5 | 5000.0 | 43.3 | 156.8 | 0.33 | 0.61 |
| comp. Ex (16) | comp. Com 5 | 5.9 | 11.4 | 5000.0 | 43.7 | 162.0 | 0.33 | 0.61 |
| comp. Ex (17) | comp. Com 6 | 5.9 | 11.1 | 5000.0 | 44.9 | 168.0 | 0.33 | 0.62 |
| comp. Ex (18) | comp. Com 7 | 6.2 | 15.0 | 5000.0 | 33.4 | 77.6 | 0.33 | 0.62 |
| comp. Ex (19) | — | 6.0 | 20.8 | 5000.0 | 24.0 | 53.0 | 0.33 | 0.61 |
| Ex. (III-1) | Com. (B6) | 5.9 | 10.1 | 5000.0 | 49.3 | 180.3 | 0.33 | 0.61 |
| Ex. (III-2) | Com. (B7) | 5.9 | 10.3 | 5000.0 | 48.5 | 176.5 | 0.33 | 0.62 |
| Ex. (III-3) | Com. (B11) | 5.9 | 10.3 | 5000.0 | 48.7 | 173.8 | 0.33 | 0.61 |
| Ex. (III-4) | Com. (B12) | 5.9 | 10.6 | 5000.0 | 47.1 | 167.2 | 0.33 | 0.61 |
| Ex. (III-5) | Com. (B17) | 5.8 | 9.7 | 5000.0 | 51.4 | 188.1 | 0.33 | 0.61 |
| Ex. (III-6) | Com. (B21) | 6.0 | 9.9 | 5000.0 | 50.4 | 183.9 | 0.33 | 0.62 |
| Ex. (III-7) | Com. (B22) | 5.9 | 10.2 | 5000.0 | 48.9 | 181.6 | 0.33 | 0.62 |
| Ex. (III-8) | Com. (B23) | 5.9 | 10.3 | 5000.0 | 48.6 | 176.9 | 0.33 | 0.62 |
| Ex. (III-9) | Com. (B24) | 5.9 | 10.3 | 5000.0 | 48.4 | 172.6 | 0.33 | 0.61 |
| Ex. (III-10) | Com. (B25) | 5.8 | 10.2 | 5000.0 | 48.8 | 177.9 | 0.33 | 0.61 |
| Ex. (III-11) | Com. (B26) | 5.8 | 10.1 | 5000.0 | 49.4 | 180.6 | 0.33 | 0.62 |
| Ex. (III-12) | Com. (B27) | 6.0 | 10.4 | 5000.0 | 48.0 | 171.1 | 0.33 | 0.62 |
| Ex. (III-13) | Com. (B47) | 5.8 | 10.6 | 5000.0 | 47.4 | 173.8 | 0.33 | 0.61 |
| Ex. (III-14) | Com. (B51) | 5.7 | 10.0 | 5000.0 | 49.8 | 181.1 | 0.33 | 0.62 |
| Ex. (III-15) | Com. (B106) | 5.9 | 10.3 | 5000.0 | 48.7 | 171.0 | 0.33 | 0.61 |
| Ex. (III-16) | Com. (B128) | 6.0 | 10.7 | 5000.0 | 46.8 | 173.3 | 0.33 | 0.61 |

TABLE 6-continued

|  | Compound | Voltage (V) | Current Density (mA/cm²) | Brightness (cd/m²) | Efficiency (cd/A) | Lifetime T(95) | CIE x | CIE y |
| --- | --- | --- | --- | --- | --- | --- | --- | --- |
| Ex. (III-17) | Com. (B129) | 5.9 | 10.9 | 5000.0 | 45.7 | 158.4 | 0.33 | 0.61 |
| Ex. (III-18) | Com. (B132) | 5.9 | 10.9 | 5000.0 | 46.0 | 162.0 | 0.33 | 0.61 |
| Ex. (III-19) | Com. (B138) | 5.9 | 10.9 | 5000.0 | 45.9 | 164.0 | 0.33 | 0.61 |
| Ex. (III-20) | Com. (B145) | 5.9 | 10.8 | 5000.0 | 46.5 | 163.3 | 0.33 | 0.61 |
| Ex. (III-21) | Com. (B157) | 5.8 | 11.0 | 5000.0 | 45.5 | 160.0 | 0.33 | 0.62 |
| Ex. (III-22) | Com. (B158) | 5.8 | 11.0 | 5000.0 | 45.6 | 164.9 | 0.33 | 0.61 |
| Ex. (III-23) | Com. (B164) | 5.8 | 10.9 | 5000.0 | 46.0 | 156.9 | 0.33 | 0.61 |
| Ex. (III-24) | Com. (B165) | 5.8 | 10.8 | 5000.0 | 46.5 | 157.5 | 0.33 | 0.61 |
| Ex. (III-25) | Com. (B167) | 5.8 | 10.5 | 5000.0 | 47.7 | 174.5 | 0.33 | 0.62 |
| Ex. (III-26) | Com. (B168) | 5.8 | 10.5 | 5000.0 | 47.6 | 168.5 | 0.33 | 0.61 |
| Ex. (III-27) | Com. (B169) | 5.9 | 10.4 | 5000.0 | 48.0 | 170.0 | 0.33 | 0.61 |
| Ex. (III-28) | Com. (B171) | 5.8 | 10.7 | 5000.0 | 46.8 | 173.3 | 0.33 | 0.61 |
| Ex. (III-29) | Com. (B172) | 5.9 | 10.6 | 5000.0 | 47.0 | 166.6 | 0.33 | 0.62 |
| Ex. (III-30) | Com. (B173) | 6.0 | 10.6 | 5000.0 | 47.3 | 171.1 | 0.33 | 0.61 |
| Ex. (III-31) | Com. (B174) | 5.8 | 10.3 | 5000.0 | 48.6 | 178.9 | 0.33 | 0.61 |
| Ex. (III-32) | Com. (B175) | 5.9 | 10.5 | 5000.0 | 47.8 | 179.9 | 0.33 | 0.62 |
| Ex. (III-33) | Com. (B176) | 6.0 | 10.4 | 5000.0 | 47.9 | 171.1 | 0.33 | 0.62 |
| Ex. (III-34) | Com. (B177) | 6.0 | 10.2 | 5000.0 | 49.0 | 180.7 | 0.33 | 0.62 |
| Ex. (III-35) | Com. (B178) | 5.7 | 10.6 | 5000.0 | 47.2 | 166.1 | 0.33 | 0.61 |
| Ex. (III-36) | Com. (B179) | 5.9 | 10.3 | 5000.0 | 48.4 | 175.6 | 0.33 | 0.62 |
| Ex. (III-37) | Com. (B182) | 5.8 | 10.8 | 5000.0 | 46.2 | 160.6 | 0.33 | 0.61 |
| Ex. (III-38) | Com. (B183) | 5.8 | 10.4 | 5000.0 | 48.0 | 178.5 | 0.33 | 0.62 |
| Ex. (III-39) | Com. (B187) | 5.8 | 10.2 | 5000.0 | 49.2 | 181.0 | 0.33 | 0.61 |
| Ex. (III-40) | Com. (B192) | 5.8 | 10.8 | 5000.0 | 46.1 | 162.9 | 0.33 | 0.61 |
| Ex. (III-41) | Com. (B195) | 5.9 | 10.1 | 5000.0 | 49.6 | 180.5 | 0.33 | 0.61 |
| Ex. (III-42) | Com. (B197) | 5.7 | 9.8 | 5000.0 | 50.9 | 187.0 | 0.33 | 0.62 |
| Ex. (III-43) | Com. (B198) | 5.9 | 10.1 | 5000.0 | 49.5 | 181.5 | 0.33 | 0.62 |
| Ex. (III-44) | Com. (B200) | 5.8 | 10.7 | 5000.0 | 46.6 | 165.2 | 0.33 | 0.62 |
| Ex. (III-45) | Com. (B203) | 5.9 | 9.8 | 5000.0 | 50.9 | 184.8 | 0.33 | 0.62 |
| Ex. (III-46) | Com. (B204) | 5.8 | 10.1 | 5000.0 | 49.3 | 180.6 | 0.33 | 0.61 |
| Ex. (III-47) | Com. (B206) | 5.8 | 10.5 | 5000.0 | 47.6 | 170.5 | 0.33 | 0.62 |
| Ex. (III-48) | Com. (B210) | 6.0 | 10.5 | 5000.0 | 47.7 | 166.6 | 0.33 | 0.62 |
| Ex. (III-49) | Com. (B213) | 5.9 | 10.7 | 5000.0 | 46.9 | 174.2 | 0.33 | 0.62 |
| Ex. (III-50) | Com. (B217) | 5.9 | 10.5 | 5000.0 | 47.7 | 174.0 | 0.33 | 0.62 |
| Ex. (III-51) | Com. (B219) | 6.0 | 10.1 | 5000.0 | 49.7 | 179.7 | 0.33 | 0.61 |
| Ex. (III-52) | Com. (B220) | 5.9 | 10.0 | 5000.0 | 50.1 | 185.2 | 0.33 | 0.61 |
| Ex. (III-53) | Com. (B221) | 5.8 | 9.9 | 5000.0 | 50.4 | 184.8 | 0.33 | 0.62 |
| Ex. (III-54) | Com. (B222) | 5.9 | 10.0 | 5000.0 | 50.2 | 187.5 | 0.33 | 0.61 |
| Ex. (III-55) | Com. (B223) | 6.0 | 9.5 | 5000.0 | 52.6 | 198.2 | 0.33 | 0.61 |
| Ex. (III-56) | Com. (B224) | 5.9 | 10.0 | 5000.0 | 50.1 | 183.1 | 0.33 | 0.61 |
| Ex. (III-57) | Com. (B225) | 5.7 | 9.8 | 5000.0 | 51.0 | 186.4 | 0.33 | 0.61 |
| Ex. (III-58) | Com. (B226) | 5.8 | 9.9 | 5000.0 | 50.6 | 182.5 | 0.33 | 0.62 |
| Ex. (III-59) | Com. (B227) | 5.7 | 9.9 | 5000.0 | 50.7 | 181.8 | 0.33 | 0.62 |
| Ex. (III-60) | Com. (B228) | 5.8 | 9.8 | 5000.0 | 50.9 | 184.1 | 0.33 | 0.61 |
| Ex. (III-61) | Com. (B229) | 5.7 | 10.0 | 5000.0 | 49.9 | 187.8 | 0.33 | 0.62 |
| Ex. (III-62) | Com. (B232) | 5.7 | 9.9 | 5000.0 | 50.4 | 185.3 | 0.33 | 0.62 |
| Ex. (III-63) | Com. (B234) | 5.8 | 10.0 | 5000.0 | 49.9 | 181.5 | 0.33 | 0.62 |
| Ex. (III-64) | Com. (B238) | 5.8 | 10.0 | 5000.0 | 49.9 | 187.7 | 0.33 | 0.62 |
| Ex. (III-65) | Com. (B239) | 5.8 | 10.0 | 5000.0 | 50.2 | 182.6 | 0.33 | 0.61 |
| Ex. (III-66) | Com. (B240) | 5.7 | 9.6 | 5000.0 | 52.1 | 191.4 | 0.33 | 0.62 |
| Ex. (III-67) | Com. (B241) | 5.7 | 9.8 | 5000.0 | 51.2 | 190.6 | 0.33 | 0.61 |
| Ex. (III-68) | Com. (B245) | 6.0 | 10.1 | 5000.0 | 49.4 | 179.4 | 0.33 | 0.62 |
| Ex. (III-69) | Com. (B248) | 5.8 | 9.8 | 5000.0 | 50.9 | 182.2 | 0.33 | 0.61 |
| Ex. (III-70) | Com. (B252) | 6.0 | 9.8 | 5000.0 | 51.2 | 191.5 | 0.33 | 0.61 |
| Ex. (III-71) | Com. (B253) | 5.9 | 9.9 | 5000.0 | 50.6 | 180.7 | 0.33 | 0.61 |
| Ex. (III-72) | Com. (B255) | 5.9 | 10.1 | 5000.0 | 49.7 | 178.9 | 0.33 | 0.62 |
| Ex. (III-73) | Com. (B259) | 5.9 | 9.7 | 5000.0 | 51.6 | 190.5 | 0.33 | 0.62 |
| Ex. (III-74) | Com. (B260) | 5.8 | 9.6 | 5000.0 | 52.0 | 190.1 | 0.33 | 0.62 |
| Ex. (III-75) | Com. (B264) | 5.7 | 9.5 | 5000.0 | 52.6 | 196.6 | 0.33 | 0.62 |
| Ex. (III-76) | Com. (B266) | 6.0 | 10.2 | 5000.0 | 49.2 | 184.0 | 0.33 | 0.62 |
| Ex. (III-77) | Com. (B267) | 5.8 | 10.1 | 5000.0 | 49.6 | 176.2 | 0.33 | 0.61 |
| Ex. (III-78) | Com. (B271) | 5.8 | 10.2 | 5000.0 | 48.9 | 183.2 | 0.33 | 0.62 |
| Ex. (III-79) | Com. (B273) | 5.9 | 10.3 | 5000.0 | 48.7 | 165.8 | 0.33 | 0.61 |
| Ex. (III-80) | Com. (B276) | 6.0 | 10.1 | 5000.0 | 49.3 | 176.6 | 0.33 | 0.61 |
| Ex. (III-81) | Com. (B277) | 5.8 | 10.1 | 5000.0 | 49.3 | 178.5 | 0.33 | 0.62 |
| Ex. (III-82) | Com. (B278) | 5.9 | 10.3 | 5000.0 | 48.7 | 172.2 | 0.33 | 0.61 |
| Ex. (III-83) | Com. (B285) | 5.9 | 9.7 | 5000.0 | 51.6 | 199.2 | 0.33 | 0.62 |
| Ex. (III-84) | Com. (B287) | 5.7 | 9.5 | 5000.0 | 52.6 | 201.9 | 0.33 | 0.61 |
| Ex. (III-85) | Com. (B288) | 5.8 | 9.6 | 5000.0 | 51.9 | 196.3 | 0.33 | 0.61 |
| Ex. (III-86) | Com. (B289) | 5.7 | 9.7 | 5000.0 | 51.5 | 195.1 | 0.33 | 0.61 |
| Ex. (III-87) | Com. (B290) | 5.9 | 9.7 | 5000.0 | 51.5 | 195.6 | 0.33 | 0.62 |
| Ex. (III-88) | Com. (B293) | 5.8 | 9.7 | 5000.0 | 51.7 | 194.6 | 0.33 | 0.62 |
| Ex. (III-89) | Com. (B296) | 5.9 | 9.6 | 5000.0 | 51.9 | 190.8 | 0.33 | 0.61 |
| Ex. (III-90) | Com. (B297) | 5.7 | 9.8 | 5000.0 | 51.1 | 191.0 | 0.33 | 0.62 |
| Ex. (III-91) | Com. (B299) | 5.9 | 9.7 | 5000.0 | 51.6 | 199.9 | 0.33 | 0.62 |

TABLE 6-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (III-92) | Com. (B303) | 5.7 | 10.1 | 5000.0 | 49.3 | 178.3 | 0.33 | 0.61 |
| Ex. (III-93) | Com. (B304) | 5.8 | 10.1 | 5000.0 | 49.7 | 177.6 | 0.33 | 0.62 |
| Ex. (III-94) | Com. (B305) | 6.0 | 10.2 | 5000.0 | 49.2 | 182.9 | 0.33 | 0.62 |
| Ex. (III-95) | Com. (B306) | 6.0 | 10.2 | 5000.0 | 48.9 | 174.7 | 0.33 | 0.61 |
| Ex. (III-96) | Com. (B308) | 5.9 | 9.8 | 5000.0 | 50.8 | 190.7 | 0.33 | 0.61 |
| Ex. (III-97) | Com. (B309) | 6.0 | 10.0 | 5000.0 | 50.2 | 189.3 | 0.33 | 0.61 |
| Ex. (III-98) | Com. (B310) | 5.8 | 9.7 | 5000.0 | 51.6 | 193.6 | 0.33 | 0.62 |
| Ex. (III-99) | Com. (B311) | 5.8 | 9.7 | 5000.0 | 51.4 | 198.2 | 0.33 | 0.62 |
| Ex. (III-100) | Com. (B313) | 5.9 | 9.7 | 5000.0 | 51.5 | 191.6 | 0.33 | 0.62 |
| Ex. (III-101) | Com. (B314) | 5.7 | 9.4 | 5000.0 | 53.0 | 201.0 | 0.33 | 0.62 |
| Ex. (III-102) | Com. (B315) | 5.7 | 9.5 | 5000.0 | 52.6 | 200.2 | 0.33 | 0.62 |
| Ex. (III-103) | Com. (B316) | 5.9 | 9.7 | 5000.0 | 51.8 | 190.7 | 0.33 | 0.61 |
| Ex. (III-104) | Com. (B317) | 5.8 | 9.8 | 5000.0 | 51.0 | 192.3 | 0.33 | 0.62 |
| Ex. (III-105) | Com. (B320) | 6.0 | 10.0 | 5000.0 | 50.1 | 190.5 | 0.33 | 0.61 |
| Ex. (III-106) | Com. (B322) | 5.9 | 10.0 | 5000.0 | 50.2 | 192.4 | 0.33 | 0.62 |
| Ex. (III-107) | Com. (B325) | 5.7 | 9.9 | 5000.0 | 50.5 | 187.9 | 0.33 | 0.61 |
| Ex. (III-108) | Com. (B327) | 5.8 | 9.8 | 5000.0 | 50.8 | 194.1 | 0.33 | 0.62 |
| Ex. (III-109) | Com. (B328) | 5.8 | 9.7 | 5000.0 | 51.3 | 197.3 | 0.33 | 0.61 |
| Ex. (III-110) | Com. (B331) | 5.9 | 9.6 | 5000.0 | 52.2 | 200.2 | 0.33 | 0.61 |
| Ex. (III-111) | Com. (B340) | 5.9 | 9.4 | 5000.0 | 53.0 | 200.7 | 0.33 | 0.61 |
| Ex. (III-112) | Com. (B343) | 5.9 | 9.4 | 5000.0 | 53.3 | 202.7 | 0.33 | 0.61 |
| Ex. (III-113) | Com. (B344) | 5.9 | 9.3 | 5000.0 | 53.7 | 202.7 | 0.33 | 0.62 |
| Ex. (III-114) | Com. (B348) | 5.9 | 9.8 | 5000.0 | 50.9 | 186.6 | 0.33 | 0.62 |
| Ex. (III-115) | Com. (B351) | 5.8 | 9.9 | 5000.0 | 50.6 | 188.4 | 0.33 | 0.62 |
| Ex. (III-116) | Com. (B358) | 5.9 | 10.0 | 5000.0 | 49.9 | 189.4 | 0.33 | 0.62 |
| Ex. (III-117) | Com. (B363) | 6.0 | 9.9 | 5000.0 | 50.5 | 192.4 | 0.33 | 0.61 |
| Ex. (III-118) | Com. (B372) | 5.9 | 10.5 | 5000.0 | 47.7 | 175.0 | 0.33 | 0.61 |
| Ex. (III-119) | Com. (B375) | 5.9 | 10.2 | 5000.0 | 49.2 | 171.6 | 0.33 | 0.62 |
| Ex. (III-120) | Com. (B386) | 5.8 | 10.2 | 5000.0 | 49.2 | 182.5 | 0.33 | 0.61 |
| Ex. (III-121) | Com. (C1) | 5.9 | 9.3 | 5000.0 | 53.6 | 186.3 | 0.33 | 0.62 |
| Ex. (III-122) | Com. (C2) | 5.8 | 9.3 | 5000.0 | 53.9 | 190.2 | 0.33 | 0.61 |
| Ex. (III-123) | Com. (C3) | 5.8 | 9.7 | 5000.0 | 51.6 | 186.5 | 0.33 | 0.61 |
| Ex. (III-124) | Com. (C4) | 5.9 | 9.8 | 5000.0 | 51.2 | 193.3 | 0.33 | 0.61 |
| Ex. (III-125) | Com. (C5) | 5.7 | 9.7 | 5000.0 | 51.4 | 189.3 | 0.33 | 0.61 |
| Ex. (III-126) | Com. (C6) | 5.9 | 9.6 | 5000.0 | 52.3 | 188.1 | 0.33 | 0.62 |
| Ex. (III-127) | Com. (C7) | 5.9 | 9.7 | 5000.0 | 51.5 | 185.8 | 0.33 | 0.62 |
| Ex. (III-128) | Com. (C8) | 5.7 | 9.3 | 5000.0 | 53.6 | 187.8 | 0.33 | 0.62 |
| Ex. (III-129) | Com. (C9) | 5.9 | 9.6 | 5000.0 | 51.8 | 190.8 | 0.33 | 0.62 |
| Ex. (III-130) | Com. (C10) | 5.8 | 10.5 | 5000.0 | 47.6 | 190.6 | 0.33 | 0.61 |
| Ex. (III-131) | Com. (C11) | 5.8 | 9.8 | 5000.0 | 51.0 | 185.9 | 0.33 | 0.61 |
| Ex. (III-132) | Com. (C12) | 5.9 | 10.0 | 5000.0 | 49.9 | 193.4 | 0.33 | 0.62 |
| Ex. (III-133) | Com. (C13) | 5.8 | 10.3 | 5000.0 | 48.7 | 187.5 | 0.33 | 0.61 |
| Ex. (III-134) | Com. (C14) | 5.8 | 9.7 | 5000.0 | 51.8 | 191.5 | 0.33 | 0.61 |
| Ex. (III-135) | Com. (C15) | 5.8 | 10.4 | 5000.0 | 48.1 | 194.1 | 0.33 | 0.62 |
| Ex. (III-136) | Com. (C16) | 5.9 | 9.3 | 5000.0 | 53.7 | 186.5 | 0.33 | 0.62 |

[Test Example IV-1] Red Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm.

Subsequently, NPB was vacuum-deposited with a thickness of 60 nm on the hole injection layer to form a hole transport layer. Next, the inventive compound B1 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with CBP as a host material and bis-(1-phenylisoquinolyl)iridium(III) acetylacetonate (hereinafter abbreviated as "(piq)$_2$Ir(acac)") as a dopant material in a weight ratio of 95:5. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

[Test Example IV-2] to [Test Example IV-135] Red Organic Light Emitting Diode (Emission-Auxiliary Layer)

The OLED was manufactured in the same manner as described in Test Example IV-1, except that any one of the compounds B6 to B386 of the present invention in the Table 7 below was used as the Emission-Auxiliary Layer material, instead of the inventive compound B1.

Comparative Example 20

An OLED was manufactured in the same manner as described in Test Example IV-1, except that Comparative Compound 2 represented above was used as the Emission-Auxiliary Layer material, instead of the inventive compound B1.

Comparative Example 21

An OLED was manufactured in the same manner as described in Test Example IV-1, except that Comparative Compound 4 represented above was used as the Emission-Auxiliary Layer material, instead of the inventive compound B1.

Comparative Example 22

An OLED was manufactured in the same manner as described in Test Example IV-1, except that Comparative Compound 5 represented above was used as the Emission-Auxiliary Layer material, instead of the inventive compound B1.

Comparative Example 23

An OLED was manufactured in the same manner as described in Test Example IV-1, except that Comparative Compound 6 represented above was used as the Emission-Auxiliary Layer material, instead of the inventive compound B1.

Comparative Example 24

An OLED was manufactured in the same manner as described in Test Example IV-1, except that Comparative Compound 7 represented above was used as the Emission-Auxiliary Layer material, instead of the inventive compound B1.

Comparative Example 25

An OLED was manufactured in the same manner as described in Test Example IV-1, except that an emission-auxiliary layer was not formed.

A forward bias DC voltage was applied to each of the OLEDs manufactured through Test Examples (IV-1) to (IV-135) and Comparative Example (20) to (25), and electro-luminescence (EL) characteristics of the OLED were measured by PR-650 (Photoresearch).

Also, T95 life span was measured by life span measuring equipment (Mcscience) at a reference brightness of 2500 cd/m$^2$. Table 7 below shows evaluation results of OLEDs manufactured Test Examples and Comparative Examples.

TABLE 7

|  | Compound | Voltage (V) | Current Density (mA/cm$^2$) | Brightness (cd/m$^2$) | Efficiency (cd/A) | Lifetime T(95) | CIE x | CIE y |
| --- | --- | --- | --- | --- | --- | --- | --- | --- |
| comp. Ex (20) | comp. Com 2 | 6.5 | 27.5 | 2500.0 | 9.1 | 84.7 | 0.66 | 0.32 |
| comp. Ex (21) | comp. Com 4 | 6.6 | 20.8 | 2500.0 | 12.0 | 120.1 | 0.66 | 0.32 |
| comp. Ex (22) | comp. Com 5 | 6.6 | 20.0 | 2500.0 | 12.5 | 129.5 | 0.66 | 0.32 |
| comp. Ex (23) | comp. Com 6 | 6.7 | 19.5 | 2500.0 | 12.8 | 137.6 | 0.66 | 0.32 |
| comp. Ex (24) | comp. Com 7 | 7.0 | 29.9 | 2500.0 | 8.3 | 81.8 | 0.66 | 0.32 |
| comp. Ex (25) | — | 7.0 | 33.3 | 2500.0 | 7.5 | 66.8 | 0.66 | 0.32 |
| Ex. (IV-1) | Com. (B1) | 6.7 | 19.3 | 2500.0 | 13.0 | 143.8 | 0.66 | 0.32 |
| Ex. (IV-2) | Com. (B6) | 6.6 | 18.4 | 2500.0 | 13.6 | 142.5 | 0.66 | 0.32 |
| Ex. (IV-3) | Com. (B7) | 6.7 | 19.4 | 2500.0 | 12.9 | 150.9 | 0.66 | 0.32 |
| Ex. (IV-4) | Com. (B11) | 6.8 | 19.1 | 2500.0 | 13.1 | 141.1 | 0.66 | 0.32 |
| Ex. (IV-5) | Com. (B12) | 6.7 | 19.0 | 2500.0 | 13.2 | 147.8 | 0.66 | 0.32 |
| Ex. (IV-6) | Com. (B17) | 6.7 | 16.8 | 2500.0 | 14.9 | 159.5 | 0.66 | 0.32 |
| Ex. (IV-7) | Com. (B21) | 6.7 | 17.2 | 2500.0 | 14.5 | 157.3 | 0.66 | 0.32 |
| Ex. (IV-8) | Com. (B22) | 6.6 | 17.8 | 2500.0 | 14.1 | 150.7 | 0.66 | 0.32 |
| Ex. (IV-9) | Com. (B23) | 6.5 | 18.2 | 2500.0 | 13.8 | 149.5 | 0.66 | 0.32 |
| Ex. (IV-10) | Com. (B24) | 6.6 | 17.6 | 2500.0 | 14.2 | 151.2 | 0.66 | 0.32 |
| Ex. (IV-11) | Com. (B25) | 6.7 | 19.7 | 2500.0 | 12.7 | 137.5 | 0.66 | 0.33 |
| Ex. (IV-12) | Com. (B26) | 6.5 | 18.6 | 2500.0 | 13.5 | 140.1 | 0.66 | 0.32 |
| Ex. (IV-13) | Com. (B47) | 6.7 | 19.3 | 2500.0 | 12.9 | 151.2 | 0.66 | 0.32 |
| Ex. (IV-14) | Com. (B51) | 6.6 | 18.8 | 2500.0 | 13.3 | 150.5 | 0.66 | 0.32 |
| Ex. (IV-15) | Com. (B62) | 6.7 | 19.0 | 2500.0 | 13.2 | 146.0 | 0.66 | 0.32 |
| Ex. (IV-16) | Com. (B106) | 6.6 | 19.6 | 2500.0 | 12.8 | 136.5 | 0.67 | 0.33 |
| Ex. (IV-17) | Com. (B128) | 6.8 | 19.0 | 2500.0 | 13.2 | 144.5 | 0.66 | 0.32 |
| Ex. (IV-18) | Com. (B129) | 6.8 | 19.1 | 2500.0 | 13.1 | 143.0 | 0.66 | 0.32 |
| Ex. (IV-19) | Com. (B132) | 6.7 | 19.4 | 2500.0 | 12.9 | 144.1 | 0.67 | 0.33 |
| Ex. (IV-20) | Com. (B138) | 6.6 | 18.9 | 2500.0 | 13.2 | 140.8 | 0.67 | 0.33 |
| Ex. (IV-21) | Com. (B145) | 6.6 | 19.3 | 2500.0 | 13.0 | 140.9 | 0.66 | 0.32 |
| Ex. (IV-22) | Com. (B157) | 6.5 | 19.0 | 2500.0 | 13.2 | 143.2 | 0.67 | 0.33 |
| Ex. (IV-23) | Com. (B158) | 6.6 | 18.8 | 2500.0 | 13.3 | 137.9 | 0.66 | 0.33 |
| Ex. (IV-24) | Com. (B164) | 6.5 | 19.1 | 2500.0 | 13.1 | 140.0 | 0.67 | 0.32 |
| Ex. (IV-25) | Com. (B165) | 6.6 | 19.3 | 2500.0 | 13.0 | 138.5 | 0.66 | 0.33 |
| Ex. (IV-26) | Com. (B167) | 6.7 | 19.2 | 2500.0 | 13.0 | 141.2 | 0.66 | 0.32 |
| Ex. (IV-27) | Com. (B168) | 6.6 | 19.0 | 2500.0 | 13.2 | 147.3 | 0.66 | 0.32 |
| Ex. (IV-28) | Com. (B169) | 6.6 | 18.4 | 2500.0 | 13.6 | 140.7 | 0.66 | 0.32 |
| Ex. (IV-29) | Com. (B170) | 6.6 | 19.4 | 2500.0 | 12.9 | 145.0 | 0.66 | 0.32 |
| Ex. (IV-30) | Com. (B171) | 6.8 | 19.0 | 2500.0 | 13.2 | 144.1 | 0.66 | 0.32 |
| Ex. (IV-31) | Com. (B172) | 6.6 | 18.8 | 2500.0 | 13.3 | 143.9 | 0.66 | 0.32 |
| Ex. (IV-32) | Com. (B173) | 6.8 | 18.9 | 2500.0 | 13.2 | 141.5 | 0.66 | 0.32 |
| Ex. (IV-33) | Com. (B174) | 6.6 | 18.7 | 2500.0 | 13.4 | 151.1 | 0.66 | 0.32 |
| Ex. (IV-34) | Com. (B175) | 6.7 | 18.6 | 2500.0 | 13.4 | 147.1 | 0.66 | 0.32 |
| Ex. (IV-35) | Com. (B176) | 6.5 | 18.6 | 2500.0 | 13.5 | 151.1 | 0.66 | 0.32 |
| Ex. (IV-36) | Com. (B177) | 6.6 | 17.9 | 2500.0 | 14.0 | 153.4 | 0.66 | 0.32 |
| Ex. (IV-37) | Com. (B178) | 6.7 | 18.8 | 2500.0 | 13.3 | 147.1 | 0.66 | 0.32 |

TABLE 7-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (IV-38) | Com. (B179) | 6.7 | 18.6 | 2500.0 | 13.4 | 140.8 | 0.66 | 0.32 |
| Ex. (IV-39) | Com. (B180) | 6.6 | 18.2 | 2500.0 | 13.7 | 151.0 | 0.66 | 0.32 |
| Ex. (IV-40) | Com. (B181) | 6.8 | 19.3 | 2500.0 | 13.0 | 149.7 | 0.66 | 0.32 |
| Ex. (IV-41) | Com. (B182) | 6.8 | 19.2 | 2500.0 | 13.0 | 142.6 | 0.66 | 0.33 |
| Ex. (IV-42) | Com. (B183) | 6.7 | 18.1 | 2500.0 | 13.8 | 147.6 | 0.66 | 0.32 |
| Ex. (IV-43) | Com. (B184) | 6.8 | 19.5 | 2500.0 | 12.8 | 144.6 | 0.66 | 0.32 |
| Ex. (IV-44) | Com. (B187) | 6.5 | 17.5 | 2500.0 | 14.3 | 152.7 | 0.66 | 0.32 |
| Ex. (IV-45) | Com. (B188) | 6.5 | 18.6 | 2500.0 | 13.4 | 145.7 | 0.66 | 0.32 |
| Ex. (IV-46) | Com. (B190) | 6.5 | 18.2 | 2500.0 | 13.7 | 141.8 | 0.66 | 0.32 |
| Ex. (IV-47) | Com. (B191) | 6.6 | 19.3 | 2500.0 | 12.9 | 147.3 | 0.66 | 0.32 |
| Ex. (IV-48) | Com. (B192) | 6.8 | 19.0 | 2500.0 | 13.1 | 137.7 | 0.66 | 0.32 |
| Ex. (IV-49) | Com. (B194) | 6.7 | 19.0 | 2500.0 | 13.2 | 142.6 | 0.66 | 0.32 |
| Ex. (IV-50) | Com. (B195) | 6.6 | 17.8 | 2500.0 | 14.1 | 150.4 | 0.66 | 0.32 |
| Ex. (IV-51) | Com. (B197) | 6.5 | 17.0 | 2500.0 | 14.7 | 156.0 | 0.66 | 0.32 |
| Ex. (IV-52) | Com. (B198) | 6.6 | 18.1 | 2500.0 | 13.8 | 151.1 | 0.66 | 0.32 |
| Ex. (IV-53) | Com. (B200) | 6.7 | 19.0 | 2500.0 | 13.1 | 149.8 | 0.66 | 0.32 |
| Ex. (IV-54) | Com. (B203) | 6.6 | 17.3 | 2500.0 | 14.4 | 158.2 | 0.66 | 0.32 |
| Ex. (IV-55) | Com. (B204) | 6.7 | 18.0 | 2500.0 | 13.9 | 152.3 | 0.66 | 0.32 |
| Ex. (IV-56) | Com. (B206) | 6.7 | 19.3 | 2500.0 | 13.0 | 144.0 | 0.66 | 0.32 |
| Ex. (IV-57) | Com. (B208) | 6.6 | 19.5 | 2500.0 | 12.9 | 148.5 | 0.66 | 0.32 |
| Ex. (IV-58) | Com. (B210) | 6.6 | 19.3 | 2500.0 | 13.0 | 144.1 | 0.66 | 0.32 |
| Ex. (IV-59) | Com. (B213) | 6.7 | 19.0 | 2500.0 | 13.2 | 142.6 | 0.66 | 0.32 |
| Ex. (IV-60) | Com. (B217) | 6.7 | 19.0 | 2500.0 | 13.1 | 141.3 | 0.66 | 0.32 |
| Ex. (IV-61) | Com. (B219) | 6.7 | 17.9 | 2500.0 | 13.9 | 156.2 | 0.66 | 0.32 |
| Ex. (IV-62) | Com. (B220) | 6.6 | 17.5 | 2500.0 | 14.3 | 150.5 | 0.66 | 0.32 |
| Ex. (IV-63) | Com. (B221) | 6.5 | 17.5 | 2500.0 | 14.3 | 159.1 | 0.66 | 0.32 |
| Ex. (IV-64) | Com. (B222) | 6.7 | 17.2 | 2500.0 | 14.5 | 159.7 | 0.66 | 0.32 |
| Ex. (IV-65) | Com. (B223) | 6.5 | 15.9 | 2500.0 | 15.7 | 169.9 | 0.66 | 0.32 |
| Ex. (IV-66) | Com. (B224) | 6.5 | 17.1 | 2500.0 | 14.6 | 151.3 | 0.66 | 0.32 |
| Ex. (IV-67) | Com. (B225) | 6.7 | 17.4 | 2500.0 | 14.3 | 149.2 | 0.66 | 0.32 |
| Ex. (IV-68) | Com. (B226) | 6.6 | 17.1 | 2500.0 | 14.6 | 159.3 | 0.66 | 0.32 |
| Ex. (IV-69) | Com. (B227) | 6.7 | 17.4 | 2500.0 | 14.4 | 151.3 | 0.66 | 0.32 |
| Ex. (IV-70) | Com. (B228) | 6.6 | 17.6 | 2500.0 | 14.2 | 149.6 | 0.66 | 0.32 |
| Ex. (IV-71) | Com. (B229) | 6.6 | 17.2 | 2500.0 | 14.5 | 152.2 | 0.66 | 0.32 |
| Ex. (IV-72) | Com. (B232) | 6.6 | 17.4 | 2500.0 | 14.4 | 159.3 | 0.66 | 0.32 |
| Ex. (IV-73) | Com. (B234) | 6.7 | 17.1 | 2500.0 | 14.6 | 155.3 | 0.66 | 0.32 |
| Ex. (IV-74) | Com. (B236) | 6.7 | 17.4 | 2500.0 | 14.3 | 149.3 | 0.66 | 0.32 |
| Ex. (IV-75) | Com. (B238) | 6.6 | 17.3 | 2500.0 | 14.4 | 159.6 | 0.66 | 0.32 |
| Ex. (IV-76) | Com. (B239) | 6.5 | 17.2 | 2500.0 | 14.5 | 153.5 | 0.66 | 0.32 |
| Ex. (IV-77) | Com. (B240) | 6.6 | 16.8 | 2500.0 | 14.9 | 162.1 | 0.66 | 0.32 |
| Ex. (IV-78) | Com. (B241) | 6.6 | 16.9 | 2500.0 | 14.8 | 162.2 | 0.66 | 0.32 |
| Ex. (IV-79) | Com. (B245) | 6.6 | 18.0 | 2500.0 | 13.9 | 153.8 | 0.66 | 0.32 |
| Ex. (IV-80) | Com. (B248) | 6.7 | 17.5 | 2500.0 | 14.3 | 158.1 | 0.66 | 0.32 |
| Ex. (IV-81) | Com. (B251) | 6.6 | 17.9 | 2500.0 | 14.0 | 150.9 | 0.66 | 0.32 |
| Ex. (IV-82) | Com. (B252) | 6.6 | 17.0 | 2500.0 | 14.7 | 160.2 | 0.66 | 0.32 |
| Ex. (IV-83) | Com. (B253) | 6.7 | 17.1 | 2500.0 | 14.6 | 155.1 | 0.66 | 0.32 |
| Ex. (IV-84) | Com. (B255) | 6.8 | 17.9 | 2500.0 | 14.0 | 160.2 | 0.66 | 0.32 |
| Ex. (IV-85) | Com. (B259) | 6.6 | 16.4 | 2500.0 | 15.2 | 162.1 | 0.66 | 0.32 |
| Ex. (IV-86) | Com. (B260) | 6.6 | 16.9 | 2500.0 | 14.8 | 159.6 | 0.66 | 0.32 |
| Ex. (IV-87) | Com. (B264) | 6.6 | 16.3 | 2500.0 | 15.4 | 167.3 | 0.66 | 0.32 |
| Ex. (IV-88) | Com. (B266) | 6.7 | 18.1 | 2500.0 | 13.8 | 157.3 | 0.66 | 0.32 |
| Ex. (IV-89) | Com. (B267) | 6.7 | 17.9 | 2500.0 | 14.0 | 155.3 | 0.66 | 0.32 |
| Ex. (IV-90) | Com. (B271) | 6.6 | 18.2 | 2500.0 | 13.7 | 149.4 | 0.66 | 0.32 |
| Ex. (IV-91) | Com. (B273) | 6.7 | 18.5 | 2500.0 | 13.5 | 144.9 | 0.66 | 0.33 |
| Ex. (IV-92) | Com. (B276) | 6.8 | 17.5 | 2500.0 | 14.3 | 149.1 | 0.66 | 0.32 |
| Ex. (IV-93) | Com. (B277) | 6.8 | 17.6 | 2500.0 | 14.2 | 151.6 | 0.66 | 0.32 |
| Ex. (IV-94) | Com. (B278) | 6.8 | 18.5 | 2500.0 | 13.5 | 139.5 | 0.67 | 0.32 |
| Ex. (IV-95) | Com. (B279) | 6.7 | 18.2 | 2500.0 | 13.7 | 155.7 | 0.66 | 0.32 |
| Ex. (IV-96) | Com. (B285) | 6.6 | 16.2 | 2500.0 | 15.5 | 168.2 | 0.66 | 0.32 |
| Ex. (IV-97) | Com. (B287) | 6.6 | 15.8 | 2500.0 | 15.8 | 168.8 | 0.66 | 0.32 |
| Ex. (IV-98) | Com. (B288) | 6.7 | 14.9 | 2500.0 | 16.8 | 177.8 | 0.66 | 0.32 |
| Ex. (IV-99) | Com. (B289) | 6.6 | 16.1 | 2500.0 | 15.5 | 166.9 | 0.66 | 0.32 |
| Ex. (IV-100) | Com. (B290) | 6.6 | 16.1 | 2500.0 | 15.6 | 164.8 | 0.66 | 0.32 |
| Ex. (IV-101) | Com. (B293) | 6.7 | 16.5 | 2500.0 | 15.1 | 164.2 | 0.66 | 0.32 |
| Ex. (IV-102) | Com. (B296) | 6.6 | 16.1 | 2500.0 | 15.6 | 163.2 | 0.66 | 0.32 |
| Ex. (IV-103) | Com. (B297) | 6.5 | 16.2 | 2500.0 | 15.4 | 166.5 | 0.66 | 0.32 |
| Ex. (IV-104) | Com. (B299) | 6.5 | 16.1 | 2500.0 | 15.5 | 168.9 | 0.66 | 0.32 |
| Ex. (IV-105) | Com. (B303) | 6.6 | 17.2 | 2500.0 | 14.5 | 151.0 | 0.67 | 0.32 |
| Ex. (IV-106) | Com. (B304) | 6.8 | 17.5 | 2500.0 | 14.3 | 149.9 | 0.67 | 0.32 |
| Ex. (IV-107) | Com. (B305) | 6.8 | 17.6 | 2500.0 | 14.2 | 149.6 | 0.67 | 0.33 |
| Ex. (IV-108) | Com. (B306) | 6.7 | 17.4 | 2500.0 | 14.4 | 160.7 | 0.67 | 0.32 |
| Ex. (IV-109) | Com. (B308) | 6.7 | 17.0 | 2500.0 | 14.7 | 165.6 | 0.66 | 0.32 |
| Ex. (IV-110) | Com. (B309) | 6.6 | 16.4 | 2500.0 | 15.2 | 166.1 | 0.66 | 0.32 |
| Ex. (IV-111) | Com. (B310) | 6.6 | 16.5 | 2500.0 | 15.2 | 168.4 | 0.66 | 0.32 |
| Ex. (IV-112) | Com. (B311) | 6.5 | 16.1 | 2500.0 | 15.6 | 167.7 | 0.66 | 0.32 |

TABLE 7-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (IV-113) | Com. (B313) | 6.6 | 16.4 | 2500.0 | 15.2 | 159.2 | 0.66 | 0.32 |
| Ex. (IV-114) | Com. (B314) | 6.6 | 16.0 | 2500.0 | 15.6 | 164.0 | 0.66 | 0.32 |
| Ex. (IV-115) | Com. (B315) | 6.6 | 15.9 | 2500.0 | 15.7 | 171.8 | 0.66 | 0.32 |
| Ex. (IV-116) | Com. (B316) | 6.6 | 15.7 | 2500.0 | 15.9 | 172.7 | 0.66 | 0.32 |
| Ex. (IV-117) | Com. (B317) | 6.8 | 16.8 | 2500.0 | 14.8 | 159.4 | 0.66 | 0.32 |
| Ex. (IV-118) | Com. (B320) | 6.8 | 17.1 | 2500.0 | 14.6 | 163.6 | 0.66 | 0.32 |
| Ex. (IV-119) | Com. (B322) | 6.7 | 16.6 | 2500.0 | 15.0 | 158.2 | 0.66 | 0.32 |
| Ex. (IV-120) | Com. (B325) | 6.6 | 16.7 | 2500.0 | 15.0 | 169.2 | 0.66 | 0.32 |
| Ex. (IV-121) | Com. (B327) | 6.8 | 16.5 | 2500.0 | 15.2 | 169.7 | 0.66 | 0.32 |
| Ex. (IV-122) | Com. (B328) | 6.6 | 16.5 | 2500.0 | 15.2 | 164.7 | 0.66 | 0.32 |
| Ex. (IV-123) | Com. (B331) | 6.6 | 15.6 | 2500.0 | 16.0 | 168.1 | 0.66 | 0.32 |
| Ex. (IV-124) | Com. (B340) | 6.7 | 15.9 | 2500.0 | 15.7 | 170.6 | 0.66 | 0.32 |
| Ex. (IV-125) | Com. (B343) | 6.6 | 15.5 | 2500.0 | 16.1 | 176.3 | 0.66 | 0.32 |
| Ex. (IV-126) | Com. (B344) | 6.6 | 15.2 | 2500.0 | 16.4 | 173.9 | 0.66 | 0.32 |
| Ex. (IV-127) | Com. (B348) | 6.7 | 17.0 | 2500.0 | 14.7 | 165.0 | 0.66 | 0.32 |
| Ex. (IV-128) | Com. (B351) | 6.7 | 16.7 | 2500.0 | 15.0 | 163.5 | 0.66 | 0.32 |
| Ex. (IV-129) | Com. (B354) | 6.8 | 16.9 | 2500.0 | 14.8 | 158.5 | 0.66 | 0.32 |
| Ex. (IV-130) | Com. (B358) | 6.6 | 16.5 | 2500.0 | 15.2 | 166.6 | 0.66 | 0.32 |
| Ex. (IV-131) | Com. (B363) | 6.8 | 16.6 | 2500.0 | 15.1 | 158.5 | 0.66 | 0.32 |
| Ex. (IV-132) | Com. (B365) | 6.6 | 19.6 | 2500.0 | 12.7 | 138.8 | 0.66 | 0.33 |
| Ex. (IV-133) | Com. (B372) | 6.6 | 18.2 | 2500.0 | 13.8 | 152.6 | 0.66 | 0.33 |
| Ex. (IV-134) | Com. (B375) | 6.7 | 18.6 | 2500.0 | 13.5 | 142.8 | 0.67 | 0.33 |
| Ex. (IV-135) | Com. (B386) | 6.6 | 17.0 | 2500.0 | 14.7 | 162.8 | 0.66 | 0.32 |

As can be seen from the data of Tables 5 to 7, the organic electroluminescent device in which the compound according to the present invention is used as a material of an auxiliary light emitting layer has improved light emitting efficiency and a remarkably improved lifespan compared to the organic electroluminescent devices of Comparative Examples 7 to 25.

Also, when used in an auxiliary light emitting layer, Comparative Compound 2 having a linear-type linker was found to be inferior to the compound of the present having a non-linear-type linker in terms of both luminous efficiency and lifespan. Moreover, Comparative Compound 7, although being of a non-linear type structure like the compound of the present invention, has poor luminous efficiency and longevity because it has a heterocyclic group rather than an amine group (—NAr²Ar³) as a main substituent. This seems to be attributed to the fact that that the a low T1 value is generated when the heterocyclic group, instead of the amine group (—NAr²Ar³), is introduced, with the consequent emission of light at an interface between the light emitting layer and the auxiliary light emitting layer, rather than the inside of the light emitting layer.

In Table 4, the shift from the non-linear meta position to position 2 of the carbazole backbone provides the main contribution in improving the device in terms of the performance of the auxiliary light emitting layer (blue fluorescence, green phosphorescence, and red phosphorescence), as well as the hole transporting layer, and there is similar trend between the two positions.

This is further confirmed from the data showing that the compound of the present invention in which the linker is linked at position 2 directly to the carbazole backbone has improved luminous efficiency and longevity, compared to Comparative Compounds 4 to 6 in which the linker is linked at position 3.

Another feature of the compound according to the present invention is that a smaller bond angle at which linker $L^1$ is connected to amine (—NAr²Ar³) makes the band gap wider, and the T1 value higher. This is confirmed by the fact that a compound linked at the ortho position is higher in luminosity than that linked at the metal or para position. In addition to the improvement in luminous efficiency, the compound linked at the ortho position is expected to reduce the process time and increase the longevity of the device because it has a relatively low deposition temperature, compared to the other compounds.

Lastly, the compound according to the present invention used in the auxiliary light emitting layer causes the backbone to be further twisted upon introduction of a bulky substituent on the nitrogen (N) atom of the carbazole, which leads to a reduction in packing density between materials within the auxiliary light emitting layer while adjusting hole mobility so as to raise the luminous efficiency.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound represented by Formula 1 below:

[Formula 1]

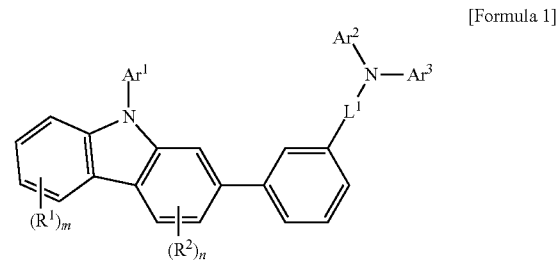

wherein, m is an integer from 1 to 4, n is an integer from 1 to 3, $R^1$ and $R^2$ are independently selected from the group consisting of hydrogen, deuterium, tritium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C1$-$C_{50}$ alkyl group, a $C_2$-$C_{20}$ alkenyl group, a $C_1$-$C_{30}$ alkoxy group, and a $C_6$-$C_{30}$ aryloxy group, $Ar^1$ is selected from the group consisting of a fluorenyl group, a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, a $C1$-$C_{50}$ alkyl group, $-L^2$-$N(Ar^2)(Ar^3)$, and a fused ring group of a $C_3$-$C_{60}$ aliphatic ring and a $C_6$-$C_{60}$ aromatic ring, $L^1$ and $L^2$ are independently selected from the group consisting of a single bond, a $C_6$-$C_{60}$ arylene group, a fluorenylene group, a $C_2$-$C_{60}$ bivalent heterocyclic group containing at least one heteroatom selected from the group consisting of O, N, S, Si, and P, a bivalent fused ring group of a $C_3$-$C_{60}$ aliphatic ring and a $C_6$-$C_{60}$ aromatic ring, and a bivalent aliphatic hydrocarbon group, $Ar^2$ and $Ar^3$ are independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, and a $C_2$-$C_{20}$ alkenyl group, and the aryl group, heterocyclic group, fluorenyl group, alkyl group, alkenyl group, fused ring group, alkoxy group, aryloxy group, arylene group, fluorenylene group and aliphatic hydrocarbon group may be substituted by one or more substituents selected from the group consisting of deuterium, halogen, a silane group, a boron group, a germanium group, a cyano group, a nitro group, $-L'$-$N(R')(R'')$, a $C_1$-$C_{20}$ alkylthio group, a $C1$-$C_{20}$ alkoxy group, a $C1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group, wherein L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring, and a $C2$-$C_{60}$ bivalent aliphatic hydrocarbon group, and R' and R" are independently from each other selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{20}$ alkyl group, and a $C_2$-$C_{20}$ alkenyl group, with the proviso that: where $Ar^1$ is a substituted $C_6$-$C_{60}$ aryl group, the substituent is selected from the group consisting of deuterium, halogen, a silane group, a boron group, a germanium group, a cyano group, a nitro group, $-L'$-$N(R')(R'')$, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{14}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group; and where $R^1$ or $R^2$ is a substituted $C_6$-$C_{60}$ aryl group, the substituent is selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group, and with the proviso that:

where $Ar^1$ is a $C_6$-$C_{60}$ aryl group, $L^1$ is a single bond, and one of $Ar^2$ and $Ar^3$ is a $C_6$-$C_{60}$ aryl group or a fluorenyl group, the other of $Ar^2$ and $Ar^3$ is selected from the group consisting of:

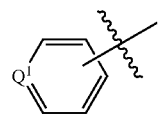

wherein $Q^1$ is $C(R^a)$;

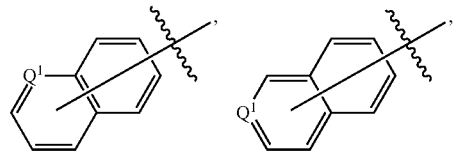

wherein $Q^1$ is $C(R^a)$;

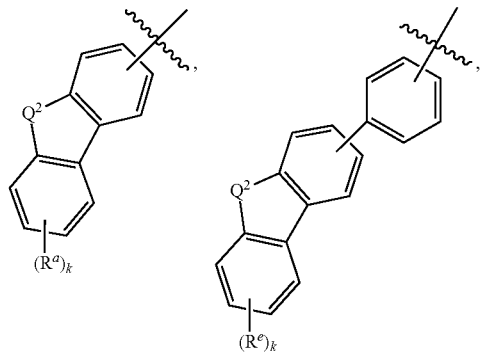

-continued

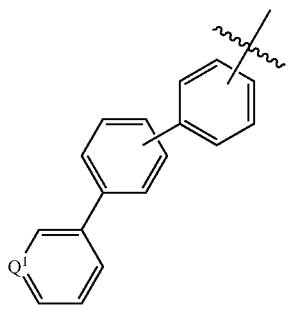

wherein Q² is C(R$^b$)(R$^c$), N(R$^d$), S, or O;

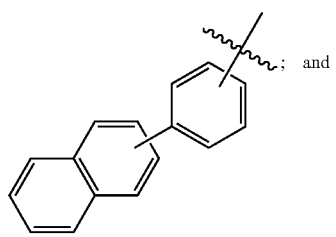; and

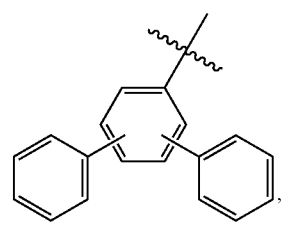, wherein R$^a$ and R$^e$ are independently selected from the group consisting of hydrogen, deuterium, a C$_6$-C$_{60}$ aryl group, a C$_2$-C$_{60}$ heterocyclic group containing at least one heteroatom selected from the group consisting of O, N, S, Si, and P, a C$_1$-C$_{50}$ alkyl group, a C$_2$-C$_{20}$ alkenyl group, a C$_1$-C$_{30}$ alkoxy group, and a fluorenyl group, or any two adjacent groups of R$^e$s can be optionally linked together to form at least one aromatic ring, R$^b$ to R$^d$ are independently selected from the group consisting of a C$_6$-C$_{60}$ aryl group, a C$_2$-C$_{60}$ heterocyclic group containing at least one heteroatom selected from the group consisting of O, N, S, Si, and P, a C$_1$-C$_{50}$ alkyl group, a C$_2$-C$_{20}$ alkenyl group, and a C$_1$-C$_{30}$ alkoxy group, wherein R$^b$ and R$^c$ are optionally linked together to form at least one spiro compound.

2. The compound as claimed in claim 1, wherein L$^1$ is any one of the compounds below:

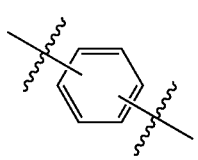 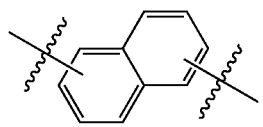

-continued

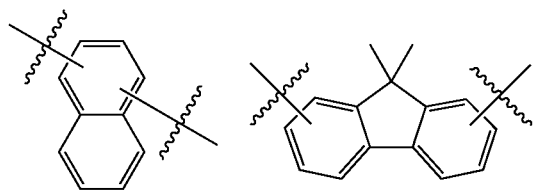

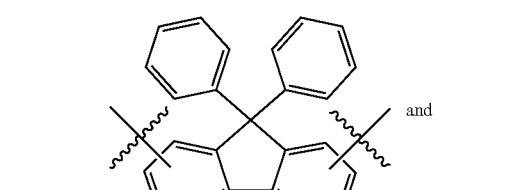

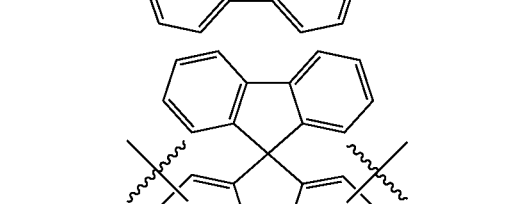 and

3. The compound as claimed in claim 1, wherein Ar² and Ar³ each are independently any one of compounds below:

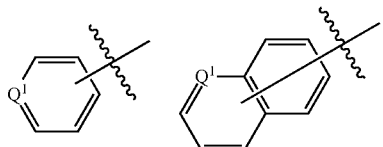

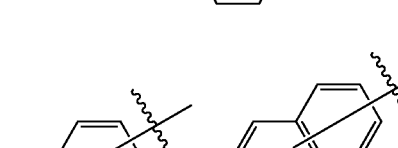

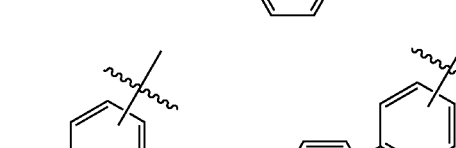

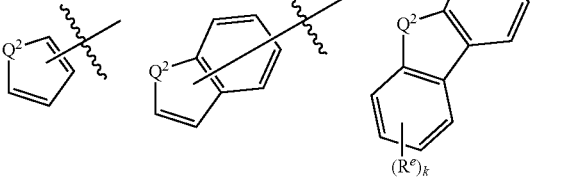

-continued

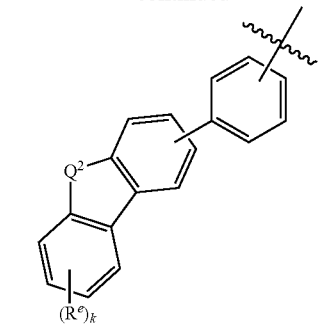

and

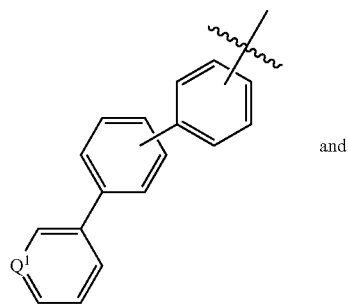

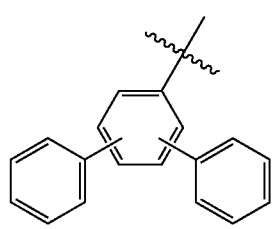

wherein, $Q^1$ is $C(R^a)$ or N, $Q^2$ is selected form the group consisting of $C(R^b)(R^c)$, $N(R^d)$, S and O, k is an integer from 1 to 4, $R^a$ and $R^e$ are independently selected from the group consisting of hydrogen, deuterium, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a fluorenyl group, wherein any two adjacent groups of $R^e$s are optionally linked together to form at least one aromatic ring, $R^b$ to $R^d$ are independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, wherein $R^b$ and $R^c$ are optionally linked together to form at least one spiro compound.

4. The compound as claimed in claim 1, wherein the compound is represented by one of Formulas below:

[Formula 2]

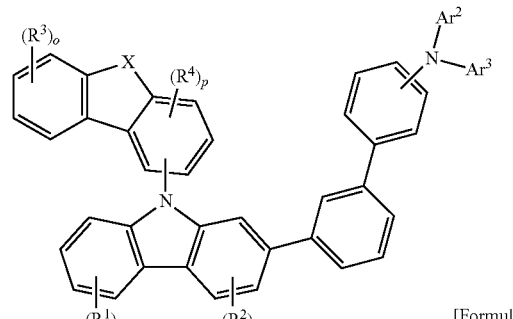

[Formula 3]

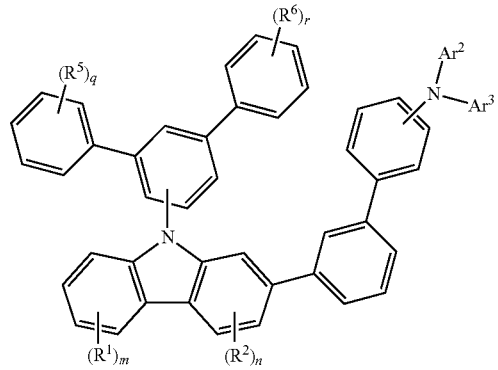

wherein,

Ar$^2$, Ar$^3$, R$^1$, R$^2$, m and n are as defined for Formula 1 in claim 1, X is selected from the group consisting of $C(R^f)(R^g)$, S and O, $R^f$ and $R^g$ are independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, wherein $R^f$ and $R^g$ are optionally linked together to form at least one spiro compound, o is an integer from 1 to 4, p is an integer from 1 to 3, q and r are independently an integer from 1 to 5, and, $R^3$ to $R^6$ are independently selected from the group consisting of hydrogen, deuterium, tritium, halogen, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a $C_6$-$C_{30}$ aryloxy group, wherein any two adjacent groups of $R^3$s to $R^6$s are optionally linked together to form at least one aromatic ring.

5. The compound as claimed in claim 1, wherein the compound is represented by one of Formulas below:

[Formula 4]

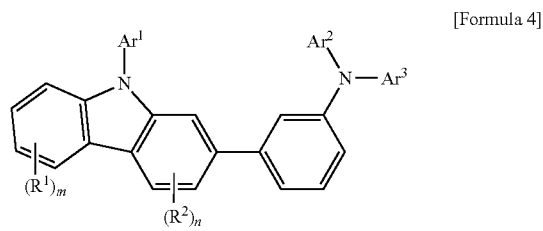

-continued

[Formula 5]

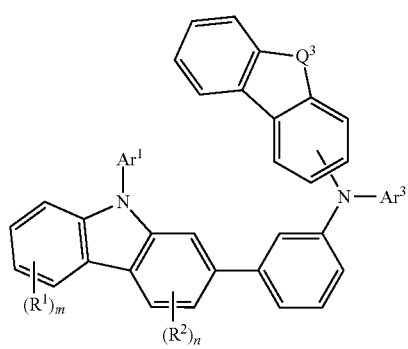

wherein,

Ar¹ to Ar³, R¹, R², m and n are as defined for Formula 1 in claim 1,

Q³ is selected from the group consisting of $C(R^h)(R^i)$, $N(R^j)$, S and O, and, $R^h$ to $R^j$ are independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, wherein $R^h$ and $R^i$ are optionally linked together to form at least one spiro compound.

6. The compound as claimed in claim 1, being any one of the compounds below:

B1

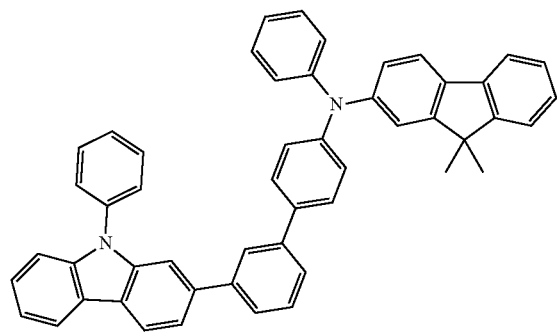

B6

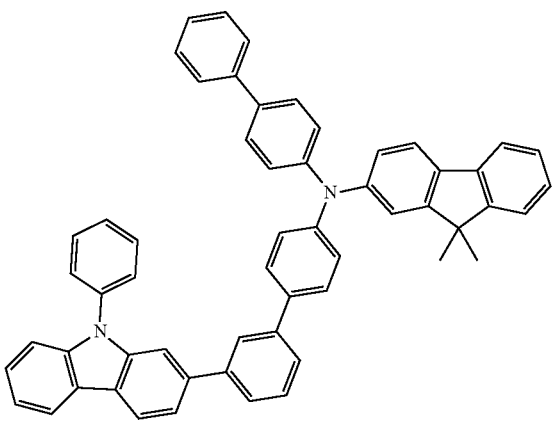

B7

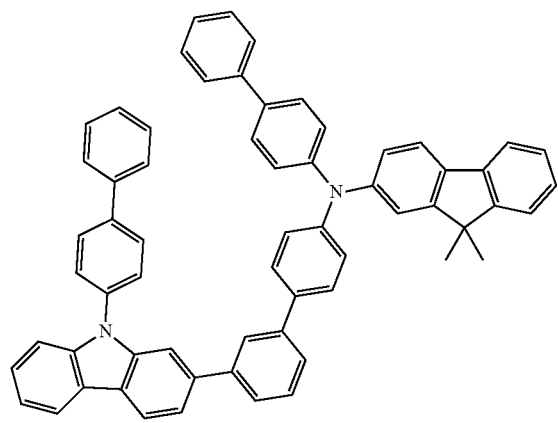

B11

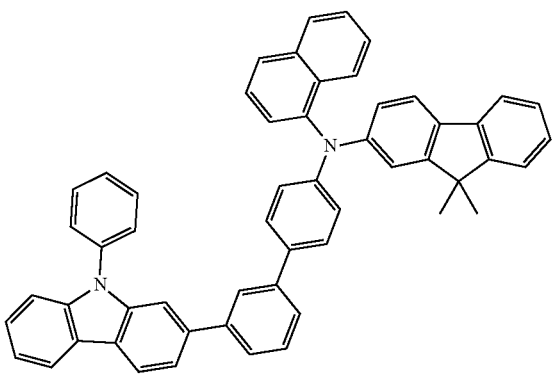

-continued
B12
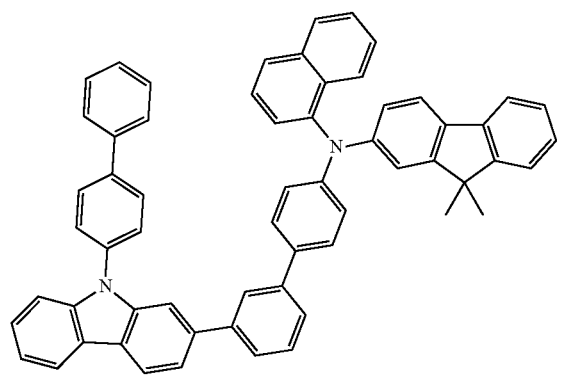
B16
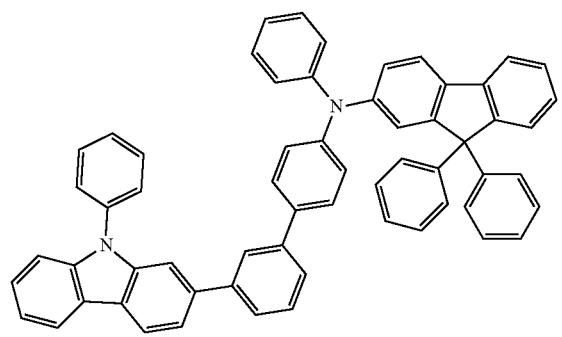
B17
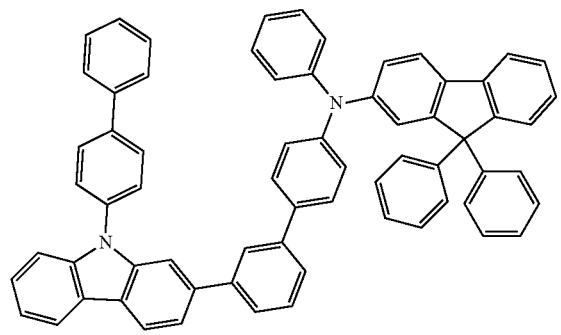
B21
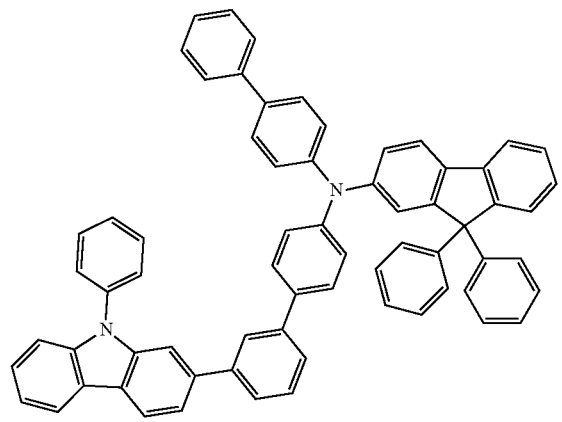
B22
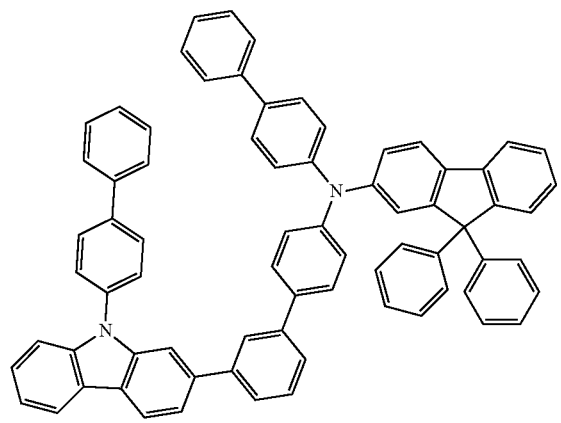
B23
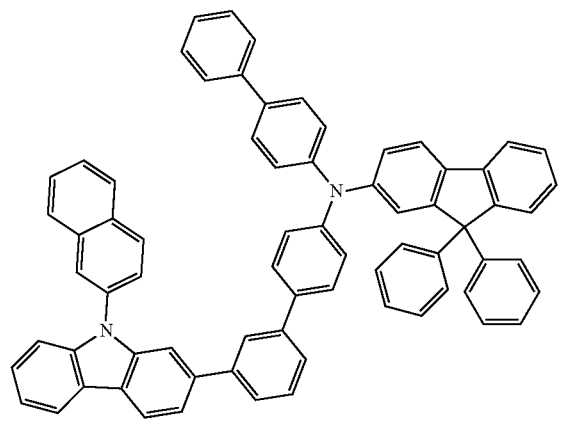

-continued
B24
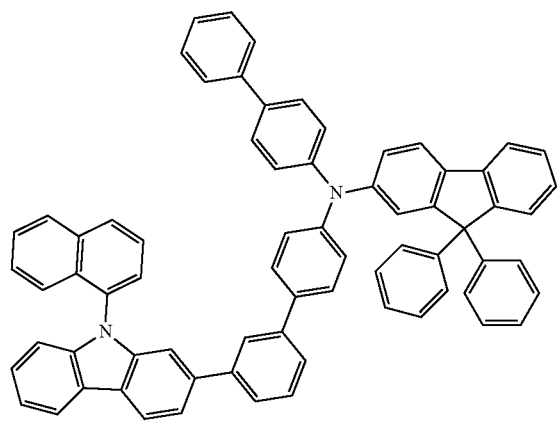
B25
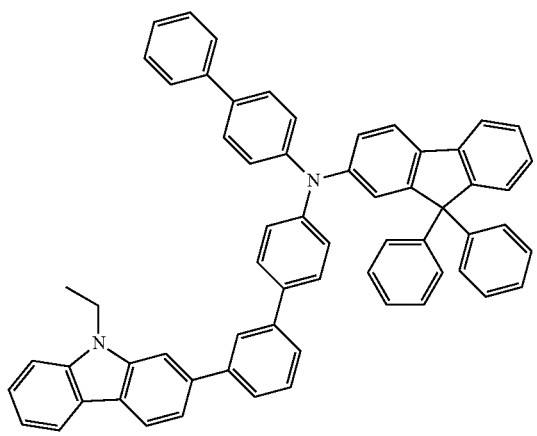
B26
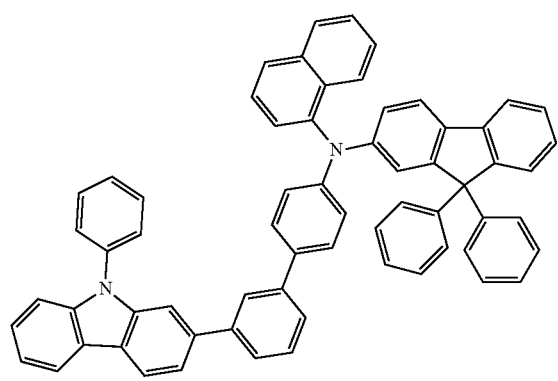
B27
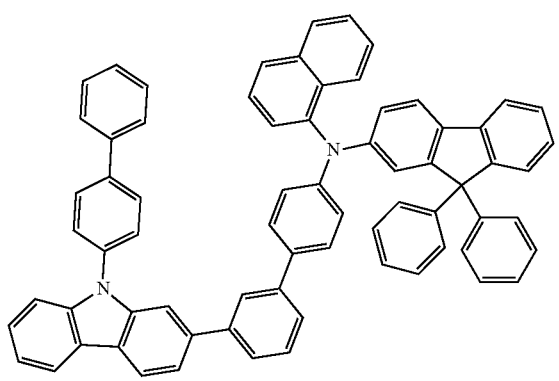
B31
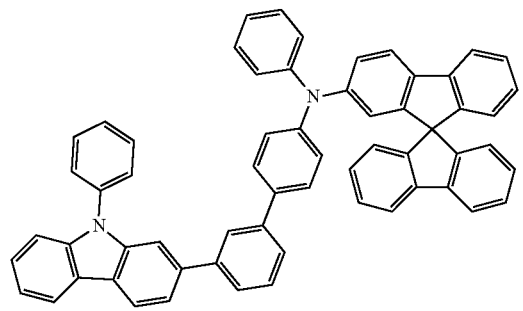
B43
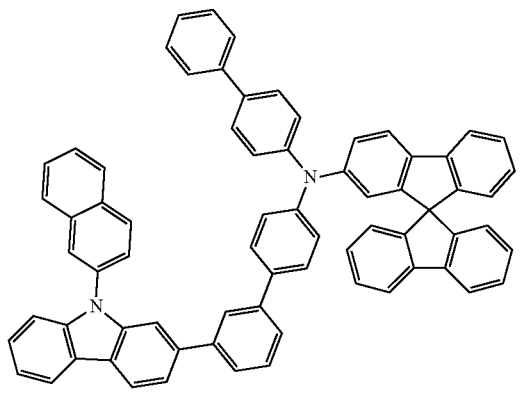

-continued
B47
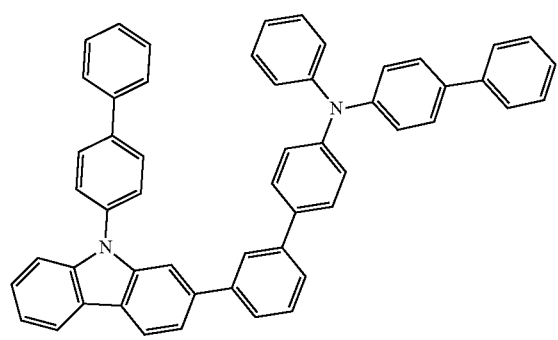
B51
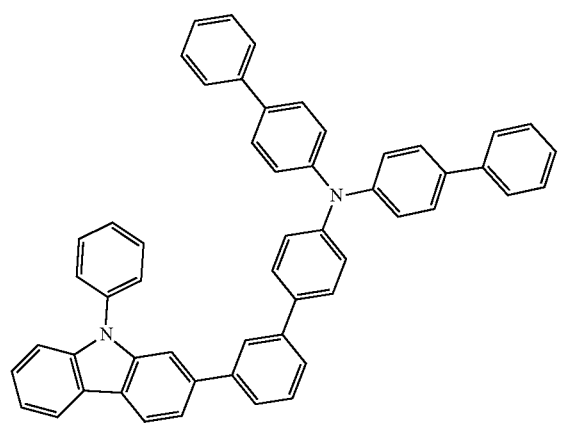
B62
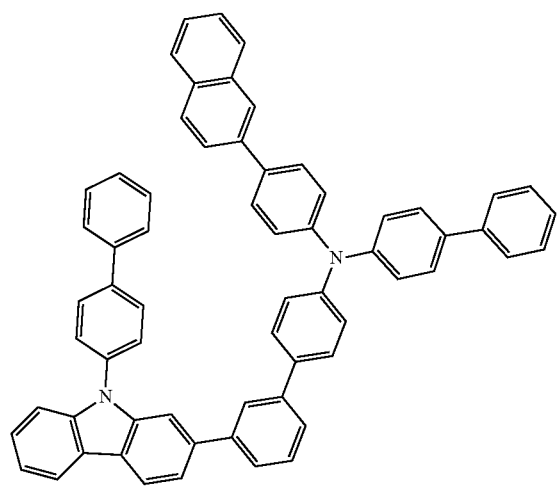
B66
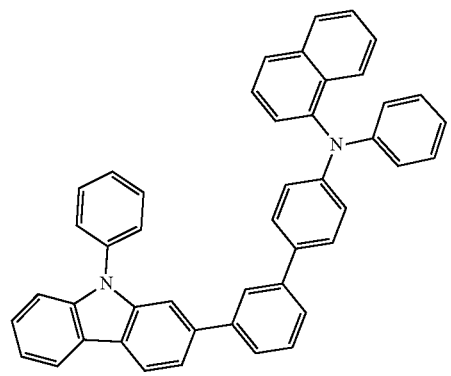
B86
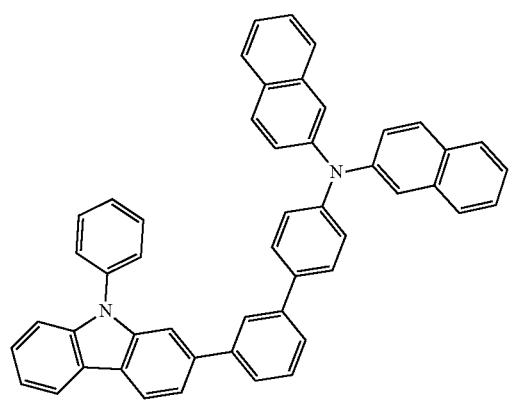
B94
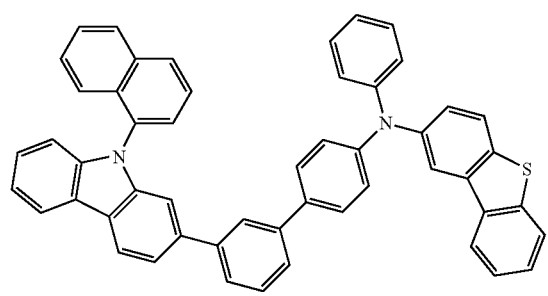

B106
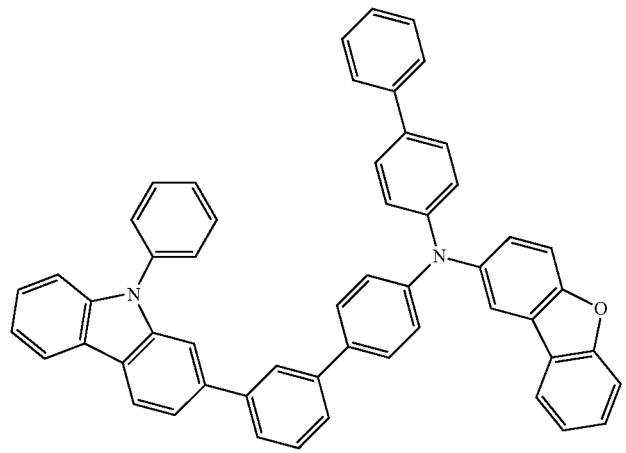
B122
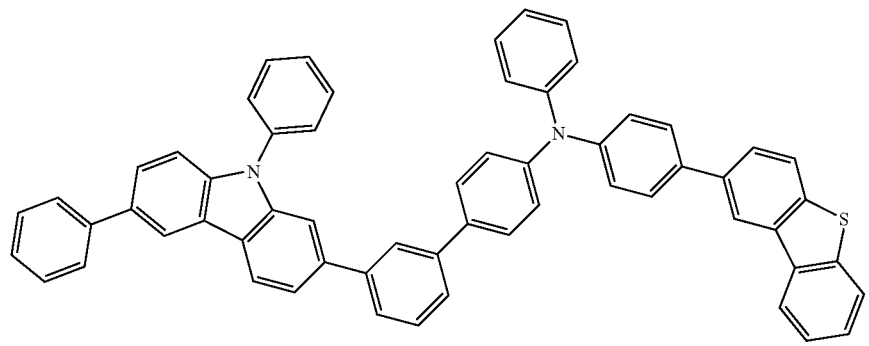
B124
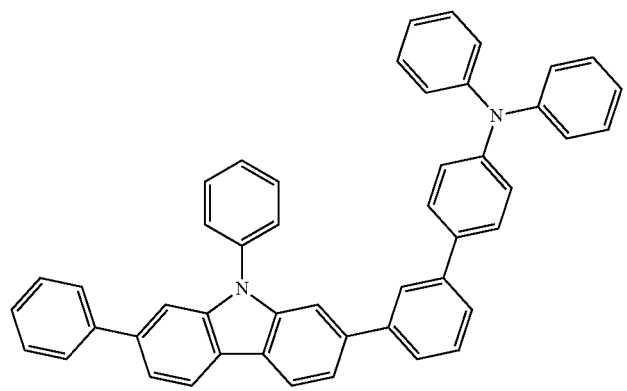

-continued
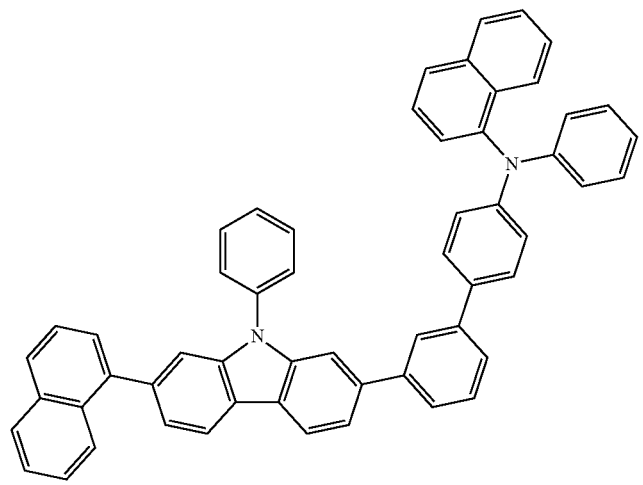
B125
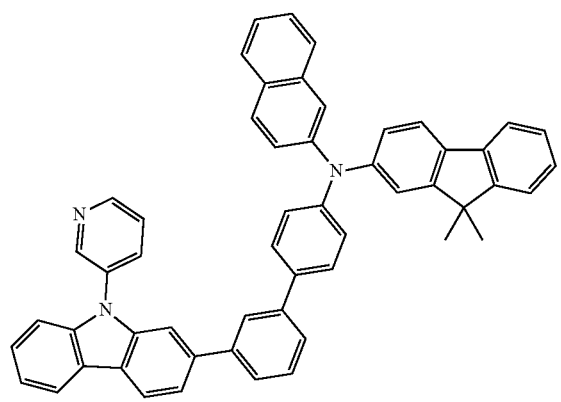
B127
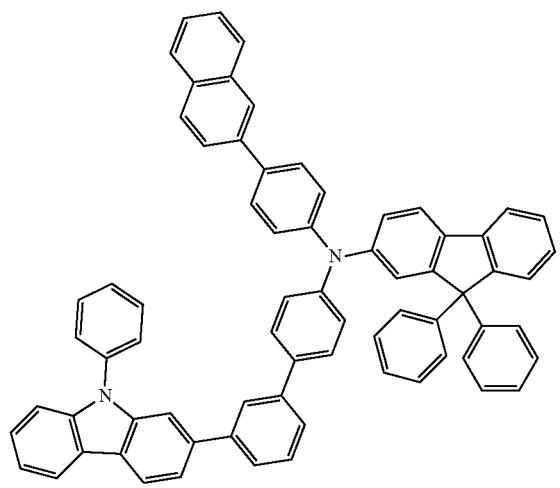
B128
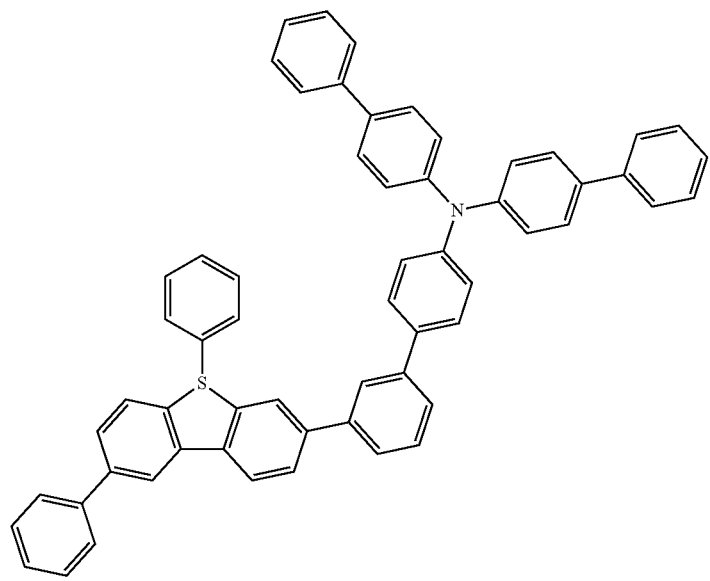
B129

-continued
B130
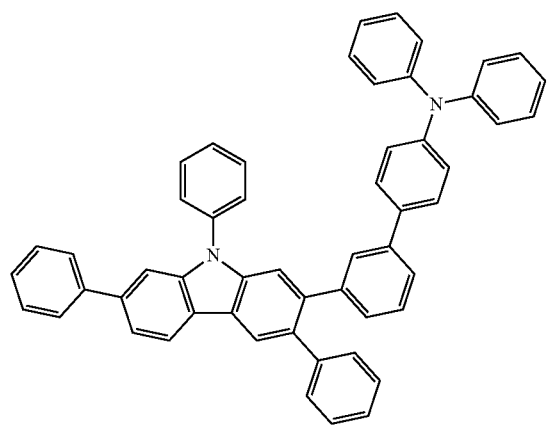
B132
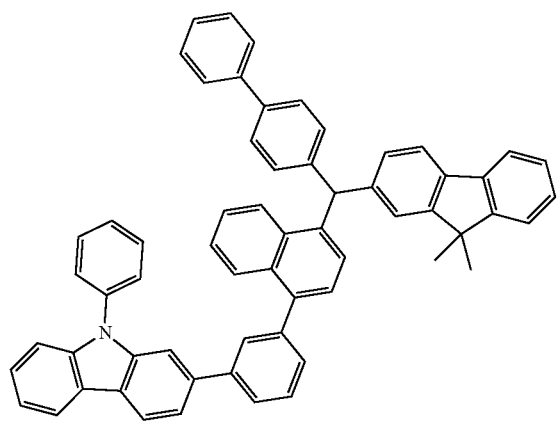
B138
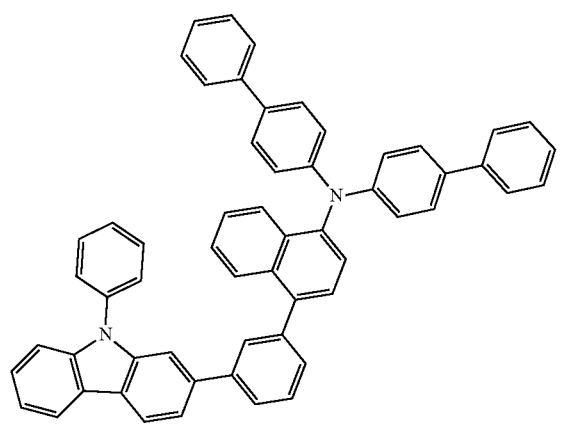
B145
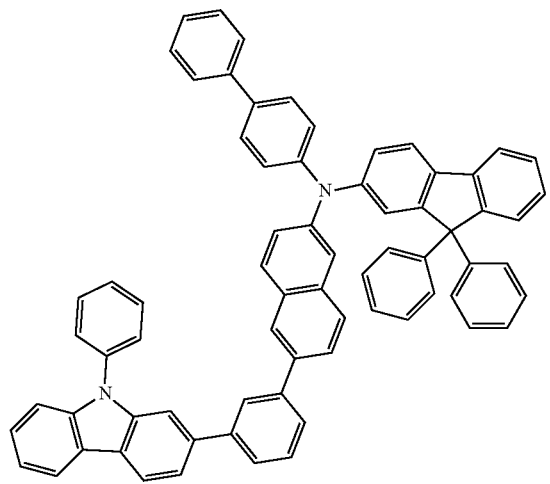
B152
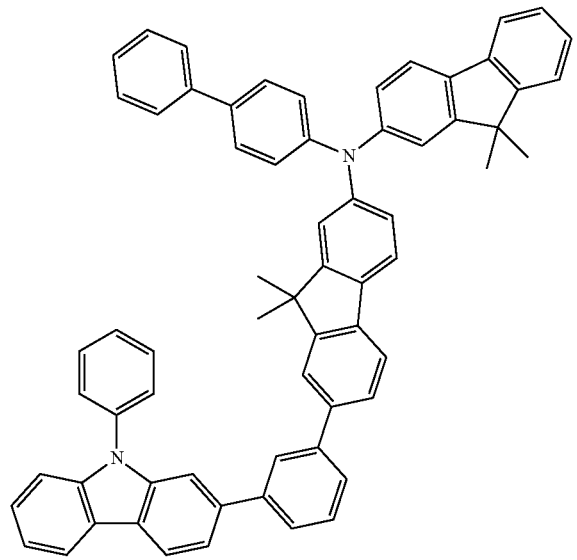
B157
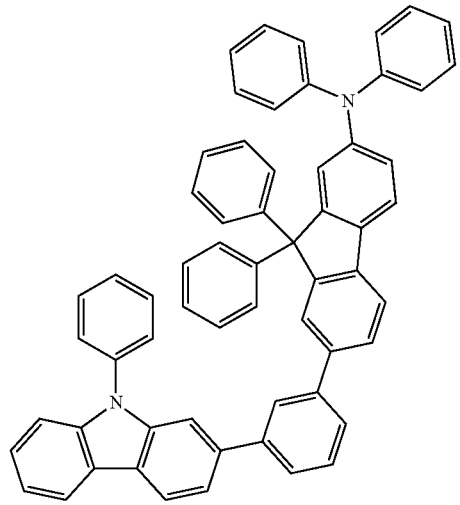

-continued
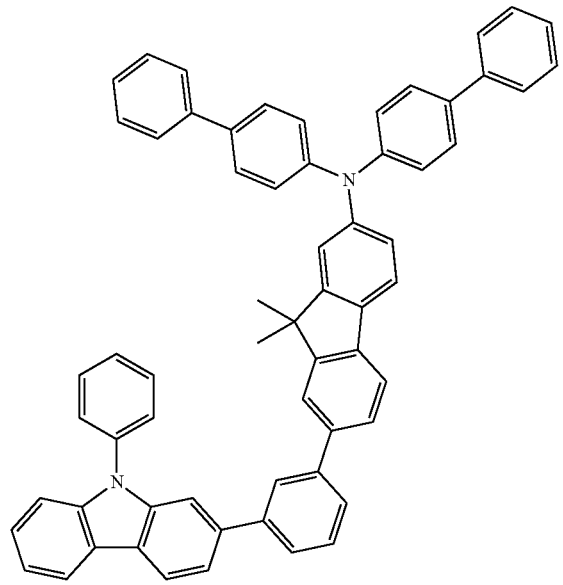
B158
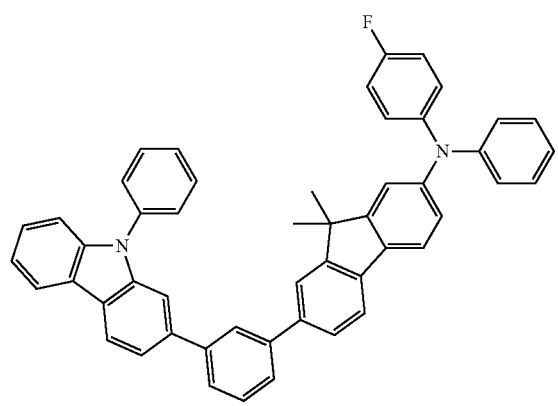
B161
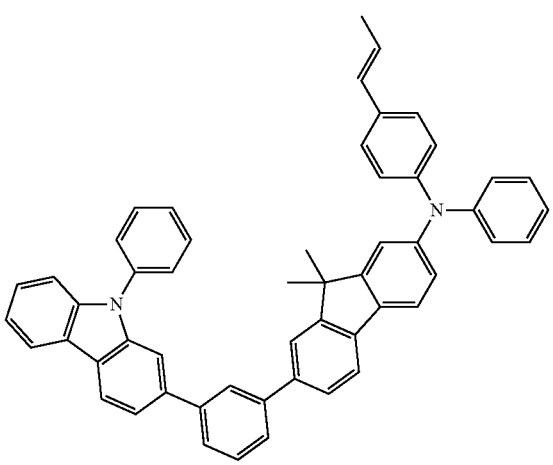
B162
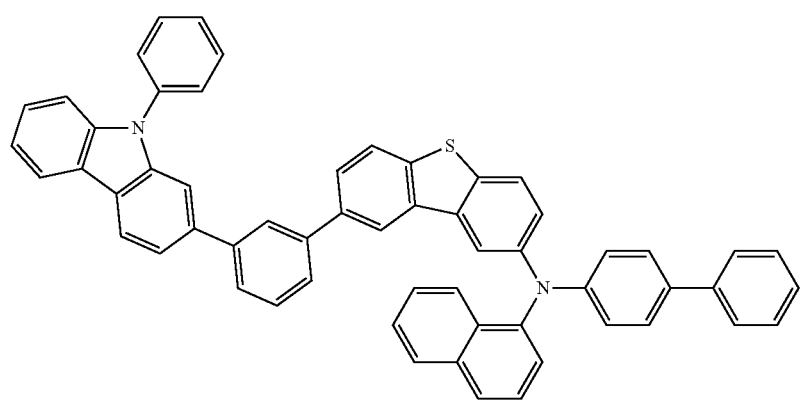
B164

B165
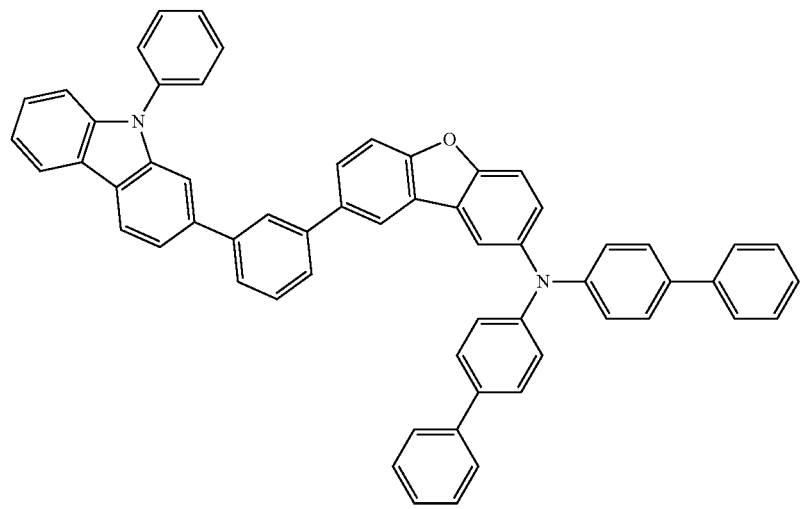
B167
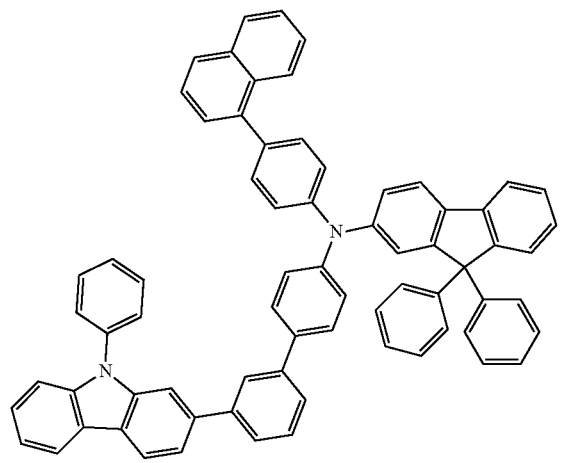
B168
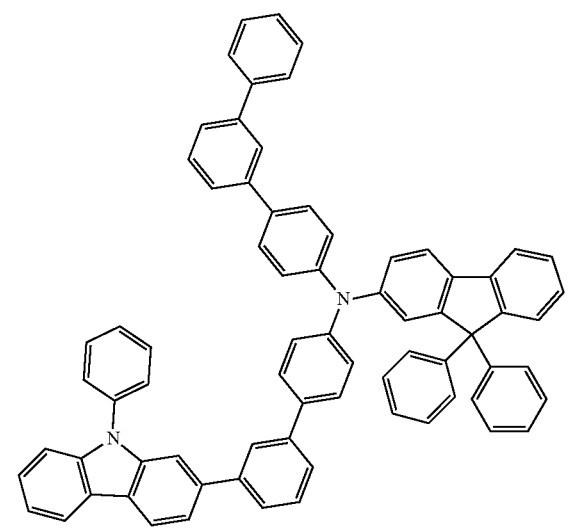
B169
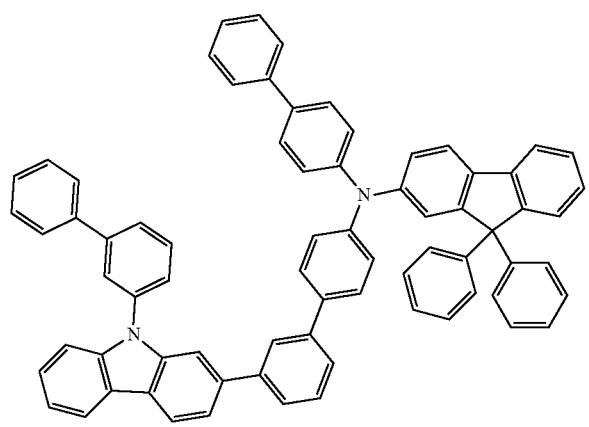
B170
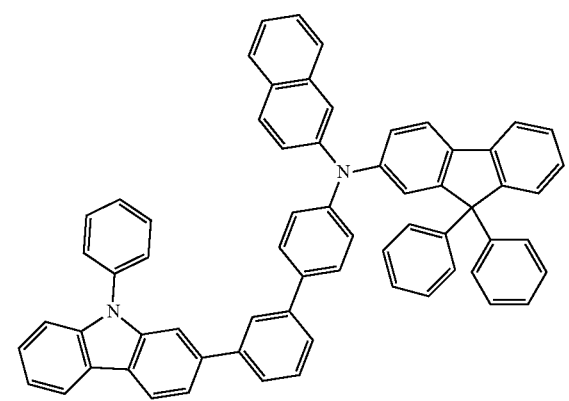

-continued
B171
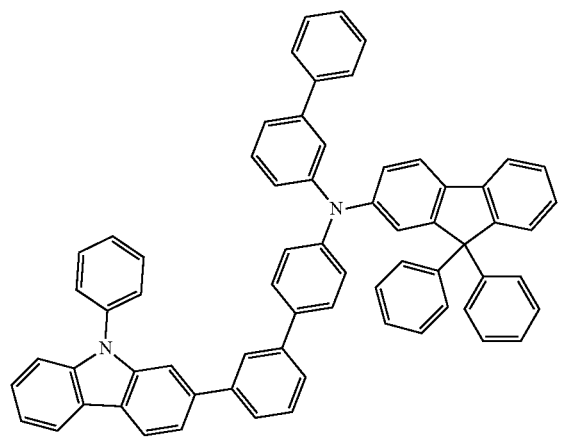
B172
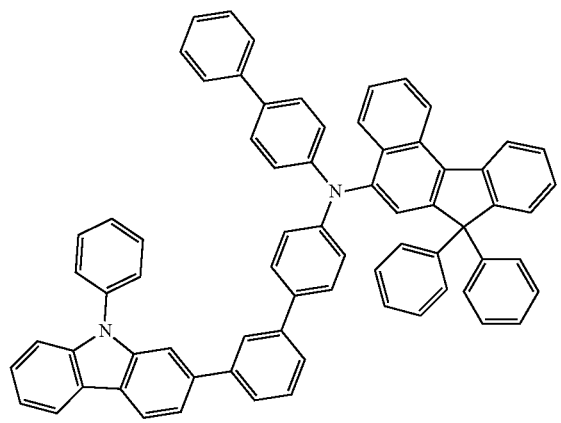
B173
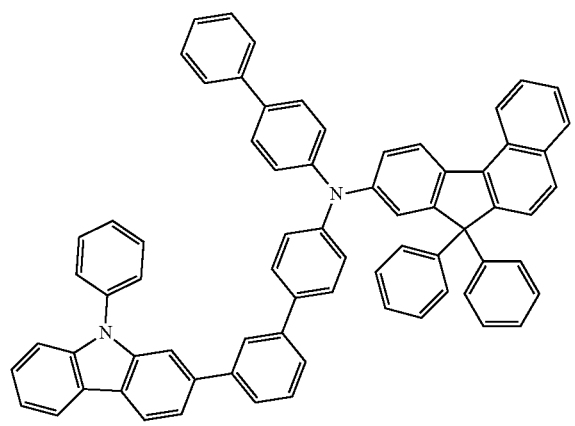
B174
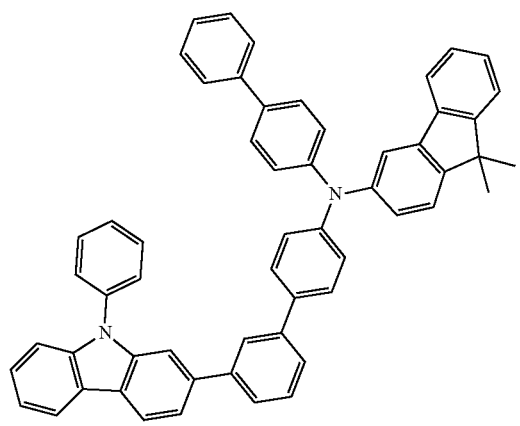
B175
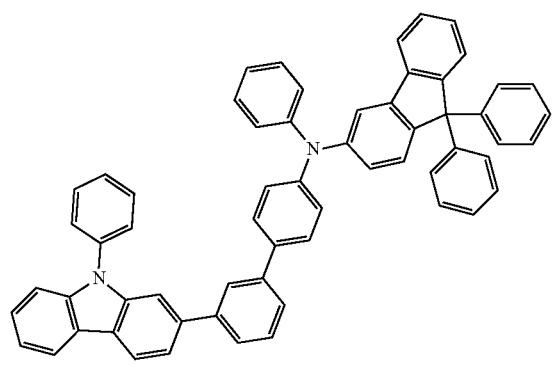
B176
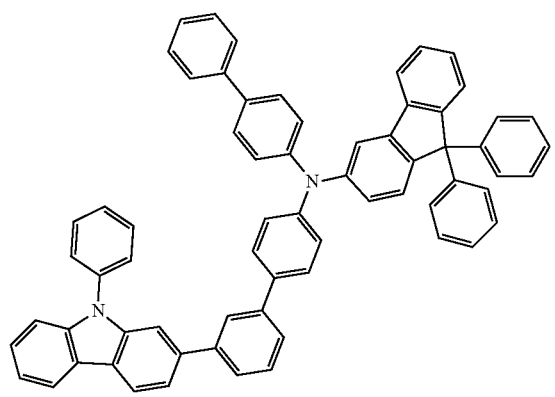

-continued
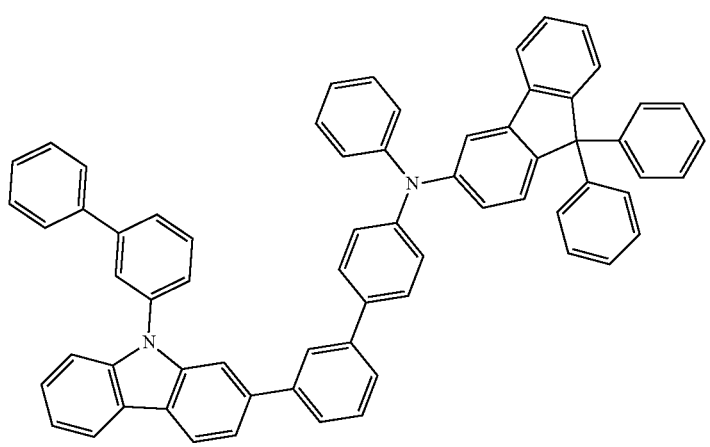
B177
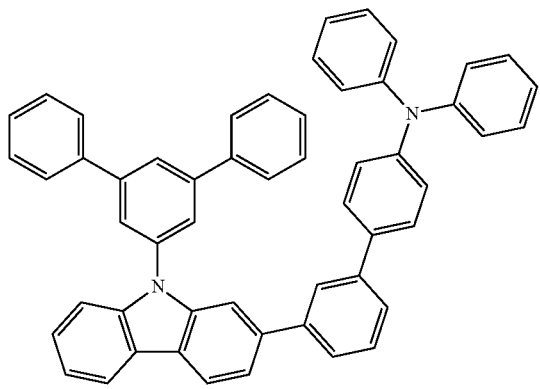
B178
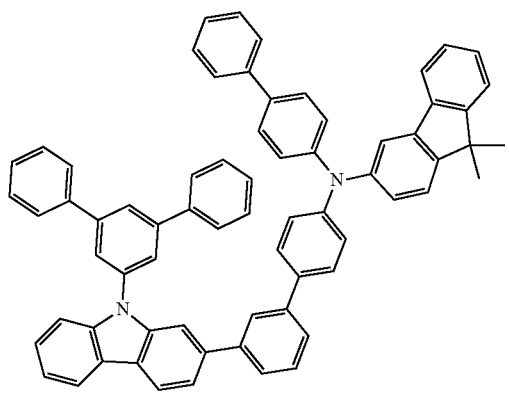
B179
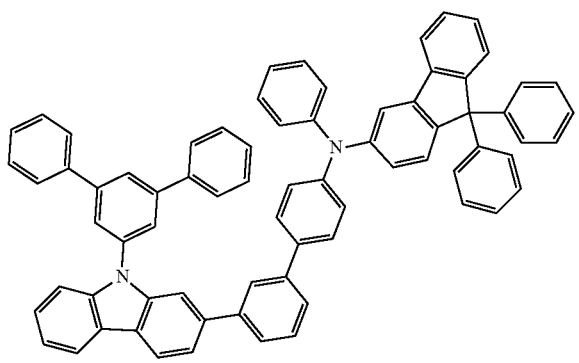
B180
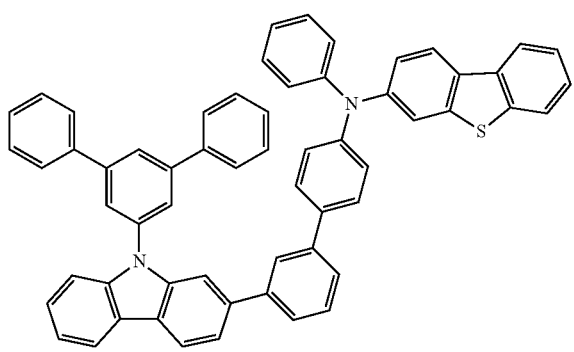
B181
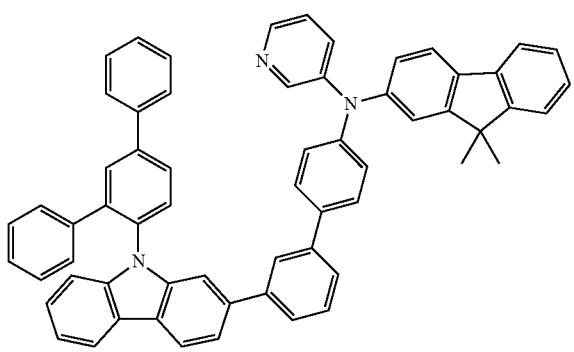
B182

-continued
B183
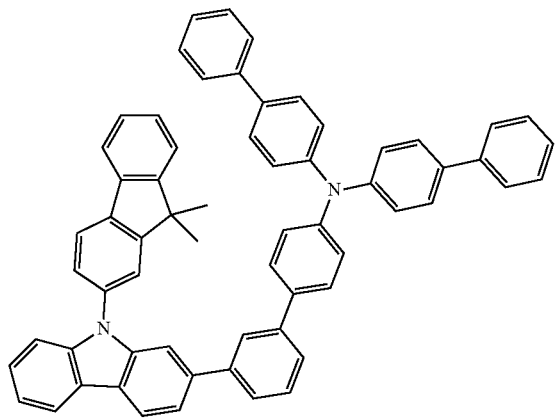
B184
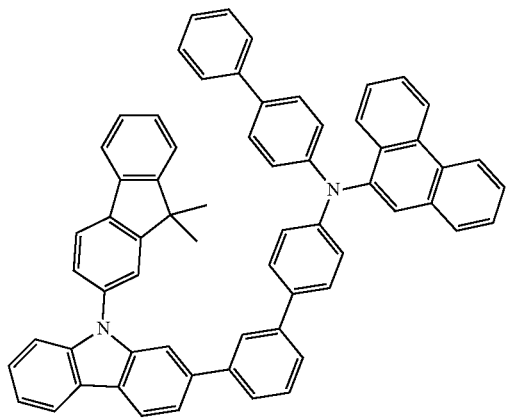
B185
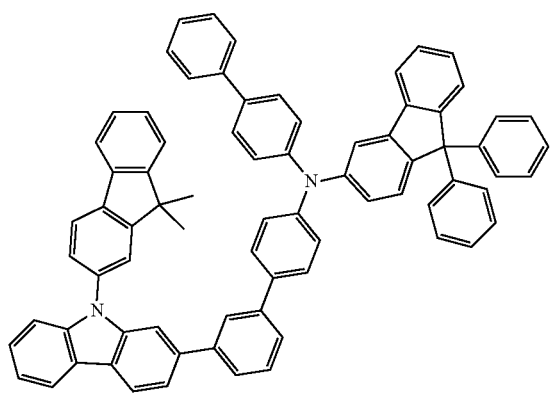
B186
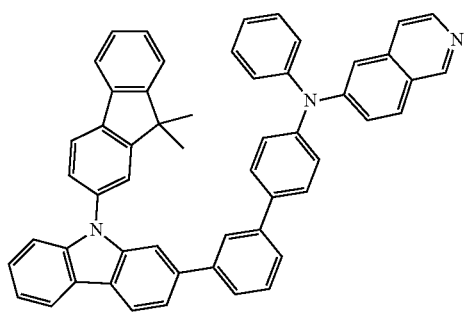
B187
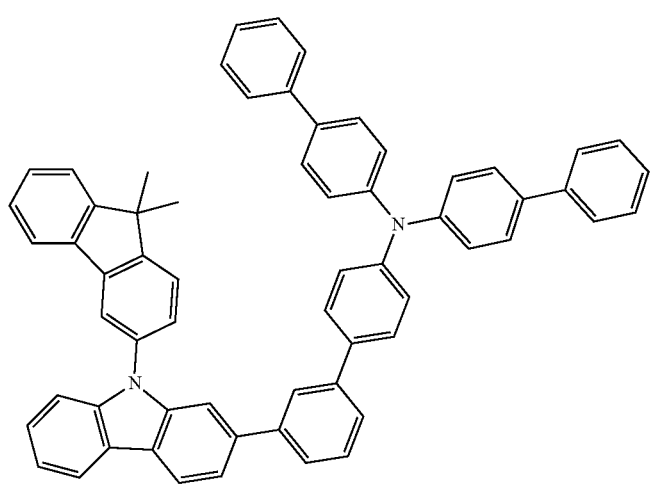

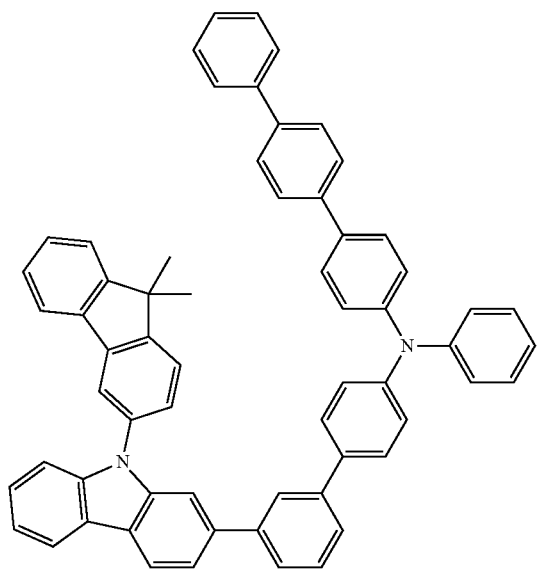
B188
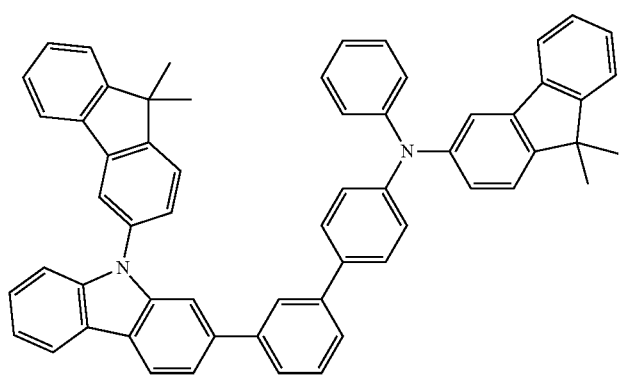
B189
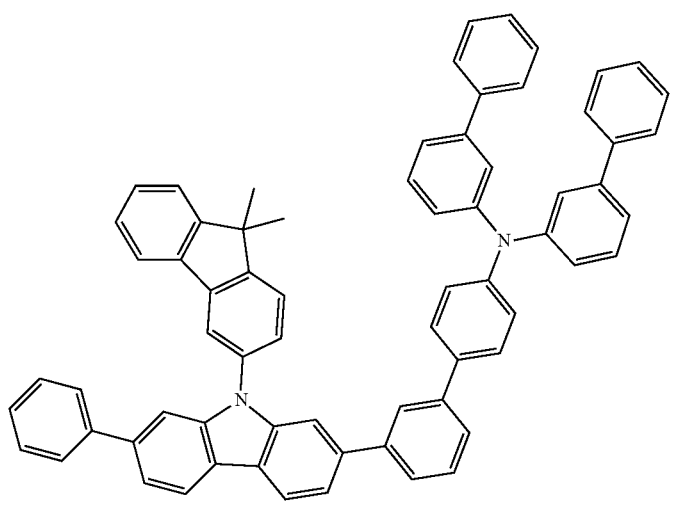
B190

-continued
B191
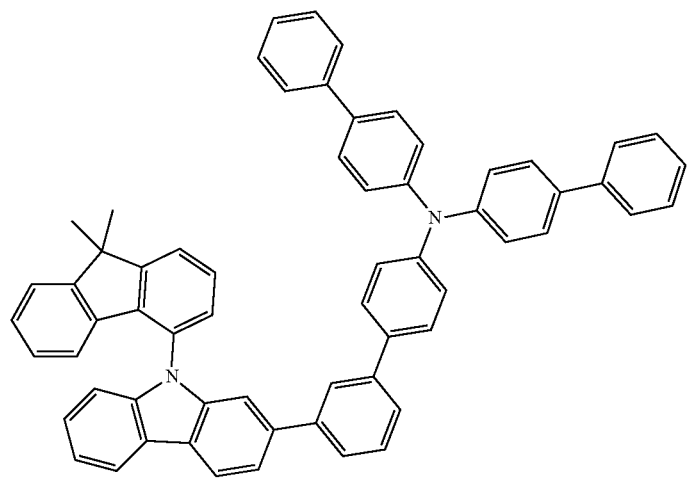
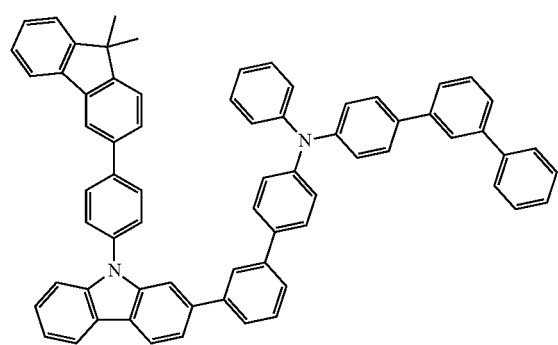
B192
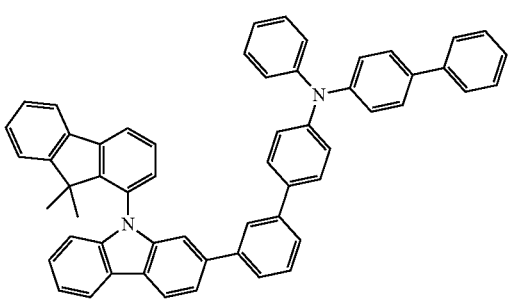
B193
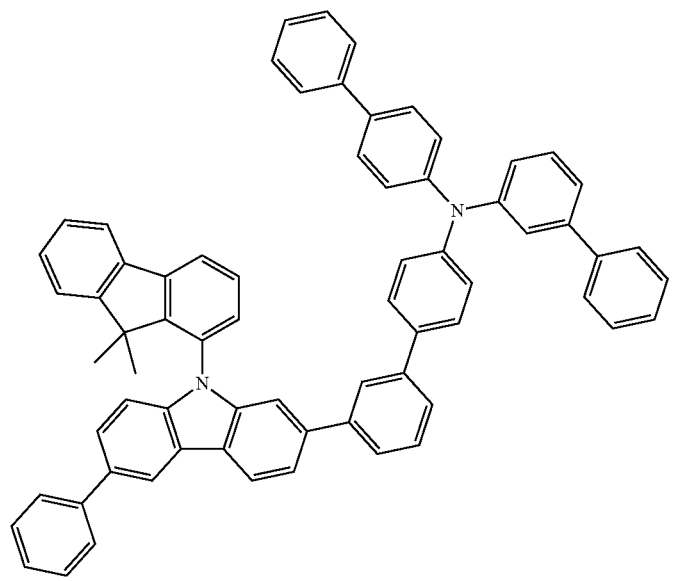
B194

-continued
B195
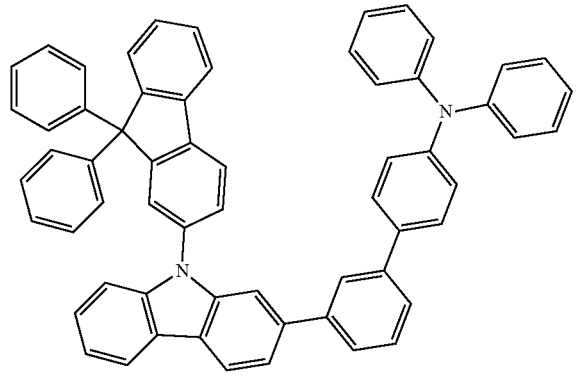
B196
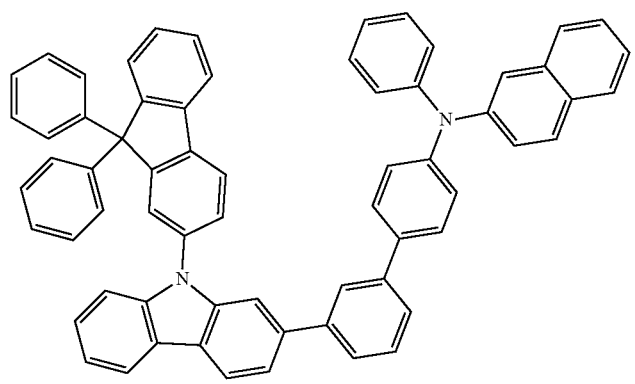
B197
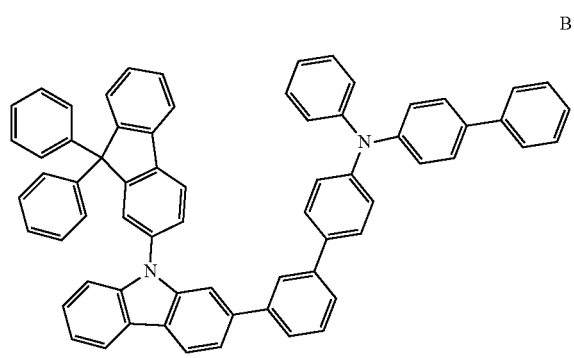
B198
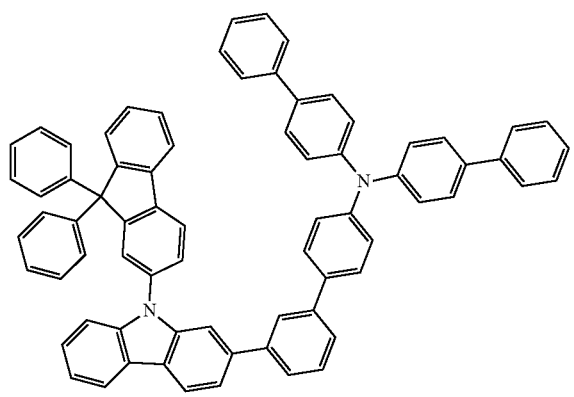
B199
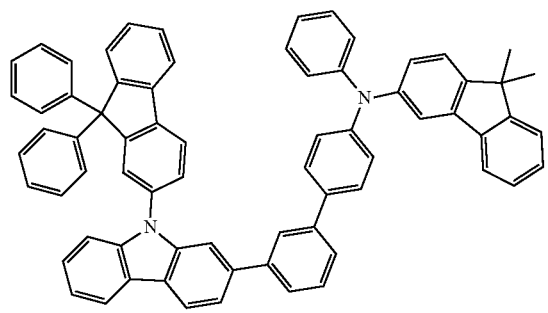
B200
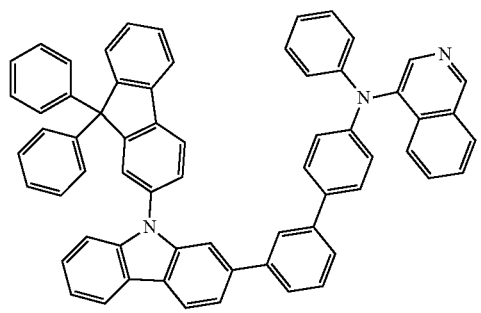

-continued
B201
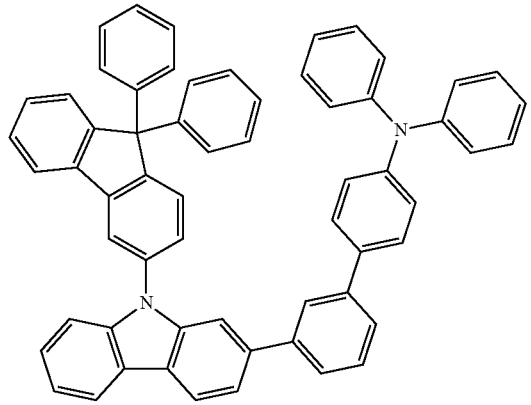
B202
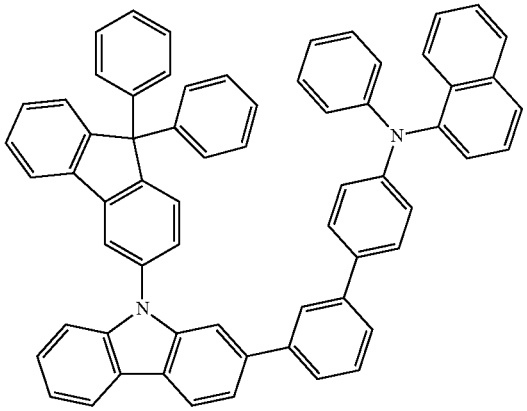
B203
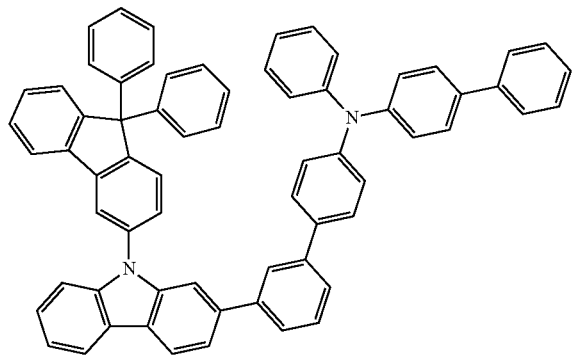
B204
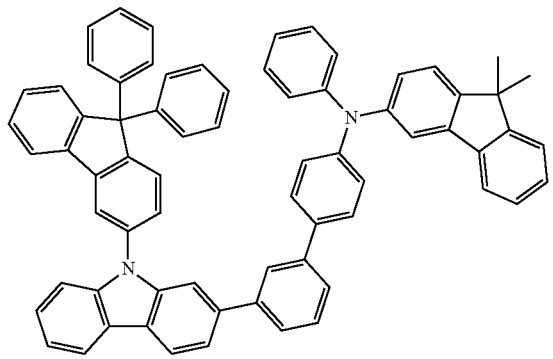
B205
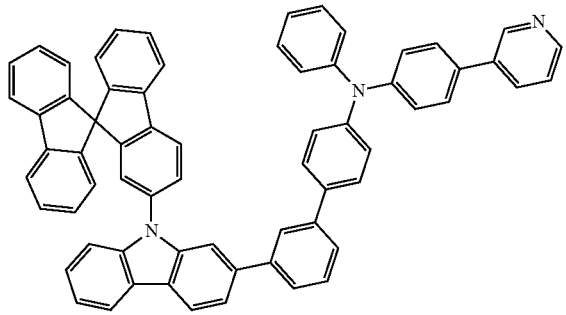
B206
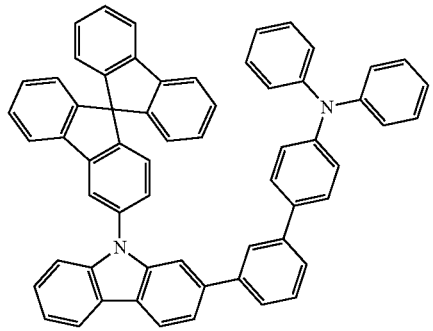
B207
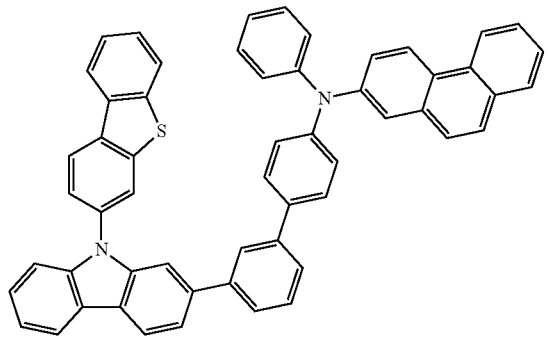
B208
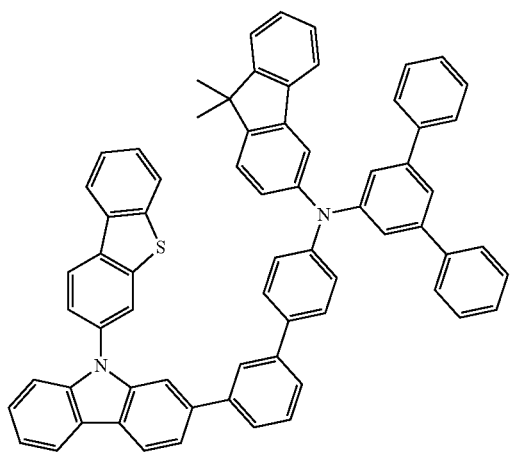

-continued
B210
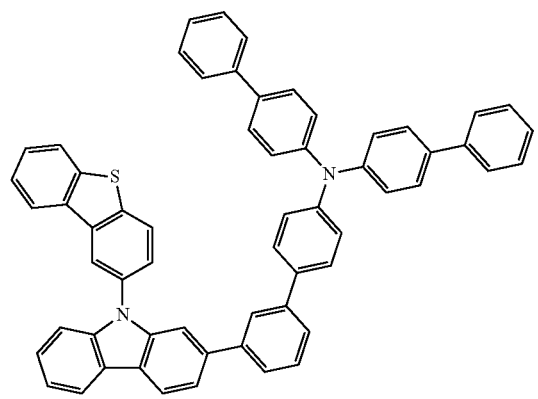
B209
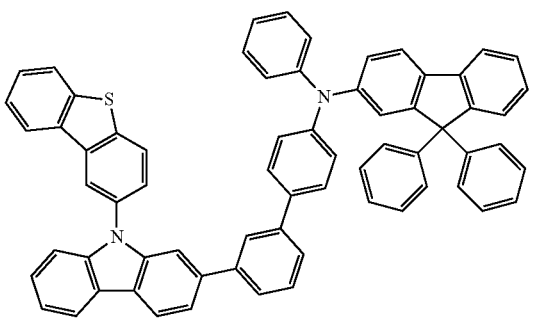
B211
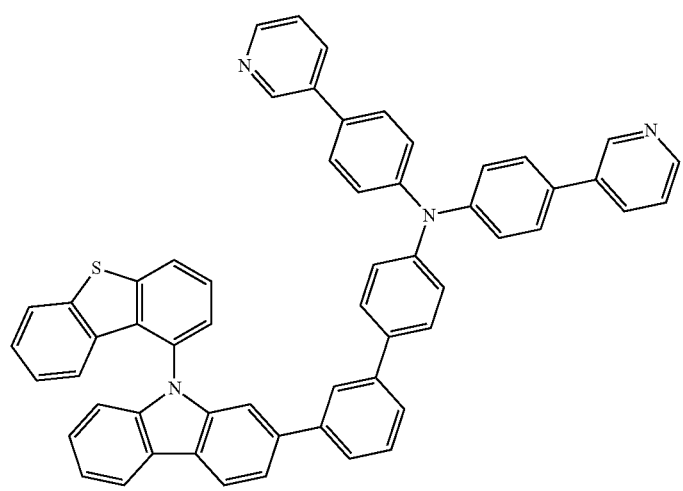
B212
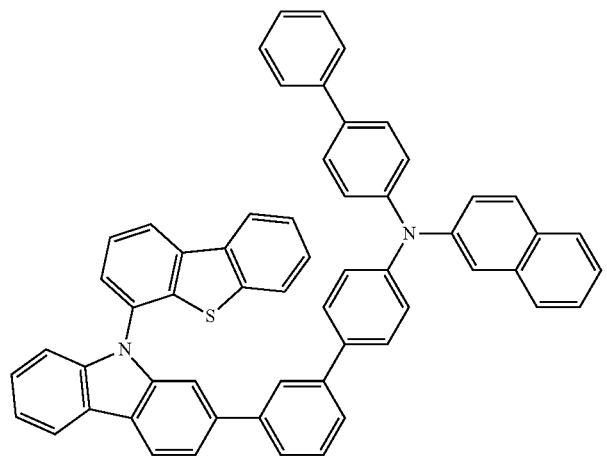

-continued
B213
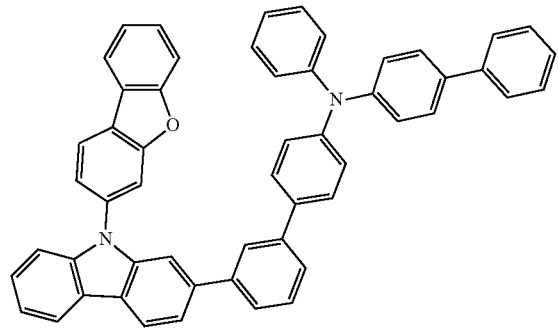
B214
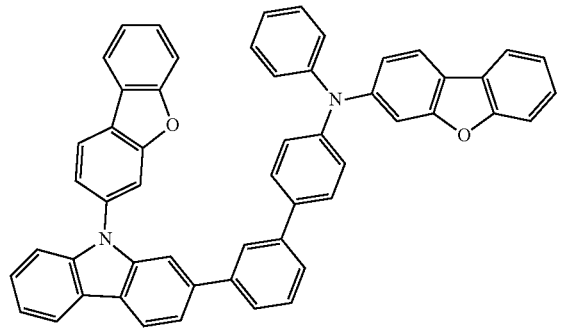
B215
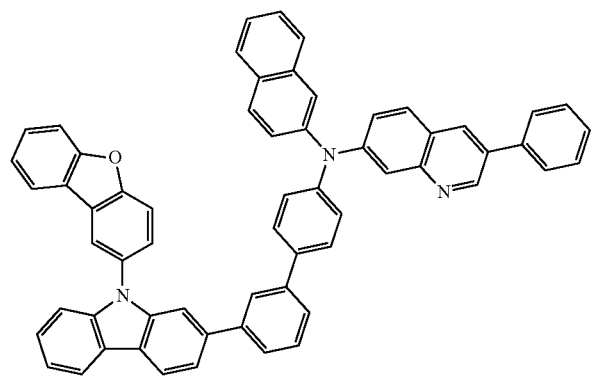
B216
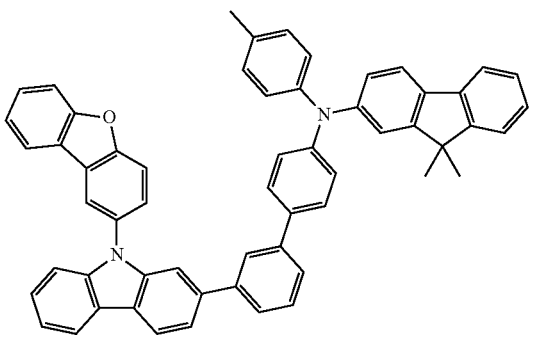
B217
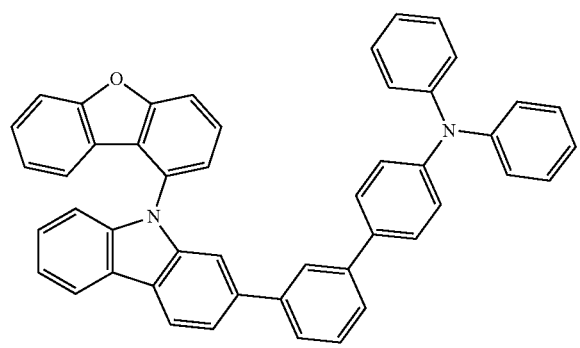
B218
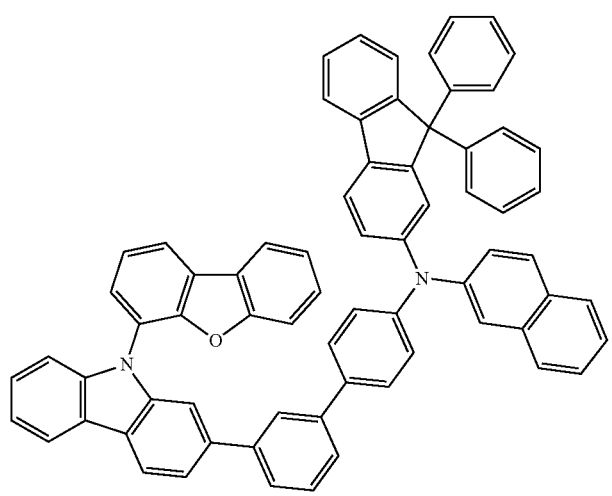

-continued
B219
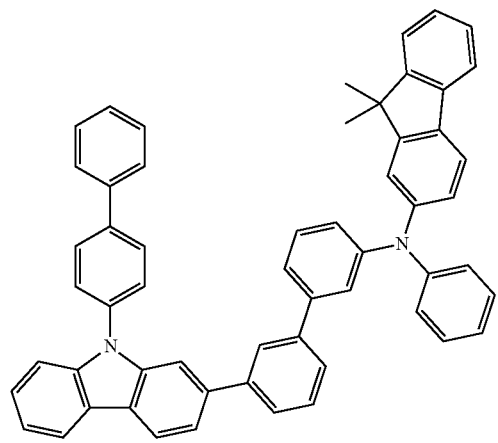
B220
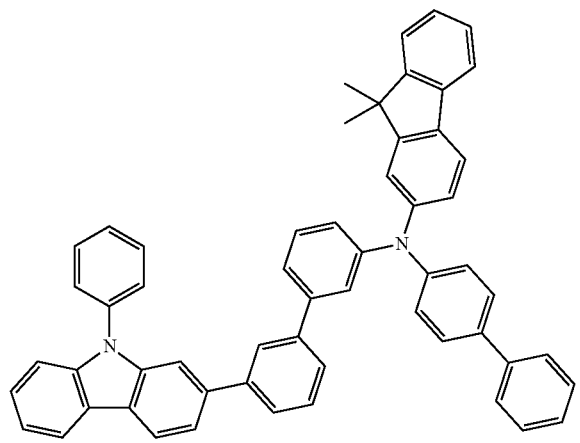
B221
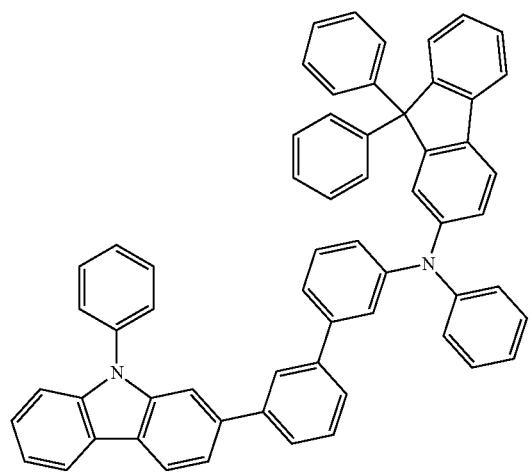
B222
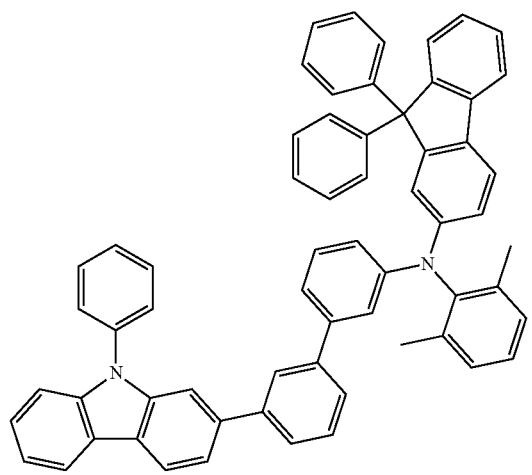
B223
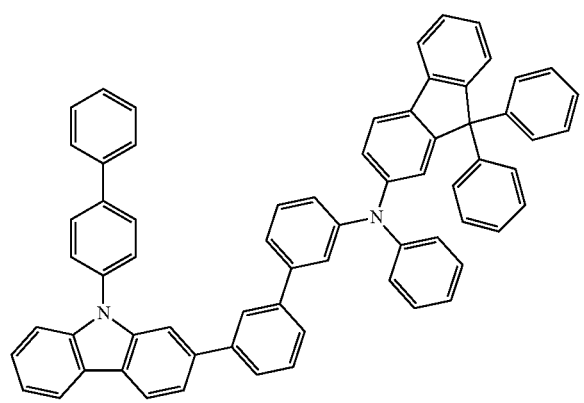
B224
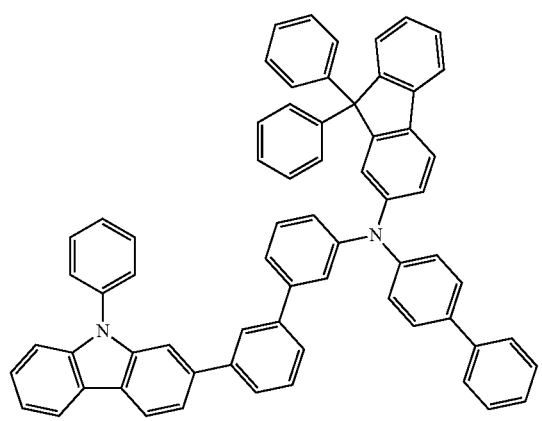

-continued
B225
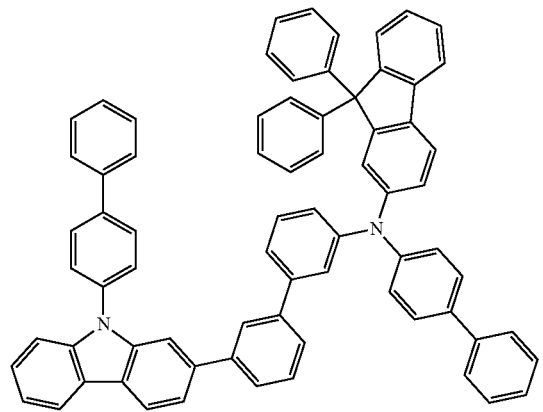
B226
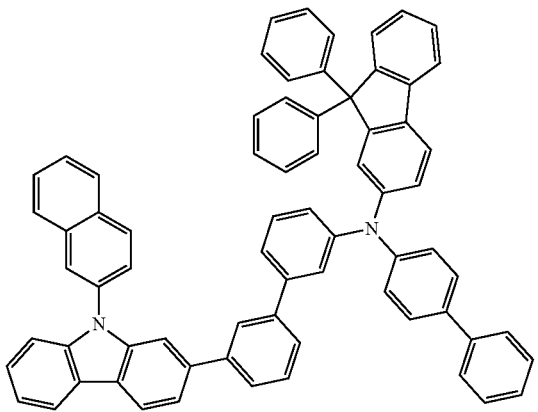
B227
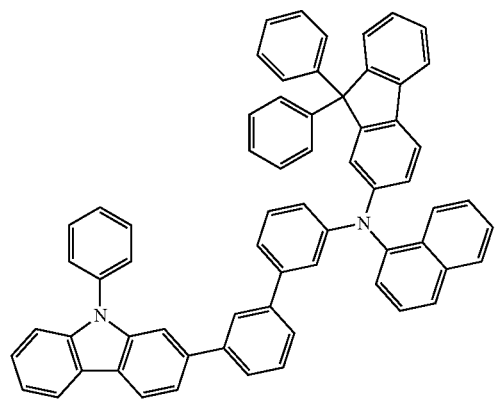
B228
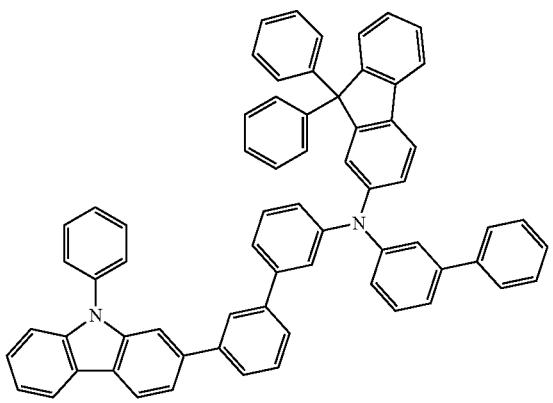
B229
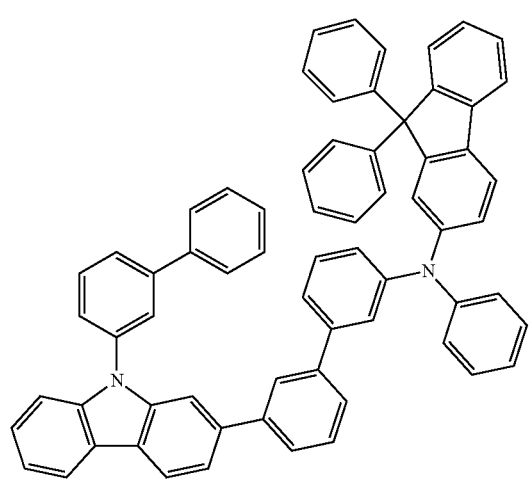

-continued
B230
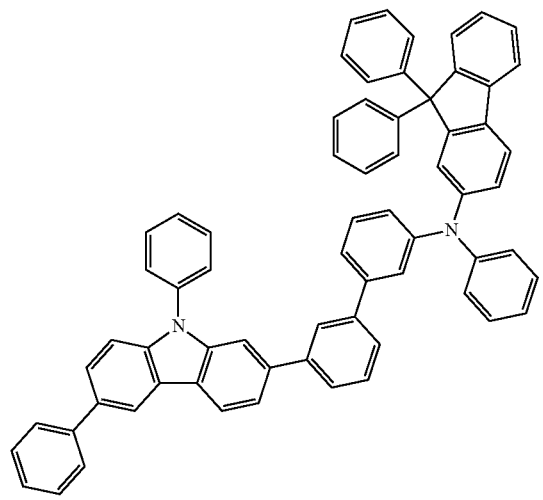
B231
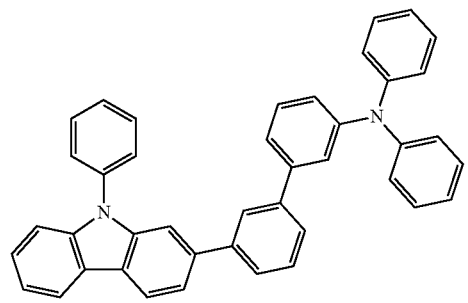
B232
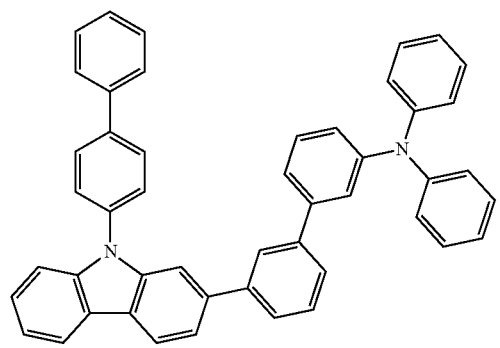
B233
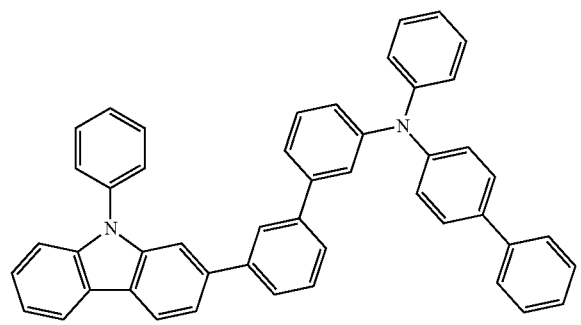
B234
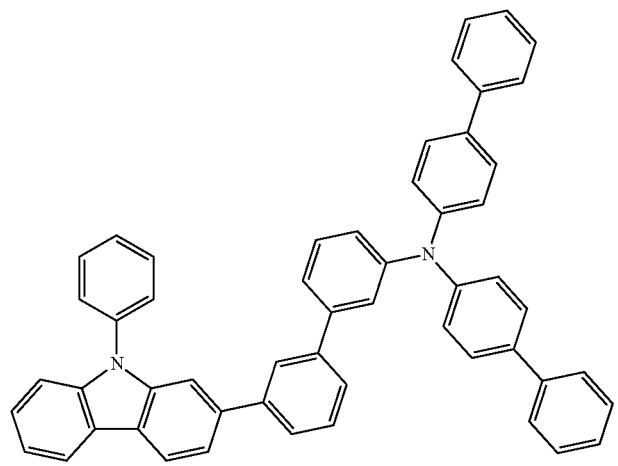

-continued
B235
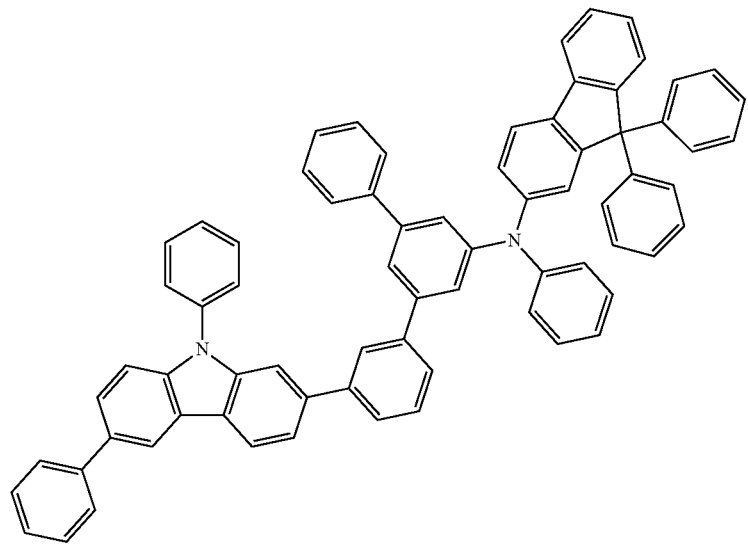
B236
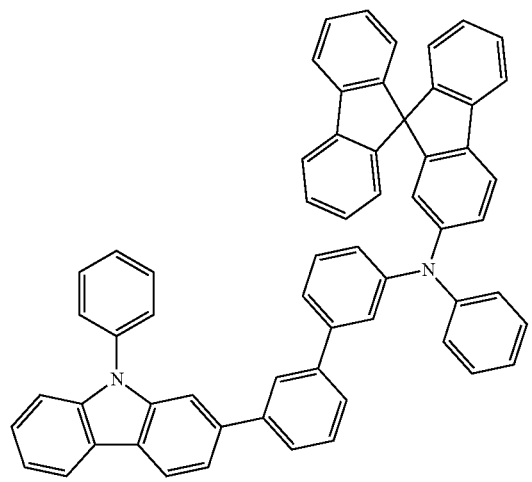
B237
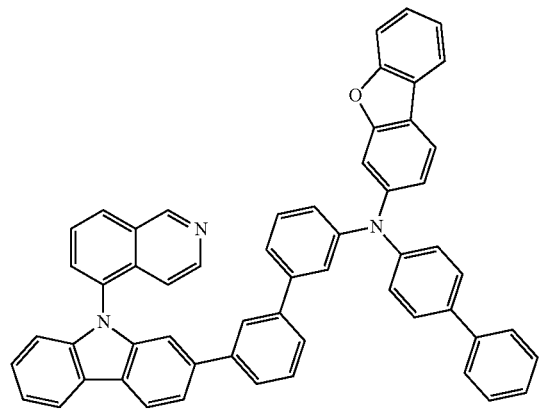
B238
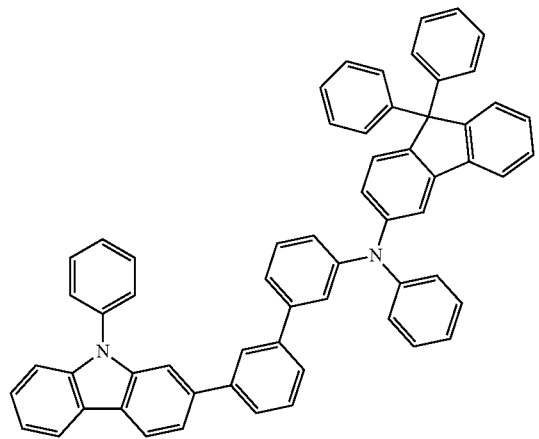

-continued
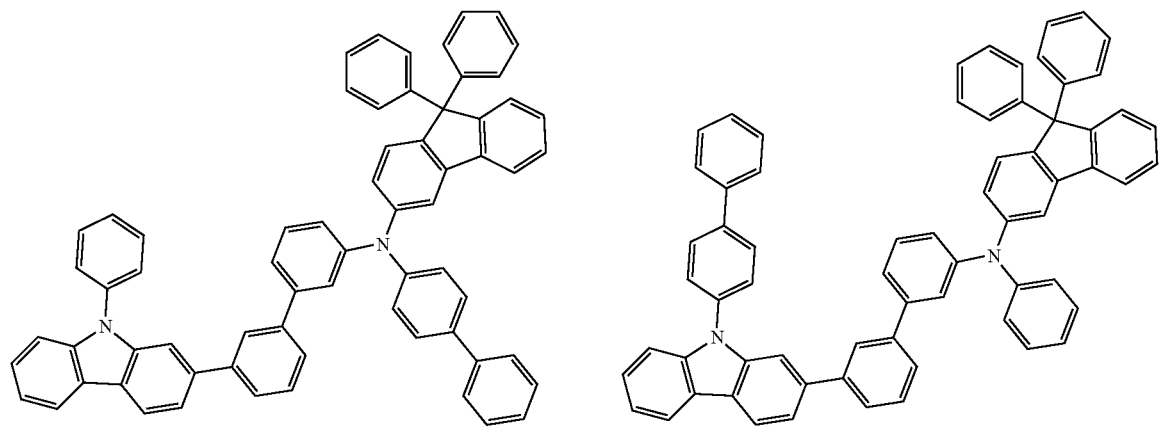
B239
B240
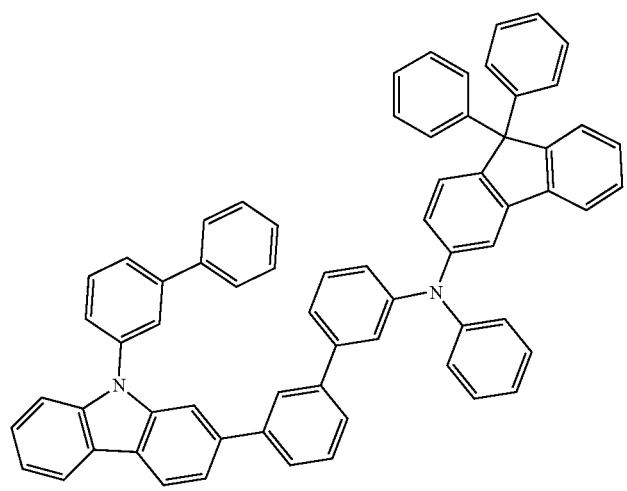
B241
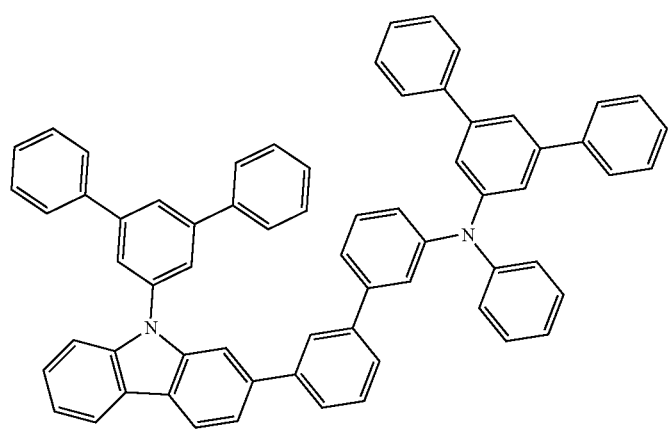
B242

-continued
B243
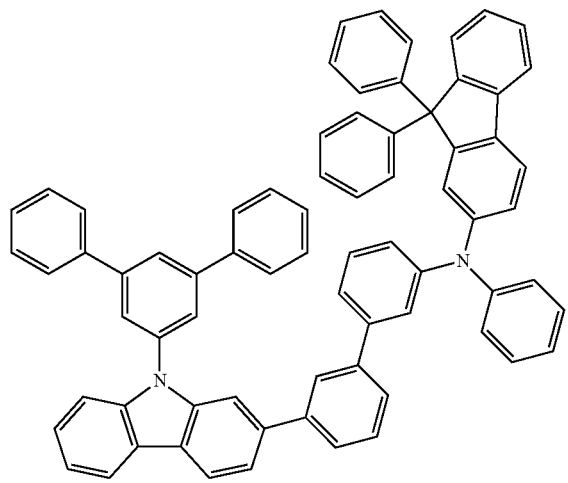
B244 B245
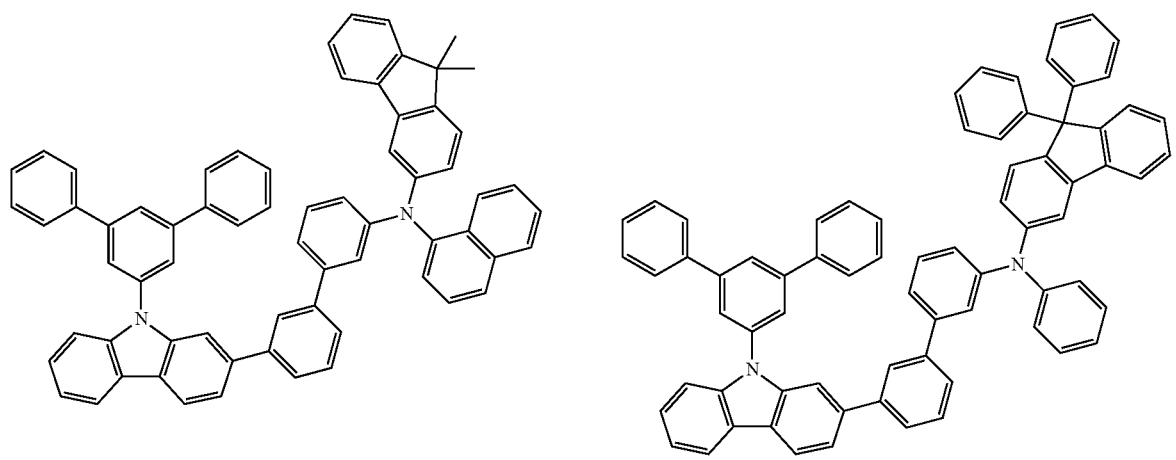
B246
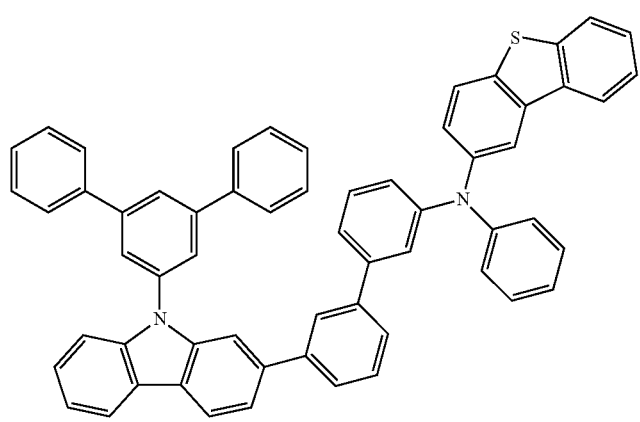

-continued
B247
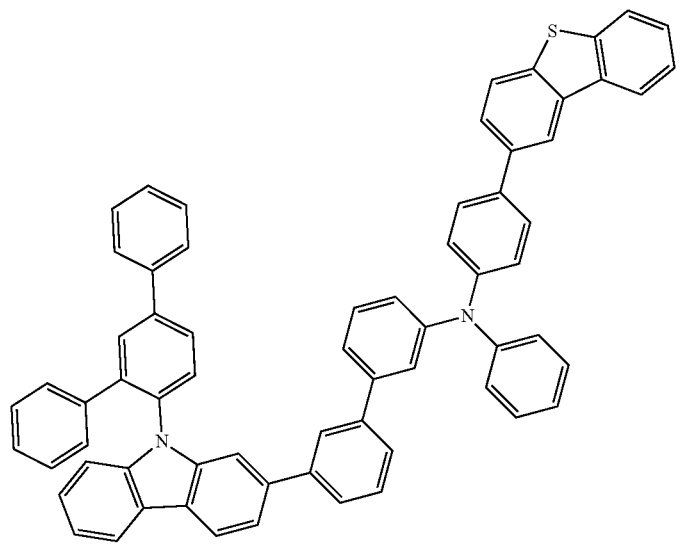
B248
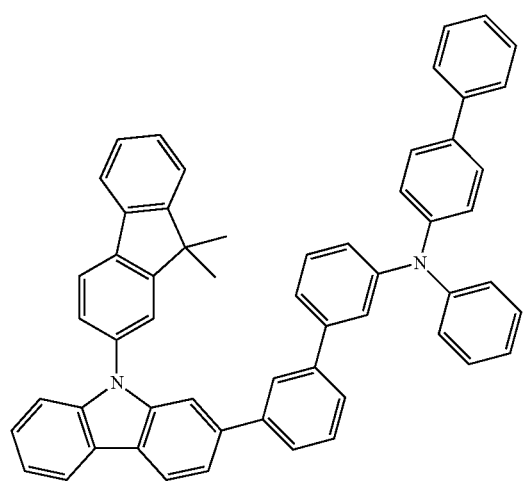
B249
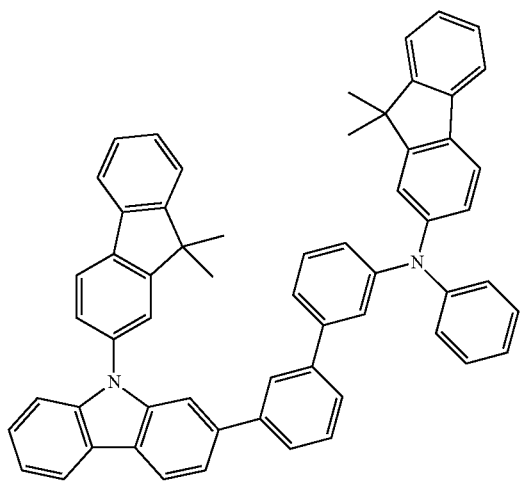
B250
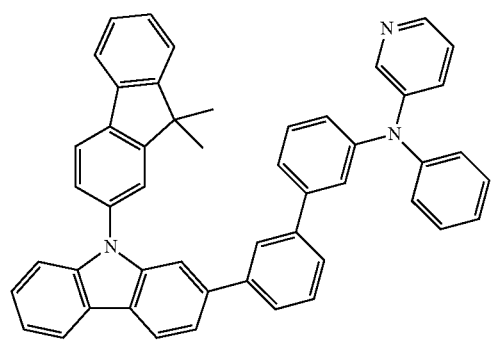
B251
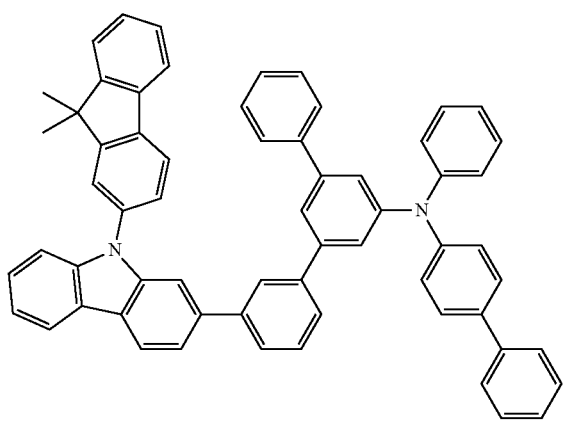

-continued
B252
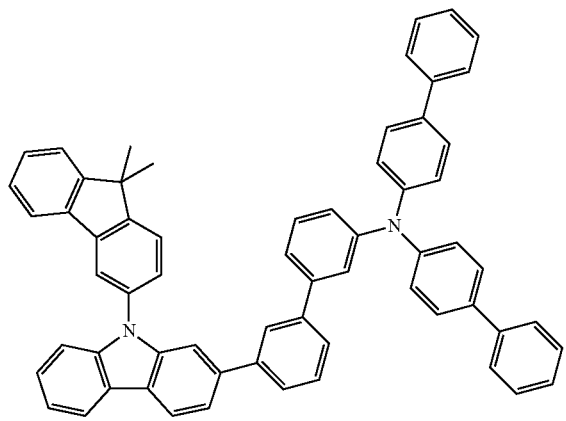
B253
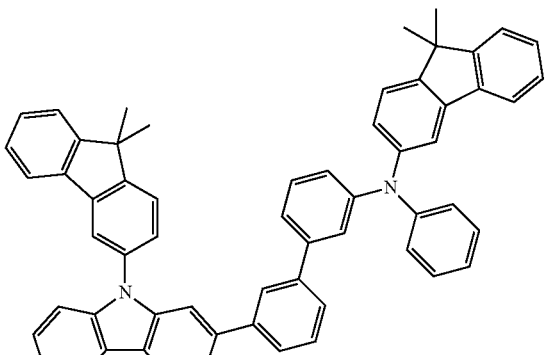
B254
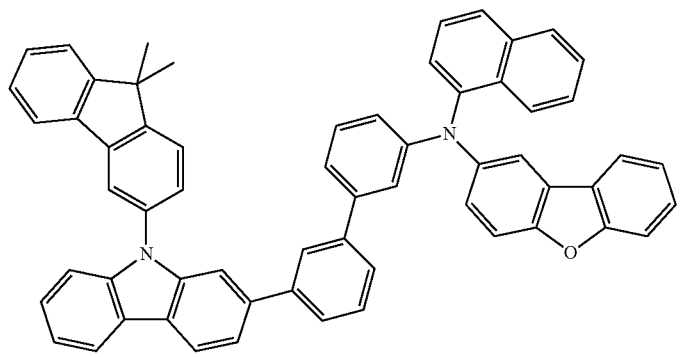
B255
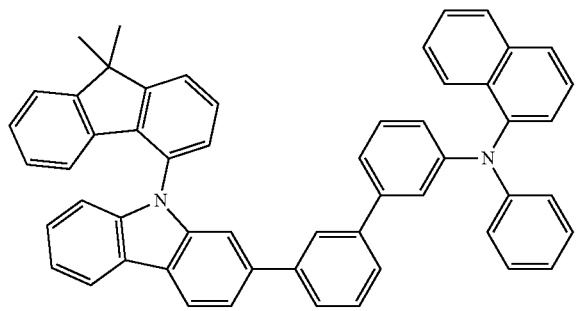
B256
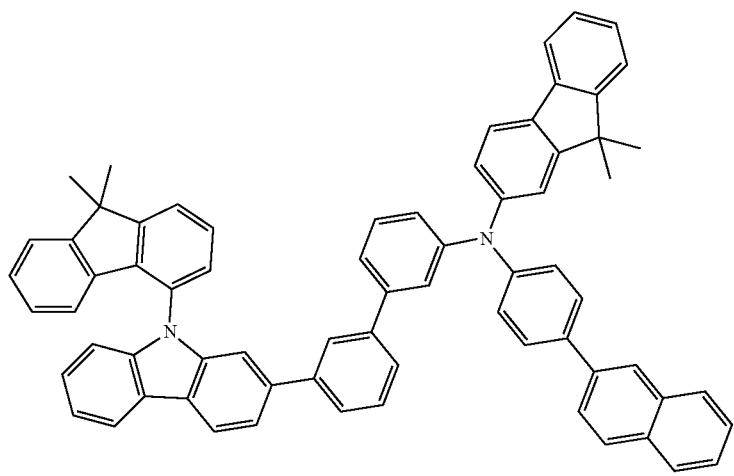

-continued
B257
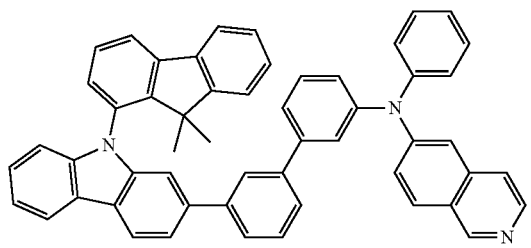
B258
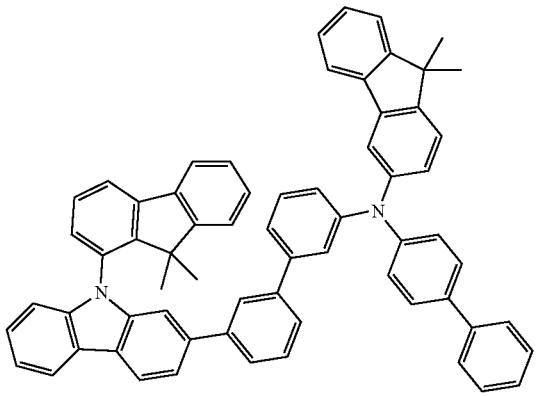
B259
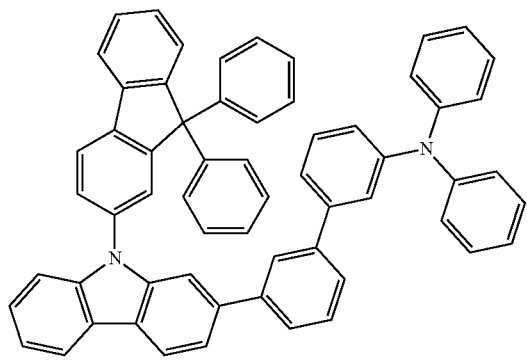
B260
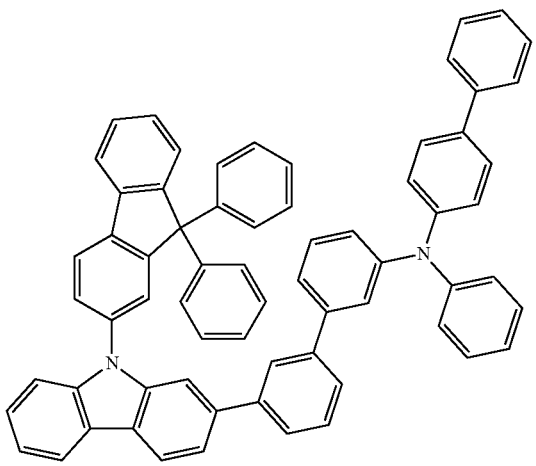
B261
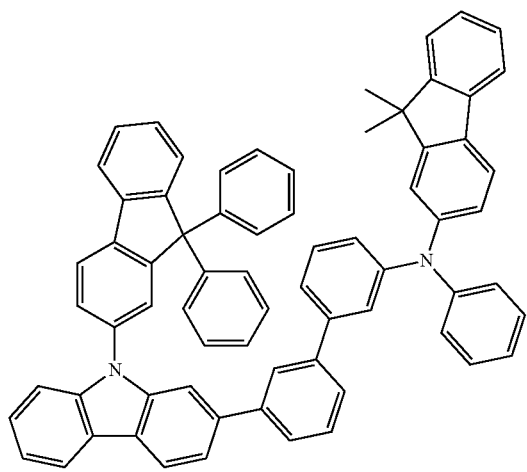

-continued
B262
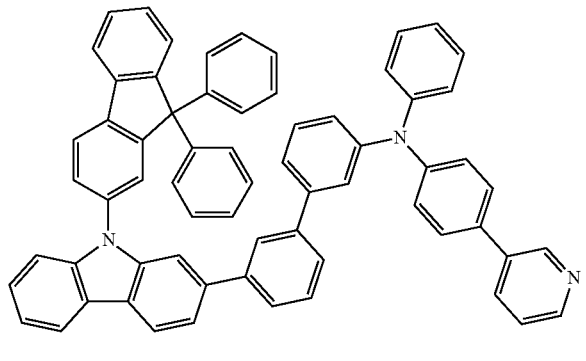
B263
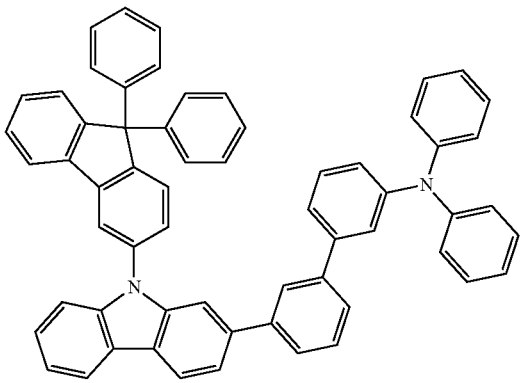
B264
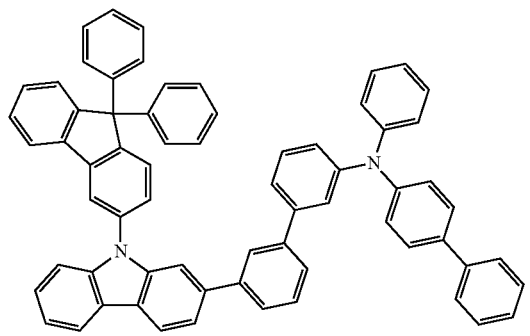
B265
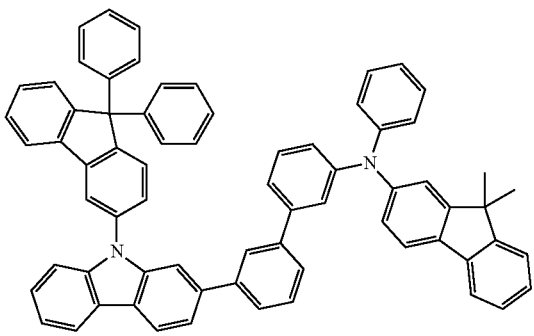
B266
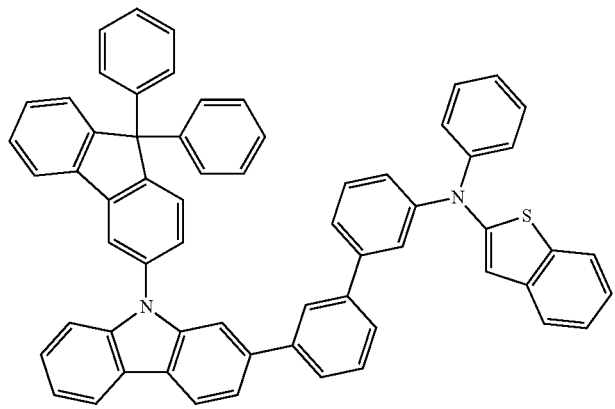
B267
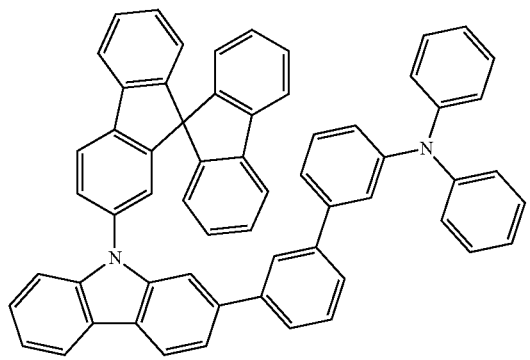

-continued
B268
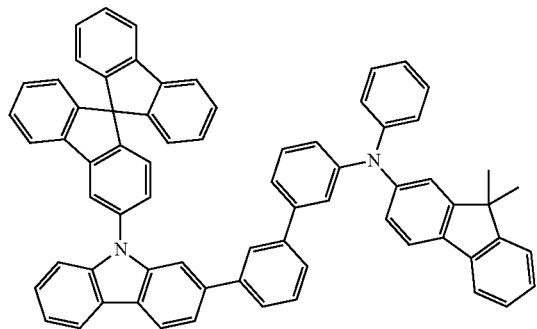
B269
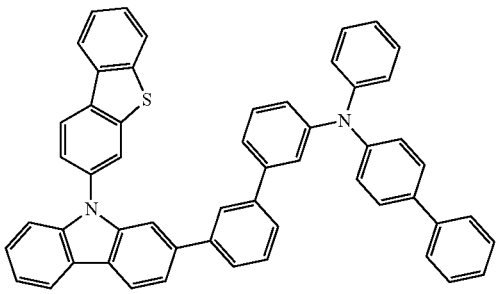
B270
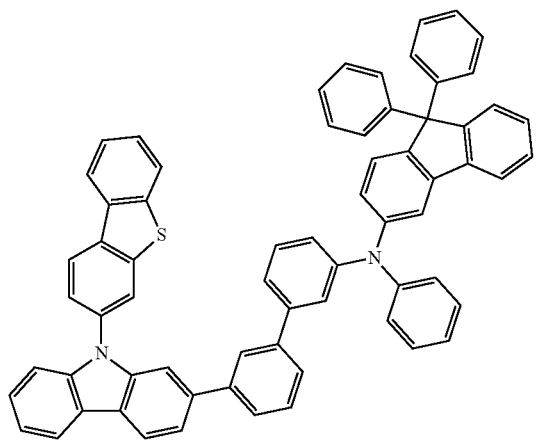
B271
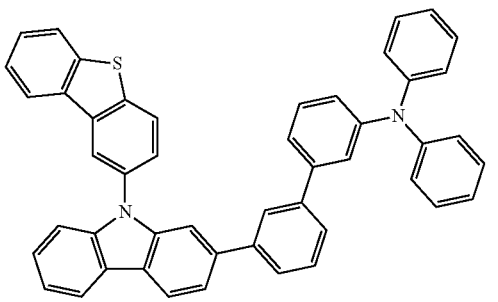
B272
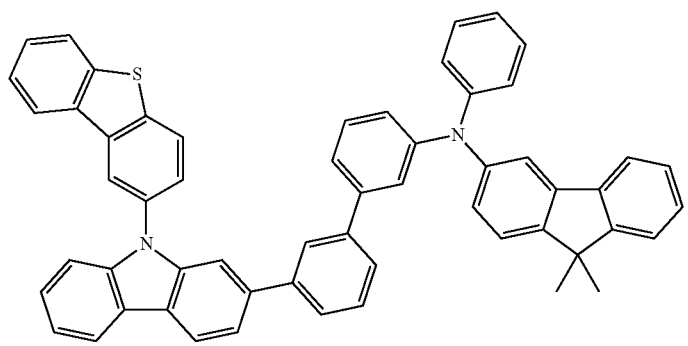
B273
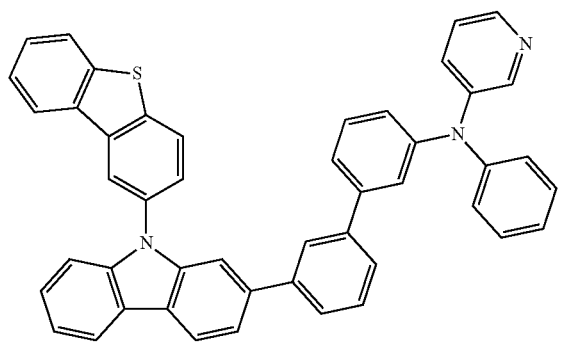

-continued
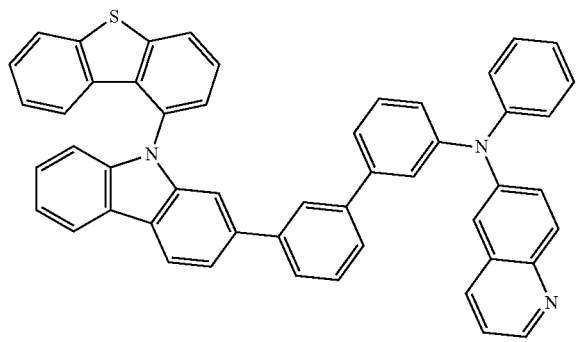
B274
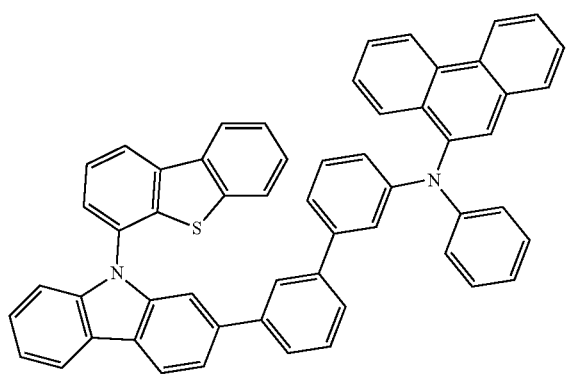
B275
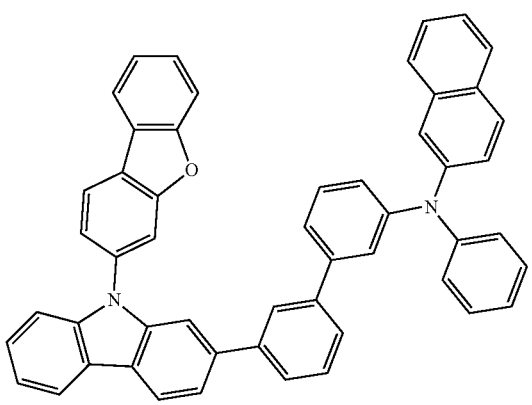
B276
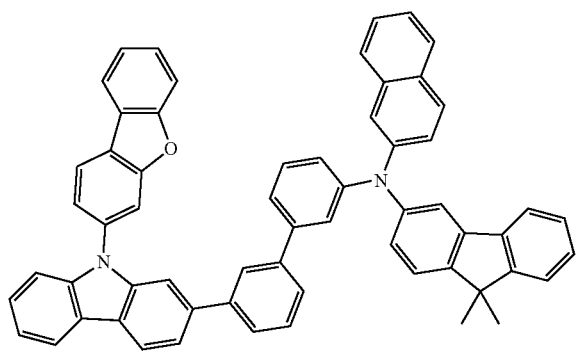
B277
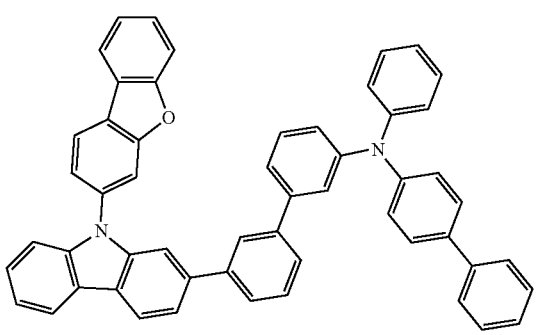
B278

-continued
B279
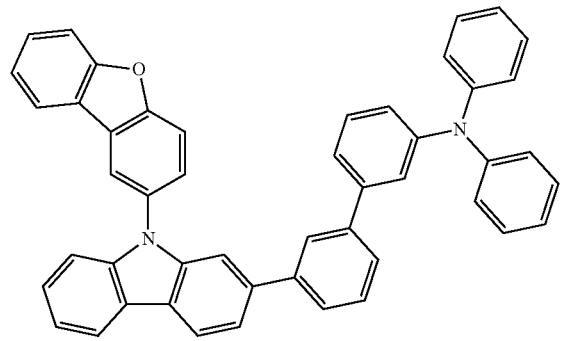
B280
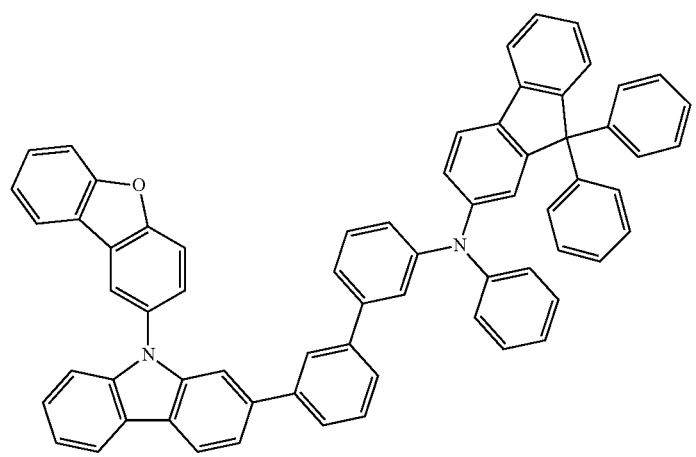
B281
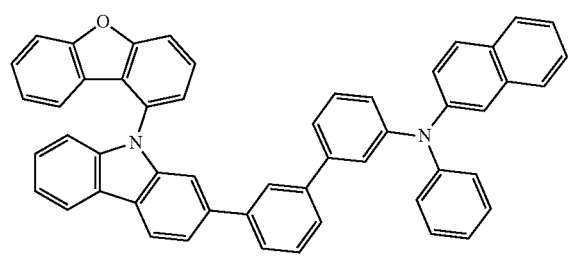
B282
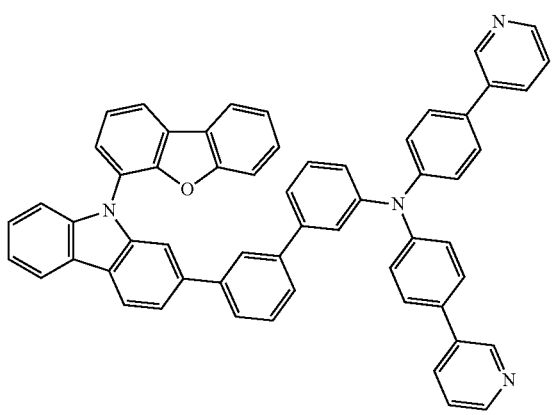
B283
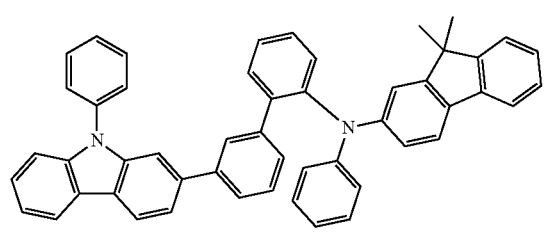
B284
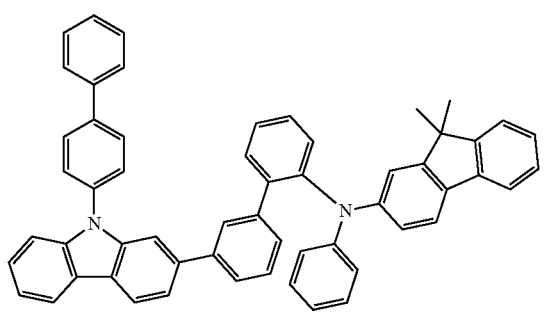

-continued
B285
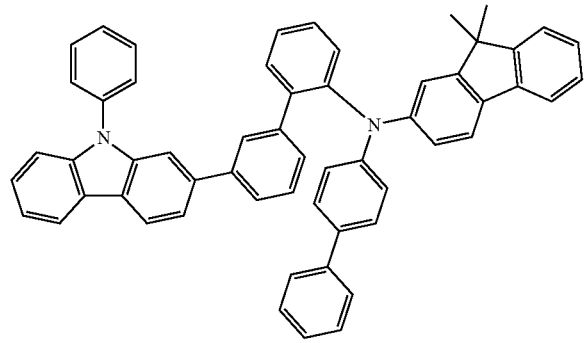
B286
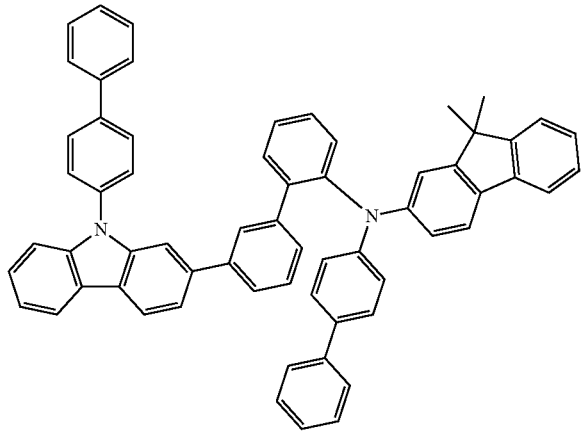
B287
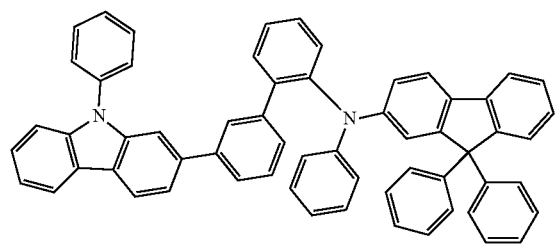
B288
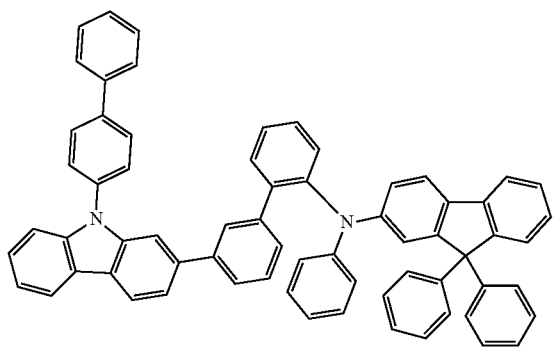
B289
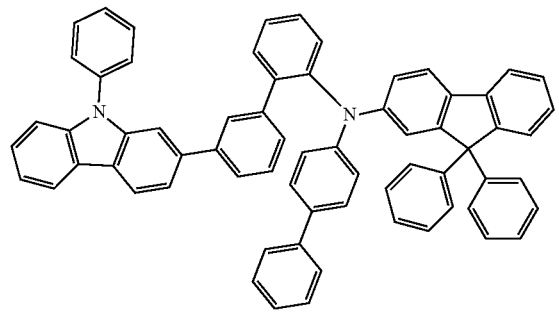
B290
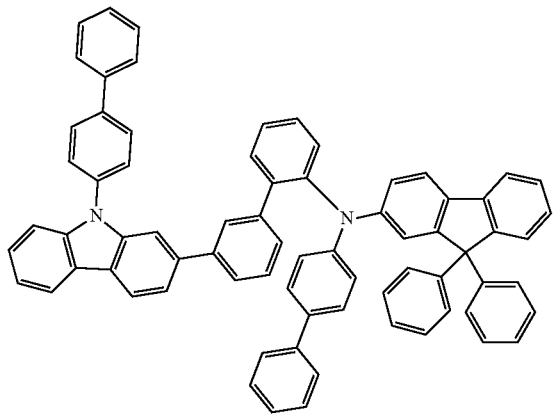
B291
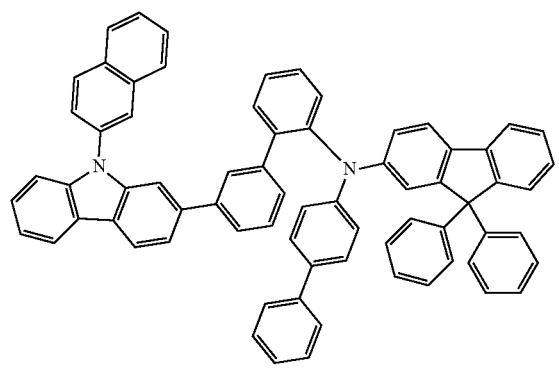

-continued
B293
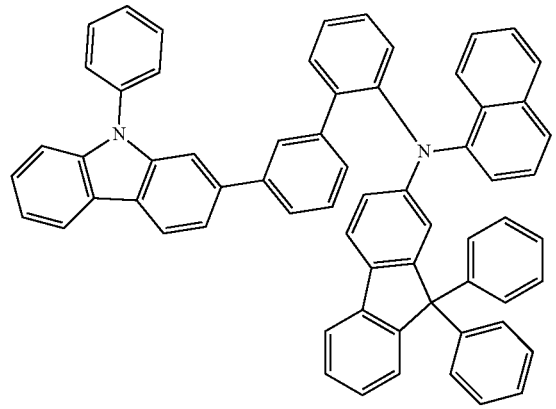
B294
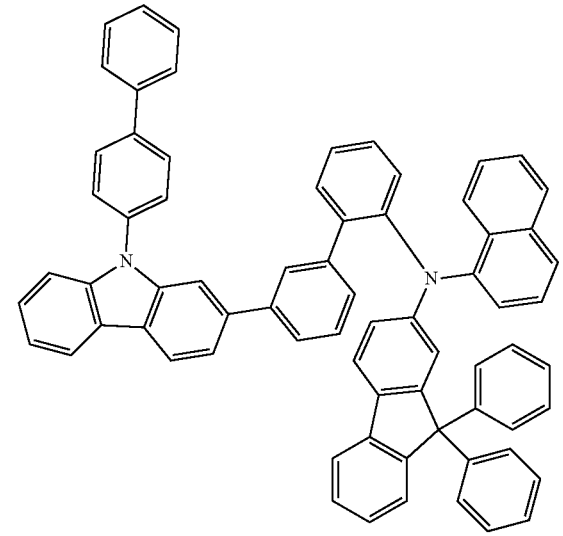
B295
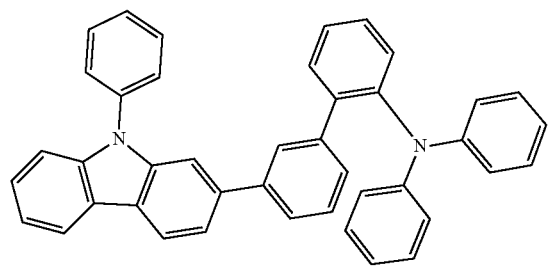
B296
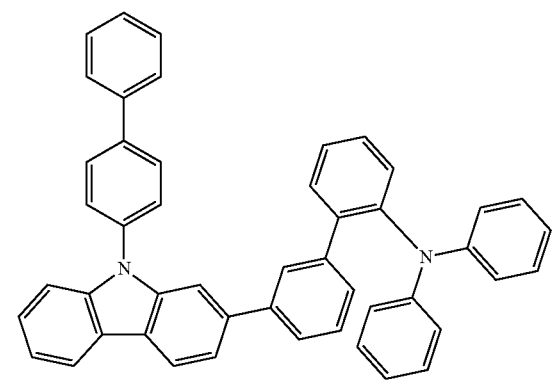
B297
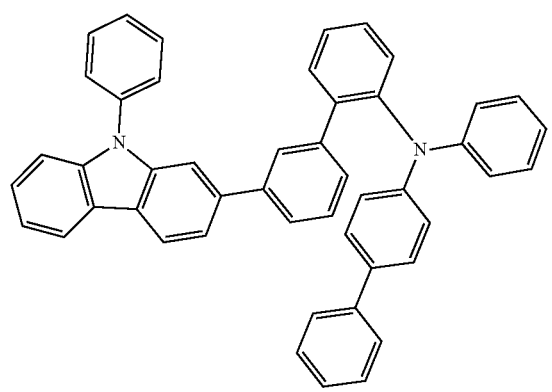
B298
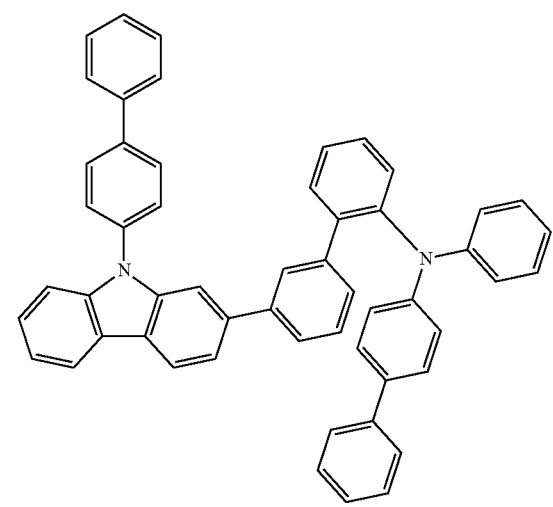

-continued
B299
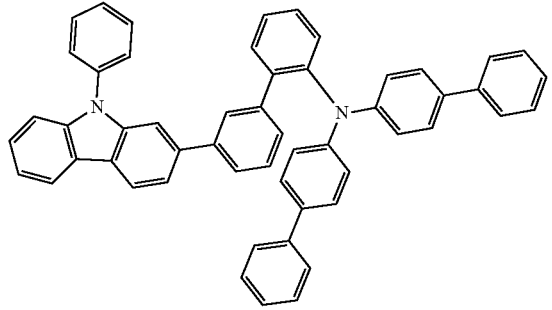
B300
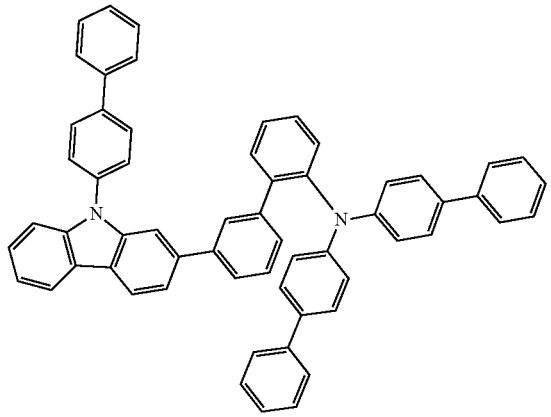
B301
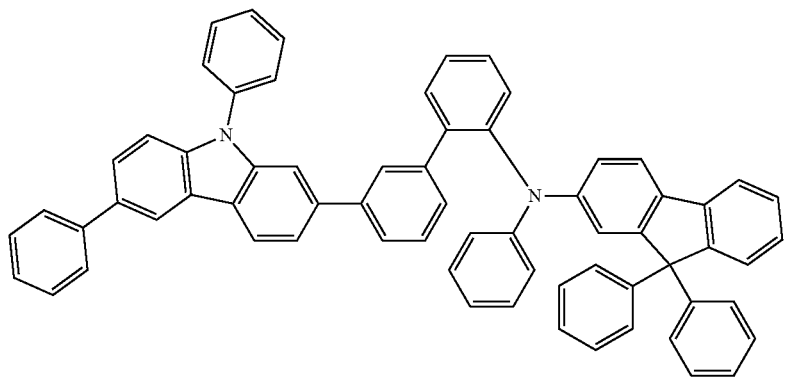
B302
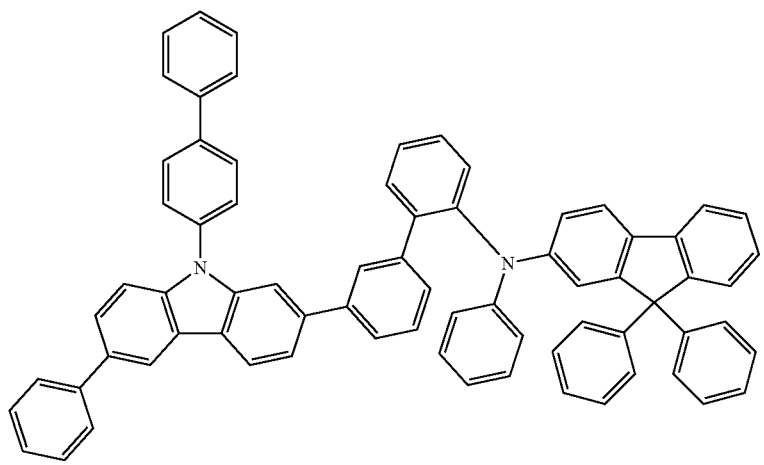
B303
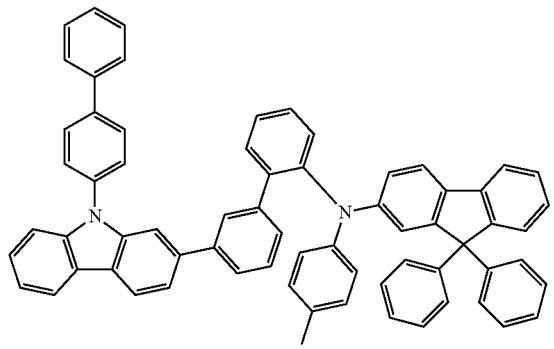
B304
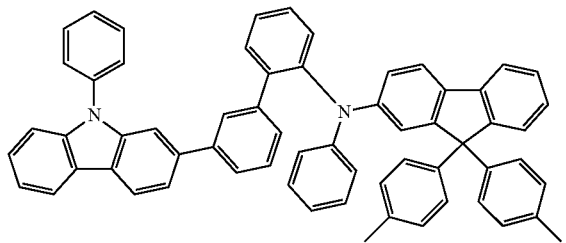

B305
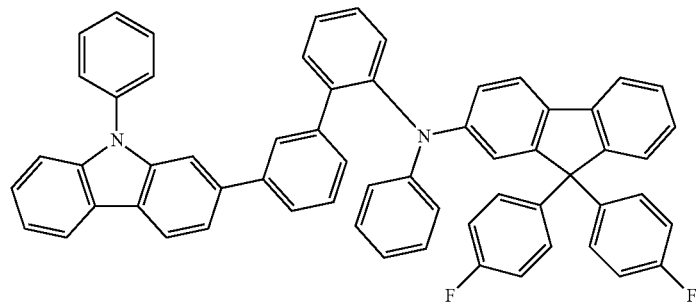
B306
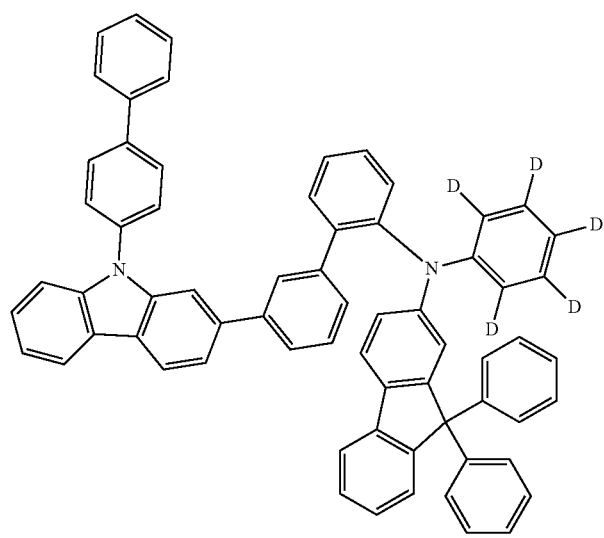
B307
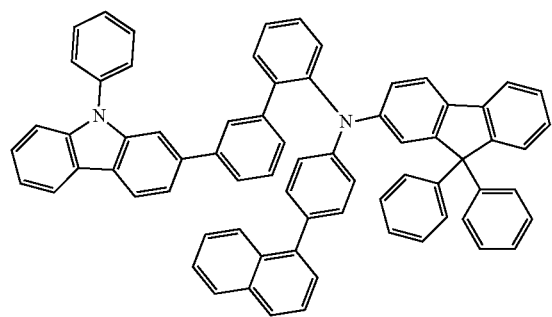
B308
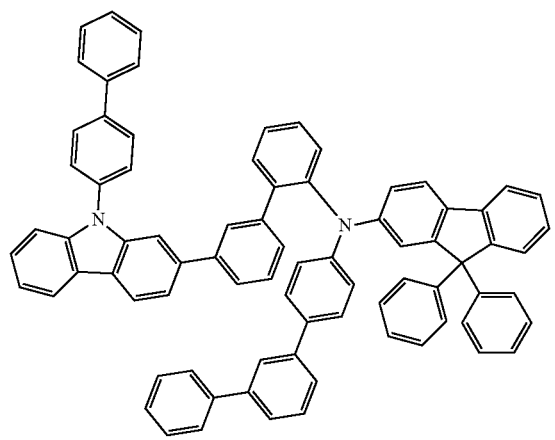

-continued
B309
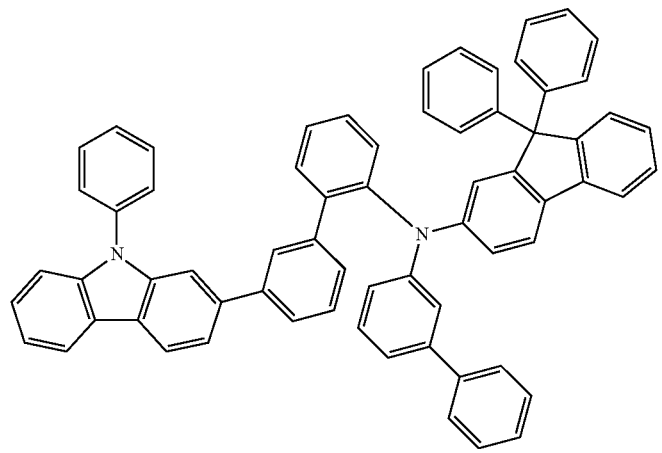
B310
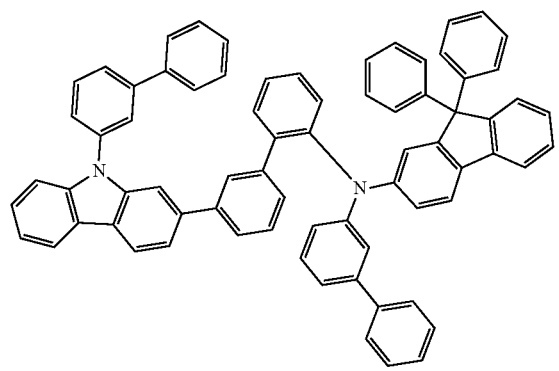
B311
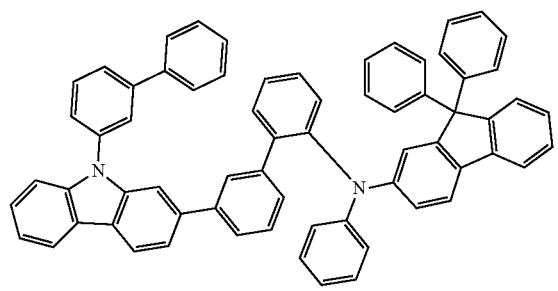
B312
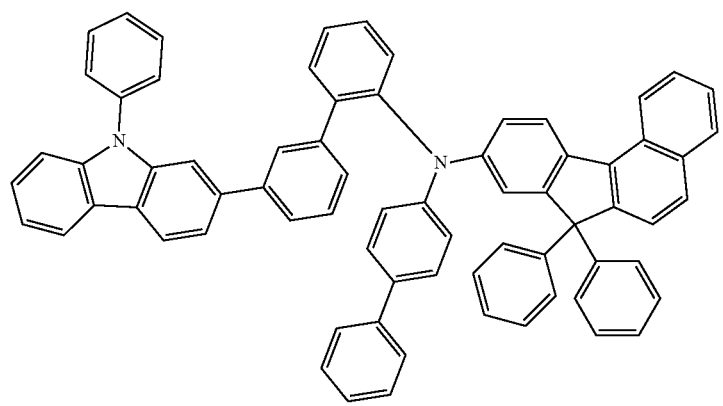
B313
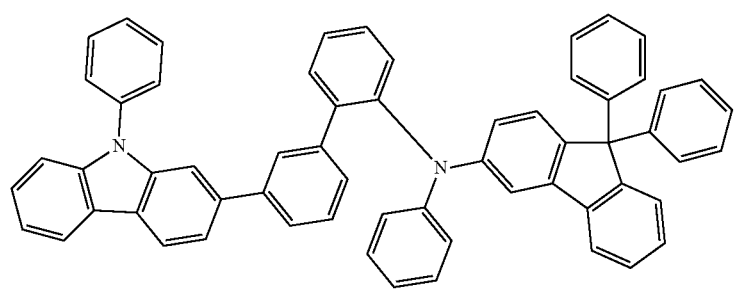

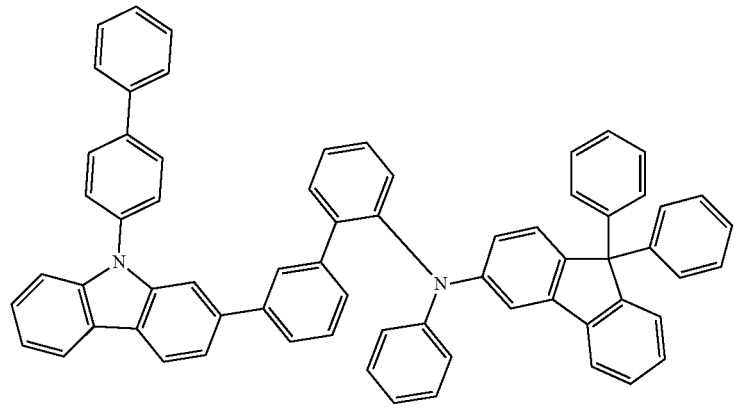
B314
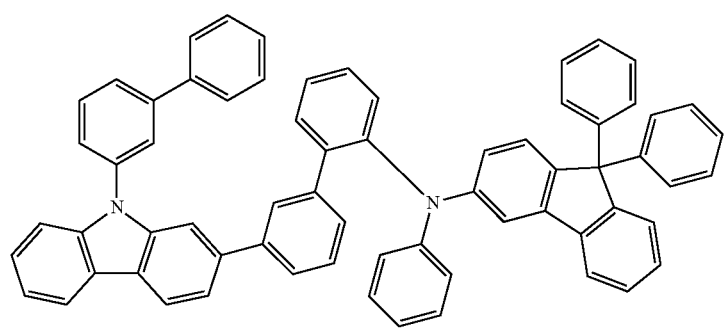
B315
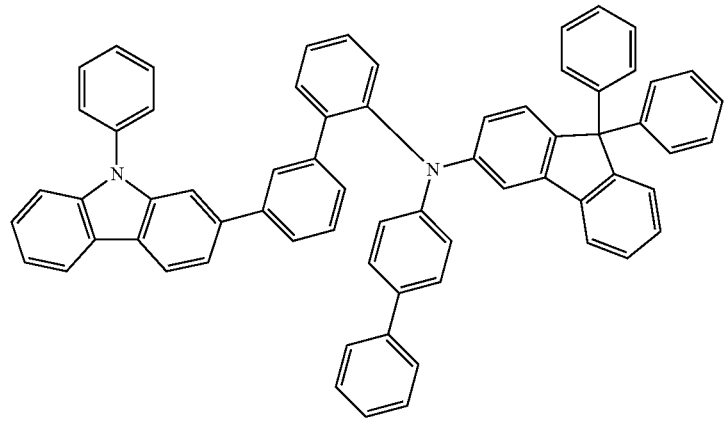
B316
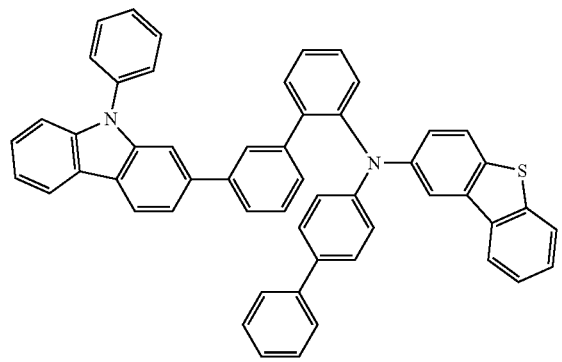
B317
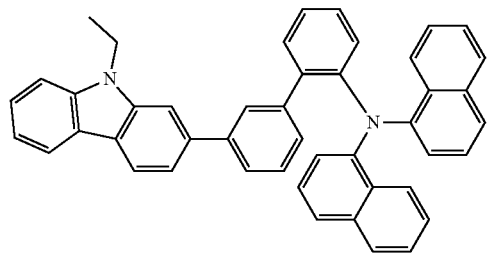
B318

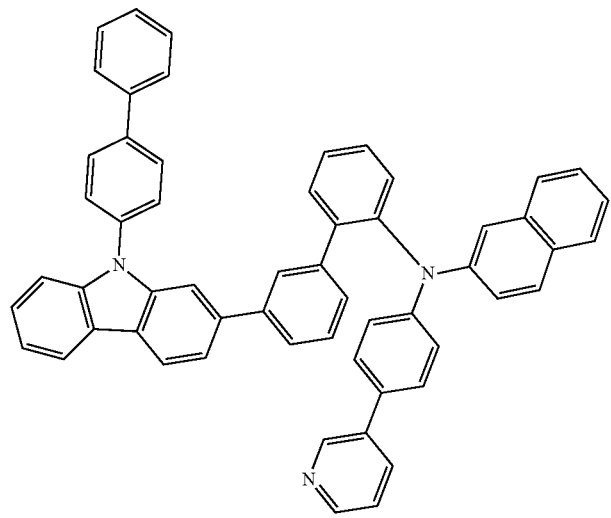
B319
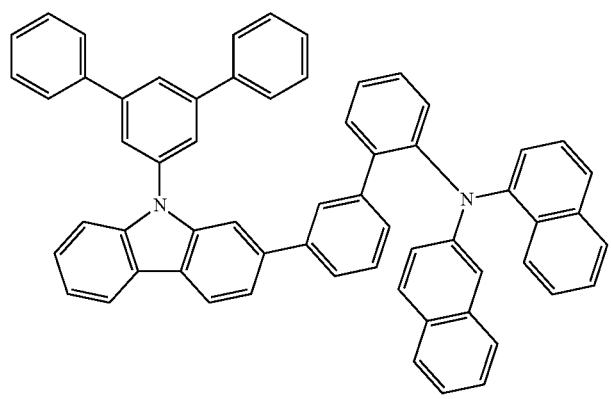
B320
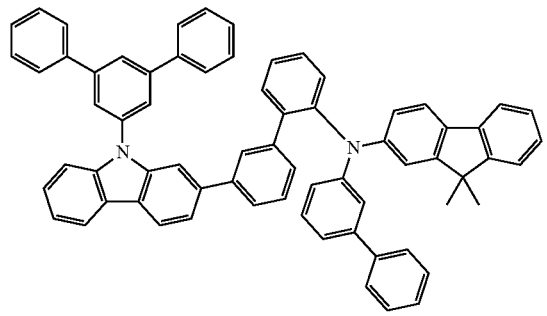
B321
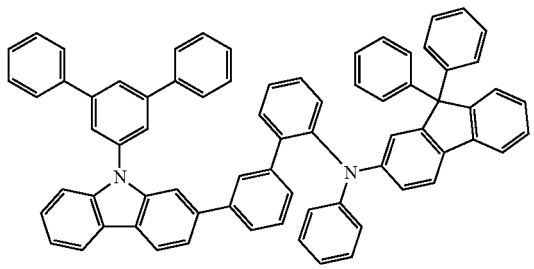
B322
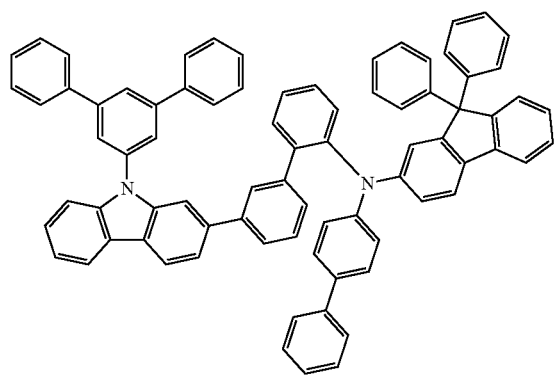
B323
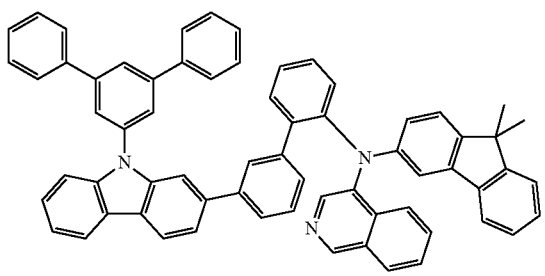
B324

-continued
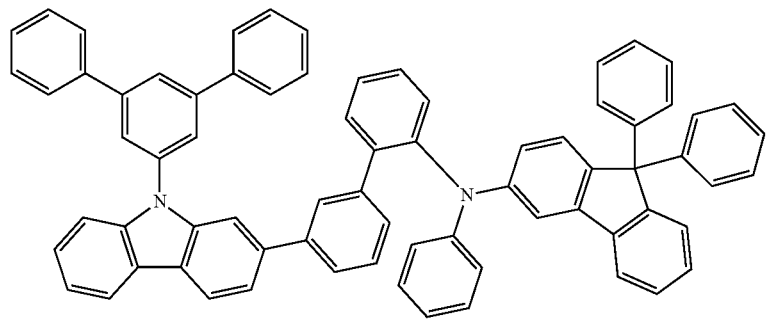
B325
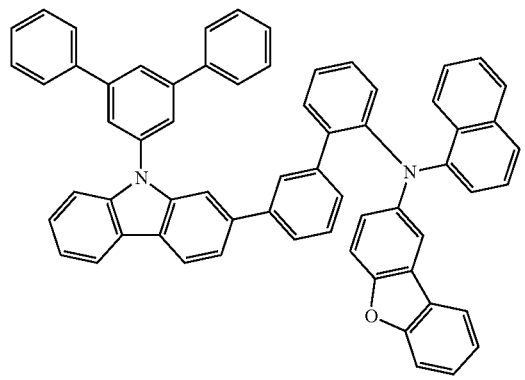
B326
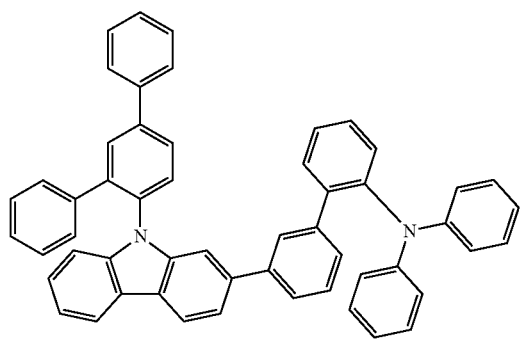
B327
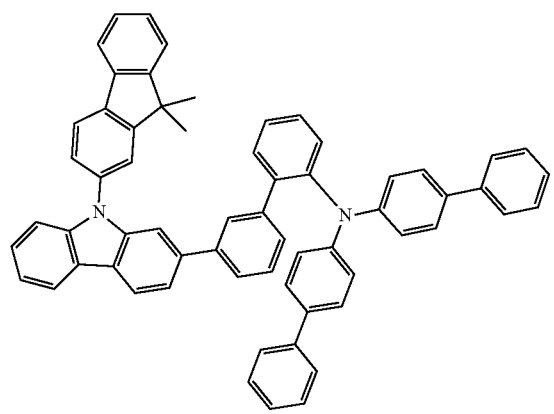
B328
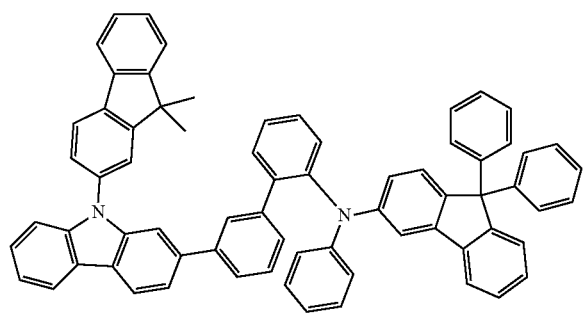
B329
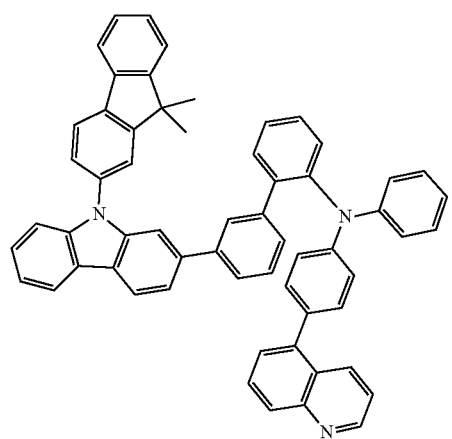
B330
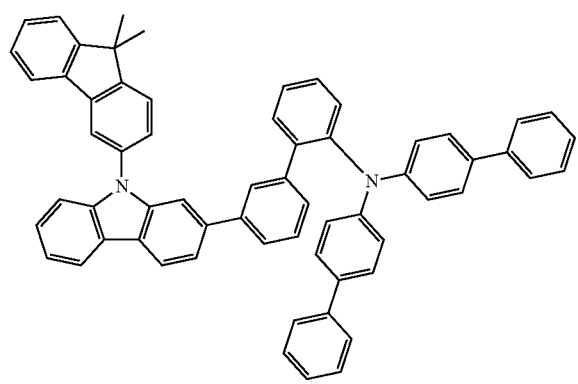
B331

-continued
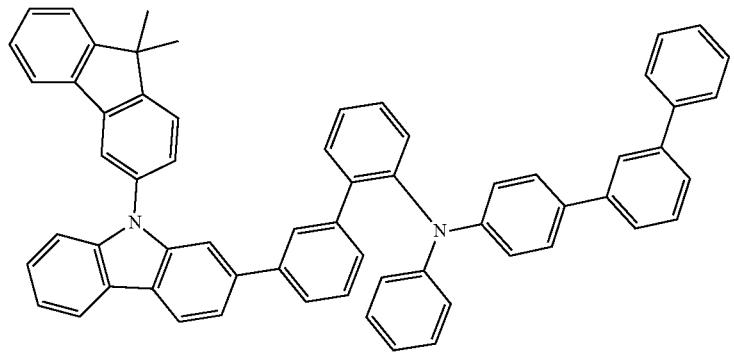
B332
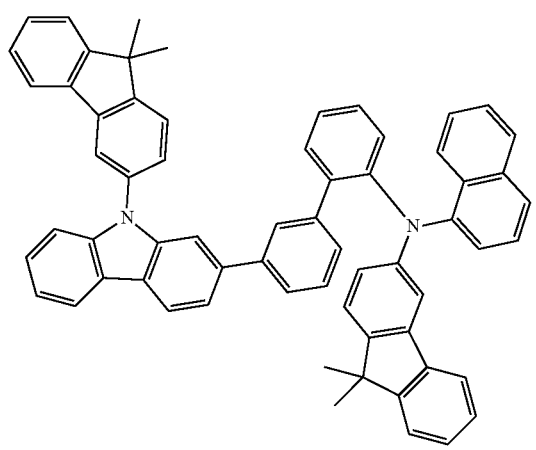
B333
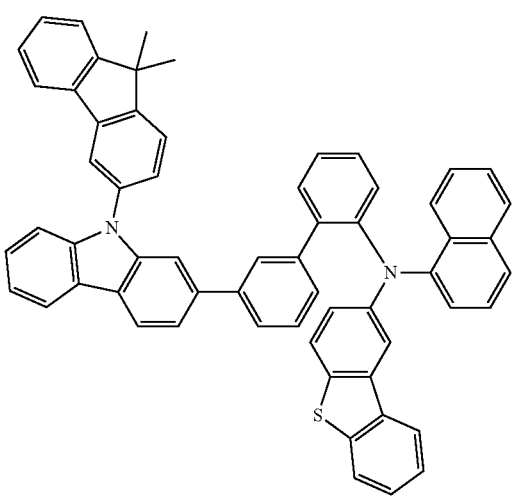
B334
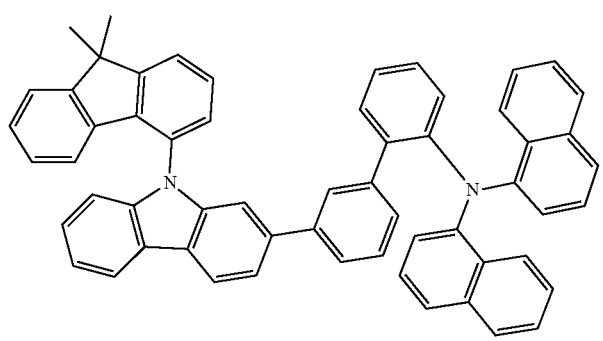
B335

B336
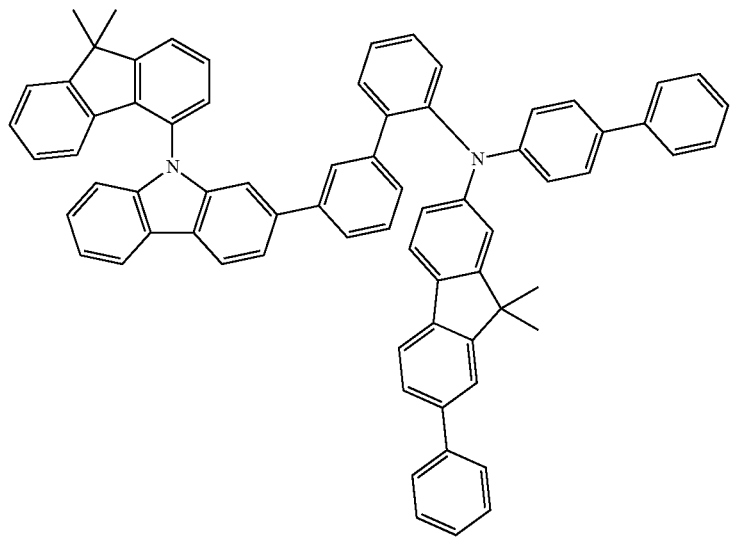
B337
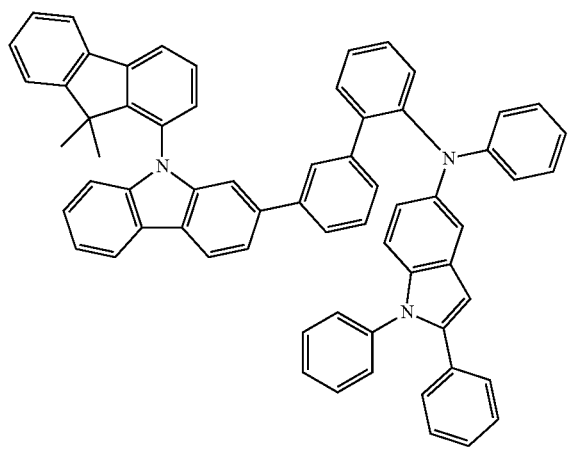
B338
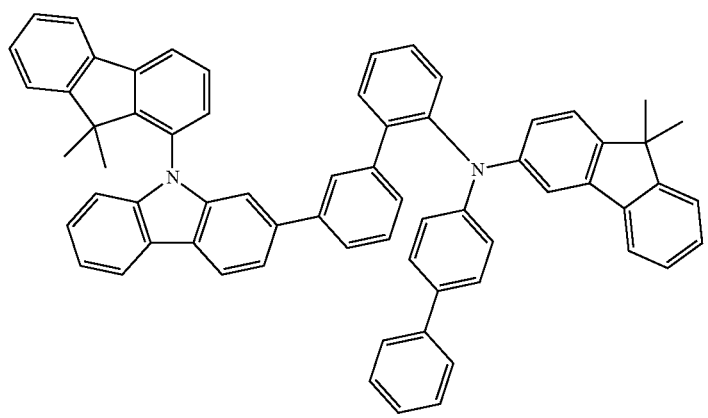

-continued
B339
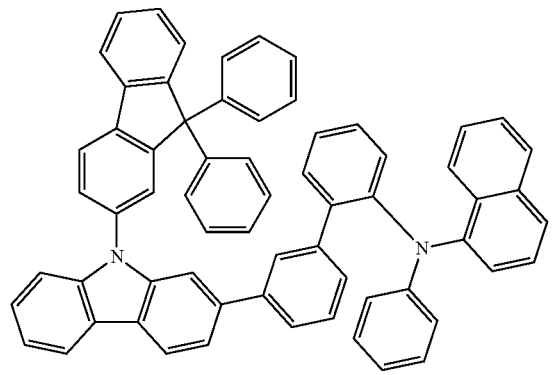
B340
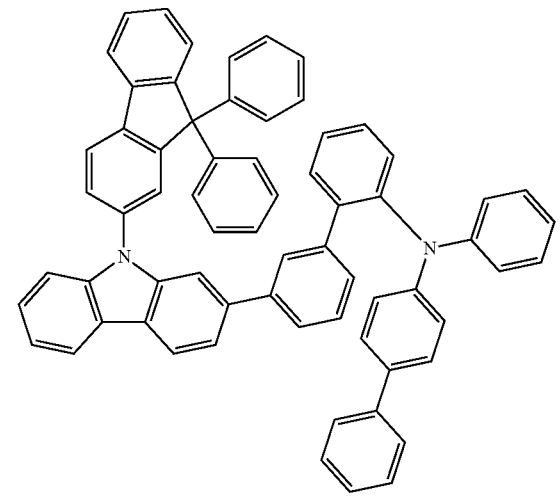
B341
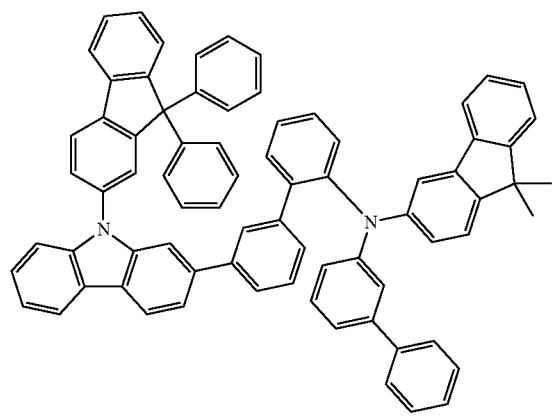
B342
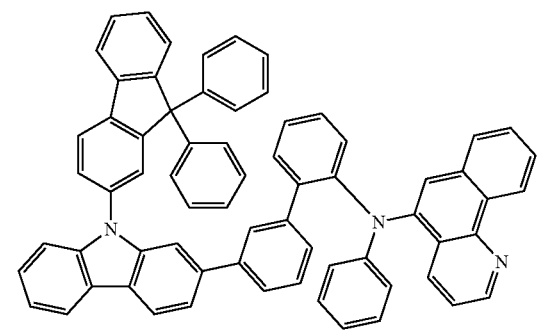
B343
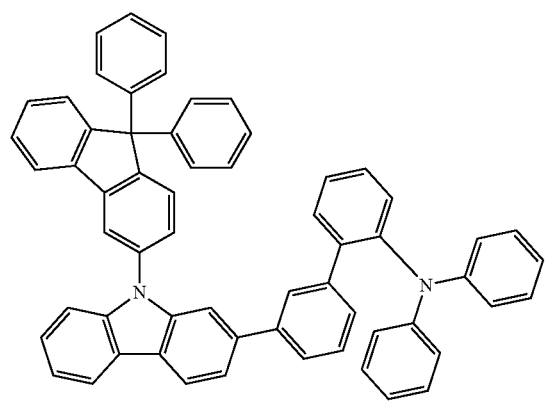
B344
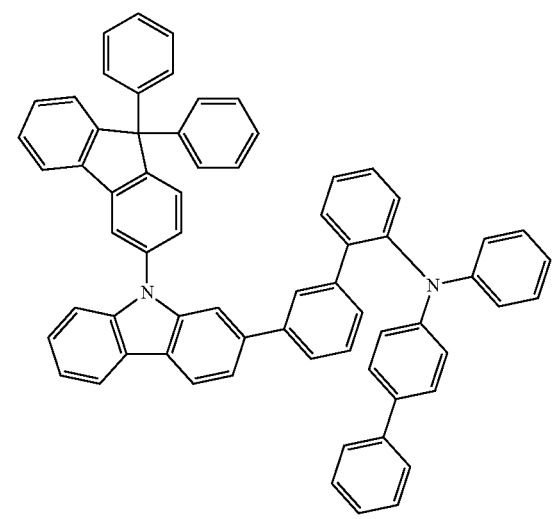

-continued
B345
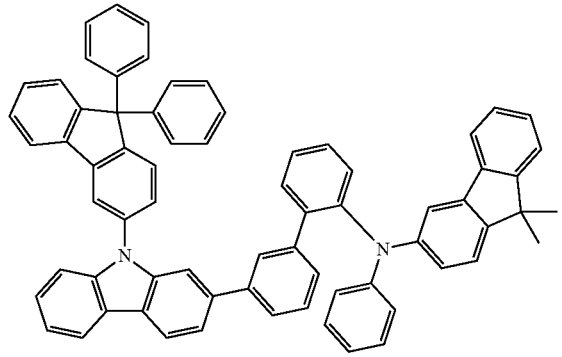
B346
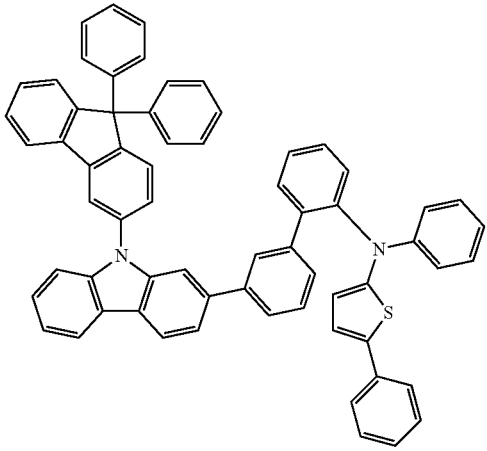
B347
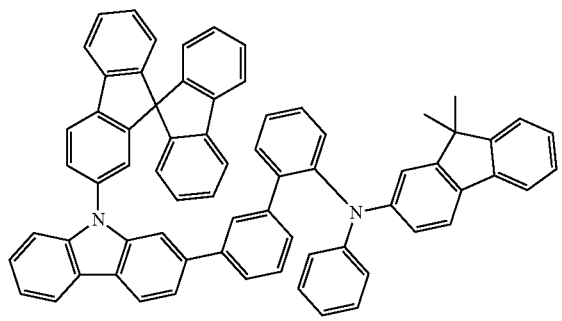
B348
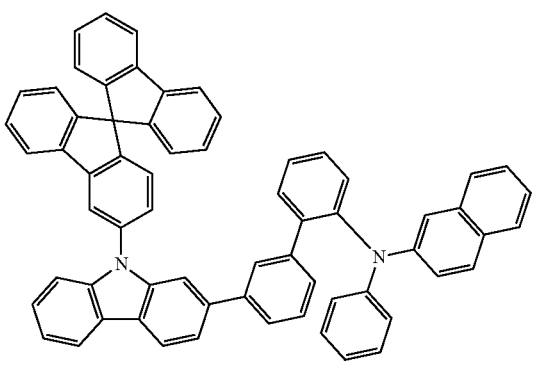
B349
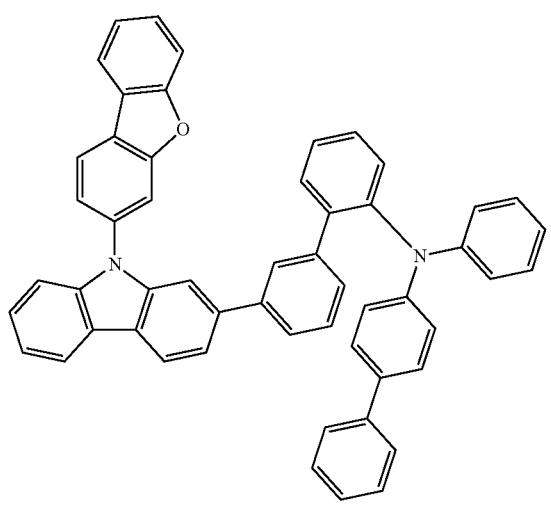

B350
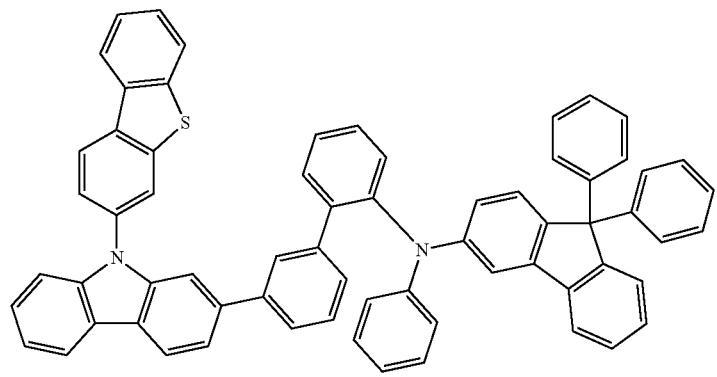
B351
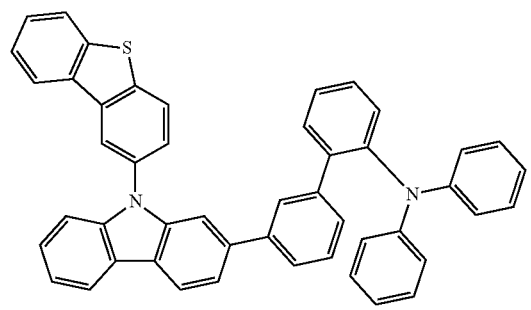
B352
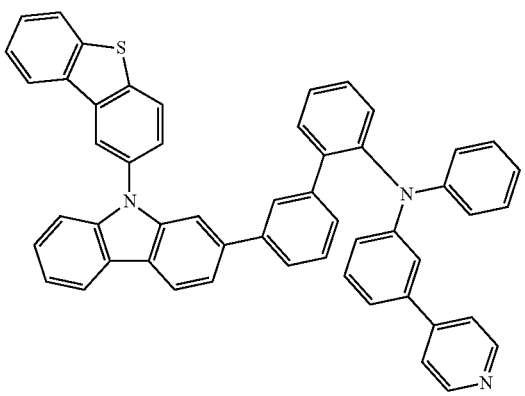
B353
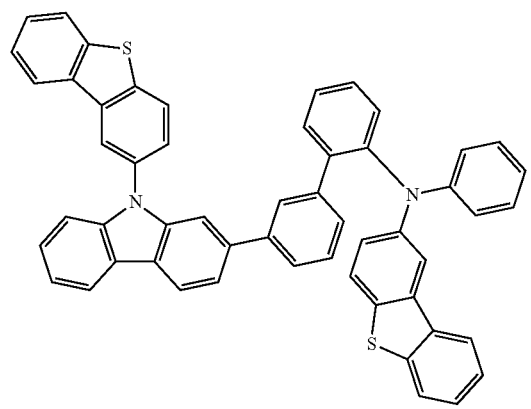
B354
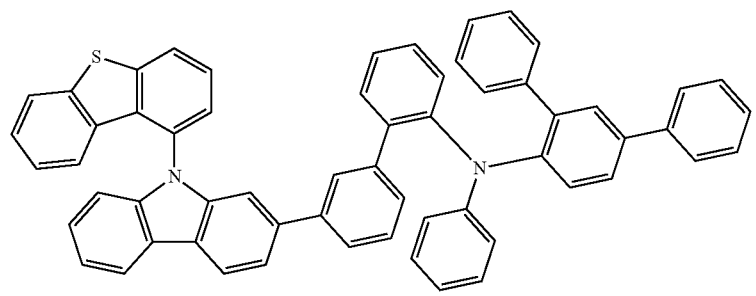

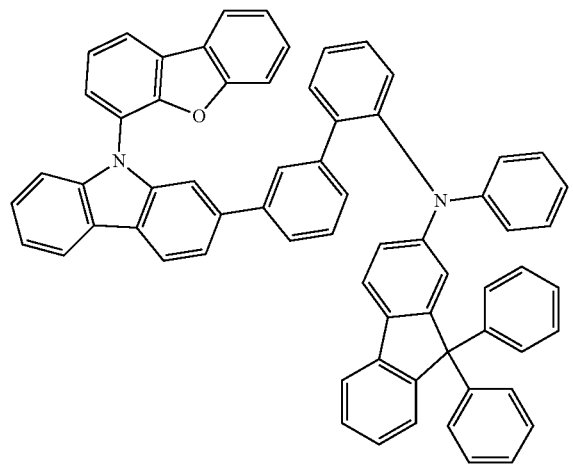
B355
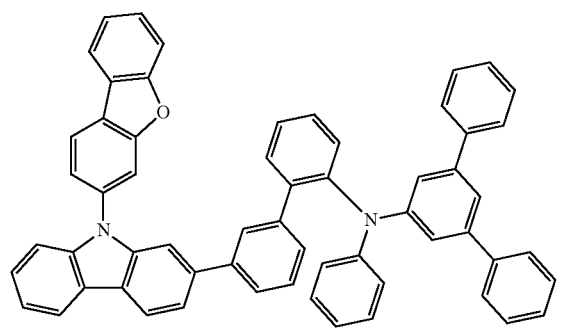
B356
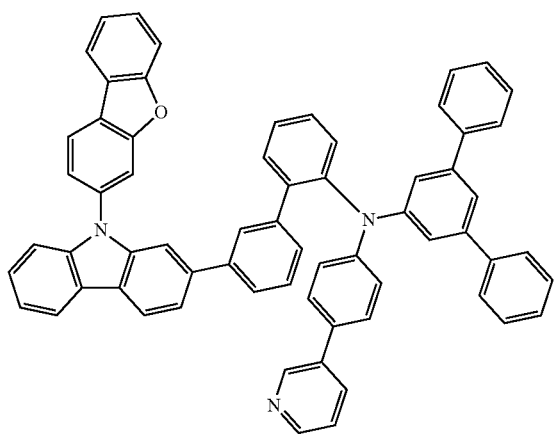
B357
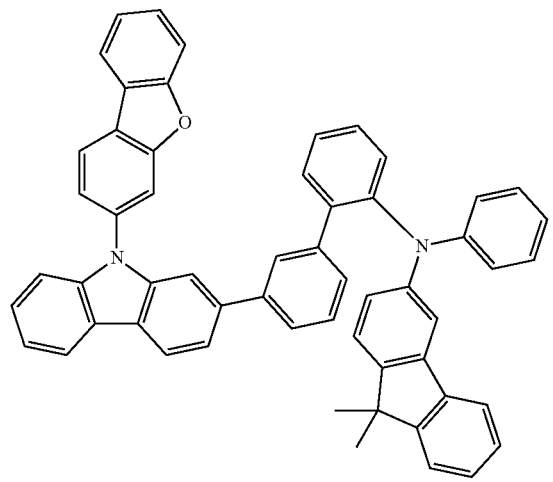
B358

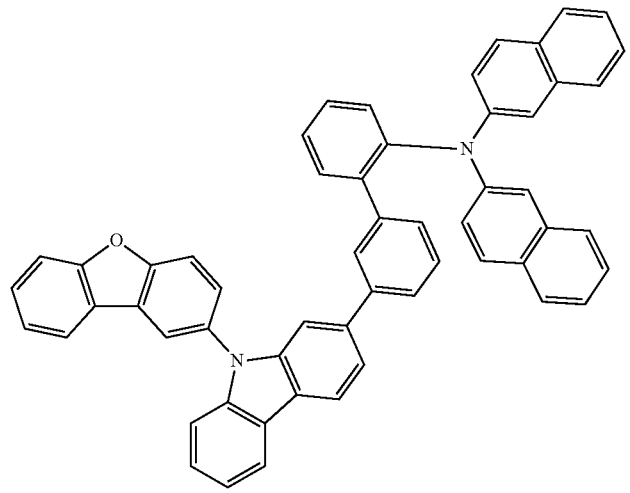
B359
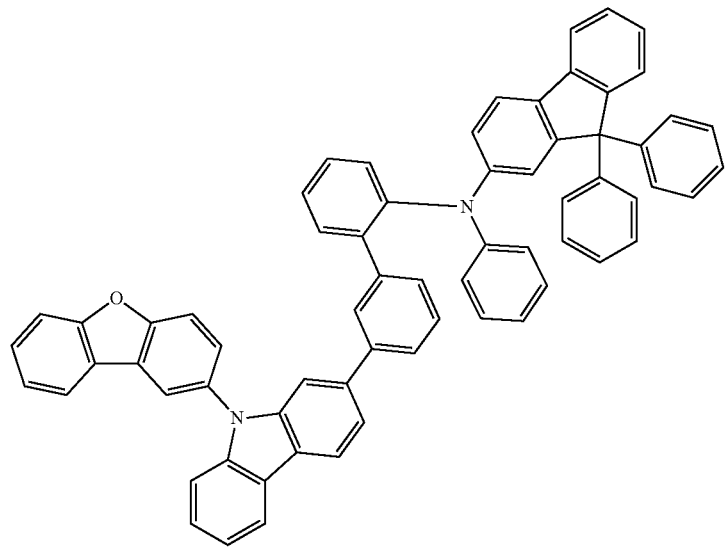
B360
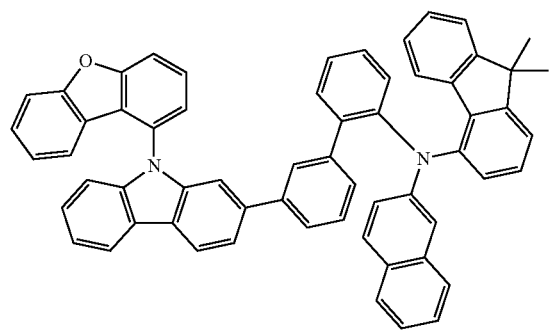
B361
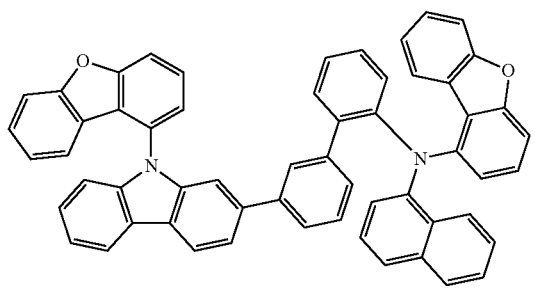
B362

-continued
B363
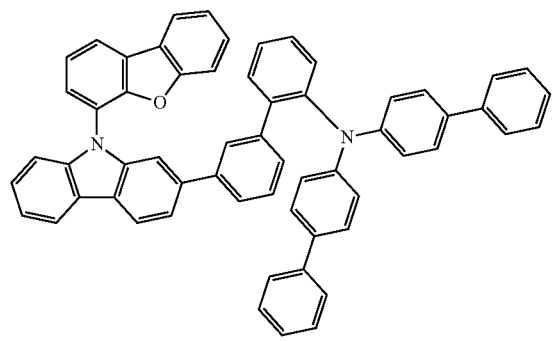
B364
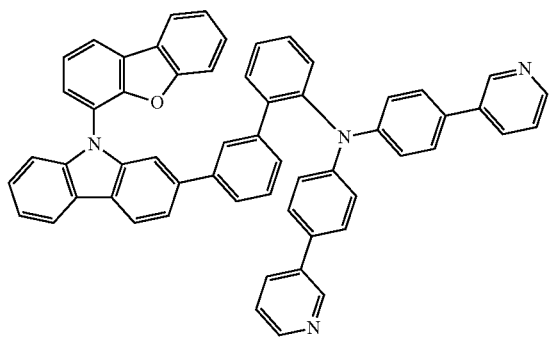
B365
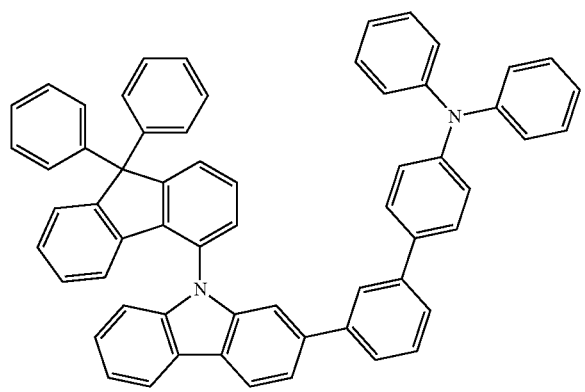
B366
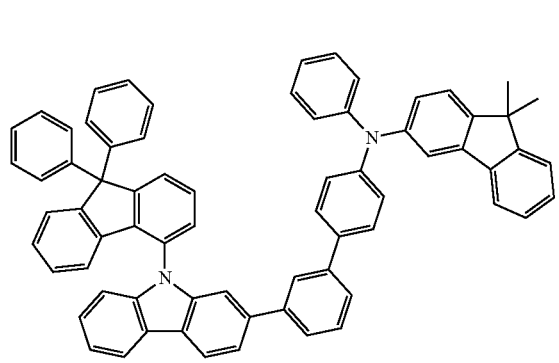
B367
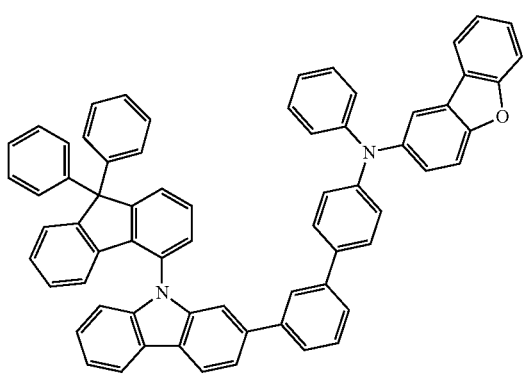
B368
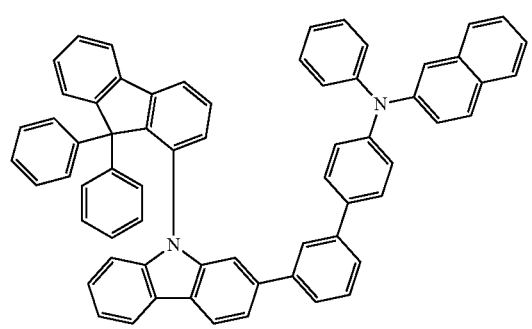
B369
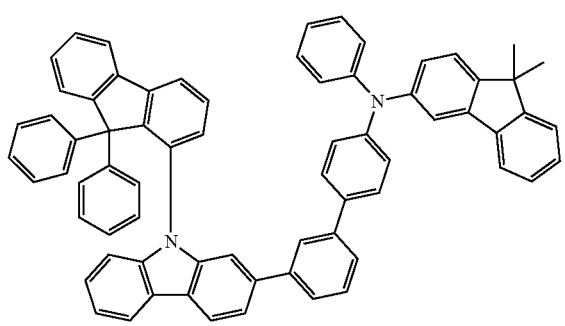

-continued
B370
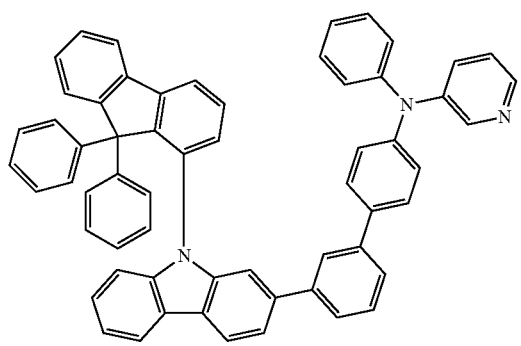
B371
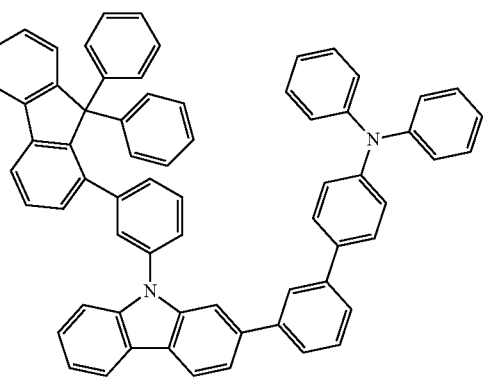
B372
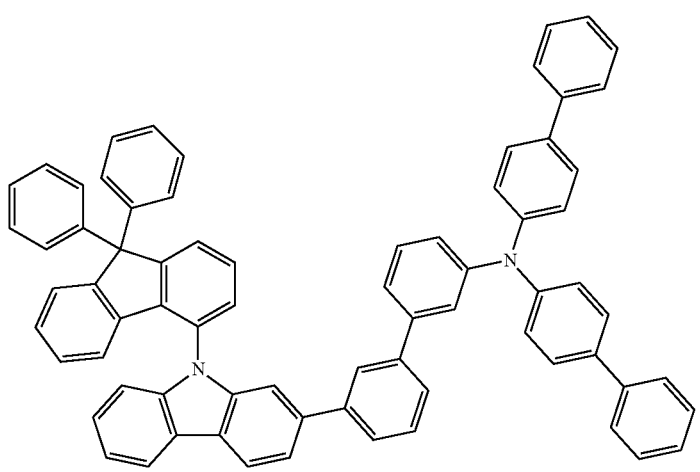
B373
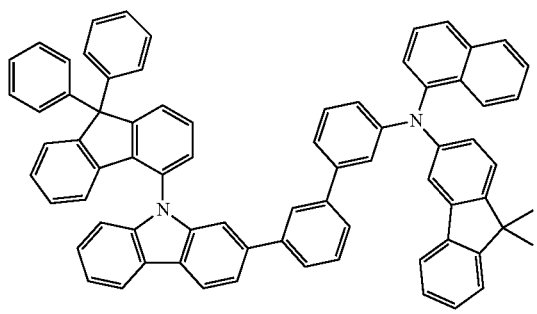
B374
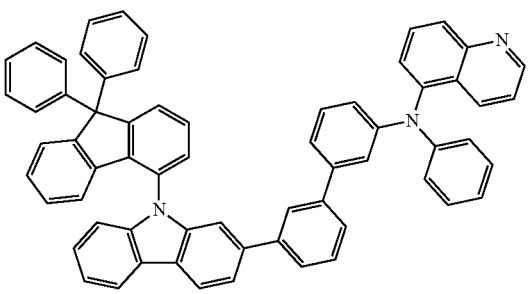
B375
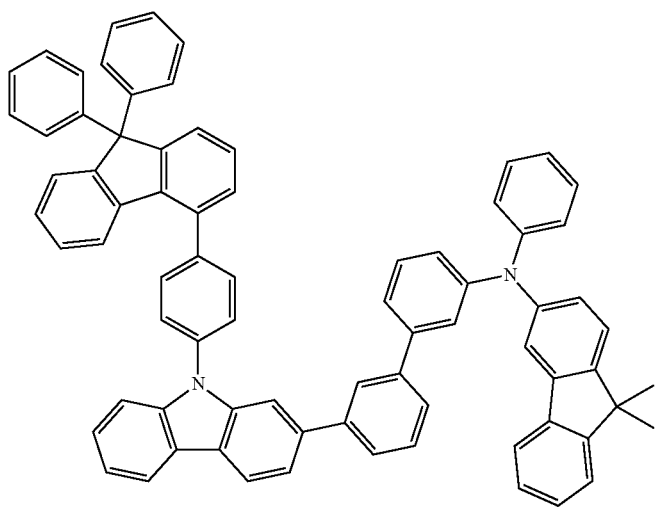

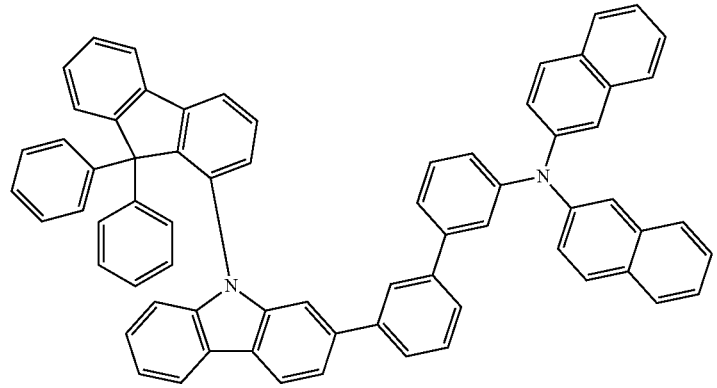
B376
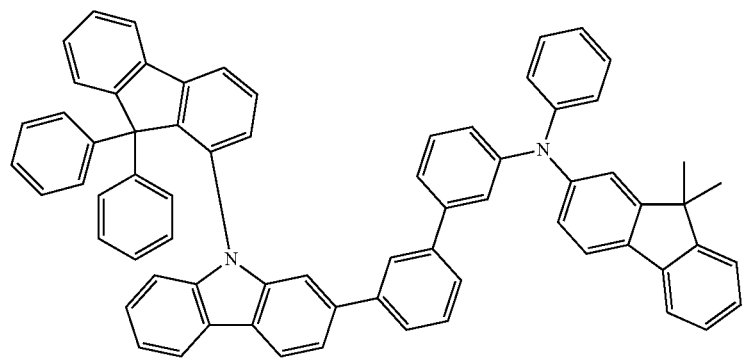
B377
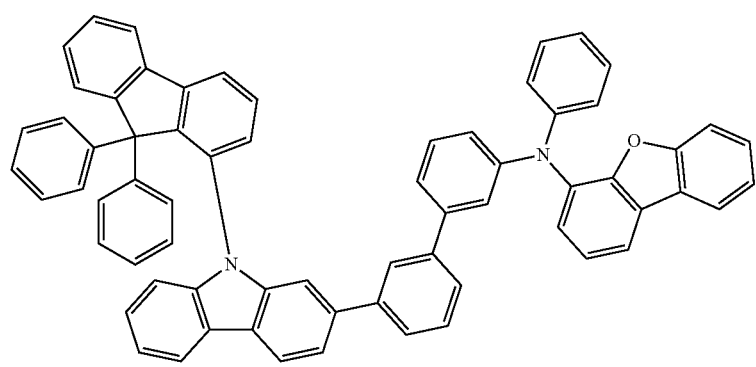
B378
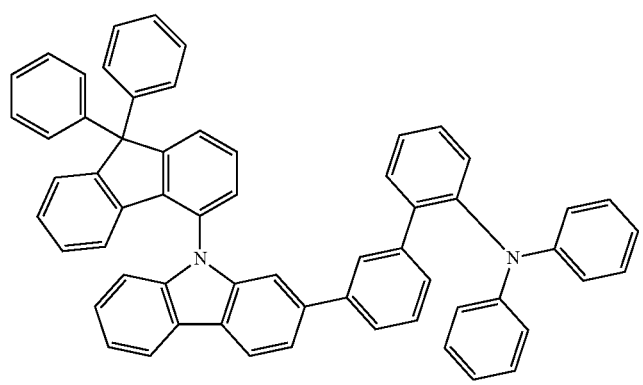
B379

-continued
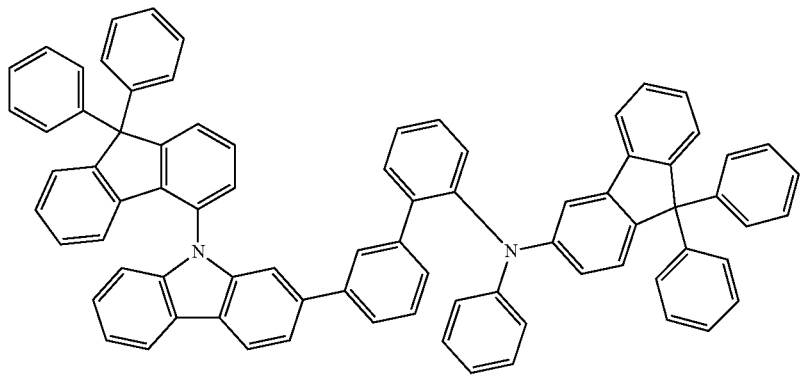
B380
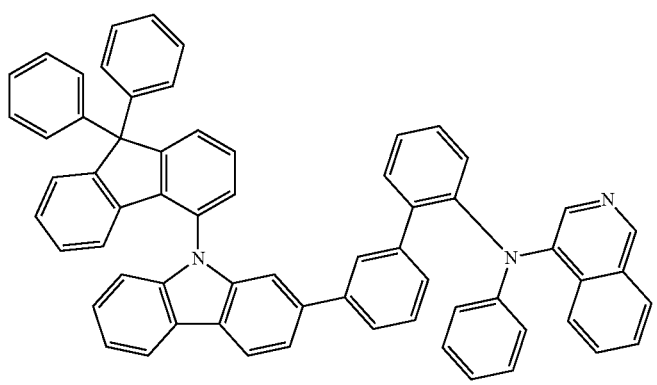
B391
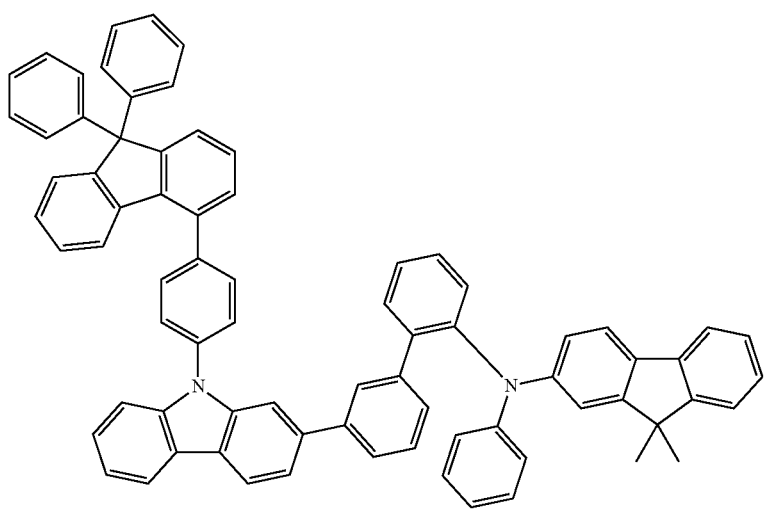
B382

B383
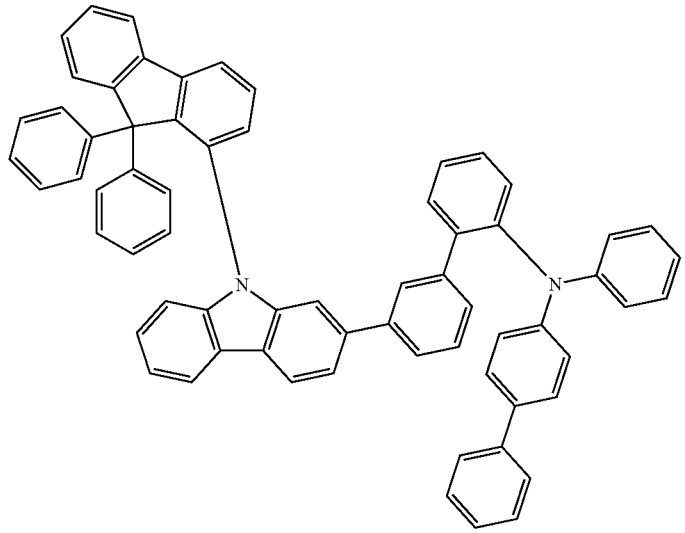
B384
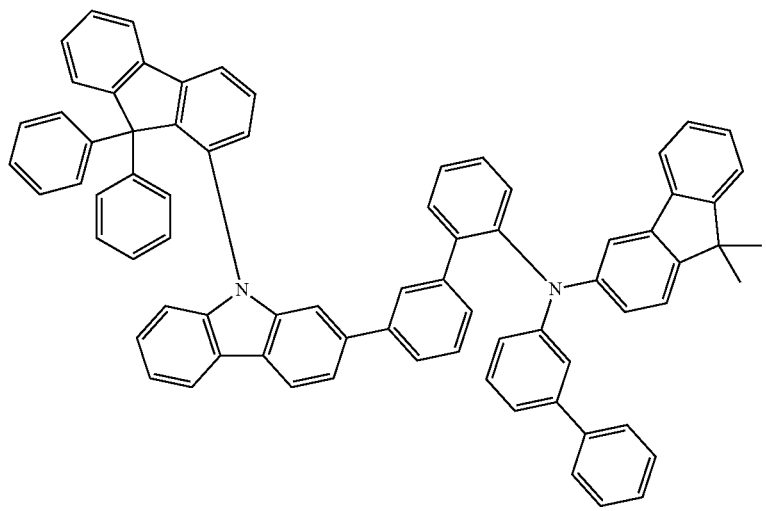
B385
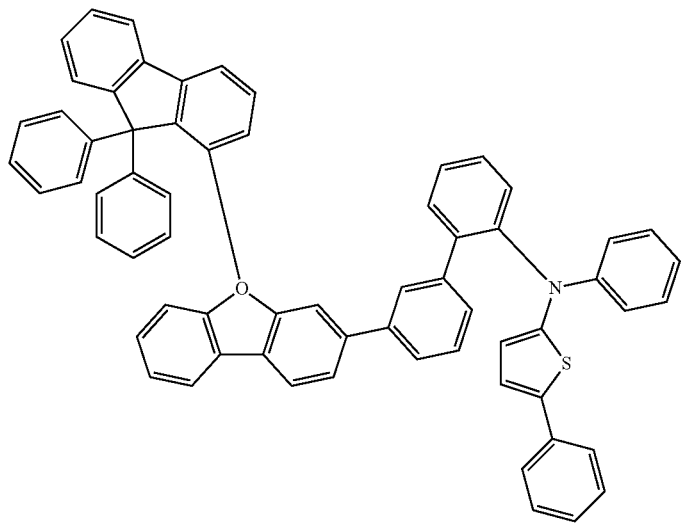

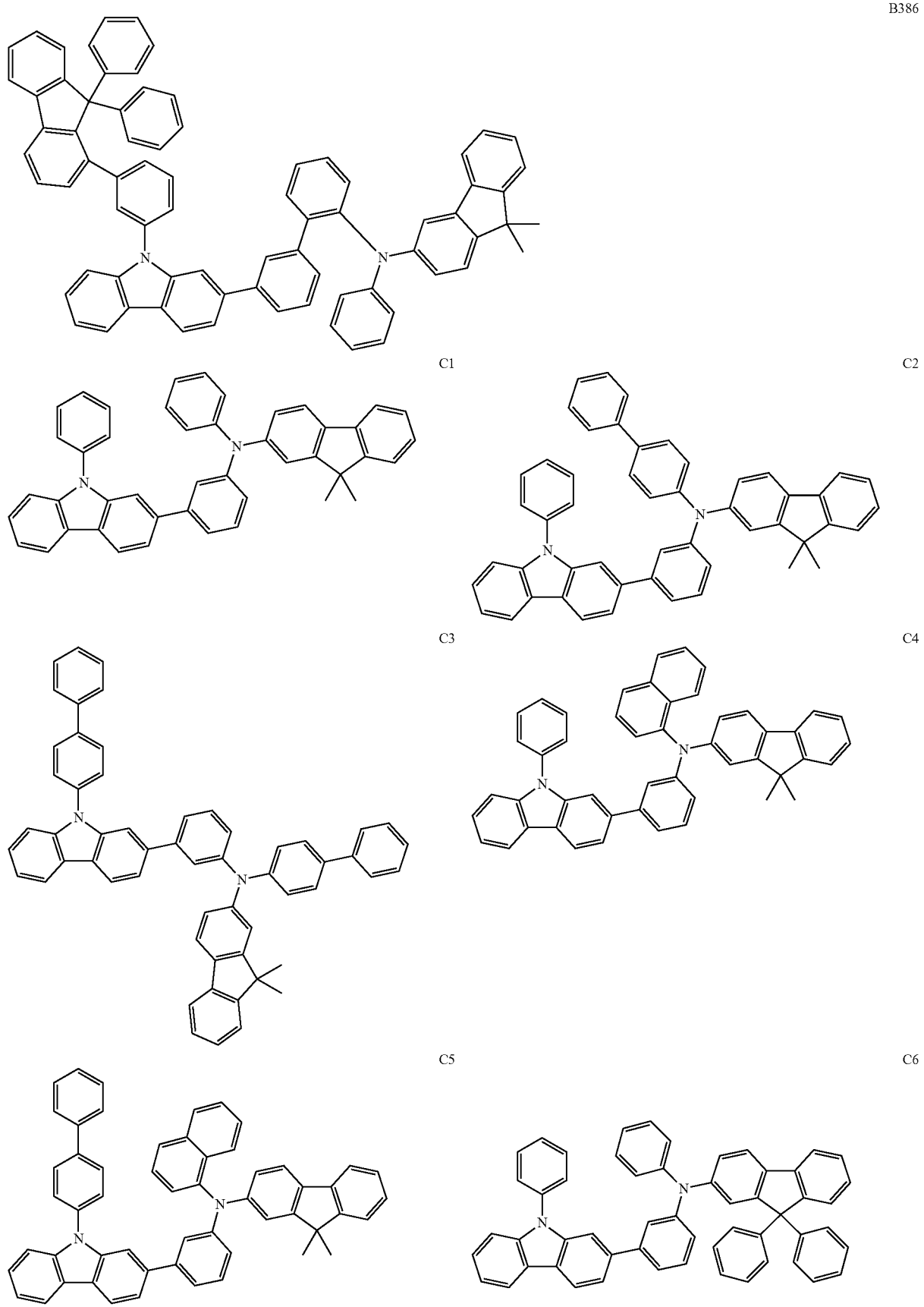

-continued
C7
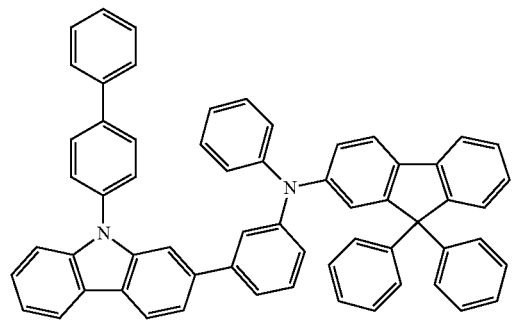
C8
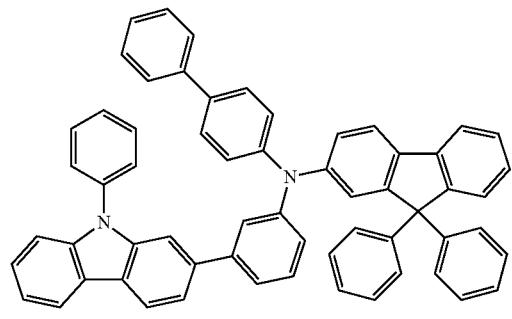
C9
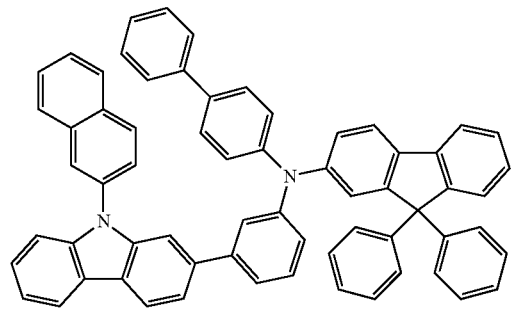
C10
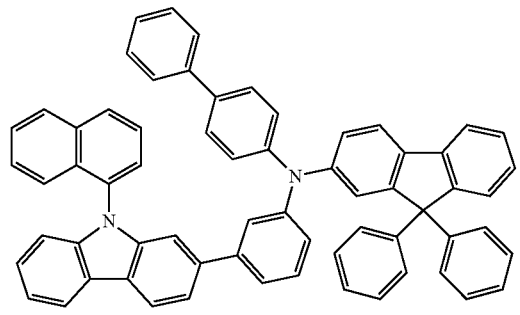
C11
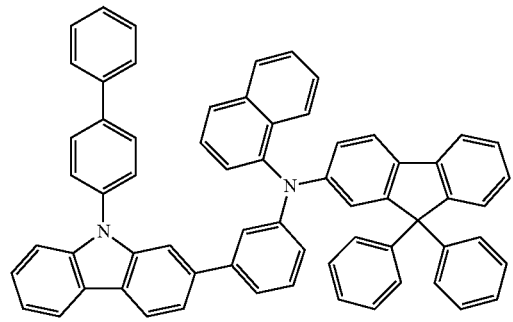
C12
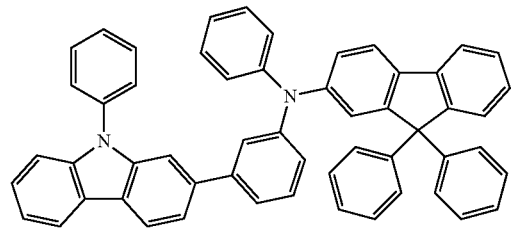
C13
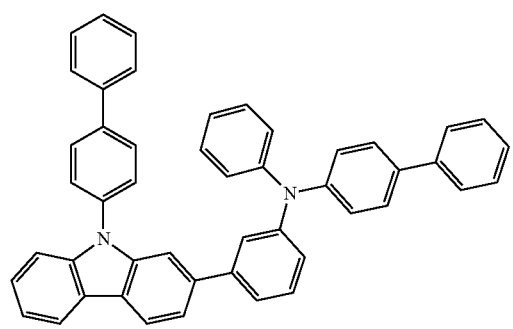
C14
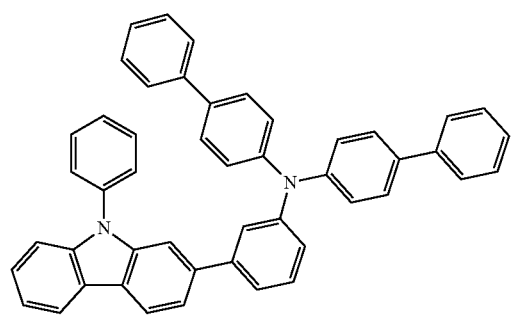
C15
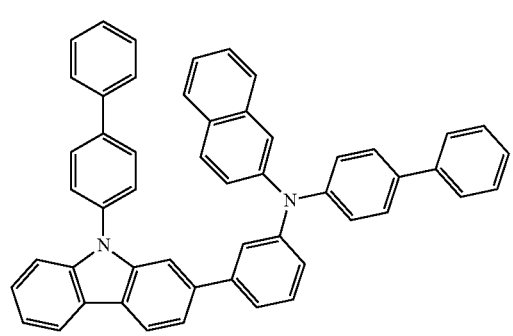
C16
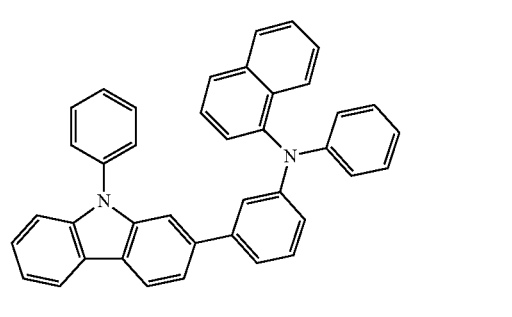

-continued
C17
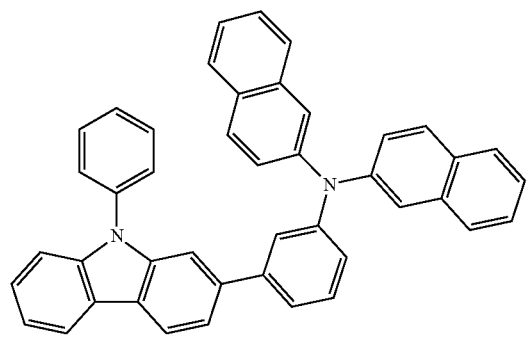
C18
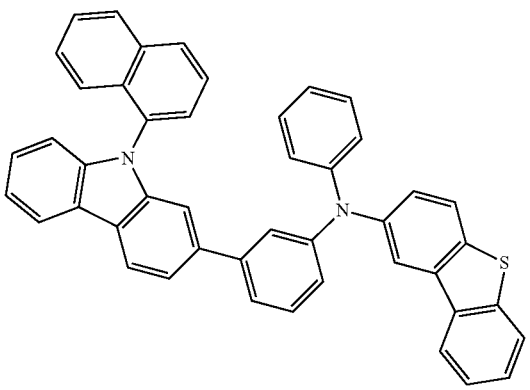
C19
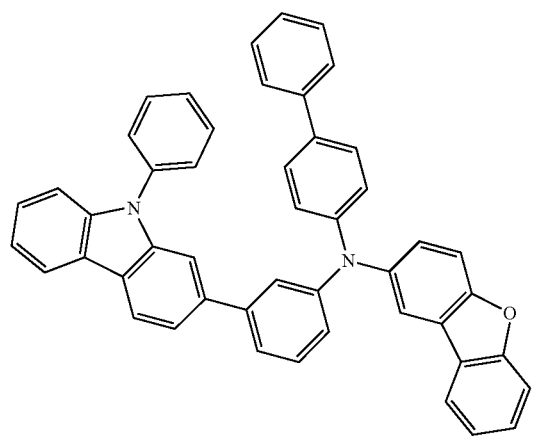
C20
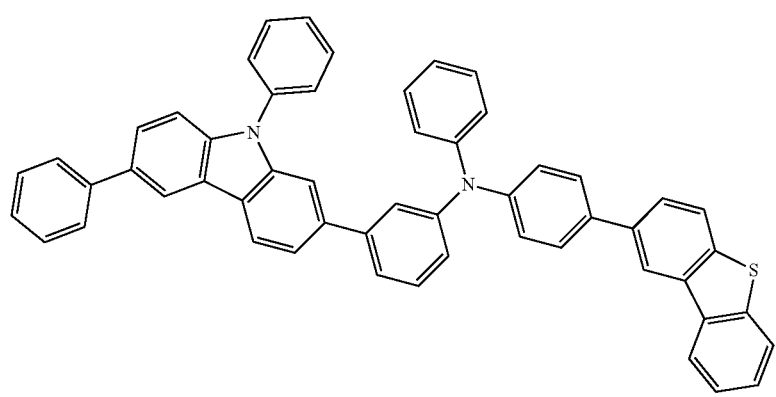

-continued
C21
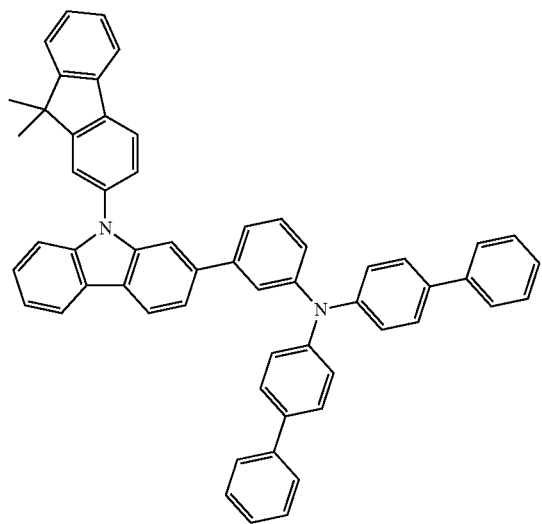
C22
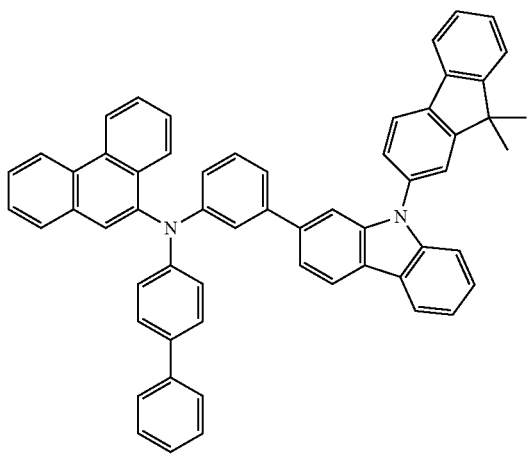
C23
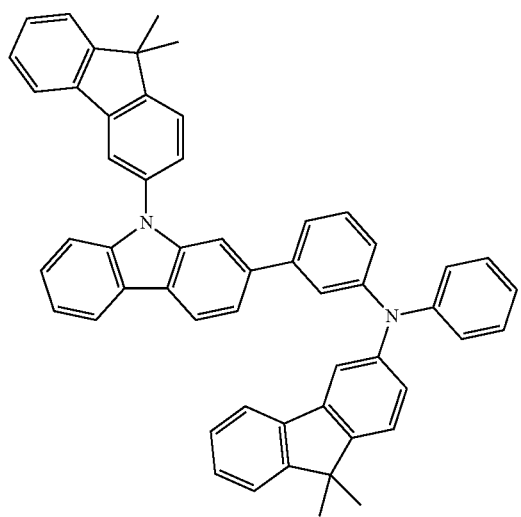
C24
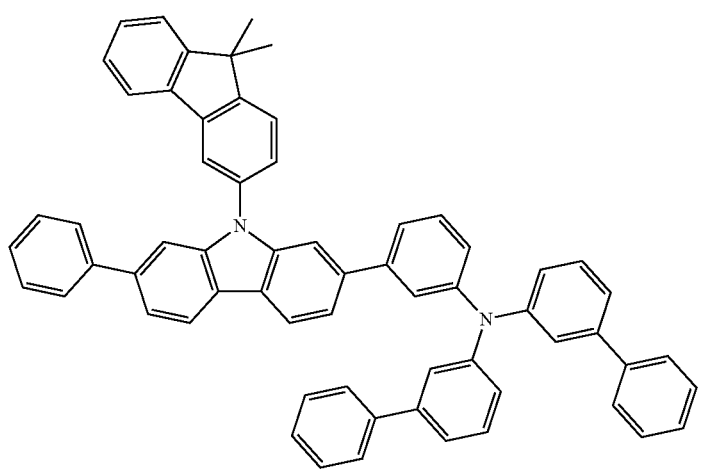

-continued
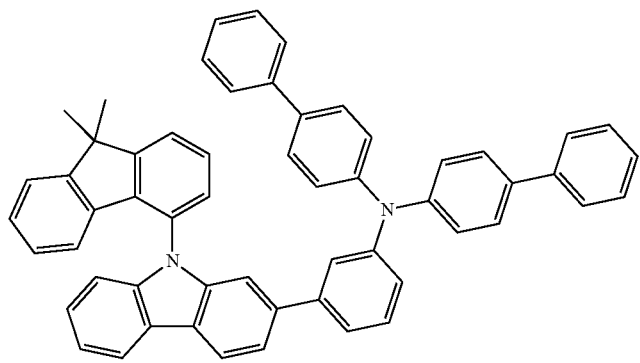
C25
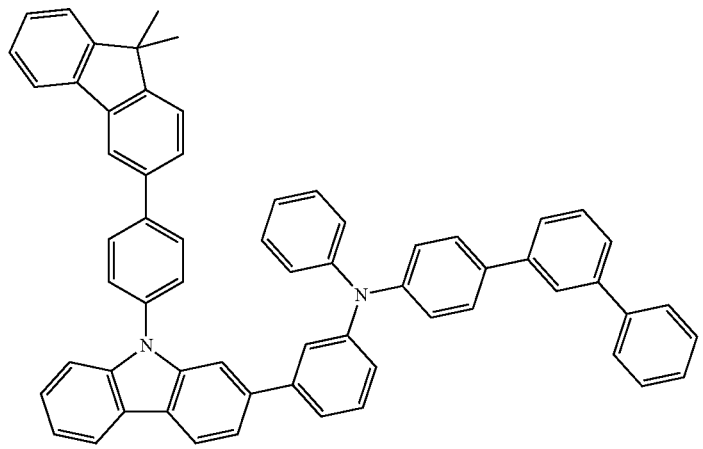
C26
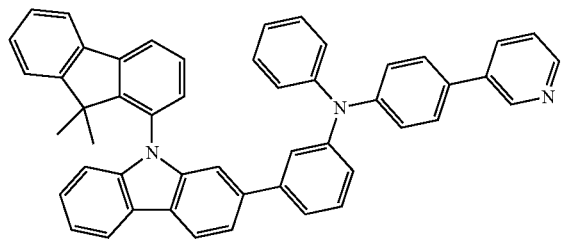
C27
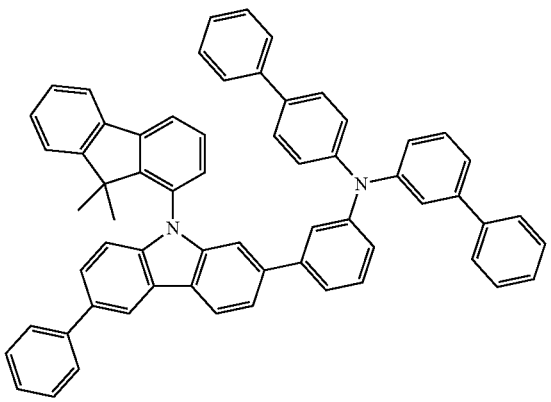
C28
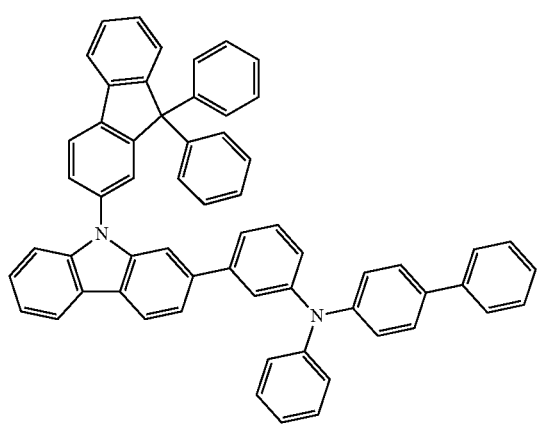
C29
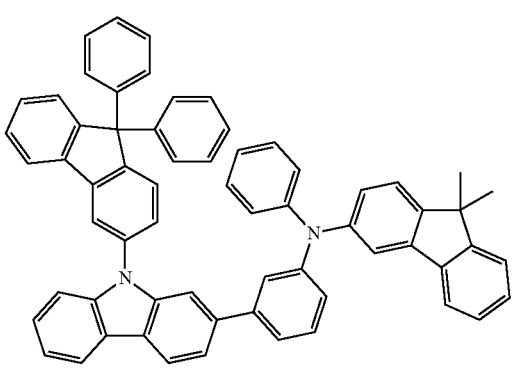
C30

-continued
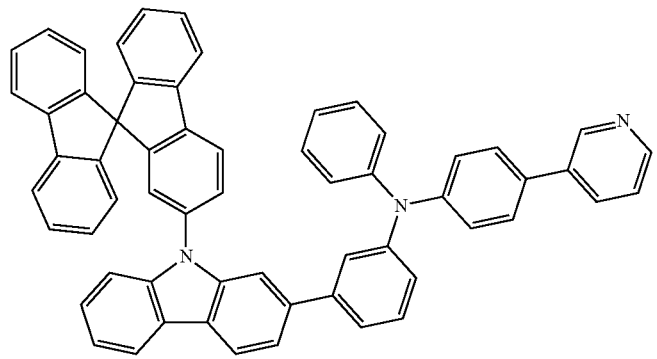
C31
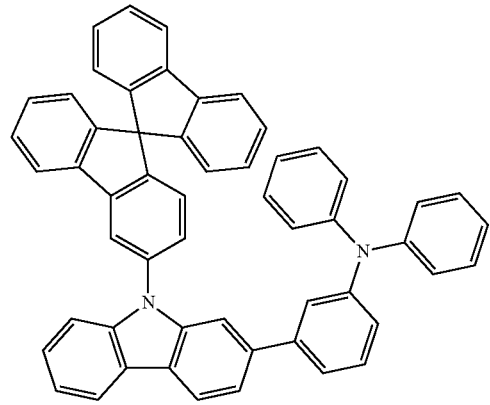
C32
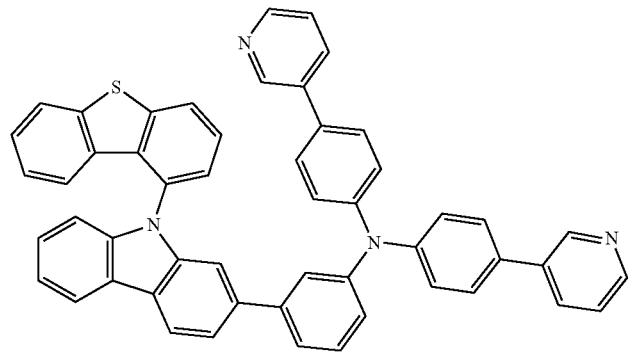
C33
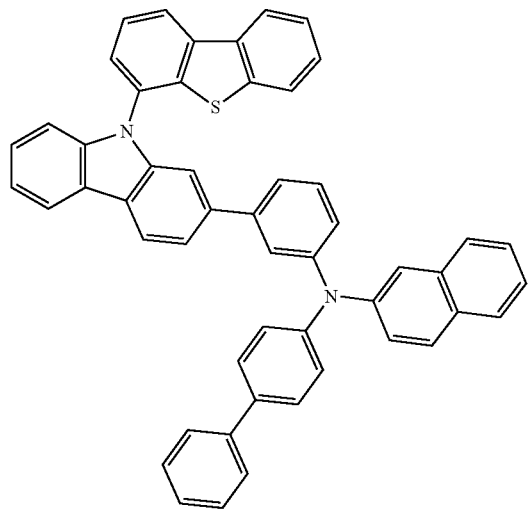
C34

C35

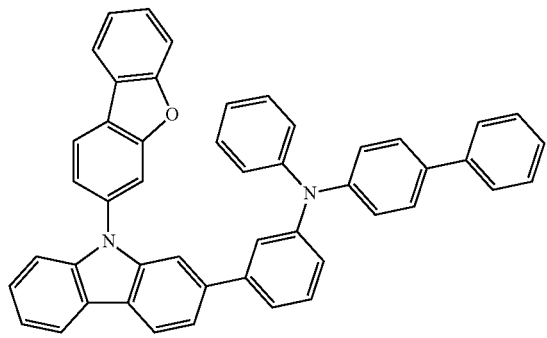

C36

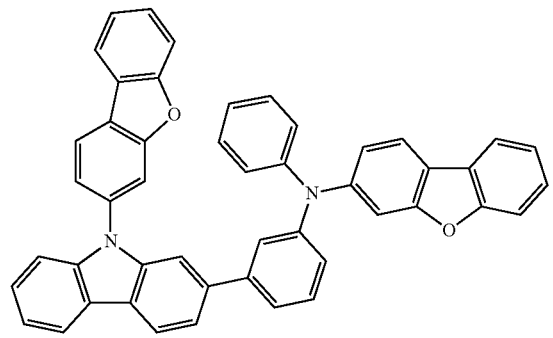

C37

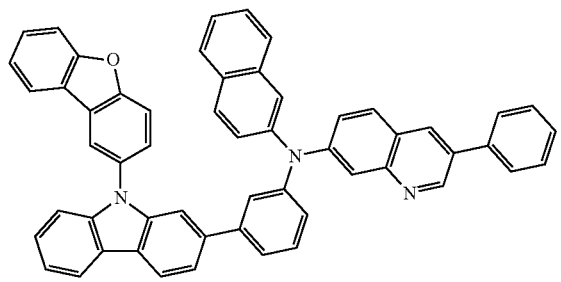

C38

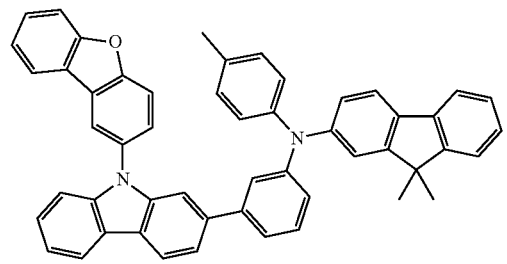

C39

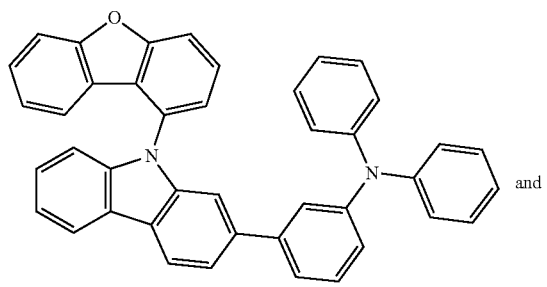

and

C40

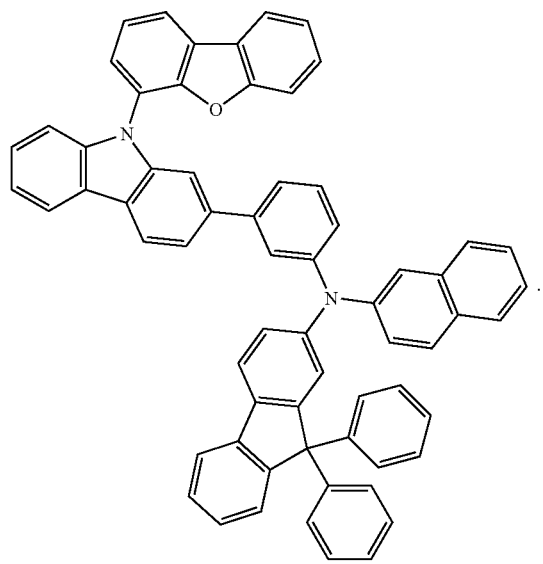

7. An organic electric element comprising the compound of claim 1.

8. The organic electric element as claimed in claim 7, wherein the organic electric element comprising a first electrode, a second electrode, and an organic material layer disposed between the first electrode and the second electrode, wherein the organic material layer comprising the compound.

9. The organic electric element as claimed in claim 8, wherein the organic material layer comprises at least one of a light emitting layer, a hole injection layer, a hole transport layer, an emission-auxiliary layer, an electron injection layer, and an electron transport layer.

10. The organic electric element as claimed in claim 8, wherein the organic electric element further including at least a layer to improve luminous efficiency which is formed on at least one of the sides the first and second electrodes, which is opposite to the organic material layer.

11. The organic electric element as claimed in claim 8, wherein the organic material layer is formed by any one of the process of spin coating, nozzle printing, inkjet printing, slot coating, dip coating and roll-to-roll.

12. An electronic device comprising a display device, which comprises the organic electric element as claimed in claim 7, and a control unit for driving the display device.

13. The electronic device as claimed in claim 12, wherein the organic electric element comprises at least one of an organic light emitting diode (OLED), an organic solar cell, an organic photo conductor (OPC), an organic transistor (organic TFT), and an element for monochromatic or white illumination.

* * * * *